US012187763B2

(12) United States Patent
Wong et al.

(10) Patent No.: US 12,187,763 B2
(45) Date of Patent: *Jan. 7, 2025

(54) CHROMATOGRAPHY RESIN AND USES THEREOF

(71) Applicant: ImmunityBio, Inc., San Diego, CA (US)

(72) Inventors: Hing C. Wong, Miramar, FL (US); Jin-an Jiao, Miramar, FL (US); Caitlin Prendes, Miramar, FL (US)

(73) Assignee: ImmunityBio, Inc., San Diego, CA (US)

( * ) Notice: Subject to any disclaimer, the term of this patent is extended or adjusted under 35 U.S.C. 154(b) by 282 days.

This patent is subject to a terminal disclaimer.

(21) Appl. No.: 17/173,767

(22) Filed: Feb. 11, 2021

(65) Prior Publication Data

US 2021/0277054 A1 Sep. 9, 2021

Related U.S. Application Data

(60) Provisional application No. 62/982,002, filed on Feb. 26, 2020, provisional application No. 62/975,141, filed on Feb. 11, 2020.

(51) Int. Cl.

| | | |
|---|---|---|
| *C07K 1/22* | (2006.01) | |
| *B01D 15/38* | (2006.01) | |
| *B01D 61/02* | (2006.01) | |
| *B01D 61/14* | (2006.01) | |
| *B01D 61/58* | (2006.01) | |
| *C07K 14/54* | (2006.01) | |
| *C07K 14/715* | (2006.01) | |
| *C07K 14/745* | (2006.01) | |
| *C07K 16/36* | (2006.01) | |

(52) U.S. Cl.
CPC ............ *C07K 1/22* (2013.01); *B01D 15/3809* (2013.01); *B01D 61/027* (2013.01); *B01D 61/145* (2013.01); *B01D 61/58* (2013.01); *C07K 14/5443* (2013.01); *C07K 14/7155* (2013.01); *C07K 14/745* (2013.01); *C07K 16/36* (2013.01); *B01D 2315/16* (2013.01); *C07K 2317/565* (2013.01); *C07K 2319/00* (2013.01)

(58) Field of Classification Search
CPC ........ C07K 1/22; C07K 14/745; C07K 16/36; B01D 15/3809; B01D 61/58
See application file for complete search history.

(56) References Cited

U.S. PATENT DOCUMENTS

| | | | |
|---|---|---|---|
| 6,117,980 A | 9/2000 | Gonzalez et al. | |
| 7,452,537 B2 | 11/2008 | Bauer et al. | |
| 7,482,436 B2 | 1/2009 | Sugimura et al. | |
| 7,488,802 B2 | 2/2009 | Collins et al. | |
| 7,521,051 B2 | 4/2009 | Collins et al. | |
| 7,612,181 B2 | 11/2009 | Wu et al. | |
| 7,691,380 B2 | 4/2010 | Thorpe et al. | |
| 7,723,482 B2 | 5/2010 | Soulillou et al. | |
| 7,968,094 B2 * | 6/2011 | Jiao ...................... | C07K 16/467 424/143.1 |
| 8,007,795 B2 | 8/2011 | Jiao et al. | |
| 8,133,485 B2 | 3/2012 | Levi-Schaffer et al. | |
| 8,217,149 B2 | 7/2012 | Irving et al. | |
| 8,258,268 B2 | 9/2012 | Wu et al. | |
| 8,475,792 B2 | 7/2013 | Dall'Acqua et al. | |
| 8,552,156 B2 | 10/2013 | Takayanagi et al. | |
| 8,586,714 B2 | 11/2013 | Ghayur et al. | |
| 8,716,450 B2 | 5/2014 | Ghayur et al. | |
| 8,722,855 B2 | 5/2014 | Ghayur et al. | |
| 8,735,546 B2 | 5/2014 | Ghayur et al. | |
| 8,741,604 B2 | 6/2014 | Campbell et al. | |
| 8,753,640 B2 | 6/2014 | Wu et al. | |
| 8,759,494 B2 | 6/2014 | Bachmann et al. | |
| 8,822,645 B2 | 9/2014 | Ghayur et al. | |
| 9,035,026 B2 | 5/2015 | Hoffmann et al. | |
| 9,067,997 B2 | 6/2015 | Romagne et al. | |
| 9,085,623 B2 | 7/2015 | Rother et al. | |
| 9,090,684 B2 | 7/2015 | Borras et al. | |
| 9,226,962 B2 | 1/2016 | Le Gall et al. | |
| 9,238,084 B2 | 1/2016 | Liu et al. | |
| 9,273,136 B2 | 3/2016 | Rader et al. | |
| 9,371,395 B2 | 6/2016 | Takahashi et al. | |
| 9,441,034 B2 | 9/2016 | Sivakumar et al. | |
| 9,505,843 B2 | 11/2016 | Kim et al. | |
| 9,617,345 B2 | 4/2017 | Berne et al. | |
| 9,701,758 B2 | 7/2017 | Cooper et al. | |
| 11,518,792 B2 | 12/2022 | Wong | |
| 11,672,826 B2 | 6/2023 | Wong | |

(Continued)

FOREIGN PATENT DOCUMENTS

| | | |
|---|---|---|
| CN | 1844150 | 10/2006 |
| CN | 101653603 | 2/2010 |

(Continued)

OTHER PUBLICATIONS

Guha et al., Affinity purification of human tissue factor: Interaction of factor VII and tissue factor in detergent micelles, 1986, Biochemistry, vol. 83, pp. 299-302 (Year: 1986).*
Urh et al., Affinity Chromatography: General Methods, 2009, Methods in Enzymology, vol. 463 (Year: 2009).*
G-Biosciences, The Basics of Affinity Purification/Affinity Chromatography, 2018, pp. 1-4 (Year: 2018).*
Helie et al., Application of the Protein Maker as a platform purification system for therapeutic antibody research and development, 2016, Computational and Structural Biotechnology Journal, vol. 14, pp. 238-244 (Year: 2016).*

(Continued)

*Primary Examiner* — Jeffrey Stucker
*Assistant Examiner* — Brittney E Donoghue
(74) *Attorney, Agent, or Firm* — Sheridan Ross P.C.

(57) ABSTRACT

An affinity chromatography resin comprising an anti-tissue factor antibody or antigen-binding fragment thereof attached to a base resin, and methods of using the same.

30 Claims, 9 Drawing Sheets

Specification includes a Sequence Listing.

(56) References Cited

U.S. PATENT DOCUMENTS

| | | | |
|---|---|---|---|
| 11,730,762 | B2 | 8/2023 | Wong |
| 11,738,052 | B2 | 8/2023 | Wong |
| 2001/0044427 | A1 | 11/2001 | Mazel et al. |
| 2003/0124678 | A1 | 7/2003 | Epstein et al. |
| 2003/0219441 | A1* | 11/2003 | Thorpe ............ A61K 47/6851 424/155.1 |
| 2005/0014224 | A1 | 1/2005 | Collins et al. |
| 2006/0159655 | A1 | 7/2006 | Collins et al. |
| 2007/0160579 | A1 | 7/2007 | Schmitz et al. |
| 2008/0025979 | A1 | 1/2008 | Honjo et al. |
| 2009/0148942 | A1 | 6/2009 | McDonagh et al. |
| 2012/0171197 | A1 | 7/2012 | Eriksson et al. |
| 2012/0264920 | A1* | 10/2012 | Wang ...................... C07K 1/36 530/416 |
| 2013/0274446 | A1 | 10/2013 | Kumagai et al. |
| 2014/0242077 | A1 | 8/2014 | Choi |
| 2015/0218274 | A1 | 8/2015 | Sabatos-Peyton et al. |
| 2015/0259429 | A1 | 9/2015 | Benaroch et al. |
| 2016/0175397 | A1 | 6/2016 | Umana et al. |
| 2016/0340413 | A1 | 11/2016 | Duerner et al. |
| 2016/0367664 | A1 | 12/2016 | Wang et al. |
| 2017/0051063 | A1 | 2/2017 | Baum et al. |
| 2017/0198042 | A1 | 7/2017 | Williams et al. |
| 2017/0283499 | A1 | 10/2017 | Delhem et al. |
| 2018/0200366 | A1 | 7/2018 | Wong |
| 2019/0078082 | A1 | 3/2019 | Amorese et al. |
| 2019/0092846 | A1 | 3/2019 | Ibebunjo et al. |
| 2019/0177406 | A1 | 6/2019 | Ledbetter et al. |
| 2019/0315850 | A1 | 10/2019 | Bedinger et al. |
| 2020/0071374 | A1* | 3/2020 | Wong ................... C07K 14/715 |
| 2020/0123607 | A1 | 4/2020 | Serrano Marugan et al. |
| 2020/0190174 | A1* | 6/2020 | Wong ........................ A61P 3/10 |
| 2020/0392221 | A1 | 12/2020 | Van Snick et al. |
| 2020/0399358 | A1 | 12/2020 | Shapiro et al. |
| 2021/0060064 | A1* | 3/2021 | Wong ................... C07K 14/715 |
| 2021/0061897 | A1 | 3/2021 | Ledbetter et al. |
| 2021/0070825 | A1* | 3/2021 | Wong ...................... C12N 15/62 |
| 2021/0070826 | A1* | 3/2021 | Wong ...................... C07K 14/54 |
| 2021/0100840 | A1 | 4/2021 | Wong et al. |
| 2021/0137981 | A1* | 5/2021 | Wong ...................... C07K 16/00 |
| 2021/0268022 | A1* | 9/2021 | Wong ...................... C12N 5/0637 |
| 2021/0338724 | A1 | 11/2021 | Wong |
| 2021/0355204 | A1 | 11/2021 | Bedinger et al. |
| 2021/0403545 | A1 | 12/2021 | Van Snick et al. |
| 2022/0073578 | A1 | 3/2022 | Wong et al. |
| 2023/0023389 | A1 | 1/2023 | Wong |
| 2023/0039157 | A1 | 2/2023 | Wong |
| 2023/0128292 | A1 | 4/2023 | Wong |
| 2023/0174666 | A1 | 6/2023 | Wong et al. |
| 2023/0272027 | A1 | 8/2023 | Wong |
| 2023/0372399 | A1 | 11/2023 | Wong |
| 2023/0372444 | A1 | 11/2023 | Wong et al. |
| 2023/0381238 | A1 | 11/2023 | Wong |
| 2023/0398151 | A1 | 12/2023 | Wong |
| 2024/0124543 | A1 | 4/2024 | Wong |
| 2024/0124544 | A1 | 4/2024 | Wong |
| 2024/0132561 | A1 | 4/2024 | Wong |

FOREIGN PATENT DOCUMENTS

| | | |
|---|---|---|
| CN | 101965364 | 2/2011 |
| CN | 102153653 | 8/2011 |
| CN | 106255703 | 12/2016 |
| CN | 109513003 | 3/2019 |
| EP | 1245676 | 10/2002 |
| EP | 1719528 | 11/2006 |
| EP | 2537933 | 12/2012 |
| EP | 3029069 | 6/2016 |
| EP | 3348276 | 7/2018 |
| JP | 2005-124568 | 5/2005 |
| JP | 2008-536487 | 9/2008 |
| JP | 2009-512433 | 3/2009 |
| JP | 4361133 | 8/2009 |
| KR | 2016/0127688 | 11/2016 |
| KR | 101778439 | 9/2017 |
| WO | WO 1995/015341 | 6/1995 |
| WO | WO 1996/001653 | 1/1996 |
| WO | WO 2001/083755 | 11/2001 |
| WO | WO 2002/083152 | 10/2002 |
| WO | WO 2003/037911 | 5/2003 |
| WO | WO 2003/104425 | 12/2003 |
| WO | WO 2004/076488 | 9/2004 |
| WO | WO 2006/096828 | 9/2006 |
| WO | WO 2006/097743 | 9/2006 |
| WO | WO 2006/119897 | 11/2006 |
| WO | WO 2008/096158 | 8/2008 |
| WO | WO 2011/127324 | 10/2011 |
| WO | WO 2012/040323 | 3/2012 |
| WO | WO 2012/120125 | 9/2012 |
| WO | WO 2012/170470 | 12/2012 |
| WO | WO 2012/175222 | 12/2012 |
| WO | WO 2012/175692 | 12/2012 |
| WO | WO 2013/068946 | 5/2013 |
| WO | WO 2014/007513 | 1/2014 |
| WO | WO 2014/026054 | 2/2014 |
| WO | WO 2014/095808 | 6/2014 |
| WO | WO 2014/130635 | 8/2014 |
| WO | WO 2014/159531 | 10/2014 |
| WO | WO 2015/089881 | 6/2015 |
| WO | WO 2016/106221 | 6/2016 |
| WO | WO 2016/154585 | 9/2016 |
| WO | WO 2016/166348 | 10/2016 |
| WO | WO 2017/053748 | 3/2017 |
| WO | WO 2017/083612 | 5/2017 |
| WO | WO 2017/149538 | 9/2017 |
| WO | WO 2017/189526 | 11/2017 |
| WO | WO 2018/067825 | 4/2018 |
| WO | WO 2018/075989 | 4/2018 |
| WO | WO 2018/129007 | 7/2018 |
| WO | WO 2018/158350 | 9/2018 |
| WO | WO 2018/183169 | 10/2018 |
| WO | WO 2018/165208 | 12/2018 |
| WO | WO 2019/046313 | 3/2019 |
| WO | WO 2020/047299 | 3/2020 |
| WO | WO 2020/047333 | 3/2020 |
| WO | WO 2020/047462 | 3/2020 |
| WO | WO 2020/047473 | 3/2020 |
| WO | WO 2021/163369 | 8/2021 |

OTHER PUBLICATIONS

Bramer et al., Membrane Adsorber for the Fast Purification of a Monoclonal Antibody Using Protein A Chromatography, 2019, Membranes, vol. 9, Issue 159, pp. 1-15 (Year: 2019).*

Amersham Pharmacia Biotech, CNBr-activated Sepharose 4 Fast Flow, 1999, Affinity Chromatography, pp. 1-4 (Year: 1999).*

ThermoFisher, Covalent Immobilization of Affinity Ligands, 2018, pp. 1-22, retrieved from: https://www.thermofisher.com/us/en/home/life-science/protein-biology/protein-biology-learning-center/protein-biology-resource-library/pierce-protein-methods/covalent-immobilization-affinity-ligands.html (Year: 2018).*

Abbott et al., "Genomic organization, exact localization, and tissue expression of the human CD26 (dipeptidyl peptidase IV) gene," Immunogenetics, Sep. 1994, 40(5):331-338.

Abdul-Aziz et al., "Acute myeloid leukemia induces protumoral p16INK4a-driven senescence in the bone marrow microenvironment," Blood, Jan. 31, 2019, 133(5):446-456.

Aertgeerts et al., "Crystal structure of human dipeptidyl peptidase IV in complex with a decapeptide reveals details on substrate specificity and tetrahedral intermediate formation," Protein Science, Feb. 2004, 13(2):412-421.

Ait-Oufella el al., "Natural regulatory T cells control the development of atherosclerosis in mice," Nature Medicine, Feb. 5, 2006, 12:178-180.

Akbari, et al., "Design, expression and evaluation of a novel humanized single chain antibody against epidermal growth factor receptor (EGFR)," Protein Expr. Purif., 2016, 127:8-15.

Ali et al., "Regulatory T cells in skin," Immunology, Jul. 12, 2017, 152(3):372-381.

(56) References Cited

OTHER PUBLICATIONS

Angevin et al., "First-in-human phase 1 of YS110, a monoclonal antibody directed against CD26 in advanced CD26-expressing cancers," British Journal of Cancer, Mar. 14, 2017, 116(9):1126-1134.
Bachelet et al., "Mast Cell Costimulation by CD226/CD112 (DNAM-1/Nectin-2) A Novel Interface in the Allergic Process," Journal of Biological Chemistry, Sep. 15, 2006, 281(37):27190-6.
Baker, et al., "Clearance of p16Ink4a-positive senescent cells delays ageing-associated disorders," Nature, 2011, 479(7372): 232-236.
Bennett et al., "Erratum: Killing the old: cell senescence in atherosclerosis," Nature Reviews Cardiology, Jan. 12, 2017, 14(3):132.
Bennett et al., "Killing the old: cell senescence in atherosclerosis," Nature Reviews Cardiology, Dec. 12, 2016, 14(1):8-9, 2 pages.
Bentebibel et al., "A First-in-Human Study and Biomarker Analysis of NKTR-214, a Novel IL2Raf Biased Cytokine, in Patients with Advanced or Metastatic Solid Tumors," Cancer Discovery, Jun. 2019, 9(6):711-721.
Bhat et al., "Astrocyte Senescence as a Component of Alzheimer's Disease," PLoS One, Sep. 12, 2012, 7(9):e45069, 10 pages.
Biran et al., "Senescent cells communicate via intercellular protein transfer," Genes & Development, Apr. 8, 2015, 29(8):791-802, 13 pages.
Borea et al., "Pharmacology of Adenosine Receptors: The State of the Art," Physiological Reviews, May 31, 2918, 98(3):1591-1625.
Borgerding et al., "B-lymphoma cells escape rituximab-triggered elimination by NK cells through increased HLA class I expression," Experimental Hematology, Mar. 1, 2010, 38(3):213-21.
Bork, "Powers and Pitfalls in Sequence Analysis: The 70% Hurdle," Genome Research, 2000, 10:398-400.
Bourgeois et al., "Regulation of cellular senescence via the FOXO4-p53 axis," FEBS Lett., 2018, 592(12): 2083-2097.
Bowie et al., "Deciphering the Message in Protein Sequences: Tolerance to Amino Acid Substitutions," Science, 1990, 247:1306-1310.
Boyman et al., "IL-7/Anti-IL-7 mAb Complexes Restore T Cell Development and Induce Homeostatic T Cell Expansion without Lymphopenia," The Journal of Immunology, Jun. 1, 2008, 180:7265-7275.
Boyman et al., "Selective Stimulation of T Cell Subsets with Antibody-Cytokine Immune Complexes," Science, Mar. 31, 2006, 311(5769):1924-1927.
Brennan et al., "Structural determination of lipid antigens captured at the CD1d-T-cell receptor interface," PNAS, 2017, 114(31):8348-8353.
Brighton et al., "Clearance of senescent decidual cells by uterine natural killer cells in cycling human endometrium," Elife, Dec. 11, 2017, 6:e31274, 23 pages.
Brooks et al., "Combined inhibition of PD1 and CD96 checkpoints improves survival in a resectable murine model of pancreatic cancer," European Journal of Cancer, Jul. 1, 2016, 61:S189, 1 page.
Broxmeyer et al., "Modulation of Hematopoietic Chemokine Effects In Vitro and In Vivo by DPP-4/CD26," Stem Cells and Development, Mar. 4, 2016, 25(8):575-585.
Brunstein et al., "Infusion of Ex Vivo Expanded T Regulatory Cells in Adults Transplanted with Umbilical Cord Blood: Safety Profile and Detection Kinetics," Blood, Jan. 20, 2011, 117(3):1061-1070.
Brunstein et al., "Umbilical cord blood-derived T regulatory cells to prevent GVHD:kinetics, toxicity profile, and clinical effect," Blood, Feb. 25, 2016, 127(8):1044-1051.
Buhling et al., "Functional role of CD26 on human B lymphocytes," Immunology Letters, Feb. 1995, 45(1-2):47-51.
Burgess et al., "Possible Dissociation of the Heparin-binding and Mitogenic Activities of Heparin-binding (Acidic Fibroblast) GrowthFactor-1 from Its Receptor-binding Activities by Site-directed Mutagenesis of a Single Lysine Residue," J. Cell Biol., 1990, 111:2129-2138.
Bussian et al., "Clearance of senescent glial cells prevents tau-dependent pathology and cognitive decline," Nature, Sep. 19, 2018, 562(7728):578-582, 21 pages.
Cai et al., "Chibby suppresses aerobic glycolysis and proliferation of nasopharyngeal carcinoma via the Wnt/β-catenin-Lin28/let7-PDK1 cascade," Journal of Experimental & Clinical Cancer Research, Dec. 1, 2018, 37(1):104.
Cao et al., "Expression and characterization of recombinant humanized anti-HER2 single-chain antibody in Pichia pastoris for targeted cancer therapy," Biotechnology Letters, Jul. 1, 2015, 37(7):1347-54.
Cao, "Self-regulation and cross-regulation of pattern-recognition receptor signaling in health and disease," Nature Reviews Immunology, Dec. 29, 2015, 16(1):35-50.
Carr et al., "NK Cell-Mediated Lysis of Autologous HCMV-Infected Skin Fibroblasts Is Highly Variable among NK Cell Clones and Polyclonal NK Cell Lines," Clinical Immunology, Nov. 2002, 105(2):126-140.
Catania et al., "The tumor-targeting immunocytokine F16-IL2 in combination with doxorubicin: dose escalation in patients with advanced solid tumors and expansion into patients with metastatic breast cancer," Cell Adhesion and Migration, Jan.-Apr. 2015, 9(1-2):14-21.
Cavinato et al., "Molecular mechanisms of UVB-induced senescence of dermal fibroblasts and its relevance for photoaging of the human skin," Experimental Gerontology. Aug. 2017, 94:78-82.
Chalan et al., "Expression of Lectin-Like Transcript 1, the Ligand for CD161, in Rheumatoid Arthritis," PLoS One, 2015, 10(7):e0132436.
Chambers et al., "Can blocking inflammation enhance immunity during aging?," Journal of Allergy and Clinical Immunology, May 2020, 145(5):1323-1331.
Chance et al., "A simple and rapid assay of oxidative phosphorylation," Nature, Jun. 1955, 175(4469):1120-1121.
Chattopadyhay et al., "Structural Basis of Inducible Costimulator Ligand Costimulatory Function: Determination of the Cell Surface Oligomeric State and Functional Mapping of the Receptor Binding Site of the Protein1," J Immunol., 2006, 3920-3929.
Chen et al., "Sterile inflammation: sensing and reacting to damage," Nature Reviews Immunology, Nov. 19, 2010, 10(12):826-837.
Chichili et al., "Linkers in the structural biology of protein-protein interactions," Protein Science, Feb. 2013, 22(2):153-67.
Childs et al., "Senescent cells: an emerging target for diseases of ageing," Nature Reviews Drug Discovery, Jul. 21, 2017, 16(10):718-735, 18 pages.
Childs et al., "Senescent intimal foam cells are deleterious at all stages of atherosclerosis," Science, Oct. 28, 2016, 354(6311):472-477.
Chinta, et al., "Cellular senescence is induced by the environmental neurotoxin paraquat and bontributes to neuropathology linked to Parkinson's Disease," Cell Rep., 2018, 22(4): 930-940.
Chong et al., "CD36 initiates the secretory phenotype during the establishment of cellular senescence," EMBO Rep., May 18, 2018, 19(6):e45274, 13 pages.
Ciaglia, et al., "Recognition by natural killer cells of N6-isopentenyladensoine-treated human glioma cell lines," Int. J. Cancer, 2018 142(1): 176-190.
Cichocki et al., "GSK3 inhibition drives maturation of NK cells and enhances their antitumor activity," Cancer Research, Oct. 15, 2017, 77(20):5664-75.
Cifaldi et al., "Boosting Natural Killer Cell-Based Immunotherapy with Anticancer Drugs: a Perspective," Trends Molecular Medicine, Dec. 2017, 23(12):1156-1175, 20 pages.
Cipriani et al., "Hippocampal Radial Glial Subtypes and Their Neurogenic Potential in Human Fetuses and Healthy and Alzheimer's Disease Adults," Cerebral Cortex, May 2, 2018, 28(7):2458-2478, 21 pages.
Clayton et al., "Soluble T Cell Immunoglobulin Mucin Domain 3 Is Shed from CD8 T Cells by the Sheddase ADAM10, Is Increased in Plasma during Untreated HIV Infection, and Correlates with HIV Disease Progression," J Viral., 2015, 89(7):3723-3736.
Collado et al., "Senescence in tumours: evidence from mice and humans," Nature Reviews Cancer, Jan. 2010, 10(1):51-57.
Conarello et al., "Mice lacking dipeptidyl peptidase IV are protected against obesity and insulin resistance," Proc. Natl. Acad. Sci. U.S.A., May 27, 2003, 100(11):6825-6830.

(56) References Cited

OTHER PUBLICATIONS

Conlon et al., "Abstract CT082: Phase (Ph) I/Ib study of NIZ985 with and without spartalizumab (PDR001) in patients (pts) with metastatic/unresectable solid tumors," Cancer Res. 79(13 Suppl.):CT082, Jul. 1, 2019, 2 pages.
Coppe et al., "Tumor Suppressor and Aging Biomarker p16INK4a Induces Cellular Senescence without the Associated Inflammatory Secretory Phenotype," Journal of Biological Chemistry, Oct. 21, 2011, 286(42): 36396-36403.
Cosman et al., "ULBPs, novel MHC class I-related molecules, bind to CMV glycoprotein UL16 and stimulate NK cytotoxicity through the NKG2D receptor," Immunity, Feb. 1, 2001, 14(2):123-33.
Costa et al., "Targeting the epidermal growth factor receptor can counteract the inhibition of natural killer cell function exerted by colorectal tumor-associated fibroblasts," Frontiers in Immunology, May 29, 2018, 9:1150, 14 pages.
Crews et al., "Molecular mechanisms of neurodegeneration in Alzheimer's disease," Human Molecular Genetics, Apr. 22, 2010, 19(R1):R12-R20, 9 pages.
Cromie et al., "Nanobodies and their use in GPCR drug discovery," Current Topics in Medicinal Chemistry, Dec. 1, 2015, 15(24):2543-57.
Czaja et al., "A comprehensive analysis of the binding of anti-KIR antibodies to activating KIRs," Genes and Immunity, Jan. 2014, 15(1), 15 pages.
Da Silva et al., "Dipeptidylpeptidase 4 inhibition enhances lymphocyte trafficking, improving both naturally occurring tumor immunity and immunotherapy," Nature Immunology, Jun. 15, 2015, 16(8):850-858, 11 pages.
Dall'Era et al., "Adoptive Regulatory T Cell Therapy in a Patient with Systemic Lupus Erythematosus," Arthritis Rheumatology, Mar. 2019, 71(3):431-440.
De Crescenzo et al., "Engineering TGF-β Traps: Artificially Dimerized Receptor Ectodomains as High-affinity Blockers of TGF-β Action," Transforming Growth Factor-β in Cancer Therapy, vol. II, 2008, Humana Press, 671-84.
De Genst et al., "Antibody repertoire development in camelids," Developmental & Comparative Immunology, Jan. 1, 2006, 30(1-2):187-98.
De Meyer et al., "Nanobody-based products as research and diagnostic tools," Trends in Biotechnology, May 1, 2014, 32(5):263-70.
De Stefano et al., "Establishing pathological cut-offs of brain atrophy rates in multiple sclerosis," Journal of Neurology, Neurosurgery, and Psychiatry, Jan. 2016, 87(1):93-99.
Deacon, "Physiology and Pharmacology of DPP-4 in Glucose Homeostasis and the Treatment of Type 2 Diabetes," Frontiers in Endocrinology, Feb. 2019, 10:80, 14 pages.
Deaglio et al., "Adenosine generation catalyzed by CD39 and CD73 expressed on regulatory T cells mediates immune suppression," Journal of Experimental Medicine, May 14, 2007, 204(6):1257-1265.
Demaria et al., "An Essential Role for Senescent Cellsin Optimal Wound Healing through Secretion of PDGF-AA," Developmental Cell, Dec. 22, 2014, 31(6):722-733.
Deyev et al., "Design of multivalent complexes using the barnase•barstar module," Nature Biotechnology, Dec. 2003, 21(12):1486-92.
Di Ianni et al., "Tregs prevent GVHD and promote immune reconstitution inHLA-haploidentical transplantation," Blood, Apr. 7, 2011, 117(14):3921-3928.
Dietel et al., "Decreased numbers of regulatory T cells are associated with human atherosclerotic lesion vulnerability and inversely correlate with infiltrated mature dendritic cells," Atherosclerosis, Sep. 2013, 230:92-99.
DiGiammarino et al., "Design and generation of DVD-Ig™ molecules for dual-specific targeting," Therapeutic Proteins: Methods and Protocols, Methods in Molecular Biology, 2012, Humana Press, Totowa, NJ, 899:145-516.
Dikov et al., "New fluorescent method for the histochemical detection of tripeptidyl peptidase I using glycyl-1-prolyl-1-met-2-anthraquinonyl hydrazide as substrate," Cellular and Molecular Biology, Jan. 1, 2004, 50 Online Pub: OL565-568, 1 page (Abstract Only).
Dimri et al., "A biomarker that identifies senescent human cells in culture and in aging skin in vivo," Proceedings of the National Academy of Sciences, Sep. 29, 1995, 92(20):9363-9367.
Dinarello, "Interleukin 1 and interleukin 18 as mediators of inflammation and the aging process," The American Journal of Clinical Nutrition, Feb. 1, 2006, 83(2):447S-455S.
Docagne et al., "A soluble transforming growth factor-β (TGF-β) type I receptor mimics TGF-β responses," Journal of Biological Chemistry, Dec. 7, 2001, 276(49):46243-50.
Dong et al., "Characterization of adenosine deaminase binding to human CD26 on T cells and its biologic role in immune response," Journal of Immunology, Feb. 15, 1996, 156(4):1349-1355.
Dong et al., "Determination of adenosine deaminase binding domain on CD26 and its immunoregulatory effect on T cell activation," Journal of Immunology, Dec. 15, 1997, 159(12):6070-6076.
Dong et al., "Loss of methylation at the IFNG promoter and CNS-1 is associated with the development of functional IFN-γ memory in human CD4+T lymphocytes," European Journal of Immunology, 2013, 43(3), 793-804.
Dou et al., "Cytoplasmic chromatin triggers inflammation in senescence and cancer," Nature, Oct. 4, 2017, 550(7676):402-406, 21 pages.
Drees, et al., "Soluble production of a biologically active single-chain antibody against murine PD-L1 in *Escherichia coli*," Protein Express. Purif., 2014, 94:60-66.
Dubois et al., "Preassociation of IL-15 with IL-15Rα-IgG1-Fc Enhances Its Activity on Proliferation of NK and CD8+/CD44high T Cells and Its Antitumor Action," The Journal of Immunology, Feb. 15, 2008, 180:2099-2106.
Edwardraja et al., "Redesigning of anti-c-met single chain Fv antibody for the cytoplasmic folding and its structural analysis," Biotechnology and Bioengineering, Jun. 15, 2010, 106(3):367-75.
Eisenhut et al., "Ion Channels in Inflammation," Pflugers Archive, Jan. 29, 2011, 461(4):401-421.
Elgueta et al., "Molecular mechanism and function of CD40/CD40L engagement in the immune system," Immunological Reviews, 2009, 229(1):152-172 doi.org/10.1111/j.1600-065X.2009.00782.x.
Elpek et al., "Mature natural killer cells with phenotypic and functional alterations accumulate upon sustained stimulation with IL-15/IL-15Rα complexes," Proceedings of the National Academy of Science, Dec. 14, 2010, 107: 21647-21652.
Engel et al., "The crystal structure of dipeptidyl peptidase IV (CD26) reveals its functional regulation and enzymatic mechanism," Proc. Natl. Acad. Sci. U.S.A., Apr. 29, 2003, 100(9):5063-5068.
Epardaud et al., "Interleukin-15/Interleukin-15RA Complexes Promote Destruction of Established Tumors by Reviving Tumor-Resident CD8+ T Cells," Cancer Research 68: Apr. 15, 2008, 2972-2983.
Esensten et al., "Regulatory T-cell therapy for autoimmune and autoinflammatory diseases: The next frontier," The Journal of Allergy and Clinical Immunology, Dec. 1, 2018, 142(6):1710-1718.
Farr, et al., "Targeting cellular senescence prevents age-related bone loss in mice," Nat. Med., 2017, 23(9): 1072-1079.
Fehniger et al., "A Phase 1 Trial of CNDO-109—Activated Natural Killer Cells in Patients with High-Risk Acute Myeloid Leukemia," Biology of Blood and Marrow Transplantation, Aug. 2018, 24(8):1581-1589.
Feng et al., "The yin and yang functions of extracellular ATP and adenosine in tumor immunity," Cancer Cell International, Apr. 7, 2020, 20:110, 11 pages.
Ferreira et al., "Next-generation regulatory T cell therapy," Nature Reviews Drug Discovery, Sep. 20, 2019, 18(10):749-769, 21 pages.
Ferrucci et al., "The origins of age-related proinflammatory state," Blood, Mar. 15, 2005, 105(6):2294-2299.
Finkelman et al., "Anti-cytokine antibodies as carrier proteins. Prolongation of in vivo effects of exogenous cytokines by injection of cytokine-anti-cytokine antibody complexes," The Journal of Immunology, Aug. 1, 1993, 151:1235-1244.

(56) References Cited

OTHER PUBLICATIONS

Finkelstein et al., "Obesity and Severe Obesity Forecasts Through 2030," American Journal of Preventative Medicine, Jun. 2012, 42(6):563-570.
Ford et al., "TREM and TREM-like receptors in inflammation and disease," Current Opinion in Immunology, Feb. 21, 2009, 21(1):38-46.
Franceschi et al., "Inflamm-aging. An evolutionary perspective on immunosenescence," Annals of the New York Academy of Sciences, Jun. 2000, 908:244-254.
Frutoso et al., "Emergence of NK Cell Hyporesponsiveness after Two IL-15 Stimulation Cycles," Journal of Immunology, May 30, 2018, 201: 493-506.
Ganesh et al., "TGF-β Inhibition and Immunotherapy: Checkmate," Immunity, Apr. 17, 2018, 48(4):626-628.
Garber, "Bispecific antibodies rise again," Nat. Rev. Drug Discov., 2014, 13:799-801.
Gaulton et al., "Characterization of a monoclonal rat anti-mouse interleukin 2 (IL-2) receptor antibody and its use in the biochemical characterization of the murine IL-2 receptor," Clinical Immunology and Immunopathology, Jul. 1, 1985, 36(1):18-29.
Gejima et al., "Human single-chain Fv (scFv) antibody specific to human IL-6 with the inhibitory activity on IL-6-signaling," Human Antibodies, Jan. 1, 2002, 11(4):121-9.
Geng et al., "A novel anti-TNF scFv constructed with human antibody frameworks and antagonistic peptides," Immunol. Res. 62(3):377-385, 2015.
Georgilis et al., "PTBP1-Mediated Alternative Splicing Regulates the Inflammatory Secretome and the Pro-tumorigenic Effects of Senescent Cells," Cancer Cell, Jul. 9, 2018, 34(1):85-102.
Ghosh et al., "The Senescence-Associated Secretory Phenotype: Critical Effector in Skin Cancer and Aging," Journal of Investigative Dermatology, Nov. 2016, 136(11):2133-2139.
Gibbs et al., "Identification of the factor VIIa binding site on tissue factor by homologous loop swap and alanine scanning mutagenesis," Biochemistry, Nov. 1, 1994, 33(47):14003-10.
Gong et al., "DAMP-sensing receptors in sterile inflammation and inflammatory diseases," Nature Reviews Immunology, Sep. 26, 2019, 20(2):95-112.
Gorrell et al., "Expression of the rat CD26 Antigen (dipeptidyl peptidase IV) on subpopulations of rat lymphocytes," Cellular Immunology, Apr. 15, 1991, 134(1):205-215.
Greenspan et al., "Defining epitopes: Its not as easy as it seems," Nature Biotechnology, 1999, 17:936-937.
Grupp et al., "Chimeric Antigen Receptor-Modified T Cells for Acute Lymphoid Leukemia," The New England Journal of Medicine, Apr. 18, 2013, 368(16):1509-1518.
Gu et al., "Human CD39hi regulatory T cells present stronger stability and function under inflammatory conditions," Cellular and Molecular Immunology, Jul. 4, 2016, 14(6):521-528.
Guo et al., "Immunobiology of the IL-15-IL-15R complex as an antitumor and antiviral agent," 2017, Cytokine & Growth Factor Reviews, 38:10-21.
Gutschmidt et al., "A quantitative histochemical study of dipeptidyl peptidase IV (DPP IV)," Histochemistry, 1981, 73(2):285-304.
Haile et al., "Soluble CD80 Restores T Cell Activation and Overcomes Tumor Cell Programmed Death Ligand 1-Mediated Immune Suppression," J. Immunol., 2013, 191(5):2829-2836.
Hayflick et al., "The serial cultivation of human diploid cell strains," Experimental Cell Research, Dec. 1961, 25:585-621.
He et al., "Senescence in Health and Disease," Cell, Jun. 1, 2017, 169(6):1000-1011.
Hebbar et al., "Detection of circulating soluble CD28 in patients with systemic lupus erythematosus, primary Sjögren's syndrome and systemic sclerosis," Clinical & Experimental Immunology, May 2004, 136(2):388-92.
Helfrich et al., "A rapid and versatile method for harnessing scFv antibody fragments with varous biological effector functions," Journal of Immunological methods, 2000, 237(1-2):131-145 DOI:1O.1O16/S0022-1759(99)OO220-3.

Heneka et al., "Inflammasome signaling in brain function and neurodegenerative disease," Nature Reviews Neuroscience, Sep. 11, 2018, 19(10):610-621.
Heneka et al., "NLRP3 is activated in Alzheimer's disease and contributes to pathology in APP/PS1 mice," Nature, Jan. 31, 2013, 493(7434):674-678, 8 pages.
Heng et al., "G Protein-Coupled Receptors Revisited: Therapeutic Applications Inspired by Synthetic Biology," Annual Review of Pharmacology and Toxicology, Jan. 2014, 54:227-249.
Heng et al., Sophea, et al. "Multiple soluble TGF-β receptors in addition to soluble endoglin are elevated in preeclamptic serum and they synergistically inhibit TGF-β signalling." Placenta, 2017 57:320 (1 page).
Highfill et al., "Overcoming Challenges in Process Development of Cellular Therapies," Current Hematologic Malignancy Reports, Jul. 6, 2019, 14(4):269-277, 9 pages.
Hoare et al., "The Power Behind the Throne: Senescence and the Hallmarks of Cancer," Annual Review of Cancer Biology, 2018, 2:175-194.
Hoffmann et al., "Large-scale in vitro expansion of polyclonal human CD4+CD25high regulatory T Cells," Blood, Aug. 2004, 104(3):895-903.
Hollande et al., "Inhibition of the dipeptidyl peptidase DPP4 (CD26) reveals IL-33-dependent eosinophil-mediated control of tumor growth," Nature Immunology, Feb. 18, 2019, 20(3):257-264.
Hombach et al., "Generation of the single chain antibody fragment conserves the idiotypic profile of the anti-CD30 monoclonal antibody HRS3," Scandinavian Journal of Immunology, Nov. 1998, 48(5):497-501.
Hu et al., "Discovery of a novel IL-15 based protein with improved developability and efficacy for cancer immunotherapy," Scientific Reports, 2018, 8:7675, 11 pages.
Huang et al., "Substrate recognition by tissue factor-factor VIIa Evidence for interaction of residues Lys165 and Lys166 of tissue factor with the 4-carboxyglutamate-rich domain of factor X," Journal of Biological Chemistry, Sep. 6, 1996, 271(36):21752-7.
Hudak et al., "Glycocalyx engineering reveals a Siglec-based mechanism for NK cell immunoevasion," Nature Chemical Biology, Jan. 2014, 10(1), 20 pages.
Hudson et al., "Targeting RAGE Signaling in Inflammatory Disease," Annual Review of Medicine, Jan. 2018, 69:349-364, 16 pages.
Huell et al., "Interleukin-6 is present in early stages of plaque formation and is restricted to the brains of Alzheimer's disease patients," Acta Neuropathologica, Nov. 1995, 89(6):544-551.
Hughes, et al., "Transfer of a TCR gene derived from a patient with a marked antitumor response conveys highly active T-cell effector functions," Hum. Gene Ther., 2005, 16:457-72.
Hynes et al., "In vitro analysis of cell metabolism using a long-decay pH-sensitive lanthanide probe and extracellular acidification assay," Analytical biochemistry, Jul. 1, 2009, 390(1):21-28.
Iannello et al., "p53-dependent chemokine production by senescent tumor cells supports NKG2D-dependent tumor elimination by natural killer cells," Journal of Experimental Medicine, Sep. 23, 2013, 210(10):2057-69.
Iihoshi et al., "Aclarubicin, an anthracycline anti-cancer drug, fluorescently contrasts mitochondria and reduces the oxygen consumption rate in living human cells," Toxicology Letters, Aug. 5, 2017, 277:109-114, 22 pages.
Inzucchi et al., "New Drugs for the Treatment of Diabetes, Part II: Incretin-Based Therapy and Beyond," Circulation, Jan. 29, 2008, 117(4):574-584, 21 pages.
Jain et al., "Mitochondrial Reactive Oxygen Species Regulate Transforming Growth Factor-β Signaling," Journal of Biological Chemistry, Jan. 11, 2013, 288(2):770-777.
Jakob et al., "Structure reveals function of the dual variable domain immunoglobulin (DVD-Ig™) molecule," Mabs, May 1, 2013, Taylor & Francis, 5(3):358-63.
Janeway, "Approaching the Asymptote? Evolution and Revolution in Immunology," Cold Spring Harbor Symposia on Quantitative Biology, 1989, 54 Pt 1:1-13.
Jeannin et al., "Soluble CD86 Is a Costimulatory Molecule for Human T Lymphocytes," Immunity, 2000, 13(3):303-312.

(56) References Cited

OTHER PUBLICATIONS

Jin et al., "Novel Insights Into the NLRP3 Inflammasome in Atherosclerosis," Journal of the American Heart Association, Jun. 11, 2019, 8(12):e012219, 12 pages.

Justice et al., "Senolytics in idiopathic pulmonary fibrosis: Results from a first-in-human, open-label, pilot study," EBioMedicine, Feb. 2019, 40:554-563.

Kain et al., "The identification of the endogenous ligands of natural killer T cells reveals the presence of mammalian α-linked glycosylceramides," Immunity, Oct. 16, 2014, 41(4):543-54.

Karin et al., "Senescent cell turnover slows with age providing an explanation for the Gompertz law," Nature Communications, 10:5495, 9 pages.

Karkera et al., "The anti-interleukin-6 antibody siltuximab down-regulates genes implicated in tumorigenesis in prostate cancer patients from a phase I study," The Prostate, Feb. 14, 2011, 71(13):1455-1465.

Katsuumi et al., "Vascular Senescence in Cardiovascular and Metabolic Diseases," Frontiers in Cardiovascular Medicine, 5:18, 13 pages.

Kellner et al., "Enhancing natural killer cell-mediated lysis of lymphoma cells by combining therapeutic antibodies with CD20-specific immunoligands engaging NKG2D or NKp30," Oncoimmunology, Jan. 2, 2016, 5(1):e1058459, 12 pages.

Kijanka et al., "Nanobody-based cancer therapy of solid tumors," Nanomedicine, Jan. 2015, 10(1):161-74.

Kim et al., "Experimental malaria infection triggers early expansion of natural killer cells," Infection and Immunity, Dec. 1, 2008, 76(12):5873-82.

Kim et al., "Identification of senescent cell surface targetable protein DPP4," Genes & Development, 2017, 31(15):1529-1534.

Kim et al., "SCAMP4 enhances the senescent cell secretome," Genes & Development, 2018, 32(13-14):909-914.

Kirchhofer et al., "The tissue factor region that interacts with substrates factor IX and factor X," Biochemistry, Jun. 27, 2000, 39(25):7380-7.

Kirkland et al., "Cellular Senescence: A Translational Perspective," EBioMedicine, Jul. 2017, 21:21-28.

Klein et al., "Cergutuzumab amunaleukin (CEA-IL2v), a CEA-targeted IL-2 variant-based immunocytokine for combination cancer immunotherapy: Overcoming limitations of aldesleukin and conventional IL-2-based immunocytokines," Oncoimmunology, 2017 6(3):e1277306, 15 pages.

Klein et al., "Design and characterization of structured protein linkers with differing flexibilities," Protein Engineering, Design & Selection, 2014, 27(10):325-30.

Klemann et al., "Cut to the chase: a review of CD26/dipeptidyl peptidase-4's (DPP4) entanglement in the immune system," Clinical and Experimental Immunology, Feb. 25, 2016, 185(1):1-21.

Klingenberg et al., "Depletion of FOXP3+ regulatory T cells promotes hypercholesterolemia and atherosclerosis," The Journal of Clinical Investigation, Feb. 15, 2013, 123:1323-1334.

Kondo et al., "Requirements for the functional expression of OX40 ligand on human activated CD4+ and CD8+ T cells," Human Immunology, 2007, 68(7):563-571.

Kovaleva et al., "Shark variable new antigen receptor biologics—a novel technology platform for therapeutic drug development," Expert Opinion on Biological Therapy, Oct. 1, 2014, 14(10):1527-39.

Krah et al., "Single-domain antibodies for biomedical applications," Immunopharmacology and Immunotoxicology, Jan. 2, 2016, 38(1):21-8.

Kritsilis et al., "Ageing, Cellular Senescence and Neurodegenerative Disease," International Journal of Molecular Sciences, Sep. 27, 2018, 19(10):2937, 37 pages.

Krizhanovsky et al., "Senescence of activated stellate cells limits liver fibrosis," Cell, Aug. 22, 2008, 134(4):657-67.

Kumagai et al., "Monitoring of glutamate-induced excitotoxicity by mitochondrial oxygen consumption," Synapse, Jan. 2019, 73(1):e22067, 24 Pages.

Lambeir et al., "Dipeptidyl-Peptidase IV from Bench to Bedside: An Update on Structural Properties, Functions, and Clinical Aspects of the Enzyme DPP IV," Critical Reviews in Clinical Laboratory Sciences, Sep. 29, 2003, 40(3):209-294.

Lamkanfi et al., "Mechanisms and Functions of Inflammasomes," Cell, May 22, 2014, 157(5):1013-1022.

Lansigan et al., "DI-Leu16-IL2, an Anti-CD20-Interleukin-2 Immunocytokine, Is Safe and Active in Patients with Relapsed and Refractory B-Cell Lymphoma: A Report of Maximum Tolerated Dose, Optimal Biologic Dose, and Recommended Phase 2 Dose," Blood, Dec. 2, 2016, 128(22):620, 3 pages (Abstract Only).

Latz et al., "Activation and regulation of the inflammasomes," Nature Reviews Immunology, May 24, 2013, 13(6):397-411.

Latz et al., "NLRP3 inflammasome activation in inflammaging," Seminars in Immunology, Dec. 2018, 40:61-73, 13 pages.

Lau et al., "RNA-associated autoantigens activate B cells by combined B cell antigen receptor/Toll-like receptor 7 engagement," The Journal of Experimental Medicine, Oct. 31, 2005, 202(9):1171-1177.

Lazar et al., "Transforming Growth Factor Alpha: Mutation of Aspartic Acid 47 and Leucine 48 Results in Different Biological Activities," Mol. Cell. Biol., 1988, 8:1247-1252.

Li et al., "A Novel I L2-based Immunotherapeutic Protein Prevents the Development of Atherosclerosis in ApoE-/mice and LDLR-/-mice," Journal of Immunology, May 1, 2020, 204(1):Supplement (Abstract Only), 2 pages.

Li et al., "Adoptive transfer of natural killer cells in combination with chemotherapy improves outcomes of patients with locally advanced colon carcinoma," Cytotherapy, Jan. 2018, 20(1):134-148, 15 pages.

Li et al., "The cGAS-cGAMP-STING pathway connects DNA damage to inflammation, senescence, and cancer," Journal of Experimental Medicine, Apr. 5, 2018, 215(5):1287-1299.

Liton et al., "Cellular senescence in the glaucomatous outflow pathway," Experimental Gerontology, Aug.-Sep. 2005, 40(8-9):745-748.

Liu et al., "A Novel Fusion of ALT-803 (IL-15 Superagonist) with an Antibody Demonstrates Antigen-specific Antitumor Responses," Journal of Biological Chemistry, 2016, 291(46):23869-23881.

Liu et al., "Evaluation of the biological activities of the IL-15 superagonist complex, ALT-803, following intravenous versus subcutaneous administration in murine models," Cytokine, Jul. 2018, 107: 105-112, 8 pages.

Loster et al., "The Cysteine-Rich Region of Dipeptidyl Peptidase IV (CD 26) Is the Collagen Binding Site," Biochemical and Biophysical Research Communications, Dec. 5, 1995, 217(1):341-348.

Lu et al., "Molecular basis of binding between novel human coronavirus MERS-CoV and its receptor CD26," Nature, Jul. 7, 2013, 500(7461):227-231.

Lujambio et al., "Non-Cell-Autonomous Tumor Suppression by p53," Cell, Apr. 11, 2013, 153(2):449-460.

Maeda et al., "Original Ligand for LTβR Is LIGHT: Insight into Evolution of the LT/LTβR System," J Immunol., 2018, 201(1):202-214.

Maganto-García et al., "Dynamic Changes in Regulatory T Cells Are Linked to Levels of Diet-Induced Hypercholesterolemia," Circulation, Jun. 20, 2011, 124:185-195.

Mandelboim et al., "Recognition of haemaglutinins on virus-infected cells by NKp46 activates lysis by human NK cells," Nature, Feb. 2001, 409(6823):1055.

Marguet et al., "Enhanced insulin secretion and improved glucose tolerance in mice lacking CD26," Proc. Natl. Acad. Sci. U.S.A., Jun. 6, 2000, 97(12):6874-6879.

Martelli et al., "HLA-haploidentical transplantation with regulatory and conventional T-cell adoptive immunotherapy prevents acute leukemia relapse," Blood, Jul. 24, 2014, 124(4):638-644.

Masoumi et al., "The role of hypoxia as the driving force for non-erythroid production of globin chains in preeclamptic placentas," Placenta. 2017;57:320.

McHugh et al., "Senescence and aging: Causes, consequences, and therapeutic avenues," Journal of Cellular Biology, Nov. 7, 2017, 217(1):65-77.

(56) References Cited

OTHER PUBLICATIONS

Mehta et al., "Why do trials for Alzheimer's disease drugs keep failing? A discontinued drug perspective for 2010-2015," Expert Opinion on Investigational Drugs, May 2017, 26(6):735-739.

Menshawy et al., "CD58; leucocyte function adhesion-3 (LFA-3) could be used as a differentiating marker between immune and non-immune thyroid disorders," Comparative Clinical Pathology, 2018, 27(3), 721-727, doi.org/10.1007/s00580-018-2657-x.

Mentlein et al., "Dipeptidyl-peptidase IV (CD26)-role in the inactivation of regulatory peptides," Regulatory Peptides, Nov. 30, 1999, 85(1):9-24.

Miah et al., "KIR2DL4 differentially signals downstream functions in human NK cells through distinct structural modules," The Journal of Immunology, Mar. 1, 2008, 180(5):2922-32.

Michelet et al., "Metabolic reprogramming of natural killer cells in obesity limits antitumor responses," Nature Immunology, Nov. 12, 2018, 19(12):1330-1340.

Milanovic et al., "Senescence-associated reprogramming promotes cancer stemness," Nature, Dec. 20, 2017, 553(7686):96-100.

Milanovic et al., "The Senescence-Stemness Alliance—A Cancer-Hijacked Regeneration Principle," Trends in Cellular Biology, Dec. 2018, 28(12):1049-1061, 13 pages.

Miller et al., "Soluble CD70: a novel immunotherapeutic agent for experimental glioblastoma," J Neurosurg., 2010, 113(2):280-285.

Miller et al., "Successful adoptive transfer and in vivo expansion of human haploidentical NK cells in patients with cancer," Blood, Apr. 15, 2005, 105(8):3051-3057.

Minamino et al., "A crucial role for adipose tissue p53 in the regulation of insulin resistance," Nature Medicine, Aug. 30, 2009, 15(9):1082-1087.

Mitterberger et al., "Adipogenic Differentiation Is Impaired in Replicative Senescent Human Subcutaneous Adipose-Derived Stromal/Progenitor Cells," The Journals of Gerontology: Series A, Biological Sciences and Medical Sciences, Jan. 2014, 69(1):13-24.

Miyazaki et al., "Abstract 3265: NKTR-255, a polymer-conjugated IL-15 enhances anti-tumor NK cell responses and synergizes with monoclonal antibodies to provide long-term survival in human lymphoma model," Proceedings: AACR Annual Meeting 2019, Atlanta, GA, Mar. 29-Apr. 3, 2019, 1 page.

Moesta et al., "Targeting CD39 in cancer," Nature Reviews Immunology, Jul. 29, 2020, 20(12):739-755, 17 pages.

Moiseeva et al., "Metformin inhibits the senescence-associated secretory phenotype by interfering with IKK/NF-κB activation," Aging Cell, Mar. 23, 2013, 12(3):489-498.

Molema et al., "The use of bispecific antibodies in tumor cell and tumor vasculature directed immunotherapy," Journal of Controlled Release, 2000, 64(1-3):229-239.

Molgora et al., "Regulatory role of IL-1R8 in immunity and disease," Frontiers in Immunology, Apr. 20, 2016, 7:149.

Mookerjee et al., "Measurement and Analysis of Extracellular Acid Production to Determine Glycolytic Rate," Journal of Visualized Experiments : Jove, Dec. 2015, (106):e53464, 9 Pages.

Moore et al., "Macrophages in atherosclerosis: a dynamic balance," Nature Reviews Immunology, Sep. 2, 2013, 13:709-721, 13 pages.

Moreno et al., "Molecular Evidence of Adenosine Deaminase Linking Adenosine A2A Receptor and CD26 Proteins," Frontiers in Pharmacology, Feb. 15, 2018, 9:106, 18 pages.

Moretta et al., "CD69-mediated pathway of lymphocyte activation: anti-CD69 monoclonal antibodies trigger the cytolytic activity of different lymphoid effector cells with the exception of cytolytic T lymphocytes expressing T cell receptor alpha/beta," Journal of Experimental Medicine, Dec. 1, 1991, 174(6):1393-8.

Mujić-Delić et al., "GPCR-targeting nanobodies: attractive research tools, diagnostics, and therapeutics," Trends in Pharmacological Sciences, May 1, 2014, 35(5):247-55.

Muller et al., "Antibody fusions with immunomodulatory proteins for cancer therapy," Pharmacology and Therapeutics, 2015, 154:57-66.

Mulvihill et al., "Pharmacology, Physiology, and Mechanisms of Action of Dipeptidyl Peptidase-4 Inhibitors," Endocrine Reviews, Dec. 1, 2014, 35(6):992-1019.

Munoz-Espin et al., "Cellular senescence: from physiology to pathology," Nature Reviews Molecular Cellular Biology, Jun. 23, 2014, 15(7):482-496.

Munoz-Espin et al., "Programmed Cell Senescence during Mammalian Embryonic Development," Cell, Nov. 21, 2013, 155(5):1104-1118.

Musi et al., "Tau protein aggregation is associated with cellular senescence in the brain," Aging Cell, Aug. 20, 2018, 17(6):e12840, 13 pages.

Must et al., "The Disease Burden Associated with Overweight and Obesity," Endotext, Feingold et al. (eds.), South Dartmouth, MA, 2000, 35 pages.

Muyldermans et al., "Recognition of antigens by single-domain antibody fragments: the superfluous luxury of paired domains," Trends in Biochemical Sciences, Apr. 1, 2001, 26(4):230-5.

Muyldermans, "Nanobodies: natural single-domain antibodies," Annual Review of Biochemistry, Jun. 2, 2013, 82:775-97.

Muyldermans, "Single domain camel antibodies: current status," Reviews in Molecular Biotechnology, Jun. 1, 2001, 74(4):277-302.

Myung et al., "Evidence of DNA damage in Alzheimer disease: phosphorylation of histone H2AX in astrocytes," Age, Apr. 23, 2008, 30(4):209-215.

Nag et al., "Soluble MHC II-peptide complexes induce antigen-specific apoptosis in T cells," Cellular Immunology, May 25, 1996, 170(1):25-33.

Nayyar et al., "Overcoming Resistance to Natural Killer Cell Based Immunotherapies for Solid Tumors," Frontiers in Oncology, 2019, 9: DOI:10.3389/fonc.2019.00051.

Nelson et al., "A senescent cell bystander effect: senescence-induced senescence," Aging Cell, Feb. 9, 2012, 11(2):345-349.

Nilsson et al., "Targeted delivery of tissue factor to the ED-B domain of fibronectin, a marker of angiogenesis, mediates the infarction of solid tumors in mice," Cancer Research, American Association for Cancer Research, Proceedings: AACR 107th Annual Meeting, 2016, Apr. 16-20, 2016, New Orleans, LA 61(2):711-716.

Nishida et al., "CD26 is a potential therapeutic target by humanized monoclonal antibody for the treatment of multiple myeloma," Blood Cancer Journal, Oct. 22, 2018, 8(11):99, 17 pages.

O'Sullivan et al., "Natural Killer Cell Memory," Immunity, Oct. 20, 2015, 43(4):634-645.

Oberle et al., "Rapid Suppression of Cytokine Transcription in Human CD4+CD25-T Cells by CD4+Foxp3+ Regulatory T Cells: Independence of IL-2 Consumption, TGF-β, and Various Inhibitors of TCR Signaling," The Journal of Immunology, Sep. 15, 2007, 179(6):3578-3587.

Ogrodnik et al., "Cellular senescence drives age-dependent hepatic steatosis," Nat Commun. Jun. 13, 2017;8:15691, 12 pages.

Ogrodnik et al., "Obesity-Induced Cellular Senescence Drives Anxiety and Impairs Neurogenesis," Cell Metabolism, May 2019, 29(5):1061-1077, 25 pages.

Ohnuma et al., "Blockade of CD26-mediated T cell costimulation with soluble caveolin-1-Ig fusion protein induces anergy in CD4+T cells," Biochemical and Biophysics Research Communications, Aug. 21, 2009, 386(2):327-332.

Ohnuma et al., "CD26 Mediates Dissociation of Tollip and IRAK-1 from Caveolin-1 and Induces Upregulation of CD86 on Antigen-Presenting Cells," Molecular and Cellular Biology, Sep. 1, 2005, 25(17):7743-7757.

Ohnuma et al., "CD26 up-regulates expression of CD86 on antigen-presenting cells by means of caveolin-1," Proc. Natl. Acad. Sci. U.S.A., Sep. 28, 2004, 101(39):14186-14191.

Ohnuma et al., "Role of CD26/dipeptidyl peptidase IV in human T cell activation and function," Frontiers in Bioscience, Jan. 1, 2008, 13:2299-2310.

Ohnuma et al., "Soluble CD26/Dipeptidyl Peptidase IV Induces T Cell Proliferation Through CD86 Up-Regulation on APCs," Journal of Immunology, Dec. 15, 2001, 167(12):6745-6755.

Ovadya et al., "Strategies targeting cellular senescence," The Journal of Clinical Investigation, Apr. 2, 2018, 128(4):1247-54.

(56) References Cited

OTHER PUBLICATIONS

Owicki et al., "Biosensors based on the energy metabolism of living cells: the physical chemistry and cell biology of extracellular acidification," Biosensors and Bioelectronics, Jan. 1, 1992, 7(4):255-272.
Padutsch et al., "Superior Treg-Expanding Properties of a Novel Dual-Acting Cytokine Fusion Protein," Frontiers in Pharmacology, Dec. 18, 2019, 10:1490, 10 pages.
Palmer et al., "Cellular Senescence in Type 2 Diabetes: A Therapeutic Opportunity," Diabetes, Jul. 2015, 64(7):2289-2298.
Parker et al., "Design, production, and characterization of a single-chain variable fragment (ScFv) derived from the prostate specific membrane antigen (PSMA) monoclonal antibody J591," Protein Expression and Purification, Jun. 1, 2013, 89(2):136-45.
PCT International Preliminary Report on Patentability in International Appln. No. PCT/US2019/048881, dated Mar. 11, 2021, 7 pages.
PCT International Preliminary Report on Patentability in International Appln. No. PCT/US2019/048930, dated Mar. 11, 2021, 9 pages.
PCT International Preliminary Report on Patentability in International Appln. No. PCT/US2019/049142, dated Mar. 11, 2021, 11 pages.
PCT International Preliminary Report on Patentability in International Appln. No. PCT/US2019/049158, dated Mar. 11, 2021, 8 pages.
PCT International Search Report and Written Opinion in International Appln. No. PCT/US2019/048881, dated Nov. 9, 2019, 16 pages.
PCT International Search Report and Written Opinion in International Appln. No. PCT/US2019/048930, dated Nov. 20, 2019, 18 pages.
PCT International Search Report and Written Opinion in International Appln. No. PCT/US2019/04912, dated Jun. 23, 2020, 20 pages.
PCT International Search Report and Written Opinion in International Appln. No. PCT/US2019/049158, dated Jan. 20, 2020, 18 pages.
PCT International Search Report and Written Opinion in International Appln. No. PCT/US2020/035598, dated Feb. 18, 2021, 12 pages.
PCT International Search Report and Written Opinion in International Appln. No. PCT/US2020/038717, dated Oct. 16, 2020, 17 pages.
PCT International Search Report and Written Opinion in International Appln. No. PCT/US2021/017620, dated Aug. 6, 2021, 22 pages.
PCT International Search Report and Written Opinion in International Appln. No. PCT/US2021/017621, dated Jun. 9, 2021, 15 pages.
PCT International Search Report and Written Opinion in International Appln. No. PCT/US2021/017714, dated Aug. 27, 2021, 22 pages.
Peipp et al., "HER2-specific immunoligands engaging NKp30 or NKp80 trigger NK-cell-mediated lysis of tumor cells and enhance antibody-dependent cell-mediated cytotoxicity," Oncotarget, Oct. 13, 2015, 6(31):32075.
Pittayapruek et al., "Role of Matrix Metalloproteinases in Photoaging and Photocarcinogenesis," International Journal of Molecular Sciences, 2016, 17(6):868, 20 pages.
Priyanka et al., "Linkers in the structural biology of protein-protein interactions," Protein Sci., 2013, 22(2):153-167.
Purohit et al., "Smad3-dependent regulation of type I collagen in human dermal fibroblasts: Impact on human skin connective tissue aging," Journal of Dermatological Science, Jul. 2016, 83(1):80-83, 4 pages.
Qin et al., "Critical Role of P2Y12 Receptor in Regulation of Th17 Differentiation and Experimental Autoimmune Encephalomyelitis Pathogenesis," The Journal of Immunology, Jul. 1, 2017, 199(1):72-81.
Rafei et al., "Off-the-shelf virus specific T-cells for therapy of adenovirus disease in immunosuppressed patients," Journal of Clinical Oncology, May 26, 2019, 37(15 Suppl.): 7008, 2 pages.
Rahbarizadeh et al., "Nanobody; an old concept and new vehicle for immunotargeting," Immunological Investigations, Jan. 1, 2011, 40(3):299-338.
Raj et al., "Adenosine Deaminase Acts as a Natural Antagonist for Dipeptidyl Peptidase 4-Mediated Entry of the Middle East Respiratory Syndrome Coronavirus," Journal of Virology, Feb. 2014, 88(3):1834-1838, 7 pages.
Ranganathan et al., "Pinpointing the putative heparin/sialic acid-binding residues in the 'sushi' domain 7 of factor H: a molecular modeling study," Biocomputing 2000, 1999, 155-67.
Rao et al., "Purification and characterization of rabbit tissue factor," Thrombosis Research, Oct. 1, 1989, 56(1):109-118.
Rasmussen et al., "Crystal structure of human dipeptidyl peptidase IV/CD26 in complex with a substrate analog," Nature Structural and Molecular Biology, 2003, 10(1):19-25.
Raz et al., "Efficacy and safety of the dipeptidyl peptidase-4 inhibitor sitagliptin as monotherapy in patients with type 2 diabetes mellitus," Diabetologia, Sep. 26, 2006, 49(11):2564-2571.
Resta et al., "Ecto-enzyme and signaling functions of lymphocyte CD 7 3," Immunological Reviews, 1998, 161:95-109.
Rhein et al., "Characterization of Human and Murine T-Cell Immunoglobulin Mucin Domain 4 (TIM-4) IgV Domain Residues Critical for Ebola Virus Entry," J Viral., 2016, 90(13):6097-6111.
Rippmann et al., "Fusion of the Tissue Factor Extracellular Domain to a Tumor Stromaspecific Single-Chain Fragment Variable Antibody Results in an Antigen-Specific Coagulation-Promoting Molecule," Biochemical Journal, 2000, 349(3):805-812.
Rittie et al., "Natural and Sun-Induced Aging of Human Skin," Cold Spring Harbor Perspective in Medicine, 2015, 5(1):a015370, 15 pages.
Rocha et al., "A novel immunofluorescent assay to investigate oxidative phosphorylation deficiency in mitochondrial myopathy: understanding mechanisms and improving diagnosis," Scientific reports, Oct. 15, 2015, 5:15037, 17 Pages.
Rodier et al., "Persistent DNA damage signaling triggers senescence-associated inflammatory cytokine secretion," Nature Cell Biology, Jul. 13, 2009, 11(8): 973-979, 15 pages.
Rogge et al., "Antibodies to the IL-12 receptor β2 chain mark human Th1 but not Th2 cells in vitro and in vivo," The Journal of Immunology, Apr. 1, 1999, 162(7):3926-32.
Roh et al., "Damage-Associated Molecular Patterns in Inflammatory Diseases," Immune Network, Aug. 2018, 18(4):e27, 14 pages.
Romano et al., "Past, Present, and Future of Regulatory T Cell Therapy in Transplantation and Autoimmunity," Frontiers in Immunology, Jan. 1, 2019, 10:43, 14 pages.
Romee et al., "Cytokine activation induces human memory-like NK cells," Blood, Dec. 6, 2012, 120(24):4751-4760.
Rossi et al., "Complex and defined biostructures with the dock-and-lock method," Trends in Pharmacological Sciences, Sep. 1, 2012, 33(9):474-81.
Rossi et al., "Stably tethered multifunctional structures of defined composition made by the dock and lock method for use in cancer targeting," Proceedings of the National Academy of Sciences, May 2, 2006, 103(18):6841-6.
Rubinstein et al., "Converting IL-15 to a superagonist by binding to soluble IL-15Rα," Proceedings of the National Academy of Sciences U.S.A., Jun. 13, 2006, 103(24):9166-9171.
Ruf et al., "Cofactor residues lysine 165 and 166 are critical for protein substrate recognition by the tissue factor-factor VIIa protease complex," Journal of Biological Chemistry, Mar. 25, 1992, 267(9):6375-81.
Ruf et al., "Tissue factor residues 157-167 are required for efficient proteolytic activation of factor X and factor VII," Journal of Biological Chemistry, Nov. 5, 1992, 267(31):22206-10.
Ruscetti et al., "NK cell-mediated cytotoxicity contributes to tumor control by a cytostatic drug combination," Science, Dec. 21, 2018, 362(6421):1416-1422, 8 pages.
Sagiv et al., "Granule exocytosis mediates immune surveillance of senescent cells," Oncogene, 2013, 32(15):1971-1977.

(56) References Cited

OTHER PUBLICATIONS

Sakaguchi et al., "Regulatory T Cells and Human Disease," Annual Review of Immunology, Apr. 26, 2020, 38:541-566.
Sakaguchi et al., "Regulatory T Cells and Immune Tolerance," Cell, May 30, 2008, 133(5):775-787.
Sakaguchi et al., "Regulatory T cells: how do they suppress immune responses?" International Immunology, Sep. 7, 2009, 21(10):1105-1111.
Sakamoto et al., "Phase I clinical trial of autologous NK cell therapy using novel expansion method in patients with advanced digestive cancer," Journal of Translational Medicine, Aug. 25, 2015, 13:277, 13 pages.
Sakamuri et al., "Measurement of respiratory function in isolated cardiac mitochondria using Seahorse XFe24 Analyzer: applications for aging research," Geroscience, Jun. 1, 2018, 40(3):347-356.
Salminen et al., "Emerging role of NF-κB signaling in the induction of senescence-associated secretory phenotype (SASP)," Cellular Signaling, Apr. 2012, 24(4):835-845.
Sandusky et al., "Regulation of 2B4 (CD244)-mediated NK cell activation by ligand-induced receptor modulation," European Journal of Immunology, Dec. 2006, 36(12):3268-76.
Sato et al., "Recombinant soluble murine IL-4 receptor can inhibit or enhance IgE responses in vivo," The Journal of Immunology, Apr. 1, 1993, 150:2717-2723.
Schafer et al., "Cellular senescence mediates fibrotic pulmonary disease," Nat Commun., Feb. 2017, 8:14532, 11 pages.
Schullek et al., "Key ligand interface residues in tissue factor contribute independently to factor VIIa binding," Journal of Biological Chemistry, Jul. 29, 1994, 269(30):19399-403.
Schwoppe et al., "Tissue-factor fusion proteins induce occlusion of tumor vessels," Thrombosis Research, Apr. 1, 2010, 125:S143-S150.
Seo et al., "Positive Feedback Loop between Plasminogen Activator Inhibitor-1 and Transforming Growth Factor-Beta1 during Renal Fibrosis in Diabetes," American Journal of Nephrology, Sep. 25, 2009, 30:481-490.
Sharkey et al., "Improved Therapeutic Results by Pretargeted Radioimmunotherapy of Non-Hodgkin's Lymphoma with a New Recombinant, Trivalent, Anti-CD20, Bispecific Antibody," Cancer Research, Jul. 1, 2008, 68(13):5282-90.
Sharma et al., "Regulatory T Cells License Macrophage Pro Resolving Functions During Atherosclerosis Regression," Circulation Research, Apr. 27, 2020, 127:335-353.
Smith et al., "Antigen Nature and Complexity Influence Human Antibody Light Chain Usage and Specificity," Vaccine, 2016, 34(25): 2813-2820.
Smith et al., "Development and evaluation of an optimal human single-chain variable fragment-derived BCMA-targeted CAR T cell vector," Molecular Therapy, Jun. 6, 2018, 26(6):1447-56.
Soerensen et al., "Safety, PK/PD, and anti-tumor activity of RO6874281, an engineered variant of interleukin-2 (IL-2v) targeted to tumor-associated fibroblasts via binding to fibroblast activation protein (FAP)," Journal of Clinical Oncology, Jun. 1, 2018, 36(No. 15 Suppl.):e15155, 2 pages.
Sondel et al., "Combination Therapy with Interleukin-2 and Anti-tumor Monoclonal Antibodies," Cancer Journal from Scientific American, Jan. 1, 1997, 3(Suppl. 1):S121-S127.
Sone et al., "Pancreatic beta cell senescence contributes to the pathogenesis of type 2 diabetes in high-fat diet-induced diabetic mice," Diabetologia, 2005, 48(1):58-67.
Song et al., "IL-12/IL-18-preactivated donor NK cells enhance GVL effects and mitigate GvHD after allogeneic hematopoietic stem cell transplantation," European Journal of Immunology, Apr. 2018, 48(4):670-682.
Soriani et al., "ATM-ATR-dependent up-regulation of DNAM-1 and NKG2D ligands on multiple myeloma cells by therapeutic agents results in enhanced NK-cell susceptibility and is associated with a senescent phenotype," Blood, Apr. 9, 2009, 113(15):3503-11.

Spiess et al., "Alternative molecular formats and therapeutic applications for bispecific antibodies," Molecular Immunology, Oct. 1, 2015, 67(2):95-106.
Stoklasek et al., "Combined IL-15/IL-15Rα Immunotherapy Maximizes IL-15 Activity In Vivo," The Journal of Immunology, Nov. 1, 2006, 177(9):6072-6080.
Storer et al., "Senescence Is a Developmental Mechanism that Contributes to Embryonic Growth and Patterning," Cell, Nov. 21, 2013, 155(5):1119-1130.
Stryer, Biochemistry Fourth Edition, W. H. Freeman and Company, New York, 1995, pp. 18-23, 8 pages.
Swanson et al., "The NLRP3 inflammasome: molecular activation and regulation to therapeutics," Nature Reviews Immunology, Apr. 29, 2019, 19(8):477-489, 13 pages.
Szalay et al., "Cutting edge: anti-CD1 monoclonal antibody treatment reverses the production patterns of TGF-β2 and Th1 cytokines and ameliorates listeriosis in mice," The Journal of Immunology, Jun. 15, 1999, 162(12):6955-8.
Tahara-Hanaoka et al., "Functional characterization of DNAM-1 (CD226) interaction with its ligands PVR (CD155) and nectin-2 (PRR-2/CD112)," International Immunology, Apr. 1, 2004, 16(4):533-8.
Takahashi et al., "Downregulation of cytoplasmic DNases is implicated in cytoplasmic DNA accumulation and SASP in senescent cells," Nature Communications, Mar. 28, 2018, 9:1249, 12 pages.
Takahashi et al., "Simple and inexpensive technique for measuring oxygen consumption rate in adherent cultured cells," The Journal of Physiological Sciences, Nov. 2017, 67(6):731-737.
Takeda et al., "Phase I study of YS110, a recombinant humanized monoclonal antibody to CD26, in Japanese patients with advanced malignant pleural mesothelioma," Lung Cancer, Nov. 2019, 137:64-70.
Tanaka et al., "Cloning and functional expression of the T cell activation antigen CD26," Journal of Immunology, Jul. 15, 1992, 149(2):481-486.
Tang et al., "The Foxp3+ regulatory T cell: a jack of all trades, master of regulation," Nature Immunology, Feb. 19, 2008, 9(3):239-244.
Teissier et al., "The receptor for advanced glycation end-products (RAGE) is an important pattern recognition receptor (PRR) for inflammaging," Biogerontology, Apr. 9, 2019, 20(3):279-301, 23 pages.
Teng et al., "Structural assessment of the effects of amino acid substitutions on protein stability and protein proteininteraction," International journal of computational biology and drug design, Feb. 7, 2011, 3(4):334-349.
Theil et al., "Adoptive transfer of allogeneic regulatory T cells into patients with chronic graft-versus-host disease," Cytotherapy, Apr. 2015, 17(4):473-486, 14 pages.
Thonhoff et al., "Expanded autologous regulatory T-lymphocyte infusions in ALS," Neurology Neuroimmunology Neuroinflammation, May 18, 2018, 5(4):e465, 8 pages.
Tobin et al., "NK cells in childhood obesity are activated, metabolically stressed, and functionally deficient," JCI Insight, Dec. 21, 2017, 2(24):e94939, 9 pages.
Tomala et al., "In Vivo Expansion of Activated Naive CD8+ T Cells and NK Cells Driven by Complexes of IL-2 and Anti-IL-2 Monoclonal Antibody as Novel Approach of Cancer Immunotherapy," The Journal of Immunology, Oct. 15, 2009, 183:4904-4912.
Tominaga et al., "TGF-β Signaling in Cellular Senescence and Aging-Related Pathology," International Journal of Molecular Sciences, Oct. 10, 2019, 20(20):5002, 18 pages.
Trevani et al., "Extracellular acidification induces human neutrophil activation," The Journal of Immunology, Apr. 15, 1999, 162(8):4849-4857.
Tse et al., "ABT-263: A Potent and Orally Bioavailable Bcl-2 Family Inhibitor," Cancer Research, May 2008, 68(9):3421-3428.
Uryga et al., "Ageing induced vascular smooth muscle cell senescence in atherosclerosis," Journal of Physiology, Apr. 15, 2016, 594(8):2115-2124.
Vaishampayan et al., "A phase I trial of ALKS 4230, an engineered cytokine activator of NK and effector T cells, in patients with

(56) References Cited

OTHER PUBLICATIONS advanced solid tumors," Journal of Clinical Oncology, 2017, 35(15 Suppl.):TPS3111, 4 pages (Abstract Only).
Van Audenhove et al., "Nanobodies as versatile tools to understand, diagnose, visualize and treat cancer," EBioMedicine, Jun. 1, 2016, 8:40-8.
Van den Bergh et al., "IL-15 receptor alpha as the magic wand to boost the success of IL-15 antitumor therapies: The upswing of IL-15 transpresentation," Pharmacology and Therapeutics, 2017, 170:73-79.
Van Deursen, "The role of senescent cells in ageing," Nature, May 21, 2014, 509(7501):439-446.
Vankadari et al., "Emerging COVID-19 coronavirus: glycan shield and structure prediction of spike glycoprotein and its interaction with human CD26," Emerging Microbes and Infection, Mar. 17, 2020, 9(1):601-604.
Vidarsson et al., "IgG subclasses and allotypes: from structure to effector functions," Frontiers in immunology, Oct. 20, 2014, 5:520, 17 Pages.
Vincke et al., "Introduction to heavy chain antibodies and derived Nanobodies," Single Domain Antibodies, Humana Press, Totowa, NJ, 2012, pp. 15-26.
Von Kobbe, "Cellular senescence: a view throughout organismal life," Cellular and Molecular Life Sciences, Jul. 20, 2018, 75:3553-3567, 15 pages.
Waaijer et al., "Do senescence markers correlate in vitro and in situ within individual human donors?," Aging Feb. 2018, 10(2):278-289.
Walsh et al., "Inflammasomes in the CNS," Nature Reviews Neuroscience, Jan. 8, 2014, 15(2):84-97, 14 pages.
Wang et al., A New Recombinant Single Chain Trispecific Antibody Recruits T Lymphocytes to Kill CEA (Carcinoma Embryonic Antigen) Positive Tumor Cells In Vitro Efficiently, Journal of Biochemisty, 2004, 135(4):555-565 DOI: 10.1093/jb/mvh065.
Wang et al., "Biomarkers of Cellular Senescence and Skin Aging," Frontiers in Genetics, Aug. 23, 2018, 9:247, 14 pages.
Wang et al., "Loss of lamin B1 is a biomarker to quantify cellular senescence in photoaged skin," Scientific Reports, Nov. 15, 2017, 7(1):15678, 8 pages.
Wang et al., "Recombinant human CD137L for cancer immunotherapy: effects of different fusions and linkers on its activity," Cancer Immunol Immunother., 2012, 61(4):489-495.
Washburn et al., "A potential role for shed soluble major histocompatibility class I molecules as modulators of neurite outgrowth," PLoS One, Mar. 31, 2011, 6(3):e18439.
Weber et al., "Specific low-affinity recognition of major histocompatibility complex plus peptide by soluble T-cell receptor," Nature, Apr. 1992, 356(6372):793.
Weihermann et al., "Elastin structure and its involvement in skin photoageing," International Journal of Cosmetic Science, Jun. 2017, 39(3):241-247.
Weihofen et al., "Crystal Structure of CD26/Dipeptidyl-peptidase IV in Complex with Adenosine Deaminase Reveals a Highly Amphiphilic Interface," Journal of Biological Chemistry, Oct. 2004, 279(41):43330-43335.
Weiner et al., "Antibody-based immunotherapy of cancer," Cell, Mar. 16, 2012, 148(6):1081-4.
Weiss et al., "Formyl-Peptide Receptors in Infection, Inflammation, and Cancer," Trends in Immunology, Oct. 2018, 39(10):815-829, 15 pages.
Wesolowski et al., "Single domain antibodies: promising experimental and therapeutic tools in infection and immunity," Medical Microbiology and Immunology. Aug. 1, 2009, 198(3):157-74.
Wiemann et al., "Hepatocyte telomere shortening and senescence are general markers of human liver cirrhosis," The FASEB Journal, Jul. 2002, 16(9):935-942.
Wiley et al., "Mitochondrial Dysfunction Induces Senescence with a Distinct Secretory Phenotype," Cell Metabolism, Feb. 9, 2016, 23(2):303-314.
Witkowsa et al., "Soluble intercellular adhesion molecule-1 (sICAM-1): an overview," Eur Cytokine Netw. 2004, 15(2):91-98.
Xiong et al., "Maternal uterine NK cell-activating receptor KIR2DS1 enhances placentation," The Journal of Clinical Investigation, Oct. 1, 2013, 123(10):4264-72.
Xu et al., "JAK inhibition alleviates the cellular senescence-associated secretory phenotype and frailty in old age," Proceedings of the National Academy of Sciences U.S.A., Nov. 17, 2015, 112(46):E6301-6310, 10 pages.
Xu et al., "Senolytics improve physical function and increase lifespan in old age," Nature Medicine, Aug. 2018, 24(8):1246, 15 pages.
Xu et al., "Transplanted senescent cells induce an osteoarthritis-like condition in mice," The Journals of Gerontology: Series A, Jun. 1, 2017, 72(6):780-5.
Yamamoto et al., "Measurement of glucose uptake in cultured cells," Curr Protoc Pharmacol, Dec. 2011, Chapter 12:12.14.1-12.14.22.
Yamazaki et al., "Vascular Cell Senescence Contributes to Blood-Brain Barrier Breakdown," Stroke, Feb. 16, 2016, 47(4):1068-1077, 15 pages.
Yan et al., "Obesity- and aging-induced excess of central transforming growth factor-$\beta$ potentiates diabetic development via an RNA stress response," Nature Medicine, Aug. 3, 2014, 20:1001-1008, 9 pages.
Yanai et al., "Cellular senescence-like features of lung fibroblasts derived from idiopathic pulmonary fibrosis patients," Aging (Albany NY), Sep. 2015, 7(9):664-672.
Yigit et al., "A combination of an anti-SLAMF6 antibody and ibrutinib efficiently abrogates expansion of chronic lymphocytic leukemia cells," Oncotarget, May 3, 2016, 7(18):26346.
Yousefzadeh et al., "An aged immune system drives senescence and ageing of solid organs," Nature, May 12, 2021, 594:100-105, 34 pages.
Yu et al., "Targeting the Senescence-Overriding Cooperative Activity of Structurally Unrelated H3K9 Demethylases in Melanoma," Cancer Cell, Feb. 12, 2018, 33(2):322-336, 23 pages.
Yu et al., "The dipeptidyl peptidase IV family in cancer and cell biology," FEBS Journal, Feb. 5, 2010, 277(5):1126-1144.
Yun et al., "Recurrent turnover of senescent cells during regeneration of a complex structure," Elife, May 5, 2015, 4:e05505, 16 pages.
Yung et al., "A selective transforming growth factor-$\beta$ ligand trap attenuates pulmonary hypertension," American Journal of Respiratory and Critical Care Medicine, Nov. 1, 2016, 194(9):1140-51.
Zhang et al., "AAED1 modulates proliferation and glycolysis in gastric cancer," Oncology Reports, Aug. 1, 2018, 40(2):1156-1164.
Zhang et al., "The bone anabolic effects of irisin are through preferential stimulation of aerobic glycolysis," Bone, Sep. 1, 2018, 114:150-160.
Zhao et al., "Histone Deacetylase-3 Modification of MicroRNA-31 Promotes Cell Proliferation and Aerobic Glycolysis in Breast Cancer and Is Predictive of Poor Prognosis," Journal of breast cancer, Jun. 1, 2018, 21(2):112-123.
Zheng et al., "Acquisition of Suppressive Function by Activated Human CD4+CD25-T Cells Is Associated with the Expression of CTLA-4 Not FoxP3," The Journal of Immunology, Aug. 1, 2008, 181(3):1683-1691.
Zhong et al., "A Potential Role for Dendritic Cell/Macrophage-Expressing DPP4 in Obesity-Induced Visceral Inflammation," Diabetes, Jan. 2013, 62(1):149-157.
Zhou et al., "A novel chimeric antigen receptor redirecting T-cell specificity towards CD26cancer cells," Leukemia, Apr. 2020, 35(1):119-129, 11 pages.
Zhu et al., "New agents that target senescent cells: the flavone, fisetin, and the BCL-XL inhibitors, A1331852 and A1155463," Aging (Albany NY), Mar. 2017, 9(3):955-963.
Zhu et al., "Novel Human Interleukin-15 Agonists," The Journal of Immunology, Sep. 15, 2009, 183(6):3598-3607.
Zou et al., "2-NBDG as a fluorescent indicator for direct glucose uptake measurement," Journal of biochemical and biophysical methods, Sep. 30, 2005, 64(3):207-215.

(56) References Cited

OTHER PUBLICATIONS

Zwaagstra et al., "Engineering and therapeutic application of single-chain bivalent TGF-β family traps," Molecular Cancer Therapeutics, Jul. 1, 2012, 11(7):1477-87.
PCT International Preliminary Report on Patentability in International Appln. No. PCT/US2021/017620, dated Aug. 25, 2022, 12 pages.
PCT International Preliminary Report on Patentability in International Appln. No. PCT/US2021/017621, dated Aug. 25, 2022, 8 pages.
PCT International Preliminary Report on Patentability in International Appln. No. PCT/US2021/017714, dated Aug. 25, 2022, 12 pages.
Huang et al., "Targeting the vasculature of colorectal carcinoma with a fused protein of (RGD) 3-tTF" The Scientific World Journal, 2013(637086):1-11, 2013.
PCT International Preliminary Report on Patentability in International Appln. No. PCT/US2021/029920, dated Nov. 10, 2022, 11 pages.
Li et al., "Transforming Growth Factor-β Regulation of Immune Responses," Annu. Rev. Immunol., 2006, 24:99-146.
McCarron et al., "TGF-β prevents T follicular helper cell accumulation and B cell autoreactivity," J Clin Invest., 2014, 124(10):4375-4386.
Voelker et al., "Anti-TGF-β1 Antibody Therapy in Patients with Diabetic Nephropathy," J Am Soc Nephrol., 2017, 28:953-962.
Wallace et al., "B lymphocytes confer immune tolerance via cell surface GARP-TGF-β complex," JCI Insight., 2018, 3(7):e99863, 19 pages.
PCT International Preliminary Report on Patentability in International Appln. No. PCT/US2020/038717, dated Dec. 30, 2021, 9 pages.
Mikayama et al., "Molecular cloning and functional expression of a cDNA encoding glycosylation-inhibiting factor," Proc. Natl. Acad. Sci. USA, Nov. 1, 1993, 90(21):10056-10060.
Voet et al., Biochemistry, John Wiley & Sons, Inc., 1990, pp. 126-128 and 228-234, 12 pages.
Chan et al., "Molecular mechanisms of natural killer cell activation in response to cellular stress," Cell Death & Differentiation, Jan. 2014, 21(1):5-14.
Hui et al., "Butyrate inhibit collagen-induced arthritis via Treg/IL-10/Th17 axis," International immunopharmacology, Mar. 1, 2019, 68: Abstract 1 page.
Li et al., "Lipid metabolism fuels cancer's spread," Cell metabolism, Feb. 7, 2017, 25(2):228-230.
Zhang et al., "Depletion of NK cells improves cognitive function in the Alzheimer disease mouse model," The Journal of Immunology, Jul. 15, 2020, 205(2): 10pages.
PCT International Search Report and Written Opinion in International Appln. No. PCT/US2021/029920, dated Oct. 6, 2021, 21 pages.
PCT International Search Report and Written Opinion in International Appln. No. PCT/US2021/035285, dated Oct. 18, 2021, 14 pages.
Baker et al., "Chronic treatment with the beta(2)-adrenoceptor agonist prodrug BRL-47672 impairs rat skeletal muscle function by inducing a comprehensive shift to a faster muscle phenotype," J Pharmacol Exp Ther., Oct. 2006, 319(1):439-446.
Baker et al., "Effects of conjugated linoleic acid (CLA) on tissue composition parameters in a murine cachexia model," The FASEB Journal, Mar. 2006, 20(4), 2 pages (Abstract Only).
Berry et al., "Cancer Anorexia and Cachexia: Screening in an Ambulatory Infusion Service and Nutrition Consultation," Clin J Oncol Nurs., 2018, 22(1):63-68.
Chang et al., "Association Between Sarcopenia and Cognitive Impairment: A Systematic Review and Meta-Analysis," J Am Med Dir Assoc., Dec. 1, 2016, 17(12):1164e7-1164e15, 9 pages.
Chen et al., "Circulating levels of resistin and risk of type 2 diabetes in men and women: results from two prospective cohorts," Diabetes Care, Feb. 2009, 32(2):329-334.

Cosgrove et al., "Usher protein functions in hair cells and photoreceptors," Int J Biochem Cell Biol., Jan. 2014, 46:80-89.
Helman et al., "Effects of ageing and senescence on pancreatic β-cell function," Diabetes Obes Metab., Sep. 2016, 18(Suppl. 1):58-62.
Jeon et al., "Local clearance of senescent cells attenuates the development of post-traumatic osteoarthritis and creates a pro-regenerative environment," Nat Med., Jun. 2017, 23(6):775-781.
Kim et al., "Insulin resistance, inflammation, and nonalcoholic fatty liver disease in non-obese adults without metabolic syndrome components," Hepatol Int., Jun. 2013, 7(2):586-591.
Kuyinu et al., "Animal models of osteoarthritis: classification, update, and measurement of outcomes," J Orthop Surg Res., Feb. 2, 2016, 11:19, 27 pages.
Melk et al., "Expression of p16INK4a and other cell cycle regulator and senescence associated genes in aging human kidney," Kidney Int., Feb. 2004, 65(2):510-520.
Melk et al., "Senescence of renal cells: molecular basis and clinical implications," Nephrology Dialysis Transplantation, Dec. 2003, 18(12):2474-2478.
Price et al., "Comparison of collagenase-cleaved articular cartilage collagen in mice in the naturally occurring STR/ort model of osteoarthritis and in collagen-induced arthritis," Osteoarthritis Cartilage, Mar. 2002, 10(3):172-179.
Sousa-Victor et al., "Geroconversion of aged muscle stem cells under regenerative pressure," Cell Cycle, Oct. 15, 2014, 13(20):3183-3190.
Xu et al., "Celecoxib attenuates cachectic events in mice by modulating the expression of vascular endothelial growth factor," Mol Med Rep., Jan. 2015, 11(1):289-294.
Chandrudu et al., "Chemical methods for peptide and protein production," Molecules, 2013, 18(4):4373-4388.
Tam et al., "Methods and strategies of peptide ligation," Peptide Science: Original Research on Biomolecules, 2001, 60(3):194-205.
International Preliminary Report on Patentability in International Appln. No. PCT/US2020/035598, mailed Dec. 6, 2022, 7 pages.
International Preliminary Report on Patentability in International Appln. No. PCT/US2021/035285, mailed Dec. 15, 2022, 7 pages.
Fernando et al., "Targeting tumor endothelial marker 8 in the tumor vasculature of colorectal carcinomas in mice," Cancer research, Jun. 15, 2009, 69(12):5126-5132.
Mortier et al., "Soluble interleukin-15 receptor α (IL-15Rα)-sushi as a selective and potent agonist of IL-15 action through IL-15Rβ/γ: hyperagonist IL-15• IL-15Rα fusion proteins," Journal of Biological Chemistry, Jan. 20, 2006, 281(3):1612-1619.
Wong et al., "Interleukin-15: Interleukin-15 receptor α scaffold for creation of multivalent targeted immune molecules," Protein Engineering, Design & Selection, Apr. 1, 2011, 24(4):373-383.
Bartscht et al., "Dasatinib blocks transcriptional and promigratory responses to transforming growth factor-beta in pancreatic adenocarcinoma cells through inhibition of Smad signalling: implications for in vivo mode of action," Molecular Cancer, Dec. 2015, 14(199):1-12.
Bird et al., "TGFβ inhibition restores a regenerative response in acute liver injury by suppressing paracrine senescence," Science translational medicine, Aug. 15, 2018, 10(454):eaan1230, 15 pages.
Cai et al., "Quercetin inhibits transforming growth factor β1-induced epithelial-mesenchymal transition in human retinal pigment epithelial cells via the Smad pathway," Drug design, development and therapy, Dec. 6, 2018, 12:4149-4161.
Chabannon et al., "Manufacturing natural killer cells as medicinal products," Frontiers in Immunology, Nov. 15, 2016, 7(504): 1-9.
Chang et al., "The dock and lock method: a novel platform technology for building multivalent, multifunctional structures of defined composition with retained bioactivity," Clinical cancer research, Sep. 15, 2007, 13(18):5586s-5591s.
Klingemann et al., "Natural killer cells for immunotherapy—advantages of the NK-92 cell line over blood NK cells," Frontiers in immunology, Mar. 14, 2016, 7(91): 1-7.
Kozlowska et al., "Adoptive transfer of osteoclast-expanded natural killer cells for immunotherapy targeting cancer stem-like cells in humanized mice," Cancer Immunology, Immunotherapy, Jul. 2016, 65:835-845.

(56) References Cited

OTHER PUBLICATIONS

Putnam et al., "Clinical grade manufacturing of human alloantigen-reactive regulatory T cells for use in transplantation," American journal of transplantation, Nov. 1, 2013, 13(11):3010-3020.

Uppendahl et al., "Natural killer cell-based immunotherapy in gynecologic malignancy: a review," Frontiers in immunology, Jan. 5, 2018, 8(1825): 1-15.

Veluchamy et al., "The rise of allogeneic natural killer cells as a platform for cancer immunotherapy: recent innovations and future developments," Frontiers in immunology, May 31, 2017, 8(631): 1-20.

Wilchek et al., "Essentials of biorecognition: The (strept) avidin-biotin system as a model for protein-protein and protein-ligand interaction," Immunology letters, Feb. 28, 2006, 103(1): Abstract 2 pages.

Zhou, "Emerging mechanisms and applications of low-dose IL-2 therapy in autoimmunity," Cytokine & Growth Factor Reviews, Jun. 30, 2022, 67: 80-88.

Chen et al., "A novel idea for establishing Parkinson's disease mouse model by intranasal administration of paraquat," Neurological Research, 2021, 43(4):267-277.

Igarashi et al., "VEGF-C and TGF-β reciprocally regulate mesenchymal stem cell commitment to differentiation into lymphatic endothelial or osteoblastic phenotypes," International Journal of Molecular Medicine, Apr. 1, 2016, 37(4):1005-1013.

Infante-Duarte et al., "New developments in understanding and treating neuroinflammation," Journal of Molecular Medicine, Sep. 2008, 86:975-985.

International Search Report and Written Opinion in International Appln. No. PCT/US2023/065745, mailed on Jun. 26, 2023, 14 pages.

Janeway et al., "The interaction of the antibody molecule with specific antigen," In Immunobiology: The Immune System in Health and Disease, 5th edition, 5 pages, 2001.

Matsuura et al., "Pole test is a useful method for evaluating the mouse movement disorder caused by striatal dopamine depletion," 1997, Journal of Neuroscience Methods, 73(1):45-48.

Reddy et al., "Linkers in the structural biology of protein-protein interactions," Protein Science, 2013, 22(2):153-167.

Ross et al., "Signaling and function of interleukin-2 in T lymphocytes," Annual Review of Immunology, 2018, 36:411-433.

Van Bockstaele et al., "The development of nanobodies for therapeutic applications," Current Opinion in Investigational Drugs, 2009, 10(11):1212-1224.

Shen et al., "Engineering peptide linkers for scFv immunosensors," Anal Chem., Mar. 2008, 80(6):1910-1917.

\* cited by examiner

CHROMATOGRAPHY RESIN AND USES THEREOF

CROSS-REFERENCE TO RELATED APPLICATION

This application claims priority to U.S. Provisional Patent Application Ser. No. 62/982,002, filed on Feb. 26, 2020, and U.S. Provisional Patent Application Ser. No. 62/975,141, filed on Feb. 11, 2020, both of which are incorporated herein by reference in their entireties.

SEQUENCE LISTING

This application contains a Sequence Listing that has been submitted electronically in ACSII format named "20240722 47059-0018001_SL_ST25.txt". The .txt file, created on Jul. 22, 2024, is 598,981 bytes in size. The material in the .txt file is hereby incorporated by reference in its entirety.

TECHNICAL FIELD

The present disclosure relates to the field of biotechnology, and more specifically, to antigen-binding molecules.

BACKGROUND

Tissue factor (TF), a 263 amino acid integral membrane glycoprotein with a molecular weight of ~46 kDa and the trigger protein of the extrinsic blood coagulation pathway, is the primary initiator of coagulation in vivo. Tissue factor, normally not in contact with circulating blood, initiates the coagulation cascade upon exposure to the circulating coagulation serine protease factors. Vascular damage exposes sub-endothelial cells expressing tissue factor, resulting in the formation of a calcium-dependent, high-affinity complex with pre-existing plasma factor VIIa (FVIIa). Binding of the serine protease FVIIa to tissue factor promotes rapid cleavage of FX to FXa and FIX to FIXa. The proteolytic activity of the resulting FXa and an active membrane surface then inefficiently converts a small amount of prothrombin to thrombin. The thrombin generated by FXa initiates platelet activation and activates minute amounts of the pro-cofactors factor V (FV) and factor VIII (FVIII) to become active cofactors, factor Va (FVa) and factor VIIIa (FVIIIa). FIXa complexes with FVIIIa on the platelet surface forming the intrinsic tenase complex, which results in rapid generation of FXa. FXa complexes with FVa to form the pro-thrombinase complex on the activated platelet surface which results in rapid cleavage of prothrombin to thrombin.

In addition to the tissue factor-FVIIa complex, a recent study showed that the tissue factor-FVIIa-FXa complex can activate FVIII, which would provide additional levels of FVIIIa during the initiation phase. The extrinsic pathway is paramount in initiating coagulation via the activation of limited amounts of thrombin, whereas the intrinsic pathway maintains coagulation by dramatic amplification of the initial signal.

Much of the tissue factor expressed on a cell surface is "encrypted," which must be "decrypted" for full participation in coagulation. The mechanism of "decryption" of cell-surface tissue factor is still unclear at this time, however, exposure of anionic phospholipids plays a major role in this process. Healthy cells actively sequester anionic phospholipids such as phosphatidyl serine (PS) to the inner leaflet of the plasma membrane. Following cellular damage, activation, or increased levels of cytosolic $Ca^{2+}$, this bilayer asymmetry is lost, resulting in increased PS exposure on the outer leaflet, which increases the specific activity of cell-surface tissue factor-FVIIa complexes. PS exposure is known to decrease the apparent Km for activation of FIX and FX by tissue factor-FVIIa complexes, but additional mechanisms could include conformational rearrangement of tissue factor or tissue factor-FVIIa and subsequent exposure of substrate binding sites.

SUMMARY

Provided herein are affinity chromatography resins that include an anti-tissue factor antibody or antigen-binding fragment thereof attached to a base resin, and methods of using the same.

Provided herein are affinity chromatography resins that include an anti-tissue factor antibody or antigen-binding fragment thereof comprising a heavy chain variable domain comprising CDRs of SEQ ID NOs: 1, 2 or 9, and 3, and a light chain variable domain comprising CDRs of SEQ ID NOs: 4, 5, and 6, attached to a base resin.

In some embodiments of any of the affinity chromatography resins described herein, the heavy chain variable domain comprises a sequence that is at least 90% identical to SEQ ID NO: 7, and the light chain variable domain comprises a sequence that is at least 90% identical to SEQ ID NO: 8. In some embodiments of any of the affinity chromatography resins described herein, the heavy chain variable domain comprises SEQ ID NO: 7, and the light chain variable domain comprises SEQ ID NO: 8.

In some embodiments of any of the affinity chromatography resins described herein, the base resin is sepharose. In some embodiments of any of the affinity chromatography resins described herein, the base resin is any support material. In some embodiments of any of the affinity chromatography resins described herein, the support material is agarose or a capto resin. In some embodiments of any of the affinity chromatography resins described herein, the anti-tissue factor antibody or antigen-binding fragment thereof is non-covalently attached to the base resin. In some embodiments of any of the affinity chromatography resins described herein, the anti-tissue factor antibody or antigen-binding fragment thereof is covalently attached to the base resin.

In some embodiments of any of the affinity chromatography resins described herein, the anti-tissue factor antibody or antigen-binding fragment thereof is covalently attached to the base resin through the formation of a disulfide bond between a cysteine in the anti-tissue factor antibody or antigen-binding fragment thereof and a chemical group on the base resin. In some embodiments of any of the affinity chromatography resins described herein, the anti-tissue factor antibody or antigen-binding fragment thereof is covalently attached to the base resin through the formation of a covalent bond between a free amine of the anti-tissue factor antibody or antigen-binding domain and a chemical group on the base resin.

In some embodiments of any of the affinity chromatography resins described herein, the base resin is CNBr-activated or N-hydroxysuccinimide (NHS)-activated solid support material. In some embodiments of any of the affinity chromatography resins described herein, the covalent bond is represented by Formula I below:

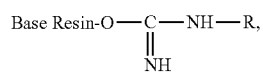

where R represents the anti-tissue factor antibody or antigen-binding fragment thereof.

Also provided herein are kits that include any of the affinity chromatography resins described herein.

Also provided herein are methods of purifying a tissue factor-containing protein that include the use of any of the affinity chromatography resins described herein. Some embodiments of any of the methods described herein further include: loading the affinity chromatography resin with a liquid comprising the tissue factor-containing protein; washing the affinity chromatography resin using one or more wash buffer(s); and eluting the tissue factor-containing protein using an elution buffer. In some embodiments of any of the methods described herein, the liquid comprising the tissue factor-containing protein is a clarified liquid culture medium. In some embodiments of any of the methods described herein, the liquid comprising the tissue factor-containing protein comprises a cell lysate.

In some embodiments of any of the methods described herein, the one or more wash buffer(s) are: (i) a first wash buffer comprising phosphate buffered saline; and (ii) a second wash buffer comprising about 0.01 M to about 0.2 M citrate and having a pH of about 4.5 to about 5.5. In some embodiments of any of the methods described herein, (i) the first wash buffer is phosphate buffered saline; and (ii) the second wash buffer is 0.1 M citrate, pH 5.0.

In some embodiments of any of the methods described herein, the elution buffer comprises 0.01 M to about 0.2 M acetate and has a pH of about 2.5 to about 3.5. In some embodiments of any of the methods described herein, the elution buffer comprises 0.1 M acetate and has a pH of about 2.9.

Also provided herein are methods of manufacturing a tissue factor-containing protein that include: (i) purifying a tissue factor-containing protein using any of the methods described herein that include the use of any of the affinity chromatography resins described herein; and (ii) performing one or more additional unit operations on an eluate obtained from step (i). In some embodiments of any of the methods described herein, the one or more additional unit operations comprises, in sequential order: performing low pH viral inactivation; performing depth filtration; performing polishing chromatography; performing nanofiltration; and performing ultrafiltration and diafiltration (UF/DF).

In some embodiments of any of the methods described herein, the tissue factor-containing protein is a single-chain chimeric polypeptide. In some embodiments of any of the methods described herein, the single-chain chimeric polypeptide comprises: (i) a first target-binding domain; (ii) a soluble tissue factor domain; and (iii) a second target-binding domain. In some embodiments of any of the methods described herein, the first target-binding domain and the soluble tissue factor domain directly abut each other. In some embodiments of any of the methods described herein, the single-chain chimeric polypeptide further comprises a linker sequence between the first target-binding domain and the soluble tissue factor domain. In some embodiments of any of the methods described herein, the soluble tissue factor domain and the second target-binding domain directly abut each other. In some embodiments of any of the methods described herein, the single-chain chimeric polypeptide further comprises a linker sequence between the soluble tissue factor domain and the second target-binding domain.

In some embodiments of any of the methods described herein, the first target-binding domain and the second target-binding domain bind specifically to the same antigen. In some embodiments of any of the methods described herein, the first target-binding domain and the second target-binding domain bind specifically to the same epitope. In some embodiments of any of the methods described herein, the first target-binding domain and the second target-binding domain comprise the same amino acid sequence. In some embodiments of any of the methods described herein, the first target-binding domain and the second target-binding domain bind specifically to different antigens.

In some embodiments of any of the methods described herein, one or both of the first target-binding domain and the second target-binding domain is an antigen-binding domain. In some embodiments of any of the methods described herein, one or both of the first target-binding domain and the second target-binding domain bind to a target selected from the group of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

In some embodiments of any of the methods described herein, one or both of the first target-binding domain and the second target-binding domain is a soluble interleukin, a soluble cytokine protein, or a soluble cell surface protein. In some embodiments of any of the methods described herein, the soluble interleukin, soluble cytokine protein, or soluble cell surface protein is selected from the group of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

In some embodiments of any of the methods described herein, one or both of the first target-binding domain and the second target-binding domain is a soluble interleukin receptor, a soluble cytokine receptor, or a soluble cell surface receptor. In some embodiments of any of the methods described herein, the soluble interleukin receptor, the soluble cytokine receptor, or the soluble cell surface receptor is a soluble TGF-β receptor II (TGF-βRII), a soluble TGF-βRIII, a soluble NKG2D, a soluble NKp30, a soluble NKp44, a soluble NKp46, a soluble DNAM-1, a scMHCI, a scMHCII, a scTCR, a soluble CD155, or a soluble CD28.

In some embodiments of any of the methods described herein, the soluble tissue factor domain is a soluble human tissue factor domain. In some embodiments of any of the methods described herein, the soluble human tissue factor domain comprises a sequence that is at least 80% identical to SEQ ID NO: 10. In some embodiments of any of the methods described herein, the soluble tissue factor domain does not comprise any of: a lysine at an amino acid position that corresponds to amino acid position 20 of mature wild-type human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein.

In some embodiments of any of the methods described herein, the soluble tissue factor domain comprises one or more of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein.

In some embodiments of any of the methods described herein, the single-chain chimeric polypeptide further comprises one or more additional target-binding domains at its N- and/or C-terminus.

In some embodiments of any of the methods described herein, the tissue factor-containing protein is a multi-chain chimeric polypeptide. In some embodiments of any of the methods described herein, the multi-chain chimeric polypeptide comprises: (a) a first chimeric polypeptide comprising: (i) a first target-binding domain; (ii) a soluble tissue factor domain; and (iii) a first domain of a pair of affinity domains; (b) a second chimeric polypeptide comprising: (i) a second domain of a pair of affinity domains; and (ii) a second target-binding domain, where the first chimeric polypeptide and the second chimeric polypeptide associate through the binding of the first domain and the second domain of the pair of affinity domains. In some embodiments of any of the methods described herein, the first target-binding domain and the soluble tissue factor domain directly abut each other in the first chimeric polypeptide. In some embodiments of any of the methods described herein, the first chimeric polypeptide further comprises a linker sequence between the first target-binding domain and the soluble tissue factor domain in the first chimeric polypeptide. In some embodiments of any of the methods described herein, the soluble tissue factor domain and the first domain of the pair of affinity domains directly abut each other in the first chimeric polypeptide. In some embodiments of any of the methods described herein, the first chimeric polypeptide further comprises a linker sequence between the soluble tissue factor domain and the first domain of the pair of affinity domains in the first chimeric polypeptide. In some embodiments of any of the methods described herein, the second domain of the pair of affinity domains and the second target-binding domain directly abut each other in the second chimeric polypeptide. In some embodiments of any of the methods described herein, the second chimeric polypeptide further comprises a linker sequence between the second domain of the pair of affinity domains and the second target-binding domain in the second chimeric polypeptide.

In some embodiments of any of the methods described herein, the first target-binding domain and the second target-binding domain bind specifically to the same antigen. In some embodiments of any of the methods described herein, the first target-binding domain and the second target-binding domain bind specifically to different antigens.

In some embodiments of any of the methods described herein, one or both of the first target-binding domain and the second target-binding domain is an antigen-binding domain. In some embodiments of any of the methods described herein, one or both of the first target-binding domain and the second target-binding domain bind specifically to a target selected from the group of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

In some embodiments of any of the methods described herein, one or both of the first target-binding domain and the second target-binding domain is a soluble interleukin or cytokine protein. In some embodiments of any of the methods described herein, the soluble interleukin, cytokine, or ligand protein is selected from the group of: IL-1, IL-2, IL-3, IL-7, IL-8, IL-10, IL-12, IL-15, IL-17, IL-18, IL-21, PDGF-DD, SCF, and FLT3L.

In some embodiments of any of the methods described herein, one or both of the first target-binding domain and the second target-binding domain is a soluble interleukin or cytokine receptor. In some embodiments of any of the methods described herein, the soluble receptor is a soluble TGF-β receptor II (TGF-βRII), a soluble TGF-βRIII, a soluble NKG2D, a soluble NKp30, a soluble NKp44, a soluble NKp46, a soluble DNAM-1, a scMHCI, a scMHCII, a scTCR, a soluble CD155, or a soluble CD28.

In some embodiments of any of the methods described herein, the first chimeric polypeptide further comprises one or more additional target-binding domain(s). In some embodiments of any of the methods described herein, the second chimeric polypeptide further comprises one or more additional target-binding domains.

In some embodiments of any of the methods described herein, the soluble tissue factor domain is a soluble human tissue factor domain. In some embodiments of any of the methods described herein, the soluble human tissue factor domain comprises a sequence that is at least 80% identical to SEQ ID NO: 10.

In some embodiments of any of the methods described herein, the soluble tissue factor domain does not comprise any of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein.

In some embodiments of any of the methods described herein, the soluble tissue factor domain comprises one or more of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein.

In some embodiments of any of the methods described herein, the pair of affinity domains is a sushi domain from an alpha chain of human IL-15 receptor (IL15Rα) and a soluble IL-15. In some embodiments of any of the methods described herein, the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Also provided are tissue factor-containing proteins manufactured by any of the methods described herein. Also provided herein are pharmaceutical compositions that include any of the manufactured tissue factor-containing proteins described herein.

As used herein, the term "chimeric" refers to a polypeptide that includes amino acid sequences (e.g., domains) originally derived from two different sources (e.g., two different naturally-occurring proteins, e.g., from the same or different species). For example, a chimeric polypeptide can include domains from at least two different naturally occurring human proteins. In some examples, a chimeric polypeptide can include a domain that is a synthetic sequence (e.g., an scFv) and a domain that is derived from a naturally-occurring protein (e.g., a naturally-occurring human protein). In some embodiments, a chimeric polypeptide can include at least two different domains that are synthetic sequences (e.g., two different scFvs).

An "antigen-binding domain" is one or more protein domain(s) (e.g., formed from amino acids from a single polypeptide or formed from amino acids from two or more polypeptides (e.g., the same or different polypeptides) that is capable of specifically binding to one or more different antigen(s). In some examples, an antigen-binding domain can bind to an antigen or epitope with specificity and affinity similar to that of naturally-occurring antibodies. In some embodiments, the antigen-binding domain can be an antibody or a fragment thereof. In some embodiments, an antigen-binding domain can include an alternative scaffold. Non-limiting examples of antigen-binding domains are described herein. Additional examples of antigen-binding domains are known in the art.

A "soluble tissue factor domain" refers to a polypeptide having at least 70% identity (e.g., at least 75% identity, at least 80% identity, at least 85% identity, at least 90% identity, at least 95% identity, at least 99% identity, or 100% identical) to a segment of a wildtype mammalian tissue factor protein (e.g., a wildtype human tissue factor protein) that lacks the transmembrane domain and the intracellular domain. Non-limiting examples of soluble tissue factor domains are described herein.

The term "soluble interleukin protein" is used herein to refer to a mature and secreted interleukin protein or a biologically active fragment thereof. In some examples, a soluble interleukin protein can include a sequence that is at least 70% identical, at least 75% identical, at least 80% identical, at least 85% identical, at least 90% identical, at least 95% identical, at least 99% identical, or 100% identical to a wildtype mature and secreted mammalian interleukin protein (e.g., a wildtype human interleukin protein) and retains its biological activity. Non-limiting examples of soluble interleukin proteins are described herein.

The term "soluble cytokine protein" is used herein to refer to a mature and secreted cytokine protein or a biologically active fragment thereof. In some examples, a soluble cytokine protein can include a sequence that is at least 70% identical, at least 75% identical, at least 80% identical, at least 85% identical, at least 90% identical, at least 95% identical, at least 99% identical, or 100% identical to a wildtype mature and secreted mammalian interleukin protein (e.g., a wildtype human interleukin protein) and retains its biological activity. Non-limiting examples of soluble cytokine proteins are described herein.

The term "soluble interleukin receptor" is used herein in the broadest sense to refer to a polypeptide that lacks a transmembrane domain (and optionally an intracellular domain) that is capable of binding one or more of its natural ligands (e.g., under physiological conditions, e.g., in phosphate buffered saline at room temperature). For example, a soluble interleukin receptor can include a sequence that is at least 70% identical (e.g., at least 75% identical, at least 80% identical, at least 85% identical, at least 90% identical, at least 95% identical, at least 99% identical, or 100% identical) to an extracellular domain of wildtype interleukin receptor and retains its ability to specifically bind to one or more of its natural ligands, but lacks its transmembrane domain (and optionally, further lacks its intracellular domain). Non-limiting examples of soluble interleukin receptors are described herein.

The term "soluble cytokine receptor" is used herein in the broadest sense to refer to a polypeptide that lacks a transmembrane domain (and optionally an intracellular domain) that is capable of binding one or more of its natural ligands (e.g., under physiological conditions, e.g., in phosphate buffered saline at room temperature). For example, a soluble cytokine receptor can include a sequence that is at least 70% identical (e.g., at least 75% identical, at least 80% identical, at least 85% identical, at least 90% identical, at least 95% identical, at least 99% identical, or 100% identical) to an extracellular domain of wildtype cytokine receptor and retains its ability to specifically bind to one or more of its natural ligands, but lacks its transmembrane domain (and optionally, further lacks its intracellular domain). Non-limiting examples of soluble cytokine receptors are described herein.

The term "antibody" is used herein in its broadest sense and includes certain types of immunoglobulin molecules that include one or more antigen-binding domains that specifically bind to an antigen or epitope. An antibody specifically includes, e.g., intact antibodies (e.g., intact immunoglobulins), antibody fragments, and multi-specific antibodies. One example of an antigen-binding domain is an antigen-binding domain formed by a VH-VL dimer. Additional examples of an antibody are described herein. Additional examples of an antibody are known in the art.

"Affinity" refers to the strength of the sum total of non-covalent interactions between an antigen-binding site and its binding partner (e.g., an antigen or epitope). Unless indicated otherwise, as used herein, "affinity" refers to intrinsic binding affinity, which reflects a 1:1 interaction between members of an antigen-binding domain and an antigen or epitope. The affinity of a molecule X for its partner Y can be represented by the dissociation equilibrium constant ($K_D$). The kinetic components that contribute to the dissociation equilibrium constant are described in more detail below. Affinity can be measured by common methods known in the art, including those described herein. Affinity can be determined, for example, using surface plasmon resonance (SPR) technology (e.g., BIACORE®) or biolayer interferometry (e.g., FORTEBIO®). Additional methods for determining the affinity for an antigen-binding domain and its corresponding antigen or epitope are known in the art.

A "multi-chain polypeptide" as used herein to refers to a polypeptide comprising two or more (e.g., three, four, five, six, seven, eight, nine, or ten) protein chains (e.g., at least a first chimeric polypeptide and a second polypeptide), where the two or more proteins chains associate through non-covalent bonds to form a quaternary structure.

A "single-chain polypeptide" as used herein to refers to a single protein chain.

The term "pair of affinity domains" is two different protein domain(s) that bind specifically to each other with a $K_D$ of less than of less than $1 \times 10^{-7}$ M (e.g., less than $1 \times 10^{-8}$ M, less than $1 \times 10^{-9}$ M, less than $1 \times 10^{-10}$ M, or less than $1 \times 10^{-11}$ M). In some examples, a pair of affinity domains can be a pair of naturally-occurring proteins. In some embodiments, a pair of affinity domains can be a pair of synthetic proteins. Non-limiting examples of pairs of affinity domains are described herein.

The term "epitope" means a portion of an antigen that specifically binds to an antigen-binding domain. Epitopes can, e.g., consist of surface-accessible amino acid residues and/or sugar side chains and may have specific three-dimensional structural characteristics, as well as specific charge characteristics. Conformational and non-conformational epitopes are distinguished in that the binding to the former but not the latter may be lost in the presence of denaturing solvents. An epitope may comprise amino acid residues that are directly involved in the binding, and other amino acid residues, which are not directly involved in the binding. Methods for identifying an epitope to which an antigen-binding domain binds are known in the art.

The term "treatment" means to ameliorate at least one symptom of a disorder. In some examples, the disorder being treated is cancer and to ameliorate at least one symptom of cancer includes reducing aberrant proliferation, gene expression, signaling, translation, and/or secretion of factors. Generally, the methods of treatment include administering a therapeutically effective amount of composition that reduces at least one symptom of a disorder to a subject who is in need of, or who has been determined to be in need of such treatment.

The term "purifying" means a step performed to isolate a protein (e.g., any of the exemplary single-chain or multi-chain chimeric polypeptides described herein) from one or more other impurities (e.g., bulk impurities) or components present in a fluid containing a protein (e.g., liquid culture medium proteins or one or more other components (e.g., DNA, RNA, other proteins, endotoxins, viruses, etc.) present in or secreted from a mammalian cell). Purification can be performed using a resin, membrane, or any other solid support that binds either a protein or contaminants (e.g., through the use of affinity chromatography, hydrophobic interaction chromatography, anion or cation exchange chromatography, or molecular sieve chromatography). A protein can be purified from a fluid containing the protein using at least one chromatography column (e.g., any of the chromatography columns described herein that include any of the affinity chromatography resins described herein).

The term "polishing" is a term of art and means a step performed to remove remaining trace or small amounts of contaminants or impurities from a fluid containing a protein (e.g., any of the single-chain or multi-chain chimeric polypeptides described herein) that is close to a final desired purity. For example, polishing can be performed by passing a fluid containing the protein through a chromatographic column(s) or membrane absorber(s) that selectively binds to either the protein or small amounts of contaminants or impurities present in a fluid containing the protein. In such an example, the eluate/filtrate of the chromatographic column(s) or membrane absorber(s) contains the protein.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
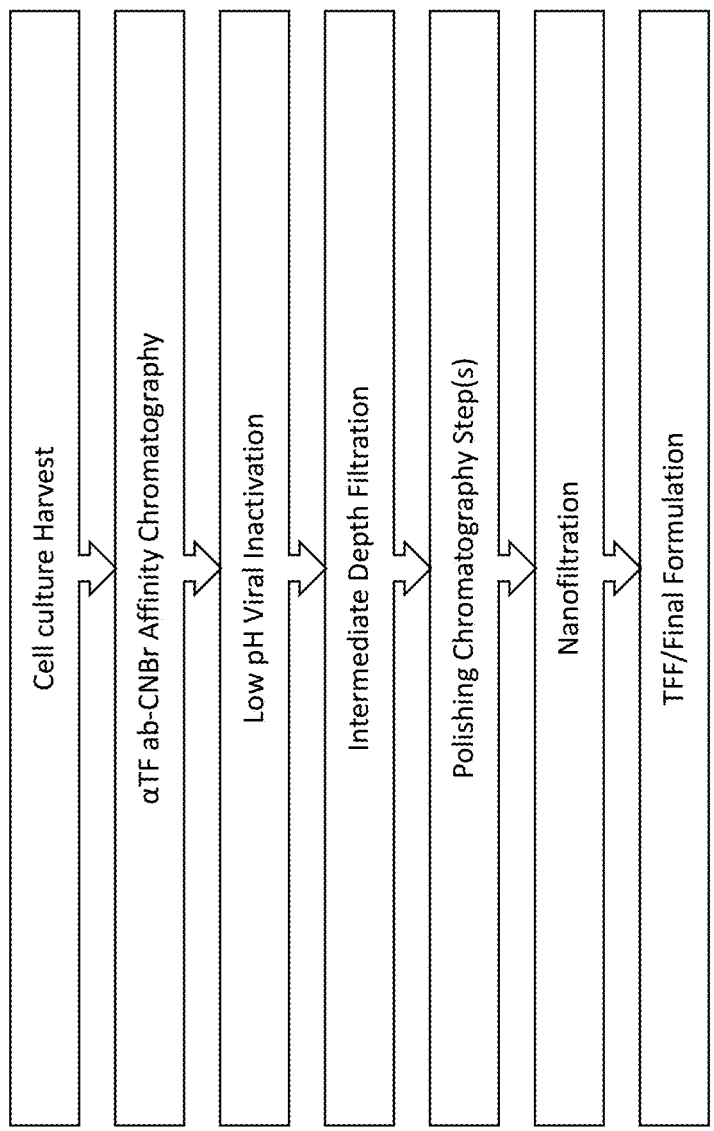
FIG. 1 is a workflow schematic showing an exemplary workflow for manufacturing a tissue-factor containing protein that include providing a harvested cell culture (e.g., a substantially cell-free (e.g., at least 99% free of cells) liquid culture medium), purifying the tissue-factor containing protein using any of the affinity chromatography resins described herein, performing low pH viral inactivation, performing depth filtration, performing polishing chromatography, performing nanofiltration, and performing ultrafiltration/diafiltration (shown as "TFF/final formulation" in the schematic).

Provided herein is an affinity chromatography resin comprising an anti-tissue factor antibody or antigen-binding fragment thereof comprising a heavy chain variable domain comprising CDRs of SEQ ID NOs: 1, 2 or 9, and 3, and a light chain variable domain comprising CDRs of SEQ ID NOs: 4, 5, and 6, attached to a base resin.

Also provided herein is a kit including any of the affinity chromatography resins described herein. Also provided herein are methods of purifying a tissue factor-containing protein comprising the use of any of the affinity chromatography resins described herein. Also provided herein are methods of manufacturing a tissue factor-containing protein comprising: (i) purifying a tissue factor-containing protein using any of the methods of purifying a tissue factor-containing protein described herein; and (ii) performing one or more additional unit operations on an eluate obtained from step (i). Also provided herein is a tissue factor-containing protein manufactured by any of the methods described herein. Also provided herein is a pharmaceutical composition comprising any of the manufactured tissue factor-containing proteins described herein.

In some embodiments, an affinity chromatography resin as described herein can have a binding capacity for a tissue factor-containing protein of about 0.5 mg/mL to about 6.0 mg/mL (e.g., about 0.5 mg/mL to about 5.5 mg/mL, about 0.5 mg/mL to about 5.0 mg/mL, about 0.5 mg/mL to about 4.5 mg/mL, about 0.5 mg/mL to about 4.0 mg/mL, about 0.5 mg/mL to about 3.5 mg/mL, about 0.5 mg/mL to about 3.0 mg/mL, about 0.5 mg/mL to about 2.5 mg/mL, about 0.5 mg/mL to about 2.0 mg/mL, about 0.5 mg/mL to about 1.5 mg/mL, about 0.5 mg/mL to about 1.0 mg/mL, about 1.0 mg/mL to about 6.0 mg/mL, about 1.0 mg/mL to about 5.5 mg/mL, about 1.0 mg/mL to about 5.0 mg/mL, about 1.0 mg/mL to about 4.5 mg/mL, about 1.0 mg/mL to about 4.0 mg/mL, about 1.0 mg/mL to about 3.5 mg/mL, about 1.0 mg/mL to about 3.0 mg/mL, about 1.0 mg/mL to about 2.5 mg/mL, about 1.0 mg/mL to about 2.0 mg/mL, about 1.0 mg/mL to about 1.5 mg/mL, about 1.5 mg/mL to about 6.0 mg/mL, about 1.5 mg/mL to about 5.5 mg/mL, about 1.5 mg/mL to about 5.0 mg/mL, about 1.5 mg/mL to about 4.5 mg/mL, about 1.5 mg/mL to about 4.0 mg/mL, about 1.5 mg/mL to about 3.5 mg/mL, about 1.5 mg/mL to about 3.0 mg/mL, about 1.5 mg/mL to about 2.5 mg/mL, about 1.5 mg/mL to about 2.0 mg/mL, about 2.0 mg/mL to about 6.0 mg/mL, about 2.0 mg/mL to about 5.5 mg/mL, about 2.0 mg/mL to about 5.0 mg/mL, about 2.0 mg/mL to about 4.5 mg/mL, about 2.0 mg/mL to about 4.0 mg/mL, about 2.0 mg/mL to about 3.5 mg/mL, about 2.0 mg/mL to about 3.0 mg/mL, about 2.0 mg/mL to about 2.5 mg/mL, about 2.5 mg/mL to about 6.0 mg/mL, about 2.5 mg/mL to about 5.5 mg/mL, about 2.5 mg/mL to about 5.0 mg/mL, about 2.5 mg/mL to about 4.5 mg/mL, about 2.5 mg/mL to about 4.0 mg/mL, about 2.5 mg/mL to about 3.5 mg/mL, about 2.5 mg/mL to about 3.0 mg/mL, about 3.0 mg/mL to about 6.0 mg/mL, about 3.0 mg/mL to about 5.5 mg/mL, about 3.0 mg/mL to about 5.0 mg/mL, about 3.0 mg/mL to about 4.5 mg/mL, about 3.0 mg/mL to about 4.0 mg/mL, about 3.0 mg/mL to about 3.5 mg/mL, about 3.5 mg/mL to about 6.0 mg/mL, about 3.5 mg/mL to about 5.5 mg/mL, about 3.5 mg/mL to about 5.0 mg/mL, about 3.5 mg/mL to about 4.5 mg/mL, about 3.5 mg/mL to about 4.0 mg/mL, about 4.0 mg/mL to about 6.0 mg/mL, about 4.0 mg/mL to about 5.5 mg/mL, about 4.0 mg/mL to about 5.0 mg/mL, about 4.5 mg/mL to about 6.0 mg/mL, about 4.5 mg/mL to about 5.5 mg/mL, about 4.5 mg/mL to about 5.0 mg/mL, about 5.0 mg/mL to about 6.0 mg/mL, about 5.0 mg/mL to about 5.5 mg/mL, or about 5.5 mg/mL to about 6.0 mg/mL).

As used herein, "affinity chromatography" refers to a method of separating a solution or mixture based on a highly specific interaction between antigen and antibody, enzyme and substrate, receptor and ligand, or protein and nucleic acid. Affinity chromatography (e.g., Protein A, Protein G, Protein L, or metal chelate affinity chromatography) is an effective method to specifically purify target proteins with high yield recovery and low levels of contaminating proteins and other components in the starting mixture such as cell culture supernatants, serum, and plasma. Once a clarified liquid or mixture comprising the target protein is obtained, affinity chromatography can be used with a combination of one or more different purification techniques (e.g., ion exchange separation, hydrophobic interaction separation) for the purification of the target protein.

Antibody (e.g., monoclonal or polyclonal) based immunoaffinity chromatography has been widely used as a method/process to purify specific antigens or antigen-containing proteins (e.g., human tissue factor-containing proteins) in the fields of research, development, and manufacturing. For the immunoaffinity method, an antibody (e.g., monoclonal) or a mixture of antibodies (e.g., polyclonal) is immobilized (e.g., coupled) covalently onto solid support materials such as CNBr-activated Sepharose, NHS-Sepharose, and other related beads/resins suitable for protein coupling or immobilization. A solid support material is any material to which a biospecific ligand is covalently attached wherein examples of the materials used in affinity chromatography include agarose, cellulose, dextran, polyacrylamide, latex, and controlled pore glass. Useful support materials can have properties such as high surface-area to volume ratio, chemical groups that are easily modified for covalent attachment of ligands, minimal nonspecific binding properties, good flow characteristics and mechanical and chemical stability.

Tissue Factor

Human tissue factor is a 263 amino-acid transmembrane protein containing three domains: (1) a 219-amino acid N-terminal extracellular domain (residues 1-219); (2) a 22-amino acid transmembrane domain (residues 220-242); and (3) a 21-amino acid cytoplasmic C-terminal tail (residues 242-263) ((UniProtKB Identifier Number: P13726). The cytoplasmic tail contains two phosphorylation sites at Ser253 and Ser258, and one S-palmitoylation site at Cys245. Deletion or mutation of the cytoplasmic domain was not found to affect tissue factor coagulation activity. Tissue factor has one S-palmitoylation site in the intracellular domain of the protein at Cys245. The Cys245 is located at the amino acid terminus of the intracellular domain and close to the membrane surface. The tissue factor transmembrane domain is composed of a single-spanning α-helix.

The extracellular domain of tissue factor, composed of two fibronectin type III domains, is connected to the transmembrane domain through a six-amino acid linker. This linker provides conformational flexibility to decouple the tissue factor extracellular domain from its transmembrane and cytoplasmic domains. Each tissue factor fibronectin type III module is composed of two overlapping β sheets with the top sheet domain containing three antiparallel β-strands and the bottom sheet containing four-strands. The β-strands are connected by β-loops between strand BA and BB, BC and BD, and BE and BF, all of which are conserved in conformation in the two modules. There are three short α-helix segments connecting the β-strands. A unique feature of tissue factor is a 17-amino acid β-hairpin between strand β10 and strand β11, which is not a common element of the fibronectin superfamily. The N-terminal domain also contains a 12 amino acid loop between β6F and β7G that is not present in the C-terminal domain and is unique to tissue factor. Such a fibronectin type III domain structure is a feature of the immunoglobulin-like family of protein folds and is conserved among a wide variety of extracellular proteins.

The zymogen FVII is rapidly converted to FVIIa by limited proteolysis once it binds to tissue to form the active tissue factor-FVIIa complex. The FVIIa, which circulates as an enzyme at a concentration of approximately 0.1 nM (1% of plasma FVII), can also bind directly to tissue factor. The allosteric interaction between tissue factor and FVIIa on the tissue factor-FVIIa complex greatly increases the enzymatic activity of FVIIa: an approximate 20- to 100-fold increase in the rate of hydrolysis of small, chromogenic peptidyl substrates, and nearly a million-fold increase in the rate of activation of the natural macromolecular substrates FIX and FX. In concert with allosteric activation of the active site of FVIIa upon binding to tissue factor, the formation of tissue factor-FVIIa complex on phospholipid bilayer (i.e., upon exposure of phosphatidyl-L-serine on membrane surfaces) increases the rate of FIX or FX activation, in a $Ca^{2+}$-dependent manner, an additional 1,000-fold. The roughly million-fold overall increase in FX activation by tissue factor-FVIIa-phospholipid complex relative to free FVIIa is a critical regulatory point for the coagulation cascade.

FVII is a ~50 kDa, single-chain polypeptide consisting of 406 amino acid residues, with an N-terminal γ-carboxyglutamate-rich (GLA) domain, two epidermal growth factor-like domains (EGF1 and EFG2), and a C-terminal serine protease domain. FVII is activated to FVIIa by a specific proteolytic cleavage of the $Ile^{154}$-$Arg^{152}$ bond in the short linker region between the EGF2 and the protease domain. This cleavage results in the light and heavy chains being held together by a single disulfide bond of $Cys^{135}$ and $Cys^{262}$. FVIIa binds phospholipid membrane in a $Ca^{2+}$-dependent manner through its N-terminal GLA-domain. Immediately C-terminal to the GLA domain is an aromatic stack and two EGF domains. The aromatic stack connects the GLA to EGF1 domain which binds a single $Ca^{2+}$ ion. Occupancy of this $Ca^{2+}$-binding site increases FVIIa amidolytic activity and tissue factor association. The catalytic triad consist of $His^{193}$, $Asp^{242}$, and $Ser^{344}$, and binding of a single $Ca^{2+}$ ion within the FVIIa protease domain is critical for its catalytic activity. Proteolytic activation of FVII to FVIIa frees the newly formed amino terminus at $Ile^{153}$ to fold back and be inserted into the activation pocket forming a salt bridge with the carboxylate of $Asp^{343}$ to generate the oxyanion hole. Formation of this salt bridge is critical for FVIIa activity. However, oxyanion hole formation does not occur in free FVIIa upon proteolytic activation. As a result, FVIIa circulates in a zymogen-like state that is poorly recognized by plasma protease inhibitors, allowing it to circulate with a half-life of approximately 90 minutes.

Tissue factor-mediated positioning of the FVIIa active site above the membrane surface is important for FVIIa towards cognate substrates. Free FVIIa adopts a stable, extended structure when bound to the membrane with its active site positioned ~80 Å above the membrane surface. Upon FVIIa binding to tissue factor, the FVa active site is repositioned ~6 Å closer to the membrane. This modulation may aid in a proper alignment of the FVIIa catalytic triad with the target substrate cleavage site. Using GLA-domainless FVIIa, it has been shown that the active site was still positioned a similar distance above the membrane, demonstrating that tissue factor is able to fully support FVIIa active site positioning even in the absence of FVIIa-membrane interaction. Additional data showed that tissue factor supported full FVIIa proteolytic activity as long as the tissue factor extracellular domain was tethered in some way to the membrane surface. However, raising the active site of FVIIa greater than 80 Å above the membrane surface greatly reduced the ability of the tissue factor-FVIIa complex to activate FX but did not diminish tissue factor-FVIIa amidolytic activity.

Alanine scanning mutagenesis has been used to assess the role of specific amino acid side chains in the tissue factor extracellular domain for interaction with FVIIa (Gibbs et al., *Biochemistry* 33 (47): 14003-14010, 1994; Schullek et al., *J Biol Chem* 269 (30): 19399-19403, 1994). Alanine substitution identified a limited number of residue positions at which alanine replacements cause 5- to 10-fold lower affinity for FVIIa binding. Most of these residue side chains were found to be well-exposed to solvent in the crystal structure, concordant with macromolecular ligand interaction. The FVIIa ligand-binding site is located over an extensive region at the boundary between the two modules. In the C-module, residues $Arg^{135}$ and $Phe^{140}$ located on the protruding B-C loop provide an independent contact with FVIIa. $Leu^{133}$ is located at the base of the fingerlike structure and packed into the cleft between the two modules. This provides continuity to a major cluster of important binding residues consisting of $Lys^{20}$, $Thr^{60}$, $Asp^{58}$, and $Ile^{22}$. $Thr^{60}$ is only partially solvent-exposed and may play a local structural role rather than making a significant contact with ligand. The binding site extends onto the concave side of the intermodule angle involving $Glu^{24}$ and $Gln^{110}$, and potentially the more distant residue $Val^{207}$. The binding region extends from $Asp^{58}$ onto a convex surface area formed by $Lys^{48}$, $Lys^{46}$, $Gln^{37}$, $Asp^{44}$, and $Trp^{45}$. $Trp^{45}$ and $Asp^{44}$ do not interact independently with FVIIa, indicating that the mutational effect at the $Trp^{45}$ position may reflect a structural importance of this side chain for the local packing of the adjacent $Asp^{44}$ and $Gln^{37}$ side chain. The interactive area further includes two surface-exposed aromatic residues, $Phe^{76}$ and $Tyr^{78}$, which form part of the hydrophobic cluster in the N-module.

The known physiologic substrates of tissue factor-FVIIa are FVII, FIX, and FX and certain proteinase-activated receptors. Mutational analysis has identified a number of residues that, when mutated, support full FVIIa amidolytic activity towards small peptidyl substrates but are deficient in their ability to support macromolecular substrate (i.e., FVII, FIX, and FX) activation (Ruf et al., *J Biol Chem* 267 (31): 22206-22210, 1992; Ruf et al., *J Biol Chem* 267 (9): 6375-6381, 1992; Huang et al., *J Biol Chem* 271 (36): 21752-21757, 1996; Kirchhofer et al., *Biochemistry* 39 (25): 7380-7387, 2000). The tissue factor loop region at residues 159-165, and residues in or adjacent to this flexible loop have been shown to be critical for the proteolytic activity of the tissue factor-FVIIa complex. This defines the proposed substrate-binding exosite region of tissue factor that is quite distant from the FVIIa active site. A substitution of the glycine residue by a marginally bulkier residue alanine, significantly impairs tissue factor-FVIIa proteolytic activity. This suggests that the flexibility afforded by glycine is critical for the loop of residues 159-165 for tissue factor macromolecular substrate recognition.

The residues $Lys^{165}$ and $Lys^{166}$ have also been demonstrated to be important for substrate recognition and binding. Mutation of either of these residues to alanine results in a significant decrease in the tissue factor co-factor function. $Lys^{165}$ and $Lys^{166}$ face away from each other, with $Lys^{165}$ pointing towards FVIIa in most tissue factor-FVIIa structures, and $Lys^{166}$ pointing into the substrate binding exosite region in the crystal structure. Putative salt bridge formation between $Lys^{165}$ of and $Gla^{35}$ of FVIIa would support the notion that tissue factor interaction with the GLA domain of FVIIa modulates substrate recognition. These results suggest that the C-terminal portion of the tissue factor ectodomain directly interacts with the GLA-domain, the possible adjacent EGF1 domains, of FIX and FX, and that the presence of the FVIIa GLA-domain may modulate these interactions either directly or indirectly.

Anti-Tissue Factor Antibodies and Antigen-Binding Antibody Fragments

In some examples, an anti-tissue factor antibody is a humanized or fully human anti-tissue factor antibody (see, e.g., the anti-tissue factor antibodies described in U.S. Pat. Nos. 7,968,094 and 8,007,795).

In some embodiments, an anti-tissue factor antibody can include a heavy chain variable domain that includes the following set of CDR sequences: a CDR1 including DYNVY (SEQ ID NO: 1); a CDR2 including YIDPYNGITIYDQNFKG (SEQ ID NO: 2); and a CDR3 including DVTTALDF (SEQ ID NO: 3).

In some embodiments, an anti-tissue factor antibody can include a heavy chain variable domain that includes the following set of CDR sequences: a CDR1 including DYNVY (SEQ ID NO: 1); a CDR2 including YIDPYNGITIYDQNLKG (SEQ ID NO: 9); and a CDR3 including DVTTALDF (SEQ ID NO: 3).

```
Exemplary heavy chain variable domain
                                  (SEQ ID NO: 7)
QIQLVQSGGEVKKPGASVRVSCKASGYSFTDYNVYWVRQSPGKGLEWIG
YIDPYNGITIYDQNFKGKATLTVDKSTSTAYMELSSLRSEDTAVYFCAR
DVTTALDFWGQGTTVTVSS Exemplary heavy chain
                                (SEQ ID NO: 127)
QIQLVQSGGEVKKPGASVRVSCKASGYSFTDYNVYWVRQSPGKGLEWIG
YIDPYNGITIYDQNFKGKATLTVDKSTSTAYMELSSLRSEDTAVYFCAR
DVTTALDFWGQGTTVTVSSEFASTKGPSVFPLAPSSKSTSGGTAALGCL
VKDYFPEPVTVSWNSGALTSGVHTFPAVLQSSGLYSLSSVVTVPSSSLG
TQTYICNVNHKPSNTKVDKKVEPKSCDKTHTCPPCPAPELLGGPSVFLF
PPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKG
QPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQK
SLSLSPGK cDNA encoding exemplary heavy chain
                                (SEQ ID NO: 128)
CAGATCCAGCTGGTGCAGAGCGGCGGCGAGGTGAAGAAGCCCGGCGCCA
GCGTGAGGGTGAGCTGCAAGGCCAGCGGCTACAGCTTCACCGACTACAA
CGTGTACTGGGTGAGGCAGAGCCCCGGCAAGGGCCTGGAGTGGATCGGC
TACATCGACCCCTACAACGGCATCACCATCTACGACCAGAACTTCAAGG
GCAAGGCCACCCTGACCGTGGACAAGAGCACCAGCACCGCCTACATGGA
GCTGAGCAGCCTGAGGAGCGAGGACACCGCCGTGTACTTCTGCGCCAGG
GACGTGACCACCGCCCTGGACTTCTGGGGCCAGGGCACCACCGTGACCG
TGAGCAGCGAGTTCGCCAGCACCAAGGGCCCCAGCGTGTTCCCCCTGGC
CCCCAGCAGCAAGAGCACCAGCGGCGGCACCGCCGCCCTGGGCTGCCTG
GTGAAGGACTACTTCCCCGAGCCCGTGACCGTGAGCTGGAACAGCGGCG
CCCTGACCAGCGGCGTGCACACCTTCCCCGCCGTGCTGCAGAGCAGCGG
CCTGTACAGCCTGAGCAGCGTGGTGACCGTGCCCAGCAGCAGCCTGGGC
ACCCAGACCTACATCTGCAACGTGAACCACAAGCCCAGCAACACCAAGG
TGGACAAGAAGGTGGAGCCCAAGAGCTGCGACAAGACCCACACCTGCCC
CCCCTGCCCCGCCCCCGAGCTGCTGGGCGGCCCCAGCGTGTTCCTGTTC
CCCCCCAAGCCCAAGGACACCCTGATGATCAGCAGGACCCCCGAGGTGA
CCTGCGTGGTGGTGGACGTGAGCCACGAGGACCCCGAGGTGAAGTTCAA
CTGGTACGTGGACGGCGTGGAGGTGCACAACGCCAAGACCAAGCCCAGG
GAGGAGCAGTACAACAGCACCTACAGGGTGGTGAGCGTGCTGACCGTGC
TGCACCAGGACTGGCTGAACGGCAAGGAGTACAAGTGCAAGGTGAGCAA
CAAGGCCCTGCCCGCCCCCATCGAGAAGACCATCAGCAAGGCCAAGGGC
CAGCCCAGGGAGCCCCAGGTGTACACCCTGCCCCCCAGCAGGGACGAGC
TGACCAAGAACCAGGTGAGCCTGACCTGCCTGGTGAAGGGCTTCTACCC
CAGCGACATCGCCGTGGAGTGGGAGAGCAACGGCCAGCCCGAGAACAAC
TACAAGACCACCCCCCCCGTGCTGGACAGCGACGGCAGCTTCTTCCTGT
ACAGCAAGCTGACCGTGGACAAGAGCAGGTGGCAGCAGGGCAACGTGTT
CAGCTGCAGCGTGATGCACGAGGCCCTGCACAACCACTACACCCAGAAG
AGCCTGAGCCTGAGCCCCGGCAAGTGA
```

In some embodiments, an anti-tissue factor antibody can include a heavy chain variable domain that includes a sequence that is at least 70% identical (e.g., at least 72%, at least 74%, at least 75%, at least 76%, at least 78%, at least 80%, at least 82%, at least 84%, at least 85%, at least 86%, at least 88%, at least 90%, at least 92%, at least 94%, at least 95%, at least 96%, at least 97%, at least 98%, at least 99%, or 100% identical) to SEQ ID NO: 7.

In some embodiments, an anti-tissue factor antibody can include a heavy chain variable domain that includes a sequence that is at least 70% identical (e.g., at least 72%, at least 74%, at least 75%, at least 76%, at least 78%, at least 80%, at least 82%, at least 84%, at least 85%, at least 86%, at least 88%, at least 90%, at least 92%, at least 94%, at least 95%, at least 96%, at least 97%, at least 98%, at least 99%, or 100% identical) to SEQ ID NO: 127.

In some embodiments, an anti-tissue factor antibody can include a light chain variable domain that includes the following set of CDR sequences: a CDR1 including LASQTIDTWLA (SEQ ID NO: 4); a CDR2 including AATNLAD (SEQ ID NO: 5); and a CDR3 including QQVYSSPFT (SEQ ID NO: 6).

```
Exemplary light chain variable domain
                                         (SEQ ID NO: 8)
DIQMTQSPASLSASVGDRVTITCLASQTIDTWLAWYLQKPGKSPQLLIY
AATNLADGVPSRFSGSGSGTDFSFTISSLQPEDFATYYCQQVYSSPFTF
GQGTKLEIK Exemplary light chain
                                       (SEQ ID NO: 129)
DIQMTQSPASLSASVGRVTITCLASQTIDTWLAWLQKPGKSPQLLIYAA
TNLDGVPSRFSGSGSGTDFSFISSLQPEDFATYYCQQVYSSPFTFGQGT
KLEIKRTVAAPSVFIFPPSDEQLKSGTASVVCLLNNFYPREAKVQWKVD
NALQSGNSQESVTEQDSKDSTYSLSSTLTLSKADYEKHKVYACEVTHQG
LSSPVTKSFNRGEC cDNA encoding an exemplary light chain
                                       (SEQ ID NO: 130)
GACATCCAGATGACCCAGAGCCCCGCCAGCCTGAGCGCCAGCGTGGGCG
ACAGGGTGACCATCACCTGCCTGGCCAGCCAGACCATCGACACCTGGCT
GGCCTGGTACCTGCAGAAGCCCGGCAAGAGCCCCCAGCTGCTGATCTAC
GCCGCCACCAACCTGGCCGACGGCGTGCCCAGCAGGTTCAGCGGCAGCG
GCAGCGGCACCGACTTCAGCTTCAACCATCAGCAGCCTGCAGCCCGAGG
ACTTCGCCACCTACTACTGCCAGCAGGTGTACTAGCAGCCCCTTCACCT
TCGGCCAGGGCACCAAGCTGGAGATCAAGAGGACCGTGGCCGCCCCCAG
CGTGTTCATCTTCCCCCCCAGCGACGAGCAGCTGAAGAGCGGCACCGCC
AGCGTGGTGTGCCTGCTGAACAACTTCTACCCCAGGGAGGCCAAGGTGC
AGTGGAAGGTGGACAACGCCCTGCAGAGCGGCAACAGCCAGGAGAGCGT
GACCGAGCAGGACAGCAAGGACAGCACCTACAGCCTGAGCAGCACCCTG
ACCCTGAGCAAGGCCGACTACGAGAAGCACAAGGTGTACGCCTGCGAGG
TGACCCACCAGGGCCTGAGCAGCCCCGTGACCAAGAGCTTCAACAGGGG
CGAGTGCTGA
```

In some embodiments, an anti-tissue factor antibody can include a light chain variable domain that includes a sequence that is at least 70% identical (e.g., at least 72%, at least 74%, at least 75%, at least 76%, at least 78%, at least 80%, at least 82%, at least 84%, at least 85%, at least 86%, at least 88%, at least 90%, at least 92%, at least 94%, at least 95%, at least 96%, at least 97%, at least 98%, at least 99%, or 100% identical) to SEQ ID NO: 8.

In some embodiments, an anti-tissue factor antibody can include a light chain variable domain that includes a sequence that is at least 70% identical (e.g., at least 72%, at least 74%, at least 75%, at least 76%, at least 78%, at least 80%, at least 82%, at least 84%, at least 85%, at least 86%, at least 88%, at least 90%, at least 92%, at least 94%, at least 95%, at least 96%, at least 97%, at least 98%, at least 99%, or 100% identical) to SEQ ID NO: 129.

Non-limiting examples of anti-tissue factor antibodies can include: a heavy chain variable domain including a sequence that is at least 70% identical (e.g., at least 72%, at least 74%, at least 75%, at least 76%, at least 78%, at least 80%, at least 82%, at least 84%, at least 85%, at least 86%, at least 88%, at least 90%, at least 92%, at least 94%, at least 95%, at least 96%, at least 97%, at least 98%, at least 99%, or 100% identical) to SEQ ID NO: 7, and a light chain variable domain including a sequence that is at least 70% identical (e.g., at least 72%, at least 74%, at least 75%, at least 76%, at least 78%, at least 80%, at least 82%, at least 84%, at least 85%, at least 86%, at least 88%, at least 90%, at least 92%, at least 94%, at least 95%, at least 96%, at least 97%, at least 98%, at least 99%, or 100% identical) to SEQ ID NO: 8.

Non-limiting examples of anti-tissue factor antibodies can include: a heavy chain variable domain including a sequence that is at least 70% identical (e.g., at least 72%, at least 74%, at least 75%, at least 76%, at least 78%, at least 80%, at least 82%, at least 84%, at least 85%, at least 86%, at least 88%, at least 90%, at least 92%, at least 94%, at least 95%, at least 96%, at least 97%, at least 98%, at least 99%, or 100% identical) to SEQ ID NO: 127, and a light chain variable domain including a sequence that is at least 70% identical (e.g., at least 72%, at least 74%, at least 75%, at least 76%, at least 78%, at least 80%, at least 82%, at least 84%, at least 85%, at least 86%, at least 88%, at least 90%, at least 92%, at least 94%, at least 95%, at least 96%, at least 97%, at least 98%, at least 99%, or 100% identical) to SEQ ID NO: 129.

In some embodiments of any of the anti-tissue factor antibodies described herein, the anti-tissue factor antibody binds to tissue factor with a binding constant ($K_D$) of about 0.1 nM to about 1 µM (e.g., about 0.1 nM to about 800 nM, about 0.1 nM to about 750 nM, about 0.1 nM to about 700 nM, about 0.1 nM to about 650 nM, about 0.1 nM to about 600 nM, about 0.1 nM to about 550 nM, about 0.1 nM to about 500 nM, about 0.1 nM to about 450 nM, about 0.1 nM to about 400 nM, about 0.1 nM to about 350 nM, about 0.1 nM to about 300, about 0.1 nM to about 250 nM, about 0.1 nM to about 200 nM, about 0.1 nM to about 150 nM, about 0.1 nM to about 100 nM, about 0.1 nM to about 80 nM, about 0.1 nM to about 60 nM, about 0.1 nM to about 50 nM, about 0.1 nM to about 40 nM, about 0.1 nM to about 25 nm, about 0.1 nM to about 20 nM, about 0.1 nM to about 15 nM, about 0.1 nM to about 10 nM, about 0.1 nM to about 8 nM, about 0.1 nM to about 6 nM, about 0.1 nM to about 5 nM, about 0.1 nM to about 4 nM, about 0.1 nM to about 3 nM, about 0.1 nM to about 2 nM, about 0.1 nM to about 1 nM, about 0.1 nM to about 0.8 nM, about 0.1 nM to about 0.6 nM, about 0.1 nM to about 0.4 nM, about 0.1 nM to about 0.2 nM; about 0.2 nM to about 1 µM, about 0.2 nM to about 800 nM, about 0.2 nM to about 750 nM, about 0.2 nM to about 700 nM, about 0.2 nM to about 650 nM, about 0.2 nM to about 600 nM, about 0.2 nM to about 550 nM, about 0.2 nM to about 500 nM, about 0.2 nM to about 450 nM, about 0.2 nM to about 400 nM, about 0.2 nM to about 350 nM, about 0.2 nM to about 300, about 0.2 nM to about 250 nM, about 0.2 nM to about 200 nM, about 0.2 nM to about 150 nM, about 0.2 nM to about 100 nM, about 0.2 nM to about 80 nM, about 0.2 nM to about 60 nM, about 0.2 nM to about 50 nM, about 0.2 nM to about 40 nM, about 0.2 nM to about 25 nm, about 0.2 nM to about 20 nM, about 0.2 nM to about 15 nM, about 0.2 nM to about 10 nM, about 0.2 nM to about 8 nM, about 0.2 nM to about 6 nM, about 0.2 nM to about 5 nM, about 0.2 nM to about 4 nM, about 0.2 nM to about 3 nM, about 0.2 nM to about 2 nM, about 0.2 nM to about 1 nM, about 0.2 nM to about 0.8 nM, about 0.2 nM to about 0.6 nM, about 0.2 nM to about 0.4 nM, about 0.2 nM to about 0.2 nM, about 0.4 nM to about 1 µM, about 0.4 nM to about 800 nM, about 0.4 nM to about 750 nM, about 0.4 nM to about 700 nM, about 0.4 nM to about 650 nM, about 0.4 nM to about 600 nM, about 0.4 nM to about 550 nM, about 0.4 nM to about 500 nM, about 0.4 nM to about 450 nM, about 0.4 nM to about 400 nM, about 0.4 nM to about 350 nM, about 0.4 nM to about 300, about 0.4 nM to about 250 nM, about 0.4 nM to about 200 nM, about 0.4 nM to about 150 nM, about 0.4 nM to about 100 nM, about 0.4 nM to about 80 nM, about 0.4 nM to about 60 nM, about 0.4 nM to about 50 nM, about 0.4 nM to about 40 nM, about 0.4 nM to about 25 nm, about 0.4 nM to about 20 nM, about 0.4 nM to about 15 nM, about 0.4 nM to about 10 nM, about 0.4 nM to about 8 nM, about 0.4 nM to about 6 nM, about 0.4 nM to about 5 nM, about 0.4 nM to about 4 nM, about 0.4 nM to about 3 nM, about 0.4 nM to about 2 nM, about 0.4 nM to about 1 nM, about 0.4 nM to about 0.8 nM, about 0.4 nM to about 0.6 nM, about 0.5 nM to about 1 µM, about 0.5 nM to about 800 nM, about 0.5 nM to about 750 nM, about 0.5 nM to about 700 nM, about 0.5 nM to about 650 nM, about 0.5 nM to about 600 nM, about 0.5 nM to about 550 nM, about 0.5 nM to about 500 nM, about 0.5 nM to about 450 nM, about 0.5 nM to about 400 nM, about 0.5 nM to about 350 nM, about 0.5 nM to about 300, about 0.5 nM to about 250 nM, about 0.5 nM to about 200 nM, about 0.5 nM to about 150 nM, about 0.5 nM to about 100 nM, about 0.5 nM to about 80 nM, about 0.5 nM to about 60 nM, about 0.5 nM to about 50 nM, about 0.5 nM to about 40 nM, about 0.5 nM to about 25 nm, about 0.5 nM to about 20 nM, about 0.5 nM to about 15 nM, about 0.5 nM to about 10 nM, about 0.5 nM to about 8 nM, about 0.5 nM to about 6 nM, about 0.5 nM to about 5 nM, about 0.5 nM to about 4 nM, about 0.5 nM to about 3 nM, about 0.5 nM to about 2 nM, about 0.5 nM to about 1 nM, about 0.5 nM to about 0.8 nM, about 0.5 nM to about 0.6 nM, about 0.6 nM to about 1 µM, about 0.6 nM to about 800 nM, about 0.6 nM to about 750 nM, about 0.6 nM to about 700 nM, about 0.6 nM to about 650 nM, about 0.6 nM to about 600 nM, about 0.6 nM to about 550 nM, about 0.6 nM to about 500 nM, about 0.6 nM to about 450 nM, about 0.6 nM to about 400 nM, about 0.6 nM to about 350 nM, about 0.6 nM to about 300, about 0.6 nM to about 250 nM, about 0.6 nM to about 200 nM, about 0.6 nM to about 150 nM, about 0.6 nM to about 100 nM, about 0.6 nM to about 80 nM, about 0.6 nM to about 60 nM, about 0.6 nM to about 50 nM, about 0.6 nM to about 40 nM, about 0.6 nM to about 25 nm, about 0.6 nM to about 20 nM, about 0.6 nM to about 15 nM, about 0.6 nM to about 10 nM, about 0.6 nM to about 8 nM, about 0.6 nM to about 6 nM, about 0.6 nM to about 5 nM, about 0.6 nM to about 4 nM, about 0.6 nM to about 3 nM, about 0.6 nM to about 2 nM, about 0.6 nM to about 1 nM, about 0.6 nM to about 0.8 nM, about 1 nM to about 1 µM, about 1 nM to about 800 nM, about 1 nM to about 750 nM, about 1 nM to about 700 nM, about 1 nM to about 650 nM, about 1 nM to about 600 nM, about 1 nM to about 550 nM, about 1 nM to about 500 nM, about 1 nM to about 450 nM, about 1 nM to about 400 nM, about 1 nM to about 350 nM, about 1 nM to about 300, about 1 nM to about 250 nM, about 1 nM to about 200 nM, about 1 nM to about 150 nM, about 1 nM to about 100 nM, about 1 nM to about 80 nM, about 1 nM to about 60 nM, about 1 nM to about 50 nM, about 1 nM to about 40 nM, about 1 nM to about 25 nm, about 1 nM to about 20 nM, about 1 nM to about 15 nM, about 1 nM to about 10 nM, about 1 nM to about 8 nM, about 1 nM to about 6 nM, about 1 nM to about 5 nM, about 1 nM to about 4 nM, about 1 nM to about 3 nM, about 1 nM to about 2 nM, about 2 nM to about 1 µM, about 2 nM to about 800 nM, about 2 nM to about 750 nM, about 2 nM to about 700 nM, about 2 nM to about 650 nM, about 2 nM to about 600 nM, about 2 nM to about 550 nM, about 2 nM to about 500 nM, about 2 nM to about 450 nM, about 2 nM to about 400 nM, about 2 nM to about 350 nM, about 2 nM to about 300, about 2 nM to about 250 nM, about 2 nM to about 200 nM, about 2 nM to about 150 nM, about 2 nM to about 100 nM, about 2 nM to about 80 nM, about 2 nM to about 60 nM, about 2 nM to about 50 nM, about 2 nM to about 40 nM, about 2 nM to about 25 nm, about 2 nM to about 20 nM, about 2 nM to about 15 nM, about 2 nM to about 10 nM, about 2 nM to about 8 nM, about 2 nM to about 6 nM, about 2 nM to about 5 nM, about 2 nM to about 4 nM, about 2 nM to about 3 nM, about 5 nM to about 1 µM, about 5 nM to about 800 nM, about 5 nM to about 750 nM, about 5 nM to about 700 nM, about 5 nM to about 650 nM, about 5 nM to about 600 nM, about 5 nM to about 550 nM, about 5 nM to about 500 nM, about 5 nM to about 450 nM, about 5 nM to about 400 nM, about 5 nM to about 350 nM, about 5 nM to about 300, about 5 nM to about 250 nM, about 5 nM to about 200 nM, about 5 nM to about 150 nM, about 5 nM to about 100 nM, about 5 nM to about 80 nM, about 5 nM to about 60 nM, about 5 nM to about 50 nM, about 5 nM to about 40 nM, about 5 nM to about 25 nm, about 5 nM to about 20 nM, about 5 nM to about 15 nM, about 5 nM to about 10 nM, about 5 nM to about 8 nM, about 5 nM to about 6 nM, about 10 nM to about 1 µM, about 10 nM to about 800 nM, about 10 nM to about 750 nM, about 10 nM to about 700 nM, about 10 nM to about 650 nM, about 10 nM to about 600 nM, about 10 nM to about 550 nM, about 10 nM to about 500 nM, about 10 nM to about 450 nM, about 10 nM to about 400 nM, about 10 nM to about 350 nM, about 10 nM to about 300, about 10 nM to about 250 nM, about 10 nM to about 200 nM, about 10 nM to about 150 nM, about 10 nM to about 100 nM, about 10 nM to about 80 nM, about 10 nM to about 60 nM, about 10 nM to about 50 nM, about 10 nM to about 40 nM, about 10 nM to about 25 nm, about 10 nM to about 20 nM, about 10 nM to about 15 nM, about 20 nM to about 1 µM, about 20 nM to about 800 nM, about 20 nM to about 750 nM, about 20 nM to about 700 nM, about 20 nM to about 650 nM, about 20 nM to about 600 nM, about 20 nM to about 550 nM, about 20 nM to about 500 nM, about 20 nM to about 450 nM, about 20 nM to about 400 nM, about 20 nM to about 350 nM, about 20 nM to about 300, about 20 nM to about 250 nM, about 20 nM to about 200 nM, about 20 nM to about 150 nM, about 20 nM to about 100 nM, about 20 nM to about 80 nM, about 20 nM to about 60 nM, about 20 nM to about 50 nM, about 20 nM to about 40 nM, about 50 nM to about 1 µM, about 50 nM to about 800 nM, about 50 nM to about 750 nM, about 50 nM to about 700 nM, about 50 nM to about 650 nM, about 50 nM to about 600 nM, about 50 nM to about 550 nM, about 50 nM to about 500 nM, about 50 nM to about 450 nM, about 50 nM to about 400 nM, about 50 nM to about 350 nM, about 50 nM to about 300, about 50 nM to about 250 nM, about 50 nM to about 200 nM, about 50 nM to about 150 nM, about 50 nM to about 100 nM, about 50 nM to about 80 nM, about 100 nM to about 1 µM, about 100 nM to about 800 nM, about 100 nM to about 750 nM, about 100 nM to about 700 nM, about 100 nM to about 650 nM, about 100 nM to about 600 nM, about 100 nM to about 550 nM, about 100 nM to about 500 nM, about 100 nM to about 450 nM, about 100 nM to about 400 nM, about 100 nM to about 350 nM, about 100 nM to about 300, about 100 nM to about 250 nM, about 100 nM to about 200 nM, about 100 nM to about 150 nM, about 250 nM to about 1 µM, about 250 nM to about 800 nM, about 250 nM to about 750 nM, about 250 nM to about 700 nM, about 250 nM to about 650 nM, about 250 nM to about 600 nM, about 250 nM to about 550 nM, about 250 nM to about 500 nM, about 250 nM to about 450 nM, about 250 nM to about 400 nM, about 250 nM to about 350 nM, about 250 nM to about 300, about 400 nM to about 1 µM, about 400 nM to about 800 nM, about 400 nM to about 750 nM, about 400 nM to about 700 nM, about 400 nM to about 650 nM, about 400 nM to about 600 nM, about 400 nM to about 550 nM, about 400 nM to about 500 nM, about 400 nM to about 450 nM, about 500 nM to about 1 µM, about 500 nM to about 800 nM, about 500 nM to about 750 nM, about 500 nM to about 700 nM, about 500 nM to about 650 nM, about 500 nM to about 600 nM, about 500 nM to about 550 nM, about 600 nM to about 1 µM, about 600 nM to about 800 nM, about 600 nM to about 750 nM, about 600 nM to about 700 nM, about 600 nM to about 650 nM, about 750 nM to about 1 µM, about 750 nM to about 800 nM, about 800 nM to about 1 µM, or about 950 nM to about 1 µM).

In some embodiments, the anti-tissue factor antibody can be an IgG (e.g., IgG1, IgG2, IgG3, and IgG4) (e.g., human IgG1, human IgG2, human IgG3, and human IgG4), an IgA (e.g., a human IgA), an IgE (e.g., a human IgE), or an IgM (e.g., a human IgM).

In some embodiments, the anti-tissue factor antibody is a human or humanized IgG1 antibody. In some embodiments, the anti-tissue factor antibody is a human or humanized IgG4 antibody.

In some embodiments, the anti-tissue factor antibody can include an IgG1 Fc region. In some embodiments, the anti-tissue factor antibody can include a heavy chain constant domain comprising a sequence that is at least 70% identical (e.g., at least 75% identical, at least 80% identical, at least 85% identical, at least 90% identical, at least 95% identical, at least 99% identical, or 100% identical) to SEQ ID NO: 102 or SEQ ID NO: 103.

Heavy Chain Constant Region
(SEQ ID NO: 102)
EFASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDK
KVEPKSCDKTHTCPPCPAPELLGGPSVFLFPPKPKDTLMISRTPEVTCV
VVDVSHEDPEVKFNWYVDGVEVHNAKTKPREEQYNSTYRVVSVLTVLHQ
DWLNGKEYKCKVSNKALPAPIEKTISKAKGQPREPQVYTLPPSRDELTK
NQVSLTCLVKGFYPSDIAVEWESNGQPENNYKTTPPVLDSDGSFFLYSK
LTVDKSRWQQGNVFSCSVMHEALHNHYTQKSLSLSPGK Heavy Chain Constant Region
(SEQ ID NO: 103)
EFASTKGPSVFPLAPCSRSTSESTAALGCLVKDYFPEPVTVSWNSGALT
SGVHTFPAVLQSSGLYSLSSVVTVPSSSLGTKTYTCNVDHKPSNTKVDK
RVESKYGPPCPSCPAPEFLGGPSVFLFPPKPKDTLMISRTPEVTCVVVD
VSQEDPEVQFNWYVDGVEVHNAKTKPREEQFNSTYRVVSVLTVLHQDWL
NGKEYKCKVSNKGLPSSIEKTISKAKGQPREPQVYTLPPSQEEMTKNQV
SLTCLVKGFYPSDIAVEWESNGQPENNYKTTPPVLDSDGSFFLYSRLTV
DKSRWQEGNVFSCSVMHEALHNHYTQKSLSLSLGK Affinity Chromatography Resin Provided herein is an affinity chromatography resin comprising an anti-tissue factor antibody or antigen-binding fragment thereof comprising a heavy chain variable domain comprising CDRs of SEQ ID NOs: 1, 2 or 9, and 3, and a light chain variable domain comprising CDRs of SEQ ID NOs: 4, 5, and 6, attached to a base resin. In some embodiments, the heavy chain variable domain comprises a sequence that is at least 90% identical to SEQ ID NO: 7, and the light chain variable domain comprises a sequence that is at least 90% identical to SEQ ID NO: 8. In some embodiments, the heavy chain variable domain comprises SEQ ID NO: 7, and the light chain variable domain comprises SEQ ID NO: 8.

In some embodiments, the base resin is Sepharose. In some embodiments, the base resin is Capto or agarose. In some embodiments, the base resin (or matrix or stationary phase) is a natural polymer including but not limited to cellulose, agarose or chitosan; a synthetic polymer including but not limited to acrylomido and vinyl co-polymers, acrylic polymers or poly-metacrylate, poly(styrene-divinyl-benzene) co-polymers; or an inorganic material, including but not limited to hydroxyapatite, silica, glass, or zirconia. In some embodiments, the anti-tissue factor antibody or antigen-binding fragment thereof is non-covalently attached to the base resin. In some embodiments, the anti-tissue factor antibody or antigen-binding fragment thereof is covalently attached to the base resin. In some embodiments, the anti-tissue factor antibody or antigen-binding fragment thereof is covalently attached to the base resin through the formation of a disulfide bond between a cysteine in the anti-tissue factor antibody or antigen-binding fragment thereof and a chemical group on the base resin. In some embodiments, the anti-tissue factor antibody or antigen-binding fragment thereof is covalently attached to the base resin through the formation of a covalent bond between a free amine of the anti-tissue factor antibody or antigen-binding domain and a chemical group on the base resin. In some embodiments, the base resin is CNBr-activated or N-hydroxysuccinimide (NHS)-activated solid support material. In some embodiments, the covalent bond is represented by Formula I below:

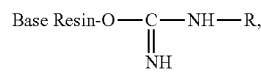

wherein, R represents the anti-tissue factor antibody or antigen-binding fragment thereof.

Figure 7:
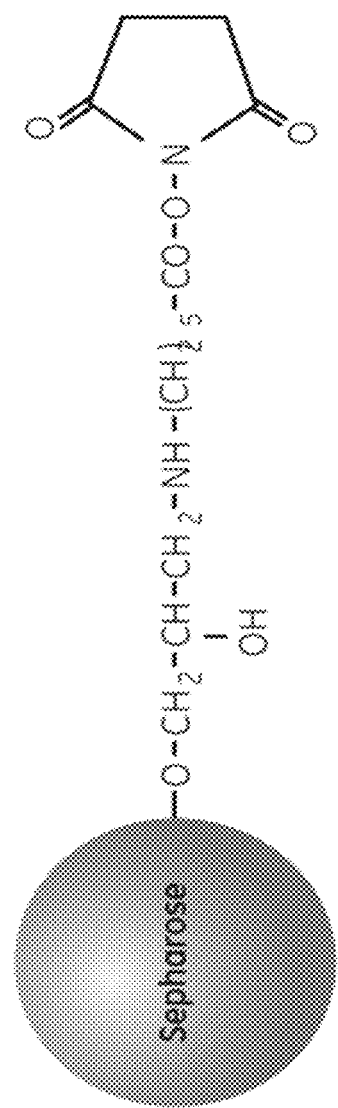
FIG. 7 shows a partial structure of NHS-activated Sepharose High Performance resin bearing activated spacer arms.
Figure 8:
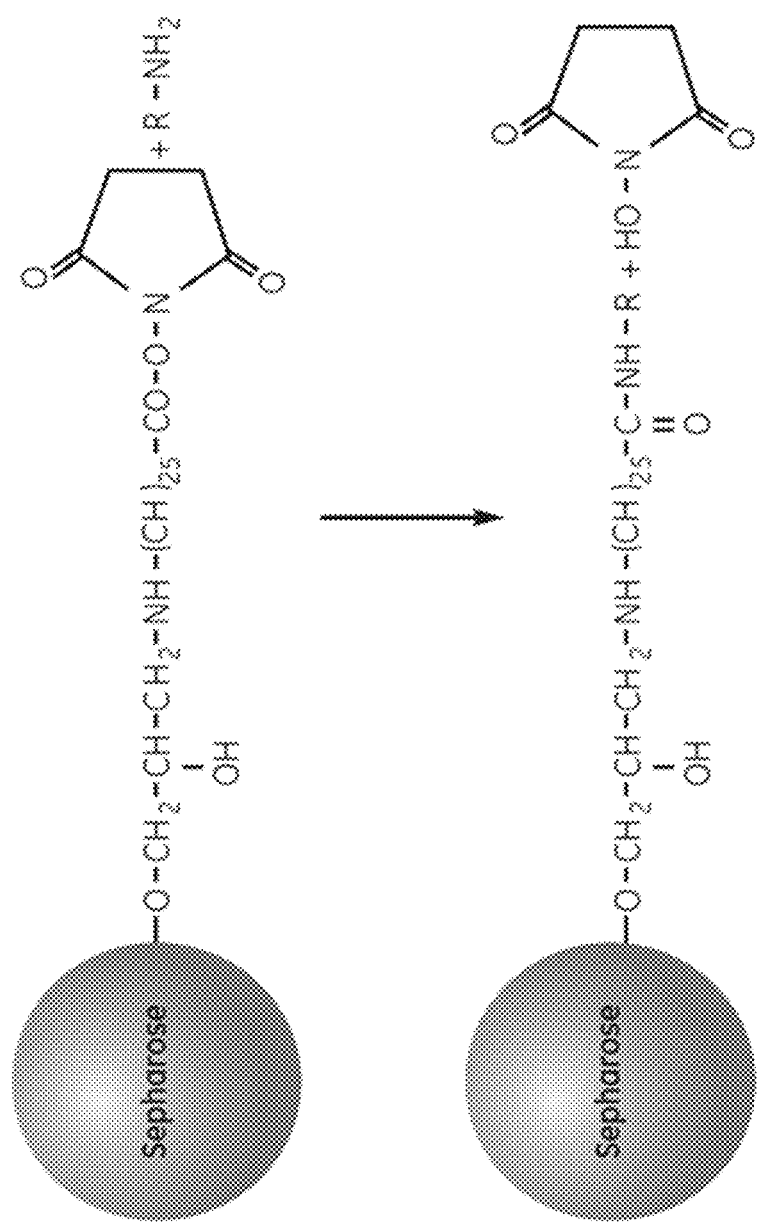
FIG. 8 shows coupling of a protein ligand containing primary amino group (R—NH$_2$) to NHS-activated Sepharose resin.

In some embodiments, NHS-activated Sepharose is designed for the covalent coupling of ligands (often antigens or antibodies) containing primary amino groups (the most common form of attachment). In some embodiments, the matrix of NHS-activated Sepharose is based on highly cross-linked agarose beads with 10-atom spacer arms (6-aminohexanoic acid) attached by epichlorohydrin and activated by N-hydroxysuccinimide (FIG. 7). In some embodiments, the matrix of NHS-activated Sepharose 4 Fast Flow is based on highly cross-linked agarose beads with 14-atom spacer arms. In some embodiments, nonspecific adsorption of proteins to NHS-activated Sepharose (which can reduce binding capacity of the target protein) is negligible due to the excellent hydrophilic properties of the base matrix. In some embodiments, the matrix is stable at high pH to allow stringent washing procedures (subject to the pH stability of the coupled ligand). In some embodiments, ligands containing amino groups such as proteins couple rapidly and spontaneously by nucleophilic attack at the ester linkage to give a very stable amide linkage (FIG. 8). In some embodiments, the amide bond is stable up to pH 13.0, making NHS-activated Sepharose suitable for applications that require conditions at high pH.

In some embodiments, CNBr-activated Sepharose is a pre-activated resin for coupling antibodies or other large proteins containing —NH$_2$ groups to the Sepharose media, by the cyanogen bromide method, without an intermediate spacer arm. In some embodiments, the CNBr-activated Sepharose is used for immobilizing antibodies or other large proteins containing —NH$_2$ groups by coupling them to the matrix of CNBr-activated Sepharose. In some embodiments, CNBr-activated Sepharose 4 Fast Flow is a bead-formed, highly cross-linked pre-activated matrix produced by reacting Sepharose 4 Fast Flow with cyanogen bromide (CNBr). In some embodiments, CNBr-activated Sepharose 4 Fast Flow is based on antigen-antibody reactions with immobilized monoclonal antibodies as ligands.

In some embodiments, a kit comprises an affinity chromatography resin of any one of the affinity chromatography resins described herein.

Antibody (e.g., monoclonal or polyclonal) based immunoaffinity chromatography is a widely used method/process to purify specific antigens or antigen-containing proteins (e.g., human tissue factor-containing proteins) using affinity chromatography resin comprising an antibody or antigen-binding fragment attached to the base resin. For the immunoaffinity method, an antibody (e.g., monoclonal) or a mixture of antibodies (e.g., polyclonal) is immobilized (e.g., coupled) covalently onto solid support materials (e.g., base resin) such as CNBr-activated Sepharose, NHS-Sepharose, and other related beads/resins suitable for protein coupling or immobilization. In some embodiments, a base resin is any material to which a biospecific ligand is covalently attached. In some embodiments, a base resin is any material to which a biospecific ligand is non-covalently attached. In some embodiments, examples of the base resin used in affinity chromatography include agarose, Capto, cellulose, ceramics, dextran, polystyrene, polyacrylamide, silica, latex, controlled pore glass, and synthetic/organic polymers. Useful base resins can have properties such as high surface-area to volume ratio, chemical groups that are easily modified for covalent attachment of ligands, minimal nonspecific binding properties, good flow characteristics and mechanical and chemical stability.

In some embodiments, the base resin is a sulfhydryl coupling resin, wherein an antibody or antigen-binding fragment thereof is covalently attached to the base resin through free sulfhydryls and an iodoacetyl group on the base resin. In some embodiments, the base resin is an amine coupling resin, wherein the amine coupling resin has reactive aldehyde groups that react with primary amines to form Schiff's bases which are then reduced with a suitable reducing agent (e.g., sodium cyanoborohydride) to form a covalent bond between an antibody or antigen-binding fragment thereof and the base resin. In some embodiments, the base resin is an NHS-activated resin, wherein an antibody or antigen-binding fragment binds to the resin through a reactive NHS group and primary amines forming a covalent bond. In some embodiments, the base resin is an immobilized protein A, immobilized protein B, or immobilized protein A/G, wherein the base resin binds the constant domain of an antibody or antigen-binding fragment thereof ensuring the antigen binding domain is facing away from the base resin for optimal binding.

In some embodiments, a chromatography column is used for affinity chromatography wherein the chromatography column comprises an affinity chromatography resin selected from the group consisting of: CNBr-activated Sepharose, NHS-Sepharose, agarose, Capto, cellulose, ceramics, dextran, polystyrene, polyacrylamide, silica, latex, controlled pore glass, and synthetic/organic polymers.

Methods of Purifying a Tissue Factor-Containing Protein

Provided herein are methods of purifying a tissue factor-containing protein comprising the use of any of the affinity chromatography resins described herein. In some embodiments, the method comprises: loading the affinity chromatography resin with a liquid comprising the tissue factor-containing protein; washing the affinity chromatography resin using one or more wash buffer(s); and eluting the tissue factor-containing protein using an elution buffer. In some embodiments, the liquid comprising the tissue factor-containing protein is a clarified liquid culture medium. In some embodiments, the liquid comprising the tissue factor-containing protein comprises a cell lysate.

In some embodiments, the one or more wash buffer(s) are: (i) a first wash buffer comprising phosphate buffered saline; and (ii) a second wash buffer comprising about 0.01 M to about 0.2 M citrate and having a pH of about 4.5 to about 5.5. In some embodiments, the first wash buffer is phosphate buffered saline and the second wash buffer is 0.1 M citrate, pH 5.0. In some embodiments, the elution buffer comprises 0.01 M to about 0.2 M acetate and has a pH of about 2.5 to about 3.5. In some embodiments, the elution buffer comprises 0.1 M acetate and has a pH of about 2.9.

In some embodiments, the second wash buffer comprises about 0.01 M to about 0.2 M (e.g., about 0.01 M to about 0.18 M, about 0.01 M to about 0.16 M, about 0.01 M to about 0.14 M, about 0.01 M to about 0.12 M, about 0.01 M to about 0.1 M, about 0.01 M to about 0.08 M, about 0.01 M to about 0.06 M, about 0.01 M to about 0.05 M, about 0.01 M to about 0.04 M, about 0.01 M to about 0.03 M, about 0.01 M to about 0.02 M, about 0.02 M to about 0.2 M, about 0.02 M to about 0.18 M, about 0.02 M to about 0.16 M, about 0.02 M to about 0.14 M, about 0.02 M to about 0.12 M, about 0.02 M to about 0.1 M, about 0.02 M to about 0.08 M, about 0.02 M to about 0.06 M, about 0.02 M to about 0.05 M, about 0.02 M to about 0.04 M, about 0.02 M to about 0.03 M, about 0.03 M to about 0.2 M, about 0.03 M to about 0.18 M, about 0.03 M to about 0.16 M, about 0.03 M to about 0.14 M, about 0.03 M to about 0.12 M, about 0.03 M to about 0.1 M, about 0.03 M to about 0.08 M, about 0.03 M to about 0.06 M, about 0.03 M to about 0.05 M, about 0.03 M to about 0.04 M, about 0.04 M to about 0.2 M, about 0.04 M to about 0.18 M, about 0.04 M to about 0.16 M, about 0.04 M to about 0.14 M, about 0.04 M to about 0.12 M, about 0.04 M to about 0.1 M, about 0.04 M to about 0.08 M, about 0.04 M to about 0.06 M, about 0.04 M to about 0.05 M, about 0.05 M to about 0.2 M, about 0.05 M to about 0.18 M, about 0.05 M to about 0.16 M, about 0.05 M to about 0.14 M, about 0.05 M to about 0.12 M, about 0.05 M to about 0.1 M, about 0.05 M to about 0.08 M, about 0.05 M to about 0.06 M, about 0.06 M to about 0.2 M, about 0.06 M to about 0.18 M, about 0.06 M to about 0.16 M, about 0.06 M to about 0.14 M, about 0.06 M to about 0.12 M, about 0.06 M to about 0.1 M, about 0.06 M to about 0.08 M, about 0.08 M to about 0.2 M, about 0.08 M to about 0.18 M, about 0.08 M to about 0.16 M, about 0.08 M to about 0.14 M, about 0.08 M to about 0.12 M, about 0.08 M to about 0.1 M, about 0.1 M to about 0.2 M, about 0.1 M to about 0.18 M, about 0.1 M to about 0.16 M, about 0.1 M to about 0.14 M, about 0.1 M to about 0.12 M, about 0.12 M to about 0.2 M, about 0.12 M to about 0.18 M, about 0.12 M to about 0.16 M, about 0.12 M to about 0.14 M, about 0.14 M to about 0.2 M, about 0.14 M to about 0.18 M, about 0.14 M to about 0.16 M, about 0.16 M to about 0.2 M, about 0.16 M to about 0.18 M, or about 0.18 M to about 0.2 M) citrate.

In some embodiments, the second wash buffer has a pH of about 4.5 to about 5.5 (e.g., about 4.5 to about 5.4, about 4.5 to about 5.3, about 4.5 to about 5.2, about 4.5 to about 5.1, about 4.5 to about 5.0, about 4.5 to about 4.9, about 4.5 to about 4.8, about 4.5 to about 4.7, about 4.5 to about 4.6, about 4.6 to about 5.5, about 4.6 to about 5.4, about 4.6 to about 5.3, about 4.6 to about 5.2, about 4.6 to about 5.1, about 4.6 to about 5.0, about 4.6 to about 4.9, about 4.6 to about 4.8, about 4.6 to about 4.7, about 4.7 to about 5.5, about 4.7 to about 5.4, about 4.7 to about 5.3, about 4.7 to about 5.2, about 4.7 to about 5.1, about 4.7 to about 5.0, about 4.7 to about 4.9, about 4.7 to about 4.8, about 4.8 to about 5.5, about 4.8 to about 5.4, about 4.8 to about 5.3, about 4.8 to about 5.2, about 4.8 to about 5.1, about 4.8 to about 5.0, about 4.8 to about 4.9, about 4.9 to about 5.5, about 4.9 to about 5.4, about 4.9 to about 5.3, about 4.9 to about 5.2, about 4.9 to about 5.1, about 4.9 to about 5.0, about 5.0 to about 5.5, about 5.0 to about 5.4, about 5.0 to about 5.3, about 5.0 to about 5.2, about 5.0 to about 5.1, about 5.1 to about 5.5, about 5.1 to about 5.4, about 5.1 to about 5.3, about 5.1 to about 5.2, about 5.2 to about 5.5, about 5.2 to about 5.4, about 5.2 to about 5.3, about 5.3 to about 5.5, about 5.3 to about 5.4, or about 5.4 to about 5.5).

In some embodiments, the elution buffer comprises about 0.01 M to about 0.2 M (e.g., about 0.01 M to about 0.18 M, about 0.01 M to about 0.16 M, about 0.01 M to about 0.14 M, about 0.01 M to about 0.12 M, about 0.01 M to about 0.1 M, about 0.01 M to about 0.08 M, about 0.01 M to about 0.06 M, about 0.01 M to about 0.05 M, about 0.01 M to about 0.04 M, about 0.01 M to about 0.03 M, about 0.01 M to about 0.02 M, about 0.02 M to about 0.2 M, about 0.02 M to about 0.18 M, about 0.02 M to about 0.16 M, about 0.02 M to about 0.14 M, about 0.02 M to about 0.12 M, about 0.02 M to about 0.1 M, about 0.02 M to about 0.08 M, about 0.02 M to about 0.06 M, about 0.02 M to about 0.05 M, about 0.02 M to about 0.04 M, about 0.02 M to about 0.03 M, about 0.03 M to about 0.2 M, about 0.03 M to about 0.18 M, about 0.03 M to about 0.16 M, about 0.03 M to about 0.14 M, about 0.03 M to about 0.12 M, about 0.03 M to about 0.1 M, about 0.03 M to about 0.08 M, about 0.03 M to about 0.06 M, about 0.03 M to about 0.05 M, about 0.03 M to about 0.04 M, about 0.04 M to about 0.2 M, about 0.04 M to about 0.18 M, about 0.04 M to about 0.16 M, about 0.04 M to about 0.14 M, about 0.04 M to about 0.12 M, about 0.04 M to about 0.1 M, about 0.04 M to about 0.08 M, about 0.04 M to about 0.06 M, about 0.04 M to about 0.05 M, about 0.05 M to about 0.2 M, about 0.05 M to about 0.18 M, about 0.05 M to about 0.16 M, about 0.05 M to about 0.14 M, about 0.05 M to about 0.12 M, about 0.05 M to about 0.1 M, about 0.05 M to about 0.08 M, about 0.05 M to about 0.06 M, about 0.06 M to about 0.2 M, about 0.06 M to about 0.18 M, about 0.06 M to about 0.16 M, about 0.06 M to about 0.14 M, about 0.06 M to about 0.12 M, about 0.06 M to about 0.1 M, about 0.06 M to about 0.08 M, about 0.08 M to about 0.2 M, about 0.08 M to about 0.18 M, about 0.08 M to about 0.16 M, about 0.08 M to about 0.14 M, about 0.08 M to about 0.12 M, about 0.08 M to about 0.1 M, about 0.1 M to about 0.2 M, about 0.1 M to about 0.18 M, about 0.1 M to about 0.16 M, about 0.1 M to about 0.14 M, about 0.1 M to about 0.12 M, about 0.12 M to about 0.2 M, about 0.12 M to about 0.18 M, about 0.12 M to about 0.16 M, about 0.12 M to about 0.14 M, about 0.14 M to about 0.2 M, about 0.14 M to about 0.18 M, about 0.14 M to about 0.16 M, about 0.16 M to about 0.2 M, about 0.16 M to about 0.18 M, or about 0.18 M to about 0.2 M) acetate.

In some embodiments, the elution buffer has a pH of about 2.5 to about 3.5 (e.g., about 2.5 to about 3.4, about 2.5 to about 3.3, about 2.5 to about 3.2, about 2.5 to about 3.1, about 2.5 to about 3.0, about 2.5 to about 2.9, about 2.5 to about 2.8, about 2.5 to about 2.7, about 2.5 to about 2.6, about 2.6 to about 3.5, about 2.6 to about 3.4, about 2.6 to about 3.3, about 2.6 to about 3.2, about 2.6 to about 3.1, about 2.6 to about 3.0, about 2.6 to about 2.9, about 2.6 to about 2.8, about 2.6 to about 2.7, about 2.7 to about 3.5, about 2.7 to about 3.4, about 2.7 to about 3.3, about 2.7 to about 3.2, about 2.7 to about 3.1, about 2.7 to about 3.0, about 2.7 to about 2.9, about 2.7 to about 2.8, about 2.8 to about 3.5, about 2.8 to about 3.4, about 2.8 to about 3.3, about 2.8 to about 3.2, about 2.8 to about 3.1, about 2.8 to about 3.0, about 2.8 to about 2.9, about 2.9 to about 3.5, about 2.9 to about 3.4, about 2.9 to about 3.3, about 2.9 to about 3.2, about 2.9 to about 3.1, about 2.9 to about 3.0, about 3.0 to about 3.5, about 3.0 to about 3.4, about 3.0 to about 3.3, about 3.0 to about 3.2, about 3.0 to about 3.1, about 3.1 to about 3.5, about 3.1 to about 3.4, about 3.1 to about 3.3, about 3.1 to about 3.2, about 3.2 to about 3.5, about 3.2 to about 3.4, about 3.2 to about 3.3, about 3.3 to about 3.5, about 3.3 to about 3.4, or about 3.4 to about 3.5).

Methods of Manufacturing a Tissue Factor-Containing Protein

Provided herein are methods of manufacturing a tissue factor-containing protein comprising: (i) purifying a tissue factor-containing protein using any of the methods described herein; and (ii) performing one or more addition unit operations on an eluate obtained from step (i). Non-limiting examples of unit operations that can be performed in a process for manufacturing a tissue factor-containing protein include: capturing the protein, purifying the protein, polishing the protein, inactivating viruses, adjusting the ionic concentration and/or pH of a fluid containing the protein, and filtering a fluid containing the protein. A non-limiting method of manufacturing a tissue factor-containing protein is depicted in FIG. 1.

In some embodiments, the one or more additional unit operations includes, in sequential order: performing low pH viral inactivation, performing depth filtration, performing polishing chromatography, performing nanofiltration, and performing ultrafiltration and diafiltration (UF/DF).

Also provided herein is a tissue factor-containing protein manufactured by any of the methods described herein. In some embodiments, a pharmaceutical composition comprises the manufactured tissue factor-containing protein.

Single-Chain Chimeric Polypeptides

Non-limiting examples of tissue factor-containing proteins are single-chain chimeric polypeptides that include: (i) a first target-binding domain (e.g., any of the target-binding domains described herein or known in the art), (ii) a soluble tissue factor domain (e.g., any of the exemplary soluble tissue factor domains described herein or known in the art), and (iii) as second target-binding domain (e.g., any of the target-binding domains described herein or known in the art).

In some embodiments of any of the single-chain chimeric polypeptides described herein, the first target-binding domain (e.g., any of the exemplary target-binding domains described herein or known in the art) and the soluble tissue factor domain (e.g., any of the exemplary soluble tissue factor domains described herein) directly abut each other. In some embodiments of any of the single-chain chimeric polypeptides described herein, the single-chain chimeric polypeptide further comprises a linker sequence (e.g., any of the exemplary linker sequences described herein or known in the art) between the first target-binding domain (e.g., any of the exemplary target-binding domains described herein or known in the art) and the soluble tissue factor domain (e.g., any of the exemplary soluble tissue factor domains described herein). In some embodiments of any of the single-chain chimeric polypeptides described herein, the soluble tissue factor domain (e.g., any of the exemplary soluble tissue factor domains described herein) and the second target-binding domain (e.g., any of the exemplary target-binding domains described herein or known in the art) directly abut each other. In some embodiments of any of the single-chain chimeric polypeptides described herein, the single-chain chimeric polypeptide further comprises a linker sequence (e.g., any of the exemplary linker sequences described herein or known in the art) between the soluble tissue factor domain (e.g., any of the exemplary soluble tissue factor domains described herein) and the second target-binding domain (e.g., any of the exemplary target-binding domains described herein or known in the art).

In some embodiments of any of the single-chain chimeric polypeptides described herein, the first target-binding domain (e.g., any of the exemplary target-binding domains described herein or known in the art) and the second target-binding domain (e.g., any of the exemplary target-binding domains described herein or known in the art) directly abut each other. In some embodiments of any of the single-chain chimeric polypeptides described herein, the single-chain chimeric polypeptide further comprises a linker sequence (e.g., any of the exemplary linker sequences described herein or known in the art) between the first target-binding domain (e.g., any of the exemplary target-binding domains described herein or known in the art) and the second target-binding domain (e.g., any of the exemplary target-binding domains described herein or known in the art). In some embodiments of any of the single-chain chimeric polypeptides described herein, the second target-binding domain (e.g., any of the exemplary target-binding domains described herein or known in the art) and the soluble tissue factor domain (e.g., any of the exemplary soluble tissue factor domains described herein) directly abut each other. In some embodiments of any of the single-chain chimeric polypeptides described herein, the single-chain chimeric polypeptide further comprises a linker sequence (e.g., any of the exemplary linker sequences described herein or known in the art) between the second target-binding domain (e.g., any of the exemplary target-binding domains described herein or known in the art) and the soluble tissue factor domain (e.g., any of the exemplary soluble tissue factor domains described herein or known in the art).

Some embodiments of any of the single-chain chimeric polypeptides described herein can further include one or more (e.g., two, three, four, five, six, seven, eight, nine, or ten) additional target-binding domains (e.g., any of the exemplary target-binding domains described herein or known in the art) at its N- and/or C-terminus.

In some embodiments, the single-chain chimeric polypeptides can include one or more (e.g., two, three, four, five, six, seven, eight, nine, or ten) additional target-binding domains (e.g., any of the exemplary target-binding domains described herein or known in the art) at its N-terminus. In some embodiments, one of the one or more additional target-binding domains (e.g., any of the exemplary target-binding domains described herein or known in the art) at the N-terminus of the single-chain chimeric polypeptide can directly abut the first target-binding domain (e.g., any of the exemplary target-binding domains described herein or known in the art), the second target-binding domain (e.g., any of the exemplary target-binding domains described herein or known in the art), or the soluble tissue factor domain (e.g., any of the exemplary soluble tissue factor domains described herein). In some embodiments, the single-chain chimeric polypeptide further includes a linker sequence (e.g., any of the exemplary linker sequences described herein or known in the art) between one of the at least one additional target-binding domains (e.g., any of the exemplary target-binding domains described herein or known in the art) at the N-terminus of the single-chain chimeric polypeptide and the first target-binding domain (e.g., any of the exemplary target-binding domains described herein or known in the art), the second target-binding domain (e.g., any of the exemplary target-binding domains described herein or known in the art), or the soluble tissue factor domain (e.g., any of the exemplary soluble tissue factor domains described herein).

In some embodiments of any of the single-chain chimeric polypeptides described herein, the single-chain chimeric polypeptide includes one or more (e.g., two, three, four, five, six, seven, eight, nine, or ten) additional target-binding domains (e.g., any of the exemplary target-binding domains described herein or known in the art) at its C-terminus. In some embodiments, one of the one or more additional target-binding domains (e.g., any of the exemplary target-binding domains described herein or known in the art) at the C-terminus of the single-chain chimeric polypeptide directly abuts the first target-binding domain (e.g., any of the exemplary target-binding domains described herein or known in the art), the second target-binding domain (e.g., any of the exemplary target-binding domains described herein or known in the art), or the soluble tissue factor domain (e.g., any of the exemplary soluble tissue factor domains described herein or known in the art). In some embodiments, the single-chain chimeric polypeptide further comprises a linker sequence (e.g., any of the exemplary linker sequences described herein or known in the art) between one of the at least one additional target-binding domains (e.g., any of the exemplary target-binding domains described herein or known in the art) at the C-terminus of the single-chain chimeric polypeptide and the first target-binding domain (e.g., any of the exemplary target-binding domains described herein or known in the art), the second target-binding domain (e.g., any of the exemplary target-binding domains described herein or known in the art), or the soluble tissue factor domain (e.g., any of the exemplary soluble tissue factor domains described herein).

In some embodiments of any of the single-chain chimeric polypeptides described herein, the single-chain chimeric polypeptide comprises one or more (e.g., two, three, four, five, six, seven, eight, nine, or ten) additional target binding domains (e.g., any of the exemplary target-binding domains described herein or known in the art) at its N-terminus and its C-terminus. In some embodiments, one of the one or more additional antigen binding domains (e.g., any of the exemplary target-binding domains described herein or known in the art) at the N-terminus of the single-chain chimeric polypeptide directly abuts the first target-binding domain (e.g., any of the exemplary target-binding domains described herein or known in the art), the second target-binding domain (e.g., any of the exemplary target-binding domains described herein or known in the art), or the soluble tissue factor domain (e.g., any of the exemplary soluble tissue factor domains described herein). In some embodiments, the single-chain chimeric polypeptide further includes a linker sequence (e.g., any of the exemplary linker sequences described herein or known in the art) between one of the one or more additional antigen-binding domains (e.g., any of the exemplary target-binding domains described herein or known in the art) at the N-terminus and the first target-binding domain (e.g., any of the exemplary target-binding domains described herein or known in the art), the second target-binding domain (e.g., any of the exemplary target-binding domains described herein or known in the art), or the soluble tissue factor domain (e.g., any of the exemplary soluble tissue factor domains). In some embodiments, one of the one or more additional antigen binding domains (e.g., any of the exemplary target-binding domains described herein or known in the art) at the C-terminus directly abuts the first target-binding domain (e.g., any of the exemplary target-binding domains described herein or known in the art), the second target-binding domain (e.g., any of the exemplary target-binding domains described herein or known in the art), or the soluble tissue factor domain (e.g., any of the exemplary soluble tissue factor domains). In some embodiments, the single-chain chimeric polypeptide further includes a linker sequence (e.g., any of the exemplary linker sequences described herein or known in the art) between one of the one or more additional antigen-binding domains (e.g., any of the exemplary target-binding domains described herein or known in the art) at the C-terminus and the first target-binding domain (e.g., any of the exemplary target-binding domains described herein or known in the art), the second target-binding domain (e.g., any of the exemplary target-binding domains described herein or known in the art), or the soluble tissue factor domain (e.g., any of the exemplary soluble tissue factor domains described herein).

In some embodiments of any of the single-chain chimeric polypeptides described herein, two or more (e.g., three, four, five, six, seven, eight, nine, or ten) of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) bind specifically to the same antigen. In some embodiments, two or more (e.g., three, four, five, six, seven, eight, nine, or ten) of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) bind specifically to the same epitope. In some embodiments, two or more (e.g., three, four, five, six, seven, eight, nine, or ten) of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) include the same amino acid sequence.

In some embodiments of any of the single-chain chimeric polypeptides described herein, the first target-binding domain (e.g., any of the exemplary target-binding domains described herein or known in the art), the second target-binding domain (e.g., any of the exemplary target-binding domains described herein or known in the art), and the one or more (e.g., two, three, four, five, six, seven, eight, nine, or ten) additional target-binding domains (e.g., any of the exemplary target-binding domains described herein or known in the art) each bind specifically to the same antigen. In some embodiments, the first target-binding domain (e.g., any of the exemplary target-binding domains described herein or known in the art), the second target-binding domain (e.g., any of the exemplary target-binding domains described herein or known in the art), and the one or more (e.g., two, three, four, five, six, seven, eight, nine, or ten) additional target-binding domains (e.g., any of the exemplary target-binding domains described herein or known in the art) each bind specifically to the same epitope. In some embodiments, the first target-binding domain, the second target-binding domain, and the one or more (e.g., two, three, four, five, six, seven, eight, nine, or ten) additional target-binding domains each comprise the same amino acid sequence.

In some embodiments of any of the single-chain chimeric polypeptides described herein, the first target-binding domain (e.g., any of the exemplary target-binding domains described herein or known in the art), the second target-binding domain (e.g., any of the exemplary target-binding domains described herein or known in the art), and the one or more (e.g., two, three, four, five, six, seven, eight, nine, or ten) additional target-binding domains (e.g., any of the exemplary target-binding domains described herein or known in the art) bind specifically to different antigens.

In some embodiments of any of the single-chain chimeric polypeptides, one or more of the first target-binding domain, the second target-binding domain, and the one or more target-binding domains is an antigen-binding domain (e.g., any of the exemplary antigen-binding domains described herein or known in the art). In some embodiments of any of the single-chain chimeric polypeptides described herein, the first target-binding domain, the second target-binding domain, and the one or more additional target-binding domains are each an antigen-binding domain (e.g., any of the exemplary antigen-binding domains described herein or known in the art). In some embodiments, the antigen-binding domain can include a scFv or a single domain antibody.

In some embodiments of any of the single-chain chimeric polypeptides described herein, one or more (e.g., two, three, four, five, six, seven, eight, nine, or ten) of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

In some embodiments of any of the single-chain chimeric polypeptides described herein, one or more of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) is a soluble interleukin or cytokine protein. Non-limiting examples of soluble interleukin proteins and soluble cytokine proteins include: IL-1, IL-2, IL-3, IL-7, IL-8, IL-10, IL-12, IL-15, IL-17, IL-18, IL-21, PDGF-DD, and SCF.

In some embodiments of any of the single-chain chimeric polypeptides described herein, one or more of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) is a soluble interleukin or cytokine receptor. Non-limiting examples of soluble interleukin receptors and soluble cytokine receptors include: a soluble TGF-β receptor II (TGF-βRII), a soluble TGF-βRIII, a soluble NKG2D, a soluble NKP30, a soluble NKp44, a soluble NKp46, a soluble DNAM-1, a scMHCI, a scMHCII, a scTCR, a soluble CD155, a soluble CD122, a soluble CD3, or a soluble CD28.

In some embodiments of any of the single-chain chimeric polypeptides described herein, the first target-binding domain (e.g., any of the target-binding domains described herein), the second target-binding domain (e.g., any of the target-binding domains described herein), and the one or more additional target-binding domains (e.g., any of the target-binding domains described herein) can each, independently, bind specifically to a target selected from the group of: CD16a, CD33, CD20, CD19, CD22, CD123, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKP30, a ligand for a scMHCI, a ligand for a scMHCII, a ligand for a scTCR, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD122.

In some embodiments of any of the single-chain chimeric polypeptides described herein, one or more of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) is a soluble interleukin or cytokine protein. In some embodiments of any of the multi-chain chimeric polypeptides described herein, the soluble interleukin or cytokine protein is selected from the group of: IL-1, IL-2, IL-3, IL-7, IL-8, IL-10, IL-12, IL-15, IL-17, IL-18, IL-21, PDGF-DD, and SCF.

In some embodiments of any of the single-chain chimeric polypeptides described herein, one or more of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) is a soluble interleukin or cytokine receptor. In some embodiments of any of the multi-chain chimeric polypeptides described herein, the soluble receptor is a soluble TGF-β receptor II (TGF-βRII) a soluble TGF-βRIII, a soluble receptor for TNFα, a soluble receptor for IL-4, or a soluble receptor for IL-10.

In some embodiments, a single-chain chimeric polypeptide has a nucleic acid sequence or an amino acid sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to SEQ ID NOs: 22-29.

Soluble Tissue Factor Domain

In some embodiments of any of the polypeptides, compositions, or methods described herein, the soluble tissue factor domain can be a wildtype tissue factor polypeptide lacking the signal sequence, the transmembrane domain, and the intracellular domain. In some examples, the soluble tissue factor domain can be a tissue factor mutant, wherein a wildtype tissue factor polypeptide lacking the signal sequence, the transmembrane domain, and the intracellular domain, and has been further modified at selected amino acids. In some examples, the soluble tissue factor domain can be a soluble human tissue factor domain. In some examples, the soluble tissue factor domain can be a soluble mouse tissue factor domain. In some examples, the soluble tissue factor domain can be a soluble rat tissue factor domain. Non-limiting examples of soluble human tissue factor domains, a mouse soluble tissue factor domain, a rat soluble tissue factor domain, and mutant soluble tissue factor domains are shown below.

```
Exemplary Soluble Human Tissue Factor Domain
                                         (SEQ ID NO: 10)
SGTTNTVAAYNLTWKSTNFKTILEWEPKPVNQVYTVQISTKSGDWKSKC
FYTTDTECDLTDEIVKDVKQTYLARVFSYPAGNVESTGSAGEPLYENSP
EFTPYLETNLGQPTIQSFEQVGTKVNVTVEDERTLVRRNNTFLSLRDVF
GKDLIYTLYYWKSSSSGKKTAKTNTNEFLIDVDKGENYCFSVQAVIPSR
TVNRKSTDSPVECMGQEKGEFRE Exemplary Nucleic Acid Encoding Soluble Human
Tissue Factor Domain
                                         (SEQ ID NO: 11)
AGCGGCACAACCAACACAGTCGCTGCCTATAACCTCACTTGGAAGAGCA
CCAACTTCAAAACCATCCTCGAATGGGAACCCAAACCCGTTAACCAAGT
TTACACCGTGCAGATCAGCACCAAGTCCGGCGACTGGAAGTCCAAATGT
TTCTATACCACCGACACCGAGTGCGATCTCACCGATGAGATCGTGAAAG
ATGTGAAACAGACCTACCTCGCCCGGGTGTTTAGCTACCCCGCCGGCAA
TGTGGAGAGCACTGGTTCCGCTGGCGAGCCTTTATACGAGAACAGCCCC
GAATTTACCCCTTACCTCGAGACCAATTTAGGACAGCCCACCATCCAAA
GCTTTGAGCAAGTTGGCACAAAGGTGAATGTGACAGTGGAGGACGAGCG
GACTTTAGTGCGGCGGAACAACACCTTTCTCAGCCTCCGGGATGTGTTC
GGCAAAGATTTAATCTACACACTGTATTACTGGAAGTCCTCTTCCTCCG
GCAAGAAGACAGCTAAAACCAACACAAACGAGTTTTTAATCGACGTGGA
TAAAGGCGAAAACTACTGTTTCAGCGTGCAAGCTGTGATCCCCTCCCGG
ACCGTGAATAGGAAAAGCACCGATAGCCCCGTTGAGTGCATGGGCCAAG
AAAAGGGCGAGTTCCGGGAG Exemplary Soluble Mouse Tissue Factor Domain
                                         (SEQ ID NO: 12)
agipekafnltwistdfktilewqpkptnytytvqisdrsrnwknkcfs
ttdtecdltdeivkdvtwayeakvlsvprinsvhgdgdqlvihgeeppf
tnapkflpyrdtnlgqpviqqfeqdgrklnvvvkdsltlvrkngtfltl
rqvfgkdlgyiityrkgsstgkktnitntnefsidveegvsycffvqam
ifsrktnqnspgsstvcteqwksflge Exemplary Soluble Rat Tissue Factor Domain
                                         (SEQ ID NO: 13)
agtppgkafnltwistdfktilewqpkptnytytvqisdrsrnwkykct
gttdtecdltdeivkdvnwtyearvlsvpwinsthgketlfgthgeepp
ftnarkflpyrdtkigqpviqkyeqggtklkvtvkdsftlvrkngtflt
lrqvfgndlgyiltyrkdsstgrktntthtneflidvekgvsycffaqa
vifsrktnhkspesitkcteqwksvlge Exemplary Mutant Soluble Human Tissue Factor
Domain
                                         (SEQ ID NO: 14)
SGTTNTVAAYNLTWKSTNFATALEWEPKPVNQVYTVQISTKSGDWKSKC
FYTTDTECALTDEIVKDVKQTYLARVFSYPAGNVESTGSAGEPLYENSP
EFTPYLETNLGQPTIQSFEQVGTKVNVTVEDERTLVARNNTALSLRDVF
GKDLIYTLYYWKSSSSGKKTAKTNTNEFLIDVDKGENYCFSVQAVIPSR
TVNRKSTDSPVECMGQEKGEFRE
```

-continued
Exemplary Mutant Soluble Human Tissue Factor
Domain (SEQ ID NO: 15)
SGTTNTVAAYNLTWKSTNFATALEWEPKPVNQVYTVQISTKSGDAKSKC
FYTTDTECALTDEIVKDVKQTYLARVFSYPAGNVESTGSAGEPLAENSP
EFTPYLETNLGQPTIQSFEQVGTKVNVTVEDERTLVARNNTALSLRDVF
GKDLIYTLYYWKSSSSGKKTAKTNTNEFLIDVDKGENYCFSVQAVIPSR
TVNRKSTDSPVECMGQEKGEFRE In some embodiments, a soluble tissue factor domain can include a sequence that is at least 70% identical, at least 72% identical, at least 74% identical, at least 76% identical, at least 78% identical, at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 10, 12, 13, 14, or 15. In some embodiments, a soluble tissue factor domain can include a sequence of SEQ ID NO: 10, 12, 13, 14, or 15, with one to twenty amino acids (e.g., 2, 3, 4, 5, 6, 7, 8, 9, 10, 11, 12, 13, 14, 15, 16, 17, 18, 19, or 20) amino acids removed from its N-terminus and/or one to twenty amino acids (e.g., 2, 3, 4, 5, 6, 7, 8, 9, 10, 11, 12, 13, 14, 15, 16, 17, 18, 19, or 20) amino acids removed from its C-terminus.

As can be appreciated in the art, one skilled in the art would understand that mutation of amino acids that are conserved between different mammalian species is more likely to decrease the activity and/or structural stability of the protein, while mutation of amino acids that are not conserved between different mammalian species is less likely to decrease the activity and/or structural stability of the protein.

In some examples of any of the multi-chain chimeric polypeptides described herein, the soluble tissue factor domain is not capable of binding to Factor VIIa. In some examples of any of the multi-chain chimeric polypeptides described herein, the soluble tissue factor domain does not convert inactive Factor X into Factor Xa. In some embodiments of any of the multi-chain chimeric polypeptides described herein, the multi-chain chimeric polypeptide does not stimulate blood coagulation in a mammal.

In some examples, the soluble tissue factor domain can be a soluble human tissue factor domain. In some embodiments, the soluble tissue factor domain can be a soluble mouse tissue factor domain. In some embodiments, the soluble tissue factor domain can be a soluble rat tissue factor domain.

In some examples, the soluble tissue factor domain does not include one or more (e.g., two, three, four, five, six, or seven) of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the mutant soluble tissue factor possesses the amino acid sequence of SEQ ID NO: 14 or SEQ ID NO: 15.

In some examples, the soluble tissue factor domain can be encoded by a nucleic acid including a sequence that is at least 70% identical, at least 72% identical, at least 74% identical, at least 76% identical, at least 78% identical, at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 11.

In some embodiments, the soluble tissue factor domain can have a total length of about 20 amino acids to about 220 amino acids, about 20 amino acids to about 215 amino acids, about 20 amino acids to about 210 amino acids, about 20 amino acids to about 205 amino acids, about 20 amino acids to about 200 amino acids, about 20 amino acids to about 195 amino acids, about 20 amino acids to about 190 amino acids, about 20 amino acids to about 185 amino acids, about 20 amino acids to about 180 amino acids, about 20 amino acids to about 175 amino acids, about 20 amino acids to about 170 amino acids, about 20 amino acids to about 165 amino acids, about 20 amino acids to about 160 amino acids, about 20 amino acids to about 155 amino acids, about 20 amino acids to about 150 amino acids, about 20 amino acids to about 145 amino acids, about 20 amino acids to about 140 amino acids, about 20 amino acids to about 135 amino acids, about 20 amino acids to about 130 amino acids, about 20 amino acids to about 125 amino acids, about 20 amino acids to about 120 amino acids, about 20 amino acids to about 115 amino acids, about 20 amino acids to about 110 amino acids, about 20 amino acids to about 105 amino acids, about 20 amino acids to about 100 amino acids, about 20 amino acids to about 95 amino acids, about 20 amino acids to about 90 amino acids, about 20 amino acids to about 85 amino acids, about 20 amino acids to about 80 amino acids, about 20 amino acids to about 75 amino acids, about 20 amino acids to about 70 amino acids, about 20 amino acids to about 60 amino acids, about 20 amino acids to about 50 amino acids, about 20 amino acids to about 40 amino acids, about 20 amino acids to about 30 amino acids.

Linker Sequences

In some embodiments, the linker sequence can be a flexible linker sequence. Non-limiting examples of linker sequences that can be used are described in Klein et al., Protein Engineering, Design & Selection 27 (10): 325-330, 2014; Priyanka et al., Protein Sci. 22 (2): 153-167, 2013. In some examples, the linker sequence is a synthetic linker sequence.

In some embodiments of any of the single-chain chimeric polypeptides described herein can include one, two, three, four, five, six, seven, eight, nine, or ten linker sequence(s) (e.g., the same or different linker sequences, e.g., any of the exemplary linker sequences described herein or known in the art). In some embodiments of any of the single-chain chimeric polypeptides described herein can include one, two, three, four, five, six, seven, eight, nine, or ten linker sequence(s) (e.g., the same or different linker sequences, e.g., any of the exemplary linker sequences described herein or known in the art).

In some embodiments of any of the multi-chain chimeric polypeptides described herein, the first chimeric polypeptide can include one, two, three, four, five, six, seven, eight, nine, or ten linker sequence(s) (e.g., the same or different linker sequences, e.g., any of the exemplary linker sequences described herein or known in the art). In some embodiments of any of the multi-chain chimeric polypeptides described herein, the second chimeric polypeptide can include one, two, three, four, five, six, seven, eight, nine, or ten linker sequence(s) (e.g., the same or different linker sequences, e.g., any of the exemplary linker sequences described herein or known in the art).

In some embodiments, a linker sequence can have a total length of 1 amino acid to about 100 amino acids, 1 amino acid to about 90 amino acids, 1 amino acid to about 80 amino acids, 1 amino acid to about 70 amino acids, 1 amino acid to about 60 amino acids, 1 amino acid to about 50 amino acids, 1 amino acid to about 45 amino acids, 1 amino acid to about 40 amino acids, 1 amino acid to about 35 amino acids, 1 amino acid to about 30 amino acids, 1 amino acid to about 25 amino acids, 1 amino acid to about 24 amino acids, 1 amino acid to about 22 amino acids, 1 amino acid to about 20 amino acids, 1 amino acid to about 18 amino acids, 1 amino acid to about 16 amino acids, 1 amino acid to about 14 amino acids, 1 amino acid to about 12 amino acids, 1 amino acid to about 10 amino acids, 1 amino acid to about 8 amino acids, 1 amino acid to about 6 amino acids, 1 amino acid to about 4 amino acids.

In some embodiments, the linker is rich in glycine (Gly or G) residues. In some embodiments, the linker is rich in serine (Ser or S) residues. In some embodiments, the linker is rich in glycine and serine residues. In some embodiments, the linker has one or more glycine-serine residue pairs (GS), e.g., 1, 2, 3, 4, 5, 6, 7, 8, 9, or 10 or more GS pairs. In some embodiments, the linker has one or more Gly-Gly-Gly-Ser (GGGS) (SEQ ID NO: 16) sequences, e.g., 1, 2, 3, 4, 5, 6, 7, 8, 9, or 10 or more GGGS (SEQ ID NO: 16) sequences. In some embodiments, the linker has one or more Gly-Gly-Gly-Gly-Ser (GGGGS) (SEQ ID NO: 17) sequences, e.g., 1, 2, 3, 4, 5, 6, 7, 8, 9, or 10 or more GGGGS (SEQ ID NO: 17) sequences. In some embodiments, the linker has one or more Gly-Gly-Ser-Gly (GGSG) (SEQ ID NO: 18) sequences, e.g., 1, 2, 3, 4, 5, 6, 7, 8, 9, or 10 or more GGSG (SEQ ID NO: 18) sequences.

In some embodiments, the linker sequence can comprise or consist of GGGGSGGGGSGGGGS (SEQ ID NO: 19). In some embodiments, the linker sequence can be encoded by a nucleic acid comprising or consisting of: GGCGGTG-GAGGATCCGGAGGAGGTGGCTCCGGCGGCGGAG-GATCT (SEQ ID NO: 20). In some embodiments, the linker sequence can comprise or consist of: GGGSGGGS (SEQ ID NO: 21).

Target-Binding Domains

In some embodiments of any of the single- or multi-chain chimeric polypeptides described herein, the first target-binding domain, the second target-binding domain, and/or the additional one or more target-binding domains can be an antigen-binding domain (e.g., any of the exemplary antigen-binding domains described herein or known in the art), a soluble interleukin or cytokine protein (e.g., any of the exemplary soluble interleukin proteins or soluble cytokine proteins described herein), and a soluble interleukin or cytokine receptor (e.g., any of the exemplary soluble interleukin receptors or soluble cytokine receptors described herein).

In some embodiments of any of the single- or multi-chain chimeric polypeptides described herein, the first target-binding domain, the second target-binding domain, and/or the one or more additional target-binding domains can each independent have a total number of amino acids of about 5 amino acids to about 1000 amino acids, about 5 amino acids to about 950 amino acids, about 5 amino acids to about 900 amino acids, about 5 amino acids to about 850 amino acids, about 5 amino acids to about 800 amino acids, about 5 amino acids to about 750 amino acids, about 5 amino acids to about 700 amino acids, about 5 amino acids to about 650 amino acids, about 5 amino acids to about 600 amino acids, about 5 amino acids to about 550 amino acids, about 5 amino acids to about 500 amino acids, about 5 amino acids to about 450 amino acids, about 5 amino acids to about 400 amino acids, about 5 amino acids to about 350 amino acids, about 5 amino acids to about 300 amino acids, about 5 amino acids to about 280 amino acids, about 5 amino acids to about 260 amino acids, about 5 amino acids to about 240 amino acids, about 5 amino acids to about 220 amino acids, about 5 amino acids to about 200 amino acids, about 5 amino acids to about 195 amino acids, about 5 amino acids to about 190 amino acids, about 5 amino acids to about 185 amino acids, about 5 amino acids to about 180 amino acids, about 5 amino acids to about 175 amino acids, about 5 amino acids to about 170 amino acids, about 5 amino acids to about 165 amino acids, about 5 amino acids to about 160 amino acids, about 5 amino acids to about 155 amino acids, about 5 amino acids to about 150 amino acids, about 5 amino acids to about 145 amino acids, about 5 amino acids to about 140 amino acids, about 5 amino acids to about 135 amino acids, about 5 amino acids to about 130 amino acids, about 5 amino acids to about 125 amino acids, about 5 amino acids to about 120 amino acids, about 5 amino acids to about 115 amino acids, about 5 amino acids to about 110 amino acids, about 5 amino acids to about 105 amino acids, about 5 amino acids to about 100 amino acids, about 5 amino acids to about 95 amino acids, about 5 amino acids to about 90 amino acids, about 5 amino acids to about 85 amino acids, about 5 amino acids to about 80 amino acids, about 5 amino acids to about 75 amino acids, about 5 amino acids to about 70 amino acids, about 5 amino acids to about 65 amino acids, about 5 amino acids to about 60 amino acids, about 5 amino acids to about 55 amino acids, about 5 amino acids to about 50 amino acids, about 5 amino acids to about 45 amino acids, about 5 amino acids to about 40 amino acids, about 5 amino acids to about 35 amino acids, about 5 amino acids to about 30 amino acids, about 5 amino acids to about 25 amino acids, about 5 amino acids to about 20 amino acids, about 5 amino acids to about 15 amino acids, about 5 amino acids to about 10 amino acids, Any of the target-binding domains described herein can bind to its target with a dissociation equilibrium constant ($K_D$) of less than $1\times10^{-7}$ M, less than $1\times10^{-8}$ M, less than $1\times10^{-9}$ M, less than $1\times10^{-10}$ M, less than $1\times10^{-11}$ M, less than $1\times10^{-12}$ M, or less than $1\times10^{-13}$ M. In some embodiments, the antigen-binding protein construct provided herein can bind to an identifying antigen with a $K_D$ of about $1\times10^{-3}$ M to about $1\times10^{-5}$ M, about $1\times10^{-4}$ M to about $1\times10^{-6}$ M, about $1\times10^{-5}$ M to about $1\times10^{-7}$ M, about $1\times10^{-6}$ M to about $1\times10^{-8}$ M, about $1\times10^{-7}$ M to about $1\times10^{-9}$ M, about $1\times10^{-8}$ M to about $1\times10^{-10}$ M, or about $1\times10^{-9}$ M to about $1\times10^{-11}$ M (inclusive).

Any of the target-binding domains described herein can bind to its target with a $K_D$ of between about 1 pM to about 30 nM (e.g., about 1 pM to about 25 nM, about 1 pM to about 20 nM, about 1 pM to about 15 nM, about 1 pM to about 10 nM, about 1 pM to about 5 nM, about 1 pM to about 2 nM, about 1 pM to about 1 nM, about 1 pM to about 950 pM, about 1 pM to about 900 pM, about 1 pM to about 850 pM, about 1 pM to about 800 pM, about 1 pM to about 750 pM, about 1 pM to about 700 pM, about 1 pM to about 650 pM, about 1 pM to about 600 pM, about 1 pM to about 550 pM, about 1 pM to about 500 pM, about 1 pM to about 450 pM, about 1 pM to about 400 pM, about 1 pM to about 350 pM, about 1 pM to about 300 pM, about 1 pM to about 250 pM, about 1 pM to about 200 pM, about 1 pM to about 150 pM, about 1 pM to about 100 pM, about 1 pM to about 90 pM, about 1 pM to about 80 pM, about 1 pM to about 70 pM, about 1 pM to about 60 pM, about 1 pM to about 50 pM, about 1 pM to about 40 pM, about 1 pM to about 30 pM, about 1 pM to about 20 pM, about 1 pM to about 10 pM, about 1 pM to about 5 pM, about 1 pM to about 4 pM, about 1 pM to about 3 pM, about 1 pM to about 2 pM).

Any of the target-binding domains described herein can bind to its target with a $K_D$ of between about 1 nM to about 10 nM (e.g., about 1 nM to about 9 nM, about 1 nM to about 8 nM, about 1 nM to about 7 nM, about 1 nM to about 6 nM, about 1 nM to about 5 nM, about 1 nM to about 4 nM, about 1 nM to about 3 nM, about 1 nM to about 2 nM, about 2 nM to about 10 nM, about 2 nM to about 9 nM, about 2 nM to about 8 nM, about 2 nM to about 7 nM, about 2 nM to about 6 nM, about 2 nM to about 5 nM, about 2 nM to about 4 nM, about 2 nM to about 3 nM, about 3 nM to about 10 nM, about 3 nM to about 9 nM, about 3 nM to about 8 nM, about 3 nM to about 7 nM, about 3 nM to about 6 nM, about 3 nM to about 5 nM, about 3 nM to about 4 nM, about 4 nM to about 10 nM, about 4 nM to about 9 nM, about 4 nM to about 8 nM, about 4 nM to about 7 nM, about 4 nM to about 6 nM, about 4 nM to about 5 nM, about 5 nM to about 10 nM, about 5 nM to about 9 nM, about 5 nM to about 8 nM, about 5 nM to about 7 nM, about 5 nM to about 6 nM, about 6 nM to about 10 nM, about 6 nM to about 9 nM, about 6 nM to about 8 nM, about 6 nM to about 7 nM, about 7 nM to about 10 nM, about 7 nM to about 9 nM, about 7 nM to about 8 nM, about 8 nM to about 10 nM, about 8 nM to about 9 nM, and about 9 nM to about 10 nM).

A variety of different methods known in the art can be used to determine the $K_D$ values of any of the antigen-binding protein constructs described herein (e.g., an electrophoretic mobility shift assay, a filter binding assay, surface plasmon resonance, and a biomolecular binding kinetics assay, etc.).

Antigen-Binding Domains

In some embodiments of any of the single-chain or multi-chain chimeric polypeptides described herein, the first target-binding domain and the second target-binding domain bind specifically to the same antigen. In some embodiments of these single-chain or multi-chain chimeric polypeptides, the first target-binding domain and the second target-binding domain bind specifically to the same epitope. In some embodiments of these single-chain or multi-chain chimeric polypeptides, the first target-binding domain and the second target-binding domain include the same amino acid sequence.

In some embodiments of any of the single-chain or multi-chain chimeric polypeptides described herein, the first target-binding domain and the second target-binding domain bind specifically to different antigens.

In some embodiments of any of the single-chain or multi-chain chimeric polypeptides described herein, one or both of the first target-binding domain and the second target-binding domain is an antigen-binding domain. In some embodiments of any of the single-chain or multi-chain chimeric polypeptides described herein, the first target-binding domain and the second target-binding domain are each antigen-binding domains. In some embodiments of any of the single-chain or multi-chain chimeric polypeptides described herein, the antigen-binding domain includes or is a scFv or a single domain antibody (e.g., a VHH or a VNAR domain).

In some examples, an antigen-binding domain (e.g., any of the antigen-binding domains described herein) can bind specifically to any one of CD16a (see, e.g., those described in U.S. Pat. No. 9,035,026), CD28 (see, e.g., those described in U.S. Pat. No. 7,723,482), CD3 (see, e.g., those described in U.S. Pat. No. 9,226,962), CD33 (see, e.g., those described in U.S. Pat. No. 8,759,494), CD20 (see, e.g., those described in WO 2014/026054), CD19 (see, e.g., those described in U.S. Pat. No. 9,701,758), CD22 (see, e.g., those described in WO 2003/104425), CD123 (see, e.g., those described in WO 2014/130635), IL-1R (see, e.g., those described in U.S. Pat. No. 8,741,604), IL-1 (see, e.g., those described in WO 2014/095808), VEGF (see, e.g., those described in U.S. Pat. No. 9,090,684), IL-6R (see, e.g., those described in U.S. Pat. No. 7,482,436), IL-4 (see, e.g., those described in U.S. Patent Application Publication No. 2012/0171197), IL-10 (see, e.g., those described in U.S. Patent Application Publication No. 2016/0340413), PDL-1 (see, e.g., those described in Drees et al., *Protein Express. Purif.* 94:60-66, 2014), TIGIT (see, e.g., those described in U.S. Patent Application Publication No. 2017/0198042), PD-1 (see, e.g., those described in U.S. Pat. No. 7,488,802), TIM3 (see, e.g., those described in U.S. Pat. No. 8,552,156), CTLA4 (see, e.g., those described in WO 2012/120125), MICA (see, e.g., those described in WO 2016/154585), MICB (see, e.g., those described in U.S. Pat. No. 8,753,640), IL-6 (see, e.g., those described in Gejima et al., *Human Antibodies* 11 (4): 121-129, 2002), IL-8 (see, e.g., those described in U.S. Pat. No. 6,117,980), TNFα (see, e.g., those described in Geng et al., *Immunol. Res.* 62 (3): 377-385, 2015), CD26 (see, e.g., those described in WO 2017/189526), CD36 (see, e.g., those described in U.S. Patent Application Publication No. 2015/0259429), ULBP2 (see, e.g., those described in U.S. Pat. No. 9,273,136), CD30 (see, e.g., those described in Homach et al., *Scand. J. Immunol.* 48 (5): 497-501, 1998), CD200 (see, e.g., those described in U.S. Pat. No. 9,085,623), IGF-1R (see, e.g., those described in U.S. Patent Application Publication No. 2017/0051063), MUC4AC (see, e.g., those described in WO 2012/170470), MUC5AC (see, e.g., those described in U.S. Pat. No. 9,238,084), Trop-2 (see, e.g., those described in WO 2013/068946), CMET (see, e.g., those described in Edwardraja et al., *Biotechnol. Bioeng.* 106 (3): 367-375, 2010), EGFR (see, e.g., those described in Akbari et al., *Protein Expr. Purif.* 127:8-15, 2016), HER1 (see, e.g., those described in U.S. Patent Application Publication No. 2013/0274446), HER2 (see, e.g., those described in Cao et al., *Biotechnol. Lett.* 37 (7): 1347-1354, 2015), HER3 (see, e.g., those described in U.S. Pat. No. 9,505,843), PSMA (see, e.g., those described in Parker et al., *Protein Expr. Purif.* 89 (2): 136-145, 2013), CEA (see, e.g., those described in WO 1995/015341), B7H3 (see, e.g., those described in U.S. Pat. No. 9,371,395), EPCAM (see, e.g., those described in WO 2014/159531), BCMA (see, e.g., those described in Smith et al., *Mol. Ther.* 26 (6): 1447-1456, 2018), P-cadherin (see, e.g., those described in U.S. Pat. No. 7,452,537), CEACAM5 (see, e.g., those described in U.S. Pat. No. 9,617,345), a UL16-binding protein (see, e.g., those described in WO 2017/083612), HLA-DR (see, e.g., Pistillo et al., *Exp. Clin. Immunogenet.* 14 (2): 123-130, 1997), DLL4 (see, e.g., those described in WO 2014/007513), TYRO3 (see, e.g., those described in WO 2016/166348), AXL (see, e.g., those described in WO 2012/175692), MER (see, e.g., those described in WO 2016/106221), CD122 (see, e.g., those described in U.S. Patent Application Publication No. 2016/0367664), CD155 (see, e.g., those described in WO 2017/149538), or PDGF-DD (see, e.g., those described in U.S. Pat. No. 9,441,034).

The antigen-binding domains present in any of the single-chain or multi-chain chimeric polypeptides described herein are each independently selected from the group consisting of: a VHH domain, a VNAR domain, and a scFv. In some embodiments, any of the antigen-binding domains described herein is a BiTe, a (scFv)₂, a nanobody, a nanobody-HSA, a DART, a TandAb, a scDiabody, a scDiabody-CH3, scFv-CH-CL-scFv, a HSAbody, scDiabody-HAS, or a tandem-scFv. Additional examples of antigen-binding domains that can be used in any of the single-chain or multi-chain chimeric polypeptide are known in the art.

A VHH domain is a single monomeric variable antibody domain that can be found in camelids. A VNAR domain is a single monomeric variable antibody domain that can be found in cartilaginous fish. Non-limiting aspects of V$_H$H domains and VNAR domains are described in, e.g., Cromie et al., *Curr. Top. Med. Chem.* 15:2543-2557, 2016; De Genst et al., *Dev. Comp. Immunol.* 30:187-198, 2006; De Meyer et al., *Trends Biotechnol.* 32:263-270, 2014; Kijanka et al., *Nanomedicine* 10:161-174, 2015; Kovaleva et al., *Expert. Opin. Biol. Ther.* 14:1527-1539, 2014; Krah et al., *Immunopharmacol. Immunotoxicol.* 38:21-28, 2016; Mujic-Delic et al., *Trends Pharmacol. Sci.* 35:247-255, 2014; Muyldermans, *J. Biotechnol.* 74:277-302, 2001; Muyldermans et al., *Trends Biochem. Sci.* 26:230-235, 2001; Muyldermans, *Ann. Rev. Biochem.* 82:775-797, 2013; Rahbarizadeh et al., *Immunol. Invest.* 40:299-338, 2011; Van Audenhove et al., *EBioMedicine* 8:40-48, 2016; Van Bockstaele et al., *Curr. Opin. Investig. Drugs* 10:1212-1224, 2009; Vincke et al., *Methods Mol. Biol.* 911:15-26, 2012; and Wesolowski et al., *Med. Microbiol. Immunol.* 198:157-174, 2009.

In some embodiments, each of the antigen-binding domains in the single-chain or multi-chain chimeric polypeptides described herein are both VHH domains, or at least one antigen-binding domain is a VHH domain. In some embodiments, each of the antigen-binding domains in the single-chain or multi-chain chimeric polypeptides described herein are both VNAR domains, or at least one antigen-binding domain is a VNAR domain. In some embodiments, each of the antigen-binding domains in the single-chain or multi-chain chimeric polypeptides described herein are both scFv domains, or at least one antigen-binding domain is a scFv domain.

In some embodiments, two or more of polypeptides present in the single-chain or multi-chain chimeric polypeptide can assemble (e.g., non-covalently assemble) to form any of the antigen-binding domains described herein, e.g., an antigen-binding fragment of an antibody (e.g., any of the antigen-binding fragments of an antibody described herein), a VHH-scAb, a VHH-Fab, a Dual scFab, a F(ab')2, a diabody, a crossMab, a DAF (two-in-one), a DAF (four-in-one), a DutaMab, a DT-IgG, a knobs-in-holes common light chain, a knobs-in-holes assembly, a charge pair, a Fab-arm exchange, a SEEDbody, a LUZ-Y, a Fcab, a KA-body, an orthogonal Fab, a DVD-IgG, a IgG(H)-scFv, a scFv-(H)IgG, IgG(L)-scFv, scFv-(L)IgG, IgG(L,H)-Fv, IgG(H)-V, V(H)-IgG, IgG(L)-V, V(L)-IgG, KIH IgG-scFab, 2scFv-IgG, IgG-2scFv, scFv4-Ig, Zybody, DVI-IgG, Diabody-CH3, a triple body, a miniantibody, a minibody, a TriBi minibody, scFv-CH3 KIH, Fab-scFv, a F(ab')₂-scFv2, a scFv-KIH, a Fab-scFv-Fc, a tetravalent HCAb, a scDiabody-Fc, a Diabody-Fc, a tandem scFv-Fc, an Intrabody, a dock and lock, a ImmTAC, an IgG-IgG conjugate, a Cov-X-Body, and a scFv1-PEG-scFv2. See, e.g., Spiess et al., *Mol. Immunol.* 67:95-106, 2015, incorporated in its entirety herewith, for a description of these elements. Non-limiting examples of an antigen-binding fragment of an antibody include an Fv fragment, a Fab fragment, a F(ab')₂ fragment, and a Fab' fragment. Additional examples of an antigen-binding fragment of an antibody is an antigen-binding fragment of an IgG (e.g., an antigen-binding fragment of IgG1, IgG2, IgG3, or IgG4) (e.g., an antigen-binding fragment of a human or humanized IgG, e.g., human or humanized IgG1, IgG2, IgG3, or IgG4); an antigen-binding fragment of an IgA (e.g., an antigen-binding fragment of IgA1 or IgA2) (e.g., an antigen-binding fragment of a human or humanized IgA, e.g., a human or humanized IgA1 or IgA2); an antigen-binding fragment of an IgD (e.g., an antigen-binding fragment of a human or humanized IgD); an antigen-binding fragment of an IgE (e.g., an antigen-binding fragment of a human or humanized IgE); or an antigen-binding fragment of an IgM (e.g., an antigen-binding fragment of a human or humanized IgM).

An "Fv" fragment includes a non-covalently-linked dimer of one heavy chain variable domain and one light chain variable domain.

A "Fab" fragment includes, the constant domain of the light chain and the first constant domain ($C_{H1}$) of the heavy chain, in addition to the heavy and light chain variable domains of the Fv fragment.

A "F(ab')₂" fragment includes two Fab fragments joined, near the hinge region, by disulfide bonds.

A "dual variable domain immunoglobulin" or "DVD-Ig" refers to multivalent and multispecific binding proteins as described, e.g., in DiGiammarino et al., *Methods Mol. Biol.* 899: 145-156, 2012; Jakob et al., *MABs* 5:358-363, 2013; and U.S. Pat. Nos. 7,612,181; 8,258,268; 8,586,714; 8,716,450; 8,722,855; 8,735,546; and 8,822,645, each of which is incorporated by reference in its entirety.

DARTs are described in, e.g., Garber, Nature Reviews Drug Discovery 13:799-801, 2014.

In some embodiments of any of the antigen-binding domains described herein can bind to an antigen selected from the group consisting of: a protein, a carbohydrate, a lipid, and a combination thereof.

Additional examples and aspects of antigen-binding domains are known in the art.

Soluble Interleukin or Cytokine Protein

In some embodiments of any of the single-chain or multi-chain chimeric polypeptides described herein, one or both of the first target-binding domain and the second target-binding domain can be a soluble interleukin protein or soluble cytokine protein. In some embodiments, the soluble interleukin or soluble cytokine protein is selected from the group of: IL-2, IL-3, IL-7, IL-8, IL-10, IL-12, IL-15, IL-17, IL-18, IL-21, PDGF-DD, SCF, and FLT3L. Non-limiting examples of soluble IL-2, IL-3, IL-7, IL-8, IL-10, IL-15, IL-17, IL-18, IL-21, PDGF-DD, SCF, and FLT3L are provided below.

Human Soluble IL-2

(SEQ ID NO: 104)

aptssstkkt qlqlehllld lqmilnginn yknpkltrml tfkfympkka
telkhlqcle eelkpleevl nlaqsknfhl rprdlisnin vivlelkgse
ttfmceyade tativeflnr witfcqsiis tlt Human Soluble IL-3
(SEQ ID NO: 105)
apmtqttplkt swvncsnmid eiithlkqpp lplldfnnln gedqdilmen
nlrrpnleaf nravkslqna saiesilknl lpclplataa ptrhpihikd
gdwnefrrkl tfylktlena qaqqttlsla if Human Soluble IL-7
(SEQ ID NO: 106)
dcdiegkdgkqyesv lmvsidqlld smkeigsncl nnefnffkrh icdankegmf
lfraarklrq flkmnstgdf dlhllkvseg ttillnctgq vkgrkpaalg
eaqptkslee nkslkeqkkl ndlcflkrll qeiktcwnki lmgtkeh Human Soluble IL-8
(SEQ ID NO: 107)
egavlprsak elrcqcikty skpfhpkfik elrviesgph canteiivkl
sdgrelcldp kenwvqrvve kflkraens Human Soluble IL-10
(SEQ ID NO: 108)
spgqgtqsensc thfpgnlpnm lrdlrdafsr vktffqmkdq ldnlllkesl
ledfkgylgc qalsemiqfy leevmpqaen qdpdikahvn slgenlktlr
lrlrrchrfl pcenkskave qvknafnklq ekgiykamse fdifinyiea
ymtmkirn Human Soluble IL-15
(SEQ ID NO: 109)
nwvnvisdlkki edliqsmhid atlytesdvh psckvtamkc fllelqvisl
esgdasihdt venliilann slssngnvte sgckeceele eknikeflqs
fvhivqmfin ts Human Soluble IL-17
(SEQ ID NO: 110)
gitiprn pgcpnsedkn fprtvmvnln ihnrntntnp krssdyynrs
tspwnlhrne dperypsviw eakcrhlgci nadgnvdyhm nsvpiqqeil
vlrrepphcp nsfrlekilv svgctcvtpi vhhva Human Soluble IL-18
(SEQ ID NO: 111)
yfgklesklsvirn lndqvlfidq gnrplfedmt dsdcrdnapr tifiismykd
sqprgmavti svkcekistl scenkiisfk emnppdnikd tksdiiffqr
svpghdnkmq fesssyegyf lacekerdlf klilkkedel gdrsimftvq ned Human Soluble PDGF-DD
(SEQ ID NO: 112)
rdtsatpqsasi kalrnanlrr desnhltdly rrdetiqvkg ngyvqsprfp
nsyprnlllt wrlhsqentr iqlvfdnqfg leeaendicr ydfvevedis
etstiirgrw cghkevppri ksrtnqikit fksddyfvak pgfkiyysll
edfqpaaase tnwesvtssi sgvsynspsv tdptliadal dkkiaefdtv
edllkyfnpe swqedlenmy ldtpryrgrs yhdrkskvdl drlnddakry
sctprnysvn ireelklanv vffprcllvq rcggncgcgt vnwrsctons
gktvkkyhev lqfepghikr rgraktmalv diqldhherc dcicssrppr Human Soluble SCF
(SEQ ID NO: 113)
egicrnrvtnnvkdv tklvanlpkd ymitlkyvpg mdvlpshcwi semvvqlsds
ltdlldkfsn iseglsnysi idklvnivdd lvecvkenss kdlkksfksp
eprlftpeef frifnrsida fkdfvvaset sdcvvsstls pekdsrvsvt
kpfmlppvaa sslrndsssss nrkaknppgd sslhwaamal palfsliigf
afgalywkkr qpsltraven iqineednei smlekeref qev Human Soluble FLT3L
(SEQ ID NO: 114)
tqdcsfqhspissd favkirelsd yllqdypvtv asnlqdeelc gglwrlvlaq
rwmerlktva gskmqgller vnteihfvtk cafqpppscl rfvqtnisrl
lqetseqlva lkpwitrqnf srclelqcqp dsstlpppws prpleatapt
apqppllllll llpvgllllla aawclhwqrt rrrtprpgeq vppvpspqdl
llveh Non-limiting examples of soluble MICA, MICB, ULBP1, ULBP2, ULBP3, ULBP4, ULBP5, and ULBP6 are provided below.

Human Soluble MICA
(SEQ ID NO: 115)
ephslry nltvlswdgs vqsgfltevh ldgqpflrcd rqkcrakpqg
qwaedvlgnk twdretrdlt gngkdlrmtl ahikdqkegl hslqeirvce
ihednstrss qhfyydgelf lsqnletkew tmpqssraqt lamvrnflk
edamktkthy hamhadclqe lrrylksgvv lrrtvppmvn vtrseasegn
itvtcrasgf ypwnitlswr qdgvslshdt qqwgdvlpdg ngtyqtwvat
ricqgeeqrf tcymehsgnh sthpvpsgkv lvlqshwqtf hvsavaaaai
fviiifyvrc ckkktsaaeg pelvslqvld qhpvgtsdhr datqlgfqpl
msdlgstgst ega -continued Human Soluble MICB
(SEQ ID NO: 116)
aephslry nlmvlsqdes vqsgflaegh ldgqpflryd rqkrrakpqg
qwaedvlgak twdtetedlt engqdlrrtl thikdqkggl hslqeirvce
ihedsstrgs rhfyydgelf lsqnletqes tvpqssraqt lamnvtnfwk
edamktkthy ramqadclqk lqrylksgva irrtvppmvn vtcsevsegn
itvtcrassf yprnitltwr qdgvslshnt qqwgdvlpdg ngtyqtwvat
rirqgeeqrf tcymehsgnh gthpvpsgkv lvlqsqrtdf pyvsaampcf
viiiilcvpc ckkktsaaeg pelvslqvld qhpvgtgdhr
daaqlgfqpl msatgstgst ega Human Soluble ULBP1
(SEQ ID NO: 117)
wvdthclcydfiit pksrpepqwc evqglvderp flhydcvnhk akafaslgkk
vnvtktweeq tetlrdvvdf lkgqlldiqv enlipieplt lqarmscehe
ahghgrgswq flfngqkfll fdsnnrkwta lhpgakkmte kweknrdvtm
ffqkislgdc kmwleeflmy weqmldptkp pslapg Human Soluble ULBP2
(SEQ ID NO: 118)
gradphslcyditvi pkfrpgprwc avqgqvdekt flhydcgnkt vtpvsplgkk
lnvttawkaq npvlrevvdi lteqlrdiql enytpkeplt lqarmsceqk
aeghssgswq fsfdgqifll fdsekrmwtt vhpgarkmke kwendkvvam
sfhyfsmgdc igwledflmg mdstlepsag aplams Human Soluble ULBP3
(SEQ ID NO: 119)
dahslwynfti ihlprhgqqw cevqsqvdqk nflsydcgsd kvlsmghlee
qlyatdawgk qlemlrevgq rlrleladte ledftpsgpl tlqvrmscec
eadgyirgsw qfsfdgrkfl lfdsnnrkwt vvhagarrmk ekwekdsglt
tffkmvsmrd ckswirdflm hrkkrlepta pptmapg Human Soluble ULBP4
(SEQ ID NO: 120)
hslcfnftik slsrpgqpwc eaqvflnknl flynsdnnm vkplgllgkk
vyatstwgel tqtlgevgrd lrmllcdikp qiktsdpstl qvemfcqrea
erctgaswqf atngeksllf damnmtwtvi nheaskiket wkkdrgleky
frklskgdcd hwlreflghw eampeptvsp vnasdihwss sslpdrwiil
gafillvlmg ivlicvwwqn gewqaglwpl rts Human Soluble ULBP5
(SEQ ID NO: 121)
gladp hslcyditvi pkfrpgprwc avqgqvdekt flhydcgskt
vtpvsplgkk lnvttawkaq npvlrevvdi lteqlldiql enyipkeplt
lqarmsceqk aeghgsgswq lsfdgqifll fdsenrmwtt vhpgarkmke
kwendkdmtm sfhyismgdc tgwledflmg mdstlepsag apptmssg Human Soluble ULBP6
(SEQ ID NO: 122)
rrddp hslcyditvi pkfrpgprwc avqgqvdekt flhydcgnkt
vtpvsplgkk lnvtmawkaq npvlrevvdi lteqlldiql enytpkeplt
lqarmsceqk aeghssgswq fsidgqtfll fdsekrmwtt vhpgarkmke
kwendkdvam sfhyismgdc igwledflmg mdstlepsag aplamssg Additional examples of soluble interleukin proteins and soluble cytokine proteins are known in the art.

Soluble Receptor

In some embodiments of any of the single-chain or multi-chain chimeric polypeptides described herein, one or both of the first target-binding domain and the second target-binding domain is a soluble interleukin receptor or a soluble cytokine receptor. In some embodiments, the soluble receptor is a soluble TGF-β receptor II (TGF-β RII) (see, e.g., those described in Yung et al., *Am. J. Resp. Crit. Care Med.* 194 (9): 1140-1151, 2016), a soluble TGF-βRIII (see, e.g., those described in Heng et al., *Placenta* 57:320, 2017), a soluble NKG2D (see, e.g., Cosman et al., Immunity 14 (2): 123-133, 2001; Costa et al., *Front. Immunol.*, Vol. 9, Article 1150 May 29, 2018; doi: 10.3389/fimmu.2018.01150), a soluble NKp30 (see, e.g., Costa et al., Front. Immunol., Vol. 9, Article 1150 May 29, 2018; doi: 10.3389/fimmu.2018.01150), a soluble NKp44 (see, e.g., those described in Costa et al., *Front. Immunol.*, Vol. 9, Article 1150 May 29, 2018; doi: 10.3389/fimmu.2018.01150), a soluble NKp46 (see, e.g., Mandelboim et al., *Nature* 409: 1055-1060, 2001; Costa et al., *Front. Immunol.*, Vol. 9, Article 1150 May 29, 2018; doi: 10.3389/fimmu.2018.01150), a soluble DNAM1 (see, e.g., those described in Costa et al., *Front. Immunol.*, Vol. 9, Article 1150 May 29, 2018; doi: 10.3389/fimmu.2018.01150), a scMHCI (see, e.g., those described in Washburn et al., *PLOS One* 6 (3): e18439, 2011), a scMHCII (see, e.g., those described in Bishwajit et al., *Cellular Immunol.* 170 (1): 25-33, 1996), a scTCR (see, e.g., those described in Weber et al., *Nature* 356 (6372): 793-796, 1992), a soluble CD155 (see, e.g., those described in Tahara-Hanaoka et al., *Int. Immunol.* 16 (4): 533-538, 2004), or a soluble CD28 (see, e.g., Hebbar et al., *Clin. Exp. Immunol.* 136:388-392, 2004). Additional examples of soluble interleukin receptors and soluble cytokine receptors are known in the art.

Exemplary Embodiments of Single-Chain Chimeric Polypeptides—Type A

In some embodiments of any of the single-chain chimeric polypeptides described herein, the first target-binding domain and/or the second target-binding domain can independently bind specifically to CD3 (e.g., human CD3) or CD28 (e.g., human CD28). In some embodiments, the first target-binding domain binds specifically to CD3 (e.g., human CD3) and the second target-binding domain binds specifically to CD28 (e.g., human CD28). In some embodiments, the first target-binding domain binds specifically to CD28 (e.g., human CD28) and the second target-binding domain binds specifically to CD3 (e.g., human CD3).

Exemplary Embodiments of Single-Chain Chimeric Polypeptides—Type B

In some embodiments of any of the single-chain chimeric polypeptides described herein, the first target-binding domain and/or the second target-binding domain can independently bind specifically to an IL-2 receptor (e.g., human IL-2 receptor).

Exemplary Embodiments of Single-Chain Chimeric Polypeptides—Type C

In some embodiments of any of the single-chain chimeric polypeptides described herein, the first target-binding domain and/or the second target-binding domain can independently bind specifically to an IL-15 receptor (e.g., a human IL-15 receptor).

Sequences of Exemplary Single-Chain Chimeric Polypeptides

The nucleic acid encoding a αCD3scFv/TF/αCD28scFv single-chain polypeptide is as follows

```
(SEQ ID NO: 22):
(Signal peptide)
ATGAAGTGGGTGACCTTCATCAGCTTATTATTTTTATTCAGCTCCGCCT
ATTCC (αCD3 light chain variable region)
CAGATCGTGCTGACCCAAAGCCCCGCCATCATGAGCGCTAGCCCCGGTG
AGAAGGTGACCATGACATGCTCCGCTTCCAGCTCCGTGTCCTACATGAA
CTGGTATCAGCAGAAAAGCGGAACCAGCCCCAAAAGGTGGATCTACGAC
ACCAGCAAGCTGGCCTCCGGAGTGCCCGCTCATTTCCGGGGCTCTGGAT
CCGGCACCAGCTACTCTTTAACCATTTCCGGCATGGAAGCTGAAGCGC
TGCCACCTACTATTGCCAGCAATGGAGCAGCAACCCCTTCACATTCGGA
TCTGGCACCAAGCTCGAAATCAATCGT (Linker)
GGAGGAGGTGGCAGCGGCGGCGGTGGATCCGGCGGAGGAGGAAGC (αCD3 heavy chain variable region)
CAAGTTCAACTCCAGCAGAGCGGCGCTGAACTGGCCCGGCCCGGCGCCT
CCGTCAAGATGAGCTGCAAGGCTTCCGGCTATACATTTACTCGTTACAC
AATGCATTGGGTCAAGCAGAGGCCCGGTCAAGGTTTAGAGTGGATCGGA
TATATCAACCCTTCCCGGGGCTACACCAACTATAACCAAAAGTTCAAGG
ATAAAGCCACTTTAACCACTGACAAGAGCTCCTCCACCGCCTACATGCA
GCTGTCCTCTTTAACCAGCGAGGACTCCGCTGTTTACTACTGCGCTAGG
TATTACGACGACCACTACTGTTTAGACTATTGGGGACAAGGTACCACTT
TAACCGTCAGCAGC (Human tissue factor 219 form)
TCCGGCACCACCAATACCGTGGCCGCTTATAACCTCACATGGAAGAGCA
CCAACTTCAAGACAATTCTGGAATGGGAACCCAAGCCCGTCAATCAAGT
TTACACCGTGCAGATCTCCACCAAATCCGGAGACTGGAAGAGCAAGTGC
TTCTACACAACAGACACCGAGTGTGATTTAACCGACGAAATCGTCAAGG
ACGTCAAGCAAACCTATCTGGCTCGGGTCTTTTCCTACCCCGCTGGCAA
TGTCGAGTCCACCGGCTCCGCTGGCGAGCCTCTCTACGAGAATTCCCCC
GAATTCACCCCTTATTAGAGACCAATTTAGGCCAGCCTACCATCCAGA
GCTTCGAGCAAGTTGGCACCAAGGTGAACGTCACCGTCGAGGATGAAAG
GACTTTAGTGCGGCGGAATAACACATTTTTATCCCTCCGGGATGTGTTC
GGCAAAGACCTCATCTACACACTGTACTATTGGAAGTCCAGCTCCTCCG
GCAAAAAGACCGCTAAGACCAACACCAACGAGTTTTTAATTGACGTGGA
CAAAGGCGAGAACTACTGCTTCAGCGTGCAAGCCGTGATCCCTTCTGT
ACCGTCAACCGGAAGAGCACAGATTCCCCCGTTGAGTGCATGGGCCAAG
AAAAGGGCGAGTTCCGGGAG (αCD28 light chain variable region)
GTCCAGCTGCAGCAGAGCGGACCCGAACTCGTGAAACCCGGTGCTTCCG
TGAAAATGTCTTGTAAGGCCAGCGGATACACCTTCACCTCCTATGTGAT
CCAGTGGGTCAAACAGAAGCCCGGACAAGGTCTCGAGTGGATCGGCAGC
ATCAACCCTTACAACGACTATACCAAATACAACGAGAAGTTTAAGGGAA
AGGCTACTTTAACCTCCGACAAAAGCTCCATCACAGCCTACATGGAGTT
CAGCTCTTTAACATCCGAGGACAGCGCTCTGTACTATTGCGCCCGGTGG
GGCGACGGCAATTACTGGGGACGGGGCACAACACTGACCGTGAGCAGC
```

(Linker)
GGAGGCGGAGGCTCCGGCGGAGGCGGATCTGGCGGTGGCGGCTCC (αCD28 light chain variable region)
GACATCGAGATGACCCAGTCCCCCGCTATCATGTCCGCCTCTTTAGGCG
AGCGGGTCACAATGACTTGTACAGCCTCCTCCAGCGTCTCCTCCTCCTA
CTTCCATTGGTACCAACAGAAACCCGGAAGCTCCCCTAAACTGTGCATC
TACAGCACCAGCAATCTCGCCAGCGGCGTGCCCCCTAGGTTTTCCGGAA
GCGGAAGCACCAGCTACTCTTTAACCATCTCCTCCATGGAGGCTGAGGA
TGCCGCCACCTACTTTTGTCACCAGTACCACCGGTCCCCCACCTTCGGA
GGCGGCACCAAACTGGAGACAAAGAGG The amino acid sequence of a αCD3scFv/TF/αCD28scFv single-chain chimeric polypeptide is as follows

```
(SEQ ID NO: 23):
(Signal peptide)
MKWVTFISLLFLFSSAYS (αCD3 light chain variable region)
QIVLTQSPAIMSASPGEKVTMTCSASSSVSYMNWYQQKSGTSPKRWIYD
TSKLASGVPAHFRGSGSGTSYSLTISGMEAEDAATYYCQQWSSNPFTFG
SGTKLEINR (Linker)
GGGGSGGGGSGGGGS (αCD3 heavy chain variable region)
QVQLQQSGAELARPGASVKMSCKASGYTFTRYTMHWVKQRPGQGLEWIG
YINPSRGYTNYNQKFKDKATLTTDKSSSTAYMQLSSLTSEDSAVYYCAR
YYDDHYCLDYWGQGTTLTVSS (Human tissue factor 219)
SGTTNTVAAYNLTWKSTNFKTILEWEPKPVNQVYTVQISTKSGDWKSKC
FYTTDTECDLTDEIVKDVKQTYLARVFSYPAGNVESTGSAGEPLYENSP
EFTPYLETNLGQPTIQSFEQVGTKVNVTVEDERTLVRRNNTFLSLRDVF
GKDLIYTLYYWKSSSSGKKTAKTNTNEFLIDVDKGENYCFSVQAVIPSR
TVNRKSTDSPVECMGQEKGEFRE (αCD28 light chain variable region)
VQLQQSGPELVKPGASVKMSCKASGYTFTSYVIQWVKQKPGQGLEWIGS
INPYNDYTKYNEKFKGKATLTSDKSSITAYMEFSSLTSEDSALYYCARW
GDGNYWGRGTTLTVSS (Linker)
GGGGSGGGGSGGGGS (αCD28 heavy chain variable region)
DIEMTQSPAIMSASLGERVTMTCTASSSVSSSYFHWYQQKPGSSPKLCI
YSTSNLASGVPPRFSGSGSTSYSLTISSMEAEDAATYFCHQYHRSPTFG
GGTKLETKR
```

The nucleic acid sequence encoding a αCD28scFv/TF/αCD3scFv single-chain polypeptide is as follows

```
(SEQ ID NO: 24):
(Signal peptide)
ATGAAATGGGTCACCTTCATCTCTTTACTGTTTTTATTTAGCAGCGCCT
ACAGC (αCD28 light chain variable region)
GTGCAGCTGCAGCAGTCCGGACCCGAACTGGTCAAGCCCGGTGCCTCCG
TGAAAATGTCTTGTAAGGCTTCTGGCTACACCTTTACCTCCTACGTCAT
CCAATGGGTGAAGCAGAAGCCCGGTCAAGGTCTCGAGTGGATCGGCAGC
ATCAATCCCTACAACGATTACACCAAGTATAACGAAAAGTTTAAGGGCA
AGGCCACTCTGACAAGCGACAAGAGCTCCATTACCGCCTACATGGAGTT
TTCCTCTTTAACTTCTGAGGACTCCGCTTTATACTATTGCGCTCGTTGG
GGCGATGGCAATTATTGGGGCCGGGGAACTACTTTAACAGTGAGCTCC (Linker)
GGCGGCGGCGGAAGCGGAGGTGGAGGATCTGGCGGTGGAGGCAGC (αCD28 heavy chain variable region)
GACATCGAGATGACACAGTCCCCCGCTATCATGAGCGCCTCTTTAGGAG
AACGTGTGACCATGACTTGTACAGCTTCCTCCAGCGTGAGCAGCTCCTA
TTTCCACTGGTACCAGCAGAAACCCGGCTCCTCCCCTAAACTGTGTATC
```

-continued
TACTCCACAAGCAATTTAGCTAGCGGCGTGCCTCCTCGTTTTAGCGGCT
CCGGCAGCACCTCTTACTCTTTAACCATTAGCTCTATGGAGGCCGAAGA
TGCCGCCACATACTTTTGCCATCAGTACCACCGGTCCCCTACCTTTGGC
GGAGGCACAAAGCTGGAGACCAAGCGG (Human tissue factor 219 form)
AGCGGCACCACCAACACAGTGGCCGCCTACAATCTGACTTGGAAATCCA
CCAACTTCAAGACCATCCTCGAGTGGGAGCCCAAGCCCGTTAATCAAGT
TTATACCGTGCAGATTTCCACCAAGAGCGGCGACTGGAAATCCAAGTGC
TTCTATACCACAGACACCGAGTGCGATCTCACCGACGAGATCGTCAAAG
ACGTGAAGCAGACATATTTAGCTAGGGTGTTCTCCTACCCCGCTGGAAA
CGTGGAGAGCACCGGATCCGCTGGAGAGCCTTTATACGAGAACTCCCCC
GAATTCACCCCCTATCTGGAAACCAATTTAGGCCAGCCCACCATCCAGA
GCTTCGAACAAGTTGGCACAAAGGTGAACGTCACCGTCGAAGATGAGAG
GACTTTAGTGCGGAGGAACAATACATTTTTATCCTTACGTGACGTCTTC
GGCAAGGATTTAATCTACACACTGTATTACTGGAAGTCTAGCTCCTCCG
GCAAGAAGACCGCCAAGACCAATACCAACGAATTTTTAATTGACGTGGA
CAAGGGCGAGAACTACTGCTTCTCCGTGCAAGCTGTGATCCCCTCCCGG
ACAGTGAACCGGAAGTCCACCGACTCCCCCGTGGAGTGCATGGGCCAAG
AGAAGGGAGAGTTTCGTGAG (αCD3 light chain variable region)
CAGATCGTGCTGACCCAGTCCCCCGCTATTATGAGCGCTAGCCCCGGTG
AAAAGGTGACTATGACATGCAGCGCCAGCTCTTCCGTGAGCTACATGAA
CTGGTATCAGCAGAAGTCCGGCACCAGCCCTAAAAGGTGGATCTACGAC
ACCAGCAAGCTGGCCAGCGGCGTCCCCGCTCACTTTCGGGGCTCCGGCT
CCGGAACAAGCTACTCTCTGACCATCAGCGGCATGGAAGCCGAGGATGC
CGCTACCTATTACTGTCAGCAGTGGAGCTCCAACCCCTTCACCTTTGGA
TCCGGCACCAAGCTCGAGATTAATCGT (Linker)
GGAGGCGGAGGTAGCGGAGGAGGCGGATCCGGCGGTGGAGGTAGC (αCD3 heavy chain variable region)
CAAGTTCAGCTCCAGCAAAGCGGCGCCGAACTCGCTCGGCCCGGCGCTT
CCGTGAAGATGTCTTGTAAGGCCTCCGGCTATACCTTCACCCGGTACAC
AATGCACTGGGTCAAGCAACGCCCGGTCAAGGTTTAGAGTGGATTGGC
TATATCAACCCCTCCCGGGGCTATACCAACTACAACCAGAAGTTCAAGG
ACAAAGCCACCCTCACCACCGACAAGTCCAGCAGCACCGCTTACATGCA
GCTGAGCTCTTTAACATCCGAGGATTCCGCCGTGTACTACTGCGCTCGG
TACTACGACGATCATTACTGCCTCGATTACTGGGGCAAGGTACCACCT
TAACAGTCTCCTCC The amino acid sequence of a αCD28scFv/TF/αCD3scFv single-chain chimeric polypeptide is as follows (SEQ ID NO: 25):
(Signal peptide)
MKWVTFISLLFLFSSAYS (αCD28 light chain variable region)
VQLQQSGPELVKPGASVKMSCKASGYTFTSYVIQWVKQPGQGLEWIGS
INPYNDYTKYNEKFKGKATLTSDKSSITAYMEFSSLTSEDSALYYCARW
GDGNYWGRGTTLTVSS (Linker)
GGGGGGGGSGGGGS (αCD28 heavy chain variable region)
DIEMTQSPAIMSASLGERVTMTCTASSSVSSSYFHWYQQKPGSSPKLCI
YSTSNLASGVPPRFSGSGSTSYSLTISSMEAEDAATYFCHQYHRSPTFG
GGTKLETKR (Human tissue factor 219)
SGTTNTVAAYNLTWKSTNFKTILEWEPKPVNQVYTVQISTKSGDWKSKC
FYTTDTECDLTDEIVKDVKQTYLARVFSYPAGNVESTGSAGEPLYENSP
EFTPYLETNLGQPTIQSFEQVGTKVNVTVEDERTLVRRNNTFLSLRDVF
GKDLIYTLYYWKSSSSGKKTAKTNTNEFLIDVDKGENYCFSVQAVIPSR
TVNRKSTDSPVECMGQEKGEFRE (αCD3 light chain variable region)
QIVLTQSPAIMSASPGEKVTMTCSASSSVSYMNWYQQKSGTSPKRWIYD
TSKLASGVPAHFRGSGSGTSYSLTISGMEAEDAATYYCQQWSSNPFTFG
SGTKLEINR (Linker)
GGGGSGGGGSGGGGS (αCD3 heavy chain variable region)
QVQLQQSGAELARPGASVKMSCKASGYTFTRYTMHWVKQRPGQGLEWIG
YINPSRGYTNYNQKFKDKATLTTDKSSSTAYMQLSSLTSEDSAVYYCAR
YYDDHYCLDYWGQGTTLTVSS The nucleic acid sequence encoding an IL-2/TF/IL-2 single-chain chimeric polypeptide is as follows (SEQ ID NO: 26):
(Signal peptide)
ATGAAGTGGGTGACCTTCATCAGCCTGCTGTTCCTGTTCTCCAGCGCCT
ACTCC (First IL-2 fragment)
GCCCCCACCTCCTCCTCCACCAAGAAGACCCAGCTGCAGCTGGAGCATT
TACTGCTGGATTTACAGATGATTTTAAACGGCATCAACAACTACAAGAA
CCCCAAGCTGACTCGTATGCTGACCTTCAAGTTCTACATGCCCAAGGAA
GCCACCGAGCTGAAGCATTTACAGTGTTTAGAGGAGGAGCTGAAGCCCC
TCGAGGAGGTGCTGAATTTAGCCCAGTCCAAGAATTTCCATTTAAGGCC
CCGGGATTTAATCAGCAACATCAACGTGATCGTTTTAGAGCTGAAGGGC
TCCGAGACCACCTTCATGTGCGAGTACGCCGACGAGACCGCCACCATCG
TGGAGTTTTTAAATCGTTGGATCACCTTCTGCCAGTCCATCATCTCCAC
TTTAACC (Human tissue factor 219 form)
AGCGGCACAACCAACACAGTCGCTGCCTATAACCTCACTTGGAAGAGCA
CCAACTTCAAAACCATCCTCGAATGGGAACCCAAACCCGTTAACCAAGT
TTACACCGTGCAGATCAGCACCAAGTCCGGCGACTGGAAGTCCAAATGT
TTCTATACCACCGACACCGAGTGCGATCTCACCGATGAGATCGTGAAAG
ATGTGAAACAGACCTACCTCGCCCGGGTGTTTAGCTACCCCGCCGGCAA
TGTGGAGAGCACTGGTTCCGCTGGCGAGCCTTTATACGAGAACAGCCCC
GAATTTACCCCTTACCTCGAGACCAATTTAGGACAGCCCACCATCCAAA
GCTTTGAGCAAGTTGGCACAAAGGTGAATGTGACAGTGGAGGACGAGCG
GACTTTAGTGCGGCGGAACAACACCTTTCTCAGCCTCCGGGATGTGTTC
GGCAAAGATTTAATCTACACACTGTATTACTGGAAGTCCTCTTCCTCCG
GCAAGAAGACAGCTAAAACCAACACAAACGAGTTTTTAATCGACGTGGA
TAAAGGCGAAAACTACTGTTTCAGCGTGCAAGCTGTGATCCCCTCCCGG
ACCGTGAATAGGAAAAGCACCGATAGCCCCGTTGAGTGCATGGGCCAAG
AAAAGGGCGAGTTCCGGGAG (Second IL-2 fragment)
GCACCTACTTCAAGTTCTACAAAGAAAACACAGCTACAACTGGAGCATT
TACTGCTGGATTTACAGATGATTTTGAATGGAATTAATAATTACAAGAA
TCCCAAACTCACCAGGATGCTCACATTTAAGTTTTACATGCCCAAGAAG
GCCACAGAACTGAAACATCTTCAGTGTCTAGAAGAAGAACTCAAACCTC
TGGAGGAAGTGCTAAATTTAGCTCAAAGCAAAAACTTTCACTTAAGACC
CAGGGACTTAATCAGCAATATCAACGTAATAGTTCTGGAACTAAAGGGA
TCTGAAACAACATTCATGTGTGAATATGCTGATGAGACAGCAACCATTG
TAGAATTTCTGAACAGATGGATTACCTTTTGTCAAAGCATCATCTCAAC
ACTAACT The amino acid sequence of an IL-2/TF/IL-2 single-chain chimeric polypeptide is as follows (SEQ ID NO: 27):
(Signal peptide)
MKWVTFISLLFLFSSAYS (Human IL-2)
APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSIISTLT (Human Tissue Factor 219)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE

-continued (Human IL-2)
APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSIISTLT

The nucleic acid sequence encoding an IL-15/TF/IL-15 single-chain chimeric polypeptide is as follows (SEQ ID NO: 28):
(Signal peptide)
ATGAAGTGGGTGACCTTCATCAGCCTGCTGTTCCTGTTCTCCAGCGCCTA

CTCC (First IL-15 fragment)
AACTGGGTGAACGTGATCAGCGATTTAAAGAAGATCGAGGATTTAATCCA

GAGCATGCACATCGACGCCACTCTGTACACTGAGAGCGACGTGCACCCTA

GCTGCAAGGTGACTGCCATGAAGTGCTTTTTACTGGAGCTGCAAGTTATC

TCTTTAGAGAGCGGCGATGCCAGCATCCACGACACTGTGGAGAATTTAAT

CATTTTAGCCAACAACTCTTTAAGCAGCAACGGCAACGTGACAGAGAGCG

GCTGCAAGGAGTGCGAGGAGCTGGAGGAGAAGAACATCAAGGAGTTTTTA

CAGAGCTTCGTGCACATCGTGCAGATGTTCATCAACACTAGC (Human tissue factor 219 form)
AGCGGCACAACCAACACAGTCGCTGCCTATAACCTCACTTGGAAGAGCAC

CAACTTCAAAACCATCCTCGAATGGGAACCCAAACCCGTTAACCAAGTTT

ACACCGTGCAGATCAGCACCAAGTCCGGCGACTGGAAGTCCAAATGTTTC

TATACCACCGACACCGAGTGCGATCTCACCGATGAGATCGTGAAAGATGT

GAAACAGACCTACCTCGCCCGGGTGTTTAGCTACCCCGCCGGCAATGTGG

AGAGCACTGGTTCCGCTGGCGAGCCTTTATACGAGAACAGCCCCGAATTT

ACCCCTTACCTCGAGACCAATTTAGGACAGCCCACCATCCAAAGCTTTGA

GCAAGTTGGCACAAAGGTGAATGTGACAGTGGAGGACGAGCGGACTTTAG

TGCGGCGGAACAACACCTTTCTCAGCCTCCGGGATGTGTTCGGCAAAGAT

TTAATCTACACACTGTATTACTGGAAGTCCTCTTCCTCCGGCAAGAAGAC

AGCTAAAACCAACACAAACGAGTTTTTAATCGACGTGGATAAAGGCGAAA

ACTACTGTTTCAGCGTGCAAGCTGTGATCCCCTCCCGGACCGTGAATAGG

AAAAGCACCGATAGCCCCGTTGAGTGCATGGGCCAAGAAAAGGGCGAGTT

CCGGGAG (Second IL-15 fragment)
AACTGGGTGAACGTCATCAGCGATTTAAAGAAGATCGAAGATTTAATTCA

GTCCATGCATATCGACGCCACTTTATACACAGAATCCGACGTGCACCCCT

CTTGTAAGGTGACCGCCATGAAATGTTTTTACTGGAGCTGCAAGTTATC

TCTTTAGAGAGCGGAGACGCTAGCATCCACGACACCGTGGAGAATTTAAT

CATTTTAGCCAATAACTCTTTATCCAGCAACGGCAACGTGACAGAGTCCG

GCTGCAAGGAGTGCGAAGAGCTGGAGGAGAAGAACATCAAGGAGTTTCTG

CAATCCTTTGTGCACATTGTCCAGATGTTCATCAATACCTCC

The amino acid sequence of an IL-15/TF/IL-15 single-chain chimeric polypeptide is as follows (SEQ ID NO: 29):
(Signal peptide)
MKWVTFISLLFLFSSAYS (Human IL-15)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS (Human Tissue Factor 219)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE (Human IL-15)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS

Multi-Chain Chimeric Polypeptides

Non-limiting examples of tissue factor-containing proteins are multi-chain chimeric polypeptides that include: (a) a first chimeric polypeptide including: (i) a first target-binding domain; (ii) a soluble tissue factor domain; and (iii) a first domain of a pair of affinity domains; and (b) a second chimeric polypeptide including: (i) a second domain of a pair of affinity domains; and (ii) a second target-binding domain, where the first chimeric polypeptide and the second chimeric polypeptide associate through the binding of the first domain and the second domain of the pair of affinity domains.

In some embodiments of any of the multi-chain chimeric polypeptides described herein, the first target-binding domain (e.g., any of the first target-binding domains described herein) and the soluble tissue factor domain (e.g., any of the exemplary soluble tissue factor domains described herein) directly abut each other in the first chimeric polypeptide. In some embodiments of any of the multi-chain chimeric polypeptides described herein, the first chimeric polypeptide further comprises a linker sequence (e.g., any of the exemplary linker sequences described herein or known in the art) between the first target-binding domain (e.g., any of the exemplary first target-binding domains described herein) and the soluble tissue factor domain (e.g., any of the exemplary soluble tissue factor domains described herein) in the first chimeric polypeptide.

In some embodiments of any of the multi-chain chimeric polypeptides described herein, the soluble tissue factor domain (e.g., any of the exemplary soluble tissue factor domains described herein) and the first domain of the pair of affinity domains (e.g., any of the exemplary first domains of any of the exemplary pairs of affinity domains described herein) directly abut each other in the first chimeric polypeptide. In some embodiments of any of the multi-chain chimeric polypeptides described herein, the first chimeric polypeptide further comprises a linker sequence (e.g., any of the exemplary linker sequences described herein or known in the art) between the soluble tissue factor domain (e.g., any of the exemplary soluble tissue factor domains described herein) and the first domain of the pair of affinity domains (e.g., any of the exemplary first domains of any of the exemplary pairs of affinity domains described herein) in the first chimeric polypeptide.

In some embodiments of any of the multi-chain chimeric polypeptides described herein, the second domain of the pair of affinity domains (e.g., any of the exemplary second domains of any of the exemplary pairs of affinity domains described herein) and the second target-binding domain (e.g., any of the exemplary second target-binding domains described herein) directly abut each other in the second chimeric polypeptide. In some embodiments of any of the multi-chain chimeric polypeptides described herein, the second chimeric polypeptide further comprises a linker sequence (e.g., any of the exemplary linker sequences described herein or known in the art) between the second domain of the pair of affinity domains (e.g., any of the exemplary second domains of any of the exemplary pairs of affinity domains described herein) and the second target-binding domain (e.g., any of the exemplary second target-binding domains described herein) in the second chimeric polypeptide.

In some embodiments of any of the multi-chain chimeric polypeptides, the first chimeric polypeptide further includes one or more (e.g., two, three, four, five, six, seven, eight, nine, or ten) additional target-binding domain(s) (e.g., any of the exemplary target-binding domains described herein or known in the art), where at least one of the one or more additional antigen-binding domain(s) is positioned between the soluble tissue factor domain (e.g., any of the exemplary soluble tissue factor domains described herein or known in the art) and the first domain of the pair of affinity domains (e.g., any of the exemplary first domains of any of the exemplary pairs of affinity domains described herein). In some embodiments, the first chimeric polypeptide can further include a linker sequence (e.g., any of the exemplary linker sequences described herein or known in the art) between the soluble tissue factor domain (e.g., any of the exemplary soluble tissue factor domains described herein) and the at least one of the one or more additional target-binding domain(s) (e.g., any of the exemplary target-binding domains described herein or known in the art), and/or a linker sequence (e.g., any of the exemplary linker sequences described herein or known in the art) between the at least one of the one or more additional target-binding domain(s) (e.g., any of the exemplary target-binding domains described herein or known in the art) and the first domain of the pair of affinity domains (e.g., any of the exemplary first domains described herein of any of the exemplary pairs of affinity domains described herein).

In some embodiments of any of the multi-chain chimeric polypeptides described herein, the first chimeric polypeptide further includes one or more (e.g., two, three, four, five, six, seven, eight, nine, or ten) additional target-binding domains at the N-terminal and/or C-terminal end of the first chimeric polypeptide. In some embodiments, at least one of the one or more additional target-binding domains (e.g., any of the exemplary target-binding domains described herein or known in the art) directly abuts the first domain of the pair of affinity domains (e.g., any of the exemplary first domains described herein of any of the exemplary pairs of affinity domains described herein) in the first chimeric polypeptide. In some embodiments, the first chimeric polypeptide further includes a linker sequence (e.g., any of the exemplary linker sequences described herein or known in the art) between the at least one of the one or more additional target-binding domains (e.g., any of the exemplary target-binding domains described herein or known in the art) and the first domain of the pair of affinity domains (e.g., any of the exemplary first domains described herein of any of the exemplary pairs of affinity domains described herein). In some embodiments, the at least one of the one or more additional target-binding domains (e.g., any of the exemplary target-binding domains described herein or known in the art) directly abuts the first target-binding domain (e.g., any of the exemplary target-binding domains described herein or known in the art) in the first chimeric polypeptide. In some embodiments, the first chimeric polypeptide further comprises a linker sequence (e.g., any of the exemplary linker sequences described herein or known in the art) between the at least one of the one or more additional target-binding domains (e.g., any of the exemplary target-binding domains described herein or known in the art) and the first target-binding domain (e.g., any of the exemplary target-binding domains described herein or known in the art).

In some embodiments of any of the multi-chain chimeric polypeptides described herein, at least one of the one or more additional target-binding domains (e.g., any of the exemplary target-binding domains described herein or known in the art) is disposed at the N- and/or C-terminus of the first chimeric polypeptide, and at least one of the one or more additional target-binding domains (e.g., any of the exemplary target-binding domains described herein or known in the art) is positioned between the soluble tissue factor domain (e.g., any of the exemplary soluble tissue factor domains described herein or known in the art) and the first domain of the pair of affinity domains (e.g., any of the exemplary first domains of any of the exemplary pairs of affinity domains described herein) in the first chimeric polypeptide. In some embodiments, the at least one additional target-binding domain (e.g., any of the exemplary target-binding domains described herein or known in the art) of the one or more additional target-binding domains disposed at the N-terminus directly abuts the first target-binding domain (e.g., any of the exemplary target-binding domains described herein or known in the art) or the first domain of the pair of affinity domains (e.g., any of the exemplary first domains described herein of any of the exemplary pairs of affinity domains described herein) in the first chimeric polypeptide. In some embodiments, the first chimeric polypeptide further comprises a linker sequence (e.g., any of the linker sequences described herein or known in the art) disposed between the at least one additional target-binding domain (e.g., any of the exemplary target-binding domains described herein or known in the art) and the first target-binding domain (e.g., any of the exemplary target-binding domains described herein or known in the art) or the first domain of the pair of affinity domains (e.g., any of the exemplary first domains described herein of any of the exemplary pairs of affinity domains described herein) in the first chimeric polypeptide. In some embodiments, the at least one additional target-binding domain (e.g., any of the exemplary target-binding domains described herein or known in the art) of the one or more additional target-binding domains disposed at the C-terminus directly abuts the first target-binding domain (e.g., any of the exemplary target-binding domains described herein or known in the art) or the first domain of the pair of affinity domains (e.g., any of the exemplary first domains of any of the exemplary pairs of affinity domains described herein) in the first chimeric polypeptide. In some embodiments, the first chimeric polypeptide further includes a linker sequence (e.g., any of the exemplary linker sequences described herein or known in the art) disposed between the at least one additional target-binding domain (e.g., any of the exemplary target-binding domains described herein or known in the art) and the first target-binding domain (e.g., any of the exemplary target-binding domains described herein or known in the art) or the first domain of the pair of affinity domains (e.g., any of the exemplary first domains described herein of any of the exemplary pairs of affinity domains described herein) in the first chimeric polypeptide. In some embodiments, the at least one of the one or more additional target-binding domains (e.g., any of the exemplary target-binding domains described herein or known in the art) positioned between the soluble tissue factor domain (e.g., any of the exemplary soluble tissue factor domains described herein) and the first domain of the pair of affinity domains (e.g., any of the first domains described herein or any of the exemplary pairs of affinity domains described herein), directly abuts the soluble tissue factor domain and/or the first domain of the pair of affinity domains. In some embodiments, the first chimeric polypeptide further comprises a linker sequence (e.g., any of the exemplary linker sequences described herein or known in the art) disposed (i) between the soluble tissue factor domain (e.g., any of the exemplary soluble tissue factor domains described herein) and the at least one of the one or more additional target-binding domains (e.g., any of the exemplary target-binding domains described herein or known in the art) positioned between the soluble tissue factor domain (e.g., any of the exemplary soluble tissue factor domains described herein) and the first domain of the pair of affinity domains (e.g., any of the exemplary first domains of any of the exemplary pairs of affinity domains described herein), and/or (ii) between the first domain of the pair of affinity domains and the at least one of the one or more additional target-binding domains positioned between the soluble tissue factor domain and the first domain of the pair of affinity domains.

In some embodiments of any of the multi-chain chimeric polypeptides described herein, the second chimeric polypeptide further includes one or more (e.g., two, three, four, five, six, seven, eight, nine, or ten) additional target-binding domains (e.g., any of the exemplary target-binding domains described herein or known in the art) at the N-terminal end and/or the C-terminal end of the second chimeric polypeptide. In some embodiments, at least one of the one or more additional target-binding domains (e.g., any of the exemplary target-binding domains described herein or known in the art) directly abuts the second domain of the pair of affinity domains (e.g., any of the exemplary second domains of any of the exemplary pairs of affinity domains described herein) in the second chimeric polypeptide. In some embodiments, the second chimeric polypeptide further includes a linker sequence (e.g., any of the exemplary linker sequences described herein or known in the art) between at least one of the one or more additional target-binding domains (e.g., any of the exemplary target-binding domains described herein or known in the art) and the second domain of the pair of affinity domains (e.g., any of the second domains described herein of any of the exemplary pairs of affinity domains described herein) in the second chimeric polypeptide. In some embodiments, at least one of the one or more additional target-binding domains (e.g., any of the exemplary target-binding domains described herein or known in the art) directly abuts the second target-binding domain (e.g., any of the target-binding domains described herein or known in the art) in the second chimeric polypeptide. In some embodiments, the second chimeric polypeptide further includes a linker sequence (e.g., any of the exemplary linker sequences described herein or known in the art) between at least one of the one or more additional target-binding domains (e.g., any of the exemplary target binding domains described herein or known in the art) and the second target-binding domain (e.g., any of the exemplary target binding domains described herein or known in the art) in the second chimeric polypeptide.

In some embodiments of any of the multi-chain chimeric polypeptides described herein, two or more (e.g., three or more, four or more, five or more, six or more, seven or more, eight or more, nine or more, or ten or more) of the first target-binding domain, the second target-binding domain, and the one or more additional target-binding domains bind specifically to the same antigen. In some embodiments, two or more (e.g., three or more, four or more, five or more, six or more, seven or more, eight or more, nine or more, or ten or more) of the first target-binding domain, the second target-binding domain, and the one or more additional target-binding domains bind specifically to the same epitope. In some embodiments, two or more (e.g., three or more, four or more, five or more, six or more, seven or more, eight or more, nine or more, or ten or more) of the first target-binding domain, the second target-binding domain, and the one or more additional target-binding domains include the same amino acid sequence. In some embodiments, the first target-binding domain, the second target-binding domain, and the one or more additional target-binding domains each bind specifically to the same antigen. In some embodiments, the first target-binding domain, the second target-binding domain, and the one or more additional target-binding domains each bind specifically to the same epitope. In some embodiments, the first target-binding domain, the second target-binding domain, and the one or more additional target-binding domains each include the same amino acid sequence.

In some embodiments of any of the multi-chain chimeric polypeptides described herein, the first target-binding domain, the second target-binding domain, and the one or more additional target-binding domains bind specifically to different antigens. In some embodiments of any of the multi-chain chimeric polypeptides described herein, one or more (e.g., two or more, three or more, four or more, five or more, six or more, seven or more, eight or more, nine or more, or ten or more) of the first target-binding domain, the second target-binding domain, and the one or more additional target-binding domains is an antigen-binding domain. In some embodiments, the first target-binding domain, the second target-binding domain, and the one or more additional target-binding domains are each an antigen-binding domain (e.g., a scFv or a single-domain antibody).

In some embodiments of any of the multi-chain chimeric polypeptides described herein, one or more (e.g., two, three, four, five, six, seven, eight, nine, or ten) of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKP30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

In some embodiments of any of the multi-chain chimeric polypeptides described herein, one or more of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) is a soluble interleukin or cytokine protein. Non-limiting examples of soluble interleukin proteins and soluble cytokine proteins include: IL-1, IL-2, IL-3, IL-7, IL-8, IL-10, IL-12, IL-15, IL-17, IL-18, IL-21, PDGF-DD, and SCF.

In some embodiments of any of the multi-chain chimeric polypeptides described herein, one or more of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) is a soluble interleukin or cytokine receptor. Non-limiting examples of soluble interleukin receptors and soluble cytokine receptors include: a soluble TGF-β receptor II (TGF-βRII), a soluble TGF-βRIII, a soluble NKG2D, a soluble NKP30, a soluble NKp44, a soluble NKp46, a soluble DNAM1, a scMHCI, a scMHCII, a scTCR, a soluble CD155, a soluble CD122, a soluble CD3, or a soluble CD28.

In some embodiments of any of the multi-chain chimeric polypeptides described herein, the first target-binding domain (e.g., any of the target-binding domains described herein, the second target-binding domain (e.g., any of the target-binding domains described herein), and the one or more additional target-binding domains (e.g., any of the target-binding domains described herein) can each, independently, bind specifically to a target selected from the group of: CD16a, CD33, CD20, CD19, CD22, CD123, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD122.

In some embodiments of any of the multi-chain chimeric polypeptides described herein, one or both of the first target-binding domain (e.g., any of the target-binding domains described herein), the second target-binding domain (e.g., any of the target-binding domains described herein), and the one or more additional binding domains (e.g., any of the target-binding described herein) is a soluble interleukin or cytokine protein. In some embodiments of any of the multi-chain chimeric polypeptides described herein, the soluble interleukin or cytokine protein is selected from the group of: IL-1, IL-2, IL-3, IL-7, IL-8, IL-10, IL-12, IL-15, IL-17, IL-18, IL-21, PDGF-DD, and SCF.

In some embodiments of any of the multi-chain chimeric polypeptides described herein, one or both of the first target-binding domain and the second target-binding domain is a soluble interleukin or cytokine receptor. In some embodiments of any of the multi-chain chimeric polypeptides described herein, the soluble receptor is a soluble TGF-β receptor II (TGF-βRII) a soluble TGF-βRIII, a soluble receptor for TNFα, a soluble receptor for IL-4, or a soluble receptor for IL-10.

Non-limiting examples of cell activating agents are multi-chain chimeric polypeptides that include: (a) a first and second chimeric polypeptide each including: (i) a first target-binding domain; (ii) a Fc domain; and (iii) a first domain of a pair of affinity domains; and (b) a third and fourth chimeric polypeptide each including: (i) a second domain of a pair of affinity domains; and (ii) a second target-binding domain, where the first and second chimeric polypeptides and the third and fourth chimeric polypeptides associate through the binding of the first domain and the second domain of the pair of affinity domains, and the first and second chimeric polypeptides associate through their Fc domains.

In some embodiments of any of the multi-chain chimeric polypeptides described herein, the first target-binding domain (e.g., any of the first target-binding domains described herein) and the Fc domain (e.g., any of the exemplary Fc domains described herein) directly abut each other in the first and second chimeric polypeptides. In some embodiments of any of the multi-chain chimeric polypeptides described herein, the first and second chimeric polypeptides further comprise a linker sequence (e.g., any of the exemplary linker sequences described herein or known in the art) between the first target-binding domain (e.g., any of the exemplary first target-binding domains described herein) and the Fc domain (e.g., any of the exemplary Fc domains described herein) in the first and second chimeric polypeptides.

In some embodiments of any of the multi-chain chimeric polypeptides described herein, the Fc domain (e.g., any of the exemplary Fc domains described herein) and the first domain of the pair of affinity domains (e.g., any of the exemplary first domains of any of the exemplary pairs of affinity domains described herein) directly abut each other in the first and second chimeric polypeptide. In some embodiments of any of the multi-chain chimeric polypeptides described herein, the first and second chimeric polypeptide further comprises a linker sequence (e.g., any of the exemplary linker sequences described herein or known in the art) between the Fc domain (e.g., any of the exemplary Fc domains described herein) and the first domain of the pair of affinity domains (e.g., any of the exemplary first domains of any of the exemplary pairs of affinity domains described herein) in the first and second chimeric polypeptide.

In some embodiments of any of the multi-chain chimeric polypeptides described herein, the second domain of the pair of affinity domains (e.g., any of the exemplary second domains of any of the exemplary pairs of affinity domains described herein) and the second target-binding domain (e.g., any of the exemplary second target-binding domains described herein) directly abut each other in the third and fourth chimeric polypeptide. In some embodiments of any of the multi-chain chimeric polypeptides described herein, the third and fourth chimeric polypeptide further comprise a linker sequence (e.g., any of the exemplary linker sequences described herein or known in the art) between the second domain of the pair of affinity domains (e.g., any of the exemplary second domains of any of the exemplary pairs of affinity domains described herein) and the second target-binding domain (e.g., any of the exemplary second target-binding domains described herein) in the third and fourth chimeric polypeptide.

In some embodiments of any of the multi-chain chimeric polypeptides described herein, the first target-binding domain and the second target-binding domain bind specifically to the same antigen. In some embodiments of any of the multi-chain chimeric polypeptides described herein, the first target-binding domain and the second target-binding domain bind specifically to the same epitope. In some embodiments of any of the multi-chain chimeric polypeptides described herein, the first target-binding domain and the second target-binding domain include the same amino acid sequence. In some embodiments of any of the multi-chain chimeric polypeptides described herein, the first target-binding domain and the second target-binding domain bind specifically to different antigens. In some embodiments of any of the multi-chain chimeric polypeptides described herein, one or both of the first target-binding domain and the second target-binding domain is an antigen-binding domain (e.g., any of the exemplary second target-binding domains described herein). In some embodiments of any of the multi-chain chimeric polypeptides described herein, the first target-binding domain and the second target-binding domain are each antigen-binding domains (e.g., any of the exemplary second target-binding domains described herein). In some embodiments of any of the multi-chain chimeric polypeptides described herein, the antigen-binding domain (e.g., any of the exemplary second target-binding domains described herein) includes a scFv or a single domain antibody.

In some embodiments of any of the multi-chain chimeric polypeptides described herein, one or both of the first target-binding domain (e.g., any of the exemplary target-binding domains described herein or known in the art) and the second target-binding domain (e.g., any of the exemplary target-binding domains described herein or known in the art) bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

In some embodiments of any of the multi-chain chimeric polypeptides described herein, one or both of the first target-binding domain (e.g., any of the exemplary target-binding domains described herein or known in the art) and the second target-binding domain (e.g., any of the exemplary target-binding domains described herein or known in the art) is a soluble interleukin or cytokine protein. Non-limiting examples of soluble interleukin proteins and soluble cytokine proteins include: IL-1, IL-2, IL-3, IL-7, IL-8, IL-10, IL-12, IL-15, IL-17, IL-18, IL-21, PDGF-DD, and SCF.

In some embodiments of any of the multi-chain chimeric polypeptides described herein, one or both of the first target-binding domain and the second target-binding domain (e.g., any of the exemplary target-binding domains described herein or known in the art) is a soluble interleukin or cytokine receptor. Non-limiting examples of soluble interleukin receptors and soluble cytokine receptors include: a soluble TGF-β receptor II (TGF-βRII), a soluble TGF-βRIII, a soluble NKG2D, a soluble NKp30, a soluble NKp44, a soluble NKp46, a soluble DNAM1, a scMHCI, a scMHCII, a scTCR, a soluble CD155, a soluble CD122, a soluble CD3, or a soluble CD28.

In some embodiments of any of the multi-chain chimeric polypeptides described herein, the first target-binding domain and the second target-binding domain can each, independently, bind specifically to a target selected from the group of: CD16a, CD33, CD20, CD19, CD22, CD123, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD122.

In some embodiments of any of the multi-chain chimeric polypeptides described herein, one or both of the first target-binding domain and the second target-binding domain is a soluble interleukin or cytokine protein. In some embodiments of any of the multi-chain chimeric polypeptides described herein, the soluble interleukin or cytokine protein is selected from the group of: IL-1, IL-2, IL-3, IL-7, IL-8, IL-10, IL-12, IL-15, IL-17, IL-18, IL-21, PDGF-DD, and SCF.

In some embodiments of any of the multi-chain chimeric polypeptides described herein, one or both of the first target-binding domain and the second target-binding domain is a soluble interleukin or cytokine receptor. In some embodiments of any of the multi-chain chimeric polypeptides described herein, the soluble receptor is a soluble TGF-β receptor II (TGF-βRII) a soluble TGF-βRIII, a soluble receptor for TNFα, a soluble receptor for IL-4, or a soluble receptor for IL-10.

In some embodiments, a multi-chain chimeric polypeptide has a nucleic acid sequence or an amino acid that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to: SEQ ID NOs: 30-101.

Additional Antigen-Binding Domains

In some embodiments of any of the single- or multi-chain chimeric polypeptides, the first chimeric polypeptide further includes one or more (e.g., two, three, four, five, six, seven, eight, nine, or ten) additional target-binding domain(s) (e.g., any of the exemplary target-binding domains described herein or known in the art). In some embodiments of any of the multi-chain chimeric polypeptides, at least one of the one or more additional antigen-binding domain(s) can be positioned between the soluble tissue factor domain (e.g., any of the exemplary soluble tissue factor domains described herein or known in the art) and the first domain of the pair of affinity domains (e.g., any of the exemplary first domains of any of the exemplary pairs of affinity domains described herein). In some embodiments, the first chimeric polypeptide can further include a linker sequence (e.g., any of the exemplary linker sequences described herein or known in the art) between the soluble tissue factor domain (e.g., any of the exemplary soluble tissue factor domains described herein) and the at least one of the one or more additional target-binding domain(s) (e.g., any of the exemplary target-binding domains described herein or known in the art), and/or a linker sequence (e.g., any of the exemplary linker sequences described herein or known in the art) between the at least one of the one or more additional target-binding domain(s) (e.g., any of the exemplary target-binding domains described herein or known in the art) and the first domain of the pair of affinity domains (e.g., any of the exemplary first domains described herein of any of the exemplary pairs of affinity domains described herein).

In some embodiments of any of the multi-chain chimeric polypeptides described herein, the first chimeric polypeptide further includes one or more (e.g., two, three, four, five, six, seven, eight, nine, or ten) additional target-binding domains at the N-terminal and/or C-terminal end of the first chimeric polypeptide. In some embodiments, at least one of the one or more additional target-binding domains (e.g., any of the exemplary target-binding domains described herein or known in the art) directly abuts the first domain of the pair of affinity domains (e.g., any of the exemplary first domains described herein of any of the exemplary pairs of affinity domains described herein) in the first chimeric polypeptide. In some embodiments, the first chimeric polypeptide further includes a linker sequence (e.g., any of the exemplary linker sequences described herein or known in the art) between the at least one of the one or more additional target-binding domains (e.g., any of the exemplary target-binding domains described herein or known in the art) and the first domain of the pair of affinity domains (e.g., any of the exemplary first domains described herein of any of the exemplary pairs of affinity domains described herein). In some embodiments, the at least one of the one or more additional target-binding domains (e.g., any of the exemplary target-binding domains described herein or known in the art) directly abuts the first target-binding domain (e.g., any of the exemplary target-binding domains described herein or known in the art) in the first chimeric polypeptide. In some embodiments, the first chimeric polypeptide further comprises a linker sequence (e.g., any of the exemplary linker sequences described herein or known in the art) between the at least one of the one or more additional target-binding domains (e.g., any of the exemplary target-binding domains described herein or known in the art) and the first target-binding domain (e.g., any of the exemplary target-binding domains described herein or known in the art).

In some embodiments of any of the multi-chain chimeric polypeptides described herein, at least one of the one or more additional target-binding domains (e.g., any of the exemplary target-binding domains described herein or known in the art) is disposed at the N- and/or C-terminus of the first chimeric polypeptide, and at least one of the one or more additional target-binding domains (e.g., any of the exemplary target-binding domains described herein or known in the art) is positioned between the soluble tissue factor domain (e.g., any of the exemplary soluble tissue factor domains described herein or known in the art) and the first domain of the pair of affinity domains (e.g., any of the exemplary first domains of any of the exemplary pairs of affinity domains described herein) in the first chimeric polypeptide. In some embodiments, the at least one additional target-binding domain (e.g., any of the exemplary target-binding domains described herein or known in the art) of the one or more additional target-binding domains disposed at the N-terminus directly abuts the first target-binding domain (e.g., any of the exemplary target-binding domains described herein or known in the art) or the first domain of the pair of affinity domains (e.g., any of the exemplary first domains described herein of any of the exemplary pairs of affinity domains described herein) in the first chimeric polypeptide. In some embodiments, the first chimeric polypeptide further comprises a linker sequence (e.g., any of the linker sequences described herein or known in the art) disposed between the at least one additional target-binding domain (e.g., any of the exemplary target-binding domains described herein or known in the art) and the first target-binding domain (e.g., any of the exemplary target-binding domains described herein or known in the art) or the first domain of the pair of affinity domains (e.g., any of the exemplary first domains described herein of any of the exemplary pairs of affinity domains described herein) in the first chimeric polypeptide. In some embodiments, the at least one additional target-binding domain (e.g., any of the exemplary target-binding domains described herein or known in the art) of the one or more additional target-binding domains disposed at the C-terminus directly abuts the first target-binding domain (e.g., any of the exemplary target-binding domains described herein or known in the art) or the first domain of the pair of affinity domains (e.g., any of the exemplary first domains of any of the exemplary pairs of affinity domains described herein) in the first chimeric polypeptide. In some embodiments, the first chimeric polypeptide further includes a linker sequence (e.g., any of the exemplary linker sequences described herein or known in the art) disposed between the at least one additional target-binding domain (e.g., any of the exemplary target-binding domains described herein or known in the art) and the first target-binding domain (e.g., any of the exemplary target-binding domains described herein or known in the art) or the first domain of the pair of affinity domains (e.g., any of the exemplary first domains described herein of any of the exemplary pairs of affinity domains described herein) in the first chimeric polypeptide. In some embodiments, the at least one of the one or more additional target-binding domains (e.g., any of the exemplary target-binding domains described herein or known in the art) positioned between the soluble tissue factor domain (e.g., any of the exemplary soluble tissue factor domains described herein) and the first domain of the pair of affinity domains (e.g., any of the first domains described herein or any of the exemplary pairs of affinity domains described herein), directly abuts the soluble tissue factor domain and/or the first domain of the pair of affinity domains. In some embodiments, the first chimeric polypeptide further comprises a linker sequence (e.g., any of the exemplary linker sequences described herein or known in the art) disposed (i) between the soluble tissue factor domain (e.g., any of the exemplary soluble tissue factor domains described herein) and the at least one of the one or more additional target-binding domains (e.g., any of the exemplary target-binding domains described herein or known in the art) positioned between the soluble tissue factor domain (e.g., any of the exemplary soluble tissue factor domains described herein) and the first domain of the pair of affinity domains (e.g., any of the exemplary first domains of any of the exemplary pairs of affinity domains described herein), and/or (ii) between the first domain of the pair of affinity domains and the at least one of the one or more additional target-binding domains positioned between the soluble tissue factor domain and the first domain of the pair of affinity domains.

In some embodiments of any of the multi-chain chimeric polypeptides described herein, the second chimeric polypeptide further includes one or more (e.g., two, three, four, five, six, seven, eight, nine, or ten) additional target-binding domains (e.g., any of the exemplary target-binding domains described herein or known in the art) at the N-terminal end and/or the C-terminal end of the second chimeric polypeptide. In some embodiments, at least one of the one or more additional target-binding domains (e.g., any of the exemplary target-binding domains described herein or known in the art) directly abuts the second domain of the pair of affinity domains (e.g., any of the exemplary second domains of any of the exemplary pairs of affinity domains described herein) in the second chimeric polypeptide. In some embodiments, the second chimeric polypeptide further includes a linker sequence (e.g., any of the exemplary linker sequences described herein or known in the art) between at least one of the one or more additional target-binding domains (e.g., any of the exemplary target-binding domains described herein or known in the art) and the second domain of the pair of affinity domains (e.g., any of the second domains described herein of any of the exemplary pairs of affinity domains described herein) in the second chimeric polypeptide. In some embodiments, at least one of the one or more additional target-binding domains (e.g., any of the exemplary target-binding domains described herein or known in the art) directly abuts the second target-binding domain (e.g., any of the target-binding domains described herein or known in the art) in the second chimeric polypeptide. In some embodiments, the second chimeric polypeptide further includes a linker sequence (e.g., any of the exemplary linker sequences described herein or known in the art) between at least one of the one or more additional target-binding domains (e.g., any of the exemplary target binding domains described herein or known in the art) and the second target-binding domain (e.g., any of the exemplary target binding domains described herein or known in the art) in the second chimeric polypeptide.

In some embodiments of any of the multi-chain chimeric polypeptides described herein, two or more (e.g., three or more, four or more, five or more, six or more, seven or more, eight or more, nine or more, or ten or more) of the first target-binding domain, the second target-binding domain, and the one or more additional target-binding domains bind specifically to the same antigen. In some embodiments, two or more (e.g., three or more, four or more, five or more, six or more, seven or more, eight or more, nine or more, or ten or more) of the first target-binding domain, the second target-binding domain, and the one or more additional target-binding domains bind specifically to the same epitope. In some embodiments, two or more (e.g., three or more, four or more, five or more, six or more, seven or more, eight or more, nine or more, or ten or more) of the first target-binding domain, the second target-binding domain, and the one or more additional target-binding domains include the same amino acid sequence. In some embodiments, the first target-binding domain, the second target-binding domain, and the one or more additional target-binding domains each bind specifically to the same antigen. In some embodiments, the first target-binding domain, the second target-binding domain, and the one or more additional target-binding domains each bind specifically to the same epitope. In some embodiments, the first target-binding domain, the second target-binding domain, and the one or more additional target-binding domains each include the same amino acid sequence.

In some embodiments of any of the multi-chain chimeric polypeptides described herein, the first target-binding domain, the second target-binding domain, and the one or more additional target-binding domains bind specifically to different antigens. In some embodiments of any of the multi-chain chimeric polypeptides described herein, one or more (e.g., two or more, three or more, four or more, five or more, six or more, seven or more, eight or more, nine or more, or ten or more) of the first target-binding domain, the second target-binding domain, and the one or more target-binding domains is an antigen-binding domain. In some embodiments, the first target-binding domain, the second target-binding domain, and the one or more additional target-binding domains are each an antigen-binding domain (e.g., a scFv or a single-domain antibody).

Pairs of Affinity Domains

In some embodiments, a multi-chain chimeric polypeptide includes: 1) a first chimeric polypeptide that includes a first domain of a pair of affinity domains, and 2) a second chimeric polypeptide that includes a second domain of a pair of affinity domains such that the first chimeric polypeptide and the second chimeric polypeptide associate through the binding of the first domain and the second domain of the pair of affinity domains. In some embodiments, the pair of affinity domains is a sushi domain from an alpha chain of human IL-15 receptor (IL15Rα) and a soluble IL-15. A sushi domain, also known as a short consensus repeat or type 1 glycoprotein motif, is a common motif in protein-protein interaction. Sushi domains have been identified on a number of protein-binding molecules, including complement components C1r, C1s, factor H, and C2m, as well as the nonimmunologic molecules factor XIII and B2-glycoprotein. A typical Sushi domain has approximately 60 amino acid residues and contains four cysteines (Ranganathan, Pac. Symp Biocomput. 2000:155-67). The first cysteine can form a disulfide bond with the third cysteine, and the second cysteine can form a disulfide bridge with the fourth cysteine. In some embodiments in which one member of the pair of affinity domains is a soluble IL-15, the soluble IL15 has a D8N or D8A amino acid substitution. In some embodiments in which one member of the pair of affinity domains is an alpha chain of human IL-15 receptor (IL15Rα), the human IL15Rα is a mature full-length IL15Rα. In some embodiments, the pair of affinity domains is barnase and barnstar. In some embodiments, the pair of affinity domains is a PKA and an AKAP. In some embodiments, the pair of affinity domains is an adapter/docking tag module based on mutated RNase I fragments (Rossi, *Proc Natl Acad Sci USA*. 103:

6841-6846, 2006; Sharkey et al., *Cancer Res.* 68:5282-5290, 2008; Rossi et al., *Trends Pharmacol Sci.* 33:474-481, 2012) or SNARE modules based on interactions of the proteins syntaxin, synaptotagmin, synaptobrevin, and SNAP25 (Deyev et al., *Nat Biotechnol.* 1486-1492, 2003).

In some embodiments, a first chimeric polypeptide of a multi-chain chimeric polypeptide includes a first domain of a pair of affinity domains and a second chimeric polypeptide of the multi-chain chimeric polypeptide includes a second domain of a pair of affinity domains, wherein the first domain of the pair of affinity domains and the second domain of the pair of affinity domains bind to each other with a dissociation equilibrium constant ($K_D$) of less than $1 \times 10^{-7}$ M, less than $1 \times 10^{-8}$ M, less than $1 \times 10^{-9}$ M, less than $1 \times 10^{-10}$ M, less than $1 \times 10^{-11}$ M, less than $1 \times 10^{-12}$ M, or less than $1 \times 10^{-13}$ M. In some embodiments, the first domain of the pair of affinity domains and the second domain of the pair of affinity domains bind to each other with a $K_D$ of about $1 \times 10^{-4}$ M to about $1 \times 10^{-6}$ M, about $1 \times 10^{-5}$ M to about $1 \times 10^{-7}$ M, about $1 \times 10^{-6}$ M to about $1 \times 10^{-8}$ M, about $1 \times 10^{-7}$ M to about $1 \times 10^{-9}$ M, about $1 \times 10^{-8}$ M to about $1 \times 10^{-10}$ M, about $1 \times 10^{-9}$ M to about $1 \times 10^{-11}$ M, about $1 \times 10^{-10}$ M to about $1 \times 10^{-12}$ M, about $1 \times 10^{-11}$ M to about $1 \times 10^{-13}$ M, about $1 \times 10^{-4}$ M to about $1 \times 10^{-5}$ M, about $1 \times 10^{-5}$ M to about $1 \times 10^{-6}$ M, about $1 \times 10^{-6}$ M to about $1 \times 10^{-7}$ M, about $1 \times 10^{-7}$ M to about $1 \times 10^{-8}$ M, about $1 \times 10^{-8}$ M to about $1 \times 10^{-9}$ M, about $1 \times 10^{-9}$ M to about $1 \times 10^{-10}$ M, about $1 \times 10^{-10}$ M to about $1 \times 10^{-11}$ M, about $1 \times 10^{-11}$ M to about $1 \times 10^{-12}$ M, or about $1 \times 10^{-12}$ M to about $1 \times 10^{-13}$ M (inclusive). Any of a variety of different methods known in the art can be used to determine the $K_D$ value of the binding of the first domain of the pair of affinity domains and the second domain of the pair of affinity domains (e.g., an electrophoretic mobility shift assay, a filter binding assay, surface plasmon resonance, and a biomolecular binding kinetics assay, etc.).

In some embodiments, a first chimeric polypeptide of a multi-chain chimeric polypeptide includes a first domain of a pair of affinity domains and a second chimeric polypeptide of the multi-chain chimeric polypeptide includes a second domain of a pair of affinity domains, wherein the first domain of the pair of affinity domains, the second domain of the pair of affinity domains, or both is about 10 to 100 amino acids in length. For example, a first domain of a pair of affinity domains, a second domain of a pair of affinity domains, or both can be about 10 to 100 amino acids in length, about 15 to 100 amino acids in length, about 20 to 100 amino acids in length, about 25 to 100 amino acids in length, about 30 to 100 amino acids in length, about 35 to 100 amino acids in length, about 40 to 100 amino acids in length, about 45 to 100 amino acids in length, about 50 to 100 amino acids in length, about 55 to 100 amino acids in length, about 60 to 100 amino acids in length, about 65 to 100 amino acids in length, about 70 to 100 amino acids in length, about 75 to 100 amino acids in length, about 80 to 100 amino acids in length, about 85 to 100 amino acids in length, about 90 to 100 amino acids in length, about 95 to 100 amino acids in length, about 10 to 95 amino acids in length, about 10 to 90 amino acids in length, about 10 to 85 amino acids in length, about 10 to 80 amino acids in length, about 10 to 75 amino acids in length, about 10 to 70 amino acids in length, about 10 to 65 amino acids in length, about 10 to 60 amino acids in length, about 10 to 55 amino acids in length, about 10 to 50 amino acids in length, about 10 to 45 amino acids in length, about 10 to 40 amino acids in length, about 10 to 35 amino acids in length, about 10 to 30 amino acids in length, about 10 to 25 amino acids in length, about 10 to 20 amino acids in length, about 10 to 15 amino acids in length, about 20 to 30 amino acids in length, about 30 to 40 amino acids in length, about 40 to 50 amino acids in length, about 50 to 60 amino acids in length, about 60 to 70 amino acids in length, about 70 to 80 amino acids in length, about 80 to 90 amino acids in length, about 90 to 100 amino acids in length, about 20 to 90 amino acids in length, about 30 to 80 amino acids in length, about 40 to 70 amino acids in length, about 50 to 60 amino acids in length, or any range in between. In some embodiments, a first domain of a pair of affinity domains, a second domain of a pair of affinity domains, or both is about 10, 15, 20, 25, 30, 35, 40, 45, 50, 55, 60, 65, 70, 75, 80, 85, 90, 95, or 100 amino acids in length.

In some embodiments, any of the first and/or second domains of a pair of affinity domains disclosed herein can include one or more additional amino acids (e.g., 1, 2, 3, 5, 6, 7, 8, 9, 10, or more amino acids) at its N-terminus and/or C-terminus, so long as the function of the first and/or second domains of a pair of affinity domains remains intact. For example, a sushi domain from an alpha chain of human IL-15 receptor (IL15Rα) can include one or more additional amino acids at the N-terminus and/or the C-terminus, while still retaining the ability to bind to a soluble IL-15. Additionally or alternatively, a soluble IL-15 can include one or more additional amino acids at the N-terminus and/or the C-terminus, while still retaining the ability to bind to a sushi domain from an alpha chain of human IL-15 receptor (IL15Rα).

A non-limiting example of a sushi domain from an alpha chain of IL-15 receptor alpha (IL15Rα) can include a sequence that is at least 70% identical, at least 75% identical, at least 80% identical, at least 85% identical, at least 90% identical, at least 95% identical, at least 99% identical, or 100% identical to (SEQ ID NO: 123)
ITCPPPMSVEHADIWVKSYSLYSRERYICNSGFKRKAGTSSLTECVLNKA

TNVAHWTTPSLKCIR.

In some embodiments, a sushi domain from an alpha chain of IL15Rα can be encoded by a nucleic acid including (SEQ ID NO: 124)
ATTACATGCCCCCCTCCCATGAGCGTGGAGCACGCCGACATCTGGGTGAA

GAGCTATAGCCTCTACAGCCGGGAGAGGTATATCTGTAACAGCGGCTTCA

AGAGGAAGGCCGGCACCAGCAGCCTCACCGAGTGCGTGCTGAATAAGGCT

ACCAACGTGGCTCACTGGACAACACCCTCTTTAAAGTGCATCCGG.

In some embodiments, a soluble IL-15 can include a sequence that is at least 70% identical, at least 75% identical, at least 80% identical, at least 85% identical, at least 90% identical, at least 95% identical, at least 99% identical, or 100% identical to (SEQ ID NO: 125)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS.

In some embodiments, a soluble IL-15 can be encoded by a nucleic acid including the sequence of

```
                                          (SEQ ID NO: 126)
AACTGGGTGAACGTCATCAGCGATTTAAAGAAGATCGAAGATTTAATTCA

GTCCATGCATATCGACGCCACTTTATACACAGAATCCGACGTGCACCCCT

CTTGTAAGGTGACCGCCATGAAATGTTTTTTACTGGAGCTGCAAGTTATC

TCTTTAGAGAGCGGAGACGCTAGCATCCACGACACCGTGGAGAATTTAAT

CATTTTAGCCAATAACTCTTTATCCAGCAACGGCAACGTGACAGAGTCCG

GCTGCAAGGAGTGCGAAGAGCTGGAGGAGAAGAACATCAAGGAGTTTCTG

CAATCCTTTGTGCACATTGTCCAGATGTTCATCAATACCTCC.
```

Exemplary Multi-Chain Chimeric Polypeptides—Type A

In some embodiments of any of the multi-chain chimeric polypeptides described herein, the first target-binding domain and the second targeting-binding domain each independently bind specifically to a receptor of IL-18 or a receptor of IL-12. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, one or both of the first target-binding domain and the second target-binding domain is a soluble IL-15 or a soluble IL-18. In some embodiments of these multi-chain chimeric polypeptides, the first target-binding domain and the second target-binding domain are each independently a soluble IL-15 or a soluble IL-18. In some embodiments of these multi-chain chimeric polypeptides, the first target-binding domain and the second target-binding domain both bind specifically to a receptor of IL-18 or a receptor of IL-12. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain binds specifically to a receptor for IL-12, and the second target-binding domain binds specifically to a receptor for IL-18. In some embodiments of these multi-chain chimeric polypeptides, the first target-binding domain binds specifically to a receptor for IL-18, and the second target-binding domain bind specifically to a receptor for IL-12.

In some embodiments of these multi-chain chimeric polypeptides, the first target-binding domain includes a soluble IL-18 (e.g., a soluble human IL-18).

In some embodiments of these multi-chain chimeric polypeptides, the second target-binding domain includes a soluble IL-12 (e.g., a soluble human IL-12). In some embodiments of these multi-chain chimeric polypeptides, the soluble human IL-15 includes a sequence of soluble human IL-12β (p40) and a sequence of soluble human IL-12α (p35). In some embodiments of these multi-chain chimeric polypeptides, the soluble IL-15 human IL-15 further includes a linker sequence (e.g., any of the exemplary linker sequences described herein) between the sequence of soluble IL-12β (p40) and the sequence of soluble human IL-12α (p35).

Exemplary Multi-Chain Chimeric Polypeptides—Type B

In some embodiments of any of the multi-chain chimeric polypeptides described herein, the first target-binding domain and the second targeting-binding domain each independently bind specifically to a receptor of IL-21 or to TGF-β. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, one or both of the first target-binding domain and the second target-binding domain is a soluble IL-21 (e.g., a soluble human IL-21 polypeptide) or a soluble TGF-β receptor (e.g., a soluble TGFRβRII receptor). In some embodiments of these multi-chain chimeric polypeptides, the first target-binding domain and the second target-binding domain are each independently a soluble IL-21 or a soluble TGF-β receptor (e.g., a soluble TGFRβRII receptor). In some embodiments of these multi-chain chimeric polypeptides, the first target-binding domain and the second target-binding domain both bind specifically to a receptor of IL-21 or to TGF-β. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain binds specifically to a receptor for IL-21, and the second target-binding domain binds specifically to TGF-β. In some embodiments of these multi-chain chimeric polypeptides, the first target-binding domain binds specifically to TGF-β, and the second target-binding domain bind specifically to a receptor for IL-21.

In some embodiments of these multi-chain chimeric polypeptides, the second target-binding domain includes a soluble TGF-β receptor (e.g., a soluble TGFRβRII receptor (e.g., a soluble human TGFRβRII receptor)). In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII.

Exemplary Multi-Chain Chimeric Polypeptides—Type C

In some embodiments of any of the multi-chain chimeric polypeptides described herein, the first target-binding domain and the second targeting-binding domain each independently bind specifically to a receptor of IL-7 or a receptor of IL-21. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, one or both of the first target-binding domain and the second target-binding domain is a soluble IL-21 (e.g., a soluble human IL-21 polypeptide) or a soluble IL-7 (e.g., a soluble human IL-7 polypeptide). In some embodiments of these multi-chain chimeric polypeptides, the first target-binding domain and the second target-binding domain are each independently a soluble IL-21 or a soluble IL-7. In some embodiments of these multi-chain chimeric polypeptides, the first target-binding domain and the second target-binding domain both bind specifically to a receptor of IL-21 or a receptor of IL-7. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain binds specifically to a receptor for IL-21, and the second target-binding domain binds specifically to a receptor for IL-7. In some embodiments of these multi-chain chimeric polypeptides, the first target-binding domain binds specifically to a receptor for IL-7, and the second target-binding domain binds specifically to a receptor for IL-21.

In some embodiments of these multi-chain chimeric polypeptides, the first target-binding domain includes a soluble IL-21 (e.g., a soluble human IL-21).

Exemplary Multi-Chain Chimeric Polypeptides—Type D

In some embodiments of any of the multi-chain chimeric polypeptides described herein, the first target-binding domain and the second targeting-binding domain each independently bind specifically to a receptor of IL-7 or a receptor of IL-21. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, one or both of the first target-binding domain and the second target-binding domain is a soluble IL-21 (e.g., a soluble human IL-21 polypeptide) or a soluble IL-7 (e.g., a soluble human IL-7 polypeptide). In some embodiments of these multi-chain chimeric polypeptides, the first target-binding domain and the second target-binding domain are each independently a soluble IL-21 or a soluble IL-7. In some embodiments of these multi-chain chimeric polypeptides, the first target-binding domain and the second target-binding domain both bind specifically to a receptor of IL-21 or a receptor of IL-7. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain binds specifically to a receptor for IL-21, and the second target-binding domain binds specifically to a receptor for IL-7. In some embodiments of these multi-chain chimeric polypeptides, the first target-binding domain binds specifically to a receptor for IL-7, and the second target-binding domain binds specifically to a receptor for IL-21.

Exemplary Multi-Chain Chimeric Polypeptides—Type E

In some embodiments of any of the multi-chain chimeric polypeptides described herein, the first target-binding domain and the second targeting-binding domain each independently bind specifically to a receptor for IL-18 (e.g., a soluble human IL-18), a receptor for IL-12 (e.g., a soluble human IL-12), or CD16 (e.g., an anti-CD16 scFv). In some embodiments of these multi-chain chimeric polypeptides described herein, the first chimeric polypeptide further includes the additional target-binding domain. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to CD16 or a receptor for IL-12.

In some embodiments of these multi-chain chimeric polypeptides, one or both of the first target-binding domain and the second target-binding domain is a soluble IL-15 or a soluble IL-18. In some embodiments of these multi-chain chimeric polypeptides, the first target-binding domain and the second target-binding domain are each independently a soluble IL-15 or a soluble IL-18. In some embodiments of these multi-chain chimeric polypeptides, the first target-binding domain and the second target-binding domain both bind specifically to a receptor of IL-18 or a receptor of IL-12. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain binds specifically to a receptor for IL-12, and the second target-binding domain binds specifically to a receptor for IL-18. In some embodiments of these multi-chain chimeric polypeptides, the first target-binding domain binds specifically to a receptor for IL-18, and the second target-binding domain bind specifically to a receptor for IL-12. In some embodiments of these multi-chain chimeric polypeptides, the first target-binding domain binds specifically to CD16, and the second target-binding domain binds specifically to a receptor for IL-18. In some embodiments of these multi-chain chimeric polypeptides, the first target-binding domain binds specifically to a receptor for IL-18, and the second target-binding domain bind specifically to CD16.

In some embodiments of these multi-chain chimeric polypeptides, two or more of the first target-binding domain, the second target-binding domain, and the one or more additional target-binding domains bind specifically to the same antigen. In some embodiments, two or more of the first target-binding domain, the second target-binding domain, and the one or more additional target-binding domains bind specifically to the same epitope. In some embodiments, two or more of the first target-binding domain, the second target-binding domain, and the one or more additional target-binding domains comprise the same amino acid sequence.

In some embodiments of these multi-chain chimeric polypeptides, the first target-binding domain includes a soluble IL-18 (e.g., a soluble human IL-18).

Exemplary Multi-Chain Chimeric Polypeptides—Type F

In some embodiments of any of the multi-chain chimeric polypeptides described herein, the first target-binding domain and the second targeting-binding domain each independently bind specifically to a receptor for IL-7 (e.g., a soluble human IL-7), CD16 (e.g., an anti-CD16 scFv), or a receptor for IL-21 (e.g., a soluble human IL-21). In some embodiments of these multi-chain chimeric polypeptides described herein, the first chimeric polypeptide further includes the additional target-binding domain. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to CD16 or a receptor for IL-21.

In some embodiments of any of the multi-chain chimeric polypeptides described herein, the first target-binding domain binds specifically to a receptor IL-7 and the second target-binding domain binds specifically to CD16 or a receptor for IL-21. In some embodiments of any of the multi-chain chimeric polypeptides described herein, the first target-binding domain includes a soluble IL-7 protein. In some embodiments of any of the multi-chain chimeric polypeptides described herein, the soluble IL-7 protein is a soluble human IL-7. In some embodiments of any of the multi-chain chimeric polypeptides described herein, the second antigen-binding domain includes a target-binding domain that binds specifically to CD16. In some embodiments of any of the multi-chain chimeric polypeptides described herein, the second target-binding domain includes an scFv that binds specifically to CD16. In some embodiments of any of the multi-chain chimeric polypeptides described herein, the second target-binding domain binds specifically to a receptor for IL-21. In some embodiments of any of the multi-chain chimeric polypeptides described herein, the second target-binding domain includes a soluble IL-21. In some embodiments of any of the multi-chain chimeric polypeptides described herein, the soluble IL-21 is a soluble human IL-21. In some embodiments of any of the multi-chain chimeric polypeptides described herein, the second chimeric polypeptide further includes an additional target-binding domain that binds specifically to a receptor for IL-21. In some embodiments of any of the multi-chain chimeric polypeptides described herein, the additional target-binding domain includes a soluble IL-21. In some embodiments of any of the multi-chain chimeric polypeptides described herein, the soluble IL-21 is a soluble human IL-21. In some embodiments of any of the multi-chain chimeric polypeptides described herein, the second chimeric polypeptide further includes an additional target-binding domain that binds specifically to CD16.

In some embodiments of these multi-chain chimeric polypeptides, two or more of the first target-binding domain, the second target-binding domain, and the one or more additional target-binding domains bind specifically to the same antigen. In some embodiments, two or more of the first target-binding domain, the second target-binding domain, and the one or more additional target-binding domains bind specifically to the same epitope. In some embodiments, two or more of the first target-binding domain, the second target-binding domain, and the one or more additional target-binding domains comprise the same amino acid sequence.

In some embodiments of these multi-chain chimeric polypeptides, the first target-binding domain includes a soluble IL-7 (e.g., a soluble human IL-7).

Exemplary Multi-Chain Chimeric Polypeptides—Type G

In some embodiments of any of the multi-chain chimeric polypeptides described herein, the first target-binding domain and the second targeting-binding domain each independently bind specifically to TGFβ (e.g., a human TGFβRII receptor), CD16 (e.g., an anti-CD16 scFv), or a receptor for IL-21 (e.g., a soluble human IL-21). In some embodiments of these multi-chain chimeric polypeptides described herein, the first chimeric polypeptide further includes the additional target-binding domain. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to CD16 or a receptor for IL-21.

In some embodiments of any of the multi-chain chimeric polypeptides described herein, the first target-binding domain and the second targeting-binding domain each independently bind specifically to TGF-β, CD16, or a receptor for IL-21. In some embodiments of any of the multi-chain chimeric polypeptides described herein, the first target-binding domain binds specifically to a TGF-β and the second target-binding domain binds specifically to CD16 or a receptor of IL-21. In some embodiments of any of the multi-chain chimeric polypeptides described herein, the first target-binding domain is a soluble TGF-β receptor. In some embodiments of any of the multi-chain chimeric polypeptides described herein, soluble TGF-β receptor is a soluble TGFβRII receptor. In some embodiments of any of the multi-chain chimeric polypeptides described herein, the second target-binding domain binds specifically to CD16. In some embodiments of any of the multi-chain chimeric polypeptides described herein, the second antigen-binding domain includes an antigen-binding domain that binds specifically to CD16. In some embodiments of any of the multi-chain chimeric polypeptides described herein, the second antigen-binding domain includes an scFv that binds specifically to CD16. In some embodiments of any of the multi-chain chimeric polypeptides described herein, the second target-binding domain binds specifically to a receptor for IL-21. In some embodiments of any of the multi-chain chimeric polypeptides described herein, the second target-binding domain includes a soluble IL-21. In some embodiments of any of the multi-chain chimeric polypeptides described herein, the second target-binding domain includes a soluble human IL-21. In some embodiments of any of the multi-chain chimeric polypeptides described herein, the second chimeric polypeptide further includes an additional target-binding domain that binds specifically to a receptor for IL-21. In some embodiments of any of the multi-chain chimeric polypeptides described herein, the additional target-binding domain includes a soluble IL-21. In some embodiments of any of the multi-chain chimeric polypeptides described herein, the soluble IL-21 is a soluble human IL-21. In some embodiments of any of the multi-chain chimeric polypeptides described herein, the second chimeric polypeptide further includes an additional target-binding domain that binds specifically to CD16.

In some embodiments of these multi-chain chimeric polypeptides, two or more of the first target-binding domain, the second target-binding domain, and the one or more additional target-binding domains bind specifically to the same antigen. In some embodiments, two or more of the first target-binding domain, the second target-binding domain, and the one or more additional target-binding domains bind specifically to the same epitope. In some embodiments, two or more of the first target-binding domain, the second target-binding domain, and the one or more additional target-binding domains comprise the same amino acid sequence.

In some embodiments of these multi-chain chimeric polypeptides, the first target-binding domain includes a TGFβRII receptor (e.g., a soluble human TGFβRII receptor). In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII.

Exemplary Multi-Chain Chimeric Polypeptides—Type H

In some embodiments of any of the multi-chain chimeric polypeptides described herein, the first target-binding domain and the second targeting-binding domain each independently bind specifically to a receptor of IL-7. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

Exemplary Multi-Chain Chimeric Polypeptides—Type I

In some embodiments of any of the multi-chain chimeric polypeptides described herein, the first target-binding domain and the second targeting-binding domain each independently bind specifically to TGF-β. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the first target-binding domain and the second target-binding domain each independently bind specifically to TGF-β. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain and the second target-binding domain is a soluble TGF-β receptor (e.g., a soluble TGFβRII receptor, e.g., a soluble human TGFβRII). In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII.

Exemplary Multi-Chain Chimeric Polypeptides—Type J

In some embodiments of any of the multi-chain chimeric polypeptides described herein, the first target-binding domain and the second targeting-binding domain each independently bind specifically to a receptor of IL-7, a receptor of IL-21, or a receptor of CD137L. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to a receptor for IL-21 (e.g., a soluble IL-21, e.g., a soluble human IL-21) or a receptor for CD137L (e.g., a soluble CD137L, e.g., a soluble human CD137L).

In some embodiments of these multi-chain chimeric polypeptides, the first target-binding domain binds specifically to a receptor for IL-7, and the second target-binding domain binds specifically to a receptor for IL-21 or a receptor for CD137L. In some embodiments, the additional target-binding domain binds specifically to a receptor for IL-21 or a receptor for CD137L.

Exemplary Multi-Chain Chimeric Polypeptides—Type K

In some embodiments of any of the multi-chain chimeric polypeptides described herein, the first target-binding domain and the second targeting-binding domain each independently bind specifically to a receptor of IL-7 or TGF-β. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the first target-binding domain binds specifically to a receptor for IL-7, and the second target-binding domain binds specifically to TGF-β. In some embodiments of these multi-chain chimeric polypeptides, the first target-binding domain binds specifically to TGF-β, and the second target-binding domain binds specifically to a receptor for IL-7.

In some embodiments of these multi-chain chimeric polypeptides, the second target-binding domain comprises a target-binding domain that binds specifically to TGF-β. In some embodiments of these multi-chain chimeric polypeptides, the second target-binding domain is a soluble TGF-β receptor (e.g., a soluble TGFβRII receptor, e.g., a soluble human TGFβRII receptor). In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII.

Exemplary Multi-Chain Chimeric Polypeptides—Type L

In some embodiments of any of the multi-chain chimeric polypeptides described herein, the first target-binding domain and the second targeting-binding domain each independently bind specifically to TGF-β, a receptor of IL-21, or a receptor of CD137L. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to a receptor for IL-21 (e.g., a soluble IL-21, e.g., a soluble human IL-21) or a receptor for CD137L (e.g., a soluble CD137L, e.g., a soluble human CD137L).

In some embodiments of these multi-chain chimeric polypeptides, the first target-binding domain binds specifically to TGF-β and the second target-binding domain binds specifically to a receptor for IL-21 or a receptor for CD137L.

In some embodiments of these multi-chain chimeric polypeptides, the first target-binding domain is a soluble TGF-β receptor (e.g., a soluble TGFβRII receptor, e.g., a soluble human TGFβRII receptor). In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII.

Exemplary Multi-Chain Chimeric Polypeptides—Type M

In some embodiments of any of the multi-chain chimeric polypeptides described herein, the first target-binding domain and the second targeting-binding domain each independently bind specifically to TGF-β or a receptor of IL-21. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to a receptor for IL-21 (e.g., a soluble IL-21, e.g., a soluble human IL-21) or a TGF-β (e.g., a soluble TGF-β receptor, e.g., a soluble TGFβRII receptor).

In some embodiments of these multi-chain chimeric polypeptides, the first target-binding domain binds specifically to TGF-β, and the second target-binding domain binds specifically to TGF-β or a receptor for IL-21. In some embodiments of these multi-chain chimeric polypeptides, the first target-binding domain is a soluble TGF-β receptor (e.g., a soluble TGFβRII receptor, e.g., a soluble human TGFβRII receptor). In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII.

Exemplary Multi-Chain Chimeric Polypeptides—Type N

In some embodiments of any of the multi-chain chimeric polypeptides described herein, the first target-binding domain and the second targeting-binding domain each independently bind specifically to TGF-β or CD16. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to CD16 (e.g., an anti-CD16 scFv) or a TGF-β (e.g., a soluble TGF-β receptor, e.g., a soluble TGFβRII receptor).

In some embodiments of these multi-chain chimeric polypeptides, the first target-binding domain binds specifically to TGF-β, and the second target-binding domain binds specifically to TGF-β or CD16. In some embodiments of these multi-chain chimeric polypeptides, the first target-binding domain is a soluble TGF-β receptor (e.g., a soluble TGFβRII receptor, e.g., a soluble human TGFβRII receptor). In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII.

Exemplary Multi-Chain Chimeric Polypeptides—Type O

In some embodiments of any of the multi-chain chimeric polypeptides described herein, the first target-binding domain and the second targeting-binding domain each independently bind specifically to TGF-β or a receptor of CD137L. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to a receptor to TGF-β (e.g., a soluble TGF-β receptor, e.g., a soluble TGFβRII receptor) or CD137L.

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide. In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, the first target-binding domain binds specifically to TGF-β, and the second target-binding domain binds specifically to CD137L. In some embodiments of these multi-chain chimeric polypeptides, the first target-binding domain or the additional target-binding domain is a soluble TGF-β receptor (e.g., a soluble TGFβRII receptor, e.g., a soluble human TGFβRII receptor).

In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII.

Sequences of Exemplary Multi-Chain Chimeric Polypeptides

The nucleic acid sequence of an IL12/IL-15RαSu construct (including signal peptide sequence) is as follows

```
(SEQ ID NO: 30):
(Signal peptide)
                                      (SEQ ID NO: 131)
ATGAAATGGGTGACCTTTATTTCTTTACTGTTCCTCTTTAGCAGCGCCTA

CTCC (Human IL-12 subunit beta (p40))
                                      (SEQ ID NO: 132)
ATTTGGGAACTGAAGAAGGACGTCTACGTGGTCGAACTGGACTGGTATCC

CGATGCTCCCGGCGAAATGGTGGTGCTCACTTGTGACACCCCCGAAGAAG

ACGGCATCACTTGGACCCTCGATCAGAGCAGCGAGGTGCTGGGCTCCGGA

AAGACCCTCACAATCCAAGTTAAGGAGTTCGGAGACGCTGGCCAATACAC

ATGCCACAAGGGAGGCGAGGTGCTCAGCCATTCCTTATTATTATTACACA

AGAAGGAAGACGGAATCTGGTCCACCGACATTTTAAAAGATCAGAAGGAG

CCCAAGAATAAGACCTTTTTAAGGTGTGAGGCCAAAAACTACAGCGGTCG

TTTCACTTGTTGGTGGCTGACCACCATTTCCACCGATTTAACCTTCTCCG

TGAAAAGCAGCCGGGGAAGCTCCGACCCTCAAGGTGTGACATGTGGAGCC

GCTACCCTCAGCGCTGAGAGGGTTCGTGGCGATAACAAGGAATACGAGTA

CAGCGTGGAGTGCCAAGAAGATAGCGCTTGTCCCGCTGCCGAAGAATCTT

TACCCATTGAGGTGATGGTGGACGCCGTGCACAAACTCAAGTACGAGAAC

TACACCTCCTCCTTCTTTATCCGGGACATCATTAAGCCCGATCCTCCTAA

GAATTTACAGCTGAAGCCTCTCAAAAATAGCCGGCAAGTTGAGGTCTCTT
```

```
GGGAATATCCCGACACTTGGAGCACACCCCACAGCTACTTCTCTTTAACC

TTTTGTGTGCAAGTTCAAGGTAAAAGCAAGCGGGAGAAGAAAGACCGGGT

GTTTACCGACAAAACCAGCGCCACCGTCATCTGTCGGAAGAACGCCTCCA

TCAGCGTGAGGGCTCAAGATCGTTATTACTCCAGCAGCTGGTCCGAGTGG

GCCAGCGTGCCTTGTTCC (Linker)
                                      (SEQ ID NO: 133)
GGCGGTGGAGGATCCGGAGGAGGTGGCTCCGGCGGCGGAGGATCT (Human IL-12 subunit alpha (p35))
                                      (SEQ ID NO: 134)
CGTAACCTCCCCGTGGCTACCCCCGATCCCGGAATGTTCCCTTGTTTACA

CCACAGCCAGAATTTACTGAGGGCCGTGAGCAACATGCTGCAGAAAGCTA

GGCAGACTTTAGAATTTTACCCTTGCACCAGCGAGGAGATCGACCATGAA

GATATCACCAAGGACAAGACATCCACCGTGGAGGCTTGTTTACCTCTGGA

GCTGACAAAGAACGAGTCTTGTCTCAACTCTCGTGAAACCAGCTTCATCA

CAAATGGCTCTTGTTTAGCTTCCCGGAAGACCTCCTTTATGATGGCTTTA

TGCCTCAGCTCCATCTACGAGGATTTAAAGATGTACCAAGTGGAGTTCAA

GACCATGAACGCCAAGCTGCTCATGGACCCTAAACGGCAGATCTTTTTAG

ACCAGAACATGCTGGCTGTGATTGATGAGCTGATGCAAGCTTTAAACTTC

AACTCCGAGACCGTCCCTCAGAAGTCCTCCCTCGAGGAGCCCGATTTTTA

CAAGACAAAGATCAAACTGTGCATTTTACTCCACGCCTTTAGGATCCGGG

CCGTGACCATTGACCGGGTCATGAGCTATTTAAACGCCAGC (Human IL-15R a sushi domain)
                                      (SEQ ID NO: 135)
ATTACATGCCCCCCTCCCATGAGCGTGGAGCACGCCGACATCTGGGTGAA

GAGCTATAGCCTCTACAGCCGGGAGAGGTATATCTGTAACAGCGGCTTCA

AGAGGAAGGCCGGCACCAGCAGCCTCACCGAGTGCGTGCTGAATAAGGCT

ACCAACGTGGCTCACTGGACAACACCCTCTTTAAAGTGCATCCGG
```

The amino acid sequence of an IL12/IL-15RαSu fusion protein (including signal peptide sequence) is as follows

```
(SEQ ID NO: 31):
(Signal peptide)
                                      (SEQ ID NO: 136)
MKWVTFISLLFLFSSAYS (Human IL-12 subunit beta (p40))
                                      (SEQ ID NO: 137)
IWELKKDVYVVELDWYPDAPGEMVVLTCDTPEEDGITWTLDQSSEVLGSG

KTLTIQVKEFGDAGQYTCHKGGEVLSHSLLLLHKKEDGIWSTDILKDQKE

PKNKTFLRCEAKNYSGRFTCWWLTTISTDLTFSVKSSRGSSDPQGVTCGA

ATLSAERVRGDNKEYEYSVECQEDSACPAAEESLPIEVMVDAVHKLKYEN

YTSSFFIRDIIKPDPPKNLQLKPLKNSRQVEVSWEYPDTWSTPHSYFSLT

FCVQVQGKSKREKKDRVFTDKTSATVICRKNASISVRAQDRYYSSSWSEW

ASVPCS
```

```
(Linker)
                                         (SEQ ID NO: 138)
GGGGSGGGGSGGGGS (Human IL-12 subunit alpha (p35))
                                         (SEQ ID NO: 139)
RNLPVATPDPGMFPCLHHSQNLLRAVSNMLQKARQTLEFYPCTSEEIDHE

DITKDKTSTVEACLPLELTKNESCLNSRETSFITNGSCLASRKTSFMMAL

CLSSIYEDLKMYQVEFKTMNAKLLMDPKRQIFLDQNMLAVIDELMQALNF

NSETVPQKSSLEEPDFYKTKIKLCILLHAFRIRAVTIDRVMSYLNAS (Human IL-15R a sushi domain)
                                         (SEQ ID NO: 140)
ITCPPPMSVEHADIWVKSYSLYSRERYICNSGFKRKAGTSSLTECVLNKA

TNVAHWTTPSLKCIR
```

The nucleic acid sequence of an IL-18/TF/IL-15 construct is as follows

```
(SEQ ID NO: 32):
(Signal peptide)
                                         (SEQ ID NO: 141)
ATGAAGTGGGTCACATTTATCTCTTTACTGTTCCTCTTCTCCAGCGCCTA

CAGC (Human IL-18)
                                         (SEQ ID NO: 142)
TACTTCGGCAAACTGGAATCCAAGCTGAGCGTGATCCGGAATTTAAACGA

CCAAGTTCTGTTTATCGATCAAGGTAACCGGCCTCTGTTCGAGGACATGA

CCGACTCCGATTGCCGGGACAATGCCCCCCGGACCATCTTCATTATCTCC

ATGTACAAGGACAGCCAGCCCCGGGGCATGGCTGTGACAATTAGCGTGAA

GTGTGAGAAAATCAGCACTTTATCTTGTGAGAACAAGATCATCTCCTTTA

AGGAAATGAACCCCCCGATAACATCAAGGACACCAAGTCCGATATCATC

TTCTTCCAGCGGTCCGTGCCCGGTCACGATAACAAGATGCAGTTCGAATC

CTCCTCCTACGAGGGCTACTTTTTAGCTTGTGAAAAGGAGAGGGATTTAT

TCAAGCTGATCCTCAAGAAGGAGGACGAGCTGGGCGATCGTTCCATCATG

TTCACCGTCCAAAACGAGGAT (Human Tissue Factor 219)
                                         (SEQ ID NO: 143)
AGCGGCACAACCAACACAGTCGCTGCCTATAACCTCACTTGGAAGAGCAC

CAACTTCAAAACCATCCTCGAATGGGAACCCAAACCCGTTAACCAAGTTT

ACACCGTGCAGATCAGCACCAAGTCCGGCGACTGGAAGTCCAAATGTTTC

TATACCACCGACACCGAGTGCGATCTCACCGATGAGATCGTGAAAGATGT

GAAACAGACCTACCTCGCCCGGGTGTTTAGCTACCCCGCCGGCAATGTGG

AGAGCACTGGTTCCGCTGGCGAGCCTTTATACGAGAACAGCCCCGAATTT

ACCCCTTACCTCGAGACCAATTTAGGACAGCCCACCATCCAAAGCTTTGA

GCAAGTTGGCACAAAGGTGAATGTGACAGTGGAGGACGAGCGGACTTTAG

TGCGGCGGAACAACACCTTTCTCAGCCTCCGGGATGTGTTCGGCAAAGAT

TTAATCTACACACTGTATTACTGGAAGTCCTCTTCCTCCGGCAAGAAGAC

AGCTAAAACCAACACAAACGAGTTTTTAATCGACGTGGATAAAGGCGAAA

ACTACTGTTTCAGCGTGCAAGCTGTGATCCCCTCCCGGACCGTGAATAGG

AAAAGCACCGATAGCCCCGTTGAGTGCATGGGCCAAGAAAAGGGCGAGTT

CCGGGAG (Human IL-15)
                                         (SEQ ID NO: 144)
AACTGGGTGAACGTCATCAGCGATTTAAAGAAGATCGAAGATTTAATTCA

GTCCATGCATATCGACGCCACTTTATACACAGAATCCGACGTGCACCCCT

CTTGTAAGGTGACCGCCATGAAATGTTTTTTACTGGAGCTGCAAGTTATC

TCTTTAGAGAGCGGAGACGCTAGCATCCACGACACCGTGGAGAATTTAAT

CATTTTAGCCAATAACTCTTTATCCAGCAACGGCAACGTGACAGAGTCCG

GCTGCAAGGAGTGCGAAGAGCTGGAGGAGAAGAACATCAAGGAGTTTCTG

CAATCCTTTGTGCACATTGTCCAGATGTTCATCAATACCTCC
```

The amino acid sequence of an IL-18/TF/IL-15 fusion protein (including signal peptide sequence) is as follows

```
(SEQ ID NO: 33):
(Signal peptide)
                                         (SEQ ID NO: 145)
MKWVTFISLLFLFSSAYS (Human IL-18)
                                         (SEQ ID NO: 146)
YFGKLESKLSVIRNLNDQVLFIDQGNRPLFEDMTDSDCRDNAPRTIFIIS

MYKDSQPRGMAVTISVKCEKISTLSCENKIISFKEMNPPDNIKDTKSDII

FFQRSVPGHDNKMQFESSSYEGYFLACEKERDLFKLILKKEDELGDRSIM

FTVQNED (Human Tissue Factor 219)
                                         (SEQ ID NO: 147)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE (Human IL-15)
                                         (SEQ ID NO: 148)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS
```

The nucleic acid sequence of an IL-12/IL-15RαSu/αCD16scFv construct is as follows

```
(SEQ ID NO: 34):
(Signal peptide)
                                         (SEQ ID NO: 149)
ATGAAATGGGTGACCTTTATTTCTTTACTGTTCCTCTTTAGCAGCGCCTA

CTCC (Human IL-12 subunit beta (p40))
                                         (SEQ ID NO: 150)
ATTTGGGAACTGAAGAAGGACGTCTACGTGGTCGAACTGGACTGGTATCC

CGATGCTCCCGGCGAAATGGTGGTGCTCACTTGTGACACCCCCGAAGAAG

ACGGCATCACTTGGACCCTCGATCAGAGCAGCGAGGTGCTGGGCTCCGGA
```

-continued

AAGACCCTCACAATCCAAGTTAAGGAGTTCGGAGACGCTGGCCAATACAC

ATGCCACAAGGGAGGCGAGGTGCTCAGCCATTCCTTATTATTATTACACA

AGAAGGAAGACGGAATCTGGTCCACCGACATTTTAAAAGATCAGAAGGAG

CCCAAGAATAAGACCTTTTTAAGGTGTGAGGCCAAAAACTACAGCGGTCG

TTTCACTTGTTGGTGGCTGACCACCATTTCCACCGATTTAACCTTCTCCG

TGAAAAGCAGCCGGGGAAGCTCCGACCCTCAAGGTGTGACATGTGGAGCC

GCTACCCTCAGCGCTGAGAGGGTTCGTGGCGATAACAAGGAATACGAGTA

CAGCGTGGAGTGCCAAGAAGATAGCGCTTGTCCCGCTGCCGAAGAATCTT

TACCCATTGAGGTGATGGTGGACGCCGTGCACAAACTCAAGTACGAGAAC

TACACCTCCTCCTTCTTTATCCGGGACATCATTAAGCCCGATCCTCCTAA

GAATTTACAGCTGAAGCCTCTCAAAAATAGCCGGCAAGTTGAGGTCTCTT

GGGAATATCCCGACACTTGGAGACACACCCCACAGCTACTTCTCTTTAACC

TTTTGTGTGCAAGTTCAAGGTAAAAGCAAGCGGGAGAAGAAAGACCGGGT

GTTTACCGACAAAACCAGCGCCACCGTCATCTGTCGGAAGAACGCCTCCA

TCAGCGTGAGGGCTCAAGATCGTTATTACTCCAGCAGCTGGTCCGAGTGG

GCCAGCGTGCCTTGTTCC (Linker)
(SEQ ID NO: 151)
GGCGGTGGAGGATCCGGAGGAGGTGGCTCCGGCGGCGGAGGATCT (Human IL-12 subunit alpha (p35))
(SEQ ID NO: 152)
CGTAACCTCCCCGTGGCTACCCCCGATCCCGGAATGTTCCCTTGTTTACA

CCACAGCCAGAATTTACTGAGGGCCGTGAGCAACATGCTGCAGAAAGCTA

GGCAGACTTTAGAATTTTACCCTTGCACCAGCGAGGAGATCGACCATGAA

GATATCACCAAGGACAAGACATCCACCGTGGAGGCTTGTTTACCTCTGGA

GCTGACAAAGAACGAGTCTTGTCTCAACTCTCGTGAAACCAGCTTCATCA

CAAATGGCTCTTGTTTAGCTTCCCGGAAGACCTCCTTTATGATGGCTTTA

TGCCTCAGCTCCATCTACGAGGATTTAAAGATGTACCAAGTGGAGTTCAA

GACCATGAACGCCAAGCTGCTCATGGACCCTAAACGGCAGATCTTTTTAG

ACCAGAACATGCTGGCTGTGATTGATGAGCTGATGCAAGCTTTAAACTTC

AACTCCGAGACCGTCCCTCAGAAGTCCTCCCTCGAGGAGCCCGATTTTTA

CAAGACAAAGATCAAACTGTGCATTTTACTCCACGCCTTTAGGATCCGGG

CCGTGACCATTGACCGGGTCATGAGCTATTTAAACGCCAGC (Human IL-15R a sushi domain)
(SEQ ID NO: 153)
ATTACATGCCCCCCTCCCATGAGCGTGGAGCACGCCGACATCTGGGTGAA

GAGCTATAGCCTCTACAGCCGGGAGAGGTATATCTGTAACAGCGGCTTCA

AGAGGAAGGCCGGCACCAGCAGCCTCACCGAGTGCGTGCTGAATAAGGCT

ACCAACGTGGCTCACTGGACAACACCCTCTTTAAAGTGCATCCGG (anti-Human CD16 light chain variable domain)
(SEQ ID NO: 154)
TCCGAGCTGACCCAGGACCCTGCTGTGTCCGTGGCTCTGGGCCAGACCGT

GAGGATCACCTGCCAGGGCGACTCCCTGAGGTCCTACTACGCCTCCTGGT

ACCAGCAGAAGCCCGGCCAGGCTCCTGTGCTGGTGATCTACGGCAAGAAC

AACAGGCCCTCCGGCATCCCTGACAGGTTCTCCGGATCCTCCTCCGGCAA

CACCGCCTCCCTGACCATCACAGGCGCTCAGGCCGAGGACGAGGCTGACT

ACTACTGCAACTCCAGGGACTCCTCCGGCAACCATGTGGTGTTCGGCGGC

GGCACCAAGCTGACCGTGGGCCAT (Linker)
(SEQ ID NO: 155)
GGCGGCGGCGGCTCCGGAGGCGGCGGCAGCGGCGGAGGAGGATCC (anti-Human CD16 heavy chain variable domain)
(SEQ ID NO: 156)
GAGGTGCAGCTGGTGGAGTCCGGAGGAGGAGTGGTGAGGCCTGGAGGCTC

CCTGAGGCTGAGCTGTGCTGCCTCCGGCTTCACCTTCGACGACTACGGCA

TGTCCTGGGTGAGGCAGGCTCCTGGAAAGGGCCTGGAGTGGGTGTCCGGC

ATCAACTGGAACGGCGGATCCACCGGCTACGCCGATTCCGTGAAGGGCAG

GTTCACCATCAGCAGGGACAACGCCAAGAACTCCCTGTACCTGCAGATGA

ACTCCCTGAGGGCCGAGGACACCGCCGTGTACTACTGCGCCAGGGGCAGG

TCCCTGCTGTTCGACTACTGGGGACAGGGCACCCTGGTGACCGTGTCCAG

G

The amino acid sequence of an IL-12/IL-15RαSu/αCD16scFv fusion protein (including signal peptide sequence) is as follows (SEQ ID NO: 35):
(Signal peptide)
(SEQ ID NO: 157)
MKWVTFISLLFLFSSAYS (Human IL-12 subunit beta (p40))
(SEQ ID NO: 158)
IWELKKDVYVVELDWYPDAPGEMVVLTCDTPEEDGITWTLDQSSEVLGSG

KTLTIQVKEFGDAGQYTCHKGGEVLSHSLLLLHKKEDGIWSTDILKDQKE

PKNKTFLRCEAKNYSGRFTCWWLTTISTDLTFSVKSSRGSSDPQGVTCGA

ATLSAERVRGDNKEYEYSVECQEDSACPAAEESLPIEVMVDAVHKLKYEN

YTSSFFIRDIIKPDPPKNLQLKPLKNSRQVEVSWEYPDTWSTPHSYFSLT

FCVQVQGKSKREKKDRVFTDKTSATVICRKNASISVRAQDRYYSSSWSEW

ASVPCS (Linker)
(SEQ ID NO: 159)
GGGGSGGGGSGGGGS (Human IL-12 subunit alpha (p35))
(SEQ ID NO: 160)
RNLPVATPDPGMFPCLHHSQNLLRAVSNMLQKARQTLEFYPCTSEEIDHE

DITKDKTSTVEACLPLELTKNESCLNSRETSFITNGSCLASRKTSFMMAL

CLSSIYEDLKMYQVEFKTMNAKLLMDPKRQIFLDQNMLAVIDELMQALNF

NSETVPQKSSLEEPDFYKTKIKLCILLHAFRIRAVTIDRVMSYLNAS (Human IL-15R a sushi domain)
(SEQ ID NO: 161)
ITCPPPMSVEHADIWVKSYSLYSRERYICNSGFKRKAGTSSLTECVLNKA

TNVAHWTTPSLKCIR

-continued
(anti-Human CD16 light chain variable domain)
(SEQ ID NO: 162)
SELTQDPAVSVALGQTVRITCQGDSLRSYYASWYQQKPGQAPVLVIYGKN

NRPSGIPDRFSGSSSGNTASLTITGAQAEDEADYYCNSRDSSGNHVVFGG

GTKLTVGH (Linker)
(SEQ ID NO: 163)
GGGGSGGGGSGGGGS (anti-Human CD16 heavy chain variable domain)
(SEQ ID NO: 164)
EVQLVESGGGVVRPGGSLRLSCAASGFTFDDYGMSWVRQAPGKGLEWVSG

INWNGGSTGYADSVKGRFTISRDNAKNSLYLQMNSLRAEDTAVYYCARGR

SLLFDYWGQGTLVTVSR

The nucleic acid sequence of an IL-18/IL-15RαSu construct (including signal peptide sequence) is as follows (SEQ ID NO: 36):
(Signal peptide)
(SEQ ID NO: 165)
ATGAAGTGGGTCACATTTATCTCTTTACTGTTCCTCTTCTCCAGCGCCTA

CAGC (Human IL-18)
(SEQ ID NO: 166)
TACTTCGGCAAACTGGAATCCAAGCTGAGCGTGATCCGGAATTTAAACGA

CCAAGTTCTGTTTATCGATCAAGGTAACCGGCCTCTGTTCGAGGACATGA

CCGACTCCGATTGCCGGGACAATGCCCCCCGGACCATCTTCATTATCTCC

ATGTACAAGGACAGCCAGCCCCGGGGCATGGCTGTGACAATTAGCGTGAA

GTGTGAGAAAATCAGCACTTTATCTTGTGAGAACAAGATCATCTCCTTTA

AGGAAATGAACCCCCCCGATAACATCAAGGACACCAAGTCCGATATCATC

TTCTTCCAGCGGTCCGTGCCCGGTCACGATAACAAGATGCAGTTCGAATC

CTCCTCCTACGAGGGCTACTTTTTAGCTTGTGAAAAGGAGAGGGATTTAT

TCAAGCTGATCCTCAAGAAGGAGGACGAGCTGGGCGATCGTTCCATCATG

TTCACCGTCCAAAACGAGGAT (Human IL-15R a sushi domain)
(SEQ ID NO: 167)
ATTACATGCCCCCCCTCCCATGAGCGTGGAGCACGCCGACATCTGGGTGAA

GAGCTATAGCCTCTACAGCCGGGAGAGGTATATCTGTAACAGCGGCTTCA

AGAGGAAGGCCGGCACCAGCAGCCTCACCGAGTGCGTGCTGAATAAGGCT

ACCAACGTGGCTCACTGGACAACACCCTCTTTAAAGTGCATCCGG

The amino acid sequence of an IL-18/IL-15RαSu fusion protein (including signal peptide sequence) is as follows (SEQ ID NO: 37):
(Signal peptide)
(SEQ ID NO: 168)
MKWVTFISLLFLFSSAYS (Human IL-18)
(SEQ ID NO: 169)
YFGKLESKLSVIRNLNDQVLFIDQGNRPLFEDMTDSDCRDNAPRTIFII
SMYKDSQPRGMAVTISVKCEKISTLSCENKIISFKEMNPPDNIKDTKSD
IIFFQRSVPGHDNKMQFESSSYEGYFLACEKERDLFKLILKKEDELGDR
SIMFTVQNED -continued
(Human IL-15R α sushi domain)
(SEQ ID NO: 170)
ITCPPPMSVEHADIWVKSYSLYSRERYICNSGFKRKAGTSSLTECVLNK
ATNVAHWTTPSLKCIR The nucleic acid sequence of an IL-12/TF/IL-15 construct (including leader sequence) is as follows (SEQ ID NO: 38):
(Signal peptide)
(SEQ ID NO: 171)
ATGAAATGGGTGACCTTTATTTCTTTACTGTTCCTCTTTAGCAGCGCCT
ACTCC (Human IL-12 subunit beta (p40))
(SEQ ID NO: 172)
ATTTGGGAACTGAAGAAGGACGTCTACGTGGTCGAACTGGACTGGTATC
CCGATGCTCCCGGCGAAATGGTGGTGCTCACTTGTGACACCCCCGAAGA
AGACGGCATCACTTGGACCCTCGATCAGAGCAGCGAGGTGCTGGGCTCC
GGAAAGACCCTCACAATCCAAGTTAAGGAGTTCGGAGACGCTGGCCAAT
ACACATGCCACAAGGGAGGCGAGGTGCTCAGCCATTCCTTATTATTATT
ACACAAGAAGGAAGACGGAATCTGGTCCACCGACATTTTAAAAGATCAG
AAGGAGCCCAAGAATAAGACCTTTTTAAGGTGTGAGGCCAAAAACTACA
GCGGTCGTTTCACTTGTTGGTGGCTGACCACCATTTCCACCGATTTAAC
CTTCTCCGTGAAAAGCAGCCGGGGAAGCTCCGACCCTCAAGGTGTGACA
TGTGGAGCCGCTACCCTCAGCGCTGAGAGGGTTCGTGGCGATAACAAGG
AATACGAGTACAGCGTGGAGTGCCAAGAAGATAGCGCTTGTCCCGCTGC
CGAAGAATCTTTACCCATTGAGGTGATGGTGGACGCCGTGCACAAACTC
AAGTACGAGAACTACACCTCCTCCTTCTTTATCCGGGACATCATTAAGC
CCGATCCTCCTAAGAATTTACAGCTGAAGCCTCTCAAAAATAGCCGGCA
AGTTGAGGTCTCTTGGGAATATCCCGACACTTGGAGCACACCCCACAGC
TACTTCTCTTTAACCTTTTGTGTGCAAGTTCAAGGTAAAAGCAAGCGGG
AGAAGAAAGACCGGGTGTTTACCGACAAAACCAGCGCCACCGTCATCTG
TCGGAAGAACGCCTCCATCAGCGTGAGGGCTCAAGATCGTTATTACTCC
AGCAGCTGGTCCGAGTGGGCCAGCGTGCCTTGTTCC (Linker)
(SEQ ID NO: 173)
GGCGGTGGAGGATCCGGAGGAGGTGGCTCCGGCGGCGGAGGATCT (Human IL-12 subunit alpha (p35))
(SEQ ID NO: 174)
CGTAACCTCCCCGTGGCTACCCCCGATCCCGGAATGTTCCCTTGTTTAC
ACCACAGCCAGAATTTACTGAGGGCCGTGAGCAACATGCTGCAGAAAGC
TAGGCAGACTTTAGAATTTTACCCTTGCACCAGCGAGGAGATCGACCAT
GAAGATATCACCAAGGACAAGACATCCACCGTGGAGGCTTGTTTACCTC
TGGAGCTGACAAAGAACGAGTCTTGTCTCAACTCTCGTGAAACCAGCTT
CATCACAAATGGCTCTTGTTTAGCTTCCCGGAAGACCTCCTTTATGATG
GCTTTATGCCTCAGCTCCATCTACGAGGATTTAAAGATGTACCAAGTGG
AGTTCAAGACCATGAACGCCAAGCTGCTCATGGACCCTAAACGGCAGAT
CTTTTTAGACCAGAACATGCTGGCTGTGATTGATGAGCTGATGCAAGCT
TTAAACTTCAACTCCGAGACCGTCCCTCAGAAGTCCTCCCTCGAGGAGC
CCGATTTTTACAAGACAAAGATCAAACTGTGCATTTTACTCCACGCCTT
TAGGATCCGGGCCGTGACCATTGACCGGGTCATGAGCTATTTAAACGCC
AGC (Human Tissue Factor 219)
(SEQ ID NO: 175)
AGCGGCACAACCAACACAGTCGCTGCCTATAACCTCACTTGGAAGAGCA
CCAACTTCAAAACCATCCTCGAATGGGAACCCAAACCCGTTAACCAAGT
TTACACCGTGCAGATCAGCACCAAGTCCGGCGACTGGAAGTCCAAATGT
TTCTATACCACCGACACCGAGTGCGATCTCACCGATGAGATCGTGAAAG
ATGTGAAACAGACCTACCTCGCCCGGGTGTTTAGCTACCCCGCCGGCAA
TGTGGAGAGCACTGGTTCCGCTGGCGAGCCTTTATACGAGAACAGCCCC
GAATTTACCCCTTACCTCGAGACCAATTTAGGACAGCCCACCATCCAAA
GCTTTGAGCAAGTTGGCACAAAGGTGAATGTGACAGTGGAGGACGAGCG
GACTTTAGTGCGGCGGAACAACACCTTTCTCAGCCTCCGGGATGTGTTC
GGCAAAGATTTAATCTACACACTGTATTACTGGAAGTCCTCTTCCTCCG
GCAAGAAGACAGCTAAAACCAACACAAACGAGTTTTTAATCGACGTGGA
TAAAGGCGAAAACTACTGTTTCAGCGTGCAAGCTGTGATCCCTCCCGG
ACCGTGAATAGGAAAAGCACCGATAGCCCCGTTGAGTGCATGGGCCAAG
AAAAGGGCGAGTTCCGGGAG (Human IL-15)
(SEQ ID NO: 176)
AACTGGGTGAACGTCATCAGCGATTTAAAGAAGATCGAAGATTTAATTC
AGTCCATGCATATCGACGCCACTTTATACACAGAATCCGACGTGCACCC
CTCTTGTAAGGTGACCGCCATGAAATGTTTTTTACTGGAGCTGCAAGTT
ATCTCTTTAGAGAGCGGAGACGCTAGCATCCACGACACCGTGGAGAATT -continued
TAATCATTTTAGCCAATAACTCTTTATCCAGCAACGGCAACGTGACAGA
GTCCGGCTGCAAGGAGTGCGAAGAGCTGGAGGAGAAGAACATCAAGGAG
TTTCTGCAATCCTTTGTGCACATTGTCCAGATGTTCATCAATACCTCC The amino acid sequence of an IL-12/TF/IL-15 fusion protein (including leader sequence) is as follows (SEQ ID NO: 39):
(Signal peptide)
(SEQ ID NO: 177)
MKWVTFISLLFLFSSAYS (Human IL-12 subunit beta (p40))
(SEQ ID NO: 178)
IWELKKDVYVVELDWYPDAPGEMVVLTCDTPEEDGITWTLDQSSEVLGS
GKTLTIQVKEFGDAGQYTCHKGGEVLSHSLLLLHKKEDGIWSTDILKDQ
KEPKNKTFLRCEAKNYSGRFTCWWLTTISTDLTFSVKSSRGSSDPQGVT
CGAATLSAERVRGDNKEYEYSVECQEDSACPAAEESLPIEVMVDAVHKL
KYENYTSSFFIRDIIKPDPPKNLQLKPLKNSRQVEVSWEYPDTWSTPHS
YFSLTFCVQVQGKSKREKKDRVFTDKTSATVICRKNASISVRAQDRYYS
SSWSEWASVPCS (Linker)
(SEQ ID NO: 179)
GGGGSGGGGSGGGGS (Human IL-12 subunit alpha (p35))
(SEQ ID NO: 180)
RNLPVATPDPGMFPCLHHSQNLLRAVSNMLQKARQTLEFYPCTSEEIDH
EDITKDKTSTVEACLPLELTKNESCLNSRETSFITNGSCLASRKTSFMM
ALCLSSIYEDLKMYQVEFKTMNAKLLMDPKRQIFLDQNMLAVIDELMQA
LNFNSETVPQKSSLEEPDFYKTKIKLCILLHAFRIRAVTIDRVMSYLNA
S (Human Tissue Factor 219)
(SEQ ID NO: 181)
SGTTNTVAAYNLTWKSTNFKTILEWEPKPVNQVYTVQISTKSGDWKSKC
FYTTDTECDLTDEIVKDVKQTYLARVFSYPAGNVESTGSAGEPLYENSP
EFTPYLETNLGQPTIQSFEQVGTKVNVTVEDERTLVRRNNTFLSLRDVF
GKDLIYTLYYWKSSSSGKKTAKTNTNEFLIDVDKGENYCFSVQAVIPSR
TVNRKSTDSPVECMGQEKGEFRE (Human IL-15)
(SEQ ID NO: 182)
NWVNVISDLKKIEDLIQSMHIDATLYTESDVHPSCKVTAMKCFLLELQV
ISLESGDASIHDTVENLIILANNSLSSNGNVTESGCKECEELEEKNIKE
FLQSFVHIVQMFINTS The nucleic acid sequences of a TGFβRII/IL-15RαSu construct (including signal sequence) is as follows (SEQ ID NO: 40):
(Signal peptide)
(SEQ ID NO: 183)
ATGAAGTGGGTGACCTTCATCAGCCTGCTGTTCCTGTTCTCCAGCGCCT
ACTCC (Human TGF βRII-1st fragment)
(SEQ ID NO: 184)
ATCCCCCCCCATGTGCAAAAGAGCGTGAACAACGATATGATCGTGACCG
ACAACAACGGCGCCGTGAAGTTTCCCCAGCTCTGCAAGTTCTGCGATGT
CAGGTTCAGCACCTGCGATAATCAGAAGTCCTGCATGTCCAACTGCACG
ATCACCTCCATCTGCGAGAAGCCCCAAGAAGTGTGCGTGGCCGTGTGGC
GGAAAAATGACGAGAACATCACCCTGGAGACCGTGTGTCACGACCCCAA
GCTCCCTTATCACGACTTCATTCTGGAGGACGCTGCCTCCCCCAAATGC
ATCATGAAGGAGAAGAAGAAGCCCGGAGAGACCTTCTTTATGTGTTCCT
GTAGCAGCGACGAGTGTAACGACAACATCATCTTCAGCGAAGAGTACAA
CACCAGCAACCCTGAT (Linker)
(SEQ ID NO: 185)
GGAGGTGGCGGATCCGGAGGTGGAGGTTCTGGTGGAGGTGGGAGT (Human TGF βRII-2nd fragment)
(SEQ ID NO: 186)
ATTCCTCCCCACGTGCAGAAGAGCGTGAATAATGACATGATCGTGACCG
ATAACAATGGCGCCGTGAAATTTCCCCAGCTGTGCAAATTCTGCGATGT -continued
GAGGTTTTCCACCTGCGACAACCAGAAGTCCTGTATGAGCAACTGCACA
ATCACCTCCATCTGTGAGAAGCCTCAGGAGGTGTGCGTGGCTGTCTGGC
GGAAGAATGACGAGAATATCACCCTGGAAACCGTCTGCCACGATCCCAA
GCTGCCCTACCACGATTTCATCCTGGAAGACGCCGCCAGCCCTAAGTGC
ATCATGAAAGAGAAAAAGAAGCCTGGCGAGACCTTTTTCATGTGCTCCT
GCAGCAGCGACGAATGCAACGACAATATCATCTTTAGCGAGGAATACAA
TACCAGCAACCCCGAC (Human IL-15R α sushi domain)
(SEQ ID NO: 187)
ATCACGTGTCCTCCTCCTATGTCCGTGGAACACGCAGACATCTGGGTCA
AGAGCTACAGCTTGTACTCCAGGGAGCGGTACATTTGTAACTCTGGTTT
CAAGCGTAAAGCCGGCACGTCCAGCCTGACGGAGTGCGTGTTGAACAAG
GCCACGAATGTCGCCCACTGGACAACCCCCAGTCTCAAATGTATTAGA The amino acid sequence of a TGFβRII/IL-15RαSu construct (including signal peptide sequence) is as follows (SEQ ID NO: 41):
(Signal peptide)
(SEQ ID NO: 188)
MKWVTFISLLFLFSSAYS (Human TGF βRII-1st fragment)
(SEQ ID NO: 189)
IPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKC
IMKEKKKPGETFFMCSCSSDECNDNIIFSEEYNTSNPD (Linker)
(SEQ ID NO: 190)
GGGGSGGGGSGGGGS (Human TGF βRII-2nd fragment)
(SEQ ID NO: 191)
IPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKC
IMKEKKKPGETFFMCSCSSDECNDNIIFSEEYNTSNPD (Human IL-15R α sushi domain)
(SEQ ID NO: 192)
ITCPPPMSVEHADIWVKSYSLYSRERYICNSGFKRKAGTSSLTECVLNK
ATNVAHWTTPSLKCIR The nucleic acid sequence of the IL-21/TF/IL-15 construct (including leader sequence) is as follows (Signal peptide)
(SEQ ID NO: 42):
(SEQ ID NO: 193)
ATGAAGTGGGTGACCTTCATCAGCCTGCTGTTCCTGTTCTCCAGCGCCT
ACTCC (Human IL-21)
(SEQ ID NO: 194)
CAGGGCCAGGACAGGCACATGATCCGGATGAGGCAGCTCATCGACATCG
TCGACCAGCTGAAGAACTACGTGAACGACCTGGTGCCCGAGTTTCTGCC
TGCCCCCGAGGACGTGGAGACCAACTGCGAGTGGTCCGCCTTCTCCTGC
TTTCAGAAGGCCCAGCTGAAGTCCGCCAACACCGGCAACAACGAGCGGA
TCATCAACGTGAGCATCAAGAAGCTGAAGCGGAAGCCTCCCTCCACAAA
CGCCGGCAGGAGGCAGAAGCACAGGCTGACCTGCCCCAGCTGTGACTCC
TACGAGAAGAAGCCCCCCAAGGAGTTCCTGGAGAGGTTCAAGTCCCTGC
TGCAGAAGATGATCCATCAGCACCTGTCCTCCAGGACCCACGGCTCCGA
GGACTCC (Human Tissue Factor 219)
(SEQ ID NO: 195)
TCCGGCACCACCAATACCGTGGCCGCTTATAACCTCACATGGAAGAGCA
CCAACTTCAAGACAATTCTGGAATGGGAACCCAAGCCCGTCAATCAAGT
TTACACCGTGCAGATCTCCACCAAATCCGGAGACTGGAAGAGCAAGTGC
TTCTACACAACAGACACCGAGTGTGATTTAACCGACGAAATCGTCAAGG
ACGTCAAGCAAACCTATCTGGCTCGGGTCTTTTCCTACCCCGCTGGCAA
TGTCGAGTCCACCGGCTCCGCTGGCGAGCCTCTCTACGAGAATTCCCCC
GAATTCACCCCTTATTTAGAGACCAATTTAGGCCAGCCTACCATCCAGA
GCTTCGAGCAAGTTGGCACCAAGGTGAACGTCACCGTCGAGGATGAAAG
GACTTTAGTGCGGCGGAATAACACATTTTTATCCCTCCGGGATGTGTTC

```
GGCAAAGACCTCATCTACACACTGTACTATTGGAAGTCCAGCTCCTCCG
GCAAAAAGACCGCTAAGACCAACACCAACGAGTTTTTAATTGACGTGGA
CAAAGGCGAGAACTACTGCTTCAGCGTGCAAGCCGTGATCCCTTCTCGT
ACCGTCAACCGGAAGAGCACAGATTCCCCCGTTGAGTGCATGGGCCAAG
AAAAGGGCGAGTTCCGGGAG
```

(Human IL-15)
(SEQ ID NO: 196)
```
AACTGGGTGAACGTCATCAGCGATTTAAAGAAGATCGAAGATTTAATTC
AGTCCATGCATATCGACGCCACTTTATACACAGAATCCGACGTGCACCC
CTCTTGTAAGGTGACCGCCATGAAATGTTTTTACTGGAGCTGCAAGTT
ATCTCTTTAGAGAGCGGAGACGCTAGCATCCACGACACCGTGGAGAATT
TAATCATTTTAGCCAATAACTCTTTATCCAGCAACGGCAACGTGACAGA
GTCCGGCTGCAAGGAGTGCGAAGAGCTGGAGGAGAAGAACATCAAGGAG
TTTCTGCAATCCTTTGTGCACATTGTCCAGATGTTCATCAATACCTCC
```

The amino acid sequence of the mature IL-21/TF/IL-15 fusion protein (including signal peptide sequence) is as follows (SEQ ID NO: 43):
(Signal peptide)
(SEQ ID NO: 197)
MKWVTFISLLFLFSSAYS (Human IL-21)
(SEQ ID NO: 198)
QGQDRHMIRMRQLIDIVDQLKNYVNDLVPEFLPAPEDVETNCEWSAFSC
FQKAQLKSANTGNNERIINVSIKKLKRKPPSTNAGRRQKHRLTCPSCDS
YEKKPPKEFLERFKSLLQKMIHQHLSSRTHGSEDS (Human Tissue Factor 219)
(SEQ ID NO: 199)
SGTTNTVAAYNLTWKSTNFKTILEWEPKPVNQVYTVQISTKSGDWKSKC
FYTTDTECDLTDEIVKDVKQTYLARVFSYPAGNVESTGSAGEPLYENSP
EFTPYLETNLGQPTIQSFEQVGTKVNVTVEDERTLVRRNNTFLSLRDVF
GKDLIYTLYYWKSSSSGKKTAKTNTNEFLIDVDKGENYCFSVQAVIPSR
TVNRKSTDSPVECMGQEKGEFRE (Human IL-15)
(SEQ ID NO: 200)
NWVNVISDLKKIEDLIQSMHIDATLYTESDVHPSCKVTAMKCFLLELQV
ISLESGDASIHDTVENLIILANNSLSSNGNVTESGCKECEELEEKNIKE
FLQSFVHIVQMFINTS The nucleic acid sequence of the IL-21/TF mutant/IL-15 construct (including signal peptide sequence) is as follows (SEQ ID NO: 44, bold nucleotides are mutant and the mutant codons are underlined):

(Signal sequence)
(SEQ ID NO: 201)
ATGAAGTGGGTGACCTTCATCAGCCTGCTGTTCCTGTTCTCCAGCGCCT
ACTCC (Human IL-21)
(SEQ ID NO: 202)
CAGGGCCAGGACAGGCACATGATCCGGATGAGGCAGCTCATCGACATCG
TCGACCAGCTGAAGAACTACGTGAACGACCTGGTGCCCGAGTTTCTGCC
TGCCCCCGAGGACGTGGAGACCAACTGCGAGTGGTCCGCCTTCTCCTGC
TTTCAGAAGGCCCAGCTGAAGTCCGCCAACACCGGCAACAACGAGCGGA
TCATCAACGTGAGCATCAAGAAGCTGAAGCGGAAGCCTCCCTCCACAAA
CGCCGGCAGGAGGCAGAAGCACAGGCTGACCTGCCCCAGCTGTGACTCC
TACGAGAAGAAGCCCCCCAAGGAGTTCCTGGAGAGGTTCAAGTCCCTGC
TGCAGAAGATGATCCATCAGCACCTGTCCTCCAGGACCCACGGCTCCGA
GGACTCC (Human Tissue Factor 219 mutants)
(SEQ ID NO: 203)
TCCGGCACCACCAATACCGTGGCCGCTTATAACCTCACATGGAAGAGCA
CCAACTTCGCGACAGCTCTGGAATGGGAACCCAAGCCCGTCAATCAAGT
TTACACCGTGCAGATCTCCACCAAATCCGGAGACTGGAAGAGCAAGTGC
TTCTACACAACAGACACCGAGTGTGCTTTAACCGACGAAATCGTCAAGG
ACGTCAAGCAAACCTATCTGGCTCGGGTCTTTTCCTACCCCGCTGGCAA
TGTCGAGTCCACCGGCTCCGCTGGCGAGCCTCTCTACGAGAATTCCCCC
GAATTCACCCCTTATTTAGAGACCAATTTAGGCCAGCCTACCATCCAGA
GCTTCGAGCAAGTTGGCACCAAGGTGAACGTCACCGTCGAGGATGAAAG
```

```
GACTTTAGTGGCGCGGAATAACACAGCTTTATCCCTCCGGGATGTGTTC
GGCAAAGACCTCATCTACACACTGTACTATTGGAAGTCCAGCTCCTCCG
GCAAAAAGACCGCTAAGACCAACACCAACGAGTTTTTAATTGACGTGGA
CAAAGGCGAGAACTACTGCTTCAGCGTGCAAGCCGTGATCCCTTCTCGT
ACCGTCAACCGGAAGAGCACAGATTCCCCCGTTGAGTGCATGGGCCAAG
AAAAGGGCGAGTTCCGGGAG
```

(Human IL-15)
(SEQ ID NO: 204)
```
AACTGGGTGAACGTCATCAGCGATTTAAAGAAGATCGAAGATTTAATTC
AGTCCATGCATATCGACGCCACTTTATACACAGAATCCGACGTGCACCC
CTCTTGTAAGGTGACCGCCATGAAATGTTTTTACTGGAGCTGCAAGTT
ATCTCTTTAGAGACGGGAGACGCTAGCATCCACGACACCGTGGAGAATT
TAATCATTTTAGCCAATAACTCTTTATCCAGCAACGGCAACGTGACAGA
GTCCGGCTGCAAGGAGTGCGAAGAGCTGGAGGAGAAGAACATCAAGGAG
TTTCTGCAATCCTTTGTGCACATTGTCCAGATGTTCATCAATACCTCC
```

The amino acid sequence of the IL-21/TF mutant/IL-15 construct (including signal peptide sequence) is as follows (SEQ ID NO: 45, substituted residues are shown in bold and underlined):

(Signal peptide)
(SEQ ID NO: 205)
MKWVTFISLLFLFSSAYS (Human IL-21)
(SEQ ID NO: 206)
QGQDRHMIRMRQLIDIVDQLKNYVNDLVPEFLPAPEDVETNCEWSAFSC
FQKAQLKSANTGNNERIINVSIKKLKRKPPSTNAGRRQKHRLTCPSCDS
YEKKPPKEFLERFKSLLQKMIHQHLSSRTHGSEDS (Human Tissue Factor 219)
(SEQ ID NO: 207)
SGTTNTVAAYNLTWKSTNFATALEWEPKPVNQVYTVQISTKSGDWKSKC
FYTTDTECALTDEIVKDVKQTYLARVFSYPAGNVESTGSAGEPLYENSP
EFTPYLETNLGQPTIQSFEQVGTKVNVTVEDERTLVARNNTALSLRDVF
GKDLIYTLYYWKSSSSGKKTAKTNTNEFLIDVDKGENYCFSVQAVIPSR
TVNRKSTDSPVECMGQEKGEFRE (Human IL-15)
(SEQ ID NO: 208)
NWVNVISDLKKIEDLIQSMHIDATLYTESDVHPSCKVTAMKCFLLELQV
ISLESGDASIHDTVENLIILANNSLSSNGNVTESGCKECEELEEKNIKE
FLQSFVHIVQMFINTS The nucleic acid sequence of the IL-21/IL-15RαSu construct (including signal sequence) is as follows (SEQ ID NO: 46):
(Signal sequence)
(SEQ ID NO: 209)
ATGAAGTGGGTGACCTTCATCAGCCTGCTGTTCCTGTTCTCCAGCGCCT
ACTCC (Human IL-21)
(SEQ ID NO: 210)
CAGGGCCAGGACAGGCACATGATCCGGATGAGGCAGCTCATCGACATCG
TCGACCAGCTGAAGAACTACGTGAACGACCTGGTGCCCGAGTTTCTGCC
TGCCCCCGAGGACGTGGAGACCAACTGCGAGTGGTCCGCCTTCTCCTGC
TTTCAGAAGGCCCAGCTGAAGTCCGCCAACACCGGCAACAACGAGCGGA
TCATCAACGTGAGCATCAAGAAGCTGAAGCGGAAGCCTCCCTCCACAAA
CGCCGGCAGGAGGCAGAAGCACAGGCTGACCTGCCCCAGCTGTGACTCC
TACGAGAAGAAGCCCCCCAAGGAGTTCCTGGAGAGGTTCAAGTCCCTGC
TGCAGAAGATGATCCATCAGCACCTGTCCTCCAGGACCCACGGCTCCGA
GGACTCC (Human IL-15R α sushi domain)
(SEQ ID NO: 211)
ATTACATGCCCCCTCCCATGAGCGTGGAGCACGCCGACATCTGGGTGA
AGAGCTATAGCCTCTACAGCCGGGAGAGGTATATCTGTAACAGCGGCTT
CAAGAGGAAGGCCGGCACCAGCAGCCTCACCGAGTGCGTGCTGAATAAG
GCTACCAACGTGGCTCACTGGACAACACCCTCTTTAAAGTGCATCCGG The amino acid sequence of the IL-21/IL-15RαSu construct (including signal peptide sequence) is as follows (SEQ ID NO: 101):
(Signal peptide)
(SEQ ID NO: 212)
MKWVTFISLLFLFSSAYS (Human IL-21)
(SEQ ID NO: 213)
QGQDRHMIRMRQLIDIVDQLKNYVNDLVPEFLPAPEDVETNCEWSAFSC
FQKAQLKSANTGNNERIINVSIKKLKRKPPSTNAGRRQKHRLTCPSCDS
YEKKPPKEFLERFKSLLQKMIHQHLSSRTHGSEDS (Human IL-15R α sushi domain)
(SEQ ID NO: 214)
ITCPPPMSVEHADIWVKSYSLYSRERYICNSGFKRKAGTSSLTECVLNK
ATNVAHWTTPSLKCIR The nucleic acid sequence of the TGFβRII/TF/IL-15 construct (including leader sequence) is as follows (SEQ ID NO: 47):
(Signal peptide)
(SEQ ID NO: 215)
ATGAAGTGGGTGACCTTCATCAGCCTGCTGTTCCTGTTCTCCAGCGCCT
ACTCC (Human TGF βRII-1$^{st}$ fragment)
(SEQ ID NO: 216)
ATCCCCCCCCATGTGCAAAAGAGCGTGAACAACGATATGATCGTGACCG
ACAACAACGGCGCCGTGAAGTTTCCCCAGCTCTGCAAGTTCTGCGATGT
CAGGTTCAGCACCTGCGATAATCAGAAGTCCTGCATGTCCAACTGCACG
ATCACCTCCATCTGCGAGAAGCCCCAAGAAGTGTGCGTGGCCGTGTGGC
GGAAAAATGACGAGAACATCACCCTGGAGACCGTGTGTCACGACCCCAA
GCTCCCTTATCACGACTTCATTCTGGAGGACGCTGCCTCCCCCAAATGC
ATCATGAAGGAGAAGAAGAAGCCCGGAGAGACCTTCTTTATGTGTTCCT
GTAGCAGCGACGAGTGTAACGACAACATCATCTTCAGCGAAGAGTACAA
CACCAGCAACCCTGAT (Linker)
(SEQ ID NO: 217)
GGAGGTGGCGGATCCGGAGGTGGAGGTTCTGGTGGAGGTGGGAGT (Human TGF βRII-2$^{nd}$ fragment)
(SEQ ID NO: 218)
ATTCCTCCCCACGTGCAGAAGAGCGTGAATAATGACATGATCGTGACCG
ATAACAATGGCGCCGTGAAATTTCCCCAGCTGTGCAAATTCTGCGATGT
GAGGTTTTCCACCTGCGACAACCAGAAGTCCTGTATGAGCAACTGCACA
ATCACCTCCATCTGTGAGAAGCCTCAGGAGGTGTGCGTGGCTGTCTGGC
GGAAGAATGACGAGAATATCACCCTGGAAACCGTCTGCCACGATCCCAA
GCTGCCCTACCACGATTTCATCCTGGAAGACGCCGCCAGCCCTAAGTGC
ATCATGAAAGAGAAAAAGAAGCCTGGCGAGACCTTTTTCATGTGCTCCT
GCAGCAGCGACGAATGCAACGACAATATCATCTTTAGCGAGGAATACAA
TACCAGCAACCCCGAC (Human Tissue Factor 219)
(SEQ ID NO: 219)
TCCGGCACCACCAATACCGTGGCCGCTTATAACCTCACATGAAGAGCA
CCAACTTCAAGACAATTCTGGAATGGGAACCCAAGCCCGTCAATCAAGT
TTACACCGTGCAGATCTCCACCAAATCCGGAGACTGGAAGAGCAAGTGC
TTCTACACAACAGACACCGAGTGTGATTTAACCGACGAAATCGTCAAGG
ACGTCAAGCAAACCTATCTGGCTCGGGTCTTTTCCTACCCCGCTGGCAA
TGTCGAGTCCACCGGCTCCGCTGGCGAGCCTCTCTACGAGAATTCCCCC
GAATTCACCCCTTATTTAGAGACCAATTTAGGCCAGCCTACCATCCAGA
GCTTCGAGCAAGTTGGCACCAAGGTGAACGTCACCGTCGAGGATGAAAG
GACTTTAGTGCGGCGGAATAACACATTTTTATCCCTCCGGGATGTGTTC
GGCAAAGACCTCATCTACACACTGTACTATTGGAAGTCCAGCTCCTCCG
GCAAAAAGACCGCTAAGACCAACACCAACGAGTTTTTAATTGACGTGGA
CAAAGGCGAGAACTACTGCTTCAGCGTGCAAGCCGTGATCCCTTCTCGT
ACCGTCAACCGGAAGAGCACAGATTCCCCCGTTGAGTGCATGGGCCAAG
AAAAGGGCGAGTTCCGGGAG (Human IL-15)
(SEQ ID NO: 220)
AACTGGGTGAACGTCATCAGCGATTTAAAGAAGATCGAAGATTTAATTC
AGTCCATGCATATCGACGCCACTTTATACACAGAATCCGACGTGCACCC
CTCTTGTAAGGTGACCGCCATGAAATGTTTTTTACTGGAGCTGCAAGTT ATCTCTTTAGAGAGCGGAGACGCTAGCATCCACGACACCGTGGAGAATT
TAATCATTTTAGCCAATAACTCTTTATCCAGCAACGGCAACGTGACAGA
GTCCGGCTGCAAGGAGTGCGAAGAGCTGGAGGAGAAGAACATCAAGGAG
TTTCTGCAATCCTTTGTGCACATTGTCCAGATGTTCATCAATACCTCC The amino acid sequence of the TGFβRII/TF/IL-15 fusion protein (including signal peptide) is as follows (SEQ ID NO: 48):
(Signal peptide)
(SEQ ID NO: 221)
MKWVTFISLLFLFSSAYS (Human TGFβRII-1$^{st}$ fragment)
(SEQ ID NO: 222)
IPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKC
IMKEKKKPGETFFMCSCSSDECNDNIIFSEEYNTSNPD (Linker)
(SEQ ID NO: 223)
GGGGSGGGGSGGGGS (Human TGFβRII-2$^{nd}$ fragment)
(SEQ ID NO: 224)
IPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKC
IMKEKKKPGETFFMCSCSSDECNDNIIFSEEYNTSNPD (Human Tissue Factor 219)
(SEQ ID NO: 225)
SGTTNTVAAYNLTWKSTNFKTILEWEPKPVNQVYTVQISTKSGDWKSKC
FYTTDTECDLTDEIVKDVKQTYLARVFSYPAGNVESTGSAGEPLYENSP
EFTPYLETNLGQPTIQSFEQVGTKVNVTVEDERTLVRRNNTFLSLRDVF
GKDLIYTLYYWKSSSSGKKTAKTNTNEFLIDVDKGENYCFSVQAVIPSR
TVNRKSTDSPVECMGQEKGEFRE (Human IL-15)
(SEQ ID NO: 226)
NWVNVISDLKKIEDLIQSMHIDATLYTESDVHPSCKVTAMKCFLLELQV
ISLESGDASIHDTVENLIILANNSLSSNGNVTESGCKECEELEEKNIKE
FLQSFVHIVQMFINTS The nucleic acid sequence encoding the second chimeric polypeptide of IL-7/IL-15RαSu construct (including signal peptide sequence) is as follows (SEQ ID NO: 49):
(Signal peptide)
(SEQ ID NO: 227)
ATGGGAGTGAAAGTTCTTTTTGCCCTTATTTGTATTGCTGTGGCCGAGG
CC (Human IL-7)
(SEQ ID NO: 228)
GATTGTGATATTGAAGGTAAAGATGGCAAACAATATGAGAGTGTTCTAA
TGGTCAGCATCGATCAATTATTGGACAGCATGAAAGAAATTGGTAGCAA
TTGCCTGAATAATGAATTTAACTTTTTTAAAAGACATATCTGTGATGCT
AATAAGGAAGGTATGTTTTTATTCCGTGCTGCTCGCAAGTTGAGGCAAT
TTCTTAAAATGAATAACGACTGGTGATTTTGATCTCCACTTATTAAAAGT
TTCAGAAGGCACAACAATACTGTTGAACTGCACTGGCCAGGTTAAAGGA
AGAAAACCAGCTGCCCTGGGTGAAGCCCAACCAACAAAGAGTTTGGAAG
AAAATAAATCTTTAAAGGAACAGAAAAAACTGAATGACTTGTGTTTCCT
AAAGAGACTATTACAAGAGATAAAAACTTGTTGGAATAAAATTTTGATG
GGCACTAAAGAACAC (Human IL-15R α sushi domain)
(SEQ ID NO: 229)
ATCACGTGCCCTCCCCCCATGTCCGTGGAACACGCAGACATCTGGGTCA
AGAGCTACAGCTTGTACTCCAGGGAGCGGTACATTTGTAACTCTGGTTT
CAAGCGTAAAGCCGGCACGTCCAGCCTGACGGAGTGCGTGTTGAACAAG
GCCACGAATGTCGCCCACTGGACAACCCCCAGTCTCAAATGCATTAGA The second chimeric polypeptide of IL-7/IL-15RαSu construct (including signal peptide sequence) is as follows (SEQ ID NO: 50):
(Signal peptide)
(SEQ ID NO: 230)
MKWVTFISLLFLFSSAYS (Human IL-7)
(SEQ ID NO: 231)
DCDIEGKDGKQYESVLMVSIDQLLDSMKEIGSNCLNNEFNFFKRHICDA
NKEGMFLFRAARKLRQFLKMNSTGDFDLHLLKVSEGTTILLNCTGQVKG
RKPAALGEAQPTKSLEENKSLKEQKKLNDLCFLKRLLQEIKTCWNKILM
GTKEH (Human Tissue Factor 219)
(SEQ ID NO: 232)
SGTTNTVAAYNLTWKSTNFKTILEWEPKPVNQVYTVQISTKSGDWKSKC
FYTTDTECDLTDEIVKDVKQTYLARVFSYPAGNVESTGSAGEPLYENSP
EFTPYLETNLGQPTIQSFEQVGTKVNVTVEDERTLVRRNNTFLSLRDVF
GKDLIYTLYYWKSSSSGKKTAKTNTNEFLIDVDKGENYCFSVQAVIPSR
TVNRKSTDSPVECMGQEKGEFRE (Human IL-15)
(SEQ ID NO: 233)
NWVNVISDLKKIEDLIQSMHIDATLYTESDVHPSCKVTAMKCFLLELQV
ISLESGDASIHDTVENLIILANNSLSSNGNVTESGCKECEELEEKNIKE
FLQSFVHIVQMFINTS The nucleic acid sequence encoding the first chimeric polypeptide of IL-21/TF/IL-15 construct (including leader sequence), synthesized by Genewiz, is as follows (SEQ ID NO: 51):
(Signal peptide)
(SEQ ID NO: 234)
ATGGGAGTGAAAGTTCTTTTTGCCCTTATTTGTATTGCTGTGGCCGAGG
CC
(Human IL-21 fragment)
(SEQ ID NO: 235)
CAAGGTCAAGATCGCCACATGATTAGAATGCGTCAACTTATAGATATTG
TTGATCAGCTGAAAAATTATGTGAATGACTTGGTCCCTGAATTTCTGC
AGCTCCAGAAGATGTAGAGACAAACTGTGAGTGGTCAGCTTTTTCCTGT
TTTCAGAAGGCCCAACTAAAGTCAGCAAATACAGGAAACAATGAAAGGA
TAATCAATGTATCAATTAAAAAGCTGAAGAGGAAACCACCTTCCACAAA
TGCAGGGAGAAGACAGAAACACAGACTAACATGCCCTTCATGTGATTCT
TATGAGAAAAAACCACCCAAAGAATTCCTAGAAAGATTCAAATCACTTC
TCCAAAAGATGATTCATCAGCATCTGTCCTCTAGAACACACGGAAGTGA
AGATTCC
(Human Tissue Factor 219)
(SEQ ID NO: 236)
TCAGGCACTACAAATACTGTGGCAGCATATAATTTAACTTGGAAATCAA
CTAATTTCAAGACAATTTTGGAGTGGGAACCCAAACCCGTCAATCAAGT
CTACACTGTTCAAATAAGCACTAAGTCAGGAGATTGGAAAAGCAAATGC
TTTTACACAACAGACACAGAGTGTGACCTCACCGACGAGATTGTGAAGG
ATGTGAAGCAGACGTACTTGGCACGGGTCTTCTCCTACCCGGCAGGGAA
TGTGGAGAGCACCGGTTCTGCTGGGGAGCCTCTGTATGAGAACTCCCCA
GAGTTCACACCTTACCTGGAGACAAACCTCGGACAGCCAACAATTCAGA
GTTTTGAACAGGTGGGAACAAAAGTGAATGTGACCGTAGAAGATGAACG
GACTTTAGTCAGAAGGAACAACACTTTCCTAAGCCTCCGGGATGTTTTT
GGCAAGGACTTAATTTATACACTTTATTATTGGAAATCTTCAAGTTCAG
GAAAGAAAACAGCCAAACAAACACTAATGAGTTTTTGATTGATGTGGA
TAAAGGAGAAAACTACTGTTTCAGTGTTCAAGCAGTGATTCCCTCCCGA
ACAGTTAACCGGAAGAGTACAGACAGCCCGGTAGAGTGTATGGGCCAGG
AGAAAGGGGAATTCAGAGAA
(Human IL-15)
(SEQ ID NO: 237)
AACTGGGTGAACGTCATCAGCGATTTAAAGAAGATCGAAGATTTAATTC
AGTCCATGCATATCGACGCCACTTTATACACAGAATCCGACGTGCACCC
CTCTTGTAAGGTGACCGCCATGAAATGTTTTTTACTGGAGCTGCAAGTT
ATCTCTTTAGAGAGCGGAGACGCTAGCATCCACGACACCGTGGAGAATT
TAATCATTTTAGCCAATAACTCTTTATCCAGCAACGGCAACGTGACAGA
GTCCGGCTGCAAGGAGTGCGAAGAGCTGGAGGAGAAGAACATCAAGGAG
TTTCTGCAATCCTTTGTGCACATTGTCCAGATGTTCATCAATACCTCC The first chimeric polypeptide of IL-21/TF/IL-15 construct including leader sequence is as follows (SEQ ID NO: 52):
(Signal peptide)
(SEQ ID NO: 238)
MGVKVLFALICIAVAEA (Human IL-21)
(SEQ ID NO: 239)
QGQDRHMIRMRQLIDIVDQLKNYVNDLVPEFLPAPEDVETNCEWSAFSC
FQKAQLKSANTGNNERIINVSIKKLKRKPPSTNAGRRQKHRLTCPSCDS
YEKKPPKEFLERFKSLLQKMIHQHLSSRTHGSEDS (Human Tissue Factor 219)
(SEQ ID NO: 240)
SGTTNTVAAYNLTWKSTNFKTILEWEPKPVNQVYTVQISTKSGDWKSKC
FYTTDTECDLTDEIVKDVKQTYLARVFSYPAGNVESTGSAGEPLYENSP
EFTPYLETNLGQPTIQSFEQVGTKVNVTVEDERTLVRRNNTFLSLRDVF
GKDLIYTLYYWKSSSSGKKTAKTNTNEFLIDVDKGENYCFSVQAVIPSR
TVNRKSTDSPVECMGQEKGEFRE (Human IL-15)
(SEQ ID NO: 241)
NWVNVISDLKKIEDLIQSMHIDATLYTESDVHPSCKVTAMKCFLLELQV
ISLESGDASIHDTVENLIILANNSLSSNGNVTESGCKECEELEEKNIKE
FLQSFVHIVQMFINTS The nucleic acid sequence encoding the second chimeric polypeptide of IL-21/IL-15RαSu domain (including leader sequence), synthesized by Genewiz, is as follows (SEQ ID NO: 53):
(Signal peptide)
(SEQ ID NO: 242)
ATGAAGTGGGTGACCTTCATCAGCCTGCTGTTCCTGTTCTCCAGCGCCT
ACTCC (Human IL-21)
(SEQ ID NO: 243)
CAGGGCCAGGACAGGCACATGATCCGGATGAGGCAGCTCATCGACATCG
TCGACCAGCTGAAGAACTACGTGAACGACCTGGTGCCCGAGTTTCTGCC
TGCCCCCGAGGACGTGGAGACCAACTGCGAGTGGTCCGCCTTCTCCTGC
TTTCAGAAGGCCCAGCTGAAGTCCGCCAACACCGGCAACAACGAGCGGA
TCATCAACGTGAGCATCAAGAAGCTGAAGCGGAAGCCTCCCTCCACAAA
CGCCGGCAGGAGGCAGAAGCACAGGCTGACCTGCCCCAGCTGTGACTCC
TACGAGAAGAAGCCCCCCAAGGAGTTCCTGGAGAGGTTCAAGTCCCTGC
TGCAGAAGATGATCCATCAGCACCTGTCCTCCAGGACCCACGGCTCCGA
GGACTCC (Human IL-15R α sushi domain)
(SEQ ID NO: 244)
ATTACATGCCCCCCTCCCATGAGCGTGGAGCACGCCGACATCTGGGTGA
AGAGCTATAGCCTCTACAGCCGGGAGAGGTATATCTGTAACAGCGGCTT
CAAGAGGAAGGCCGGCACCAGCAGCCTCACCGAGTGCGTGCTGAATAAG
GCTACCAACGTGGCTCACTGGACAACACCCTCTTTAAAGTGCATCCGG The second chimeric polypeptide of IL-21/IL-15Rα sushi domain (including leader sequence) is as follows (SEQ ID NO: 54):
(Signal Sequence)
(SEQ ID NO: 245)
MKWVTFISLLFLFSSAYS (Human IL-21)
(SEQ ID NO: 246)
QGQDRHMIRMRQLIDIVDQLKNYVNDLVPEFLPAPEDVETNCEWSAFSC
FQKAQLKSANTGNNERIINVSIKKLKRKPPSTNAGRRQKHRLTCPSCDS
YEKKPPKEFLERFKSLLQKMIHQHLSSRTHGSEDS (Human IL-15Rα sushi domain)
(SEQ ID NO: 247)
ITCPPPMSVEHADIWVKSYSLYSRERYICNSGFKRKAGTSSLTECVLNK
ATNVAHWTTPSLKCIR The nucleic acid sequence encoding the first chimeric polypeptide of IL-7/TF/IL-15 is as follows (SEQ ID NO: 55):
(Signal peptide)
(SEQ ID NO: 248)
ATGAAGTGGGTGACCTTCATCAGCCTGCTGTTCCTGTTCTCCAGCGCCT
ACTCC (Human IL-7 fragment)
(SEQ ID NO: 249)
GATTGCGACATCGAGGGCAAGGACGGCAAGCAGTACGAGAGCGTGCTGA
TGGTGTCCATCGACCAGCTGCTGGACAGCATGAAGGAGATCGGCTCCAA
CTGCCTCAACAACGAGTTCAACTTCTTCAAGCGGCACATCTGCGACGCC
AACAAGGAGGGCATGTTCCTGTTCAGGGCCGCCAGGAAACTGCGGCAGT
TCCTGAAGATGAACTCCACCGGCGACTTCGACCTGCACCTGCTGAAGGT
GTCCGAGGGCACCACCATCCTGCTGAACTGCACCGGACAGGTGAAGGGC
CGGAAACCTGCTGCTCTGGGAGAGGCCCAACCCACCAAGAGCCTGGAGG
AGAACAAGTCCCTGAAGGAGCAGAAGAAGCTGAACGACCTGTGCTTCCT
GAAGAGGCTGCTGCAGGAGATCAAGACCTGCTGGAACAAGATCCTGATG
GGCACCAAGGAGCAT (Human Tissue Factor 219)
(SEQ ID NO: 250)
AGCGGCACAACCAACACAGTCGCTGCCTATAACCTCACTTGGAAGAGCA
CCAACTTCAAAACCATCCTCGAATGGGAACCCAAACCCGTTAACCAAGT
TTACACCGTGCAGATCAGCACCAAGTCCGGCGACTGGAAGTCCAAATGT
TTCTATACCACCGACACCGAGTGCGATCTCACCGATGAGATCGTGAAAG
ATGTGAAACAGACCTACCTCGCCCGGGTGTTTAGCTACCCCGCCGGCAA
TGTGGAGAGCACTGGTTCCGCTGGCGAGCCTTTATACGAGAACAGCCCC
GAATTTACCCCTTACCTCGAGACCAATTTAGGACAGCCCACCATCCAAA
GCTTTGAGCAAGTTGGCACAAAGGTGAATGTGACAGTGGAGGACGAGCG
GACTTTAGTGCGGCGGAACAACACCTTTCTCAGCCTCCGGGATGTGTTC
GGCAAAGATTTAATCTACACACTGTATTACTGGAAGTCCTCTTCCTCCG
GCAAGAAGACAGCTAAAACCAACACAAACGAGTTTTTAATCGACGTGGA
TAAAGGCGAAAACTACTGTTTCAGCGTGCAAGCTGTGATCCCCTCCCGG
ACCGTGAATAGGAAAAGCACCGATAGCCCCGTTGAGTGCATGGGCCAAG
AAAAGGGCGAGTTCCGGGAG (Human IL-15)
(SEQ ID NO: 251)
AACTGGGTGAACGTCATCAGCGATTTAAAGAAGATCGAAGATTTAATTC
AGTCCATGCATATCGACGCCCACTTTATACACAGAATCCGACGTGCACCC
CTCTTGTAAGGTGACCGCCATGAAATGTTTTTTACTGGAGCTGCAAGTT
ATCTCTTTAGAGAGCGGAGACGCTAGCATCCACGACACCGTGGAGAATT
TAATCATTTTAGCCAATAACTCTTTATCCAGCAACGGCAACGTGACAGA
GTCCGGCTGCAAGGAGTGCGAAGAGCTGGAGGAGAAGAACATCAAGGAG
TTTCTGCAATCCTTTGTGCACATTGTCCAGATGTTCATCAATACCTCC The chimeric polypeptide of IL-7/TF/IL-15 (including leader sequence), is as follows (SEQ ID NO: 56):
(Signal peptide)
(SEQ ID NO: 252)
MKWVTFISLLFLFSSAYS (Human IL-7)
(SEQ ID NO: 253)
DCDIEGKDGKQYESVLMVSIDQLLDSMKEIGSNCLNNEFNFFKRHICDA
NKEGMFLFRAARKLRQFLKMNSTGDFDLHLLKVSEGTTILLNCTGQVKG
RKPAALGEAQPTKSLEENKSLKEQKKLNDLCFLKRLLQEIKTCWNKILM
GTKEH (Human Tissue Factor 219)
(SEQ ID NO: 254)
SGTTNTVAAYNLTWKSTNFKTILEWEPKPVNQVYTVQISTKSGDWKSKC
FYTTDTECDLTDEIVKDVKQTYLARVFSYPAGNVESTGSAGEPLYENSP
EFTPYLETNLGQPTIQSFEQVGTKVNVTVEDERTLVRRNNTFLSLRDVF
GKDLIYTLYYWKSSSSGKKTAKTNTNEFLIDVDKGENYCFSVQAVIPSR
TVNRKSTDSPVECMGQEKGEFRE (Human IL-15)
(SEQ ID NO: 255)
NWVNVISDLKKIEDLIQSMHIDATLYTESDVHPSCKVTAMKCFLLELQV
ISLESGDASIHDTVENLIILANNSLSSNGNVTESGCKECEELEEKNIKE
FLQSFVHIVQMFINTS The nucleic acid sequence of an IL-7/TF/IL-15 construct (including signal peptide sequence) is as follows (SEQ ID NO: 57):
(Signal peptide)
(SEQ ID NO: 256)
ATGAAGTGGGTGACCTTCATCAGCCTGCTGTTCCTGTTCTCCAGCGCCT
ACTCC (Human IL-7)
(SEQ ID NO: 257)
GATTGCGACATCGAGGGCAAGGACGGCAAGCAGTACGAGAGCGTGCTGA
TGGTGTCCATCGACCAGCTGCTGGACAGCATGAAGGAGATCGGCTCCAA
CTGCCTCAACAACGAGTTCAACTTCTTCAAGCGGCACATCTGCGACGCC
AACAAGGAGGGCATGTTCCTGTTCAGGGCCGCCAGGAAACTGCGGCAGT
TCCTGAAGATGAACTCCACCGGCGACTTCGACCTGCACCTGCTGAAGGT
GTCCGAGGGCACCACCATCCTGCTGAACTGCACCGGACAGGTGAAGGGC
CGGAAACCTGCTGCTCTGGGAGAGGCCCAACCCACCAAGAGCCTGGAGG
AGAACAAGTCCCTGAAGGAGCAGAAGAAGCTGAACGACCTGTGCTTCCT
GAAGAGGCTGCTGCAGGAGATCAAGACCTGCTGGAACAAGATCCTGATG
GGCACCAAGGAGCAT (Human Tissue Factor 219)
(SEQ ID NO: 258)
AGCGGCACAACCAACACAGTCGCTGCCTATAACCTCACTTGGAAGAGCA
CCAACTTCAAAACCATCCTCGAATGGGAACCCAAACCCGTTAACCAAGT
TTACACCGTGCAGATCAGCACCAAGTCCGGCGACTGGAAGTCCAAATGT
TTCTATACCACCGACACCGAGTGCGATCTCACCGATGAGATCGTGAAAG
ATGTGAAACAGACCTACCTCGCCCGGGTGTTTAGCTACCCCGCCGGCAA
TGTGGAGAGCACTGGTTCCGCTGGCGAGCCTTTATACGAGAACAGCCCC
GAATTTACCCCTTACCTCGAGACCAATTTAGGACAGCCCACCATCCAAA
GCTTTGAGCAAGTTGGCACAAAGGTGAATGTGACAGTGGAGGACGAGCG
GACTTTAGTGCGGCGGAACAACACCTTTCTCAGCCTCCGGGATGTGTTC
GGCAAAGATTTAATCTACACACTGTATTACTGGAAGTCCTCTTCCTCCG
GCAAGAAGACAGCTAAAACCAACACAAACGAGTTTTTAATCGACGTGGA
TAAAGGCGAAAACTACTGTTTCAGCGTGCAAGCTGTGATCCCCTCCCGG
ACCGTGAATAGGAAAAGCACCGATAGCCCCGTTGAGTGCATGGGCCAAG
AAAAGGGCGAGTTCCGGGAG (Human IL-15)
(SEQ ID NO: 259)
AACTGGGTGAACGTCATCAGCGATTTAAAGAAGATCGAAGATTTAATTC
AGTCCATGCATATCGACGCCCACTTTATACACAGAATCCGACGTGCACCC
CTCTTGTAAGGTGACCGCCATGAAATGTTTTTTACTGGAGCTGCAAGTT
ATCTCTTTAGAGAGCGGAGACGCTAGCATCCACGACACCGTGGAGAATT
TAATCATTTTAGCCAATAACTCTTTATCCAGCAACGGCAACGTGACAGA
GTCCGGCTGCAAGGAGTGCGAAGAGCTGGAGGAGAAGAACATCAAGGAG
TTTCTGCAATCCTTTGTGCACATTGTCCAGATGTTCATCAATACCTCC The amino acid sequence of IL-7/TF/IL-15 fusion protein (including the leader sequence) is as follows (SEQ ID NO: 58):
(Signal peptide)
(SEQ ID NO: 260)
MKWVTFISLLFLFSSAYS (Human IL-7)
(SEQ ID NO: 261)
DCDIEGKDGKQYESVLMVSIDQLLDSMKEIGSNCLNNEFNFFKRHICDA
NKEGMFLFRAARKLRQFLKMNSTGDFDLHLLKVSEGTTILLNCTGQVKG
RKPAALGEAQPTKSLEENKSLKEQKKLNDLCFLKRLLQEIKTCWNKILM
GTKEH (Human Tissue Factor 219)
(SEQ ID NO: 262)
SGTTNTVAAYNLTWKSTNFKTILEWEPKPVNQVYTVQISTKSGDWKSKC
FYTTDTECDLTDEIVKDVKQTYLARVFSYPAGNVESTGSAGEPLYENSP
EFTPYLETNLGQPTIQSFEQVGTKVNVTVEDERTLVRRNNTFLSLRDVF
GKDLIYTLYYWKSSSSGKKTAKTNTNEFLIDVDKGENYCFSVQAVIPSR
TVNRKSTDSPVECMGQEKGEFRE (Human IL-15)
(SEQ ID NO: 263)
NWVNVISDLKKIEDLIQSMHIDATLYTESDVHPSCKVTAMKCFLLELQV
ISLESGDASIHDTVENLIILANNSLSSNGNVTESGCKECEELEEKNIKE
FLQSFVHIVQMFINTS The nucleic acid sequence of an anti-CD16SscFv/IL-15 RαSu/IL-21 construct (including signal peptide sequence) is as follows (SEQ ID NO: 59):
(Signal peptide)
(SEQ ID NO: 264)
ATGAAGTGGGTGACCTTCATCAGCCTGCTGTTCCTGTTCTCCAGCGCCT
ACTCC ((Anti-human CD16scFv)
(SEQ ID NO: 265)
TCCGAGCTGACCCAGGACCCTGCTGTGTCCGTGGCTCTGGGCCAGACCG
TGAGGATCACCTGCCAGGGCGACTCCCTGAGGTCCTACTACGCCTCCTG
GTACCAGCAGAAGCCCGGCCAGGCTCCTGTGCTGGTGATCTACGGCAAG
AACAACAGGCCCTCCGGCATCCCTGACAGGTTCTCCGGATCCTCCTCCG
GCAACACCGCCTCCCTGACCATCACAGGCGCTCAGGCCGAGGACGAGGC
TGACTACTACTGCAACTCCAGGGACTCCTCCGGCAACCATGTGGTGTTC
GGCGGCGGCACCAAGCTGACCGTGGGCATGGCGGCGGCGGCTCCGGAG
GCGGCGGCAGCGGCGGAGGAGGATCCGAGGTGCAGCTGGTGGAGTCCGG
AGGAGGAGTGGTGAGGCCTGGAGGCTCCCTGAGGCTGAGCTGTGCTGCA
TCCGGCTTCACCTTCGACGACTACGGCATGTCCTGGGTGAGGCAGGCTC
CTGGAAAGGGCCTGGAGTGGGTGTCCGGCATCAACTGGAACGGCGGATC
CACCGGCTACGCCGATTCCGTGAAGGGCAGGTTCACCATCAGCAGGGAC
AACGCCAAGAACTCCCTGTACCTGCAGATGAACTCCCTGAGGGCCGAGG
ACACCGCCGTGTACTACTGCGCCAGGGGCAGGTCCCTGCTGTTCGACTA
CTGGGGACAGGGCACCCTGGTGACCGTGTCCAGG (Human IL-15R α sushi domain)
(SEQ ID NO: 266)
ATTACATGCCCCCCTCCCATGAGCGTGGAGCACGCCGACATCTGGGTGA
AGAGCTATAGCCTCTACAGCCGGGAGAGGTATATCTGTAACAGCGGCTT
CAAGAGGAAGGCCGGCACCAGCAGCCTCACCGAGTGCGTGCTGAATAAG
GCTACCAACGTGGCTCACTGGACAACACCCTCTTTAAAGTGCATCCGG (Human IL-21)
(SEQ ID NO: 267)
CAGGGCCAGGACAGGCACATGATCCGGATGAGGCAGCTCATCGACATCG
TCGACCAGCTGAAGAACTACGTGAACGACCTGGTGCCCGAGTTTCTGCC
TGCCCCCGAGGACGTGGAGACCAACTGCGAGTGGTCCGCCTTCTCCTGC
TTTCAGAAGGCCCAGCTGAAGTCCGCCAACACCGGCAACAACGAGCGGA
TCATCAACGTGAGCATCAAGAAGCTGAAGCGGAAGCCTCCCTCCACAAA
CGCCGGCAGGAGGCAGAAGCACAGGCTGACCTGCCCCAGCTGTGACTCC
TACGAGAAGAAGCCCCCCAAGGAGTTCCTGGAGAGGTTCAAGTCCCTGC
TGCAGAAGATGATCCATCAGCACCTGTCCTCCAGGACCCACGGCTCCGA
GGACTCC The amino acid sequence of the anti-CD16scFv/IL-15RαSu/IL-21 construct (including signal peptide sequence) is as follows (SEQ ID NO: 60):
(Signal peptide)
(SEQ ID NO: 268)
MKWVTFISLLFLFSSAYS (Anti-human CD16scFv)
(SEQ ID NO: 269)
SELTQDPAVSVALGQTVRITCQGDSLRSYYASWYQQKPGQAPVLVIYGK
NNRPSGIPDRFSGSSSGNTASLTITGAQAEDEADYYCNSRDSSGNHVVF
GGGTKLTVGHGGGGSGGGGSGGGGSEVQLVESGGGVVRPGGSLRLSCAA
SGFTEDDYGMSWVRQAPGKGLEWVSGINWNGGSTGYADSVKGRFTISRD
NAKNSLYLQMNSLRAEDTAVYYCARGRSLLFDYWGQGTLVTVSR (Human IL-15R α sushi domain)
(SEQ ID NO: 270)
ITCPPPMSVEHADIWVKSYSLYSRERYICNSGFKRKAGTSSLTECVLNK
ATNVAHWTTPSLKCIR (Human IL-21)
(SEQ ID NO: 271)
QGQDRHMIRMRQLIDIVDQLKNYVNDLVPEFLPAPEDVETNCEWSAFSC
FQKAQLKSANTGNNERIINVSIKKLKRKPPSTNAGRRQKHRLTCPSCDS
YEKKPPKEFLERFKSLLQKMIHQHLSSRTHGSEDS The nucleic acid sequence of the two TGFβ Receptor II/TF/IL-15 construct (including signal peptide sequence) is as follows (SEQ ID NO: 61):
(Signal peptide)
(SEQ ID NO: 272)
ATGAAGTGGGTGACCTTCATCAGCCTGCTGTTCCTGTTCTCCAGCGCCT
ACTCC (Two Human TGFβ Receptor II fragments)
(SEQ ID NO: 273)
ATCCCCCCCCATGTGCAAAAGAGCGTGAACAACGATATGATCGTGACCG
ACAACAACGGCGCCGTGAAGTTTCCCCAGCTCTGCAAGTTCTGCGATGT
CAGGTTCAGCACCTGCGATAATCAGAAGTCCTGCATGTCCAACTGCAGC
ATCACCTCCATCTGCGAGAAGCCCCAAGAAGTGTGCGTGGCCGTGTGGC
GGAAAAATGACGAGAACATCACCCTGGAGACCGTGTGTCACGACCCCAA
GCTCCCTTATCACGACTTCATTCTGGAGGACGCTGCCTCCCCCAAATGC
ATCATGAAGGAGAAGAAGAAGCCCGGAGAGACCTTCTTTATGTGTTCCT
GTAGCAGCGACGAGTGTAACGACAACATCATCTTCAGCGAAGAGTACAA
CACCAGCAACCCTGATGGAGGTGGCGGATCCGGAGGTGGAGGTTCTGGT
GGAGGTGGAGGTATTCCTCCCCACGTGCAGAAGAGCGTGAATAATGACA
TGATCGTGACCGATAACAATGGCGCCGTGAAATTTCCCCAGCTGTGCAA
ATTCTGCGATGTGAGGTTTTCCACCTGCGACAACCAGAAGTCCTGTATG
AGCAACTGCTCCATCACCTCCATCTGTGAGAAGCCTCAGGAGGTGTGCG
TGGCTGTCTGGCGGAAGAATGACGAGAATATCACCCTGGAAACCGTCTG
CCACGATCCCAAGCTGCCCTACCACGATTTCATCCTGGAAGACGCCGCC
AGCCCTAAGTGCATCATGAAAGAGAAAAAGAAGCCTGGCGAGACCTTTT
TCATGTGCTCCTGCAGCAGCGACGAATGCAACGACAATATCATCTTTAG
CGAGGAATACAATACCAGCAACCCCGAC (Human Tissue Factor 219)
(SEQ ID NO: 274)
AGCGGCACAACCAACACAGTCGCTGCCTATAACCTCACTTGGAAGAGCA
CCAACTTCAAAACCATCCTGAATGGGAACCCAAACCCGTTAACCAAGT
TTACACCGTGCAGATCAGCACCAAGTCCGGCGACTGGAAGTCCAAATGT
TTCTATACCACCGACACCGAGTGCGATCTCACCGATGAGATCGTGAAAG
ATGTGAAACAGACCTACCTCGCCCGGGTGTTTAGCTACCCCGCCGGCAA
TGTGGAGAGCACTGGTTCCGCTGGCGAGCCTTTATACGAGAACAGCCCC
GAATTTACCCCTTACCTCGAGACCAATTTAGGACAGCCCACCATCCAAA
GCTTTGAGCAAGTTGGCACAAAGGTGAATGTGACAGTGGAGGACGAGCG
GACTTTAGTGCGGCGGAACAACACCTTTCTCAGCCTCCGGGATGTGTTC
GGCAAAGATTTAATCTACACACTGTATTACTGGAAGTCCTCTTCCTCCG
GCAAGAAGACAGCTAAAACCAACACAAACGAGTTTTTAATCGACGTGGA
TAAAGGCGAAAACTACTGTTTCAGCGTGCAAGCTGTGATCCCCTCCCGG
ACCGTGAATAGGAAAAGCACCGATAGCCCCGTTGAGTGCATGGGCCAAG
AAAAGGGCGAGTTCCGGGAG (Human IL-15)
(SEQ ID NO: 275)
AACTGGGTGAACGTCATCAGCGATTTAAAGAAGATCGAAGATTTAATTC
AGTCCATGCATATCGACGCCACTTTATACACAGAATCCGACGTGCACCC
CTCTTGTAAGGTGACCGCCATGAAATGTTTTTTACTGGAGCTGCAAGTT
ATCTCTTTAGAGAGCGGAGACGCTAGCATCCACGACACCGTGGAGAATT
TAATCATTTTAGCCAATAACTCTTTATCCAGCAACGGCAACGTGACAGA
GTCCGGCTGCAAGGAGTGCGAAGAGCTGGAGGAGAAGAACATCAAGGAG
TTTCTGCAATCCTTTGTGCACATTGTCCAGATGTTCATCAATACCTCC The amino acid sequence of TGFβ Receptor II/TF/IL-15 fusion protein (including the leader sequence) is as follows (SEQ ID NO: 62):
(Signal peptide)
(SEQ ID NO: 276)
MKWVTFISLLFLFSSAYS (Human TGFβ Receptor II)
(SEQ ID NO: 277)
IPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKC
IMKEKKKPGETFFMCSCSSDECNDNIIFSEEYNTSNPDGGGGSGGGGSG
GGGSIPPHVQKSVNNDMIVTDNNGAVKFPQLCKFCDVRFSTCDNQKSCM
SNCSITSICEKPQEVCVAVWRKNDENITLETVCHDPKLPYHDFILEDAA
SPKCIMKEKKKPGETFFMCSCSSDECNDNIIFSEEYNTSNPD (Human Tissue Factor 219)
(SEQ ID NO: 278)
SGTTNTVAAYNLTWKSTNFKTILEWEPKPVNQVYTVQISTKSGDWKSKC
FYTTDTECDLTDEIVKDVKQTYLARVFSYPAGNVESTGSAGEPLYENSP
EFTPYLETNLGQPTIQSFEQVGTKVNVTVEDERTLVRRNNTFLSLRDVF
GKDLIYTLYYWKSSSSGKKTAKTNTNEFLIDVDKGENYCFSVQAVIPSR
TVNRKSTDSPVECMGQEKGEFRE (Human IL-15)

(SEQ ID NO: 279)
NWVNVISDLKKIEDLIQSMHIDATLYTESDVHPSCKVTAMKCFLLELQV
ISLESGDASIHDTVENLIILANNSLSSNGNVTESGCKECEELEEKNIKE
FLQSFVHIVQMFINTS

The nucleic acid sequence of the anti-CD16scFv/IL-15 RαSu/IL-21 construct (including signal peptide sequence) is as follows (SEQ ID NO: 63):
(Signal peptide)

(SEQ ID NO: 280)
ATGAAGTGGGTGACCTTCATCAGCCTGCTGTTCCTGTTCTCCAGCGCCT
ACTCC (Anti-human CD16scFv)

(SEQ ID NO: 281)
TCCGAGCTGACCCAGGACCCTGCTGTGTCCGTGGCTCTGGGCCAGACCG
TGAGGATCACCTGCCAGGGCGACTCCCTGAGGTCCTACTACGCCTCCTG
GTACCAGCAGAAGCCCGGCCAGGCTCCTGTGCTGGTGATCTACGGCAAG
AACAACAGGCCCTCCGGCATCCCTGACAGGTTCTCCGGATCCTCCTCCG
GCAACACCGCCTCCCTGACCATCACAGGCGCTCAGGCCGAGGACGAGGC
TGACTACTACTGCAACTCCAGGGACTCCTCCGGCAACCATGTGGTGTTC
GGCGGCGGCACCAAGCTGACCGTGGGCCATGGCGGCGGCGGCTCCGGAG
GCGGCGGCAGCGGCGGAGGAGGATCCGAGGTGCAGCTGGTGGAGTCCGG
AGGAGGAGTGGTGAGGCCTGGAGGCTCCCTGAGGCTGAGCTGTGCTGCC
TCCGGCTTCACCTTCGACGACTACGGCATGTCCTGGGTGAGGCAGGCTC
CTGGAAAGGGCCTGGAGTGGGTGTCCGGCATCAACTGGAACGGCGGATC
CACCGGCTACGCCGATTCCGTGAAGGGCAGGTTCACCATCAGCAGGGAC
AACGCCAAGAACTCCCTGTACCTGCAGATGAACTCCCTGAGGGCCGAGG
ACACCGCCGTGTACTACTGCGCCAGGGGCAGGTCCCTGCTGTTCGACTA
CTGGGGACAGGGCACCCTGGTGACCGTGTCCAGG (Human IL-15R α sushi domain)

(SEQ ID NO: 282)
ATTACATGCCCCCCTCCCATGAGCGTGGAGCACGCCGACATCTGGGTGA
AGAGCTATAGCCTCTACAGCCGGGAGAGGTATATCTGTAACAGCGGCTT
CAAGAGGAAGGCCGGCACCAGCAGCCTCACCGAGTGCGTGCTGAATAAG
GCTACCAACGTGGCTCACTGGACAACACCCTCTTTAAAGTGCATCCGG (Human IL-21)

(SEQ ID NO: 283)
CAGGGCCAGGACAGGCACATGATCCGGATGAGGCAGCTCATCGACATCG
TCGACCAGCTGAAGAACTACGTGAACGACCTGGTGCCCGAGTTTCTGCC
TGCCCCCGAGGACGTGGAGACCAACTGCGAGTGGTCCGCCTTCTCCTGC
TTTCAGAAGGCCCAGCTGAAGTCCGCCAACACCGGCAACAACGAGCGGA
TCATCAACGTGAGCATCAAGAAGCTGAAGCGGAAGCCTCCCTCCACAAA
CGCCGGCAGGAGGCAGAAGCACAGGCTGACCTGCCCCAGCTGTGACTCC
TACGAGAAGAAGCCCCCCAAGGAGTTCCTGGAGAGGTTCAAGTCCCTGC
TGCAGAAGATGATCCATCAGCACCTGTCCTCCAGGACCCACGGCTCCGA
GGACTCC

The amino acid sequence of the anti-CD16scFv/IL-15RαSu/IL-21 construct (including signal peptide sequence) is as follows (SEQ ID NO: 64):
(Signal peptide)

(SEQ ID NO: 284)
MKWVTFISLLFLFSSAYS (Anti-human CD16scFv)

(SEQ ID NO: 285)
SELTQDPAVSVALGQTVRITCQGDSLRSYYASWYQQKPGQAPVLVIYGK
NNRPSGIPDRFSGSSSGNTASLTITGAQAEDEADYYCNSRDSSGNHVVF
GGGTKLTVGHGGGGSGGGGSGGGGSEVQLVESGGGVVRPGGSLRLSCAA
SGFTFDDYGMSWVRQAPKGLEWVSGINWNGGSTGYADSVKGRFTISRD
NAKNSLYLQMNSLRAEDTAVYYCARGRSLLFDYWGQGTLVTVSR
(Human IL-15R α sushi domain)

(SEQ ID NO: 286)
ITCPPPMSVEHADIWVKSYSLYSRERYICNSGFKRKAGTSSLTECVLNK
ATNVAHWTTPSLKCIR (Human IL-21)

(SEQ ID NO: 287)
QGQDRHMIRMRQLIDIVDQLKNYVNDLVPEFLPAPEDVETNCEWSAFSC
FQKAQLKSANTGNNERIINVSIKKLKRKPPSTNAGRRQKHRLTCPSCDS
YEKKPPKEFLERFKSLLQKMIHQHLSSRTHGSEDS

The nucleic acid sequence of 7t15 construct (including signal peptide sequence) is as follows (SEQ ID NO: 65):
(Signal peptide)

(SEQ ID NO: 288)
ATGAAGTGGGTGACCTTCATCAGCCTGCTGTTCCTGTTCTCCAGCGCCT
ACTCC (Human IL7)

(SEQ ID NO: 289)
GATTGCGACATCGAGGGCAAGGACGGCAAGCAGTACGAGAGCGTGCTGA
TGGTGTCCATCGACCAGCTGCTGGACAGCATGAAGGAGATCGGCTCCAA
CTGCCTCAACAACGAGTTCAACTTCTTCAAGCGGCACATCTGCGACGCC
AACAAGGAGGGCATGTTCCTGTTCAGGGCCGCCAGGAAACTGCGGCAGT
TCCTGAAGATGAACTCCACCGGCGACTTCGACCTGCACCTGCTGAAGGT
GTCCGAGGGCACCACCATCCTGCTGAACTGCACCGGACAGGTGAAGGGC
CGGAAACCTGCTGCTCTGGGAGAGGCCCAACCCACCAAGAGCCTGGAGG
AGAACAAGTCCCTGAAGGAGCAGAAGAAGCTGAACGACCTGTGCTTCCT
GAAGAGGCTGCTGCAGGAGATCAAGACCTGCTGGAACAAGATCCTGATG
GGCACCAAGGAGCAT (Human Tissue Factor 219)

(SEQ ID NO: 290)
AGCGGCACAACCAACACAGTCGCTGCCTATAACCTCACTTGGAAGAGCA
CCAACTTCAAAACCATCCTCGAATGGGAACCCAAACCCGTTAACCAAGT
TTACACCGTGCAGATCAGCACCAAGTCCGGCGACTGGAAGTCCAAATGT
TTCTATACCACCGACACCGAGTGCGATCTCACCGATGAGATCGTGAAAG
ATGTGAAACAGACCTACCTCGCCCGGGTGTTTAGCTACCCCGCCGGCAA
TGTGGAGAGCACTGGTTCCGCTGGCGAGCCTTTATACGAGAACAGCCCC
GAATTTACCCCTTACCTCGAGACCAATTTAGGACAGCCCACCATCCAAA
GCTTTGAGCAAGTTGGCACAAAGGTGAATGTGACAGTGGAGGACGAGCG
GACTTTAGTGCGGCGGAACAACACCTTTCTCAGCCTCCGGGATGTGTTC
GGCAAAGATTTAATCTACACACTGTATTACTGGAAGTCCTCTTCCTCCG
GCAAGAAGACAGCTAAAACCAACACAAACGAGTTTTTAATCGACGTGGA
TAAAGGCGAAAACTACTGTTTCAGCGTGCAAGCTGTGATCCCCTCCCGG
ACCGTGAATAGGAAAAGCACCGATAGCCCCGTTGAGTGCATGGGCCAAG
AAAAGGGCGAGTTCCGGGAG (Human IL-15)

(SEQ ID NO: 291)
AACTGGGTGAACGTCATCAGCGATTTAAAGAAGATCGAAGATTTAATTC
AGTCCATGCATATCGACGCCACTTTATACACAGAATCCGACGTGCACCC
CTCCTGTAAGGTGACCGCCATGAAATGTTTTTTACTGGAGCTGCAAGTT
ATCTCTTTAGAGAGCGGAGACGCTAGCATCCACGACACCGTGGAGAATT
TAATCATTTTAGCCAATAACTCTTTATCCAGCAACGGCAACGTGACAGA
GTCCGGCTGCAAGGAGTGCGAAGAGCTGGAGGAGAAGAACATCAAGGAG
TTTCTGCAATCCTTTGTGCACATTGTCCAGATGTTCATCAATACCTCC

The amino acid sequence of 7t15 fusion protein (including the leader sequence) is as follows (SEQ ID NO: 66):
(Signal peptide)

(SEQ ID NO: 292)
MKWVTFISLLFLFSSAYS (Human IL7)

(SEQ ID NO: 293)
DCDIEGKDGKQYESVLMVSIDQLLDSMKEIGSNCLNNEFNFFKRHICDA
NKEGMFLFRAARKLRQFLKMNSTGDFDLHLLKVSEGTTILLNCTGQVKG
RKPAALGEAQPTKSLEENKSLKEQKKLNDLCFLKRLLQEIKTCWNKILM
GTKEH (Human Tissue Factor 219)

(SEQ ID NO: 294)
SGTTNTVAAYNLTWKSTNFKTILEWEPKPVNQVYTVQISTKSGDWKSKC
FYTTDTECDLTDEIVKDVKQTYLARVFSYPAGNVESTGSAGEPLYENSP
EFTPYLETNLGQPTIQSFEQVGTKVNVTVEDERTLVRRNNTFLSLRDVF
GKDLIYTLYYWKSSSSGKKTAKTNTNEFLIDVDKGENYCFSVQAVIPSR
TVNRKSTDSPVECMGQEKGEFRE (Human IL-15)

(SEQ ID NO: 295)
NWVNVISDLKKIEDLIQSMHIDATLYTESDVHPSCKVTAMKCFLLELQV
ISLESGDASIHDTVENLIILANNSLSSNGNVTESGCKECEELEEKNIKE
FLQSFVHIVQMFINTS

The nucleic acid sequence of 7s construct (including signal peptide sequence) is as follows (SEQ ID NO: 67):
(Signal peptide)

(SEQ ID NO: 296)
ATGGGAGTGAAAGTTCTTTTTGCCCTTATTTGTATTGCTGTGGCCGAGG
CC (Human IL7)

(SEQ ID NO: 297)
GATTGTGATATTGAAGGTAAAGATGGCAAACAATATGAGAGTGTTCTAA
TGGTCAGCATCGATCAATTATTGGACAGCATGAAAGAAATTGGTAGCAA
TTGCCTGAATAATGAATTTAACTTTTTTAAAAGACATATCTGTGATGCT
AATAAGGAAGGTATGTTTTATTCCGTGCTGCTCGCAAGTTGAGGCAAT
TTCTTAAAATGAATAGCACTGGTGATTTTGATCTCCACTTATTAAAAGT
TTCAGAAGGCACAACAATACTGTTGAACTGCACTGGCCAGGTTAAAGGA
AGAAAACCAGCTGCCCTGGGTGAAGCCCAACCAACAAAGAGTTTGGAAG
AAAATAAATCTTTAAAGGAACAGAAAAAACTGAATGACTTGTGTTTCCT
AAAGAGACTATTACAAGAGATAAAAACTTGTTGGAATAAAATTTTGATG
GGCACTAAAGAACAC (Human IL-15R α sushi domain)

(SEQ ID NO: 298)
ATCACGTGCCCTCCCCCCATGTCCGTGGAACACGAGACATCTGGGTCA
AGAGCTACAGCTTGTACTCCAGGGAGCGGTACATTTGTAACTCTGGTTT
CAAGCGTAAAGCCGGCACGTCCAGCCTGACGGAGTGCGTGTTGAACAAG
GCCACGAATGTCGCCCACTGGACAACCCCCAGTCTCAAATGCATTAGA

The amino acid sequence of 7s fusion protein (including the leader sequence) is as follows (SEQ ID NO: 68):
(Signal peptide)

(SEQ ID NO: 299)
MGVKVLFALICIAVAEA (Human IL7)

(SEQ ID NO: 300)
DCDIEGKDGKQYESVLMVSIDQLLDSMKEIGSNCLNNEFNFFKRHICDA
NKEGMFLFRAARKLRQFLKMNSTGDFDLHLLKVSEGTTILLNCTGQVKG
RKPAALGEAQPTKSLEENKSLKEQKKLNDLCFLKRLLQEIKTCWNKILM
GTKEH (Human IL-15R α sushi domain)

(SEQ ID NO: 301)
ITCPPPMSVEHADIWVKSYSLYSRERYICNSGFKRKAGTSSLTECVLNK
ATNVAHWTTPSLKCIR

The nucleic acid sequence of the two TGFβ Receptor II/TF/IL-15 construct (including signal peptide sequence) is as follows (SEQ ID NO: 69):
(Signal peptide)

(SEQ ID NO: 302)
ATGAAGTGGGTGACCTTCATCAGCCTGCTGTTCCTGTTCTCCAGCGCCT
ACTCC (Two Human TGFβ Receptor Il fragments)

(SEQ ID NO: 303)
ATCCCCCCCCATGTGCAAAAGAGCGTGAACAACGATATGATCGTGACCG
ACAACAACGGCGCCGTGAAGTTTCCCCAGCTCTGCAAGTTCTGCGATGT
CAGGTTCAGCACCTGCGATAATCAGAAGTCCTGCATGTCCAACTGCAGC
ATCACCTCCATCTGCGAGAAGCCCCAAGAAGTGTGCGTGGCCGTGTGGC
GGAAAAATGACGAGAACATCACCCTGGAGACCGTGTGTCACGACCCCAA
GCTCCCTTATCACGACTTCATTCTGGAGGACGCTGCCTCCCCCAAATGC
ATCATGAAGGAGAAGAAGAAGCCCGGAGAGACCTTCTTTATGTGTTCCT
GTAGCAGCGACGAGTGTAACGACAACATCATCTTCAGCGAAGAGTACAA
CACCAGCAACCCTGATGGAGGTGGCGGATCCGGAGGTGGAGGTTCTGGT
GGAGGTGGGAGTATTCCTCCCCACGTGCAGAAGAGCGTGAATAATGACA
TGATCGTGACCGATAACAATGGCGCCGTGAAATTTCCCCAGCTGTGCAA
ATTCTGCGATGTGAGGTTTTCCACCTGCGACAACCAGAAGTCCTGTATG
AGCAACTGCTCCATCACCTCCATCTGTGAGAAGCCTCAGGAGGTGTGCG
TGGCTGTCTGGCGGAAGAATGACGAGAATATCACCCTGGAAACCGTCTG
CCACGATCCCAAGCTGCCCTACCACGATTTCATCCTGGAAGACGCCGCC
AGCCCTAAGTGCATCATGAAAGAGAAAAAGAAGCCTGGCGAGACCTTTT
TCATGTGCTCCTGCAGCAGCGACGAATGCAACGACAATATCATCTTTAG
CGAGGAATACAATACCAGCAACCCCGAC (Human Tissue Factor 219)

(SEQ ID NO: 304)
AGCGGCACAACCAACACAGTCGCTGCCTATAACCTCACTTGGAAGAGCA
CCAACTTCAAAACCATCCTCGAATGGGAACCCAAACCCGTTAACCAAGT
TTACACCGTGCAGATCAGCACCAAGTCCGGCGACTGGAAGTCCAAATGT
TTCTATACCACCGACACCGAGTGCGATCTCACCGATGAGATCGTGAAAG
ATGTGAAACAGACCTACCTCGCCCGGGTGTTTAGCTACCCCGCCGGCAA
TGTGGAGAGCACTGGTTCCGCTGGCGAGCCTTTATACGAGAACAGCCCC
GAATTTACCCCTTACCTCGAGACCAATTTAGGACAGCCCACCATCCAAA
GCTTTGAGCAAGTTGGCACAAAGGTGAATGTGACAGTGGAGGACGAGCG
GACTTTAGTGCGGCGGAACAACACCTTTCTCAGCCTCCGGGATGTGTTC
GGCAAAGATTTAATCTACACACTGTATTACTGGAAGTCCTCTTCCTCCG
GCAAGAAGACAGCTAAAACCAACACAAACGAGTTTTTAATCGACGTGGA
TAAAGGCGAAAACTACTGTTTCAGCGTGCAAGCTGTGATCCCCTCCCGG
ACCGTGAATAGGAAAAGCACCGATAGCCCCGTTGAGTGCATGGGCCAAG
AAAAGGGCGAGTTCCGGGAG (Human IL-15)

(SEQ ID NO: 305)
AACTGGGTGAACGTCATCAGCGATTTAAAGAAGATCGAAGATTTAATTC
AGTCCATGCATATCGACGCCACTTTATACACAGAATCCGACGTGCACCC
CTCTTGTAAGGTGACCGCCATGAAATGTTTTTTACTGGAGCTGCAAGTT
ATCTCTTTAGAGAGCGGAGACGCTAGCATCCACGACACCGTGGAGAATT
TAATCATTTTAGCCAATAACTCTTTATCCAGCAACGGCAACGTGACAGA
GTCCGGCTGCAAGGAGTGCGAAGAGCTGGAGGAGAAGAACATCAAGGAG
TTTCTGCAATCCTTTGTGCACATTGTCCAGATGTTCATCAATACCTCC

The amino acid sequence of TGFβ Receptor II/TF/IL-15 fusion protein (including the leader sequence) is as follows (SEQ ID NO: 70):
(Signal peptide)

(SEQ ID NO: 306)
MKWVTFISLLFLFSSAYS (Human TGFβ Receptor II)

(SEQ ID NO: 307)
IPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKC
IMKEKKKPGETFFMCSCSSDECNDNIIFSEEYNTSNPDGGGGSGGGGSG
GGGSIPPHVQKSVNNDMIVTDNNGAVKFPQLCKFCDVRFSTCDNQKSCM
SNCSITSICEKPQEVCVAVWRKNDENITLETVCHDPKLPYHDFILEDAA
SPKCIMKEKKKPGETFFMCSCSSDECNDNIIFSEEYNTSNPD (Human Tissue Factor 219)

(SEQ ID NO: 308)
SGTTNTVAAYNLTWKSTNFKTILEWEPKPVNQVYTVQISTKSGDWKSKC
FYTTDTECDLTDEIVKDVKQTYLARVFSYPAGNVESTGSAGEPLYENSP
EFTPYLETNLGQPTIQSFEQVGTKVNVTVEDERTLVRRNNTFLSLRDVF
GKDLIYTLYYWKSSSSGKKTAKTNTNEFLIDVDKGENYCFSVQAVIPSR
TVNRKSTDSPVECMGQEKGEFRE (Human IL-15)

(SEQ ID NO: 309)
NWVNVISDLKKIEDLIQSMHIDATLYTESDVHPSCKVTAMKCFLLELQV
ISLESGDASIHDTVENLIILANNSLSSNGNVTESGCKECEELEEKNIKE
FLQSFVHIVQMFINTS

2The nucleic acid sequence of the TGFβ Receptor II/IL-15 RαSu construct (including signal peptide sequence) is as follows (SEQ ID NO: 71):
(Signal peptide)
(SEQ ID NO: 310)
ATGAAGTGGGTGACCTTCATCAGCCTGCTGTTCCTGTTCTCCAGCGCCTA

CTCC (Two human TGFβ Receptor II fragments)
(SEQ ID NO: 311)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGAC (Human IL-15R α sushi domain)
(SEQ ID NO: 312)
ATTACATGCCCCCCTCCCATGAGCGTGGAGCACGCCGACATCTGGGTGAA

GAGCTATAGCCTCTACAGCCGGGAGAGGTATATCTGTAACAGCGGCTTCA

AGAGGAAGGCCGGCACCAGCAGCCTCACCGAGTGCGTGCTGAATAAGGCT

ACCAACGTGGCTCACTGGACAACACCCTCTTTAAAGTGCATCCGG

The amino acid sequence of the two TGFβ Receptor II/IL-15RαSu construct (including signal peptide sequence) is as follows (SEQ ID NO: 72):
(Signal peptide)
(SEQ ID NO: 313)
MKWVTFISLLFLFSSAYS (Two human TGFβ Receptor II extra-cellular domains)
(SEQ ID NO: 314)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPD (Human IL-15R α sushi domain)
(SEQ ID NO: 315)
ITCPPPMSVEHADIWVKSYSLYSRERYICNSGFKRKAGTSSLTECVLNKA

TNVAHWTTPSLKCIR

The nucleic acid sequence of the 7t15 construct (including signal peptide sequence) is as follows (SEQ ID NO: 73):
(Signal peptide)
(SEQ ID NO: 316)
ATGAAGTGGGTGACCTTCATCAGCCTGCTGTTCCTGTTCTCCAGCGCCTA

CTCC (Human IL7)
(SEQ ID NO: 317)
GATTGCGACATCGAGGGCAAGGACGGCAAGCAGTACGAGAGCGTGCTGAT

GGTGTCCATCGACCAGCTGCTGGACAGCATGAAGGAGATCGGCTCCAACT

GCCTCAACAACGAGTTCAACTTCTTCAAGCGGCACATCTGCGACGCCAAC

AAGGAGGGCATGTTCCTGTTCAGGGCCGCCAGGAAACTGCGGCAGTTCCT

GAAGATGAACTCCACCGGCGACTTCGACCTGCACCTGCTGAAGGTGTCCG

AGGGCACCACCATCCTGCTGAACTGCACCGGACAGGTGAAGGGCCGGAAA

CCTGCTGCTCTGGGAGAGGCCCAACCCACCAAGAGCCTGGAGGAGAACAA

GTCCCTGAAGGAGCAGAAGAAGCTGAACGACCTGTGCTTCCTGAAGAGGC

TGCTGCAGGAGATCAAGACCTGCTGGAACAAGATCCTGATGGGCACCAAG

GAGCAT (Human Tissue Factor 219)
(SEQ ID NO: 318)
AGCGGCACAACCAACACAGTCGCTGCCTATAACCTCACTTGGAAGAGCAC

CAACTTCAAAACCATCCTCGAATGGGAACCCAAACCCGTTAACCAAGTTT

ACACCGTGCAGATCAGCACCAAGTCCGGCGACTGGAAGTCCAAATGTTTC

TATACCACCGACACCGAGTGCGATCTCACCGATGAGATCGTGAAAGATGT

GAAACAGACCTACCTCGCCCGGGTGTTTAGCTACCCCGCCGGCAATGTGG

AGAGCACTGGTTCCGCTGGCGAGCCTTTATACGAGAACAGCCCCGAATTT

ACCCCTTACCTCGAGACCAATTTAGGACAGCCCACCATCCAAAGCTTTGA

GCAAGTTGGCACAAAGGTGAATGTGACAGTGGAGGACGAGCGGACTTTAG

TGCGGCGGAACAACACCTTTCTCAGCCTCCGGGATGTGTTCGGCAAAGAT

TTAATCTACACACTGTATTACTGGAAGTCCTCTTCCTCCGGCAAGAAGAC

AGCTAAAACCAACACAAACGAGTTTTTAATCGACGTGGATAAAGGCGAAA

ACTACTGTTTCAGCGTGCAAGCTGTGATCCCCTCCCGGACCGTGAATAGG

AAAAGCACCGATAGCCCCGTTGAGTGCATGGGCCAAGAAAAGGGCGAGTT

CCGGGAG (Human IL-15)
(SEQ ID NO: 319)
AACTGGGTGAACGTCATCAGCGATTTAAAGAAGATCGAAGATTTAATTCA

GTCCATGCATATCGACGCCACTTTATACACAGAATCCGACGTGCACCCCT

-continued
CTTGTAAGGTGACCGCCATGAAATGTTTTTACTGGAGCTGCAAGTTATC

TCTTTAGAGAGCGGAGACGCTAGCATCCACGACACCGTGGAGAATTTAAT

CATTTTAGCCAATAACTCTTTATCCAGCAACGGCAACGTGACAGAGTCCG

GCTGCAAGGAGTGCGAAGAGCTGGAGGAGAAGAACATCAAGGAGTTTCTG

CAATCCTTTGTGCACATTGTCCAGATGTTCATCAATACCTCC

The amino acid sequence of 7t15 fusion protein (including the leader sequence) is as follows (SEQ ID NO: 74):
(Signal peptide)
(SEQ ID NO: 320)
MKWVTFISLLFLFSSAYS (Human IL7)
(SEQ ID NO: 321)
DCDIEGKDGKQYESVLMVSIDQLLDSMKEIGSNCLNNEFNFFKRHICDAN

KEGMFLFRAARKLRQFLKMNSTGDFDLHLLKVSEGTTILLNCTGQVKGRK

PAALGEAQPTKSLEENKSLKEQKKLNDLCFLKRLLQEIKTCWNKILMGTK

EH (Human Tissue Factor 219)
(SEQ ID NO: 322)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE (Human IL-15)
(SEQ ID NO: 323)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS

The nucleic acid and protein sequences of the 21s137L are shown below. The nucleic acid sequence of the 21s137L construct (including signal peptide sequence) is as follows (SEQ ID NO: 75):
(Signal peptide)
(SEQ ID NO: 324)
ATGAAGTGGGTGACCTTCATCAGCCTGCTGTTCCTGTTCTCCAGCGCCTA

CTCC (Human IL-21)
(SEQ ID NO: 325)
CAGGGCCAGGACAGGCACATGATCCGGATGAGGCAGCTCATCGACATCGT

CGACCAGCTGAAGAACTACGTGAACGACCTGGTGCCCGAGTTTCTGCCTG

CCCCCGAGGACGTGGAGACCAACTGCGAGTGGTCCGCCTTCTCCTGCTTT

CAGAAGGCCCAGCTGAAGTCCGCCAACACCGGCAACAACGAGCGGATCAT

CAACGTGAGCATCAAGAAGCTGAAGCGGAAGCCTCCCTCCACAAACGCCG

GCAGGAGGCAGAAGCACAGGCTGACCTGCCCCAGCTGTGACTCCTACGAG

AAGAAGCCCCCAAGGAGTTCCTGGAGAGGTTCAAGTCCCTGCTGCAGAA

GATGATCCATCAGCACCTGTCCTCCAGGACCCACGGCTCCGAGGACTCC (Human IL-15R α sushi domain)
(SEQ ID NO: 326)
ATTACATGCCCCCCTCCCATGAGCGTGGAGCACGCCGACATCTGGGTGAA

GAGCTATAGCCTCTACAGCCGGGAGAGGTATATCTGTAACAGCGGCTTCA

AGAGGAAGGCCGGCACCAGCAGCCTCACCGAGTGCGTGCTGAATAAGGCT

ACCAACGTGGCTCACTGGACAACACCCTCTTTAAAGTGCATCCGG ((G4S)3 linker)
(SEQ ID NO: 327)
GGCGGTGGAGGATCCGGAGGAGGTGGCTCCGGCGGCGGAGGATCT (Human CD137L)
(SEQ ID NO: 328)
CGCGAGGGTCCCGAGCTTTCGCCCGACGATCCCGCCGGCCTCTTGGACCT

GCGGCAGGGCATGTTTGCGCAGCTGGTGGCCCAAAATGTTCTGCTGATCG

ATGGCCCCTGAGCTGGTACAGTGACCCAGGCCTGGCAGGCGTGTCCCTG

ACGGGGGGCCTGAGCTACAAAGAGGACACGAAGGAGCTGGTGGTGGCCAA

GGCTGGAGTCTACTATGTCTTCTTTCAACTAGAGCTGCGGCGCGTGGTGG

CCGGCGAGGGCTCAGGCTCCGTTTCACTTGCGCTGCACCTGCAGCCACTG

CGCTCTGCTGCTGGGGCCGCCGCCCTGGCTTTGACCGTGGACCTGCCACC

CGCCTCCTCCGAGGCTCGGAACTCGGCCTTCGGTTTCCAGGGCCGCTTGC

TGCACCTGAGTGCCGGCCAGCGCCTGGGCGTCCATCTTCACACTGAGGCC

AGGGCACGCCATGCCTGGCAGCTTACCCAGGGCGCCACAGTCTTGGGACT

CTTCCGGGTGACCCCCGAAATCCCAGCCGGACTCCCTTCACCGAGGTCGG

AA

The amino acid sequence of 21s137L fusion protein (including the leader sequence) is as follows (SEQ ID NO: 76):
(Signal peptide)
(SEQ ID NO: 329)
MKWVTFISLLFLFSSAYS (Human IL-21)
(SEQ ID NO: 330)
QGQDRHMIRMRQLIDIVDQLKNYVNDLVPEFLPAPEDVETNCEWSAFSCF

QKAQLKSANTGNNERIINVSIKKLKRKPPSTNAGRRQKHRLTCPSCDSYE

KKPPKEFLERFKSLLQKMIHQHLSSRTHGSEDS (Human IL-15R α sushi domain)
(SEQ ID NO: 331)
ITCPPPMSVEHADIWVKSYSLYSRERYICNSGFKRKAGTSSLTECVLNKA

TNVAHWTTPSLKCIR ((G4S)3 linker)
(SEQ ID NO: 332)
GGGGSGGGGSGGGGS (Human CD137L)
(SEQ ID NO: 333)
REGPELSPDDPAGLLDLRQGMFAQLVAQNVLLIDGPLSWYSDPGLAGVSL

TGGLSYKEDTKELVVAKAGVYYVFFQLELRRVVAGEGSGSVSLALHLQPL

RSAAGAAALALTVDLPPASSEARNSAFGFQGRLLHLSAGQRLGVHLHTEA

RARHAWQLTQGATVLGLFRVTPEIPAGLPSPRSE

The nucleic acid sequence of 7t15 construct (including signal peptide sequence) is as follows (SEQ ID NO: 77):
(Signal peptide)
(SEQ ID NO: 334)
ATGAAGTGGGTGACCTTCATCAGCCTGCTGTTCCTGTTCTCCAGCGCCTA

CTCC (Human IL7)
(SEQ ID NO: 335)
GATTGCGACATCGAGGGCAAGGACGGCAAGCAGTACGAGAGCGTGCTGAT

GGTGTCCATCGACCAGCTGCTGGACAGCATGAAGGAGATCGGCTCCAACT

GCCTCAACAACGAGTTCAACTTCTTCAAGCGGCACATCTGCGACGCCAAC

AAGGAGGGCATGTTCCTGTTCAGGGCCGCCAGGAAACTGCGGCAGTTCCT

GAAGATGAACTCCACCGGCGACTTCGACCTGCACCTGCTGAAGGTGTCCG

AGGGCACCACCATCCTGCTGAACTGCACCGGACAGGTGAAGGGCCGGAAA

CCTGCTGCTCTGGGAGAGGCCCAACCCACCAAGAGCCTGGAGGAGAACAA

GTCCCTGAAGGAGCAGAAGAAGCTGAACGACCTGTGCTTCCTGAAGAGGC

TGCTGCAGGAGATCAAGACCTGCTGGAACAAGATCCTGATGGGCACCAAG

GAGCAT (Human Tissue Factor 219)
(SEQ ID NO: 336)
AGCGGCACAACCAACACAGTCGCTGCCTATAACCTCACTTGGAAGAGCAC

CAACTTCAAAACCATCCTCGAATGGGAACCCAAACCCGTTAACCAAGTTT

ACACCGTGCAGATCAGCACCAAGTCCGGCGACTGGAAGTCCAAATGTTTC

TATACCACCGACACCGAGTGCGATCTCACCGATGAGATCGTGAAAGATGT

GAAACAGACCTACCTCGCCCGGGTGTTTAGCTACCCCGCCGGCAATGTGG

AGAGCACTGGTTCCGCTGGCGAGCCTTTATACGAGAACAGCCCCGAATTT

ACCCCTTACCTCGAGACCAATTTAGGACAGCCCACCATCCAAAGCTTTGA

GCAAGTTGGCACAAAGGTGAATGTGACAGTGGAGGACGAGCGGACTTTAG

TGCGGCGGAACAACACCTTTCTCAGCCTCCGGGATGTGTTCGGCAAAGAT

TTAATCTACACACTGTATTACTGGAAGTCCTCTTCCTCCGGCAAGAAGAC

AGCTAAAACCAACACAAACGAGTTTTTAATCGACGTGGATAAAGGCGAAA

ACTACTGTTTCAGCGTGCAAGCTGTGATCCCCTCCCGGACCGTGAATAGG

AAAAGCACCGATAGCCCCGTTGAGTGCATGGGCCAAGAAAAGGGCGAGTT

CCGGGAG (Human IL-15)
(SEQ ID NO: 337)
AACTGGGTGAACGTCATCAGCGATTTAAAGAAGATCGAAGATTTAATTCA

GTCCATGCATATCGACGCCACTTTATACACAGAATCCGACGTGCACCCCT

CTTGTAAGGTGACCGCCATGAAATGTTTTTTACTGGAGCTGCAAGTTATC

TCTTTAGAGAGCGGAGACGCTAGCATCCACGACACCGTGGAGAATTTAAT

CATTTTAGCCAATAACTCTTTATCCAGCAACGGCAACGTGACAGAGTCCG

GCTGCAAGGAGTGCGAAGAGCTGGAGGAGAAGAACATCAAGGAGTTTCTG

CAATCCTTTGTGCACATTGTCCAGATGTTCATCAATACCTCC

The amino acid sequence of 7t15 fusion protein (including the leader sequence) is as follows (SEQ ID NO: 78):
(Signal peptide)
(SEQ ID NO: 338)
MKWVTFISLLFLFSSAYS (Human IL7)
(SEQ ID NO: 339)
DCDIEGKDGKQYESVLMVSIDQLLDSMKEIGSNCLNNEFNFFKRHICDAN

KEGMFLFRAARKLRQFLKMNSTGDFDLHLLKVSEGTTILLNCTGQVKGRK

PAALGEAQPTKSLEENKSLKEQKKLNDLCFLKRLLQEIKTCWNKILMGTK

EH (Human Tissue Factor 219)
(SEQ ID NO: 340)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE (Human IL-15)
(SEQ ID NO: 341)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS

The nucleic acid and protein sequences of the 21s137L (short version) are shown below. The nucleic acid sequence of 21s137L (short version) construct (including signal peptide sequence) is as follows (SEQ ID NO: 79):
(Signal peptide)
(SEQ ID NO: 342)
ATGAAGTGGGTGACCTTCATCAGCCTGCTGTTCCTGTTCTCCAGCGCCTA

CTCC (Human IL-21)
(SEQ ID NO: 343)
CAGGGCCAGGACAGGCACATGATCCGGATGAGGCAGCTCATCGACATCGT

CGACCAGCTGAAGAACTACGTGAACGACCTGGTGCCCGAGTTTCTGCCTG

CCCCCGAGGACGTGGAGACCAACTGCGAGTGGTCCGCCTTCTCCTGCTTT

CAGAAGGCCCAGCTGAAGTCCGCCAACACCGGCAACAACGAGCGGATCAT

CAACGTGAGCATCAAGAAGCTGAAGCGGAAGCCTCCCTCCACAAACGCCG

GCAGGAGGCAGAAGCACAGGCTGACCTGCCCCAGCTGTGACTCCTACGAG

AAGAAGCCCCCCAAGGAGTTCCTGGAGAGGTTCAAGTCCCTGCTGCAGAA

GATGATCCATCAGCACCTGTCCTCCAGGACCCACGGCTCCGAGGACTCC (Human IL-15R α sushi domain)
(SEQ ID NO: 344)
ATTACATGCCCCCCTCCCATGAGCGTGGAGCACGCCGACATCTGGGTGAA

GAGCTATAGCCTCTACAGCCGGGAGAGGTATATCTGTAACAGCGGCTTCA

AGAGGAAGGCCGGCACCAGCAGCCTCACCGAGTGCGTGCTGAATAAGGCT

ACCAACGTGGCTCACTGGACAACACCCTCTTTAAAGTGCATCCGG

-continued ((G4S)3 linker)
(SEQ ID NO: 345)
GGCGGTGGAGGATCCGGAGGAGGTGGCTCCGGCGGCGGAGGATCT (Human CD137 Ligand short version)
(SEQ ID NO: 346)
GATCCCGCCGGCCTCTTGGACCTGCGGCAGGGCATGTTTGCGCAGCTGGT

GGCCCAAAATGTTCTGCTGATCGATGGGCCCCTGAGCTGGTACAGTGACC

CAGGCCTGGCAGGCGTGTCCCTGACGGGGGCCTGAGCTACAAAGAGGAC

ACGAAGGAGCTGGTGGTGGCCAAGGCTGGAGTCTACTATGTCTTCTTTCA

ACTAGAGCTGCGGCGCGTGGTGGCCGGCGAGGGCTCAGGCTCCGTTTCAC

TTGCGCTGCACCTGCAGCCACTGCGCTCTGCTGCTGGGGCCGCCGCCCTG

GCTTTGACCGTGGACCTGCCACCCGCCTCCTCCGAGGCTCGGAACTCGGC

CTTCGGTTTCCAGGGCCGCTTGCTGCACCTGAGTGCCGGCCAGCGCCTGG

GCGTCCATCTTCACACTGAGGCCAGGGCACGCCATGCCTGGCAGCTTACC

CAGGGCGCCACAGTCTTGGGACTCTTCCGGGTGACCCCCGAAATC

The amino acid sequence of the 21s137L (short version) construct (including signal peptide sequence) is as follows (SEQ ID NO: 80):
(Signal peptide)
(SEQ ID NO: 347)
MKWVTFISLLFLFSSAYS (Human IL-21)
(SEQ ID NO: 348)
QGQDRHMIRMRQLIDIVDQLKNYVNDLVPEFLPAPEDVETNCEWSAFSCF

QKAQLKSANTGNNERIINVSIKKLKRKPPSTNAGRRQKHRLTCPSCDSYE

KKPPKEFLERFKSLLQKMIHQHLSSRTHGSEDS (Human IL-15R α sushi domain)
(SEQ ID NO: 349)
ITCPPPMSVEHADIWVKSYSLYSRERYICNSGFKRKAGTSSLTECVLNKA

TNVAHWTTPSLKCIR ((G4S)3 linker)
(SEQ ID NO: 350)
GGGGSGGGGSGGGGS (Human CD137 Ligand short version)
(SEQ ID NO: 351)
DPAGLLDLRQGMFAQLVAQNVLLIDGPLSWYSDPGLAGVSLTGGLSYKED

TKELVVAKAGVYYVFFQLELRRVVAGEGSGSVSLALHLQPLRSAAGAAAL

ALTVDLPPASSEARNSAFGFQGRLLHLSAGQRLGVHLHTEARARHAWQLT

QGATVLGLFRVTPEI

The nucleic acid sequence of the 7t15 construct (including signal peptide sequence) is as follows (SEQ ID NO: 81):
(Signal peptide)
(SEQ ID NO: 352)
ATGAAGTGGGTGACCTTCATCAGCCTGCTGTTCCTGTTCTCCAGCGCCTA

CTCC (Human IL7)
(SEQ ID NO: 353)
GATTGCGACATCGAGGGCAAGGACGGCAAGCAGTACGAGAGCGTGCTGAT

GGTGTCCATCGACCAGCTGCTGGACAGCATGAAGGAGATCGGCTCCAACT

GCCTCAACAACGAGTTCAACTTCTTCAAGCGGCACATCTGCGACGCCAAC

AAGGAGGGCATGTTCCTGTTCAGGGCCGCCAGGAAACTGCGGCAGTTCCT

GAAGATGAACTCCACCGGCGACTTCGACCTGCACCTGCTGAAGGTGTCCG

AGGGCACCACCATCCTGCTGAACTGCACCGGACAGGTGAAGGGCCGGAAA

CCTGCTGCTCTGGGAGAGGCCCAACCCACCAAGAGCCTGGAGGAGAACAA

GTCCCTGAAGGAGCAGAAGAAGCTGAACGACCTGTGCTTCCTGAAGAGGC

TGCTGCAGGAGATCAAGACCTGCTGGAACAAGATCCTGATGGGCACCAAG

GAGCAT (Human Tissue Factor 219)
(SEQ ID NO: 354)
AGCGGCACAACCAACACAGTCGCTGCCTATAACCTCACTTGGAAGAGCAC

CAACTTCAAAACCATCCTCGAATGGGAACCCAAACCCGTTAACCAAGTTT

ACACCGTGCAGATCAGCACCAAGTCCGGCGACTGGAAGTCCAAATGTTTC

TATACCACCGACACCGAGTGCGATCTCACCGATGAGATCGTGAAAGATGT

GAAACAGACCTACCTCGCCCGGGTGTTTAGCTACCCCGCCGGCAATGTGG

AGAGCACTGGTTCCGCTGGCGAGCCTTTATACGAGAACAGCCCCGAATTT

ACCCCTTACCTCGAGACCAATTTAGGACAGCCCACCATCCAAAGCTTTGA

GCAAGTTGGCACAAAGGTGAATGTGACAGTGGAGGACGAGCGGACTTTAG

TGCGGCGGAACAACACCTTTCTCAGCCTCCGGGATGTGTTCGGCAAAGAT

TTAATCTACACACTGTATTACTGGAAGTCCTCTTCCTCCGGCAAGAAGAC

AGCTAAAACCAACACAAACGAGTTTTTAATCGACGTGGATAAAGGCGAAA

ACTACTGTTTCAGCGTGCAAGCTGTGATCCCCTCCCGGACCGTGAATAGG

AAAAGCACCGATAGCCCCGTTGAGTGCATGGGCCAAGAAAAGGGCGAGTT

CCGGGAG (Human IL-15)
(SEQ ID NO: 355)
AACTGGGTGAACGTCATCAGCGATTTAAAGAAGATCGAAGATTTAATTCA

GTCCATGCATATCGACGCCACTTTATACACAGAATCCGACGTGCACCCCT

CTTGTAAGGTGACCGCCATGAAATGTTTTTTACTGGAGCTGCAAGTTATC

TCTTTAGAGAGCGGAGACGCTAGCATCCACGACACCGTGGAGAATTTAAT

CATTTTAGCCAATAACTCTTTATCCAGCAACGGCAACGTGACAGAGTCCG

GCTGCAAGGAGTGCGAAGAGCTGGAGGAGAAGAACATCAAGGAGTTTCTG

CAATCCTTTGTGCACATTGTCCAGATGTTCATCAATACCTCC

The amino acid sequence of 7t15 fusion protein (including the leader sequence) is as follows (SEQ ID NO: 82):
(Signal peptide)
(SEQ ID NO: 356)
MKWVTFISLLFLFSSAYS (Human IL7)
(SEQ ID NO: 357)
DCDIEGKDGKQYESVLMVSIDQLLDSMKEIGSNCLNNEFNFFKRHICDAN

KEGMFLFRAARKLRQFLKMNSTGDFDLHLLKVSEGTTILLNCTGQVKGRK

PAALGEAQPTKSLEENKSLKEQKKLNDLCFLKRLLQEIKTCWNKILMGTK
EH (Human Tissue Factor 219)
(SEQ ID NO: 358)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE (Human IL-15)
(SEQ ID NO: 359)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS

The nucleic acid sequence of the TGFRs construct (including signal peptide sequence) is as follows (SEQ ID NO: 83):
(Signal peptide)
(SEQ ID NO: 360)
ATGAAGTGGGTGACCTTCATCAGCCTGCTGTTCCTGTTCTCCAGCGCCT
ACTCC (Human TGFβ Receptor II fragments)
(SEQ ID NO: 361)
ATCCCCCCCCATGTGCAAAAGAGCGTGAACAACGATATGATCGTGACCG
ACAACAACGGCGCCGTGAAGTTTCCCCAGCTCTGCAAGTTCTGCGATGT
CAGGTTCAGCACCTGCGATAATCAGAAGTCCTGCATGTCCAACTGCAGC
ATCACCTCCATCTGCGAGAAGCCCCAAGAAGTGTGCGTGGCCGTGTGGC
GGAAAAATGACGAGAACATCACCCTGGAGACCGTGTGTCACGACCCCAA
GCTCCCTTATCACGACTTCATTCTGGAGGACGCTGCCTCCCCCAAATGC
ATCATGAAGGAGAAGAAGAAGCCCGGAGAGACCTTCTTTATGTGTTCCT
GTAGCAGCGACGAGTGTAACGACAACATCATCTTCAGCGAAGAGTACAA
CACCAGCAACCCTGATGGAGGTGGCGGATCCGGAGGTGGAGGTTCTGGT
GGAGGTGGGAGTATTCCTCCCCACGTGCAGAAGAGCGTGAATAATGACA
TGATCGTGACCGATAACAATGGCGCCGTGAAATTTCCCCAGCTGTGCAA
ATTCTGCGATGTGAGGTTTTCCACCTGCGACAACCAGAAGTCCTGTATG
AGCAACTGCTCCATCACCTCCATCTGTGAGAAGCCTCAGGAGGTGTGCG
TGGCTGTCTGGCGGAAGAATGACGAGAATATCACCCTGGAAACCGTCTG
CCACGATCCCAAGCTGCCCTACCACGATTTCATCCTGGAAGACGCCGCC
AGCCCTAAGTGCATCATGAAAGAGAAAAAGAAGCCTGGCGAGACCTTTT
TCATGTGCTCCTGCAGCAGCGACGAATGCAACGACAATATCATCTTTAG
CGAGGAATACAATACCAGCAACCCCGAC (Human IL-15R α sushi domain)
(SEQ ID NO: 362)
ATTACATGCCCCCCTCCCATGAGCGTGGAGCACGCCGACATCTGGGTGA
AGAGCTATAGCCTCTACAGCCGGGAGAGGTATATCTGTAACAGCGGCTT
CAAGAGGAAGGCCGGCACCAGCAGCCTCACCGAGTGCGTGCTGAATAAG
GCTACCAACGTGGCTCACTGGACAACACCCTCTTTAAAGTGCATCCGG The amino acid sequence of TGFRs fusion protein (including the leader sequence) is as follows (SEQ ID NO: 84):
(Signal peptide)
(SEQ ID NO: 363)
MKWVTFISLLFLFSSAYS
(SEQ ID NO: 364)
(Human TGFβ Receptor II)
IPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKC
IMKEKKKPGETFFMCSCSSDECNDNIIFSEEYNTSNPDGGGGSGGGGSG
GGGSIPPHVQKSVNNDMIVTDNNGAVKFPQLCKFCDVRFSTCDNQKSCM
SNCSITSICEKPQEVCVAVWRKNDENITLETVCHDPKLPYHDFILEDAA
SPKCIMKEKKKPGETFFMCSCSSDECNDNIIFSEEYNTSNPD (Human IL-15R α sushi domain)
(SEQ ID NO: 365)
ITCPPPMSVEHADIWVKSYSLYSRERYICNSGFKRKAGTSSLTECVLNK
ATNVAHWTTPSLKCIR The nucleic acid sequence of the TGFRt15 construct (including signal peptide sequence) is as follows (SEQ ID NO: 85):
(Signal peptide)
(SEQ ID NO: 366)
ATGAAGTGGGTGACCTTCATCAGCCTGCTGTTCCTGTTCTCCAGCGCCT
ACTCC (Human TGFβ Receptor II fragments)
(SEQ ID NO: 367)
ATCCCCCCCCATGTGCAAAAGAGCGTGAACAACGATATGATCGTGACCG
ACAACAACGGCGCCGTGAAGTTTCCCCAGCTCTGCAAGTTCTGCGATGT
CAGGTTCAGCACCTGCGATAATCAGAAGTCCTGCATGTCCAACTGCAGC
ATCACCTCCATCTGCGAGAAGCCCCAAGAAGTGTGCGTGGCCGTGTGGC
GGAAAAATGACGAGAACATCACCCTGGAGACCGTGTGTCACGACCCCAA
GCTCCCTTATCACGACTTCATTCTGGAGGACGCTGCCTCCCCCAAATGC
ATCATGAAGGAGAAGAAGAAGCCCGGAGAGACCTTCTTTATGTGTTCCT
GTAGCAGCGACGAGTGTAACGACAACATCATCTTCAGCGAAGAGTACAA
CACCAGCAACCCTGATGGAGGTGGCGGATCCGGAGGTGGAGGTTCTGGT
GGAGGTGGGAGTATTCCTCCCCACGTGCAGAAGAGCGTGAATAATGACA
TGATCGTGACCGATAACAATGGCGCCGTGAAATTTCCCCAGCTGTGCAA
ATTCTGCGATGTGAGGTTTTCCACCTGCGACAACCAGAAGTCCTGTATG
AGCAACTGCTCCATCACCTCCATCTGTGAGAAGCCTCAGGAGGTGTGCG
TGGCTGTCTGGCGGAAGAATGACGAGAATATCACCCTGGAAACCGTCTG
CCACGATCCCAAGCTGCCCTACCACGATTTCATCCTGGAAGACGCCGCC
AGCCCTAAGTGCATCATGAAAGAGAAAAAGAAGCCTGGCGAGACCTTTT
TCATGTGCTCCTGCAGCAGCGACGAATGCAACGACAATATCATCTTTAG
CGAGGAATACAATACCAGCAACCCCGAC (Human Tissue Factor 219)
(SEQ ID NO: 368)
AGCGGCACAACCAACACAGTCGCTGCCTATAACCTCACTTGGAAGAGCA
CCAACTTCAAAACCATCCTCGAATGGGAACCCAAACCCGTTAACCAAGT
TTACACCGTGCAGATCAGCACCAAGTCCGGCGACTGGAAGTCCAAATGT
TTCTATACCACCGACACCGAGTGCGATCTCACCGATGAGATCGTGAAAG
ATGTGAAACAGACCTACCTCGCCCGGGTGTTTAGCTACCCCGCCGGCAA
TGTGGAGAGCACTGGTTCCGCTGGCGAGCCTTTATACGAGAACAGCCCC
GAATTTACCCCTTACCTCGAGACCAATTTAGGACAGCCCACCATCCAAA
GCTTTGAGCAAGTTGGCACAAAGGTGAATGTGACAGTGGAGGACGAGCG
GACTTTAGTGCGGCGGAACAACACCTTTCTCAGCCTCCGGGATGTGTTC
GGCAAAGATTTAATCTACACACTGTATTACTGGAAGTCCTCTTCCTCCG
GCAAGAAGACAGCTAAAACCAACACAAACGAGTTTTTAATCGACGTGGA
TAAAGGCGAAAACTACTGTTTCAGCGTGCAAGCTGTGATCCCCTCCCGG
ACCGTGAATAGGAAAAGCACCGATAGCCCCGTTGAGTGCATGGGCCAAG
AAAAGGGCGAGTTCCGGGAG (Human IL-15)
(SEQ ID NO: 369)
AACTGGGTGAACGTCATCAGCGATTTAAAGAAGATCGAAGATTTAATTC
AGTCCATGCATATCGACGCCACTTTATACACAGAATCCGACGTGCACCC
CTCTTGTAAGGTGACCGCCATGAAATGTTTTTTACTGGAGCTGCAAGTT
ATCTCTTTAGAGAGCGGAGACGCTAGCATCCACGACACCGTGGAGAATT
TAATCATTTTAGCCAATAACTCTTTATCCAGCAACGGCAACGTGACAGA
GTCCGGCTGCAAGGAGTGCGAAGAGCTGGAGGAGAAGAACATCAAGGAG
TTTCTGCAATCCTTTGTGCACATTGTCCAGATGTTCATCAATACCTCC The amino acid sequence of TGFRt15 fusion protein (including the leader sequence) is as follows (SEQ ID NO: 86):
(Signal peptide)
(SEQ ID NO: 370)
MKWVTFISLLFLFSSAYS (Human TGFβ Receptor II)
(SEQ ID NO: 371)
IPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKC
IMKEKKKPGETFFMCSCSSDECNDNIIFSEEYNTSNPDGGGGSGGGGSG
GGGSIPPHVQKSVNNDMIVTDNNGAVKFPQLCKFCDVRFSTCDNQKSCM -continued SNCSITSICEKPQEVCVAVWRKNDENITLETVCHDPKLPYHDFILEDAA
SPKCIMKEKKKPGETFFMCSCSSDECNDNIIFSEEYNTSNPD (Human Tissue Factor 219)
(SEQ ID NO: 372)
SGTTNTVAAYNLTWKSTNFKTILEWEPKPVNQVYTVQISTKSGDWKSKC
FYTTDTECDLTDEIVKDVKQTYLARVFSYPAGNVESTGSAGEPLYENSP
EFTPYLETNLGQPTIQSFEQVGTKVNVTVEDERTLVRRNNTFLSLRDVF
GKDLIYTLYYWKSSSSGKKTAKTNTNEFLIDVDKGENYCFSVQAVIPSR
TVNRKSTDSPVECMGQEKGEFRE (Human IL-15)
(SEQ ID NO: 373)
NWVNVISDLKKIEDLIQSMHIDATLYTESDVHPSCKVTAMKCFLLELQV
ISLESGDASIHDTVENLIILANNSLSSNGNVTESGCKECEELEEKNIKE
FLQSFVHIVQMFINTS The nucleic acid and protein sequences of the 21s137L are shown below. The nucleic acid sequence of the 21s137L construct (including signal peptide sequence) is as follows (SEQ ID NO: 87):
(Signal peptide)
(SEQ ID NO: 374)
ATGAAGTGGGTGACCTTCATCAGCCTGCTGTTCCTGTTCTCCAGCGCCT
ACTCC (Human IL-21)
(SEQ ID NO: 375)
CAGGGCCAGGACAGGCACATGATCCGGATGAGGCAGCTCATCGACATCG
TCGACCAGCTGAAGAACTACGTGAACGACCTGGTGCCCGAGTTTCTGCC
TGCCCCCGAGGACGTGGAGACCAACTGCGAGTGGTCCGCCTTCTCCTGC
TTTCAGAAGGCCCAGCTGAAGTCCGCCAACACCGGCAACAACGAGCGGA
TCATCAACGTGAGCATCAAGAAGCTGAAGCGGAAGCCTCCCTCCACAAA
CGCCGGCAGGAGGCAGAAGCACAGGCTGACCTGCCCCAGCTGTGACTCC
TACGAGAAGAAGCCCCCCAAGGAGTTCCTGGAGAGGTTCAAGTCCCTGC
TGCAGAAGATGATCCATCAGCACCTGTCCTCCAGGACCCACGGCTCCGA
GGACTCC (Human IL-15R α sushi domain)
(SEQ ID NO: 376)
ATTACATGCCCCCCTCCCATGAGCGTGGAGCACGCCGACATCTGGGTGA
AGAGCTATAGCCTCTACAGCCGGGAGAGGTATATCTGTAACAGCGGCTT
CAAGAGGAAGGCCGGCACCAGCAGCCTCACCGAGTGCGTGCTGAATAAG
GCTACCAACGTGGCTCACTGGACAACACCCTCTTTAAAGTGCATCCGG ((G4S)3 linker)
(SEQ ID NO: 377)
GGCGGTGGAGGATCCGGAGGAGGTGGCTCCGGCGGCGGAGGATCT (Human CD137L)
(SEQ ID NO: 378)
CGCGAGGGTCCCGAGCTTTCGCCCGACGATCCCGCCGGCCTCTTGGACC
TGCGGCAGGGCATGTTTGCGCAGCTGGTGGCCCAAAATGTTCTGCTGAT
CGATGGGCCCCTGAGCTGGTACAGTGACCCAGGCCTGGCAGGCGTGTCC
CTGACGGGGGGCCTGAGCTACAAGGAGGACACGAAGGAGCTGGTGGTGG
CCAAGGCTGGAGTCTACTATGTCTTCTTTCAACTAGAGCTGCGGCGCGT
GGTGGCCGGCGAGGGCTCAGGCTCCGTTTCACTTGCGCTGCACCTGCAG
CCACTGCGCTCTGCTGCTGGGGCCGCCGCCCTGGCTTTGACCGTGGACC
TGCCACCCGCCTCCTCCGAGGCTCGGAACTCGGCCTTCGGTTTCCAGGG
CCGCTTGCTGCACCTGAGTGCCGGCCAGCGCCTGGGCGTCCATCTTCAC
ACTGAGGCCAGGGCACGCCATGCCTGGCAGCTTACCCAGGGCGCCACAG
TCTTGGGACTCTTCCGGGTGACCCCCGAAATCCCAGCCGGACTCCCTTC
ACCGAGGTCGGAA The amino acid sequence of 21s137L fusion protein (including the leader sequence) is as follows (SEQ ID NO: 88):
(Signal peptide)
(SEQ ID NO: 379)
MKWVTFISLLFLFSSAYS (Human IL-21)
(SEQ ID NO: 380)
QGQDRHMIRMRQLIDIVDQLKNYVNDLVPEFLPAPEDVETNCEWSAFSC
FQKAQLKSANTGNNERIINVSIKKLKRKPPSTNAGRRQKHRLTCPSCDS
YEKKPPKEFLERFKSLLQKMIHQHLSSRTHGSEDS (Human IL-15R α sushi domain)
(SEQ ID NO: 381)
ITCPPPMSVEHADIWVKSYSLYSRERYICNSGFKRKAGTSSLTECVLNK
ATNVAHWTTPSLKCIR ((G4S)3 linker)
(SEQ ID NO: 382)
GGGGSGGGGSGGGGS (Human CD137L)
(SEQ ID NO: 383)
REGPELSPDDPAGLLDLRQGMFAQLVAQNVLLIDGPLSWYSDPGLAGVS
LTGGLSYKEDTKELVVAKAGVYYVFFQLELRRVVAGEGSGSVSLALHLQ
PLRSAAGAAALALTVDLPPASSEARNSAFGFQGRLLHLSAGQRLGVHLH
TEARARHAWQLTQGATVLGLFRVTPEIPAGLPSPRSE The nucleic acid sequence of the TGFRt15 construct (including signal peptide sequence) is as follows (SEQ ID NO: 89):
(Signal peptide)
(SEQ ID NO: 384)
ATGAAGTGGGTGACCTTCATCAGCCTGCTGTTCCTGTTCTCCAGCGCCT
ACTCC (Human TGFβ Receptor II fragments)
(SEQ ID NO: 385)
ATCCCCCCCCATGTGCAAAAGAGCGTGAACAACGATATGATCGTGACCG
ACAACAACGGCGCCGTGAAGTTTCCCCAGCTCTGCAAGTTCTGCGATGT
CAGGTTCAGCACCTGCGATAATCAGAAGTCCTGCATGTCCAACTGCAGC
ATCACCTCCATCTGCGAGAAGCCCCAAGAAGTGTGCGTGGCCGTGTGGC
GGAAAAATGACGAGAACATCACCCTGGAGACCGTGTGTCACGACCCCAA
GCTCCCTTATCACGACTTCATTCTGGAGGACGCTGCCTCCCCCAAATGC
ATCATGAAGGAGAAGAAGAAGCCCGGAGGACCTTCTTTATGTGTTCCT
GTAGCAGCGACGAGTGTAACGACAACATCATCTTCAGCGAAGAGTACAA
CACCAGCAACCCTGATGGAGGTGGCGGATCCGGAGGTGGAGGTTCTGGT
GGAGGTGGGAGTATTCCTCCCCACGTGCAGAAGAGCGTGAATAATGACA
TGATCGTGACCGATAACAATGGCGCCGTGAAATTTCCCCAGCTGTGCAA
ATTCTGCGATGTGAGGTTTTCCACCTGCGACAACCAGAAGTCCTGTATG
AGCAACTGCTCCATCACCTCCATCTGTGAGAAGCCTCAGGAGGTGTGCG
TGGCTGTCTGGCGGAAGAATGACGAGAATATCACCCTGGAAACCGTCTG
CCACGATCCCAAGCTGCCCTACCACGATTTCATCCTGGAAGACGCCGCC
AGCCCTAAGTGCATCATGAAAGAGAAAAAGAAGCCTGGCGAGACCTTTT
TCATGTGCTCCTGCAGCAGCGACGAATGCAACGACAATATCATCTTTAG
CGAGGAATACAATACCAGCAACCCCGAC (Human Tissue Factor 219)
(SEQ ID NO: 386)
AGCGGCACAACCAACACAGTCGCTGCCTATAACCTCACTTGGAAGAGCA
CCAACTTCAAAACCATCCTCGAATGGGAACCCAAACCCGTTAACCAAGT
TTACACCGTGCAGATCAGCACCAAGTCCGGCGACTGGAAGTCCAAATGT
TTCTATACCACCGACACCGAGTGCGATCTCACCGATGAGATCGTGAAAG
ATGTGAAACAGACCTACCTCGCCCGGGTGTTTAGCTACCCCGCCGGCAA
TGTGGAGAGCACTGGTTCCGCTGGCGAGCCTTTATACGAGAACAGCCCC
GAATTTACCCCTTACCTCGAGACCAATTTAGGACAGCCCACCATCCAAA
GCTTTGAGCAAGTTGGCACAAAGGTGAATGTGACAGTGGAGGACGAGCG
GACTTTAGTGCGGCGGAACAACACCTTTCTCAGCCTCCGGGATGTGTTC
GGCAAAGATTTAATCTACACACTGTATTACTGGAAGTCCTCTTCCTCCG
GCAAGAAGACAGCTAAAACCAACACAAACGAGTTTTTAATCGACGTGGA
TAAAGGCGAAAACTACTGTTTCAGCGTGCAAGCTGTGATCCCCTCCCGG
ACCGTGAATAGGAAAAGCACCGATAGCCCCGTTGAGTGCATGGGCCAAG
AAAAGGGCGAGTTCCGGGAG -continued (Human IL-15)
(SEQ ID NO: 387)
AACTGGGTGAACGTCATCAGCGATTTAAAGAAGATCGAAGATTTAATTC
AGTCCATGCATATCGACGCCACTTTATACACAGAATCCGACGTGCACCC
CTCTTGTAAGGTGACCGCCATGAAATGTTTTTTACTGGAGCTGCAAGTT
ATCTCTTTAGAGAGCGGAGACGCTAGCATCCACGACACCGTGGAGAATT
TAATCATTTTAGCCAATAACTCTTTATCCAGCAACGGCAACGTGACAGA
GTCCGGCTGCAAGGAGTGCGAAGAGCTGGAGGAGAAGAACATCAAGGAG
TTTCTGCAATCCTTTGTGCACATTGTCCAGATGTTCATCAATACCTCC The amino acid sequence of TGFRt15 fusion protein (including the leader sequence) is as follows (SEQ ID NO: 90):
(Signal peptide)
(SEQ ID NO: 388)
MKWVTFISLLFLFSSAYS (Human TGFβ Receptor II)
(SEQ ID NO: 389)
IPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKC
IMKEKKKPGETFFMCSCSSDECNDNIIFSEEYNTSNPDGGGGSGGGGSG
GGGSIPPHVQKSVNNDMIVTDNNGAVKFPQLCKFCDVRFSTCDNQKSCM
SNCSITSICEKPQEVCVAVWRKNDENITLETVCHDPKLPYHDFILEDAA
SPKCIMKEKKKPGETFFMCSCSSDECNDNIIFSEEYNTSNPD (Human Tissue Factor 219)
(SEQ ID NO: 390)
SGTTNTVAAYNLTWKSTNFKTILEWEPKPVNQVYTVQISTKSGDWKSKC
FYTTDTECDLTDEIVKDVKQTYLARVFSYPAGNVESTGSAGEPLYENSP
EFTPYLETNLGQPTIQSFEQVGTKVNVTVEDERTLVRRNNTFLSLRDVF
GKDLIYTLYYWKSSSSGKKTAKTNTNEFLIDVDKGENYCFSVQAVIPSR
TVNRKSTDSPVECMGQEKGEFRE (Human IL-15)
(SEQ ID NO: 391)
NWVNVISDLKKIEDLIQSMHIDATLYTESDVHPSCKVTAMKCFLLELQV
ISLESGDASIHDTVENLIILANNSLSSNGNVTESGCKECEELEEKNIKE
FLQSFVHIVQMFINTS The nucleic acid sequence of the TGFRs21 construct (including signal peptide sequence) is as follows (SEQ ID NO: 91):
(Signal peptide)
(SEQ ID NO: 392)
ATGAAGTGGGTGACCTTCATCAGCCTGCTGTTCCTGTTCTCCAGCGCCT
ACTCC (Human TGFβ Receptor II fragments)
(SEQ ID NO: 393)
ATCCCCCCCCCATGTGCAAAAGAGCGTGAACAACGATATGATCGTGACCG
ACAACAACGGCGCCGTGAAGTTTCCCCAGCTCTGCAAGTTCTGCGATGT
CAGGTTCAGCACCTGCGATAATCAGAAGTCCTGCATGTCCAACTGCAGC
ATCACCTCCATCTGCGAGAAGCCCCAAGAAGTGTGCGTGGCCGTGTGGC
GGAAAAATGACGAGAACATCACCCTGGAGACCGTGTGTCACGACCCCAA
GCTCCCTTATCACGACTTCATTCTGGAGGACGCTGCCTCCCCCAAATGC
ATCATGAAGGAGAAGAAGAAGCCCGGAGAGACCTTCTTTATGTGTTCCT
GTAGCAGCGACGAGTGTAACGACAACATCATCTTCAGCGAAGAGTACAA
CACCAGCAACCCTGATGGAGGTGGCGGATCCGGAGGTGGAGGTTCTGGT
GGAGGTGGGAGTATTCCTCCCCACGTGCAGAAGAGCGTGAATAATGACA
TGATCGTGACCGATAACAATGGCGCCGTGAAATTTCCCCAGCTGTGCAA
ATTCTGCGATGTGAGGTTTTCCACCTGCGACAACCAGAAGTCCTGTATG
AGCAACTGCTCCATCACCTCCATCTGTGAGAAGCCTCAGGAGGTGTGCG
TGGCTGTCTGGCGGAAGAATGACGAGAATATCACCCTGGAAACCGTCTG
CCACGATCCCAAGCTGCCCTACCACGATTTCATCCTGGAAGACGCCGCC
AGCCCTAAGTGCATCATGAAAGAGAAAAAGAAGCCTGGCGAGACCTTTT
TCATGTGCTCCTGCAGCAGCGACGAATGCAACGACAATATCATCTTTAG
CGAGGAATACAATACCAGCAACCCCGAC (Human IL-15R α sushi domain)
(SEQ ID NO: 394)
ATTACATGCCCCCCTCCCATGAGCGTGGAGCACGCCGACATCTGGGTGA
AGAGCTATAGCCTCTACAGCCGGGAGAGGTATATCTGTAACAGCGGCTT
CAAGAGGAAGGCCGGCACCAGCAGCCTCACCGAGTGCGTGCTGAATAAG
GCTACCAACGTGGCTCACTGGACAACACCCTCTTTAAAGTGCATCCGG -continued (Human IL-21)
(SEQ ID NO: 395)
CAGGGCCAGGACAGGCACATGATCCGGATGAGGCAGCTCATCGACATCG
TCGACCAGCTGAAGAACTACGTGAACGACCTGGTGCCCGAGTTTCTGCC
TGCCCCCGAGGACGTGGAGACCAACTGCGAGTGGTCCGCCTTCTCCTGC
TTTCAGAAGGCCCAGCTGAAGTCCGCCAACACCGGCAACAACGAGCGGA
TCATCAACGTGAGCATCAAGAAGCTGAAGCGGAAGCCTCCCTCCACAAA
CGCCGGCAGGAGGCAGAAGCACAGGCTGACCTGCCCCAGCTGTGACTCC
TACGAGAAGAAGCCCCCCAAGGAGTTCCTGGAGAGGTTCAAGTCCCTGC
TGCAGAAGATGATCCATCAGCACCTGTCCTCCAGGACCCACGGCTCCGA
GGACTCC The amino acid sequence of TGFRs21 fusion protein (including the leader sequence) is as follows (SEQ ID NO: 92):
(Signal peptide)
(SEQ ID NO: 396)
MKWVTFISLLFLFSSAYS (Human TGFβ Receptor II)
(SEQ ID NO: 397)
IPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKC
IMKEKKKPGETFFMCSCSSDECNDNIIFSEEYNTSNPDGGGGSGGGGSG
GGGSIPPHVQKSVNNDMIVTDNNGAVKFPQLCKFCDVRFSTCDNQKSCM
SNCSITSICEKPQEVCVAVWRKNDENITLETVCHDPKLPYHDFILEDAA
SPKCIMKEKKKPGETFFMCSCSSDECNDNIIFSEEYNTSNPD (Human IL-15R α sushi domain)
(SEQ ID NO: 398)
ITCPPPMSVEHADIWVKSYSLYSRERYICNSGFKRKAGTSSLTECVLNK
ATNVAHWTTPSLKCIR (Human IL-21)
(SEQ ID NO: 399)
QGQDRHMIRMRQLIDIVDQLKNYVNDLVPEFLPAPEDVETNCEWSAFSC
FQKAQLKSANTGNNERIINVSIKKLKRKPPSTNAGRRQKHRLTCPSCDS
YEKKPPKEFLERFKSLLQKMIHQHLSSRTHGSEDS The nucleic acid sequence of the TGFRt15 construct (including signal peptide sequence) is as follows (SEQ ID NO: 93):
(Signal peptide)
(SEQ ID NO: 400)
ATGAAGTGGGTGACCTTCATCAGCCTGCTGTTCCTGTTCTCCAGCGCCT
ACTCC (Human TGFβ Receptor II fragments)
(SEQ ID NO: 401)
ATCCCCCCCCCATGTGCAAAAGAGCGTGAACAACGATATGATCGTGACCG
ACAACAACGGCGCCGTGAAGTTTCCCCAGCTCTGCAAGTTCTGCGATGT
CAGGTTCAGCACCTGCGATAATCAGAAGTCCTGCATGTCCAACTGCAGC
ATCACCTCCATCTGCGAGAAGCCCCAAGAAGTGTGCGTGGCCGTGTGGC
GGAAAAATGACGAGAACATCACCCTGGAGACCGTGTGTCACGACCCCAA
GCTCCCTTATCACGACTTCATTCTGGAGGACGCTGCCTCCCCCAAATGC
ATCATGAAGGAGAAGAAGAAGCCCGGAGAGACCTTCTTTATGTGTTCCT
GTAGCAGCGACGAGTGTAACGACAACATCATCTTCAGCGAAGAGTACAA
CACCAGCAACCCTGATGGAGGTGGCGGATCCGGAGGTGGAGGTTCTGGT
GGAGGTGGGAGTATTCCTCCCCACGTGCAGAAGAGCGTGAATAATGACA
TGATCGTGACCGATAACAATGGCGCCGTGAAATTTCCCCAGCTGTGCAA
ATTCTGCGATGTGAGGTTTTCCACCTGCGACAACCAGAAGTCCTGTATG
AGCAACTGCTCCATCACCTCCATCTGTGAGAAGCCTCAGGAGGTGTGCG
TGGCTGTCTGGCGGAAGAATGACGAGAATATCACCCTGGAAACCGTCTG
CCACGATCCCAAGCTGCCCTACCACGATTTCATCCTGGAAGACGCCGCC
AGCCCTAAGTGCATCATGAAAGAGAAAAAGAAGCCTGGCGAGACCTTTT
TCATGTGCTCCTGCAGCAGCGACGAATGCAACGACAATATCATCTTTAG
CGAGGAATACAATACCAGCAACCCCGAC (Human Tissue Factor 219)
(SEQ ID NO: 402)
AGCGGCACAACCAACACAGTCGCTGCCTATAACCTCACTTGGAAGAGCA
CCAACTTCAAAACCATCCTCGAATGGGAACCCAAACCCGTTAACCAAGT
TTACACCGTGCAGATCAGCACCAAGTCCGGCGACTGGAAGTCCAAATGT
TTCTATACCACCGACACCGAGTGCGATCTCACCGATGAGATCGTGAAAG -continued
ATGTGAAACAGACCTACCTCGCCCGGGTGTTTAGCTACCCCGCCGGCAA
TGTGGAGAGCACTGGTTCCGCTGGCGAGCCTTTATACGAGAACAGCCCC
GAATTTACCCCTTACCTCGAGACCAATTTAGGACAGCCCACCCATCCAAA
GCTTTGAGCAAGTTGGCACAAAGGTGAATGTGACAGTGGAGGACGAGCG
GACTTTAGTGCGGCGGAACAACACCTTTCTCAGCCTCCGGGATGTGTTC
GGCAAAGATTTAATCTACACACTGTATTACTGGAAGTCCTCTTCCTCCG
GCAAGAAGACAGCTAAAACCAACACAAACGAGTTTTTAATCGACGTGGA
TAAAGGCGAAAACTACTGTTTCAGCGTGCAAGCTGTGATCCCCTCCCGG
ACCGTGAATAGGAAAAGCACCGATAGCCCCGTTGAGTGCATGGGCCAAG
AAAAGGGCGAGTTCCGGGAG (Human IL-15)

(SEQ ID NO: 403)
AACTGGGTGAACGTCATCAGCGATTTAAAGAAGATCGAAGATTTAATTC
AGTCCATGCATATCGACGCCACTTTATACACAGAATCCGACGTGCACCC
CTCTTGTAAGGTGACCGCCATGAAATGTTTTTTACTGGAGCTGCAAGTT
ATCTCTTTAGAGAGCGGAGACGCTAGCATCCACGACACCGTGGAGAATT
TAATCATTTTAGCCAATAACTCTTTATCCAGCAACGGCAACGTGACAGA
GTCCGGCTGCAAGGAGTGCGAAGAGCTGGAGGAGAAGAACATCAAGGAG
TTTCTGCAATCCTTTGTGCACATTGTCCAGATGTTCATCAATACCTCC

The amino acid sequence of TGFRt15 fusion protein (including the leader sequence) is as follows (SEQ ID NO: 94):
(Signal peptide)

(SEQ ID NO: 404)
MKWVTFISLLFLFSSAYS (Human TGFβ Receptor II)

(SEQ ID NO: 405)
IPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKC
IMKEKKKPGETFFMCSCSSDECNDNIIFSEEYNTSNPDGGGGSGGGGSG
GGGSIPPHVQKSVNNDMIVTDNNGAVKFPQLCKFCDVRFSTCDNQKSCM
SNCSITSICEKPQEVCVAVWRKNDENITLETVCHDPKLPYHDFILEDAA
SPKCIMKEKKKPGETFFMCSCSSDECNDNIIFSEEYNTSNPD (Human Tissue Factor 219)

(SEQ ID NO: 406)
SGTTNTVAAYNLTWKSTNFKTILEWEPKPVNQVYTVQISTKSGDWKSKC
FYTTDTECDLTDEIVKDVKQTYLARVFSYPAGNVESTGSAGEPLYENSP
EFTPYLETNLGQPTIQSFEQVGTKVNVTVEDERTLVRRNNTFLSLRDVF
GKDLIYTLYYWKSSSSGKKTAKTNTNEFLIDVDKGENYCFSVQAVIPSR
TVNRKSTDSPVECMGQEKGEFRE (Human IL-15)

(SEQ ID NO: 407)
NWVNVISDLKKIEDLIQSMHIDATLYTESDVHPSCKVTAMKCFLLELQV
ISLESGDASIHDTVENLIILANNSLSSNGNVTESGCKECEELEEKNIKE
FLQSFVHIVQMFINTS

The nucleic acid sequence of the TGFRs16 construct (including signal peptide sequence) is as follows (SEQ ID NO: 95):
(Signal peptide)

(SEQ ID NO: 408)
ATGAAGTGGGTGACCTTCATCAGCCTGCTGTTCCTGTTCTCCAGCGCCT
ACTCC (Human TGFβ Receptor II fragments)

(SEQ ID NO: 409)
ATCCCCCCCCATGTGCAAAAGAGCGTGAACAACGATATGATCGTGACCG
ACAACAACGGCGCCGTGAAGTTTCCCCAGCTCTGCAAGTTCTGCGATGT
CAGGTTCAGCACCTGCGATAATCAGAAGTCCTGCATGTCCAACTGCAGC
ATCACCTCCATCTGCGAGAAGCCCCAAGAAGTGTGCGTGGCCGTGTGGC
GGAAAAATGACGAGAACATCACCCTGGAGACCGTGTGTCACGACCCCAA
GCTCCCTTATCACGACTTCATTCTGGAGGACGCTGCCTCCCCCAAATGC
ATCATGAAGGAGAAGAAGAAGCCCGGAGAGACCTTCTTTATGTGTTCCT
GTAGCAGCGACGAGTGTAACGACAACATCATCTTCAGCGAAGAGTACAA
CACCAGCAACCCTGATGGAGGTGGCGGATCCGGAGGTGGAGGTTCTGGT
GGAGGTGGGAGTATTCCTCCCCACGTGCAGAAGAGCGTGAATAATGACA
TGATCGTGACCGATAACAATGGCGCCGTGAAATTTCCCCAGCTGTGCAA
ATTCTGCGATGTGAGGTTTTCCACCTGCGACAACCAGAAGTCCTGTATG
AGCAACTGCTCCATCACCTCCATCTGTGAGAAGCCTCAGGAGGTGTGCG
TGGCTGTCTGGCGGAAGAATGACGAGAATATCACCCTGGAAACCGTCTG

-continued
CCACGATCCCAAGCTGCCCTACCACGATTTCATCCTGGAAGACGCCGCC
AGCCCTAAGTGCATCATGAAAGAGAAAAAGAAGCCTGGCGAGACCTTTT
TCATGTGCTCCTGCAGCAGCGACGAATGCAACGACAATATCATCTTTAG
CGAGGAATACAATACCAGCAACCCCGAC (Human IL-15R α sushi domain)

(SEQ ID NO: 410)
ATTACATGCCCCCCTCCCATGAGCGTGGAGCACGCCGACATCTGGGTGA
AGAGCTATAGCCTCTACAGCCGGGAGAGGTATATCTGTAACAGCGGCTT
CAAGAGGAAGGCCGGCACCAGCAGCCTCACCGAGTGCGTGCTGAATAAG
GCTACCAACGTGGCTCACTGGACAACACCCTCTTTAAAGTGCATCCGG (Anti-human CD16scFv)

(SEQ ID NO: 411)
TCCGAGCTGACCCAGGACCCTGCTGTGTCCGTGGCTCTGGGCCAGACCG
TGAGGATCACCTGCCAGGGCGACTCCCTGAGGTCCTACTACGCCTCCTG
GTACCAGCAGAAGCCCGGCCAGGCTCCTGTGCTGGTGATCTACGGCAAG
AACAACAGGCCCTCCGGCATCCCTGACAGGTTCTCCGGATCCTCCTCCG
GCAACACCGCCTCCCTGACCATCACAGGCGCTCAGGCCGAGGACGAGGC
TGACTACTACTGCAACTCCAGGGACTCCTCCGGCAACCATGTGGTGTTC
GGCGGCGGCACCAAGCTGACCGTGGGCCATGGCGGCGGCGGCTCCGGAG
GCGGCGGCAGCGGCGGAGGAGGATCCGAGGTGCAGCTGGTGGAGTCCGG
AGGAGGAGTGGTGAGGCCTGGAGGCTCCCTGAGGCTGAGCTGTGCTGCC
TCCGGCTTCACCTTCGACGACTACGGCATGTCCTGGGTGAGGCAGGCTC
CTGGAAAGGGCCTGGAGTGGGTGTCCGGCATCAACTGGAACGGCGGATC
CACCGGCTACGCCGATTCCGTGAAGGGCAGGTTCACCATCAGCAGGGAC
AACGCCAAGAACTCCCTGTACCTGCAGATGAACTCCCTGAGGGCCGAGG
ACACCGCCGTGTACTACTGCGCCAGGGGCAGGTCCCTGCTGTTCGACTA
CTGGGGACAGGGCACCCTGGTGACCGTGTCCAGG

The amino acid sequence of TGFRs16 fusion protein (including the leader sequence) is as follows (SEQ ID NO: 96):
(Signal peptide)

(SEQ ID NO: 412)
MKWVTFISLLFLFSSAYS (Human TGFβ Receptor II)

(SEQ ID NO: 413)
IPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKC
IMKEKKKPGETFFMCSCSSDECNDNIIFSEEYNTSNPDGGGGSGGGGSG
GGGSIPPHVQKSVNNDMIVTDNNGAVKFPQLCKFCDVRFSTCDNQKSCM
SNCSITSICEKPQEVCVAVWRKNDENITLETVCHDPKLPYHDFILEDAA
SPKCIMKEKKKPGETFFMCSCSSDECNDNIIFSEEYNTSNPD (Human IL-15R α sushi domain)

(SEQ ID NO: 414)
ITCPPPMSVEHADIWVKSYSLYSRERYICNSGFKRKAGTSSLTECVLNK
ATNVAHWTTPSLKCIR (Anti-human CD16scFv)

(SEQ ID NO: 415)
SELTQDPAVSVALGQTVRITCQGDSLRSYYASWYQQKPGQAPVLVIYGK
NNRPSGIPDRFSGSSSGNTASLTITGAQAEDEADYYCNSRDSSGNHVVF
GGGTKLTVGHGGGGSGGGGSGGGGSEVQLVESGGGVVRPGGSLRLSCAA
SGFTFDDYGMSWVRQAPGKGLEWVSGINWNGGSTGYADSVKGRFTISRD
NAKNSLYLQMNSLRAEDTAVYYCARGRSLLFDYWGQGTLVTVSR

The nucleic acid sequence of the TGFRt15 construct (including signal peptide sequence) is as follows (SEQ ID NO: 97):
(Signal peptide)

(SEQ ID NO: 416)
ATGAAGTGGGTGACCTTCATCAGCCTGCTGTTCCTGTTCTCCAGCGCCT
ACTCC (Human TGFβ Receptor II fragments)

(SEQ ID NO: 417)
ATCCCCCCCCATGTGCAAAAGAGCGTGAACAACGATATGATCGTGACCG
ACAACAACGGCGCCGTGAAGTTTCCCCAGCTCTGCAAGTTCTGCGATGT
CAGGTTCAGCACCTGCGATAATCAGAAGTCCTGCATGTCCAACTGCAGC
ATCACCTCCATCTGCGAGAAGCCCAAGAAGTGTGCGTGGCCGTGTGGC
GGAAAAATGACGAGAACATCACCCTGGAGACCGTGTGTCACGACCCCAA
GCTCCCTTATCACGACTTCATTCTGGAGGACGCTGCCTCCCCCAAATGC
ATCATGAAGGAGAAGAAGAAGCCCGGAGAGACCTTCTTTATGTGTTCCT

-continued
GTAGCAGCGACGAGTGTAACGACAACATCATCTTCAGCGAAGAGTACAA
CACCAGCAACCCTGATGGAGGTGGCGGATCCGGAGGTGGAGGTTCTGGT
GGAGGTGGGAGTATTCCTCCCCACGTGCAGAAGAGCGTGAATAATGACA
TGATCGTGACCGATAACAATGGCGCCGTGAAATTTCCCCAGCTGTGCAA
ATTCTGCGATGTGAGGTTTTCCACCTGCGACAACCAGAAGTCCTGTATG
AGCAACTGCTCCATCACCTCCATCTGTGAGAAGCCTCAGGAGGTGTGCG
TGGCTGTCTGGCGGAAGAATGACGAGAATATCACCCTGGAAACCGTCTG
CCACGATCCCAAGCTGCCCTACCACGATTTCATCCTGGAAGACGCCGCC
AGCCCTAAGTGCATCATGAAAGAGAAAAAGAAGCCTGGCGAGACCTTTT
TCATGTGCTCCTGCAGCAGCGACGAATGCAACGACAATATCATCTTTAG
CGAGGAATACAATACCAGCAACCCCGAC (Human Tissue Factor 219)
(SEQ ID NO: 418)
AGCGGCACAACCAACACAGTCGCTGCCTATAACCTCACTTGGAAGAGCA
CCAACTTCAAAACCATCCTCGAATGGGAACCCAAACCCGTTAACCAAGT
TTACACCGTGCAGATCAGCACCAAGTCCGGCGACTGGAAGTCCAAATGT
TTCTATACCACCGACACCGAGTGCGATCTCACCGATGAGATCGTGAAAG
ATGTGAAACAGACCTACCTCGCCCGGGTGTTTAGCTACCCCGCCGGCAA
TGTGGAGAGCACTGGTTCCGCTGGCGAGCCTTTATACGAGAACAGCCCC
GAATTTACCCCTTACCTCGAGACCAATTTAGGACAGCCCACCATCCAAA
GCTTTGAGCAAGTTGGCACAAAGGTGAATGTGACAGTGGAGGACGAGCG
GACTTTAGTGCGGCGGAACAACACCTTTCTCAGCCTCCGGGATGTGTTC
GGCAAAGATTTAATCTACACACTGTATTACTGGAAGTCCTCTTCCTCCG
GCAAGAAGACAGCTAAAACCAACACAACGAGTTTTTAATCGACGTGGA
TAAAGGCGAAAACTACTGTTTCAGCGTGCAAGCTGTGATCCCCTCCCGG
ACCGTGAATAGGAAAAGCACCGATAGCCCCGTTGAGTGCATGGGCCAAG
AAAAGGGCGAGTTCCGGGAG (Human IL-15)
(SEQ ID NO: 419)
AACTGGGTGAACGTCATCAGCGATTTAAAGAAGATCGAAGATTTAATTC
AGTCCATGCATATCGACGCCACTTTATACACAGAATCCGACGTGCACCC
CTCTTGTAAGGTGACCGCCATGAAATGTTTTTTACTGGAGCTGCAAGTT
ATCTCTTTAGAGAGCGGAGACGCTAGCATCCACGACACCGTGGAGAATT
TAATCATTTTAGCCAATAACTCTTTATCCAGCAACGGCAACGTGACAGA
GTCCGGCTGCAAGGAGTGCGAAGAGCTGGAGGAGAAGAACATCAAGGAG
TTTCTGCAATCCTTTGTGCACATTGTCCAGATGTTCATCAATACCTCC The amino acid sequence of TGFRt15 fusion protein (including the leader sequence) is as follows (SEQ ID NO: 98):
(Signal peptide)
(SEQ ID NO: 420)
MKWVTFISLLFLFSSAYS (Human TGFβ Receptor II)
(SEQ ID NO: 421)
IPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKC
IMKEKKKPGETFFMCSCSSDECNDNIIFSEEYNTSNPDGGGGSGGGGSG
GGGSIPPHVQKSVNNDMIVTDNNGAVKFPQLCKFCDVRFSTCDNQKSCM
SNCSITSICEKPQEVCVAVWRKNDENITLETVCHDPKLPYHDFILEDAA
SPKCIMKEKKKPGETFFMCSCSSDECNDNIIFSEEYNTSNPD (Human Tissue Factor 219)
(SEQ ID NO: 422)
SGTTNTVAAYNLTWKSTNFKTILEWEPKPVNQVYTVQISTKSGDWKSKC
FYTTDTECDLTDEIVKDVKQTYLARVFSYPAGNVESTGSAGEPLYENSP
EFTPYLETNLGQPTIQSFEQVGTKVNVTVEDERTLVRRNNTFLSLRDVF
GKDLIYTLYYWKSSSSGKKTAKTNTNEFLIDVDKGENYCFSVQAVIPSR
TVNRKSTDSPVECMGQEKGEFRE (Human IL-15)
(SEQ ID NO: 423)
NWVNVISDLKKIEDLIQSMHIDATLYTESDVHPSCKVTAMKCFLLELQV
ISLESGDASIHDTVENLIILANNSLSSNGNVTESGCKECEELEEKNIKE
FLQSFVHIVQMFINTS The nucleic acid sequence of the TGFRs137L construct (including signal peptide sequence) is as follows (SEQ ID NO: 99):
(Signal peptide)
(SEQ ID NO: 424)
ATGAAGTGGGTGACCTTCATCAGCCTGCTGTTCCTGTTCTCCAGCGCCT
ACTCC (Human TGFβ Receptor II fragments)
(SEQ ID NO: 425)
ATCCCCCCCCATGTGCAAAAGAGCGTGAACAACGATATGATCGTGACCG
ACAACAACGGCGCCGTGAAGTTTCCCCAGCTCTGCAAGTTCTGCGATGT
CAGGTTCAGCACCTGCGATAATCAGAAGTCCTGCATGTCCAACTGCAGC
ATCACCTCCATCTGCGAGAAGCCCCAAGAAGTGTGCGTGGCCGTGTGGC
GGAAAAATGACGAGAACATCACCCTGGAGACCGTGTGTCACGACCCCAA
GCTCCCTTATCACGACTTCATTCTGGAGGACGCTGCCTCCCCCAAATGC
ATCATGAAGGAGAAGAAGAAGCCCGGAGAGACCTTCTTTATGTGTTCCT
GTAGCAGCGACGAGTGTAACGACAACATCATCTTCAGCGAAGAGTACAA
CACCAGCAACCCTGATGGAGGTGGCGGATCCGGAGGTGGAGGTTCTGGT
GGAGGTGGGAGTATTCCTCCCCACGTGCAGAAGAGCGTGAATAATGACA
TGATCGTGACCGATAACAATGGCGCCGTGAAATTTCCCCAGCTGTGCAA
ATTCTGCGATGTGAGGTTTTCCACCTGCGACAACCAGAAGTCCTGTATG
AGCAACTGCTCCATCACCTCCATCTGTGAGAAGCCTCAGGAGGTGTGCG
TGGCTGTCTGGCGGAAGAATGACGAGAATATCACCCTGGAAACCGTCTG
CCACGATCCCAAGCTGCCCTACCACGATTTCATCCTGGAAGACGCCGCC
AGCCCTAAGTGCATCATGAAAGAGAAAAAGAAGCCTGGCGAGACCTTTT
TCATGTGCTCCTGCAGCAGCGACGAATGCAACGACAATATCATCTTTAG
CGAGGAATACAATACCAGCAACCCCGAC (Human IL-15R α sushi domain)
(SEQ ID NO: 426)
ATTACATGCCCCCCTCCCATGAGCGTGGAGCACGCCGACATCTGGGTGA
AGAGCTATAGCCTCTACAGCCGGGAGAGGTATATCTGTAACAGCGGCTT
CAAGAGGAAGGCCGGCACCAGCAGCCTCACCGAGTGCGTGCTGAATAAG
GCTACCAACGTGGCTCACTGGACAACACCCTCTTTAAAGTGCATCCGG ((G4S)3 linker)
(SEQ ID NO: 427)
GGCGGTGGAGGATCCGGAGGAGGTGGCTCCGGCGGCGGAGGATCT (Human CD137L)
(SEQ ID NO: 428)
CGCGAGGGTCCCGAGCTTTCGCCCGACGATCCCGCCGGCCTCTTGGACC
TGCGGCAGGGCATGTTTGCGCAGCTGGTGGCCCAAAATGTTCTGCTGAT
CGATGGGCCCCTGAGCTGGTACAGTGACCCAGGCCTGGCAGGCGTGTCC
CTGACGGGGGCCTGAGCTACAAAGAGGACACGAAGGAGCTGGTGGTGG
CCAAGGCTGGAGTCTACTATGTCTTCTTTCAACTAGAGCTGCGGCGCGT
GGTGGCCGGCGAGGGCTCAGGCTCCGTTTCACTTGCGCTGCACCTGCAG
CCACTGCGCTCTGCTGCTGGGGCGCCGCCCTGGCTTTGACCGTGGACC
TGCCACCCGCCTCCTCCGAGGCTCGGAACTCGGCCTTCGGTTTCCAGGG
CCGCTTGCTGCACCTGAGTGCCGGCCAGCGCCTGGGCGTCCATCTTCAC
ACTGAGGCCAGGGCACGCCATGCCTGGCAGCTTACCCAGGGCGCCACAG
TCTTGGGACTCTTCCGGGTGACCCCCGAAATCCCAGCCGGACTCCCTTC
ACCGAGGTCGGAA The amino acid sequence of TGFRs137L fusion protein (including the leader sequence) is as follows (SEQ ID NO: 100):
(Signal peptide)
(SEQ ID NO: 429)
MKWVTFISLLFLFSSAYS (Human TGFβ Receptor II)
(SEQ ID NO: 430)
IPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKC
IMKEKKKPGETFFMCSCSSDECNDNIIFSEEYNTSNPDGGGGSGGGGSG
GGGSIPPHVQKSVNNDMIVTDNNGAVKFPQLCKFCDVRFSTCDNQKSCM
SNCSITSICEKPQEVCVAVWRKNDENITLETVCHDPKLPYHDFILEDAA
SPKCIMKEKKKPGETFFMCSCSSDECNDNIIFSEEYNTSNPD (Human IL-15R α sushi domain)
(SEQ ID NO: 431)
ITCPPPMSVEHADIWVKSYSLYSRERYICNSGFKRKAGTSSLTECVLNK
ATNVAHWTTPSLKCIR -continued ((G4S)3 linker)

(SEQ ID NO: 432)
GGGGSGGGGSGGGGS (Human CD137L)

(SEQ ID NO: 433)
REGPELSPDDPAGLLDLRQGMFAQLVAQNVLLIDGPLSWYSDPGLAGVS
LTGGLSYKEDTKELVVAKAGVYYVFFQLELRRVVAGEGSGSVSLALHLQ
PLRSAAGAAALALTVDLPPASSEARNSAFGFQGRLLHLSAGQRLGVHLH
TEARARHAWQLTQGATVLGLFRVTPEIPAGLPSPRSE

Compositions/Kits

Also provided herein are compositions that include any of the affinity chromatography resins described herein. Also provided herein are chromatography columns that include any of the affinity chromatography resins described herein. Also provided herein are kits that include any of the affinity chromatography resins or chromatography columns described herein. Some embodiments of any of the kits described herein further include instructions for performing any of the methods described herein.

EXAMPLES

Example 1: Comparison of CNBr-activated Sepharose vs NHS Sepharose

Solid support materials for coupling proteins may contain different activation groups or use different chemical reactions. Thus, two different solid support materials for anti-tissue factor antibody coupling were evaluated to see which one is a better based resin for high yield recovery of human tissue factor (TF)-containing proteins (e.g., any of the single-chain or multi-chain chimeric proteins described herein).

Two anti-tissue factor affinity columns were produced using NHS-Activated Sepharose 4 Fast Flow resin and CNBr Activated Sepharose 4 Fast Flow resin from GE Healthcare. The anti-tissue factor used in these experiments include a heavy chain variable domain comprising SEQ ID NO: 7 and a light chain variable domain comprising SEQ ID NO: 8.

For the same amount of each resin, the same amount of anti-tissue factor antibody was conjugated under the same conditions per the manufacturer's instructions. The two anti-tissue factor affinity chromatography resins were then packed into two columns and evaluated using 18t15-12s harvest for yield recovery and performance. When the same amount of 18t15-12s was loaded onto each anti-tissue factor affinity chromatography column, the anti-tissue factor CNBr-Sepharose column yielded 50% higher (6 mg vs 4 mg) 18t15-12s in the elution peak compared to anti-tissue factor-NHS Sepharose column (NB #07, PG #08-09) (see, Table 1).

TABLE 1

Comparison of CNBr-activated Sepharose vs NHS Sepharose

| Parameters | CNBr-activated Sepharose 4 Fast Flow | NHS-activated Sepharose 4 Fast Flow |
|---|---|---|
| Resin volume or weight | 6.83 mL | 6.0 mL |
| Column volume, mL | 6.83 | 6.0 |
| Anti-TF Ab amount conjugated, mg | 30 | 30 |
| Volume of 18t15-12s harvest loaded, mL | 480 | 480 |
| Total amount of 18t15-12s in elution peak, mg | 6.04 | 4.24 |

Example 2: Elution Conditions

Figure 2:
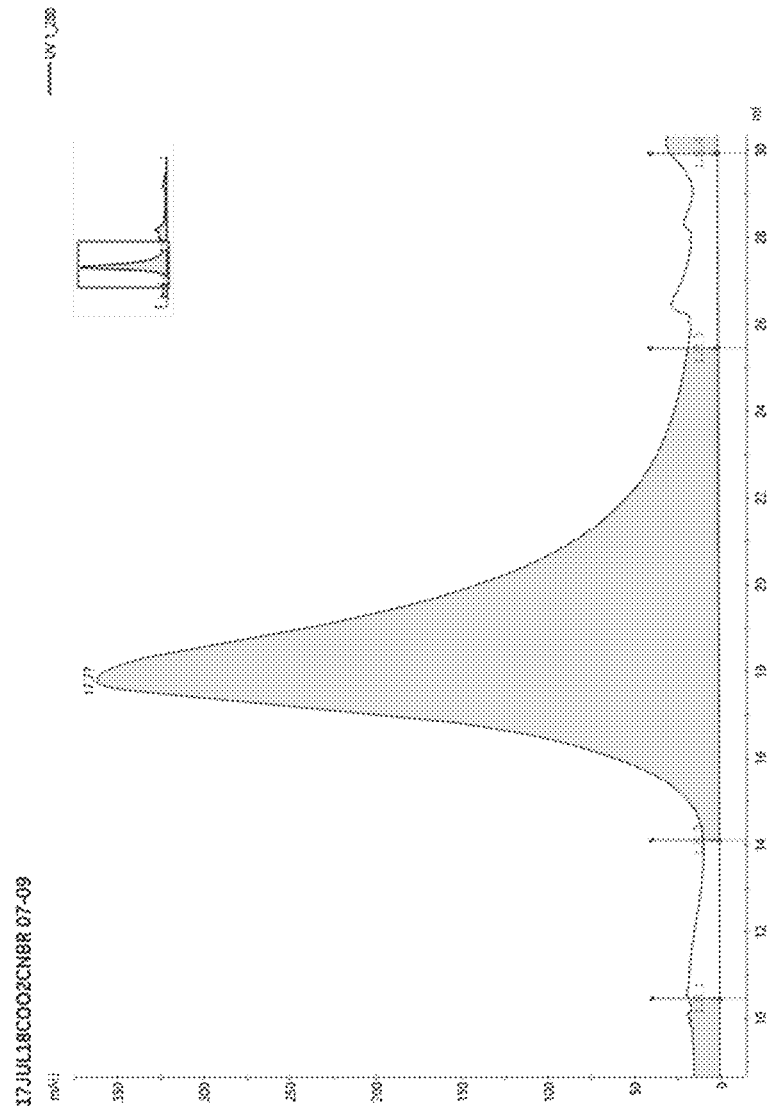
FIG. 2 is an elution profile of 18t15-12s protein from an exemplary affinity chromatography resin provided herein (αTF antibody CNBr-Sepharose affinity column) that was equilibrated with phosphate buffered saline, loaded, washed with phosphate buffered saline, and eluted using 0.1M acetic acid, pH 2.9.

An elution profile of 18t15-12s from a 1.6 cm×3.4 cm (6.83 mL CV) anti-tissue factor CNBr-Sepharose affinity column that was equilibrated with 5CVs phosphate buffered saline, loaded with 18t15-12s washed with 7CVs phosphate buffered saline, and eluted with 6CVs of 0.1 M acetic acid, pH 2.9 is shown in FIG. 2. The resulting chromatograph in FIG. 2 shows that elution using 0.1 M acetic acid resulted in a sharp protein peak with minimal tailing. In view of these data, 0.1 M acetic acid was selected as a useful elution buffer for the anti-tissue factor affinity chromatography resin.

Example 3: Coupling Density and Binding Capacity of Target Protein

Figure 3:
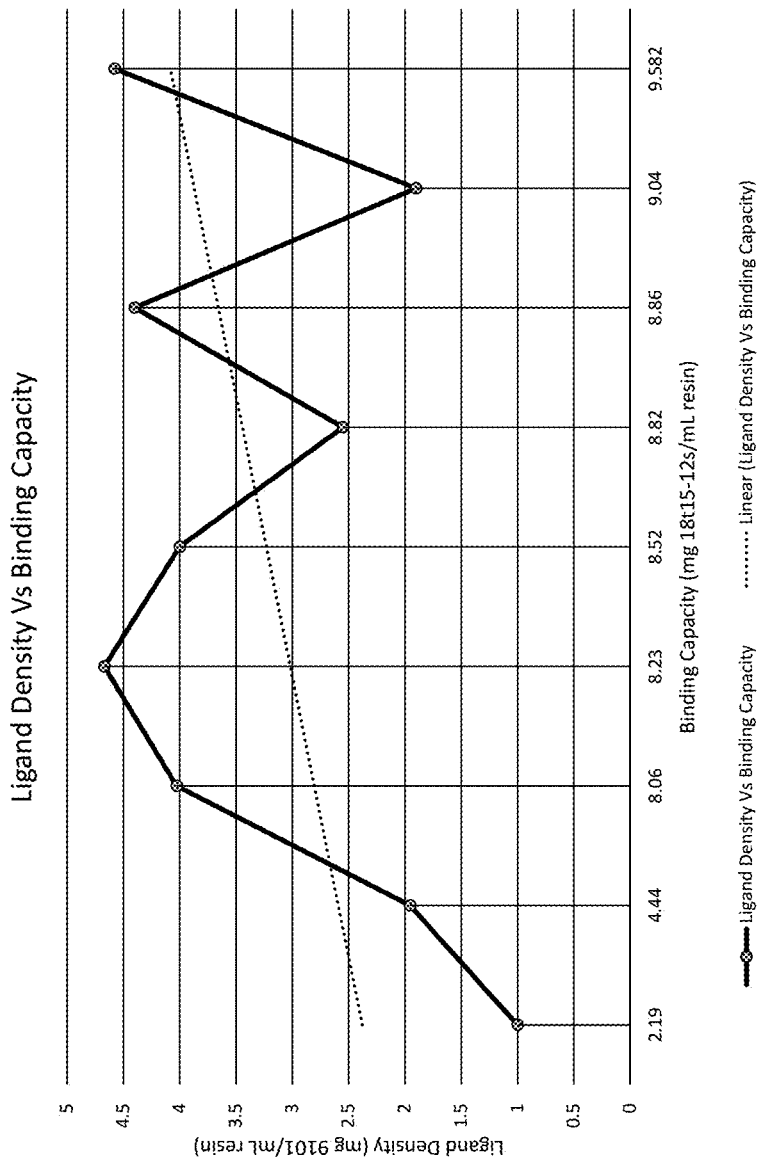
FIG. 3 is a graph of ligand density versus binding capacity for different affinity chromatography resin preparations, showing the relationship between anti-tissue factor antibody coupling density and the binding capacity of the resin for a tissue-factor containing protein, such as 18t15-12s protein.

To evaluate the binding capacity of anti-tissue factor affinity columns, resins containing different coupling densities of the anti-tissue factor were prepared using CNBr-Sepharose, and then 18t15-12s was loaded to generate yield recovery data. FIG. 3 represents historical data from many different resin preparation lots showing an increasing binding capacity with increasing quantities of anti-tissue factor conjugated to the CNBr-activated Sepharose resin. This increased binding capacity begins to level off at around 9 mg anti-tissue factor/mL CNBr-activated Sepharose resin.

Example 4: Coupling Time and Mixing Method

Different mixing methods and conjugation times were evaluated for anti-tissue factor coupling conditions. No difference was observed in coupling for 2-4 hours versus overnight conjugation time. The data is represented in Table 2 below. Also, no difference was observed for rocker versus impeller mixing method.

TABLE 2

Historical resin preparation data

| Column ID | Mixing Method | CV Column (mL) | Ligand Density (mg antibody/ mL resin) | Total mg of 18t15-12 s recovered per column | Binding capacity (mg product/mL resin) | Amount of 18t15-12 s recovered per mg of immobilized anti-tissue factor antibody |
|---|---|---|---|---|---|---|
| 1 | Rocker | 6.83 | 2.19 | 6.86 | 1 | 0.457 |
| 2 | Rocker | 9 | 4.44 | 17.6 | 1.955 | 0.44 |
| 3 | Rocker | 15.57 | 8.06 | 62.71 | 4.027 | 0.500 |
| 15-37cond2 | Impellor | 2.67 | 8.23 | 12.47 | 4.67 | 0.567 |
| 15-37cond3 | Rocker | 2.67 | 9.582 | 12.24 | 4.58 | 0.478 |
| 15-37cond1 | Impellor | 2.67 | 8.86 | 11.815 | 4.4 | 0.497 |
| 14-25 | Impellor | 40 | 8.52 | ND | 4 | 0.469 |

Example 5: Wash Studies

A set of experiments were performed to identify optimal wash conditions for the anti-tissue factor chromatography resins described herein. In these experiments, two different first wash buffers were compared: phosphate buffered saline and 20 mM Tris, 1 M NaCl, pH 8.0. Using 20 mM Tris, 1 M NaCl, pH 8.0 as the first wash buffer led to loss of material without an increase in product quality. After this initial experiment, 0.1 M sodium citrate, pH 5.0 was evaluated as a second wash buffer (after use of a first wash buffer of phosphate buffered saline).

Figure 4:
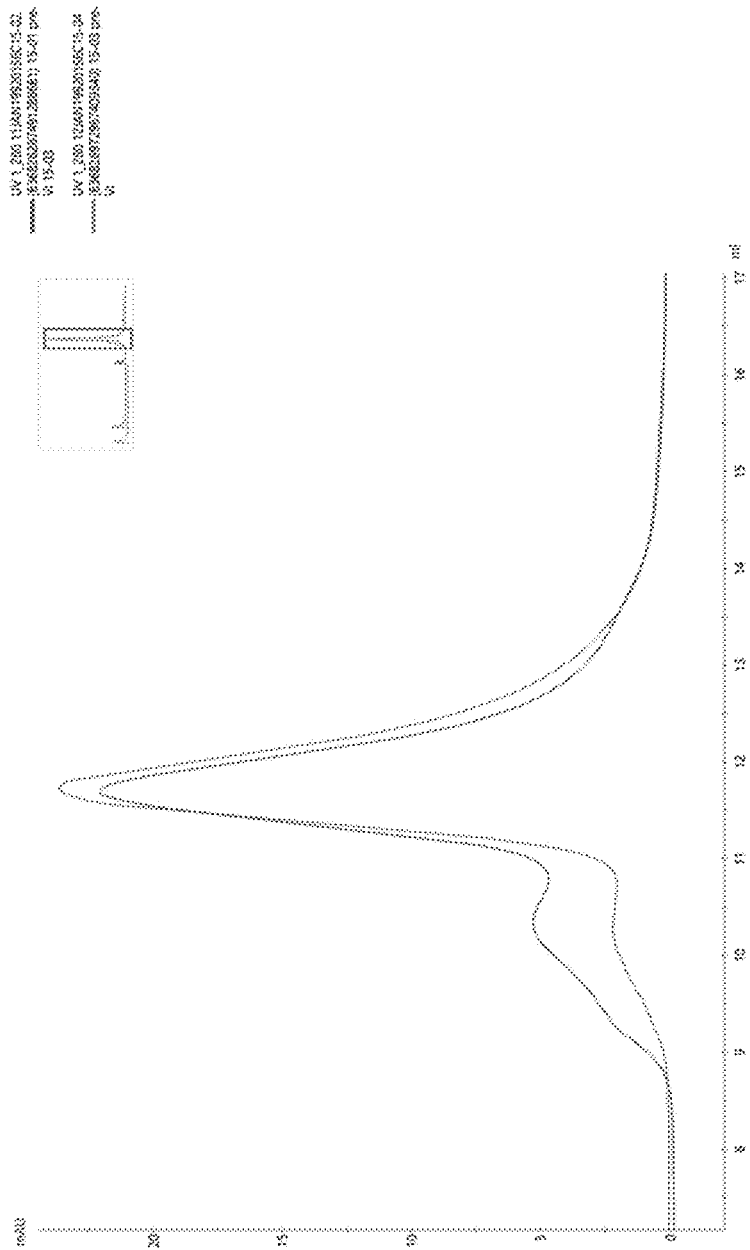
FIG. 4 is a graph showing optimization of wash conditions for 18t15-12s purification using an exemplary affinity chromatography resin provided herein (anti-tissue factor CNBr-Sepharose affinity column). Each experiment was performed using a column equilibrated with phosphate buffered saline, loaded, washed with phosphate buffered saline, and eluted using 0.1M acetic acid, pH 2.9. The data shown in blue did not include a further 5 CV wash using 0.1M sodium citrate, pH 5.0, while the data in orange included a further 5 CV wash using 0.1 M sodium citrate, pH 5.0.

The use of a first wash buffer of phosphate buffered saline, following by a second wash buffer of 0.1 M sodium citrate, pH 5.0 was adopted as it led to an increase in elution pool pH. This increased elution pool pH was found to be protective for the product quality as it relates to aggregation. FIG. 4 shows the optimization of wash conditions for 18t15-12s purification by anti-tissue factor CNBr-Sepharose affinity column. Each experiment was performed using a 2.6 cm×7.4 cm (39.27 mL CV) column equilibrated with 5 CVs of phosphate buffered saline, loaded, washed with 5CVs of phosphate buffered saline and further washed with either 5 CVs of phosphate buffered saline or 5 CVs of 0.1 M citrate, pH 5.0, and eluted with 6 CVs of 0.1M acetic acid, pH 2.9.

TABLE 3

Effect of wash 2 (0.1M sodium citrate, pH 5.0) on 18t15-12s product quality

| Experiment | Wash condition | 18t15-12s aggregates (%) | 18t15-12s main peak (%) |
|---|---|---|---|
| 15-01 | No pH 5.0 wash | 19.81 | 80.19 |
| 15-03 | Wash with 0.1M sodium citrate, pH 5.0 | 8.4 | 91.6 |

Figure 5:
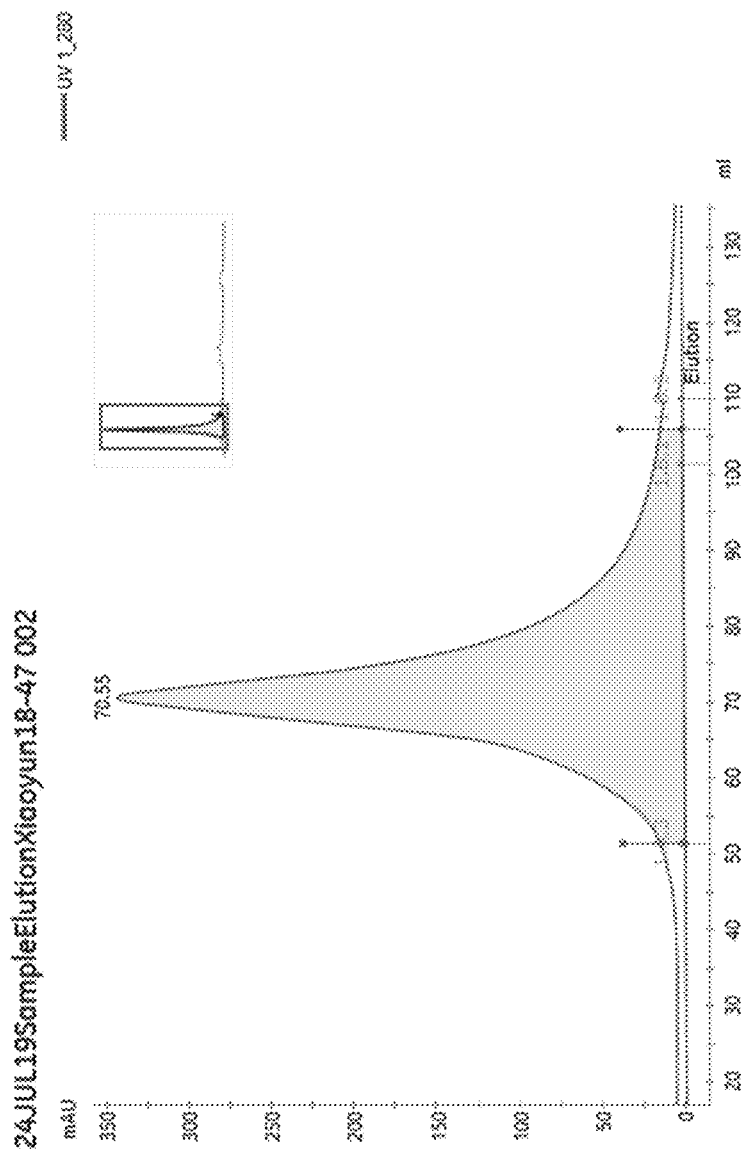
FIG. 5 shows an elution profile of the first run of a newly generated an exemplary affinity chromatography resin provided herein (anti-tissue factor CNBr column) purified by equilibrating with the resin with phosphate buffered saline, loading the resin, washing the resin using phosphate buffered saline, and eluting the resin using 0.1M acetic acid, pH 2.9.
Figure 6:
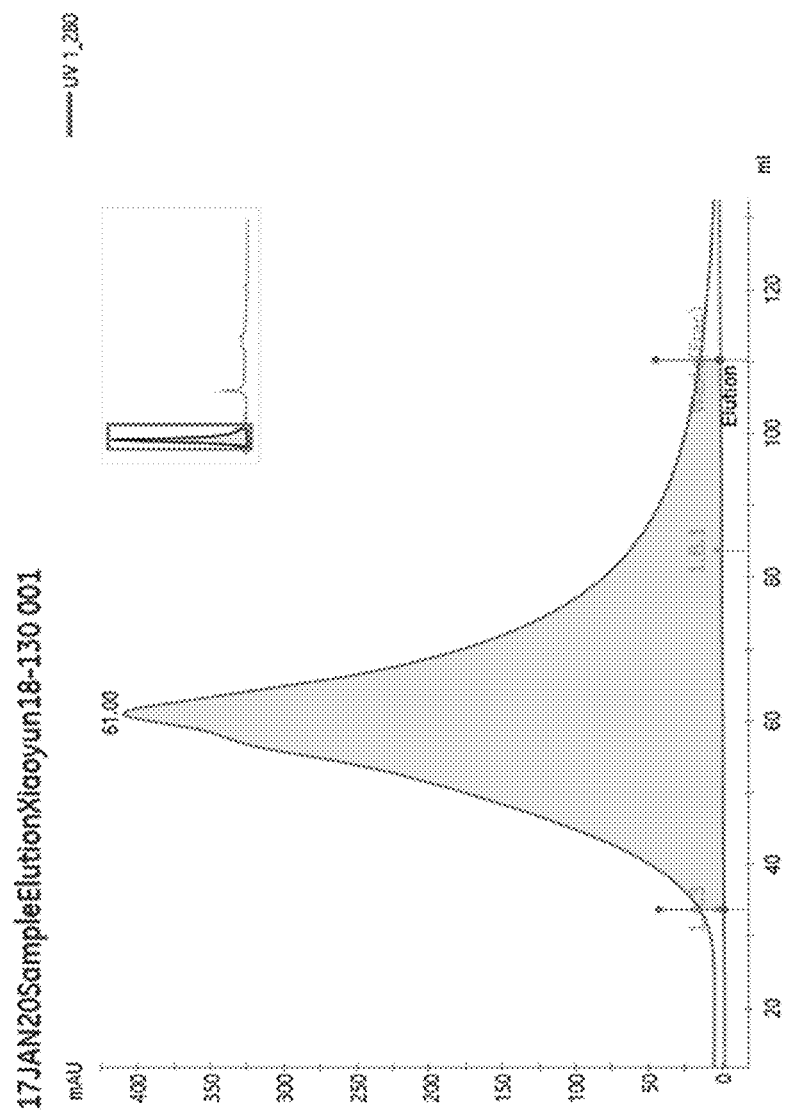
FIG. 6 shows an elution profile of the $51^{st}$ purification run using the same column used in FIG. 5. The $51^{st}$ purification run was performed by equilibrating the column with phosphate buffered saline, loading the column, washing the column with phosphate buffered saline, and eluting the column using 0.1M acetic acid, pH 2.9.

Example 6: Stripping Condition, Storage Solution, and Stability Data 0.1M Glycine pH 2.5 was selected as the strip buffer for the anti-tissue factor-CNBr Sepharose column. The conjugated column was stored in phosphate buffered saline, 0.05% sodium azide. In order to utilize a storage solution that could be easily transferred to manufacturing, 20% ethanol was adopted as the new storage solution. No column performance loss is observed when storing in 20% ethanol for up to a year. Additionally, anti-tissue factor CNBr-Sepharose columns have been used for up to a year without significant loss of binding capacity. FIGS. 5 and 6 show the elution profiles of the first run, with a newly generated anti-tissue factor-CNBr Sepharose column and the 51$^{st}$ run with the same column. FIG. 5 shows the elution profile of the first run of a newly generated 2.6 cm×9.5 cm (50.41 mL CV) anti-tissue factor-CNBr Sepharose column purified by equilibrating with 5CVs phosphate buffered saline, loaded, washed with 5 CVs phosphate buffered saline, and eluted with 6 CVs of 0.1M acetic acid, pH 2.9. FIG. 6 shows the elution profile of the 51$^{st}$ purification run (the same column used in FIG. 5), where the chromatography run was performed using the steps of equilibration using 5 CVs phosphate buffered saline, loading, washing with 5 CVs of phosphate buffered saline, and eluted with 6 CVs of 0.1 M acetic acid, pH 2.9.

Example 7: Development of Sanitation Method

In order to avoid contamination, sanitization solutions are typically used in column chromatography before column use, post use, and storage. Initially 50 mM NaOH 1 M NaCl with a 15-minute contact time was tested. This resulted in a 60% loss of the column binding capacity, and thus 50 mM NaOH, 1 M NaCl was no longer used as a sanitation solution. A commercial solution of 120 mM phosphoric acid, 167 mM acetic acid, 2.2% benzyl alcohol, pH 5.0 was also tested as a possible sanitization buffer. Although 120 mM phosphoric acid, 167 mM acetic acid, 2.2% benzyl alcohol, pH 5.0 resulted in good column stability, it was abandoned as a sanitization strategy due to its interaction with plastic containers. Then, 50 mM citrate, 2% benzyl alcohol, pH 5.0 with a 15-minute contact time was evaluated as a sanitation solution. The results indicated that there was no loss of column binding capacity. Therefore, 50 mM citrate, 2% benzyl alcohol, pH 5.0 was selected as a sanitation solution for the anti-tissue factor affinity chromatography columns.

Studies were also performed to determine if product carryover of loaded product from one run to the next was occurring. This was accomplished by equilibrating a 2.6 cm×9.5 cm (50.41 mL CV) anti-tissue factor-CNBr Sepharose column with 5CVs phosphate buffered saline, loading 18t15-12s onto the column, washing with 5 CVs of PBS, washing with 5 CVs of 0.1 M citrate, pH 5.0, eluting with 0.1 M acetic acid, pH 2.9, stripping with 4 CVs of 0.1 M glycine, pH 2.5, neutralizing with 4 CVs of phosphate buffered saline, and storing with 7 CVs of 20% ethanol. The same process was then repeated, but instead of loading 18t15-12s the column was loaded with phosphate buffered saline, and the elution pool was analyzed by ELISA for residual 18t15-12s A minimal amount-1.162 g/mL 18t15-12s was detected in the elution of the next run.

An eluate from a process demonstration run, using the same purification process listed above was tested by ELISA for residual anti-tissue factor antibody to evaluate the stability of the column, and to verify that a minimum amount of antibody leaching was occurring from the column into the elution pool during processing. A negligible quantity, 17 ppm, was detected in the elution.

Example 8: Examples of TF Fusion Proteins and TF Fusion Protein Complexes

A variety of different single-chain and multi-chain chimeric polypeptides including a soluble tissue factor domain have been successfully purified using anti-tissue factor CNBr Sepharose affinity chromatography resins provided herein. Multi-chain chimeric polypeptides that have been successfully purified using anti-tissue factor CNBr Sepharose affinity chromatography resins provided herein include 18t15-12s, 7t15-21s, TGFRt15-TGFRs, 7t15-21s137L, 21t15-TGFRs, TGFRt15-21s137L, TGFRt15-TGFRs137L, TGFRt15-TGFRs21, TGFRt15-TGFRs16, 7t15-TGFRs, 21t15-7s, 18t15-12s16, 7t15-16s21, TGFRt15-16s21, and 7t15-7s. Single-chain chimeric polypeptides that have been successfully purified using anti-tissue factor CNBr Sepharose affinity chromatography resins described herein are 2t2, 3t28, and 15t15.

A preliminary stability study was performed on 18t15-12s a fusion protein product purified through the anti-tissue factor-CNBr Sepharose column and then subsequent unit operations were performed (as outlined in FIG. 1). The resulting manufactured 18t15-12s was stable for up to 5 weeks (Table 4).

TABLE 4

Stability data for 18t15-12 s incubated at 2-8° C., 25° C.,
and 37° C., and then analyzed by HPLC-SEC 1 week timepoints up to 5 weeks.

| Time points | 18t15-12 s 2-8° C. Stability Data | | | 18t15-12 s 25° C. Stability Data | | | 18t15-12 s 37° C. Stability Data | | |
|---|---|---|---|---|---|---|---|---|---|
| | HMWS (%) | Main (%) | LMWS (%) | HMWS (%) | Main (%) | LMWS (%) | HMWS (%) | Main (%) | LMWS (%) |
| 0 week | 8.91 | 91.09 | 0 | 8.91 | 91.09 | 0 | 8.91 | 91.09 | 0 |
| 1 week | 9.46 | 90.54 | 0 | 10.45 | 89.55 | 0 | 10.83 | 89.17 | 0 |
| 2 weeks | 7.89 | 92.11 | 0 | 9.44 | 90.47 | 0.9 | 9.84 | 87.07 | 3.1 |
| 3 weeks | 10.2 | 89.65 | 0.15 | 11.19 | 88.7 | 0.11 | 12.27 | 87.69 | 0.09 |
| 4 weeks | 9.07 | 90.7 | 0.24 | 10.62 | 89.37 | 0.02 | 11.7 | 88.18 | 0.12 |
| 5 weeks | 5.1 | 94.84 | 0.06 | 7.65 | 92.32 | 0.03 | 8.23 | 90.67 | 1.1 |

Example 9: Purification of TGFRt15-TGFRs and 2t2

The conditions to purify TGFRt15-TGFRs and 2t2 using an affinity chromatograph resin as described herein (anti-tissue factor CNBr Sepharose affinity chromatography resin). In general, the anti-tissue factor CNBr Sepharose affinity chromatography resin was prepared as previously described. The anti-tissue factor CNBr Sepharose affinity chromatography resin was then packed into a column and clarified cell harvest containing either TGFRt15-TGFRs or 2t2 was loaded onto the column which had been equilibrated with 4 column volume (CV) of PBS. After sample loading, the column was washed with 5 CV of PBS and 5 CV of 0.1 M sodium citrate, pH 5.0. The target protein (TGFRt15-TGFRs or 2t2) was then eluted with 3-4 CV of 0.1 M acetic acid, pH 2.9. The eluted protein peak of TGFRt15-TGFRs or 2t2 was then adjusted to neutral pH (7-8) with 1 M Tris if the protein material is used for research purposes, adjusted to pH 3.6 with 1 M citric acid, followed by incubation at this low pH for 1 hour at room temperature if the protein material is used for clinical study. The low pH incubation serves to inactivate viruses that may be potentially present in cell culture harvest. After low pH incubation, 1 M Tris was then added to adjust pH to 6.0 for TGFRt15-TGFRs or to 5.0 for 2t2, followed by depth filtration to remove or reduce product or process-related protein contaminants. After protein elution, the column was stripped and stored as described in Example 7.

Figure 9:
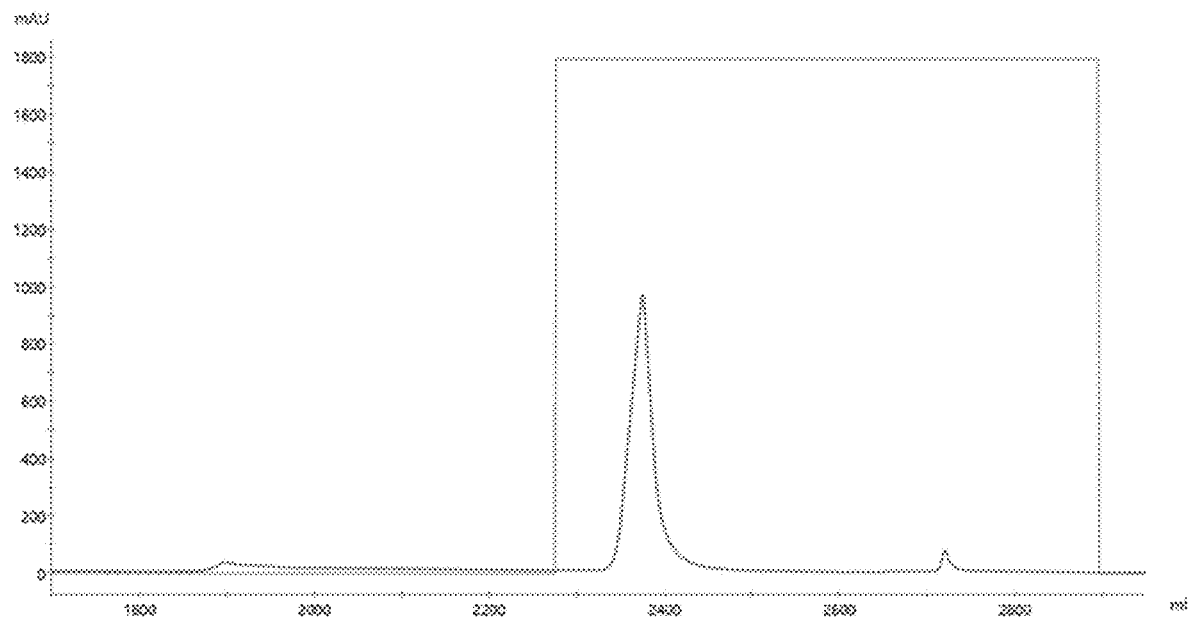
FIG. 9 shows a chromatogram of TGFRt15-TGFRs elution profile from an exemplary affinity chromatography resin provided herein (anti-tissue factor CNBr column). The dark gray line is absorbance at 280 nm, and the light gray line represents the use of the elution buffer (0.1 M acetic acid, pH 2.9).
Figure 10:
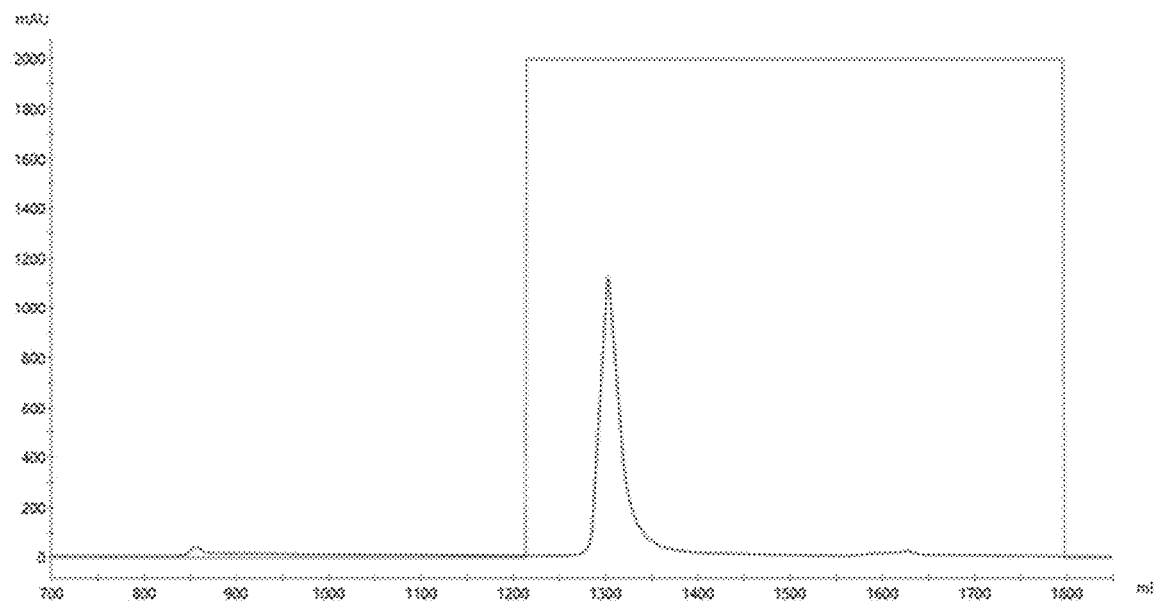
FIG. 10 shows a chromatogram of 2t2 elution profile from an exemplary affinity chromatography resin provided herein (anti-tissue factor CNBr column). The dark gray line is absorbance at 280 nm, and the light gray line represents the use of the elution buffer (0.1 M acetic acid, pH 2.9).

Chromatograms showing elution of TGFRt15-TGFRs and 2t2 are shown in FIG. 9 and FIG. 10, respectively.

---

SEQUENCE LISTING

```
<160> NUMBER OF SEQ ID NOS: 433

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asp Tyr Asn Val Tyr
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Tyr Ile Asp Pro Tyr Asn Gly Ile Thr Ile Tyr Asp Gln Asn Phe Lys
1               5                   10                  15

Gly

<210> SEQ ID NO 3
<211> LENGTH: 8
<212> TYPE: PRT
<213> ORGANISM: Artificial Sequence
<220> FEATURE:
```

<223> OTHER INFORMATION: Description of Artificial Sequence: Synthetic
       peptide

<400> SEQUENCE: 3

Asp Val Thr Thr Ala Leu Asp Phe
1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 4

Leu Ala Ser Gln Thr Ile Asp Thr Trp Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic

```
                              peptide

<400> SEQUENCE: 5

Ala Ala Thr Asn Leu Ala Asp
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Gln Val Tyr Ser Ser Pro Phe Thr
1               5

<210> SEQ ID NO 7
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Ile Gln Leu Val Gln Ser Gly Gly Glu Val Lys Lys Pro Gly Ala
1               5                   10                  15

Ser Val Arg Val Ser Cys Lys Ala Ser Gly Tyr Ser Phe Thr Asp Tyr
            20                  25                  30

Asn Val Tyr Trp Val Arg Gln Ser Pro Gly Lys Gly Leu Glu Trp Ile
        35                  40                  45

Gly Tyr Ile Asp Pro Tyr Asn Gly Ile Thr Ile Tyr Asp Gln Asn Phe
    50                  55                  60

Lys Gly Lys Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Val Thr Thr Ala Leu Asp Phe Trp Gly Gln Gly Thr Thr
            100                 105                 110

Val Thr Val Ser Ser
        115

<210> SEQ ID NO 8
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Met Thr Gln Ser Pro Ala Ser Leu Ser Ala Ser Val Gly
1               5                   10                  15

Asp Arg Val Thr Ile Thr Cys Leu Ala Ser Gln Thr Ile Asp Thr Trp
            20                  25                  30

Leu Ala Trp Tyr Leu Gln Lys Pro Gly Lys Ser Pro Gln Leu Leu Ile
        35                  40                  45

Tyr Ala Ala Thr Asn Leu Ala Asp Gly Val Pro Ser Arg Phe Ser Gly
    50                  55                  60
```

```
Ser Gly Ser Gly Thr Asp Phe Ser Phe Thr Ile Ser Ser Leu Gln Pro
 65                  70                  75                  80

Glu Asp Phe Ala Thr Tyr Tyr Cys Gln Gln Val Tyr Ser Ser Pro Phe
                 85                  90                  95

Thr Phe Gly Gln Gly Thr Lys Leu Glu Ile Lys
            100                 105
```

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

```
Tyr Ile Asp Pro Tyr Asn Gly Ile Thr Ile Tyr Asp Gln Asn Leu Lys
 1               5                  10                  15

Gly
```

<210> SEQ ID NO 10
<211> LENGTH: 219
<212> TYPE: PRT
<213> ORGANISM: Homo sapiens

<400> SEQUENCE: 10

```
Ser Gly Thr Thr Asn Thr Val Ala Ala Tyr Asn Leu Thr Trp Lys Ser
 1               5                  10                  15

Thr Asn Phe Lys Thr Ile Leu Glu Trp Glu Pro Lys Pro Val Asn Gln
                20                  25                  30

Val Tyr Thr Val Gln Ile Ser Thr Lys Ser Gly Asp Trp Lys Ser Lys
             35                  40                  45

Cys Phe Tyr Thr Thr Asp Thr Glu Cys Asp Leu Thr Asp Glu Ile Val
 50                  55                  60

Lys Asp Val Lys Gln Thr Tyr Leu Ala Arg Val Phe Ser Tyr Pro Ala
 65                  70                  75                  80

Gly Asn Val Glu Ser Thr Gly Ser Ala Gly Glu Pro Leu Tyr Glu Asn
                 85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu
    210                 215
```

<210> SEQ ID NO 11
<211> LENGTH: 657
<212> TYPE: DNA

<213> ORGANISM: Homo sapiens

<400> SEQUENCE: 11

```
agcggcacaa ccaacacagt cgctgcctat aacctcactt ggaagagcac caacttcaaa      60
accatcctcg aatgggaacc caaacccgtt aaccaagttt acaccgtgca gatcagcacc     120
aagtccggcg actggaagtc caatgtttc tataccaccg acaccgagtg cgatctcacc     180
gatgagatcg tgaaagatgt gaaacagacc tacctcgccc gggtgtttag ctaccccgcc     240
ggcaatgtgg agagcactgg ttccgctggc gagcctttat acgagaacag ccccgaattt     300
accccttacc tcgagaccaa tttaggacag cccaccatcc aaagctttga gcaagttggc     360
acaaaggtga atgtgacagt ggaggacgag cggactttag tgcggcggaa caacaccttt     420
ctcagcctcc gggatgtgtt cggcaaagat ttaatctaca cactgtatta ctggaagtcc     480
tcttcctccg gcaagaagac agctaaaacc aacacaaacg agttttaat cgacgtggat     540
aaaggcgaaa actactgttt cagcgtgcaa gctgtgatcc cctcccggac cgtgaatagg     600
aaaagcaccg atagccccgt tgagtgcatg ggccaagaaa agggcgagtt ccgggag       657
```

<210> SEQ ID NO 12
<211> LENGTH: 223
<212> TYPE: PRT
<213> ORGANISM: Mus musculus

<400> SEQUENCE: 12

```
Ala Gly Ile Pro Glu Lys Ala Phe Asn Leu Thr Trp Ile Ser Thr Asp
1               5                   10                  15

Phe Lys Thr Ile Leu Glu Trp Gln Pro Lys Pro Thr Asn Tyr Thr Tyr
            20                  25                  30

Thr Val Gln Ile Ser Asp Arg Ser Arg Asn Trp Lys Asn Lys Cys Phe
        35                  40                  45

Ser Thr Thr Asp Thr Glu Cys Asp Leu Thr Asp Glu Ile Val Lys Asp
    50                  55                  60

Val Thr Trp Ala Tyr Glu Ala Lys Val Leu Ser Val Pro Arg Arg Asn
65                  70                  75                  80

Ser Val His Gly Asp Gly Asp Gln Leu Val Ile His Gly Glu Glu Pro
                85                  90                  95

Pro Phe Thr Asn Ala Pro Lys Phe Leu Pro Tyr Arg Asp Thr Asn Leu
            100                 105                 110

Gly Gln Pro Val Ile Gln Gln Phe Glu Gln Asp Gly Arg Lys Leu Asn
        115                 120                 125

Val Val Val Lys Asp Ser Leu Thr Leu Val Arg Lys Asn Gly Thr Phe
    130                 135                 140

Leu Thr Leu Arg Gln Val Phe Gly Lys Asp Leu Gly Tyr Ile Ile Thr
145                 150                 155                 160

Tyr Arg Lys Gly Ser Ser Thr Gly Lys Lys Thr Asn Ile Thr Asn Thr
                165                 170                 175

Asn Glu Phe Ser Ile Asp Val Glu Glu Gly Val Ser Tyr Cys Phe Phe
            180                 185                 190

Val Gln Ala Met Ile Phe Ser Arg Lys Thr Asn Gln Asn Ser Pro Gly
        195                 200                 205

Ser Ser Thr Val Cys Thr Glu Gln Trp Lys Ser Phe Leu Gly Glu
    210                 215                 220
```

<210> SEQ ID NO 13
<211> LENGTH: 224

<212> TYPE: PRT
<213> ORGANISM: Rattus rattus

<400> SEQUENCE: 13

Ala Gly Thr Pro Pro Gly Lys Ala Phe Asn Leu Thr Trp Ile Ser Thr
1               5                   10                  15

Asp Phe Lys Thr Ile Leu Glu Trp Gln Pro Lys Pro Thr Asn Tyr Thr
            20                  25                  30

Tyr Thr Val Gln Ile Ser Asp Arg Ser Arg Asn Trp Lys Tyr Lys Cys
        35                  40                  45

Thr Gly Thr Thr Asp Thr Glu Cys Asp Leu Thr Asp Glu Ile Val Lys
    50                  55                  60

Asp Val Asn Trp Thr Tyr Glu Ala Arg Val Leu Ser Val Pro Trp Arg
65                  70                  75                  80

Asn Ser Thr His Gly Lys Glu Thr Leu Phe Gly Thr His Gly Glu Glu
                85                  90                  95

Pro Pro Phe Thr Asn Ala Arg Lys Phe Leu Pro Tyr Arg Asp Thr Lys
            100                 105                 110

Ile Gly Gln Pro Val Ile Gln Lys Tyr Glu Gln Gly Thr Lys Leu
        115                 120                 125

Lys Val Thr Val Lys Asp Ser Phe Thr Leu Val Arg Lys Asn Gly Thr
    130                 135                 140

Phe Leu Thr Leu Arg Gln Val Phe Gly Asn Asp Leu Gly Tyr Ile Leu
145                 150                 155                 160

Thr Tyr Arg Lys Asp Ser Ser Thr Gly Arg Lys Thr Asn Thr Thr His
                165                 170                 175

Thr Asn Glu Phe Leu Ile Asp Val Glu Lys Gly Val Ser Tyr Cys Phe
            180                 185                 190

Phe Ala Gln Ala Val Ile Phe Ser Arg Lys Thr Asn His Lys Ser Pro
        195                 200                 205

Glu Ser Ile Thr Lys Cys Thr Glu Gln Trp Lys Ser Val Leu Gly Glu
    210                 215                 220

<210> SEQ ID NO 14
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ser Gly Thr Thr Asn Thr Val Ala Ala Tyr Asn Leu Thr Trp Lys Ser
1               5                   10                  15

Thr Asn Phe Ala Thr Ala Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Ala Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

```
Ile Gln Ser Phe Glu Gln Val Gly Thr Lys Val Asn Val Thr Val Glu
            115                 120                 125

Asp Glu Arg Thr Leu Val Ala Arg Asn Asn Thr Ala Leu Ser Leu Arg
    130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
            195                 200                 205

Cys Met Gly Gln Glu Lys Gly Glu Phe Arg Glu
210                 215

<210> SEQ ID NO 15
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Ser Gly Thr Thr Asn Thr Val Ala Ala Tyr Asn Leu Thr Trp Lys Ser
1               5                   10                  15

Thr Asn Phe Ala Thr Ala Leu Glu Trp Glu Pro Lys Pro Val Asn Gln
            20                  25                  30

Val Tyr Thr Val Gln Ile Ser Thr Lys Ser Gly Asp Ala Lys Ser Lys
        35                  40                  45

Cys Phe Tyr Thr Thr Asp Thr Glu Cys Ala Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Ala Glu Asn
            85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
            115                 120                 125

Asp Glu Arg Thr Leu Val Ala Arg Asn Asn Thr Ala Leu Ser Leu Arg
    130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
            195                 200                 205

Cys Met Gly Gln Glu Lys Gly Glu Phe Arg Glu
210                 215

<210> SEQ ID NO 16
<211> LENGTH: 4
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 16

Gly Gly Gly Ser
1

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Gly Gly Gly Ser
1               5

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Gly Ser Gly
1

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Gly Gly Gly Ser Gly Gly Gly Gly Ser Gly Gly Gly Gly Ser
1               5                   10                  15

<210> SEQ ID NO 20
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ggcggtggag gatccggagg aggtggctcc ggcggcggag gatct            45

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Gly Gly Ser Gly Gly Gly Ser
1               5
```

```
<210> SEQ ID NO 22
<211> LENGTH: 2142
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
atgaagtggg tgaccttcat cagcttatta ttttttattca gctccgccta ttcccagatc      60
gtgctgaccc aaagccccgc catcatgagc gctagccccg gtgagaaggt gaccatgaca     120
tgctccgctt ccagctccgt gtcctacatg aactggtatc agcagaaaag cggaaccagc     180
cccaaaaggt ggatctacga caccagcaag ctggcctccg gagtgcccgc tcatttccgg     240
ggctctggat ccggcaccag ctactcttta accatttccg gcatggaagc tgaagacgct     300
gccacctact attgccagca atggagcagc aaccccttca cattcggatc tggcaccaag     360
ctcgaaatca tcgtggagg aggtggcagc ggcggcggtg gatccggcgg aggaggaagc     420
caagttcaac tccagcagag cggcgctgaa ctggcccggc ccggcgcctc cgtcaagatg     480
agctgcaagg cttccggcta cattact cgttacacaa tgcattgggt caagcagagg     540
cccggtcaag gtttagagtg gatcggatat atcaacccctt cccggggcta caccaactat     600
aaccaaaagt tcaaggataa agccactta accactgaca agagctcctc caccgcctac     660
atgcagctgt cctctttaac cagcgaggac tccgctgttt actactgcgc taggtattac     720
gacgaccact actgtttaga ctattgggga caaggtacca ctttaaccgt cagcagctcc     780
ggcaccacca ataccgtggc cgcttataac ctcacatgga gagcaccaa cttcaagaca     840
attctggaat gggaacccaa gcccgtcaat caagtttaca ccgtgcagat ctccaccaaa     900
tccggagact ggaagagcaa gtgcttctac acaacagaca ccgagtgtga tttaaccgac     960
gaaatcgtca aggacgtcaa gcaaacctat ctggctcggg tcttttccta ccccgctggc    1020
aatgtcgagt ccaccggctc cgctggcgag cctctctacg agaattcccc cgaattcacc    1080
ccttatttag agaccaattt aggccagcct accatccaga gcttcgagca gttggcacc    1140
aaggtgaacg tcaccgtcga ggatgaaagg actttagtgc ggcggaataa cacatttta    1200
tccctccggg atgtgttcgg caaagacctc atctacacac tgtactattg gaagtccagc    1260
tcctccggca aaaagaccgc taagaccaac accaacgagt ttttaattga cgtggacaaa    1320
ggcgagaact actgcttcag cgtgcaagcc gtgatcctt ctcgtaccgt caaccggaag    1380
agcacagatt cccccgttga gtgcatgggc caagaaaagg gcgagttccg ggaggtccag    1440
ctgcagcaga gcggacccga actcgtgaaa cccggtgctt ccgtgaaaat gtcttgtaag    1500
gccagcggat acaccttcac ctcctatgtg atccagtggg tcaaacagaa gcccggacaa    1560
ggtctcgagt ggatcggcag catcaaccct acaacgact ataccaaata caacgagaag    1620
tttaagggaa aggctacttt aacctccgac aaaagctcca tcacagccta catggagttc    1680
agctctttaa catccgagga cagcgctctg tactattgcg cccggtgggg cgacggcaat    1740
tactggggac ggggcacaac actgaccgtg agcagcggag cggaggctc cggcggaggc    1800
ggatctggcg gtgcggctc cgacatcgag atgacccagt cccccgctat catgtccgcc    1860
tctttaggcg agcgggtcac aatgacttgt acagcctcct ccagcgtctc ctcctcctac    1920
ttccattggt accaacagaa accggaagc tcccctaaac tgtgcatcta cagcaccagc    1980
aatctcgcca gcggcgtgcc ccctaggttt tccggaagcg gaagcaccag ctactctta    2040
accatctcct ccatggaggc tgaggatgcc gccacctact tttgtcacca gtaccaccgg    2100
```
tcccccacct tcggaggcgg caccaaactg gagacaaaga gg 2142

<210> SEQ ID NO 23
<211> LENGTH: 714
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 23

```
Met Lys Trp Val Thr Phe Ile Ser Leu Leu Phe Leu Phe Ser Ser Ala
1               5                   10                  15

Tyr Ser Gln Ile Val Leu Thr Gln Ser Pro Ala Ile Met Ser Ala Ser
            20                  25                  30

Pro Gly Glu Lys Val Thr Met Thr Cys Ser Ala Ser Ser Val Ser
        35                  40                  45

Tyr Met Asn Trp Tyr Gln Gln Lys Ser Gly Thr Ser Pro Lys Arg Trp
    50                  55                  60

Ile Tyr Asp Thr Ser Lys Leu Ala Ser Gly Val Pro Ala His Phe Arg
65                  70                  75                  80

Gly Ser Gly Ser Gly Thr Ser Tyr Ser Leu Thr Ile Ser Gly Met Glu
                85                  90                  95

Ala Glu Asp Ala Ala Thr Tyr Tyr Cys Gln Gln Trp Ser Ser Asn Pro
            100                 105                 110

Phe Thr Phe Gly Ser Gly Thr Lys Leu Glu Ile Asn Arg Gly Gly Gly
        115                 120                 125

Gly Ser Gly Gly Gly Gly Ser Gly Gly Gly Ser Gln Val Gln Leu
    130                 135                 140

Gln Gln Ser Gly Ala Glu Leu Ala Arg Pro Gly Ala Ser Val Lys Met
145                 150                 155                 160

Ser Cys Lys Ala Ser Gly Tyr Thr Phe Thr Arg Tyr Thr Met His Trp
                165                 170                 175

Val Lys Gln Arg Pro Gly Gln Gly Leu Glu Trp Ile Gly Tyr Ile Asn
            180                 185                 190

Pro Ser Arg Gly Tyr Thr Asn Tyr Asn Gln Lys Phe Lys Asp Lys Ala
        195                 200                 205

Thr Leu Thr Thr Asp Lys Ser Ser Ser Thr Ala Tyr Met Gln Leu Ser
    210                 215                 220

Ser Leu Thr Ser Glu Asp Ser Ala Val Tyr Tyr Cys Ala Arg Tyr Tyr
225                 230                 235                 240

Asp Asp His Tyr Cys Leu Asp Tyr Trp Gly Gln Gly Thr Thr Leu Thr
                245                 250                 255

Val Ser Ser Gly Thr Thr Asn Thr Val Ala Ala Tyr Asn Leu Thr
            260                 265                 270

Trp Lys Ser Thr Asn Phe Lys Thr Ile Leu Glu Trp Glu Pro Lys Pro
        275                 280                 285

Val Asn Gln Val Tyr Thr Val Gln Ile Ser Thr Lys Ser Gly Asp Trp
    290                 295                 300

Lys Ser Lys Cys Phe Tyr Thr Thr Asp Thr Glu Cys Asp Leu Thr Asp
305                 310                 315                 320

Glu Ile Val Lys Asp Val Lys Gln Thr Tyr Leu Ala Arg Val Phe Ser
                325                 330                 335

Tyr Pro Ala Gly Asn Val Glu Ser Thr Gly Ser Ala Gly Glu Pro Leu
            340                 345                 350
```

```
Tyr Glu Asn Ser Pro Glu Phe Thr Pro Tyr Leu Glu Thr Asn Leu Gly
            355                 360                 365

Gln Pro Thr Ile Gln Ser Phe Glu Gln Val Gly Thr Lys Val Asn Val
        370                 375                 380

Thr Val Glu Asp Glu Arg Thr Leu Val Arg Arg Asn Asn Thr Phe Leu
385                 390                 395                 400

Ser Leu Arg Asp Val Phe Gly Lys Asp Leu Ile Tyr Thr Leu Tyr Tyr
                405                 410                 415

Trp Lys Ser Ser Ser Gly Lys Lys Thr Ala Lys Thr Asn Thr Asn
            420                 425                 430

Glu Phe Leu Ile Asp Val Asp Lys Gly Glu Asn Tyr Cys Phe Ser Val
            435                 440                 445

Gln Ala Val Ile Pro Ser Arg Thr Val Asn Arg Lys Ser Thr Asp Ser
        450                 455                 460

Pro Val Glu Cys Met Gly Gln Glu Lys Gly Glu Phe Arg Glu Val Gln
465                 470                 475                 480

Leu Gln Gln Ser Gly Pro Glu Leu Val Lys Pro Gly Ala Ser Val Lys
                485                 490                 495

Met Ser Cys Lys Ala Ser Gly Tyr Thr Phe Thr Ser Tyr Val Ile Gln
            500                 505                 510

Trp Val Lys Gln Lys Pro Gly Gln Gly Leu Glu Trp Ile Gly Ser Ile
        515                 520                 525

Asn Pro Tyr Asn Asp Tyr Thr Lys Tyr Asn Glu Lys Phe Lys Gly Lys
        530                 535                 540

Ala Thr Leu Thr Ser Asp Lys Ser Ser Ile Thr Ala Tyr Met Glu Phe
545                 550                 555                 560

Ser Ser Leu Thr Ser Glu Asp Ser Ala Leu Tyr Tyr Cys Ala Arg Trp
                565                 570                 575

Gly Asp Gly Asn Tyr Trp Gly Arg Gly Thr Thr Leu Thr Val Ser Ser
            580                 585                 590

Gly Gly Gly Gly Ser Gly Gly Gly Gly Ser Gly Gly Gly Gly Ser Asp
        595                 600                 605

Ile Glu Met Thr Gln Ser Pro Ala Ile Met Ser Ala Ser Leu Gly Glu
        610                 615                 620

Arg Val Thr Met Thr Cys Thr Ala Ser Ser Ser Val Ser Ser Ser Tyr
625                 630                 635                 640

Phe His Trp Tyr Gln Gln Lys Pro Gly Ser Ser Pro Lys Leu Cys Ile
                645                 650                 655

Tyr Ser Thr Ser Asn Leu Ala Ser Gly Val Pro Pro Arg Phe Ser Gly
            660                 665                 670

Ser Gly Ser Thr Ser Tyr Ser Leu Thr Ile Ser Ser Met Glu Ala Glu
        675                 680                 685

Asp Ala Ala Thr Tyr Phe Cys His Gln Tyr His Arg Ser Pro Thr Phe
        690                 695                 700

Gly Gly Gly Thr Lys Leu Glu Thr Lys Arg
705                 710
```

<210> SEQ ID NO 24
<211> LENGTH: 2142
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 24

```
atgaaatggg tcaccttcat ctctttactg tttttattta gcagcgccta cagcgtgcag    60
ctgcagcagt ccggacccga actggtcaag cccggtgcct ccgtgaaaat gtcttgtaag   120
gcttctggct acacctttac ctcctacgtc atccaatggg tgaagcagaa gcccggtcaa   180
ggtctcgagt ggatcggcag catcaatccc tacaacgatt acaccaagta taacgaaaag   240
tttaagggca aggccactct gacaagcgac aagagctcca ttaccgccta catggagttt   300
tcctctttaa cttctgagga ctccgcttta tactattgcg ctcgttgggg cgatggcaat   360
tattggggcc ggggaactac tttaacagtg agctccggcg gcggcggaag cggaggtgga   420
ggatctggcg gtggaggcag cgacatcgag atgacacagt cccccgctat catgagcgcc   480
tctttaggag aacgtgtgac catgacttgt acagcttcct ccagcgtgag cagctccctat  540
ttccactggt accagcagaa acccggctcc tcccctaaac tgtgtatcta ctccacaagc   600
aatttagcta gcggcgtgcc tcctcgtttt agcggctccg gcagcacctc ttactcttta   660
accattagct ctatggaggc cgaagatgcc gccacatact tttgccatca gtaccaccgg   720
tcccctacct ttggcggagg cacaaagctg agaccaagc ggagcggcac caccaacaca    780
gtggccgcct acaatctgac ttggaaatcc accaacttca gaccatcct cgagtgggag    840
cccaagcccg ttaatcaagt ttataccgtg cagatttcca ccaagagcgg cgactggaaa   900
tccaagtgct ctataccac agacaccgag tgcgatctca ccgacgagat cgtcaaagac    960
gtgaagcaga catatttagc tagggtgttc tcctaccccg ctggaaacgt ggagagcacc  1020
ggatccgctg gagagccttt atacgagaac tcccccgaat tcacccccta tctggaaacc  1080
aatttaggcc agcccaccat ccagagcttc gaacaagttg gcacaaaggt gaacgtcacc  1140
gtcgaagatg agaggacttt agtgcggagg aacaatacat ttttatcctt acgtgacgtc  1200
ttcggcaagg atttaatcta cacactgtat tactggaagt ctagctcctc cggcaagaag  1260
accgccaaga ccaataccaa cgaattttta attgacgtgg acaagggcga gaactactgc  1320
ttctccgtgc aagctgtgat cccctcccgg acagtgaacc ggaagtccac cgactccccc  1380
gtggagtgca tgggccaaga gaagggagag tttcgtgagc agatcgtgct gacccagtcc  1440
cccgctatta tgagcgctag ccccggtgaa aaggtgacta tgacatgcag cgccagctct  1500
tccgtgagct acatgaactg gtatcagcag aagtccggca ccagccctaa aggtggatc   1560
tacgacacca gcaagctggc cagcggcgtc cccgctcact ttcggggctc cggctccgga  1620
acaagctact ctctgaccat cagcggcatg gaagccgagg atgccgctac ctattactgt  1680
cagcagtgga gctccaaccc cttcaccttt ggatccggca ccaagctcga gattaatcgt  1740
ggaggcggag gtagcggagg aggcggatcc ggcggtggag gtagccaagt tcagctccag  1800
caaagcggcg ccgaactcgc tcggcccggc gcttccgtga agatgtcttg taaggcctcc  1860
ggctatacct tcacccggta cacaatgcac tgggtcaagc aacggcccgg tcaaggttta  1920
gagtggattg gctatatcaa ccctcccggg gctataccaa actacaacca gaagttcaag  1980
gacaaagcca ccctcaccac cgacaagtcc agcagcaccg cttacatgca gctgagctct  2040
ttaacatccg aggattccgc cgtgtactac tgcgctcggt actacgacga tcattactgc  2100
ctcgattact ggggccaagg taccaccctta acagtctcct cc                    2142
```

<210> SEQ ID NO 25
<211> LENGTH: 714
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 25

Met Lys Trp Val Thr Phe Ile Ser Leu Leu Phe Leu Phe Ser Ser Ala
1               5                   10                  15

Tyr Ser Val Gln Leu Gln Gln Ser Gly Pro Glu Leu Val Lys Pro Gly
                20                  25                  30

Ala Ser Val Lys Met Ser Cys Lys Ala Ser Gly Tyr Thr Phe Thr Ser
            35                  40                  45

Tyr Val Ile Gln Trp Val Lys Gln Lys Pro Gly Gln Gly Leu Glu Trp
    50                  55                  60

Ile Gly Ser Ile Asn Pro Tyr Asn Asp Tyr Thr Lys Tyr Asn Glu Lys
65                  70                  75                  80

Phe Lys Gly Lys Ala Thr Leu Thr Ser Asp Lys Ser Ser Ile Thr Ala
                85                  90                  95

Tyr Met Glu Phe Ser Ser Leu Thr Ser Glu Asp Ser Ala Leu Tyr Tyr
            100                 105                 110

Cys Ala Arg Trp Gly Asp Gly Asn Tyr Trp Gly Arg Gly Thr Thr Leu
        115                 120                 125

Thr Val Ser Ser Gly Gly Gly Ser Gly Gly Gly Ser Gly Gly
130                 135                 140

Gly Gly Ser Asp Ile Glu Met Thr Gln Ser Pro Ala Ile Met Ser Ala
145                 150                 155                 160

Ser Leu Gly Glu Arg Val Thr Met Thr Cys Thr Ala Ser Ser Ser Val
                165                 170                 175

Ser Ser Ser Tyr Phe His Trp Tyr Gln Gln Lys Pro Gly Ser Ser Pro
            180                 185                 190

Lys Leu Cys Ile Tyr Ser Thr Ser Asn Leu Ala Ser Gly Val Pro Pro
        195                 200                 205

Arg Phe Ser Gly Ser Gly Ser Thr Ser Tyr Ser Leu Thr Ile Ser Ser
    210                 215                 220

Met Glu Ala Glu Asp Ala Ala Thr Tyr Phe Cys His Gln Tyr His Arg
225                 230                 235                 240

Ser Pro Thr Phe Gly Gly Gly Thr Lys Leu Glu Thr Lys Arg Ser Gly
                245                 250                 255

Thr Thr Asn Thr Val Ala Ala Tyr Asn Leu Thr Trp Lys Ser Thr Asn
            260                 265                 270

Phe Lys Thr Ile Leu Glu Trp Glu Pro Lys Pro Val Asn Gln Val Tyr
        275                 280                 285

Thr Val Gln Ile Ser Thr Lys Ser Gly Asp Trp Lys Ser Lys Cys Phe
    290                 295                 300

Tyr Thr Thr Asp Thr Glu Cys Asp Leu Thr Asp Glu Ile Val Lys Asp
305                 310                 315                 320

Val Lys Gln Thr Tyr Leu Ala Arg Val Phe Ser Tyr Pro Ala Gly Asn
                325                 330                 335

Val Glu Ser Thr Gly Ser Ala Gly Glu Pro Leu Tyr Glu Asn Ser Pro
            340                 345                 350

Glu Phe Thr Pro Tyr Leu Glu Thr Asn Leu Gly Gln Pro Thr Ile Gln
        355                 360                 365

Ser Phe Glu Gln Val Gly Thr Lys Val Asn Val Thr Val Glu Asp Glu
    370                 375                 380

Arg Thr Leu Val Arg Arg Asn Asn Thr Phe Leu Ser Leu Arg Asp Val
```

```
                385                 390                 395                 400
        Phe Gly Lys Asp Leu Ile Tyr Thr Leu Tyr Tyr Trp Lys Ser Ser Ser
                        405                 410                 415

Ser Gly Lys Lys Thr Ala Lys Thr Asn Thr Asn Glu Phe Leu Ile Asp
                        420                 425                 430

Val Asp Lys Gly Glu Asn Tyr Cys Phe Ser Val Gln Ala Val Ile Pro
                        435                 440                 445

Ser Arg Thr Val Asn Arg Lys Ser Thr Asp Ser Pro Val Glu Cys Met
                    450                 455                 460

Gly Gln Glu Lys Gly Glu Phe Arg Glu Gln Ile Val Leu Thr Gln Ser
        465                 470                 475                 480

Pro Ala Ile Met Ser Ala Ser Pro Gly Glu Lys Val Thr Met Thr Cys
                                485                 490                 495

Ser Ala Ser Ser Ser Val Ser Tyr Met Asn Trp Tyr Gln Gln Lys Ser
                        500                 505                 510

Gly Thr Ser Pro Lys Arg Trp Ile Tyr Asp Thr Ser Lys Leu Ala Ser
                        515                 520                 525

Gly Val Pro Ala His Phe Arg Gly Ser Gly Ser Gly Thr Ser Tyr Ser
                    530                 535                 540

Leu Thr Ile Ser Gly Met Glu Ala Glu Asp Ala Ala Thr Tyr Tyr Cys
        545                 550                 555                 560

Gln Gln Trp Ser Ser Asn Pro Phe Thr Phe Gly Ser Gly Thr Lys Leu
                        565                 570                 575

Glu Ile Asn Arg Gly Gly Gly Gly Ser Gly Gly Gly Gly Ser Gly Gly
                        580                 585                 590

Gly Gly Ser Gln Val Gln Leu Gln Gln Ser Gly Ala Glu Leu Ala Arg
                    595                 600                 605

Pro Gly Ala Ser Val Lys Met Ser Cys Lys Ala Ser Gly Tyr Thr Phe
        610                 615                 620

Thr Arg Tyr Thr Met His Trp Val Lys Gln Arg Pro Gly Gln Gly Leu
        625                 630                 635                 640

Glu Trp Ile Gly Tyr Ile Asn Pro Ser Arg Gly Tyr Thr Asn Tyr Asn
                        645                 650                 655

Gln Lys Phe Lys Asp Lys Ala Thr Leu Thr Thr Asp Lys Ser Ser Ser
                        660                 665                 670

Thr Ala Tyr Met Gln Leu Ser Ser Leu Thr Ser Glu Asp Ser Ala Val
                    675                 680                 685

Tyr Tyr Cys Ala Arg Tyr Tyr Asp Asp His Tyr Cys Leu Asp Tyr Trp
        690                 695                 700

Gly Gln Gly Thr Thr Leu Thr Val Ser Ser
        705                 710

<210> SEQ ID NO 26
<211> LENGTH: 1509
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
atgaagtggg tgaccttcat cagcctgctg ttcctgttct ccagcgccta ctccgccccc    60
acctcctcct ccaccaagaa gacccagctg cagctggagc atttactgct ggatttacag   120
atgattttaa acggcatcaa caactacaag aaccccaagc tgactcgtat gctgaccttc   180
```

-continued

```
aagttctaca tgcccaagaa ggccaccgag ctgaagcatt tacagtgttt agaggaggag    240
ctgaagcccc tcgaggaggt gctgaattta gcccagtcca agaatttcca tttaaggccc    300
cgggatttaa tcagcaacat caacgtgatc gttttagagc tgaagggctc cgagaccacc    360
ttcatgtgcg agtacgccga cgagaccgcc accatcgtgg agttttaaa tcgttggatc    420 accttctgcc agtccatcat ctccacttta accagcggca caaccaacac agtcgctgcc    480
tataacctca cttggaagag caccaacttc aaaaccatcc tcgaatggga acccaaaccc    540
gttaaccaag tttacaccgt gcagatcagc accaagtccg gcgactggaa gtccaaatgt    600
ttctatacca ccgacaccga gtgcgatctc accgatgaga tcgtgaaaga tgtgaaacag    660
acctacctcg cccgggtgtt tagctacccc gccggcaatg tggagagcac tggttccgct    720
ggcgagcctt tatacgagaa cagccccgaa tttacccctt acctcgagac caatttagga    780
cagcccacca tccaaagctt tgagcaagtt ggcacaaagg tgaatgtgac agtggaggac    840
gagcggactt tagtgcggcg gaacaacacc tttctcagcc tccgggatgt gttcggcaaa    900
gatttaatct acacactgta ttactggaag tcctcttcct ccggcaagaa gacagctaaa    960
accaacacaa acgagttttt aatcgacgtg gataaaggcg aaaactactg tttcagcgtg   1020
caagctgtga tcccctcccg gaccgtgaat aggaaaagca ccgatagccc cgttgagtgc   1080
atgggccaag aaaagggcga gttccgggag gcacctactt caagttctac aaagaaaaca   1140
cagctacaac tggagcattt actgctggat ttacagatga ttttgaatgg aattaataat   1200
tacaagaatc ccaaactcac caggatgctc acatttaagt tttacatgcc caagaaggcc   1260
acagaactga aacatcttca gtgtctagaa gaagaactca aacctctgga ggaagtgcta   1320
aatttagctc aaagcaaaaa ctttcactta agacccaggg acttaatcag caatatcaac   1380
gtaatagttc tggaactaaa gggatctgaa acaacattca tgtgtgaata tgctgatgag   1440
acagcaacca ttgtagaatt tctgaacaga tggattacct tttgtcaaag catcatctca   1500
acactaact                                                            1509
```

<210> SEQ ID NO 27
<211> LENGTH: 503
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 27

```
Met Lys Trp Val Thr Phe Ile Ser Leu Leu Phe Leu Phe Ser Ser Ala
1               5                   10                  15

Tyr Ser Ala Pro Thr Ser Ser Ser Thr Lys Lys Thr Gln Leu Gln Leu
            20                  25                  30

Glu His Leu Leu Leu Asp Leu Gln Met Ile Leu Asn Gly Ile Asn Asn
        35                  40                  45

Tyr Lys Asn Pro Lys Leu Thr Arg Met Leu Thr Phe Lys Phe Tyr Met
    50                  55                  60

Pro Lys Lys Ala Thr Glu Leu Lys His Leu Gln Cys Leu Glu Glu Glu
65                  70                  75                  80

Leu Lys Pro Leu Glu Glu Val Leu Asn Leu Ala Gln Ser Lys Asn Phe
                85                  90                  95

His Leu Arg Pro Arg Asp Leu Ile Ser Asn Ile Asn Val Ile Val Leu
            100                 105                 110

Glu Leu Lys Gly Ser Glu Thr Thr Phe Met Cys Glu Tyr Ala Asp Glu
```

```
            115                 120                 125
Thr Ala Thr Ile Val Glu Phe Leu Asn Arg Trp Ile Thr Phe Cys Gln
        130                 135                 140

Ser Ile Ile Ser Thr Leu Thr Ser Gly Thr Thr Asn Thr Val Ala Ala
145                 150                 155                 160

Tyr Asn Leu Thr Trp Lys Ser Thr Asn Phe Lys Thr Ile Leu Glu Trp
                165                 170                 175

Glu Pro Lys Pro Val Asn Gln Val Tyr Thr Val Gln Ile Ser Thr Lys
            180                 185                 190

Ser Gly Asp Trp Lys Ser Lys Cys Phe Tyr Thr Thr Asp Thr Glu Cys
        195                 200                 205

Asp Leu Thr Asp Glu Ile Val Lys Asp Val Lys Gln Thr Tyr Leu Ala
    210                 215                 220

Arg Val Phe Ser Tyr Pro Ala Gly Asn Val Glu Ser Thr Gly Ser Ala
225                 230                 235                 240

Gly Glu Pro Leu Tyr Glu Asn Ser Pro Glu Phe Thr Pro Tyr Leu Glu
                245                 250                 255

Thr Asn Leu Gly Gln Pro Thr Ile Gln Ser Phe Glu Gln Val Gly Thr
            260                 265                 270

Lys Val Asn Val Thr Val Glu Asp Glu Arg Thr Leu Val Arg Arg Asn
        275                 280                 285

Asn Thr Phe Leu Ser Leu Arg Asp Val Phe Gly Lys Asp Leu Ile Tyr
    290                 295                 300

Thr Leu Tyr Tyr Trp Lys Ser Ser Ser Gly Lys Lys Thr Ala Lys
305                 310                 315                 320

Thr Asn Thr Asn Glu Phe Leu Ile Asp Val Asp Lys Gly Glu Asn Tyr
                325                 330                 335

Cys Phe Ser Val Gln Ala Val Ile Pro Ser Arg Thr Val Asn Arg Lys
            340                 345                 350

Ser Thr Asp Ser Pro Val Glu Cys Met Gly Gln Glu Lys Gly Glu Phe
        355                 360                 365

Arg Glu Ala Pro Thr Ser Ser Ser Thr Lys Lys Thr Gln Leu Gln Leu
    370                 375                 380

Glu His Leu Leu Leu Asp Leu Gln Met Ile Leu Asn Gly Ile Asn Asn
385                 390                 395                 400

Tyr Lys Asn Pro Lys Leu Thr Arg Met Leu Thr Phe Lys Phe Tyr Met
                405                 410                 415

Pro Lys Lys Ala Thr Glu Leu Lys His Leu Gln Cys Leu Glu Glu Glu
            420                 425                 430

Leu Lys Pro Leu Glu Glu Val Leu Asn Leu Ala Gln Ser Lys Asn Phe
        435                 440                 445

His Leu Arg Pro Arg Asp Leu Ile Ser Asn Ile Asn Val Ile Val Leu
    450                 455                 460

Glu Leu Lys Gly Ser Glu Thr Thr Phe Met Cys Glu Tyr Ala Asp Glu
465                 470                 475                 480

Thr Ala Thr Ile Val Glu Phe Leu Asn Arg Trp Ile Thr Phe Cys Gln
                485                 490                 495

Ser Ile Ile Ser Thr Leu Thr
            500

<210> SEQ ID NO 28
<211> LENGTH: 1395
<212> TYPE: DNA
<213> ORGANISM: Artificial Sequence
```

-continued

```
<220> FEATURE:
<223> OTHER INFORMATION: Description of Artificial Sequence: Synthetic
      polynucleotide

<400> SEQUENCE: 28
atgaagtggg tgaccttcat cagcctgctg ttcctgttct ccagcgccta ctccaactgg      60
gtgaacgtga tcagcgattt aaagaagatc gaggatttaa tccagagcat gcacatcgac     120
gccactctgt acactgagag cgacgtgcac cctagctgca aggtgactgc catgaagtgc     180
tttttactgg agctgcaagt tatctcttta gagagcggcg atgccagcat ccacgacact     240
gtggagaatt taatcatttt agccaacaac tctttaagca gcaacggcaa cgtgacagag     300
agcggctgca aggagtgcga ggagctggag agaagaacaa tcaaggagtt tttacagagc     360
ttcgtgcaca tcgtgcagat gttcatcaac actagcagcg gcacaaccaa cacagtcgct     420
gcctataacc tcacttggaa gagcaccaac ttcaaaacca tcctcgaatg ggaacccaaa     480
cccgttaacc aagtttacac cgtgcagatc agcaccaagt ccggcgactg gaagtccaaa     540
tgtttctata ccaccgacac cgagtgcgat ctcaccgatg agatcgtgaa agatgtgaaa     600
cagacctacc tcgcccgggt gtttagctac cccgccggca atgtggagag cactggttcc     660
gctggcgagc ctttatacga gaacagcccc gaatttaccc cttacctcga gaccaattta     720
ggacagccca ccatccaaag ctttgagcaa gttggcacaa aggtgaatgt gacagtggag     780
gacgagcgga ctttagtgcg gcggaacaac acctttctca gcctccggga tgtgttcggc     840
aaagatttaa tctacacact gtattactgg aagtcctctt cctccggcaa gaagacagct     900
aaaaccaaca caaacgagtt tttaatcgac gtggataaag gcgaaaacta ctgtttcagc     960
gtgcaagctg tgatcccctc ccggaccgtg aataggaaaa gcaccgatag ccccgttgag    1020
tgcatgggcc aagaaaaggg cgagttccgg gagaactggg tgaacgtcat cagcgattta    1080
aagaagatcg aagatttaat tcagtccatg catatcgacg ccactttata cacagaatcc    1140
gacgtgcacc cctcttgtaa ggtgaccgcc atgaaatgtt ttttactgga gctgcaagtt    1200
atctctttag agagcggaga cgctagcatc cacgacaccg tggagaattt aatcattta    1260 gccaataact ctttatccag caacggcaac gtgacagagt ccggctgcaa ggagtgcgaa    1320
gagctggagg agaagaacat caaggagttt ctgcaatcct tgtgcacat tgtccagatg    1380 ttcatcaata cctcc                                                      1395

<210> SEQ ID NO 29
<211> LENGTH: 465
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Lys Trp Val Thr Phe Ile Ser Leu Leu Phe Leu Phe Ser Ser Ala
1               5                   10                  15

Tyr Ser Asn Trp Val Asn Val Ile Ser Asp Leu Lys Lys Ile Glu Asp
            20                  25                  30

Leu Ile Gln Ser Met His Ile Asp Ala Thr Leu Tyr Thr Glu Ser Asp
        35                  40                  45

Val His Pro Ser Cys Lys Val Thr Ala Met Lys Cys Phe Leu Leu Glu
    50                  55                  60

Leu Gln Val Ile Ser Leu Glu Ser Gly Asp Ala Ser Ile His Asp Thr
65                  70                  75                  80
```

```
Val Glu Asn Leu Ile Ile Leu Ala Asn Asn Ser Leu Ser Ser Asn Gly
                85                  90                  95

Asn Val Thr Glu Ser Gly Cys Lys Glu Cys Glu Glu Leu Glu Glu Lys
            100                 105                 110

Asn Ile Lys Glu Phe Leu Gln Ser Phe Val His Ile Val Gln Met Phe
        115                 120                 125

Ile Asn Thr Ser Ser Gly Thr Thr Asn Thr Val Ala Ala Tyr Asn Leu
    130                 135                 140

Thr Trp Lys Ser Thr Asn Phe Lys Thr Ile Leu Glu Trp Glu Pro Lys
145                 150                 155                 160

Pro Val Asn Gln Val Tyr Thr Val Gln Ile Ser Thr Lys Ser Gly Asp
                165                 170                 175

Trp Lys Ser Lys Cys Phe Tyr Thr Thr Asp Thr Glu Cys Asp Leu Thr
            180                 185                 190

Asp Glu Ile Val Lys Asp Val Lys Gln Thr Tyr Leu Ala Arg Val Phe
        195                 200                 205

Ser Tyr Pro Ala Gly Asn Val Glu Ser Thr Gly Ser Ala Gly Glu Pro
    210                 215                 220

Leu Tyr Glu Asn Ser Pro Glu Phe Thr Pro Tyr Leu Glu Thr Asn Leu
225                 230                 235                 240

Gly Gln Pro Thr Ile Gln Ser Phe Glu Gln Val Gly Thr Lys Val Asn
                245                 250                 255

Val Thr Val Glu Asp Glu Arg Thr Leu Val Arg Arg Asn Asn Thr Phe
            260                 265                 270

Leu Ser Leu Arg Asp Val Phe Gly Lys Asp Leu Ile Tyr Thr Leu Tyr
        275                 280                 285

Tyr Trp Lys Ser Ser Ser Ser Gly Lys Lys Thr Ala Lys Thr Asn Thr
    290                 295                 300

Asn Glu Phe Leu Ile Asp Val Asp Lys Gly Glu Asn Tyr Cys Phe Ser
305                 310                 315                 320

Val Gln Ala Val Ile Pro Ser Arg Thr Val Asn Arg Lys Ser Thr Asp
                325                 330                 335

Ser Pro Val Glu Cys Met Gly Gln Glu Lys Gly Glu Phe Arg Glu Asn
            340                 345                 350

Trp Val Asn Val Ile Ser Asp Leu Lys Lys Ile Glu Asp Leu Ile Gln
        355                 360                 365

Ser Met His Ile Asp Ala Thr Leu Tyr Thr Glu Ser Asp Val His Pro
    370                 375                 380

Ser Cys Lys Val Thr Ala Met Lys Cys Phe Leu Leu Glu Leu Gln Val
385                 390                 395                 400

Ile Ser Leu Glu Ser Gly Asp Ala Ser Ile His Asp Thr Val Glu Asn
                405                 410                 415

Leu Ile Ile Leu Ala Asn Asn Ser Leu Ser Ser Asn Gly Asn Val Thr
            420                 425                 430

Glu Ser Gly Cys Lys Glu Cys Glu Glu Leu Glu Glu Lys Asn Ile Lys
        435                 440                 445

Glu Phe Leu Gln Ser Phe Val His Ile Val Gln Met Phe Ile Asn Thr
    450                 455                 460

Ser
465

<210> SEQ ID NO 30
<211> LENGTH: 1803
```

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30

| | | | | | |
|---|---|---|---|---|---|
| atgaaatggg | tgacctttat | ttctttactg | ttcctcttta | gcagcgccta | ctccatttgg | 60 |
| gaactgaaga | aggacgtcta | cgtggtcgaa | ctggactggt | atcccgatgc | tcccggcgaa | 120 |
| atggtggtgc | tcacttgtga | cacccccgaa | gaagacggca | tcacttggac | cctcgatcag | 180 |
| agcagcgagg | tgctgggctc | cggaaagacc | ctcacaatcc | aagttaagga | gttcggagac | 240 |
| gctggccaat | acacatgcca | aagggaggc | gaggtgctca | gccattcctt | attattatta | 300 |
| cacaagaagg | aagacggaat | ctggtccacc | gacattttaa | agatcagaa | ggagcccaag | 360 |
| aataagacct | ttttaaggtg | tgaggccaaa | aactacagcg | gtcgtttcac | ttgttggtgg | 420 |
| ctgaccacca | tttccaccga | tttaaccttc | tccgtgaaaa | gcagccgggg | aagctccgac | 480 |
| cctcaaggtg | tgacatgtgg | agccgctacc | ctcagcgctg | agagggttcg | tggcgataac | 540 |
| aaggaatacg | agtacagcgt | ggagtgccaa | gaagatagcg | cttgtcccgc | tgccgaagaa | 600 |
| tctttaccca | ttgaggtgat | ggtggacgcc | gtgcacaaac | tcaagtacga | gaactacacc | 660 |
| tcctccttct | ttatccggga | catcattaag | cccgatcctc | ctaagaattt | acagctgaag | 720 |
| cctctcaaaa | atagccggca | agttgaggtc | tcttgggaat | atcccgacac | ttggagcaca | 780 |
| ccccacagct | acttctcttt | aacctttgt | gtgcaagttc | aaggtaaaag | caagcgggag | 840 |
| aagaaagacc | gggtgtttac | cgacaaaacc | agcgccaccg | tcatctgtcg | gaagaacgcc | 900 |
| tccatcagcg | tgagggctca | agatcgttat | tactccagca | gctggtccga | gtgggccagc | 960 |
| gtgccttgtt | ccggcggtgg | aggatccgga | ggaggtggct | ccggcggcgg | aggatctcgt | 1020 |
| aacctccccg | tggctacccc | cgatcccgga | atgttccctt | gtttacacca | cagccagaat | 1080 |
| ttactgaggg | ccgtgagcaa | catgctgcag | aaagctaggc | agactttaga | attttacct | 1140 |
| tgcaccagcg | aggagatcga | ccatgaagat | atcaccaagg | acaagacatc | caccgtggag | 1200 |
| gcttgtttac | ctctggagct | gacaaagaac | gagtcttgtc | tcaactctcg | tgaaaccagc | 1260 |
| ttcatcacaa | atggctcttg | tttagcttcc | cggaagacct | cctttatgat | ggctttatgc | 1320 |
| ctcagctcca | tctacgagga | tttaaagatg | taccaagtgg | agttcaagac | catgaacgcc | 1380 |
| aagctgctca | tggaccctaa | acggcagatc | ttttagacc | agaacatgct | ggctgtgatt | 1440 |
| gatgagctga | tgcaagcttt | aaacttcaac | tccgagaccg | tccctcagaa | gtcctccctc | 1500 |
| gaggagcccg | atttttacaa | gacaaagatc | aaactgtgca | ttttactcca | cgcctttagg | 1560 |
| atccggcccg | tgaccattga | ccgggtcatg | agctatttaa | acgccagcat | acatgcccc | 1620 |
| cctcccatga | gcgtggagca | cgccgacatc | tgggtgaaga | gctatagcct | ctacagccgg | 1680 |
| gagaggtata | tctgtaacag | cggcttcaag | aggaaggccg | gcaccagcag | cctcaccgag | 1740 |
| tgcgtgctga | ataaggctac | caacgtggct | cactggacaa | caccctcttt | aaagtgcatc | 1800 |
| cgg | | | | | | 1803 |

<210> SEQ ID NO 31
<211> LENGTH: 601
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

```
Met Lys Trp Val Thr Phe Ile Ser Leu Leu Phe Leu Phe Ser Ser Ala
1               5                   10                  15

Tyr Ser Ile Trp Glu Leu Lys Lys Asp Val Tyr Val Val Glu Leu Asp
            20                  25                  30

Trp Tyr Pro Asp Ala Pro Gly Glu Met Val Val Leu Thr Cys Asp Thr
        35                  40                  45

Pro Glu Glu Asp Gly Ile Thr Trp Thr Leu Asp Gln Ser Ser Glu Val
    50                  55                  60

Leu Gly Ser Gly Lys Thr Leu Thr Ile Gln Val Lys Glu Phe Gly Asp
65                  70                  75                  80

Ala Gly Gln Tyr Thr Cys His Lys Gly Gly Glu Val Leu Ser His Ser
                85                  90                  95

Leu Leu Leu Leu His Lys Lys Glu Asp Gly Ile Trp Ser Thr Asp Ile
            100                 105                 110

Leu Lys Asp Gln Lys Glu Pro Lys Asn Lys Thr Phe Leu Arg Cys Glu
        115                 120                 125

Ala Lys Asn Tyr Ser Gly Arg Phe Thr Cys Trp Trp Leu Thr Thr Ile
    130                 135                 140

Ser Thr Asp Leu Thr Phe Ser Val Lys Ser Ser Arg Gly Ser Ser Asp
145                 150                 155                 160

Pro Gln Gly Val Thr Cys Gly Ala Ala Thr Leu Ser Ala Glu Arg Val
                165                 170                 175

Arg Gly Asp Asn Lys Glu Tyr Glu Tyr Ser Val Glu Cys Gln Glu Asp
            180                 185                 190

Ser Ala Cys Pro Ala Ala Glu Glu Ser Leu Pro Ile Glu Val Met Val
        195                 200                 205

Asp Ala Val His Lys Leu Lys Tyr Glu Asn Tyr Thr Ser Ser Phe Phe
    210                 215                 220

Ile Arg Asp Ile Ile Lys Pro Asp Pro Pro Lys Asn Leu Gln Leu Lys
225                 230                 235                 240

Pro Leu Lys Asn Ser Arg Gln Val Glu Val Ser Trp Glu Tyr Pro Asp
                245                 250                 255

Thr Trp Ser Thr Pro His Ser Tyr Phe Ser Leu Thr Phe Cys Val Gln
            260                 265                 270

Val Gln Gly Lys Ser Lys Arg Glu Lys Lys Asp Arg Val Phe Thr Asp
        275                 280                 285

Lys Thr Ser Ala Thr Val Ile Cys Arg Lys Asn Ala Ser Ile Ser Val
    290                 295                 300

Arg Ala Gln Asp Arg Tyr Tyr Ser Ser Ser Trp Ser Glu Trp Ala Ser
305                 310                 315                 320

Val Pro Cys Ser Gly Gly Gly Ser Gly Gly Gly Ser Gly
                325                 330                 335

Gly Gly Ser Arg Asn Leu Pro Val Ala Thr Pro Asp Pro Gly Met Phe
            340                 345                 350

Pro Cys Leu His His Ser Gln Asn Leu Leu Arg Ala Val Ser Asn Met
        355                 360                 365

Leu Gln Lys Ala Arg Gln Thr Leu Glu Phe Tyr Pro Cys Thr Ser Glu
    370                 375                 380

Glu Ile Asp His Glu Asp Ile Thr Lys Asp Lys Thr Ser Thr Val Glu
385                 390                 395                 400

Ala Cys Leu Pro Leu Glu Leu Thr Lys Asn Glu Ser Cys Leu Asn Ser
                405                 410                 415
```

```
Arg Glu Thr Ser Phe Ile Thr Asn Gly Ser Cys Leu Ala Ser Arg Lys
            420                 425                 430
Thr Ser Phe Met Met Ala Leu Cys Leu Ser Ser Ile Tyr Glu Asp Leu
            435                 440                 445
Lys Met Tyr Gln Val Glu Phe Lys Thr Met Asn Ala Lys Leu Leu Met
            450                 455                 460
Asp Pro Lys Arg Gln Ile Phe Leu Asp Gln Asn Met Leu Ala Val Ile
465                 470                 475                 480
Asp Glu Leu Met Gln Ala Leu Asn Phe Asn Ser Glu Thr Val Pro Gln
                485                 490                 495
Lys Ser Ser Leu Glu Glu Pro Asp Phe Tyr Lys Thr Lys Ile Lys Leu
            500                 505                 510
Cys Ile Leu Leu His Ala Phe Arg Ile Arg Ala Val Thr Ile Asp Arg
            515                 520                 525
Val Met Ser Tyr Leu Asn Ala Ser Ile Thr Cys Pro Pro Pro Met Ser
            530                 535                 540
Val Glu His Ala Asp Ile Trp Val Lys Ser Tyr Ser Leu Tyr Ser Arg
545                 550                 555                 560
Glu Arg Tyr Ile Cys Asn Ser Gly Phe Lys Arg Lys Ala Gly Thr Ser
                565                 570                 575
Ser Leu Thr Glu Cys Val Leu Asn Lys Ala Thr Asn Val Ala His Trp
            580                 585                 590
Thr Thr Pro Ser Leu Lys Cys Ile Arg
            595                 600

<210> SEQ ID NO 32
<211> LENGTH: 1524
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
atgaagtggg tcacatttat ctctttactg ttcctcttct ccagcgccta cagctacttc      60
ggcaaactgg aatccaagct gagcgtgatc cggaatttaa cgaccaagt  tctgtttatc     120
gatcaaggta accggcctct gttcgaggac atgaccgact ccgattgccg ggacaatgcc     180
ccccggacca tcttcattat ctccatgtac aaggacagcc agccccgggg catggctgtg     240
acaattagcg tgaagtgtga aaaatcagc actttatctt gtgagaacaa gatcatctcc     300
tttaaggaaa tgaaccccc cgataacatc aaggacacca gtccgatat catcttcttc     360
cagcggtccg tgcccggtca cgataacaag atgcagttcg aatcctcctc ctacgagggc     420
tactttttag cttgtgaaaa ggagagggat ttattcaagc tgatcctcaa gaaggaggac     480
gagctgggcg atcgttccat catgttcacc gtccaaaacg aggatagcgg cacaaccaac     540
acagtcgctg cctataacct cacttggaag agcaccaact tcaaaaccat cctcgaatgg     600
gaacccaaac ccgttaacca agtttacacc gtgcagatca gcaccaagtc cggcgactgg     660
aagtccaaat gtttctatac caccgacacc gagtgcgatc tcaccgatga gatcgtgaaa     720
gatgtgaaac agacctacct cgcccgggtg tttagctacc ccgccggcaa tgtggagagc     780
actggttccg ctggcgagcc tttatacgag aacagccccg aatttacccc ttacctcgag     840
accaatttag acagcccac catccaaagc tttgagcaag ttggcacaaa ggtgaatgtg     900
acagtggagg acgagcggac tttagtgcgg cggaacaaca cctttctcag cctccgggat     960
```

```
gtgttcggca aagatttaat ctacacactg tattactgga agtcctcttc ctccggcaag    1020
aagacagcta aaaccaacac aaacgagttt ttaatcgacg tggataaagg cgaaaactac    1080
tgtttcagcg tgcaagctgt gatcccctcc cggaccgtga ataggaaaag caccgatagc    1140
cccgttgagt gcatgggcca agaaaagggc gagttccggg agaactgggt gaacgtcatc    1200
agcgatttaa agaagatcga agatttaatt cagtccatgc atatcgacgc cactttatac    1260
acagaatccg acgtgcaccc ctcttgtaag gtgaccgcca tgaaatgttt tttactggag    1320
ctgcaagtta tctctttaga gagcggagac gctagcatcc acgacaccgt ggagaattta    1380 atcatttttag ccataactc tttatccagc aacggcaacg tgacagagtc cggctgcaag    1440
gagtgcgaag agctggagga gaagaacatc aaggagtttc tgcaatcctt tgtgcacatt    1500
gtccagatgt tcatcaatac ctcc                                          1524
```

<210> SEQ ID NO 33
<211> LENGTH: 508
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

```
Met Lys Trp Val Thr Phe Ile Ser Leu Leu Phe Leu Phe Ser Ser Ala
1               5                   10                  15

Tyr Ser Tyr Phe Gly Lys Leu Glu Ser Lys Leu Ser Val Ile Arg Asn
            20                  25                  30

Leu Asn Asp Gln Val Leu Phe Ile Asp Gln Gly Asn Arg Pro Leu Phe
        35                  40                  45

Glu Asp Met Thr Asp Ser Asp Cys Arg Asp Asn Ala Pro Arg Thr Ile
    50                  55                  60

Phe Ile Ile Ser Met Tyr Lys Asp Ser Gln Pro Arg Gly Met Ala Val
65                  70                  75                  80

Thr Ile Ser Val Lys Cys Glu Lys Ile Ser Thr Leu Ser Cys Glu Asn
                85                  90                  95

Lys Ile Ile Ser Phe Lys Glu Met Asn Pro Pro Asp Asn Ile Lys Asp
            100                 105                 110

Thr Lys Ser Asp Ile Ile Phe Phe Gln Arg Ser Val Pro Gly His Asp
        115                 120                 125

Asn Lys Met Gln Phe Glu Ser Ser Ser Tyr Glu Gly Tyr Phe Leu Ala
    130                 135                 140

Cys Glu Lys Glu Arg Asp Leu Phe Lys Leu Ile Leu Lys Lys Glu Asp
145                 150                 155                 160

Glu Leu Gly Asp Arg Ser Ile Met Phe Thr Val Gln Asn Glu Asp Ser
                165                 170                 175

Gly Thr Thr Asn Thr Val Ala Ala Tyr Asn Leu Thr Trp Lys Ser Thr
            180                 185                 190

Asn Phe Lys Thr Ile Leu Glu Trp Glu Pro Lys Pro Val Asn Gln Val
        195                 200                 205

Tyr Thr Val Gln Ile Ser Thr Lys Ser Gly Asp Trp Lys Ser Lys Cys
    210                 215                 220

Phe Tyr Thr Thr Asp Thr Glu Cys Asp Leu Thr Asp Glu Ile Val Lys
225                 230                 235                 240

Asp Val Lys Gln Thr Tyr Leu Ala Arg Val Phe Ser Tyr Pro Ala Gly
                245                 250                 255
```

Asn Val Glu Ser Thr Gly Ser Ala Gly Glu Pro Leu Tyr Glu Asn Ser
            260                 265                 270

Pro Glu Phe Thr Pro Tyr Leu Glu Thr Asn Leu Gly Gln Pro Thr Ile
        275                 280                 285

Gln Ser Phe Glu Gln Val Gly Thr Lys Val Asn Val Thr Val Glu Asp
    290                 295                 300

Glu Arg Thr Leu Val Arg Arg Asn Asn Thr Phe Leu Ser Leu Arg Asp
305                 310                 315                 320

Val Phe Gly Lys Asp Leu Ile Tyr Thr Leu Tyr Tyr Trp Lys Ser Ser
                325                 330                 335

Ser Ser Gly Lys Lys Thr Ala Lys Thr Asn Thr Asn Glu Phe Leu Ile
            340                 345                 350

Asp Val Asp Lys Gly Glu Asn Tyr Cys Phe Ser Val Gln Ala Val Ile
        355                 360                 365

Pro Ser Arg Thr Val Asn Arg Lys Ser Thr Asp Ser Pro Val Glu Cys
    370                 375                 380

Met Gly Gln Glu Lys Gly Glu Phe Arg Glu Asn Trp Val Asn Val Ile
385                 390                 395                 400

Ser Asp Leu Lys Lys Ile Glu Asp Leu Ile Gln Ser Met His Ile Asp
                405                 410                 415

Ala Thr Leu Tyr Thr Glu Ser Asp Val His Pro Ser Cys Lys Val Thr
            420                 425                 430

Ala Met Lys Cys Phe Leu Leu Glu Leu Gln Val Ile Ser Leu Glu Ser
        435                 440                 445

Gly Asp Ala Ser Ile His Asp Thr Val Glu Asn Leu Ile Ile Leu Ala
    450                 455                 460

Asn Asn Ser Leu Ser Ser Asn Gly Asn Val Thr Glu Ser Gly Cys Lys
465                 470                 475                 480

Glu Cys Glu Glu Leu Glu Glu Lys Asn Ile Lys Glu Phe Leu Gln Ser
                485                 490                 495

Phe Val His Ile Val Gln Met Phe Ile Asn Thr Ser
            500                 505

<210> SEQ ID NO 34
<211> LENGTH: 2523
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
atgaaatggg tgacctttat ttctttactg ttcctcttta gcagcgccta ctccatttgg      60
gaactgaaga aggacgtcta cgtggtcgaa ctggactggt atcccgatgc tcccggcgaa     120
atggtggtgc tcacttgtga cacccccgaa gaagacggca tcacttggac cctcgatcag     180
agcagcgagg tgctgggctc cggaaagacc ctcacaatcc aagttaagga gttcggagac     240
gctggccaat acacatgcca caagggaggc gaggtgctca gccattcctt attattatta     300
cacaagaagg aagacggaat ctggtccacc gacattttaa agatcagaa ggagcccaag      360 aataagacct ttttaaggtg tgaggccaaa aactacagcg gtcgtttcac ttgttggtgg     420
ctgaccacca tttccaccga tttaaccttc tccgtgaaaa gcagccgggg aagctccgac     480
cctcaaggtg tgacatgtgg agccgctacc ctcagcgctg agagggttcg tggcgataac     540
aaggaatacg agtacagcgt ggagtgccaa gaagatagcg cttgtcccgc tgccgaagaa    600

```
tctttaccca ttgaggtgat ggtggacgcc gtgcacaaac tcaagtacga aactacacc      660 tcctccttct ttatccggga catcattaag cccgatcctc ctaagaattt acagctgaag      720
cctctcaaaa atagccggca agttgaggtc tcttgggaat atcccgacac ttggagcaca      780
ccccacagct acttctcttt aacctttgt gtgcaagttc aaggtaaaag caagcgggag       840
aagaaagacc gggtgtttac cgacaaaacc agcgccaccg tcatctgtcg aagaacgcc       900 tccatcagcg tgagggctca agatcgttat tactccagca gctggtccga gtgggccagc     960
gtgccttgtt ccggcggtgg aggatccgga ggaggtggct ccggcggcgg aggatctcgt     1020
aacctccccg tggctacccc cgatcccgga atgttccctt gtttacacca cagccagaat     1080
ttactgaggg ccgtgagcaa catgctgcag aaagctaggc agactttaga attttaccct     1140
tgcaccagcg aggagatcga ccatgaagat atcaccaagg acaagacatc caccgtggag     1200
gcttgtttac ctctggagct gacaaagaac gagtcttgtc tcaactctcg tgaaaccagc     1260
ttcatcacaa atggctcttg tttagcttcc cggaagacct cctttatgat ggctttatgc     1320
ctcagctcca tctacgagga tttaaagatg taccaagtgg agttcaagac catgaacgcc     1380
aagctgctca tggaccctaa acggcagatc tttttagacc agaacatgct ggctgtgatt     1440
gatgagctga tgcaagcttt aaacttcaac tccgagaccg tccctcagaa gtcctccctc     1500
gaggagcccg attttacaa gacaaagatc aaactgtgca ttttactcca cgcctttagg      1560
atccgggccg tgaccattga ccgggtcatg agctatttaa acgccagcat acatgcccc      1620 cctcccatga gcgtggagca cgccgacatc tgggtgaaga gctatagcct ctacagccgg     1680
gagaggtata tctgtaacag cggcttcaag aggaaggccg gcaccagcag cctcaccgag     1740
tgcgtgctga ataaggctac caacgtggct cactggacaa caccctcttt aaagtgcatc     1800
cggtccgagc tgacccagga ccctgctgtg tccgtggctc tgggccagac cgtgaggatc     1860
acctgccagg gcgactccct gaggtcctac tacgcctcct ggtaccagca gaagcccggc     1920
caggctcctg tgctggtgat ctacggcaag aacaacaggc cctccggcat ccctgacagg     1980
ttctccggat cctcctccgg caacaccgcc tccctgacca tcacaggcgc tcaggccgag     2040
gacgaggctg actactactg caactccagg gactcctccg caaccatgt ggtgttcggc      2100 ggcggcacca gctgaccgt gggccatggc ggcggcggct ccggaggcgg cggcagcggc      2160
ggaggaggat ccgaggtgca gctggtggag tccgaggag gagtggtgag gcctggaggc     2220
tccctgaggc tgagctgtgc tgcctccggc ttcaccttcg acgactacgg catgtcctgg     2280
gtgaggcagg ctcctggaaa gggcctggag tgggtgtccg gcatcaactg gaacggcgga     2340
tccaccggct acgccgattc cgtgaagggc aggttcacca tcagcaggga caacgccaag     2400
aactccctgt acctgcagat gaactccctg agggccgagg acaccgccgt gtactactgc     2460 gccagggggca ggtccctgct gttcgactac tggggacagg gcaccctggt gaccgtgtcc     2520
agg                                                                    2523
```

<210> SEQ ID NO 35
<211> LENGTH: 841
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 35

Met Lys Trp Val Thr Phe Ile Ser Leu Leu Phe Leu Phe Ser Ser Ala

```
1               5                   10                  15
Tyr Ser Ile Trp Glu Leu Lys Lys Asp Val Tyr Val Glu Leu Asp
            20                  25                  30

Trp Tyr Pro Asp Ala Pro Gly Glu Met Val Val Leu Thr Cys Asp Thr
                35                  40                  45

Pro Glu Glu Asp Gly Ile Thr Trp Thr Leu Asp Gln Ser Ser Glu Val
    50                  55                  60

Leu Gly Ser Gly Lys Thr Leu Thr Ile Gln Val Lys Glu Phe Gly Asp
65                  70                  75                  80

Ala Gly Gln Tyr Thr Cys His Lys Gly Gly Glu Val Leu Ser His Ser
                85                  90                  95

Leu Leu Leu Leu His Lys Lys Glu Asp Gly Ile Trp Ser Thr Asp Ile
                100                 105                 110

Leu Lys Asp Gln Lys Glu Pro Lys Asn Lys Thr Phe Leu Arg Cys Glu
                115                 120                 125

Ala Lys Asn Tyr Ser Gly Arg Phe Thr Cys Trp Trp Leu Thr Thr Ile
130                 135                 140

Ser Thr Asp Leu Thr Phe Ser Val Lys Ser Ser Arg Gly Ser Ser Asp
145                 150                 155                 160

Pro Gln Gly Val Thr Cys Gly Ala Ala Thr Leu Ser Ala Glu Arg Val
                165                 170                 175

Arg Gly Asp Asn Lys Glu Tyr Glu Tyr Ser Val Glu Cys Gln Glu Asp
                180                 185                 190

Ser Ala Cys Pro Ala Ala Glu Glu Ser Leu Pro Ile Glu Val Met Val
                195                 200                 205

Asp Ala Val His Lys Leu Lys Tyr Glu Asn Tyr Thr Ser Ser Phe Phe
210                 215                 220

Ile Arg Asp Ile Ile Lys Pro Asp Pro Lys Asn Leu Gln Leu Lys
225                 230                 235                 240

Pro Leu Lys Asn Ser Arg Gln Val Glu Val Ser Trp Glu Tyr Pro Asp
                245                 250                 255

Thr Trp Ser Thr Pro His Ser Tyr Phe Ser Leu Thr Phe Cys Val Gln
                260                 265                 270

Val Gln Gly Lys Ser Lys Arg Glu Lys Lys Asp Arg Val Phe Thr Asp
                275                 280                 285

Lys Thr Ser Ala Thr Val Ile Cys Arg Lys Asn Ala Ser Ile Ser Val
                290                 295                 300

Arg Ala Gln Asp Arg Tyr Tyr Ser Ser Ser Trp Ser Glu Trp Ala Ser
305                 310                 315                 320

Val Pro Cys Ser Gly Gly Gly Ser Gly Gly Gly Ser Gly Gly
                325                 330                 335

Gly Gly Ser Arg Asn Leu Pro Val Ala Thr Pro Asp Pro Gly Met Phe
                340                 345                 350

Pro Cys Leu His His Ser Gln Asn Leu Leu Arg Ala Val Ser Asn Met
                355                 360                 365

Leu Gln Lys Ala Arg Gln Thr Leu Glu Phe Tyr Pro Cys Thr Ser Glu
                370                 375                 380

Glu Ile Asp His Glu Asp Ile Thr Lys Asp Lys Thr Ser Thr Val Glu
385                 390                 395                 400

Ala Cys Leu Pro Leu Glu Leu Thr Lys Asn Glu Ser Cys Leu Asn Ser
                405                 410                 415

Arg Glu Thr Ser Phe Ile Thr Asn Gly Ser Cys Leu Ala Ser Arg Lys
                420                 425                 430
```

```
Thr Ser Phe Met Met Ala Leu Cys Leu Ser Ser Ile Tyr Glu Asp Leu
        435                 440                 445

Lys Met Tyr Gln Val Glu Phe Lys Thr Met Asn Ala Lys Leu Leu Met
    450                 455                 460

Asp Pro Lys Arg Gln Ile Phe Leu Asp Gln Asn Met Leu Ala Val Ile
465                 470                 475                 480

Asp Glu Leu Met Gln Ala Leu Asn Phe Asn Ser Glu Thr Val Pro Gln
                485                 490                 495

Lys Ser Ser Leu Glu Glu Pro Asp Phe Tyr Lys Thr Lys Ile Lys Leu
            500                 505                 510

Cys Ile Leu Leu His Ala Phe Arg Ile Arg Ala Val Thr Ile Asp Arg
        515                 520                 525

Val Met Ser Tyr Leu Asn Ala Ser Ile Thr Cys Pro Pro Met Ser
    530                 535                 540

Val Glu His Ala Asp Ile Trp Val Lys Ser Tyr Ser Leu Tyr Ser Arg
545                 550                 555                 560

Glu Arg Tyr Ile Cys Asn Ser Gly Phe Lys Arg Lys Ala Gly Thr Ser
                565                 570                 575

Ser Leu Thr Glu Cys Val Leu Asn Lys Ala Thr Asn Val Ala His Trp
            580                 585                 590

Thr Thr Pro Ser Leu Lys Cys Ile Arg Ser Glu Leu Thr Gln Asp Pro
        595                 600                 605

Ala Val Ser Val Ala Leu Gly Gln Thr Val Arg Ile Thr Cys Gln Gly
    610                 615                 620

Asp Ser Leu Arg Ser Tyr Tyr Ala Ser Trp Tyr Gln Gln Lys Pro Gly
625                 630                 635                 640

Gln Ala Pro Val Leu Val Ile Tyr Gly Lys Asn Asn Arg Pro Ser Gly
                645                 650                 655

Ile Pro Asp Arg Phe Ser Gly Ser Ser Ser Gly Asn Thr Ala Ser Leu
            660                 665                 670

Thr Ile Thr Gly Ala Gln Ala Glu Asp Glu Ala Asp Tyr Tyr Cys Asn
        675                 680                 685

Ser Arg Asp Ser Ser Gly Asn His Val Val Phe Gly Gly Gly Thr Lys
    690                 695                 700

Leu Thr Val Gly His Gly Gly Gly Ser Gly Gly Gly Ser Gly
705                 710                 715                 720

Gly Gly Gly Ser Glu Val Gln Leu Val Glu Ser Gly Gly Val Val
                725                 730                 735

Arg Pro Gly Gly Ser Leu Arg Leu Ser Cys Ala Ala Ser Gly Phe Thr
            740                 745                 750

Phe Asp Asp Tyr Gly Met Ser Trp Val Arg Gln Ala Pro Gly Lys Gly
        755                 760                 765

Leu Glu Trp Val Ser Gly Ile Asn Trp Asn Gly Gly Ser Thr Gly Tyr
    770                 775                 780

Ala Asp Ser Val Lys Gly Arg Phe Thr Ile Ser Arg Asp Asn Ala Lys
785                 790                 795                 800

Asn Ser Leu Tyr Leu Gln Met Asn Ser Leu Arg Ala Glu Asp Thr Ala
                805                 810                 815

Val Tyr Tyr Cys Ala Arg Gly Arg Ser Leu Leu Phe Asp Tyr Trp Gly
            820                 825                 830

Gln Gly Thr Leu Val Thr Val Ser Arg
        835                 840
```

<210> SEQ ID NO 36
<211> LENGTH: 720
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
atgaagtggg tcacatttat ctctttactg ttcctcttct ccagcgccta cagctacttc      60
ggcaaactgg aatccaagct gagcgtgatc cggaatttaa acgaccaagt tctgtttatc     120
gatcaaggta accggcctct gttcgaggac atgaccgact ccgattgccg ggacaatgcc     180
ccccggacca tcttcattat ctccatgtac aaggacagcc agccccgggg catggctgtg     240
acaattagcg tgaagtgtga gaaaatcagc actttatctt gtgagaacaa gatcatctcc     300
tttaaggaaa tgaaccccc cgataacatc aaggacacca gtccgatat catcttcttc       360 cagcggtccg tgcccggtca cgataacaag atgcagttcg aatcctcctc ctacgagggc     420
tactttttag cttgtgaaaa ggagagggat ttattcaagc tgatcctcaa gaaggaggac     480
gagctgggcg atcgttccat catgttcacc gtccaaaacg aggatattac atgcccccct     540
cccatgagcg tggagcacgc cgacatctgg gtgaagagct atagcctcta cagccgggag     600
aggtatatct gtaacagcgg cttcaagagg aaggccggca ccagcagcct caccgagtgc     660
gtgctgaata aggctaccaa cgtggctcac tggacaacac cctctttaaa gtgcatccgg     720

<210> SEQ ID NO 37
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Met Lys Trp Val Thr Phe Ile Ser Leu Leu Phe Leu Phe Ser Ser Ala
1               5                   10                  15

Tyr Ser Tyr Phe Gly Lys Leu Glu Ser Lys Leu Ser Val Ile Arg Asn
                20                  25                  30

Leu Asn Asp Gln Val Leu Phe Ile Asp Gln Gly Asn Arg Pro Leu Phe
            35                  40                  45

Glu Asp Met Thr Asp Ser Asp Cys Arg Asp Asn Ala Pro Arg Thr Ile
        50                  55                  60

Phe Ile Ile Ser Met Tyr Lys Asp Ser Gln Pro Arg Gly Met Ala Val
65                  70                  75                  80

Thr Ile Ser Val Lys Cys Glu Lys Ile Ser Thr Leu Ser Cys Glu Asn
                85                  90                  95

Lys Ile Ile Ser Phe Lys Glu Met Asn Pro Pro Asp Asn Ile Lys Asp
            100                 105                 110

Thr Lys Ser Asp Ile Ile Phe Phe Gln Arg Ser Val Pro Gly His Asp
        115                 120                 125

Asn Lys Met Gln Phe Glu Ser Ser Ser Tyr Glu Gly Tyr Phe Leu Ala
    130                 135                 140

Cys Glu Lys Glu Arg Asp Leu Phe Lys Leu Ile Leu Lys Lys Glu Asp
145                 150                 155                 160

Glu Leu Gly Asp Arg Ser Ile Met Phe Thr Val Gln Asn Glu Asp Ile
                165                 170                 175

```
Thr Cys Pro Pro Pro Met Ser Val Glu His Ala Asp Ile Trp Val Lys
            180                 185                 190

Ser Tyr Ser Leu Tyr Ser Arg Glu Arg Tyr Ile Cys Asn Ser Gly Phe
        195                 200                 205

Lys Arg Lys Ala Gly Thr Ser Ser Leu Thr Glu Cys Val Leu Asn Lys
    210                 215                 220

Ala Thr Asn Val Ala His Trp Thr Thr Pro Ser Leu Lys Cys Ile Arg
225                 230                 235                 240

<210> SEQ ID NO 38
<211> LENGTH: 2607
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
atgaaatggg tgacctttat ttctttactg ttcctcttta gcagcgccta ctccatttgg      60
gaactgaaga aggacgtcta cgtggtcgaa ctggactggt atcccgatgc tcccggcgaa     120
atggtggtgc tcacttgtga cacccccgaa gaagacggca tcacttggac cctcgatcag     180
agcagcgagg tgctgggctc cggaaagacc ctcacaatcc aagttaagga gttcggagac     240
gctggccaat acacatgcca caagggaggc gaggtgctca gccattcctt attattatta     300
cacaagaagg aagacggaat ctggtccacc gacatttttaa aagatcagaa ggagcccaag     360
aataagacct ttttaaggtg tgaggccaaa actacagcg tcgtttcac ttgttggtgg      420 ctgaccacca tttccaccga tttaaccttc tccgtgaaaa gcagccgggg aagctccgac     480
cctcaaggtg tgcatgtgg agccgctacc ctcagcgctg agagggttcg tggcgataac     540
aaggaatacg agtacagcgt ggagtgccaa gaagatagcg cttgtccgc tgccgaagaa     600 tctttaccca ttgaggtgat ggtggacgcc gtgcacaaac tcaagtacga gaactacacc     660
tcctccttct ttatccggga catcattaag cccgatcctc ctaagaattt acagctgaag     720
cctctcaaaa atagccggca agttgaggtc tcttgggaat atcccgacac ttggagcaca     780
ccccacagct acttctcttt aacctttttgt gtgcaagttc aaggtaaaag caagcgggag     840
aagaaagacc gggtgtttac cgacaaaaac agcgccaccg tcatctgtcg aagaacgcc      900 tccatcagcg tgagggctca agatcgttat tactccagca gctggtccga gtgggccagc     960
gtgccttgtt ccggcggtgg aggatccgga ggaggtggct ccggcggcgg aggatctcgt    1020
aacctccccg tggctacccc cgatcccgga atgttcccct gtttacacca cagccagaat    1080
ttactgaggg ccgtgagcaa catgctgcag aaagctaggc agactttaga attttaccct    1140
tgcaccagcg aggagatcga ccatgaagat atcaccaagg acaagacatc caccgtggag    1200
gcttgtttac ctctggagct gacaaagaac gagtcttgtc tcaactctcg tgaaaccagc    1260
ttcatcacaa atggctcttg tttagcttcc cggaagacct cctttatgat ggcttttatgc    1320 ctcagctcca tctacgagga tttaaagatg taccaagtgg agttcaagac catgaacgcc    1380
aagctgctca tggaccctaa acggcagatc ttttttagacc agaacatgct ggctgtgatt    1440
gatgagctga tgcaagcttt aaacttcaac tccgagaccg tccctcagaa gtcctccctc    1500
gaggagcccg atttttacaa gacaaagatc aaactgtgca ttttactcca cgcctttagg    1560
atccgggccg tgaccattga ccgggtcatg agctattaa acgccagcag cggcacaacc    1620
aacacagtcg ctgcctataa cctcacttgg aagagcacca acttcaaaac catcctcgaa    1680
```

```
tgggaaccca aacccgttaa ccaagtttac accgtgcaga tcagcaccaa gtccggcgac    1740
tggaagtcca atgtttcta taccaccgac accgagtgcg atctcaccga tgagatcgtg    1800
aaagatgtga acagaccta cctcgcccgg gtgtttagct accccgccgg caatgtggag    1860
agcactggtt ccgctggcga gcctttatac gagaacagcc ccgaatttac cccttacctc    1920
gagaccaatt taggacagcc caccatccaa agctttgagc aagttggcac aaaggtgaat    1980
gtgacagtgg aggacgagcg gactttagtg cggcggaaca cacctttct cagcctccgg    2040 gatgtgttcg gcaaagattt aatctacaca ctgtattact ggaagtcctc ttcctccggc    2100
aagaagacag ctaaaaccaa cacaaacgag ttttttaatcg acgtggataa aggcgaaaac    2160
tactgtttca gcgtgcaagc tgtgatcccc tcccggaccg tgaataggaa aagcaccgat    2220
agccccgttg agtgcatggg ccaagaaaag ggcgagttcc gggagaactg ggtgaacgtc    2280
atcagcgatt taagaagat cgaagattta attcagtcca tgcatatcga cgccactta    2340 tacacagaat ccgacgtgca cccctcttgt aaggtgaccg ccatgaaatg ttttttactg    2400
gagctgcaag ttatctcttt agagagcgga gacgctagca tccacgacac cgtggagaat    2460
ttaatcattt tagccaataa ctctttatcc agcaacggca acgtgacaga gtccggctgc    2520
aaggagtgcg aagagctgga ggagaagaac atcaaggagt tcctgcaatc ctttgtgcac    2580
attgtccaga tgttcatcaa tacctcc                                       2607
```

<210> SEQ ID NO 39
<211> LENGTH: 869
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 39

```
Met Lys Trp Val Thr Phe Ile Ser Leu Leu Phe Leu Phe Ser Ser Ala
1               5                   10                  15

Tyr Ser Ile Trp Glu Leu Lys Lys Asp Val Tyr Val Val Glu Leu Asp
                20                  25                  30

Trp Tyr Pro Asp Ala Pro Gly Glu Met Val Val Leu Thr Cys Asp Thr
            35                  40                  45

Pro Glu Glu Asp Gly Ile Thr Trp Thr Leu Asp Gln Ser Ser Glu Val
        50                  55                  60

Leu Gly Ser Gly Lys Thr Leu Thr Ile Gln Val Lys Glu Phe Gly Asp
65                  70                  75                  80

Ala Gly Gln Tyr Thr Cys His Lys Gly Gly Glu Val Leu Ser His Ser
                85                  90                  95

Leu Leu Leu Leu His Lys Lys Glu Asp Gly Ile Trp Ser Thr Asp Ile
                100                 105                 110

Leu Lys Asp Gln Lys Glu Pro Lys Asn Lys Thr Phe Leu Arg Cys Glu
            115                 120                 125

Ala Lys Asn Tyr Ser Gly Arg Phe Thr Cys Trp Trp Leu Thr Thr Ile
        130                 135                 140

Ser Thr Asp Leu Thr Phe Ser Val Lys Ser Ser Arg Gly Ser Ser Asp
145                 150                 155                 160

Pro Gln Gly Val Thr Cys Gly Ala Ala Thr Leu Ser Ala Glu Arg Val
                165                 170                 175

Arg Gly Asp Asn Lys Glu Tyr Glu Tyr Ser Val Glu Cys Gln Glu Asp
                180                 185                 190
```

```
Ser Ala Cys Pro Ala Ala Glu Glu Ser Leu Pro Ile Glu Val Met Val
        195                 200                 205

Asp Ala Val His Lys Leu Lys Tyr Glu Asn Tyr Thr Ser Ser Phe Phe
210                 215                 220

Ile Arg Asp Ile Ile Lys Pro Asp Pro Lys Asn Leu Gln Leu Lys
225                 230                 235                 240

Pro Leu Lys Asn Ser Arg Gln Val Glu Val Ser Trp Glu Tyr Pro Asp
                245                 250                 255

Thr Trp Ser Thr Pro His Ser Tyr Phe Ser Leu Thr Phe Cys Val Gln
            260                 265                 270

Val Gln Gly Lys Ser Lys Arg Glu Lys Lys Asp Arg Val Phe Thr Asp
        275                 280                 285

Lys Thr Ser Ala Thr Val Ile Cys Arg Lys Asn Ala Ser Ile Ser Val
        290                 295                 300

Arg Ala Gln Asp Arg Tyr Tyr Ser Ser Ser Trp Ser Glu Trp Ala Ser
305                 310                 315                 320

Val Pro Cys Ser Gly Gly Gly Ser Gly Gly Gly Ser Gly
                325                 330                 335

Gly Gly Ser Arg Asn Leu Pro Val Ala Thr Pro Asp Pro Gly Met Phe
            340                 345                 350

Pro Cys Leu His His Ser Gln Asn Leu Leu Arg Ala Val Ser Asn Met
        355                 360                 365

Leu Gln Lys Ala Arg Gln Thr Leu Glu Phe Tyr Pro Cys Thr Ser Glu
        370                 375                 380

Glu Ile Asp His Glu Asp Ile Thr Lys Asp Lys Thr Ser Thr Val Glu
385                 390                 395                 400

Ala Cys Leu Pro Leu Glu Leu Thr Lys Asn Glu Ser Cys Leu Asn Ser
                405                 410                 415

Arg Glu Thr Ser Phe Ile Thr Asn Gly Ser Cys Leu Ala Ser Arg Lys
                420                 425                 430

Thr Ser Phe Met Met Ala Leu Cys Leu Ser Ser Ile Tyr Glu Asp Leu
            435                 440                 445

Lys Met Tyr Gln Val Glu Phe Lys Thr Met Asn Ala Lys Leu Leu Met
450                 455                 460

Asp Pro Lys Arg Gln Ile Phe Leu Asp Gln Asn Met Leu Ala Val Ile
465                 470                 475                 480

Asp Glu Leu Met Gln Ala Leu Asn Phe Asn Ser Glu Thr Val Pro Gln
                485                 490                 495

Lys Ser Ser Leu Glu Glu Pro Asp Phe Tyr Lys Thr Lys Ile Lys Leu
                500                 505                 510

Cys Ile Leu Leu His Ala Phe Arg Ile Arg Ala Val Thr Ile Asp Arg
            515                 520                 525

Val Met Ser Tyr Leu Asn Ala Ser Ser Gly Thr Thr Asn Thr Val Ala
530                 535                 540

Ala Tyr Asn Leu Thr Trp Lys Ser Thr Asn Phe Lys Thr Ile Leu Glu
545                 550                 555                 560

Trp Glu Pro Lys Pro Val Asn Gln Val Tyr Thr Val Gln Ile Ser Thr
                565                 570                 575

Lys Ser Gly Asp Trp Lys Ser Lys Cys Phe Tyr Thr Thr Asp Thr Glu
            580                 585                 590

Cys Asp Leu Thr Asp Glu Ile Val Lys Asp Val Lys Gln Thr Tyr Leu
595                 600                 605

Ala Arg Val Phe Ser Tyr Pro Ala Gly Asn Val Glu Ser Thr Gly Ser
```

Ala Gly Glu Pro Leu Tyr Glu Asn Ser Pro Glu Phe Thr Pro Tyr Leu
625                 630                 635                 640

Glu Thr Asn Leu Gly Gln Pro Thr Ile Gln Ser Phe Glu Gln Val Gly
            645                 650                 655

Thr Lys Val Asn Val Thr Val Glu Asp Glu Arg Thr Leu Val Arg Arg
            660                 665                 670

Asn Asn Thr Phe Leu Ser Leu Arg Asp Val Phe Gly Lys Asp Leu Ile
            675                 680                 685

Tyr Thr Leu Tyr Tyr Trp Lys Ser Ser Ser Gly Lys Lys Thr Ala
    690                 695                 700

Lys Thr Asn Thr Asn Glu Phe Leu Ile Asp Val Asp Lys Gly Glu Asn
705                 710                 715                 720

Tyr Cys Phe Ser Val Gln Ala Val Ile Pro Ser Arg Thr Val Asn Arg
            725                 730                 735

Lys Ser Thr Asp Ser Pro Val Glu Cys Met Gly Gln Glu Lys Gly Glu
            740                 745                 750

Phe Arg Glu Asn Trp Val Asn Val Ile Ser Asp Leu Lys Lys Ile Glu
    755                 760                 765

Asp Leu Ile Gln Ser Met His Ile Asp Ala Thr Leu Tyr Thr Glu Ser
770                 775                 780

Asp Val His Pro Ser Cys Lys Val Thr Ala Met Lys Cys Phe Leu Leu
785                 790                 795                 800

Glu Leu Gln Val Ile Ser Leu Glu Ser Gly Asp Ala Ser Ile His Asp
            805                 810                 815

Thr Val Glu Asn Leu Ile Ile Leu Ala Asn Asn Ser Leu Ser Ser Asn
            820                 825                 830

Gly Asn Val Thr Glu Ser Gly Cys Lys Glu Cys Glu Glu Leu Glu Glu
            835                 840                 845

Lys Asn Ile Lys Glu Phe Leu Gln Ser Phe Val His Ile Val Gln Met
850                 855                 860

Phe Ile Asn Thr Ser
865

<210> SEQ ID NO 40
<211> LENGTH: 1110
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
atgaagtggg tgaccttcat cagcctgctg ttcctgttct ccagcgccta ctccatcccc      60
ccccatgtgc aaaagagcgt gaacaacgat atgatcgtga ccgacaacaa cggcgccgtg     120
aagtttcccc agctctgcaa gttctgcgat gtcaggttca gcacctgcga taatcagaag     180
tcctgcatgt ccaactgcac gatcacctcc atctgcgaga agccccaaga agtgtgcgtg     240
gccgtgtggc ggaaaaatga cgagaacatc accctggaga ccgtgtgtca cgaccccaag     300
ctcccttatc acgacttcat tctggaggac gctgcctccc ccaaatgcat catgaaggag     360
aagaagaagc ccggagagac cttctttatg tgttcctgta gcagcgacga gtgtaacgac     420
aacatcatct tcagcgaaga gtacaacacc agcaaccctg atggaggtgg cggatccgga     480
ggtggaggtt ctggtggagg tgggagtatt cctccccacg tgcagaagag cgtgaataat     540

```
gacatgatcg tgaccgataa caatggcgcc gtgaaatttc cccagctgtg caaattctgc    600
gatgtgaggt tttccacctg cgacaaccag aagtcctgta tgagcaactg cacaatcacc    660
tccatctgtg agaagcctca ggaggtgtgc gtggctgtct ggcggaagaa tgacgagaat    720
atcaccctgg aaaccgtctg ccacgatccc aagctgccct accacgattt catcctggaa    780
gacgccgcca gccctaagtg catcatgaaa gagaaaaaga gcctggcga gacctttttc    840 atgtgctcct gcagcagcga cgaatgcaac gacaatatca tctttagcga ggaatacaat    900
accagcaacc ccgacatcac gtgtcctcct cctatgtccg tggaacacgc agacatctgg    960
gtcaagagct acagcttgta ctccagggag cggtacattt gtaactctgg tttcaagcgt   1020
aaagccggca cgtccagcct gacggagtgc gtgttgaaca aggccacgaa tgtcgcccac   1080
tggacaaccc ccagtctcaa atgtattaga                                    1110
```

<210> SEQ ID NO 41
<211> LENGTH: 370
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 41

```
Met Lys Trp Val Thr Phe Ile Ser Leu Leu Phe Leu Phe Ser Ser Ala
1               5                   10                  15

Tyr Ser Ile Pro Pro His Val Gln Lys Ser Val Asn Asn Asp Met Ile
            20                  25                  30

Val Thr Asp Asn Asn Gly Ala Val Lys Phe Pro Gln Leu Cys Lys Phe
        35                  40                  45

Cys Asp Val Arg Phe Ser Thr Cys Asp Asn Gln Lys Ser Cys Met Ser
    50                  55                  60

Asn Cys Ser Ile Thr Ser Ile Cys Glu Lys Pro Gln Glu Val Cys Val
65                  70                  75                  80

Ala Val Trp Arg Lys Asn Asp Glu Asn Ile Thr Leu Glu Thr Val Cys
                85                  90                  95

His Asp Pro Lys Leu Pro Tyr His Asp Phe Ile Leu Glu Asp Ala Ala
            100                 105                 110

Ser Pro Lys Cys Ile Met Lys Glu Lys Lys Pro Gly Glu Thr Phe
        115                 120                 125

Phe Met Cys Ser Cys Ser Ser Asp Glu Cys Asn Asp Asn Ile Ile Phe
    130                 135                 140

Ser Glu Glu Tyr Asn Thr Ser Asn Pro Asp Gly Gly Gly Ser Gly
145                 150                 155                 160

Gly Gly Gly Ser Gly Gly Gly Ser Ile Pro Pro His Val Gln Lys
                165                 170                 175

Ser Val Asn Asn Asp Met Ile Val Thr Asp Asn Asn Gly Ala Val Lys
            180                 185                 190

Phe Pro Gln Leu Cys Lys Phe Cys Asp Val Arg Phe Ser Thr Cys Asp
        195                 200                 205

Asn Gln Lys Ser Cys Met Ser Asn Cys Ser Ile Thr Ser Ile Cys Glu
    210                 215                 220

Lys Pro Gln Glu Val Cys Val Ala Val Trp Arg Lys Asn Asp Glu Asn
225                 230                 235                 240

Ile Thr Leu Glu Thr Val Cys His Asp Pro Lys Leu Pro Tyr His Asp
                245                 250                 255
```

Phe Ile Leu Glu Asp Ala Ala Ser Pro Lys Cys Ile Met Lys Glu Lys
            260                 265                 270
Lys Lys Pro Gly Glu Thr Phe Phe Met Cys Ser Cys Ser Ser Asp Glu
        275                 280                 285
Cys Asn Asp Asn Ile Ile Phe Ser Glu Glu Tyr Asn Thr Ser Asn Pro
    290                 295                 300
Asp Ile Thr Cys Pro Pro Met Ser Val Glu His Ala Asp Ile Trp
305                 310                 315                 320
Val Lys Ser Tyr Ser Leu Tyr Ser Arg Glu Arg Tyr Ile Cys Asn Ser
                325                 330                 335
Gly Phe Lys Arg Lys Ala Gly Thr Ser Ser Leu Thr Glu Cys Val Leu
            340                 345                 350
Asn Lys Ala Thr Asn Val Ala His Trp Thr Thr Pro Ser Leu Lys Cys
        355                 360                 365
Ile Arg
    370

<210> SEQ ID NO 42
<211> LENGTH: 1452
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42

| | | | | | |
|---|---|---|---|---|---|
| atgaagtggg | tgaccttcat | cagcctgctg | ttcctgttct | ccagcgccta | ctcccagggc | 60 |
| caggacaggc | acatgatccg | gatgaggcag | ctcatcgaca | tcgtcgacca | gctgaagaac | 120 |
| tacgtgaacg | acctggtgcc | cgagtttctg | cctgccccg | aggacgtgga | gaccaactgc | 180 |
| gagtggtccg | ccttctcctg | ctttcagaag | gcccagctga | agtccgccaa | caccggcaac | 240 |
| aacgagcgga | tcatcaacgt | gagcatcaag | aagctgaagc | ggaagcctcc | ctccacaaac | 300 |
| gccggcagga | ggcagaagca | caggctgacc | tgccccagct | gtgactccta | cgagaagaag | 360 |
| cccccaagg | agttcctgga | gaggttcaag | tccctgctgc | agaagatgat | ccatcagcac | 420 |
| ctgtcctcca | ggaccacgg | ctccgaggac | tcctccggca | ccaccaatac | cgtggccgct | 480 |
| tataacctca | catggaagag | caccaacttc | aagacaattc | tggaatggga | acccaagccc | 540 |
| gtcaatcaag | tttacaccgt | gcagatctcc | accaaatccg | gagactggaa | gagcaagtgc | 600 |
| ttctacacaa | cagacaccga | gtgtgattta | accgacgaaa | tcgtcaagga | cgtcaagcaa | 660 |
| acctatctgg | ctcgggtctt | ttcctacccc | gctggcaatg | tcgagtccac | cggctccgct | 720 |
| ggcgagcctc | tctacgagaa | ttcccccgaa | ttcacccctt | atttagagac | caatttaggc | 780 |
| cagcctacca | tccagagctt | cgagcaagtt | ggcaccaagg | tgaacgtcac | cgtcgaggat | 840 |
| gaaaggactt | tagtgcggcg | gaataacaca | tttttatccc | tccgggatgt | gttcggcaaa | 900 |
| gacctcatct | acacactgta | ctattggaag | tccagctcct | ccggcaaaaa | gaccgctaag | 960 |
| accaacacca | acgagttttt | aattgacgtg | gacaaaggcg | agaactactg | cttcagcgtg | 1020 |
| caagccgtga | tcccttctcg | taccgtcaac | cggaagagca | cagattcccc | cgttgagtgc | 1080 |
| atgggccaag | aaaagggcga | gttccgggag | aactgggtga | acgtcatcag | cgatttaaag | 1140 |
| aagatcgaag | atttaattca | gtccatgcat | atcgacgcca | ctttatacac | agaatccgac | 1200 |
| gtgcacccct | cttgtaaggt | gaccgccatg | aaatgttttt | tactggagct | gcaagttatc | 1260 |
| tctttagaga | gcggagacgc | tagcatccac | gacaccgtgg | agaatttaat | cattttagcc | 1320 |

```
aataactctt tatccagcaa cggcaacgtg acagagtccg gctgcaagga gtgcgaagag    1380
ctggaggaga agaacatcaa ggagtttctg caatcctttg tgcacattgt ccagatgttc    1440 atcaataacct cc                                                      1452
```

<210> SEQ ID NO 43
<211> LENGTH: 484
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 43

```
Met Lys Trp Val Thr Phe Ile Ser Leu Leu Phe Leu Phe Ser Ser Ala
1               5                   10                  15

Tyr Ser Gln Gly Gln Asp Arg His Met Ile Arg Met Arg Gln Leu Ile
            20                  25                  30

Asp Ile Val Asp Gln Leu Lys Asn Tyr Val Asn Asp Leu Val Pro Glu
        35                  40                  45

Phe Leu Pro Ala Pro Glu Asp Val Glu Thr Asn Cys Glu Trp Ser Ala
    50                  55                  60

Phe Ser Cys Phe Gln Lys Ala Gln Leu Lys Ser Ala Asn Thr Gly Asn
65                  70                  75                  80

Asn Glu Arg Ile Ile Asn Val Ser Ile Lys Lys Leu Lys Arg Lys Pro
                85                  90                  95

Pro Ser Thr Asn Ala Gly Arg Arg Gln Lys His Arg Leu Thr Cys Pro
            100                 105                 110

Ser Cys Asp Ser Tyr Glu Lys Lys Pro Pro Lys Glu Phe Leu Glu Arg
        115                 120                 125

Phe Lys Ser Leu Leu Gln Lys Met Ile His Gln His Leu Ser Ser Arg
    130                 135                 140

Thr His Gly Ser Glu Asp Ser Ser Gly Thr Thr Asn Thr Val Ala Ala
145                 150                 155                 160

Tyr Asn Leu Thr Trp Lys Ser Thr Asn Phe Lys Thr Ile Leu Glu Trp
                165                 170                 175

Glu Pro Lys Pro Val Asn Gln Val Tyr Thr Val Gln Ile Ser Thr Lys
            180                 185                 190

Ser Gly Asp Trp Lys Ser Lys Cys Phe Tyr Thr Thr Asp Thr Glu Cys
        195                 200                 205

Asp Leu Thr Asp Glu Ile Val Lys Asp Val Lys Gln Thr Tyr Leu Ala
    210                 215                 220

Arg Val Phe Ser Tyr Pro Ala Gly Asn Val Glu Ser Thr Gly Ser Ala
225                 230                 235                 240

Gly Glu Pro Leu Tyr Glu Asn Ser Pro Glu Phe Thr Pro Tyr Leu Glu
                245                 250                 255

Thr Asn Leu Gly Gln Pro Thr Ile Gln Ser Phe Glu Gln Val Gly Thr
            260                 265                 270

Lys Val Asn Val Thr Val Glu Asp Glu Arg Thr Leu Val Arg Arg Asn
        275                 280                 285

Asn Thr Phe Leu Ser Leu Arg Asp Val Phe Gly Lys Asp Leu Ile Tyr
    290                 295                 300

Thr Leu Tyr Tyr Trp Lys Ser Ser Ser Gly Lys Lys Thr Ala Lys
305                 310                 315                 320

Thr Asn Thr Asn Glu Phe Leu Ile Asp Val Asp Lys Gly Glu Asn Tyr
                325                 330                 335
```

```
Cys Phe Ser Val Gln Ala Val Ile Pro Ser Arg Thr Val Asn Arg Lys
                340                 345                 350

Ser Thr Asp Ser Pro Val Glu Cys Met Gly Gln Glu Lys Gly Glu Phe
            355                 360                 365

Arg Glu Asn Trp Val Asn Val Ile Ser Asp Leu Lys Lys Ile Glu Asp
    370                 375                 380

Leu Ile Gln Ser Met His Ile Asp Ala Thr Leu Tyr Thr Glu Ser Asp
385                 390                 395                 400

Val His Pro Ser Cys Lys Val Thr Ala Met Lys Cys Phe Leu Leu Glu
                405                 410                 415

Leu Gln Val Ile Ser Leu Glu Ser Gly Asp Ala Ser Ile His Asp Thr
            420                 425                 430

Val Glu Asn Leu Ile Ile Leu Ala Asn Asn Ser Leu Ser Ser Asn Gly
        435                 440                 445

Asn Val Thr Glu Ser Gly Cys Lys Glu Cys Glu Glu Leu Glu Glu Lys
    450                 455                 460

Asn Ile Lys Glu Phe Leu Gln Ser Phe Val His Ile Val Gln Met Phe
465                 470                 475                 480

Ile Asn Thr Ser
```

<210> SEQ ID NO 44
<211> LENGTH: 1452
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44

```
atgaagtggg tgaccttcat cagcctgctg ttcctgttct ccagcgccta ctcccagggc     60
caggacaggc acatgatccg gatgaggcag ctcatcgaca tcgtcgacca gctgaagaac    120
tacgtgaacg acctggtgcc cgagtttctg cctgcccccg aggacgtgga gaccaactgc    180
gagtggtccg ccttctcctg ctttcagaag gcccagctga agtccgccaa caccggcaac    240
aacgagcgga tcatcaacgt gagcatcaag aagctgaagc ggaagcctcc ctccacaaac    300
gccggcagga ggcagaagca caggctgacc tgccccagct gtgactccta cgagaagaag    360
ccccccaagg agttcctgga gaggttcaag tccctgctgc agaagatgat ccatcagcac    420
ctgtcctcca ggacccacgg ctccgaggac tcctccggca ccaccaatac cgtggccgct    480
tataacctca catggaagag caccaacttc gcgacagctc tggaatggga acccaagccc    540
gtcaatcaag tttacaccgt gcagatctcc accaaatccg agactggaa gagcaagtgc    600 ttctacacaa cagacaccga gtgtgcttta accgacgaaa tcgtcaagga cgtcaagcaa    660
acctatctgg ctcgggtctt ttcctacccc gctggcaatg tcgagtccac cggctccgct    720
ggcgagcctc tctacgagaa ttcccccgaa ttcacccctt atttagagac caatttaggc    780
cagcctacca tccagagctt cgagcaagtt ggcaccaagg tgaacgtcac cgtcgaggat    840
gaaaggactt tagtggcgcg gaataacaca gctttatccc tccgggatgt gttcggcaaa    900
gacctcatct acacactgta ctattggaag tccagctcct ccggcaaaaa gaccgctaag    960
accaacacca acgagttttt aattgacgtg gacaaggcg agaactactg cttcagcgtg   1020
caagccgtga tcccttctcg taccgtcaac cggaagagca cagattcccc cgttgagtgc   1080
atgggccaag aaaagggcga gttccgggag aactgggtga acgtcatcag cgatttaaag   1140
```

```
aagatcgaag atttaattca gtccatgcat atcgacgcca ctttatacac agaatccgac    1200
gtgcacccct cttgtaaggt gaccgccatg aaatgttttt tactggagct gcaagttatc    1260
tctttagaga gcggagacgc tagcatccac gacaccgtgg agaatttaat cattttagcc    1320
aataactctt tatccagcaa cggcaacgtg acagagtccg gctgcaagga gtgcgaagag    1380
ctggaggaga agaacatcaa ggagtttctg caatcctttg tgcacattgt ccagatgttc    1440 atcaataccct cc                                                       1452
```

<210> SEQ ID NO 45
<211> LENGTH: 484
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 45

```
Met Lys Trp Val Thr Phe Ile Ser Leu Leu Phe Leu Phe Ser Ser Ala
1               5                   10                  15

Tyr Ser Gln Gly Gln Asp Arg His Met Ile Arg Met Arg Gln Leu Ile
            20                  25                  30

Asp Ile Val Asp Gln Leu Lys Asn Tyr Val Asn Asp Leu Val Pro Glu
        35                  40                  45

Phe Leu Pro Ala Pro Glu Asp Val Glu Thr Asn Cys Glu Trp Ser Ala
    50                  55                  60

Phe Ser Cys Phe Gln Lys Ala Gln Leu Lys Ser Ala Asn Thr Gly Asn
65                  70                  75                  80

Asn Glu Arg Ile Ile Asn Val Ser Ile Lys Lys Leu Lys Arg Lys Pro
                85                  90                  95

Pro Ser Thr Asn Ala Gly Arg Arg Gln Lys His Arg Leu Thr Cys Pro
            100                 105                 110

Ser Cys Asp Ser Tyr Glu Lys Lys Pro Pro Lys Glu Phe Leu Glu Arg
        115                 120                 125

Phe Lys Ser Leu Leu Gln Lys Met Ile His Gln His Leu Ser Ser Arg
    130                 135                 140

Thr His Gly Ser Glu Asp Ser Ser Gly Thr Thr Asn Thr Val Ala Ala
145                 150                 155                 160

Tyr Asn Leu Thr Trp Lys Ser Thr Asn Phe Ala Thr Ala Leu Glu Trp
                165                 170                 175

Glu Pro Lys Pro Val Asn Gln Val Tyr Thr Val Gln Ile Ser Thr Lys
            180                 185                 190

Ser Gly Asp Trp Lys Ser Lys Cys Phe Tyr Thr Thr Asp Thr Glu Cys
        195                 200                 205

Ala Leu Thr Asp Glu Ile Val Lys Asp Val Lys Gln Thr Tyr Leu Ala
    210                 215                 220

Arg Val Phe Ser Tyr Pro Ala Gly Asn Val Glu Ser Thr Gly Ser Ala
225                 230                 235                 240

Gly Glu Pro Leu Tyr Glu Asn Ser Pro Glu Phe Thr Pro Tyr Leu Glu
                245                 250                 255

Thr Asn Leu Gly Gln Pro Thr Ile Gln Ser Phe Glu Gln Val Gly Thr
            260                 265                 270

Lys Val Asn Val Thr Val Glu Asp Glu Arg Thr Leu Val Ala Arg Asn
        275                 280                 285

Asn Thr Ala Leu Ser Leu Arg Asp Val Phe Gly Lys Asp Leu Ile Tyr
    290                 295                 300
```

```
Thr Leu Tyr Tyr Trp Lys Ser Ser Ser Gly Lys Lys Thr Ala Lys
305                 310                 315                 320

Thr Asn Thr Asn Glu Phe Leu Ile Asp Val Asp Lys Gly Glu Asn Tyr
                325                 330                 335

Cys Phe Ser Val Gln Ala Val Ile Pro Ser Arg Thr Val Asn Arg Lys
            340                 345                 350

Ser Thr Asp Ser Pro Val Glu Cys Met Gly Gln Glu Lys Gly Glu Phe
        355                 360                 365

Arg Glu Asn Trp Val Asn Val Ile Ser Asp Leu Lys Lys Ile Glu Asp
    370                 375                 380

Leu Ile Gln Ser Met His Ile Asp Ala Thr Leu Tyr Thr Glu Ser Asp
385                 390                 395                 400

Val His Pro Ser Cys Lys Val Thr Ala Met Lys Cys Phe Leu Leu Glu
                405                 410                 415

Leu Gln Val Ile Ser Leu Glu Ser Gly Asp Ala Ser Ile His Asp Thr
            420                 425                 430

Val Glu Asn Leu Ile Ile Leu Ala Asn Asn Ser Leu Ser Ser Asn Gly
        435                 440                 445

Asn Val Thr Glu Ser Gly Cys Lys Glu Cys Glu Glu Leu Glu Glu Lys
    450                 455                 460

Asn Ile Lys Glu Phe Leu Gln Ser Phe Val His Ile Val Gln Met Phe
465                 470                 475                 480

Ile Asn Thr Ser
```

<210> SEQ ID NO 46
<211> LENGTH: 648
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 46

```
atgaagtggg tgaccttcat cagcctgctg ttcctgttct ccagcgccta ctcccagggc      60
caggacaggc acatgatccg gatgaggcag ctcatcgaca tcgtcgacca gctgaagaac     120
tacgtgaacg acctggtgcc cgagtttctg cctgcccccg aggacgtgga gaccaactgc     180
gagtggtccg ccttctcctg ctttcagaag gcccagctga gtccgccaa caccggcaac     240
aacgagcgga tcatcaacgt gagcatcaag aagctgaagc ggaagcctcc ctccacaaac     300
gccggcagga ggcagaagca caggctgacc tgccccagct gtgactccta cgagaagaag     360
cccccaagg agttcctgga gaggttcaag tccctgctgc agaagatgat ccatcagcac     420
ctgtcctcca ggaccacgg ctccgaggac tccattacat gccccctcc catgagcgtg     480
gagcacgccg acatctgggt gaagagctat agcctctaca gccgggagag gtatatctgt     540
aacagcggct tcaagaggaa ggccggcacc agcagcctca ccgagtgcgt gctgaataag     600
gctaccaacg tggctcactg gacaacaccc tctttaaagt gcatccgg                 648
```

<210> SEQ ID NO 47
<211> LENGTH: 1914
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 47

```
atgaagtggg tgaccttcat cagcctgctg ttcctgttct ccagcgccta ctccatcccc      60
ccccatgtgc aaaagagcgt gaacaacgat atgatcgtga ccgacaacaa cggcgccgtg     120
aagtttcccc agctctgcaa gttctgcgat gtcaggttca gcacctgcga taatcagaag     180
tcctgcatgt ccaactgcac gatcacctcc atctgcgaga agccccaaga agtgtgcgtg     240
gccgtgtggc ggaaaaatga cgagaacatc accctggaga ccgtgtgtca cgaccccaag     300
ctcccttatc acgacttcat tctggaggac gctgcctccc ccaaatgcat catgaaggag     360
aagaagaagc ccggagagac cttctttatg tgttcctgta gcagcgacga gtgtaacgac     420
aacatcatct tcagcgaaga gtacaacacc agcaaccctg atggaggtgg cggatccgga     480
ggtggaggtt ctggtggagg tgggagtatt cctccccacg tgcagaagag cgtgaataat     540
gacatgatcg tgaccgataa caatggcgcc gtgaaatttc cccagctgtg caaattctgc     600
gatgtgaggt tttccacctg cgacaaccag aagtcctgta tgagcaactg cacaatcacc     660
tccatctgtg agaagcctca ggaggtgtgc gtggctgtct ggcggaagaa tgacgagaat     720
atcaccctgg aaaccgtctg ccacgatccc aagctgccct accacgattt catcctggaa     780
gacgccgcca gccctaagtg catcatgaaa gagaaaaaga gcctggcga gaccttttc     840
atgtgctcct gcagcagcga cgaatgcaac gacaatatca tctttagcga ggaatacaat     900
accagcaacc ccgactccgg caccaccaat accgtggccg cttataacct cacatggaag     960
agcaccaact tcaagacaat tctggaatgg gaacccaagc ccgtcaatca gtttacacc    1020
gtgcagatct ccaccaaatc cggagactgg aagagcaagt gcttctacac aacagacacc    1080
gagtgtgatt taaccgacga aatcgtcaag gacgtcaagc aaacctatct ggctcgggtc    1140
ttttcctacc ccgctggcaa tgtcgagtcc accggctccg ctggcgagcc tctctacgag    1200
aattcccccg aattcacccc ttatttagag accaatttag gccagcctac catccagagc    1260
ttcgagcaag ttggcaccaa ggtgaacgtc accgtcgagg atgaaaggac tttagtgcgg    1320
cggaataaca cattttttatc cctccgggat gtgttcggca aagacctcat ctacacactg    1380
tactattgga gtccagctc ctccggcaaa aagaccgcta agaccaacac caacgagttt    1440
ttaattgacg tggacaaagg cgagaactac tgcttcagcg tgcaagccgt gatcccttct    1500
cgtaccgtca accggaagag cacagattcc cccgttgagt gcatgggcca agaaaagggc    1560
gagttccggg agaactgggt gaacgtcatc agcgatttaa agaagatcga agatttaatt    1620
cagtccatgc atatcgacgc cactttatac acagaatccg acgtgcaccc ctcttgtaag    1680
gtgaccgcca tgaatgtttt tttactggag ctgcaagtta tctctttaga gagcggagac    1740
gctagcatcc acgacaccgt ggagaattta atcatttag ccaataactc tttatccagc    1800
aacggcaacg tgacagagtc cggctgcaag gagtgcgaag agctggagga agaacatc    1860
aaggagtttc tgcaatcctt tgtgcacatt gtccagatgt tcatcaatac ctcc          1914
```

<210> SEQ ID NO 48
<211> LENGTH: 638
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Lys Trp Val Thr Phe Ile Ser Leu Leu Phe Leu Phe Ser Ser Ala
1               5                   10                  15

```
Tyr Ser Ile Pro Pro His Val Gln Lys Ser Val Asn Asn Asp Met Ile
             20                  25                  30

Val Thr Asp Asn Asn Gly Ala Val Lys Phe Pro Gln Leu Cys Lys Phe
         35                  40                  45

Cys Asp Val Arg Phe Ser Thr Cys Asp Asn Gln Lys Ser Cys Met Ser
     50                  55                  60

Asn Cys Ser Ile Thr Ser Ile Cys Glu Lys Pro Gln Glu Val Cys Val
 65                  70                  75                  80

Ala Val Trp Arg Lys Asn Asp Glu Asn Ile Thr Leu Glu Thr Val Cys
                 85                  90                  95

His Asp Pro Lys Leu Pro Tyr His Asp Phe Ile Leu Glu Asp Ala Ala
             100                 105                 110

Ser Pro Lys Cys Ile Met Lys Glu Lys Lys Pro Gly Glu Thr Phe
         115                 120                 125

Phe Met Cys Ser Cys Ser Ser Asp Glu Cys Asn Asp Asn Ile Ile Phe
         130                 135                 140

Ser Glu Glu Tyr Asn Thr Ser Asn Pro Asp Gly Gly Gly Gly Ser Gly
145                 150                 155                 160

Gly Gly Gly Ser Gly Gly Gly Ser Ile Pro Pro His Val Gln Lys
                 165                 170                 175

Ser Val Asn Asn Asp Met Ile Val Thr Asp Asn Asn Gly Ala Val Lys
             180                 185                 190

Phe Pro Gln Leu Cys Lys Phe Cys Asp Val Arg Phe Ser Thr Cys Asp
             195                 200                 205

Asn Gln Lys Ser Cys Met Ser Asn Cys Ser Ile Thr Ser Ile Cys Glu
210                 215                 220

Lys Pro Gln Glu Val Cys Val Ala Val Trp Arg Lys Asn Asp Glu Asn
225                 230                 235                 240

Ile Thr Leu Glu Thr Val Cys His Asp Pro Lys Leu Pro Tyr His Asp
             245                 250                 255

Phe Ile Leu Glu Asp Ala Ala Ser Pro Lys Cys Ile Met Lys Glu Lys
             260                 265                 270

Lys Lys Pro Gly Glu Thr Phe Phe Met Cys Ser Cys Ser Ser Asp Glu
         275                 280                 285

Cys Asn Asp Asn Ile Ile Phe Ser Glu Glu Tyr Asn Thr Ser Asn Pro
290                 295                 300

Asp Ser Gly Thr Thr Asn Thr Val Ala Ala Tyr Asn Leu Thr Trp Lys
305                 310                 315                 320

Ser Thr Asn Phe Lys Thr Ile Leu Glu Trp Glu Pro Lys Pro Val Asn
             325                 330                 335

Gln Val Tyr Thr Val Gln Ile Ser Thr Lys Ser Gly Asp Trp Lys Ser
             340                 345                 350

Lys Cys Phe Tyr Thr Thr Asp Thr Glu Cys Asp Leu Thr Asp Glu Ile
         355                 360                 365

Val Lys Asp Val Lys Gln Thr Tyr Leu Ala Arg Val Phe Ser Tyr Pro
     370                 375                 380

Ala Gly Asn Val Glu Ser Thr Gly Ser Ala Gly Glu Pro Leu Tyr Glu
385                 390                 395                 400

Asn Ser Pro Glu Phe Thr Pro Tyr Leu Glu Thr Asn Leu Gly Gln Pro
                 405                 410                 415

Thr Ile Gln Ser Phe Glu Gln Val Gly Thr Lys Val Asn Val Thr Val
             420                 425                 430

Glu Asp Glu Arg Thr Leu Val Arg Arg Asn Asn Thr Phe Leu Ser Leu
```

```
                  435                 440                 445
Arg Asp Val Phe Gly Lys Asp Leu Ile Tyr Thr Leu Tyr Tyr Trp Lys
450                 455                 460

Ser Ser Ser Ser Gly Lys Lys Thr Ala Lys Thr Asn Thr Asn Glu Phe
465                 470                 475                 480

Leu Ile Asp Val Asp Lys Gly Glu Asn Tyr Cys Phe Ser Val Gln Ala
                    485                 490                 495

Val Ile Pro Ser Arg Thr Val Asn Arg Lys Ser Thr Asp Ser Pro Val
                500                 505                 510

Glu Cys Met Gly Gln Glu Lys Gly Glu Phe Arg Glu Asn Trp Val Asn
            515                 520                 525

Val Ile Ser Asp Leu Lys Lys Ile Glu Asp Leu Ile Gln Ser Met His
        530                 535                 540

Ile Asp Ala Thr Leu Tyr Thr Glu Ser Asp Val His Pro Ser Cys Lys
545                 550                 555                 560

Val Thr Ala Met Lys Cys Phe Leu Leu Glu Leu Gln Val Ile Ser Leu
                565                 570                 575

Glu Ser Gly Asp Ala Ser Ile His Asp Thr Val Glu Asn Leu Ile Ile
                    580                 585                 590

Leu Ala Asn Asn Ser Leu Ser Ser Asn Gly Asn Val Thr Glu Ser Gly
                595                 600                 605

Cys Lys Glu Cys Glu Glu Leu Glu Glu Lys Asn Ile Lys Glu Phe Leu
            610                 615                 620

Gln Ser Phe Val His Ile Val Gln Met Phe Ile Asn Thr Ser
625                 630                 635

<210> SEQ ID NO 49
<211> LENGTH: 702
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
atgggagtga aagttctttt tgcccttatt tgtattgctg tggccgaggc cgattgtgat        60
attgaaggta agatggcaa acaatatgag agtgttctaa tggtcagcat cgatcaatta       120
ttggacagca tgaaagaaat tggtagcaat tgcctgaata atgaatttaa ctttttaaa       180 agacatatct gtgatgctaa taaggaaggt atgttttat ccgtgctgc tcgcaagttg       240 aggcaatttc ttaaaatgaa tagcactggt gattttgatc tccacttatt aaaagtttca       300
gaaggcacaa caatactgtt gaactgcact ggccaggtta aggaagaaa accagctgcc       360 ctgggtgaag cccaaccaac aaagagtttg aagaaaata atctttaaa ggaacagaaa       420 aaactgaatg acttgtgttt cctaaagaga ctattacaag ataaaaac ttgttggaat       480 aaaattttga tgggcactaa agaacacatc acgtgccctc cccccatgtc cgtggaacac       540
gcagacatct gggtcaagag ctacagcttg tactccaggg agcggtacat ttgtaactct       600
ggtttcaagc gtaaagccgg cacgtccagc ctgacggagt gcgtgttgaa caaggccacg       660
aatgtcgccc actggacaac ccccagtctc aaatgcatta ga                         702

<210> SEQ ID NO 50
<211> LENGTH: 503
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 50

| | | | | | | | | | | | | | | | |
|---|---|---|---|---|---|---|---|---|---|---|---|---|---|---|---|
| Met | Lys | Trp | Val | Thr | Phe | Ile | Ser | Leu | Leu | Phe | Leu | Phe | Ser | Ser | Ala |
| 1 | | | | 5 | | | | | 10 | | | | | 15 | |
| Tyr | Ser | Asp | Cys | Asp | Ile | Glu | Gly | Lys | Asp | Gly | Lys | Gln | Tyr | Glu | Ser |
| | | | 20 | | | | | 25 | | | | | 30 | | |
| Val | Leu | Met | Val | Ser | Ile | Asp | Gln | Leu | Leu | Asp | Ser | Met | Lys | Glu | Ile |
| | | | 35 | | | | | 40 | | | | | 45 | | |
| Gly | Ser | Asn | Cys | Leu | Asn | Asn | Glu | Phe | Asn | Phe | Phe | Lys | Arg | His | Ile |
| | 50 | | | | | 55 | | | | | 60 | | | | |
| Cys | Asp | Ala | Asn | Lys | Glu | Gly | Met | Phe | Leu | Phe | Arg | Ala | Ala | Arg | Lys |
| 65 | | | | | 70 | | | | | 75 | | | | | 80 |
| Leu | Arg | Gln | Phe | Leu | Lys | Met | Asn | Ser | Thr | Gly | Asp | Phe | Asp | Leu | His |
| | | | | 85 | | | | | 90 | | | | | 95 | |
| Leu | Leu | Lys | Val | Ser | Glu | Gly | Thr | Thr | Ile | Leu | Leu | Asn | Cys | Thr | Gly |
| | | | 100 | | | | | 105 | | | | | 110 | | |
| Gln | Val | Lys | Gly | Arg | Lys | Pro | Ala | Ala | Leu | Gly | Glu | Ala | Gln | Pro | Thr |
| | | | 115 | | | | | 120 | | | | | 125 | | |
| Lys | Ser | Leu | Glu | Glu | Asn | Lys | Ser | Leu | Lys | Glu | Gln | Lys | Lys | Leu | Asn |
| | 130 | | | | | 135 | | | | | 140 | | | | |
| Asp | Leu | Cys | Phe | Leu | Lys | Arg | Leu | Leu | Gln | Glu | Ile | Lys | Thr | Cys | Trp |
| 145 | | | | | 150 | | | | | 155 | | | | | 160 |
| Asn | Lys | Ile | Leu | Met | Gly | Thr | Lys | Glu | His | Ser | Gly | Thr | Thr | Asn | Thr |
| | | | | 165 | | | | | 170 | | | | | 175 | |
| Val | Ala | Ala | Tyr | Asn | Leu | Thr | Trp | Lys | Ser | Thr | Asn | Phe | Lys | Thr | Ile |
| | | | 180 | | | | | 185 | | | | | 190 | | |
| Leu | Glu | Trp | Glu | Pro | Lys | Pro | Val | Asn | Gln | Val | Tyr | Thr | Val | Gln | Ile |
| | | | 195 | | | | | 200 | | | | | 205 | | |
| Ser | Thr | Lys | Ser | Gly | Asp | Trp | Lys | Ser | Lys | Cys | Phe | Tyr | Thr | Thr | Asp |
| | 210 | | | | | 215 | | | | | 220 | | | | |
| Thr | Glu | Cys | Asp | Leu | Thr | Asp | Glu | Ile | Val | Lys | Asp | Val | Lys | Gln | Thr |
| 225 | | | | | 230 | | | | | 235 | | | | | 240 |
| Tyr | Leu | Ala | Arg | Val | Phe | Ser | Tyr | Pro | Ala | Gly | Asn | Val | Glu | Ser | Thr |
| | | | | 245 | | | | | 250 | | | | | 255 | |
| Gly | Ser | Ala | Gly | Glu | Pro | Leu | Tyr | Glu | Asn | Ser | Pro | Glu | Phe | Thr | Pro |
| | | | 260 | | | | | 265 | | | | | 270 | | |
| Tyr | Leu | Glu | Thr | Asn | Leu | Gly | Gln | Pro | Thr | Ile | Gln | Ser | Phe | Glu | Gln |
| | | | 275 | | | | | 280 | | | | | 285 | | |
| Val | Gly | Thr | Lys | Val | Asn | Val | Thr | Val | Glu | Asp | Glu | Arg | Thr | Leu | Val |
| | 290 | | | | | 295 | | | | | 300 | | | | |
| Arg | Arg | Asn | Asn | Thr | Phe | Leu | Ser | Leu | Arg | Asp | Val | Phe | Gly | Lys | Asp |
| 305 | | | | | 310 | | | | | 315 | | | | | 320 |
| Leu | Ile | Tyr | Thr | Leu | Tyr | Tyr | Trp | Lys | Ser | Ser | Ser | Ser | Gly | Lys | Lys |
| | | | | 325 | | | | | 330 | | | | | 335 | |
| Thr | Ala | Lys | Thr | Asn | Thr | Asn | Glu | Phe | Leu | Ile | Asp | Val | Asp | Lys | Gly |
| | | | 340 | | | | | 345 | | | | | 350 | | |
| Glu | Asn | Tyr | Cys | Phe | Ser | Val | Gln | Ala | Val | Ile | Pro | Ser | Arg | Thr | Val |
| | | | 355 | | | | | 360 | | | | | 365 | | |
| Asn | Arg | Lys | Ser | Thr | Asp | Ser | Pro | Val | Glu | Cys | Met | Gly | Gln | Glu | Lys |
| | 370 | | | | | 375 | | | | | 380 | | | | |
| Gly | Glu | Phe | Arg | Glu | Asn | Trp | Val | Asn | Val | Ile | Ser | Asp | Leu | Lys | Lys |
| 385 | | | | | 390 | | | | | 395 | | | | | 400 |

```
Ile Glu Asp Leu Ile Gln Ser Met His Ile Asp Ala Thr Leu Tyr Thr
            405                 410                 415
Glu Ser Asp Val His Pro Ser Cys Lys Val Thr Ala Met Lys Cys Phe
        420                 425                 430
Leu Leu Glu Leu Gln Val Ile Ser Leu Glu Ser Gly Asp Ala Ser Ile
    435                 440                 445
His Asp Thr Val Glu Asn Leu Ile Ile Leu Ala Asn Asn Ser Leu Ser
450                 455                 460
Ser Asn Gly Asn Val Thr Glu Ser Gly Cys Lys Glu Cys Glu Glu Leu
465                 470                 475                 480
Glu Glu Lys Asn Ile Lys Glu Phe Leu Gln Ser Phe Val His Ile Val
                485                 490                 495
Gln Met Phe Ile Asn Thr Ser
            500
```

<210> SEQ ID NO 51
<211> LENGTH: 1449
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51

| | | |
|---|---|---|
| atgggagtga agttcttttt tgcccttatt tgtattgctg tggccgaggc ccaaggtcaa | 60 |
| gatcgccaca tgattagaat gcgtcaactt atagatattg ttgatcagct gaaaaattat | 120 |
| gtgaatgact tggtccctga atttctgcca gctccagaag atgtagagac aaactgtgag | 180 |
| tggtcagctt tttcctgttt tcagaaggcc aactaaagt cagcaaatac aggaaacaat | 240 |
| gaaaggataa tcaatgtatc aattaaaaag ctgaagagga accaccttc cacaaatgca | 300 |
| gggagaagac agaaacacag actaacatgc ccttcatgtg attcttatga aaaaaacca | 360 |
| cccaaagaat tcctagaaag attcaaatca cttctccaaa agatgattca tcagcatctg | 420 |
| tcctctagaa cacacggaag tgaagattcc tcaggcacta caaatactgt ggcagcatat | 480 |
| aatttaactt ggaaatcaac taatttcaag acaattttgg agtgggaacc caaacccgtc | 540 |
| aatcaagtct acactgttca ataagcact aagtcaggag attggaaaag caaatgcttt | 600 |
| tacacaacag acacagagtg tgacctcacc gacgagattg tgaaggatgt gaagcagacg | 660 |
| tacttggcac gggtcttctc ctacccggca gggaatgtgg agagcaccgg ttctgctggg | 720 |
| gagcctctgt atgagaactc cccagagttc acaccttacc tggagacaaa cctcggacag | 780 |
| ccaacaattc agagttttga acaggtggga acaaaagtga atgtgaccgt agaagatgaa | 840 |
| cggactttag tcagaaggaa caacactttc ctaagcctcc gggatgtttt tggcaaggac | 900 |
| ttaatttata cactttatta ttggaaatct tcaagttcag gaaagaaaac agccaaaaca | 960 |
| aacactaatg agttttgat tgatgtggat aaaggagaaa actactgttt cagtgttcaa | 1020 |
| gcagtgattc cctcccgaac agttaaccgg aagagtacag acagcccggt agagtgtatg | 1080 |
| ggccaggaga aggggaatt cagagaaaac tgggtgaacg tcatcagcga tttaaagaag | 1140 |
| atcgaagatt taattcagtc catgcatatc gacgccactt tatacacaga atccgacgtg | 1200 |
| caccccctctt gtaaggtgac cgccatgaaa tgttttttac tggagctgca agttatctct | 1260 |
| ttagagagcg gagacgctag catccacgac accgtggaga attaatcat tttagccaat | 1320 |
| aactctttat ccagcaacgg caacgtgaca gagtccggct gcaaggagtg cgaagagctg | 1380 |

-continued

```
gaggagaaga acatcaagga gtttctgcaa tcctttgtgc acattgtcca gatgttcatc    1440
aatacctcc                                                             1449
```

<210> SEQ ID NO 52
<211> LENGTH: 483
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

```
Met Gly Val Lys Val Leu Phe Ala Leu Ile Cys Ile Ala Val Ala Glu
1               5                   10                  15

Ala Gln Gly Gln Asp Arg His Met Ile Arg Met Arg Gln Leu Ile Asp
            20                  25                  30

Ile Val Asp Gln Leu Lys Asn Tyr Val Asn Asp Leu Val Pro Glu Phe
        35                  40                  45

Leu Pro Ala Pro Glu Asp Val Glu Thr Asn Cys Glu Trp Ser Ala Phe
    50                  55                  60

Ser Cys Phe Gln Lys Ala Gln Leu Lys Ser Ala Asn Thr Gly Asn Asn
65                  70                  75                  80

Glu Arg Ile Ile Asn Val Ser Ile Lys Lys Leu Lys Arg Lys Pro Pro
                85                  90                  95

Ser Thr Asn Ala Gly Arg Arg Gln Lys His Arg Leu Thr Cys Pro Ser
            100                 105                 110

Cys Asp Ser Tyr Glu Lys Lys Pro Pro Lys Glu Phe Leu Glu Arg Phe
        115                 120                 125

Lys Ser Leu Leu Gln Lys Met Ile His Gln His Leu Ser Ser Arg Thr
    130                 135                 140

His Gly Ser Glu Asp Ser Ser Gly Thr Thr Asn Thr Val Ala Ala Tyr
145                 150                 155                 160

Asn Leu Thr Trp Lys Ser Thr Asn Phe Lys Thr Ile Leu Glu Trp Glu
                165                 170                 175

Pro Lys Pro Val Asn Gln Val Tyr Thr Val Gln Ile Ser Thr Lys Ser
            180                 185                 190

Gly Asp Trp Lys Ser Lys Cys Phe Tyr Thr Thr Asp Thr Glu Cys Asp
        195                 200                 205

Leu Thr Asp Glu Ile Val Lys Asp Val Lys Gln Thr Tyr Leu Ala Arg
    210                 215                 220

Val Phe Ser Tyr Pro Ala Gly Asn Val Glu Ser Thr Gly Ser Ala Gly
225                 230                 235                 240

Glu Pro Leu Tyr Glu Asn Ser Pro Glu Phe Thr Pro Tyr Leu Glu Thr
                245                 250                 255

Asn Leu Gly Gln Pro Thr Ile Gln Ser Phe Glu Gln Val Gly Thr Lys
            260                 265                 270

Val Asn Val Thr Val Glu Asp Glu Arg Thr Leu Val Arg Arg Asn Asn
        275                 280                 285

Thr Phe Leu Ser Leu Arg Asp Val Phe Gly Lys Asp Leu Ile Tyr Thr
    290                 295                 300

Leu Tyr Tyr Trp Lys Ser Ser Ser Gly Lys Lys Thr Ala Lys Thr
305                 310                 315                 320

Asn Thr Asn Glu Phe Leu Ile Asp Val Asp Lys Gly Glu Asn Tyr Cys
                325                 330                 335

Phe Ser Val Gln Ala Val Ile Pro Ser Arg Thr Val Asn Arg Lys Ser
```

```
            340                 345                 350
Thr Asp Ser Pro Val Glu Cys Met Gly Gln Glu Lys Gly Glu Phe Arg
            355                 360                 365

Glu Asn Trp Val Asn Val Ile Ser Asp Leu Lys Lys Ile Glu Asp Leu
        370                 375                 380

Ile Gln Ser Met His Ile Asp Ala Thr Leu Tyr Thr Glu Ser Asp Val
385                 390                 395                 400

His Pro Ser Cys Lys Val Thr Ala Met Lys Cys Phe Leu Leu Glu Leu
                405                 410                 415

Gln Val Ile Ser Leu Glu Ser Gly Asp Ala Ser Ile His Asp Thr Val
            420                 425                 430

Glu Asn Leu Ile Ile Leu Ala Asn Asn Ser Leu Ser Ser Asn Gly Asn
        435                 440                 445

Val Thr Glu Ser Gly Cys Lys Glu Cys Glu Glu Leu Glu Glu Lys Asn
    450                 455                 460

Ile Lys Glu Phe Leu Gln Ser Phe Val His Ile Val Gln Met Phe Ile
465                 470                 475                 480

Asn Thr Ser

<210> SEQ ID NO 53
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
atgaagtggg tgaccttcat cagcctgctg ttcctgttct ccagcgccta ctcccagggc      60
caggacaggc acatgatccg gatgaggcag ctcatcgaca tcgtcgacca gctgaagaac     120
tacgtgaacg acctggtgcc cgagtttctg cctgccccg aggacgtgga gaccaactgc     180
gagtggtccg ccttctcctg ctttcagaag gcccagctga gtccgccaa caccggcaac     240 aacgagcgga tcatcaacgt gagcatcaag aagctgaagc ggaagcctcc ctccacaaac     300
gccggcagga ggcagaagca caggctgacc tgccccagct gtgactccta cgagaagaag     360 cccccccaagg agttcctgga gaggttcaag tccctgctgc agaagatgat ccatcagcac     420
ctgtcctcca ggaccacgg ctccgaggac tccattacat gccccctcc catgagcgtg      480 gagcacgccg acatctgggt gaagagctat agcctctaca gccgggagag gtatatctgt     540
aacagcggct tcaagaggaa ggccggcacc agcagcctca ccgagtgcgt gctgaataag     600
gctaccaacg tggctcactg gacaacaccc tctttaaagt gcatccgg                  648

<210> SEQ ID NO 54
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Met Lys Trp Val Thr Phe Ile Ser Leu Leu Phe Leu Phe Ser Ser Ala
1               5                   10                  15

Tyr Ser Gln Gly Gln Asp Arg His Met Ile Arg Met Arg Gln Leu Ile
            20                  25                  30

Asp Ile Val Asp Gln Leu Lys Asn Tyr Val Asn Asp Leu Val Pro Glu
```

```
                35                  40                  45
Phe Leu Pro Ala Pro Glu Asp Val Glu Thr Asn Cys Glu Trp Ser Ala
 50                  55                  60
Phe Ser Cys Phe Gln Lys Ala Gln Leu Lys Ser Ala Asn Thr Gly Asn
 65                  70                  75                  80
Asn Glu Arg Ile Ile Asn Val Ser Ile Lys Lys Leu Lys Arg Lys Pro
                 85                  90                  95
Pro Ser Thr Asn Ala Gly Arg Arg Gln Lys His Arg Leu Thr Cys Pro
                100                 105                 110
Ser Cys Asp Ser Tyr Glu Lys Lys Pro Pro Lys Glu Phe Leu Glu Arg
                115                 120                 125
Phe Lys Ser Leu Leu Gln Lys Met Ile His Gln His Leu Ser Ser Arg
130                 135                 140
Thr His Gly Ser Glu Asp Ser Ile Thr Cys Pro Pro Pro Met Ser Val
145                 150                 155                 160
Glu His Ala Asp Ile Trp Val Lys Ser Tyr Ser Leu Tyr Ser Arg Glu
                165                 170                 175
Arg Tyr Ile Cys Asn Ser Gly Phe Lys Arg Lys Ala Gly Thr Ser Ser
                180                 185                 190
Leu Thr Glu Cys Val Leu Asn Lys Ala Thr Asn Val Ala His Trp Thr
                195                 200                 205
Thr Pro Ser Leu Lys Cys Ile Arg
210                 215

<210> SEQ ID NO 55
<211> LENGTH: 1509
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
atgaagtggg tgaccttcat cagcctgctg ttcctgttct ccagcgccta ctccgattgc     60
gacatcgagg gcaaggacgg caagcagtac gagagcgtgc tgatggtgtc catcgaccag    120
ctgctggaca gcatgaagga gatcggctcc aactgcctca caacgagtt caacttcttc     180 aagcggcaca tctgcgacgc caacaaggag ggcatgttcc tgttcagggc cgccaggaaa    240
ctgcggcagt tcctgaagat gaactccacc ggcgacttcg acctgcacct gctgaaggtg    300
tccgagggca ccaccatcct gctgaactgc accggacagg tgaagggccg gaaacctgct    360
gctctgggag aggcccaacc caccaagagc ctggaggaga caagtccct gaaggagcag    420 aagaagctga cgacctgtg cttcctgaag aggctgctgc aggagatcaa gacctgctgg    480
aacaagatcc tgatgggcac caaggagcat agcggcacaa ccaacacagt cgctgcctat    540
aacctcactt ggaagagcac caacttcaaa accatcctcg aatgggaacc caaaccctgtt    600 aaccaagttt acaccgtgca gatcagcacc aagtccggcg actggaagtc caaatgtttc    660
tataccaccg acaccgagtg cgatctcacc gatgagatcg tgaaagatgt gaaacagacc    720
tacctcgccc gggtgtttag ctaccccgcc ggcaatgtgg agagcactgg ttccgctggc    780
gagcctttat acgagaacag ccccgaattt accccttacc tcgagaccaa tttaggacag    840
cccaccatcc aaagctttga gcaagttggc acaaaggtga atgtgacagt ggaggacgag    900
cggactttag tgcggcggaa caacaccttt ctcagcctcc gggatgtgtt cggcaaagat    960
ttaatctaca cactgtatta ctggaagtcc tcttcctccg gcaagaagac agctaaaacc    1020
```

-continued

```
aacacaaacg agtttttaat cgacgtggat aaaggcgaaa actactgttt cagcgtgcaa    1080
gctgtgatcc cctcccggac cgtgaatagg aaaagcaccg atagcccgt tgagtgcatg    1140 ggccaagaaa agggcgagtt ccgggagaac tgggtgaacg tcatcagcga tttaaagaag    1200
atcgaagatt taattcagtc catgcatatc gacgccactt tatacacaga atccgacgtg    1260 caccccctctt gtaaggtgac cgccatgaaa tgttttttac tggagctgca agttatctct    1320
ttagagagcg gagacgctag catccacgac accgtggaga attaatcat tttagccaat    1380 aactctttat ccagcaacgg caacgtgaca gagtccggct gcaaggagtg cgaagagctg    1440
gaggagaaga acatcaagga gtttctgcaa tcctttgtgc acattgtcca gatgttcatc    1500
aatacctcc                                                            1509
```

<210> SEQ ID NO 56
<211> LENGTH: 503
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Met Lys Trp Val Thr Phe Ile Ser Leu Leu Phe Leu Phe Ser Ala
1               5                   10                  15

Tyr Ser Asp Cys Asp Ile Glu Gly Lys Asp Gly Lys Gln Tyr Glu Ser
            20                  25                  30

Val Leu Met Val Ser Ile Asp Gln Leu Leu Asp Ser Met Lys Glu Ile
        35                  40                  45

Gly Ser Asn Cys Leu Asn Asn Glu Phe Asn Phe Phe Lys Arg His Ile
    50                  55                  60

Cys Asp Ala Asn Lys Glu Gly Met Phe Leu Phe Arg Ala Ala Arg Lys
65                  70                  75                  80

Leu Arg Gln Phe Leu Lys Met Asn Ser Thr Gly Asp Phe Asp Leu His
                85                  90                  95

Leu Leu Lys Val Ser Glu Gly Thr Thr Ile Leu Leu Asn Cys Thr Gly
            100                 105                 110

Gln Val Lys Gly Arg Lys Pro Ala Ala Leu Gly Glu Ala Gln Pro Thr
        115                 120                 125

Lys Ser Leu Glu Glu Asn Lys Ser Leu Lys Glu Gln Lys Lys Leu Asn
    130                 135                 140

Asp Leu Cys Phe Leu Lys Arg Leu Leu Gln Glu Ile Lys Thr Cys Trp
145                 150                 155                 160

Asn Lys Ile Leu Met Gly Thr Lys Glu His Ser Gly Thr Thr Asn Thr
                165                 170                 175

Val Ala Ala Tyr Asn Leu Thr Trp Lys Ser Thr Asn Phe Lys Thr Ile
            180                 185                 190

Leu Glu Trp Glu Pro Lys Pro Val Asn Gln Val Tyr Thr Val Gln Ile
        195                 200                 205

Ser Thr Lys Ser Gly Asp Trp Lys Ser Lys Cys Phe Tyr Thr Thr Asp
    210                 215                 220

Thr Glu Cys Asp Leu Thr Asp Glu Ile Val Lys Asp Val Lys Gln Thr
225                 230                 235                 240

Tyr Leu Ala Arg Val Phe Ser Tyr Pro Ala Gly Asn Val Glu Ser Thr
                245                 250                 255

Gly Ser Ala Gly Glu Pro Leu Tyr Glu Asn Ser Pro Glu Phe Thr Pro

```
            260                 265                 270
Tyr Leu Glu Thr Asn Leu Gly Gln Pro Thr Ile Gln Ser Phe Glu Gln
            275                 280                 285

Val Gly Thr Lys Val Asn Val Thr Val Glu Asp Glu Arg Thr Leu Val
            290                 295                 300

Arg Arg Asn Asn Thr Phe Leu Ser Leu Arg Asp Val Phe Gly Lys Asp
305                 310                 315                 320

Leu Ile Tyr Thr Leu Tyr Tyr Trp Lys Ser Ser Ser Gly Lys Lys
                325                 330                 335

Thr Ala Lys Thr Asn Thr Asn Glu Phe Leu Ile Asp Val Asp Lys Gly
            340                 345                 350

Glu Asn Tyr Cys Phe Ser Val Gln Ala Val Ile Pro Ser Arg Thr Val
            355                 360                 365

Asn Arg Lys Ser Thr Asp Ser Pro Val Glu Cys Met Gly Gln Glu Lys
            370                 375                 380

Gly Glu Phe Arg Glu Asn Trp Val Asn Val Ile Ser Asp Leu Lys Lys
385                 390                 395                 400

Ile Glu Asp Leu Ile Gln Ser Met His Ile Asp Ala Thr Leu Tyr Thr
                405                 410                 415

Glu Ser Asp Val His Pro Ser Cys Lys Val Thr Ala Met Lys Cys Phe
            420                 425                 430

Leu Leu Glu Leu Gln Val Ile Ser Leu Glu Ser Gly Asp Ala Ser Ile
            435                 440                 445

His Asp Thr Val Glu Asn Leu Ile Ile Leu Ala Asn Asn Ser Leu Ser
450                 455                 460

Ser Asn Gly Asn Val Thr Glu Ser Gly Cys Lys Glu Cys Glu Glu Leu
465                 470                 475                 480

Glu Glu Lys Asn Ile Lys Glu Phe Leu Gln Ser Phe Val His Ile Val
                485                 490                 495

Gln Met Phe Ile Asn Thr Ser
                500

<210> SEQ ID NO 57
<211> LENGTH: 1509
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
atgaagtggg tgaccttcat cagcctgctg ttcctgttct ccagcgccta ctccgattgc      60
gacatcgagg caaggacgg caagcagtac gagagcgtgc tgatggtgtc catcgaccag     120
ctgctggaca gcatgaagga gatcggctcc aactgcctca caacgagtt caacttcttc     180 aagcggcaca tctgcgacgc caacaaggag ggcatgttcc tgttcagggc cgccaggaaa     240
ctgcggcagt tcctgaagat gaactccacc ggcgacttcg acctgcacct gctgaaggtg     300
tccgagggca ccaccatcct gctgaactgc accggacagg tgaagggccg aaacctgct      360 gctctgggag aggcccaacc caccaagagc ctggaggaga caagtccct gaaggagcag     420 aagaagctga cgacctgtg cttcctgaag aggctgctgc aggagatcaa gacctgctgg     480
aacaagatcc tgatgggcac caaggagcat agcggcacaa ccaacacagt cgctgcctat     540
aacctcactt ggaagagcac caacttcaaa accatcctcg aatgggaacc caaacccgtt     600
aaccaagttt acaccgtgca gatcagcacc aagtccggcg actggaagtc caaatgtttc     660
```

```
tataccaccg acaccgagtg cgatctcacc gatgagatcg tgaaagatgt gaaacagacc    720
tacctcgccc gggtgtttag ctaccccgcc ggcaatgtgg agagcactgg ttccgctggc    780
gagcctttat acgagaacag ccccgaattt accccttacc tcgagaccaa tttaggacag    840
cccaccatcc aaagctttga gcaagttggc acaaaggtga atgtgacagt ggaggacgag    900
cggactttag tgcggcggaa caacaccttt ctcagcctcc gggatgtgtt cggcaaagat    960
ttaatctaca cactgtatta ctggaagtcc tcttcctccg gcaagaagac agctaaaacc   1020
aacacaaacg agtttttaat cgacgtggat aaaggcgaaa actactgttt cagcgtgcaa   1080
gctgtgatcc cctcccggac cgtgaatagg aaaagcaccg atagcccgt tgagtgcatg    1140 ggccaagaaa agggcgagtt ccgggagaac tgggtgaacg tcatcagcga tttaaagaag   1200
atcgaagatt taattcagtc catgcatatc gacgccactt tatacacaga atccgacgtg   1260 caccccctctt gtaaggtgac cgccatgaaa tgttttttac tggagctgca agttatctct   1320
ttagagagcg gagacgctag catccacgac accgtggaga atttaatcat tttagccaat   1380
aactctttat ccagcaacgg caacgtgaca gagtccggct gcaaggagtg cgaagagctg   1440
gaggagaaga acatcaagga gtttctgcaa tcctttgtgc acattgtcca gatgttcatc   1500
aatacctcc                                                          1509

<210> SEQ ID NO 58
<211> LENGTH: 503
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Met Lys Trp Val Thr Phe Ile Ser Leu Leu Phe Leu Phe Ser Ser Ala
1               5                   10                  15

Tyr Ser Asp Cys Asp Ile Glu Gly Lys Asp Gly Lys Gln Tyr Glu Ser
            20                  25                  30

Val Leu Met Val Ser Ile Asp Gln Leu Leu Asp Ser Met Lys Glu Ile
        35                  40                  45

Gly Ser Asn Cys Leu Asn Asn Glu Phe Asn Phe Phe Lys Arg His Ile
    50                  55                  60

Cys Asp Ala Asn Lys Glu Gly Met Phe Leu Phe Arg Ala Ala Arg Lys
65                  70                  75                  80

Leu Arg Gln Phe Leu Lys Met Asn Ser Thr Gly Asp Phe Asp Leu His
                85                  90                  95

Leu Leu Lys Val Ser Glu Gly Thr Thr Ile Leu Leu Asn Cys Thr Gly
            100                 105                 110

Gln Val Lys Gly Arg Lys Pro Ala Ala Leu Gly Glu Ala Gln Pro Thr
        115                 120                 125

Lys Ser Leu Glu Glu Asn Lys Ser Leu Lys Glu Gln Lys Lys Leu Asn
    130                 135                 140

Asp Leu Cys Phe Leu Lys Arg Leu Leu Gln Glu Ile Lys Thr Cys Trp
145                 150                 155                 160

Asn Lys Ile Leu Met Gly Thr Lys Glu His Ser Gly Thr Thr Asn Thr
                165                 170                 175

Val Ala Ala Tyr Asn Leu Thr Trp Lys Ser Thr Asn Phe Lys Thr Ile
            180                 185                 190

Leu Glu Trp Glu Pro Lys Pro Val Asn Gln Val Tyr Thr Val Gln Ile
```

| | | 195 | | | 200 | | | 205 | | | |
|---|---|---|---|---|---|---|---|---|---|---|---|
Ser Thr Lys Ser Gly Asp Trp Lys Ser Lys Cys Phe Tyr Thr Thr Asp
210 215 220

Thr Glu Cys Asp Leu Thr Asp Glu Ile Val Lys Asp Val Lys Gln Thr
225 230 235 240

Tyr Leu Ala Arg Val Phe Ser Tyr Pro Ala Gly Asn Val Glu Ser Thr
245 250 255

Gly Ser Ala Gly Glu Pro Leu Tyr Glu Asn Ser Pro Glu Phe Thr Pro
260 265 270

Tyr Leu Glu Thr Asn Leu Gly Gln Pro Thr Ile Gln Ser Phe Glu Gln
275 280 285

Val Gly Thr Lys Val Asn Val Thr Val Glu Asp Glu Arg Thr Leu Val
290 295 300

Arg Arg Asn Asn Thr Phe Leu Ser Leu Arg Asp Val Phe Gly Lys Asp
305 310 315 320

Leu Ile Tyr Thr Leu Tyr Tyr Trp Lys Ser Ser Ser Gly Lys Lys
325 330 335

Thr Ala Lys Thr Asn Thr Asn Glu Phe Leu Ile Asp Val Asp Lys Gly
340 345 350

Glu Asn Tyr Cys Phe Ser Val Gln Ala Val Ile Pro Ser Arg Thr Val
355 360 365

Asn Arg Lys Ser Thr Asp Ser Pro Val Glu Cys Met Gly Gln Glu Lys
370 375 380

Gly Glu Phe Arg Glu Asn Trp Val Asn Val Ile Ser Asp Leu Lys Lys
385 390 395 400

Ile Glu Asp Leu Ile Gln Ser Met His Ile Asp Ala Thr Leu Tyr Thr
405 410 415

Glu Ser Asp Val His Pro Ser Cys Lys Val Thr Ala Met Lys Cys Phe
420 425 430

Leu Leu Glu Leu Gln Val Ile Ser Leu Glu Ser Gly Asp Ala Ser Ile
435 440 445

His Asp Thr Val Glu Asn Leu Ile Ile Leu Ala Asn Asn Ser Leu Ser
450 455 460

Ser Asn Gly Asn Val Thr Glu Ser Gly Cys Lys Glu Cys Glu Glu Leu
465 470 475 480

Glu Glu Lys Asn Ile Lys Glu Phe Leu Gln Ser Phe Val His Ile Val
485 490 495

Gln Met Phe Ile Asn Thr Ser
500

<210> SEQ ID NO 59
<211> LENGTH: 1368
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 59
atgaagtggg tgaccttcat cagcctgctg ttcctgttct ccagcgccta ctcctccgag    60
ctgacccagg accctgctgt gtccgtggct ctgggccaga ccgtgaggat cacctgccag   120
ggcgactccc tgaggtccta ctacgcctcc tggtaccagc agaagcccgg ccaggctcct   180
gtgctggtga tctacggcaa gaacaacagg ccctccggca tccctgacag gttctccgga   240
tcctcctccg gcaacaccgc ctccctgacc atcacaggcg ctcaggccga ggacgaggct   300

```
gactactact gcaactccag ggactcctcc ggcaaccatg tggtgttcgg cggcggcacc      360
aagctgaccg tgggccatgg cggcggcggc tccggaggcg gcggcagcgg cggaggagga      420
tccgaggtgc agctggtgga gtccggagga ggagtggtga ggcctggagg ctccctgagg      480
ctgagctgtg ctgcctccgg cttcaccttc gacgactacg gcatgtcctg ggtgaggcag      540
gctcctggaa agggcctgga gtgggtgtcc ggcatcaact ggaacggcgg atccaccggc      600
tacgccgatt ccgtgaaggg caggttcacc atcagcaggg acaacgccaa gaactccctg      660
tacctgcaga tgaactccct gagggccgag gacaccgccg tgtactactg cgccggggc       720
aggtccctgc tgttcgacta ctggggacag ggcaccctgg tgaccgtgtc caggattaca      780
tgccccctc ccatgagcgt ggagcacgcc gacatctggg tgaagagcta tagcctctac       840
agccgggaga ggtatatctg taacagcggc ttcaagagga aggccggcac cagcagcctc      900
accgagtgcg tgctgaataa ggctaccaac gtggctcact ggacaacacc ctctttaaag      960
tgcatccggc agggccagga caggcacatg atccggatga ggcagctcat cgacatcgtc     1020
gaccagctga agaactacgt gaacgacctg gtgcccgagt ttctgcctgc ccccgaggac     1080
gtggagacca actgcgagtg gtccgccttc tcctgctttc agaaggccca gctgaagtcc     1140
gccaacaccg gcaacaacga gcggatcatc aacgtgagca tcaagaagct gaagcggaag     1200
cctccctcca caaacgccgg caggaggcag aagcacaggc tgacctgccc cagctgtgac     1260
tcctacgaga gaagccccc caaggagttc ctggagaggt tcaagtccct gctgcagaag     1320
atgatccatc agcacctgtc ctccaggacc cacggctccg aggactcc                1368
```

<210> SEQ ID NO 60
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Met Lys Trp Val Thr Phe Ile Ser Leu Leu Phe Leu Phe Ser Ser Ala
1               5                   10                  15

Tyr Ser Ser Glu Leu Thr Gln Asp Pro Ala Val Ser Val Ala Leu Gly
            20                  25                  30

Gln Thr Val Arg Ile Thr Cys Gln Gly Asp Ser Leu Arg Ser Tyr Tyr
        35                  40                  45

Ala Ser Trp Tyr Gln Gln Lys Pro Gly Gln Ala Pro Val Leu Val Ile
    50                  55                  60

Tyr Gly Lys Asn Asn Arg Pro Ser Gly Ile Pro Asp Arg Phe Ser Gly
65                  70                  75                  80

Ser Ser Ser Gly Asn Thr Ala Ser Leu Thr Ile Thr Gly Ala Gln Ala
                85                  90                  95

Glu Asp Glu Ala Asp Tyr Tyr Cys Asn Ser Arg Asp Ser Ser Gly Asn
            100                 105                 110

His Val Val Phe Gly Gly Gly Thr Lys Leu Thr Val Gly His Gly Gly
        115                 120                 125

Gly Gly Ser Gly Gly Gly Gly Ser Gly Gly Gly Gly Ser Glu Val Gln
    130                 135                 140

Leu Val Glu Ser Gly Gly Gly Val Val Arg Pro Gly Gly Ser Leu Arg
145                 150                 155                 160

Leu Ser Cys Ala Ala Ser Gly Phe Thr Phe Asp Asp Tyr Gly Met Ser

|     |     |     |     | 165 |     |     |     | 170 |     |     |     | 175 |     |
| --- | --- | --- | --- | --- | --- | --- | --- | --- | --- | --- | --- | --- | --- |
| Trp | Val | Arg | Gln | Ala | Pro | Gly | Lys | Gly | Leu | Glu | Trp | Val | Ser | Gly | Ile |

Asn Trp Asn Gly Gly Ser Thr Gly Tyr Ala Asp Ser Val Lys Gly Arg
        195                 200                 205

Phe Thr Ile Ser Arg Asp Asn Ala Lys Asn Ser Leu Tyr Leu Gln Met
    210                 215                 220

Asn Ser Leu Arg Ala Glu Asp Thr Ala Val Tyr Tyr Cys Ala Arg Gly
225                 230                 235                 240

Arg Ser Leu Leu Phe Asp Tyr Trp Gly Gln Gly Thr Leu Val Thr Val
                245                 250                 255

Ser Arg Ile Thr Cys Pro Pro Pro Met Ser Val Glu His Ala Asp Ile
            260                 265                 270

Trp Val Lys Ser Tyr Ser Leu Tyr Ser Arg Glu Arg Tyr Ile Cys Asn
        275                 280                 285

Ser Gly Phe Lys Arg Lys Ala Gly Thr Ser Ser Leu Thr Glu Cys Val
    290                 295                 300

Leu Asn Lys Ala Thr Asn Val Ala His Trp Thr Thr Pro Ser Leu Lys
305                 310                 315                 320

Cys Ile Arg Gln Gly Gln Asp Arg His Met Ile Arg Met Arg Gln Leu
                325                 330                 335

Ile Asp Ile Val Asp Gln Leu Lys Asn Tyr Val Asn Asp Leu Val Pro
            340                 345                 350

Glu Phe Leu Pro Ala Pro Glu Asp Val Glu Thr Asn Cys Glu Trp Ser
        355                 360                 365

Ala Phe Ser Cys Phe Gln Lys Ala Gln Leu Lys Ser Ala Asn Thr Gly
    370                 375                 380

Asn Asn Glu Arg Ile Ile Asn Val Ser Ile Lys Lys Leu Lys Arg Lys
385                 390                 395                 400

Pro Pro Ser Thr Asn Ala Gly Arg Arg Gln Lys His Arg Leu Thr Cys
                405                 410                 415

Pro Ser Cys Asp Ser Tyr Glu Lys Lys Pro Pro Lys Glu Phe Leu Glu
            420                 425                 430

Arg Phe Lys Ser Leu Leu Gln Lys Met Ile His Gln His Leu Ser Ser
        435                 440                 445

Arg Thr His Gly Ser Glu Asp Ser
    450                 455

<210> SEQ ID NO 61
<211> LENGTH: 1914
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
atgaagtggg tgaccttcat cagcctgctg ttcctgttct ccagcgccta ctccatcccc    60
ccccatgtgc aaaagagcgt gaacaacgat atgatcgtga ccgacaacaa cggcgccgtg   120
aagtttcccc agctctgcaa gttctgcgat gtcaggttca gcacctgcga taatcagaag   180
tcctgcatgt ccaactgcag catcaccctc catctgcgag agccccaaga agtgtgcgtg   240
gccgtgtggc ggaaaaatga cgagaacatc accctggaga ccgtgtgtca cgaccccaag   300
ctcccttatc acgacttcat tctggaggac gctgcctccc ccaaatgcat catgaaggag   360

```
aagaagaagc ccggagagac cttctttatg tgttcctgta gcagcgacga gtgtaacgac    420
aacatcatct tcagcgaaga gtacaacacc agcaacctg atggaggtgg cggatccgga    480
ggtggaggtt ctggtggagg tgggagtatt cctccccacg tgcagaagag cgtgaataat    540
gacatgatcg tgaccgataa caatggcgcc gtgaaatttc cccagctgtg caaattctgc    600
gatgtgaggt tttccacctg cgacaaccag aagtcctgta tgagcaactg ctccatcacc    660
tccatctgtg agaagcctca ggaggtgtgc gtggctgtct ggcggaagaa tgacgagaat    720
atcaccctgg aaaccgtctg ccacgatccc aagctgccct accacgattt catcctggaa    780
gacgccgcca gccctaagtg catcatgaaa gagaaaaaga agcctggcga gacctttttc    840
atgtgctcct gcagcagcga cgaatgcaac gacaatatca tctttagcga ggaatacaat    900
accagcaacc ccgacagcgg cacaaccaac acagtcgctg cctataacct cacttggaag    960
agcaccaact tcaaaaccat cctcgaatgg gaacccaaac ccgttaacca agtttacacc    1020
gtgcagatca gcaccaagtc cggcgactgg aagtccaaat gtttctatac caccgacacc    1080
gagtgcgatc tcaccgatga gatcgtgaaa gatgtgaaac agacctacct cgcccgggtg    1140
tttagctacc ccgccggcaa tgtggagagc actggttccg ctggcgagcc tttatacgag    1200
aacagccccg aatttacccc ttacctcgag accaatttag acagcccac catccaaagc    1260 tttgagcaag ttggcacaaa ggtgaatgtg acagtggagg acgagcggac tttagtgcgg    1320
cggaacaaca ccttttctcag cctccgggat gtgttcggca agatttaat ctacacactg    1380 tattactgga agtcctcttc ctccggcaag aagacagcta aaaccaacac aaacgagttt    1440
ttaatcgacg tggataaagg cgaaaactac tgtttcagcg tgcaagctgt gatcccctcc    1500
cggaccgtga ataggaaaag caccgatagc cccgttgagt gcatgggcca agaaaagggc    1560
gagttccggg agaactgggt gaacgtcatc agcgatttaa agaagatcga agatttaatt    1620
cagtccatgc atatcgacgc cactttatac acagaatccg acgtgcaccc ctcttgtaag    1680
gtgaccgcca tgaaatgttt tttactggag ctgcaagtta tctctttaga gagcggagac    1740
gctagcatcc acgacaccgt ggagaattta atcatttag ccaataactc tttatccagc    1800
aacggcaacg tgacagagtc cggctgcaag gagtgcgaag agctggagga aagaacatc    1860 aaggagtttc tgcaatcctt tgtgcacatt gtccagatgt tcatcaatac ctcc    1914
```

<210> SEQ ID NO 62
<211> LENGTH: 638
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

```
Met Lys Trp Val Thr Phe Ile Ser Leu Leu Phe Leu Phe Ser Ser Ala
1               5                   10                  15

Tyr Ser Ile Pro Pro His Val Gln Lys Ser Val Asn Asn Asp Met Ile
            20                  25                  30

Val Thr Asp Asn Asn Gly Ala Val Lys Phe Pro Gln Leu Cys Lys Phe
        35                  40                  45

Cys Asp Val Arg Phe Ser Thr Cys Asp Asn Gln Lys Ser Cys Met Ser
    50                  55                  60

Asn Cys Ser Ile Thr Ser Ile Cys Glu Lys Pro Gln Glu Val Cys Val
65                  70                  75                  80

Ala Val Trp Arg Lys Asn Asp Glu Asn Ile Thr Leu Glu Thr Val Cys
```

```
                    85                  90                  95
His Asp Pro Lys Leu Pro Tyr His Asp Phe Ile Leu Glu Asp Ala Ala
                100                 105                 110

Ser Pro Lys Cys Ile Met Lys Glu Lys Lys Pro Gly Glu Thr Phe
            115                 120                 125

Phe Met Cys Ser Cys Ser Ser Asp Glu Cys Asn Asp Asn Ile Ile Phe
        130                 135                 140

Ser Glu Glu Tyr Asn Thr Ser Asn Pro Asp Gly Gly Gly Ser Gly
145                 150                 155                 160

Gly Gly Gly Ser Gly Gly Gly Ser Ile Pro Pro His Val Gln Lys
            165                 170                 175

Ser Val Asn Asn Asp Met Ile Val Thr Asp Asn Gly Ala Val Lys
            180                 185                 190

Phe Pro Gln Leu Cys Lys Phe Cys Asp Val Arg Phe Ser Thr Cys Asp
        195                 200                 205

Asn Gln Lys Ser Cys Met Ser Asn Cys Ser Ile Thr Ser Ile Cys Glu
    210                 215                 220

Lys Pro Gln Glu Val Cys Val Ala Val Trp Arg Lys Asn Asp Glu Asn
225                 230                 235                 240

Ile Thr Leu Glu Thr Val Cys His Asp Pro Lys Leu Pro Tyr His Asp
                245                 250                 255

Phe Ile Leu Glu Asp Ala Ala Ser Pro Lys Cys Ile Met Lys Glu Lys
                260                 265                 270

Lys Lys Pro Gly Glu Thr Phe Phe Met Cys Ser Cys Ser Ser Asp Glu
            275                 280                 285

Cys Asn Asp Asn Ile Ile Phe Ser Glu Glu Tyr Asn Thr Ser Asn Pro
    290                 295                 300

Asp Ser Gly Thr Thr Asn Thr Val Ala Ala Tyr Asn Leu Thr Trp Lys
305                 310                 315                 320

Ser Thr Asn Phe Lys Thr Ile Leu Glu Trp Glu Pro Lys Pro Val Asn
                325                 330                 335

Gln Val Tyr Thr Val Gln Ile Ser Thr Lys Ser Gly Asp Trp Lys Ser
                340                 345                 350

Lys Cys Phe Tyr Thr Thr Asp Thr Glu Cys Asp Leu Thr Asp Glu Ile
        355                 360                 365

Val Lys Asp Val Lys Gln Thr Tyr Leu Ala Arg Val Phe Ser Tyr Pro
        370                 375                 380

Ala Gly Asn Val Glu Ser Thr Gly Ser Ala Gly Glu Pro Leu Tyr Glu
385                 390                 395                 400

Asn Ser Pro Glu Phe Thr Pro Tyr Leu Glu Thr Asn Leu Gly Gln Pro
                405                 410                 415

Thr Ile Gln Ser Phe Glu Gln Val Gly Thr Lys Val Asn Val Thr Val
                420                 425                 430

Glu Asp Glu Arg Thr Leu Val Arg Arg Asn Asn Thr Phe Leu Ser Leu
            435                 440                 445

Arg Asp Val Phe Gly Lys Asp Leu Ile Tyr Thr Leu Tyr Tyr Trp Lys
    450                 455                 460

Ser Ser Ser Ser Gly Lys Lys Thr Ala Lys Thr Asn Thr Asn Glu Phe
465                 470                 475                 480

Leu Ile Asp Val Asp Lys Gly Glu Asn Tyr Cys Phe Ser Val Gln Ala
                485                 490                 495

Val Ile Pro Ser Arg Thr Val Asn Arg Lys Ser Thr Asp Ser Pro Val
                500                 505                 510
```

```
Glu Cys Met Gly Gln Glu Lys Gly Glu Phe Arg Glu Asn Trp Val Asn
            515                 520                 525

Val Ile Ser Asp Leu Lys Lys Ile Glu Asp Leu Ile Gln Ser Met His
        530                 535                 540

Ile Asp Ala Thr Leu Tyr Thr Glu Ser Asp Val His Pro Ser Cys Lys
545                 550                 555                 560

Val Thr Ala Met Lys Cys Phe Leu Leu Glu Leu Gln Val Ile Ser Leu
                565                 570                 575

Glu Ser Gly Asp Ala Ser Ile His Asp Thr Val Glu Asn Leu Ile Ile
            580                 585                 590

Leu Ala Asn Asn Ser Leu Ser Ser Asn Gly Asn Val Thr Glu Ser Gly
            595                 600                 605

Cys Lys Glu Cys Glu Glu Leu Glu Glu Lys Asn Ile Lys Glu Phe Leu
            610                 615                 620

Gln Ser Phe Val His Ile Val Gln Met Phe Ile Asn Thr Ser
625                 630                 635
```

<210> SEQ ID NO 63
<211> LENGTH: 1368
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 63

```
atgaagtggg tgaccttcat cagcctgctg ttcctgttct ccagcgccta ctcctccgag    60
ctgacccagg accctgctgt gtccgtggct ctgggccaga ccgtgaggat cacctgccag   120
ggcgactccc tgaggtccta ctacgcctcc tggtaccagc agaagcccgg ccaggctcct   180
gtgctggtga tctacggcaa gaacaacagg ccctccggca tccctgacag gttctccgga   240
tcctcctccg gcaacaccgc ctccctgacc atcacaggcg ctcaggccga ggacgaggct   300
gactactact gcaactccag ggactcctcc ggcaaccatg tggtgttcgg cggcggcacc   360
aagctgaccg tgggccatgg cggcggcggc tccggaggcg gcggcagcgg cggaggagga   420
tccgaggtgc agctggtgga gtccggagga ggagtggtga ggcctggagg ctccctgagg   480
ctgagctgtg ctgcctccgg cttcaccttc gacgactacg catgtcctg  ggtgaggcag   540
gctcctggaa agggcctgga gtgggtgtcc ggcatcaact ggaacggcgg atccaccggc   600
tacgccgatt ccgtgaaggg caggttcacc atcagcaggg acaacgccaa gaactccctg   660
tacctgcaga tgaactccct gagggccgag gacaccgccg tgtactactg cgccaggggc   720
aggtccctgc tgttcgacta ctggggacag ggcaccctgg tgaccgtgtc caggattaca   780
tgcccccctc ccatgagcgt ggagcacgcc gacatctggg tgaagagcta tagcctctac   840
agccgggaga gtatatctg  taacagcggc ttcaagagga aggccggcac agcagcctc   900
accgagtgcg tgctgaataa ggctaccaac gtggctcact ggacaacacc ctctttaaag   960
tgcatccggc agggccagga caggcacatg atccggatga ggcagctcat cgacatcgtc  1020
gaccagctga gaactacgt  gaacgacctg gtgcccgagt ttctgcctgc ccccgaggac  1080
gtggagacca actgcgagtg gtccgccttc tcctgctttc agaaggccca gctgaagtcc  1140
gccaacaccg gcaacaacga gcggatcatc aacgtgagca tcaagaagct gaagcggaag  1200
cctccctcca aaacgccgg  caggaggcag aagcacaggc tgacctgccc cagctgtgac  1260
tcctacgaga agaagccccc caaggagttc ctggagaggt tcaagtccct gctgcagaag  1320
```

```
atgatccatc agcacctgtc ctccaggacc cacggctccg aggactcc                    1368
```

<210> SEQ ID NO 64
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

```
Met Lys Trp Val Thr Phe Ile Ser Leu Leu Phe Leu Phe Ser Ser Ala
1               5                   10                  15

Tyr Ser Ser Glu Leu Thr Gln Asp Pro Ala Val Ser Val Ala Leu Gly
            20                  25                  30

Gln Thr Val Arg Ile Thr Cys Gln Gly Asp Ser Leu Arg Ser Tyr Tyr
        35                  40                  45

Ala Ser Trp Tyr Gln Gln Lys Pro Gly Gln Ala Pro Val Leu Val Ile
    50                  55                  60

Tyr Gly Lys Asn Asn Arg Pro Ser Gly Ile Pro Asp Arg Phe Ser Gly
65                  70                  75                  80

Ser Ser Ser Gly Asn Thr Ala Ser Leu Thr Ile Thr Gly Ala Gln Ala
                85                  90                  95

Glu Asp Glu Ala Asp Tyr Tyr Cys Asn Ser Arg Asp Ser Ser Gly Asn
            100                 105                 110

His Val Val Phe Gly Gly Gly Thr Lys Leu Thr Val Gly His Gly Gly
        115                 120                 125

Gly Gly Ser Gly Gly Gly Gly Ser Gly Gly Gly Gly Ser Glu Val Gln
    130                 135                 140

Leu Val Glu Ser Gly Gly Gly Val Val Arg Pro Gly Gly Ser Leu Arg
145                 150                 155                 160

Leu Ser Cys Ala Ala Ser Gly Phe Thr Phe Asp Asp Tyr Gly Met Ser
                165                 170                 175

Trp Val Arg Gln Ala Pro Gly Lys Gly Leu Glu Trp Val Ser Gly Ile
            180                 185                 190

Asn Trp Asn Gly Gly Ser Thr Gly Tyr Ala Asp Ser Val Lys Gly Arg
        195                 200                 205

Phe Thr Ile Ser Arg Asp Asn Ala Lys Asn Ser Leu Tyr Leu Gln Met
    210                 215                 220

Asn Ser Leu Arg Ala Glu Asp Thr Ala Val Tyr Tyr Cys Ala Arg Gly
225                 230                 235                 240

Arg Ser Leu Leu Phe Asp Tyr Trp Gly Gln Gly Thr Leu Val Thr Val
                245                 250                 255

Ser Arg Ile Thr Cys Pro Pro Met Ser Val Glu His Ala Asp Ile
            260                 265                 270

Trp Val Lys Ser Tyr Ser Leu Tyr Ser Arg Glu Arg Tyr Ile Cys Asn
        275                 280                 285

Ser Gly Phe Lys Arg Lys Ala Gly Thr Ser Ser Leu Thr Glu Cys Val
    290                 295                 300

Leu Asn Lys Ala Thr Asn Val Ala His Trp Thr Thr Pro Ser Leu Lys
305                 310                 315                 320

Cys Ile Arg Gln Gly Gln Asp Arg His Met Ile Arg Met Arg Gln Leu
                325                 330                 335

Ile Asp Ile Val Asp Gln Leu Lys Asn Tyr Val Asn Asp Leu Val Pro
            340                 345                 350
```

```
Glu Phe Leu Pro Ala Pro Glu Asp Val Glu Thr Asn Cys Glu Trp Ser
            355                 360                 365
Ala Phe Ser Cys Phe Gln Lys Ala Gln Leu Lys Ser Ala Asn Thr Gly
    370                 375                 380
Asn Asn Glu Arg Ile Ile Asn Val Ser Ile Lys Lys Leu Lys Arg Lys
385                 390                 395                 400
Pro Pro Ser Thr Asn Ala Gly Arg Arg Gln Lys His Arg Leu Thr Cys
                405                 410                 415
Pro Ser Cys Asp Ser Tyr Glu Lys Lys Pro Pro Lys Glu Phe Leu Glu
            420                 425                 430
Arg Phe Lys Ser Leu Leu Gln Lys Met Ile His Gln His Leu Ser Ser
        435                 440                 445
Arg Thr His Gly Ser Glu Asp Ser
    450                 455
```

<210> SEQ ID NO 65
<211> LENGTH: 1509
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 65

| | |
|---|---:|
| atgaagtggg tgaccttcat cagcctgctg ttcctgttct ccagcgccta ctccgattgc | 60 |
| gacatcgagg gcaaggacgg caagcagtac gagagcgtgc tgatggtgtc catcgaccag | 120 |
| ctgctggaca gcatgaagga gatcggctcc aactgcctca caacgagtt caacttcttc | 180 |
| aagcggcaca tctgcgacgc caacaaggag ggcatgttcc tgttcagggc cgccaggaaa | 240 |
| ctgcggcagt tcctgaagat aactccacc ggcgacttcg acctgcacct gctgaaggtg | 300 |
| tccgagggca ccaccatcct gctgaactgc accggacagg tgaagggccg gaaacctgct | 360 |
| gctctgggag aggcccaacc caccaagagc ctggaggaga caagtccct gaaggagcag | 420 |
| aagaagctga cgacctgtg cttcctgaag aggctgctgc aggagatcaa gacctgctgg | 480 |
| aacaagatcc tgatgggcac caaggagcat agcggcacaa ccaacacagt cgctgcctat | 540 |
| aacctcactt ggaagagcac caacttcaaa accatcctcg aatgggaacc caaacccgtt | 600 |
| aaccaagttt acaccgtgca gatcagcacc aagtccggcg actggaagtc caatgtttc | 660 |
| tataccaccg acaccgagtg cgatctcacc gatgagatcg tgaaagatgt gaaacagacc | 720 |
| tacctcgccc gggtgtttag ctaccccgcc ggcaatgtgg agagcactgg ttccgctggc | 780 |
| gagcctttat acgagaacag ccccgaattt accccttacc tcgagaccaa tttaggacag | 840 |
| cccaccatcc aaagctttga gcaagttggc acaaaggtga atgtgacagt ggaggacgag | 900 |
| cggactttag tgcggcggaa caacaccttt ctcagcctcc gggatgtgtt cggcaaagat | 960 |
| ttaatctaca cactgtatta ctggaagtcc tcttcctccg gcaagaagac agctaaaacc | 1020 |
| aacacaaacg agttttaat cgacgtggat aaaggcgaaa actactgttt cagcgtgcaa | 1080 |
| gctgtgatcc cctcccggac cgtgaatagg aaaagcaccg atagcccccgt tgagtgcatg | 1140 |
| ggccaagaaa agggcgagtt ccgggagaac tgggtgaacg tcatcagcga tttaaagaag | 1200 |
| atcgaagatt taattcagtc catgcatatc gacgccactt tatacacaga atccgacgtg | 1260 |
| cacccctctt gtaaggtgac cgccatgaaa tgttttttac tggagctgca agttatctct | 1320 |
| ttagagagcg gagacgctag catccacgac accgtggaga atttaatcat tttagccaat | 1380 |

```
aactctttat ccagcaacgg caacgtgaca gagtccggct gcaaggagtg cgaagagctg    1440
gaggagaaga acatcaagga gtttctgcaa tcctttgtgc acattgtcca gatgttcatc    1500
aatacctcc                                                            1509
```

<210> SEQ ID NO 66
<211> LENGTH: 503
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

```
Met Lys Trp Val Thr Phe Ile Ser Leu Leu Phe Leu Phe Ser Ser Ala
1               5                   10                  15

Tyr Ser Asp Cys Asp Ile Glu Gly Lys Asp Gly Lys Gln Tyr Glu Ser
            20                  25                  30

Val Leu Met Val Ser Ile Asp Gln Leu Leu Asp Ser Met Lys Glu Ile
        35                  40                  45

Gly Ser Asn Cys Leu Asn Asn Glu Phe Asn Phe Phe Lys Arg His Ile
    50                  55                  60

Cys Asp Ala Asn Lys Glu Gly Met Phe Leu Phe Arg Ala Ala Arg Lys
65                  70                  75                  80

Leu Arg Gln Phe Leu Lys Met Asn Ser Thr Gly Asp Phe Asp Leu His
                85                  90                  95

Leu Leu Lys Val Ser Glu Gly Thr Thr Ile Leu Leu Asn Cys Thr Gly
            100                 105                 110

Gln Val Lys Gly Arg Lys Pro Ala Ala Leu Gly Glu Ala Gln Pro Thr
        115                 120                 125

Lys Ser Leu Glu Glu Asn Lys Ser Leu Lys Glu Gln Lys Lys Leu Asn
    130                 135                 140

Asp Leu Cys Phe Leu Lys Arg Leu Leu Gln Glu Ile Lys Thr Cys Trp
145                 150                 155                 160

Asn Lys Ile Leu Met Gly Thr Lys Glu His Ser Gly Thr Thr Asn Thr
                165                 170                 175

Val Ala Ala Tyr Asn Leu Thr Trp Lys Ser Thr Asn Phe Lys Thr Ile
            180                 185                 190

Leu Glu Trp Glu Pro Lys Pro Val Asn Gln Val Tyr Thr Val Gln Ile
        195                 200                 205

Ser Thr Lys Ser Gly Asp Trp Lys Ser Lys Cys Phe Tyr Thr Thr Asp
    210                 215                 220

Thr Glu Cys Asp Leu Thr Asp Glu Ile Val Lys Asp Val Lys Gln Thr
225                 230                 235                 240

Tyr Leu Ala Arg Val Phe Ser Tyr Pro Ala Gly Asn Val Glu Ser Thr
                245                 250                 255

Gly Ser Ala Gly Glu Pro Leu Tyr Glu Asn Ser Pro Glu Phe Thr Pro
            260                 265                 270

Tyr Leu Glu Thr Asn Leu Gly Gln Pro Thr Ile Gln Ser Phe Glu Gln
        275                 280                 285

Val Gly Thr Lys Val Asn Val Thr Val Glu Asp Glu Arg Thr Leu Val
    290                 295                 300

Arg Arg Asn Asn Thr Phe Leu Ser Leu Arg Asp Val Phe Gly Lys Asp
305                 310                 315                 320

Leu Ile Tyr Thr Leu Tyr Tyr Trp Lys Ser Ser Ser Gly Lys Lys
                325                 330                 335
```

Thr Ala Lys Thr Asn Thr Asn Glu Phe Leu Ile Asp Val Asp Lys Gly
            340                 345                 350

Glu Asn Tyr Cys Phe Ser Val Gln Ala Val Ile Pro Ser Arg Thr Val
            355                 360                 365

Asn Arg Lys Ser Thr Asp Ser Pro Val Glu Cys Met Gly Gln Glu Lys
        370                 375                 380

Gly Glu Phe Arg Glu Asn Trp Val Asn Val Ile Ser Asp Leu Lys Lys
385                 390                 395                 400

Ile Glu Asp Leu Ile Gln Ser Met His Ile Asp Ala Thr Leu Tyr Thr
                405                 410                 415

Glu Ser Asp Val His Pro Ser Cys Lys Val Thr Ala Met Lys Cys Phe
            420                 425                 430

Leu Leu Glu Leu Gln Val Ile Ser Leu Glu Ser Gly Asp Ala Ser Ile
            435                 440                 445

His Asp Thr Val Glu Asn Leu Ile Ile Leu Ala Asn Asn Ser Leu Ser
450                 455                 460

Ser Asn Gly Asn Val Thr Glu Ser Gly Cys Lys Glu Cys Glu Glu Leu
465                 470                 475                 480

Glu Glu Lys Asn Ile Lys Glu Phe Leu Gln Ser Phe Val His Ile Val
                485                 490                 495

Gln Met Phe Ile Asn Thr Ser
            500

<210> SEQ ID NO 67
<211> LENGTH: 702
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
atgggagtga aagttctttt tgcccttatt tgtattgctg tggccgaggc cgattgtgat      60
attgaaggta agatggcaa acaatatgag agtgttctaa tggtcagcat cgatcaatta     120
ttggacagca tgaaagaaat tggtagcaat tgcctgaata atgaatttaa cttttttaaa     180
agacatatct gtgatgctaa taggaaggt atgttttat ccgtgctgc tcgcaagttg       240 aggcaatttc ttaaaatgaa tagcactggt gattttgatc tccacttatt aaaagtttca     300
gaaggcacaa caatactgtt gaactgcact ggccaggtta aggaagaaa accagctgcc    360 ctgggtgaag cccaaccaac aaagagtttg gaagaaaata atctttaaa ggaacagaaa    420 aaactgaatg acttgtgttt cctaaagaga ctattacaag ataaaaac ttgttggaat      480 aaaattttga tgggcactaa agaacacatc acgtgccctc ccccatgtc cgtggaacac    540 gcagacatct gggtcaagag ctacagcttg tactccaggg agcggtacat ttgtaactct     600
ggtttcaagc gtaaagccgg cacgtccagc ctgacggagt gcgtgttgaa caaggccacg    660
aatgtcgccc actggacaac ccccagtctc aaatgcatta ga                         702

<210> SEQ ID NO 68
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

```
Met Gly Val Lys Val Leu Phe Ala Leu Ile Cys Ile Ala Val Ala Glu
1               5                   10                  15

Ala Asp Cys Asp Ile Glu Gly Lys Gly Lys Gln Tyr Glu Ser Val
            20                  25                  30

Leu Met Val Ser Ile Asp Gln Leu Leu Asp Ser Met Lys Glu Ile Gly
                35                  40                  45

Ser Asn Cys Leu Asn Asn Glu Phe Asn Phe Phe Lys Arg His Ile Cys
        50                  55                  60

Asp Ala Asn Lys Glu Gly Met Phe Leu Phe Arg Ala Ala Arg Lys Leu
65                  70                  75                  80

Arg Gln Phe Leu Lys Met Asn Ser Thr Gly Asp Phe Asp Leu His Leu
                85                  90                  95

Leu Lys Val Ser Glu Gly Thr Thr Ile Leu Leu Asn Cys Thr Gly Gln
            100                 105                 110

Val Lys Gly Arg Lys Pro Ala Ala Leu Gly Glu Ala Gln Pro Thr Lys
        115                 120                 125

Ser Leu Glu Glu Asn Lys Ser Leu Lys Glu Gln Lys Lys Leu Asn Asp
    130                 135                 140

Leu Cys Phe Leu Lys Arg Leu Leu Gln Glu Ile Lys Thr Cys Trp Asn
145                 150                 155                 160

Lys Ile Leu Met Gly Thr Lys Glu His Ile Thr Cys Pro Pro Pro Met
                165                 170                 175

Ser Val Glu His Ala Asp Ile Trp Val Lys Ser Tyr Ser Leu Tyr Ser
            180                 185                 190

Arg Glu Arg Tyr Ile Cys Asn Ser Gly Phe Lys Arg Lys Ala Gly Thr
        195                 200                 205

Ser Ser Leu Thr Glu Cys Val Leu Asn Lys Ala Thr Asn Val Ala His
    210                 215                 220

Trp Thr Thr Pro Ser Leu Lys Cys Ile Arg
225                 230

<210> SEQ ID NO 69
<211> LENGTH: 1914
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69
atgaagtggg tgaccttcat cagcctgctg ttcctgttct ccagcgccta ctccatcccc        60
ccccatgtgc aaaagagcgt gaacaacgat atgatcgtga ccgacaacaa cggcgccgtg       120
aagtttcccc agctctgcaa gttctgcgat gtcaggttca gcacctgcga taatcagaag       180
tcctgcatgt ccaactgcag catcaccctc catctgcgaga agccccaaga agtgtgcgtg       240
gccgtgtggc ggaaaaatga cgagaacatc accctggaga ccgtgtgtca cgaccccaag       300
ctcccttatc acgacttcat tctggaggac gctgcctccc ccaaatgcat catgaaggag       360
aagaagaagc ccggagagac cttctttatg tgttcctgta gcagcgacga gtgtaacgac       420
aacatcatct tcagcgaaga gtacaacacc agcaaccctg atggaggtgg cggatccgga       480
ggtggaggtt ctggtggagg tgggagtatt cctccccacg tgcagaagag cgtgaataat       540
gacatgatcg tgaccgataa caatggcgcc gtgaaatttc cccagctgtg caaattctgc       600
gatgtgaggt tttccacctg cgacaaccag aagtcctgta tgagcaactg ctccatcacc       660
```

-continued

```
tccatctgtg agaagcctca ggaggtgtgc gtggctgtct ggcggaagaa tgacgagaat    720
atcaccctgg aaaccgtctg ccacgatccc aagctgccct accacgattt catcctggaa    780
gacgccgcca gccctaagtg catcatgaaa gagaaaaaga gcctggcga gaccttttc     840
atgtgctcct gcagcagcga cgaatgcaac gacaatatca tctttagcga ggaatacaat    900
accagcaacc ccgacagcgg cacaaccaac acagtcgctg cctataacct cacttggaag    960
agcaccaact tcaaaaccat cctcgaatgg gaacccaaac ccgttaacca agtttacacc   1020
gtgcagatca gcaccaagtc cggcgactgg aagtccaaat gtttctatac caccgacacc   1080
gagtgcgatc tcaccgatga gatcgtgaaa gatgtgaaac agacctacct cgcccgggtg   1140
tttagctacc ccgccggcaa tgtggagagc actggttccg ctggcgagcc tttatacgag   1200
aacagccccg aatttacccc ttacctcgag accaatttag gacagcccac catccaaagc   1260
tttgagcaag ttggcacaaa ggtgaatgtg acagtggagg acgagcggac tttagtgcgg   1320
cggaacaaca cctttctcag cctccgggat gtgttcggca agatttaat ctacacactg    1380
tattactgga agtcctcttc ctccggcaag aagacagcta aaaccaacac aaacgagttt   1440
ttaatcgacg tggataaagg cgaaaactac tgtttcagcg tgcaagctgt gatcccctcc   1500
cggaccgtga ataggaaaag caccgatagc cccgttgagt gcatgggcca agaaaagggc   1560
gagttccggg agaactgggt gaacgtcatc agcgatttaa agaagatcga agatttaatt    1620
cagtccatgc atatcgacgc cactttatac acagaatccg acgtgcaccc ctcttgtaag   1680
gtgaccgcca tgaaatgttt tttactggag ctgcaagtta tctctttaga gagcggagac   1740
gctagcatcc acgaccgt ggagaattta atcattttag ccaataactc tttatccagc     1800
aacggcaacg tgacagagtc cggctgcaag gagtgcgaag agctggagga agaacatc     1860
aaggagtttc tgcaatcctt tgtgcacatt gtccagatgt tcatcaatac ctcc         1914
```

<210> SEQ ID NO 70
<211> LENGTH: 638
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 70

```
Met Lys Trp Val Thr Phe Ile Ser Leu Leu Phe Leu Phe Ser Ser Ala
1               5                   10                  15

Tyr Ser Ile Pro Pro His Val Gln Lys Ser Val Asn Asn Asp Met Ile
            20                  25                  30

Val Thr Asp Asn Asn Gly Ala Val Lys Phe Pro Gln Leu Cys Lys Phe
        35                  40                  45

Cys Asp Val Arg Phe Ser Thr Cys Asp Asn Gln Lys Cys Met Ser
    50                  55                  60

Asn Cys Ser Ile Thr Ser Ile Cys Glu Lys Pro Gln Glu Val Cys Val
65                  70                  75                  80

Ala Val Trp Arg Lys Asn Asp Glu Asn Ile Thr Leu Glu Thr Val Cys
                85                  90                  95

His Asp Pro Lys Leu Pro Tyr His Asp Phe Ile Leu Glu Asp Ala Ala
            100                 105                 110

Ser Pro Lys Cys Ile Met Lys Glu Lys Lys Pro Gly Glu Thr Phe
            115                 120                 125

Phe Met Cys Ser Cys Ser Ser Asp Glu Cys Asn Asp Asn Ile Ile Phe
        130                 135                 140
```

```
Ser Glu Glu Tyr Asn Thr Ser Asn Pro Asp Gly Gly Gly Ser Gly
145                 150                 155                 160

Gly Gly Gly Ser Gly Gly Gly Ser Ile Pro Pro His Val Gln Lys
            165                 170                 175

Ser Val Asn Asn Asp Met Ile Val Thr Asp Asn Asn Gly Ala Val Lys
            180                 185                 190

Phe Pro Gln Leu Cys Lys Phe Cys Asp Val Arg Phe Ser Thr Cys Asp
        195                 200                 205

Asn Gln Lys Ser Cys Met Ser Asn Cys Ser Ile Thr Ser Ile Cys Glu
        210                 215                 220

Lys Pro Gln Glu Val Cys Val Ala Val Trp Arg Lys Asn Asp Glu Asn
225                 230                 235                 240

Ile Thr Leu Glu Thr Val Cys His Asp Pro Lys Leu Pro Tyr His Asp
                245                 250                 255

Phe Ile Leu Glu Asp Ala Ala Ser Pro Lys Cys Ile Met Lys Glu Lys
                260                 265                 270

Lys Lys Pro Gly Glu Thr Phe Phe Met Cys Ser Cys Ser Ser Asp Glu
        275                 280                 285

Cys Asn Asp Asn Ile Ile Phe Ser Glu Glu Tyr Asn Thr Ser Asn Pro
290                 295                 300

Asp Ser Gly Thr Thr Asn Thr Val Ala Ala Tyr Asn Leu Thr Trp Lys
305                 310                 315                 320

Ser Thr Asn Phe Lys Thr Ile Leu Glu Trp Glu Pro Lys Pro Val Asn
                325                 330                 335

Gln Val Tyr Thr Val Gln Ile Ser Thr Lys Ser Gly Asp Trp Lys Ser
                340                 345                 350

Lys Cys Phe Tyr Thr Thr Asp Thr Glu Cys Asp Leu Thr Asp Glu Ile
        355                 360                 365

Val Lys Asp Val Lys Gln Thr Tyr Leu Ala Arg Val Phe Ser Tyr Pro
370                 375                 380

Ala Gly Asn Val Glu Ser Thr Gly Ser Ala Gly Glu Pro Leu Tyr Glu
385                 390                 395                 400

Asn Ser Pro Glu Phe Thr Pro Tyr Leu Glu Thr Asn Leu Gly Gln Pro
                405                 410                 415

Thr Ile Gln Ser Phe Glu Gln Val Gly Thr Lys Val Asn Val Thr Val
                420                 425                 430

Glu Asp Glu Arg Thr Leu Val Arg Arg Asn Asn Thr Phe Leu Ser Leu
        435                 440                 445

Arg Asp Val Phe Gly Lys Asp Leu Ile Tyr Thr Leu Tyr Tyr Trp Lys
450                 455                 460

Ser Ser Ser Ser Gly Lys Lys Thr Ala Lys Thr Asn Thr Asn Glu Phe
465                 470                 475                 480

Leu Ile Asp Val Asp Lys Gly Glu Asn Tyr Cys Phe Ser Val Gln Ala
                485                 490                 495

Val Ile Pro Ser Arg Thr Val Asn Arg Lys Ser Thr Asp Ser Pro Val
                500                 505                 510

Glu Cys Met Gly Gln Glu Lys Gly Glu Phe Arg Glu Asn Trp Val Asn
        515                 520                 525

Val Ile Ser Asp Leu Lys Lys Ile Glu Asp Leu Ile Gln Ser Met His
530                 535                 540

Ile Asp Ala Thr Leu Tyr Thr Glu Ser Asp Val His Pro Ser Cys Lys
545                 550                 555                 560
```

```
Val Thr Ala Met Lys Cys Phe Leu Leu Glu Leu Gln Val Ile Ser Leu
            565                 570                 575

Glu Ser Gly Asp Ala Ser Ile His Asp Thr Val Glu Asn Leu Ile Ile
        580                 585                 590

Leu Ala Asn Asn Ser Leu Ser Ser Asn Gly Asn Val Thr Glu Ser Gly
            595                 600                 605

Cys Lys Glu Cys Glu Glu Leu Glu Glu Lys Asn Ile Lys Glu Phe Leu
        610                 615                 620

Gln Ser Phe Val His Ile Val Gln Met Phe Ile Asn Thr Ser
625                 630                 635
```

<210> SEQ ID NO 71
<211> LENGTH: 1110
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 71

```
atgaagtggg tgaccttcat cagcctgctg ttcctgttct ccagcgccta ctccatcccc      60
ccccatgtgc aaaagagcgt gaacaacgat atgatcgtga ccgacaacaa cggcgccgtg     120
aagtttcccc agctctgcaa gttctgcgat gtcaggttca gcacctgcga taatcagaag     180
tcctgcatgt ccaactgcag catcacctcc atctgcgaga agcccaagaa agtgtgcgtg     240
gccgtgtggc ggaaaaatga cgagaacatc accctggaga ccgtgtgtca cgaccccaag     300
ctcccttatc acgacttcat tctggaggac gctgcctccc ccaaatgcat catgaaggag     360
aagaagaagc ccggagagac cttctttatg tgttcctgta gcagcgacga gtgtaacgac     420
aacatcatct tcagcgaaga gtacaacacc agcaaccctg atggaggtgg cggatccgga     480
ggtggaggtt ctggtggagg tgggagtatt cctccccacg tgcagaagag cgtgaataat     540
gacatgatcg tgaccgataa caatggcgcc gtgaaatttc cccagctgtg caaattctgc     600
gatgtgaggt tttccacctg cgacaaccag aagtcctgta tgagcaactg ctccatcacc     660
tccatctgtg agaagcctca ggaggtgtgc gtggctgtct ggcggaagaa tgacgagaat     720
atcaccctgg aaaccgtctg ccacgatccc aagctgccct accacgattt catcctggaa     780
gacgccgcca gccctaagtg catcatgaaa gagaaaaaga gcctggcga gaccttttc      840
atgtgctcct gcagcagcga cgaatgcaac gacaatatca tctttagcga ggaatacaat     900
accagcaacc ccgacattac atgccccct cccatgagcg tggagcacgc cgacatctgg     960
gtgaagagct atagcctcta cagccgggag aggtatatct gtaacagcgg cttcaagagg    1020
aaggccggca ccagcagcct caccgagtgc gtgctgaata aggctaccaa cgtggctcac    1080
tggacaacac cctctttaaa gtgcatccgg                                    1110
```

<210> SEQ ID NO 72
<211> LENGTH: 370
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 72

```
Met Lys Trp Val Thr Phe Ile Ser Leu Leu Phe Leu Phe Ser Ser Ala
1               5                   10                  15

Tyr Ser Ile Pro Pro His Val Gln Lys Ser Val Asn Asn Asp Met Ile
```

```
            20                  25                  30
Val Thr Asp Asn Asn Gly Ala Val Lys Phe Pro Gln Leu Cys Lys Phe
        35                  40                  45
Cys Asp Val Arg Phe Ser Thr Cys Asp Asn Gln Lys Ser Cys Met Ser
 50                  55                  60
Asn Cys Ser Ile Thr Ser Ile Cys Glu Lys Pro Gln Glu Val Cys Val
 65                  70                  75                  80
Ala Val Trp Arg Lys Asn Asp Glu Asn Ile Thr Leu Glu Thr Val Cys
                 85                  90                  95
His Asp Pro Lys Leu Pro Tyr His Asp Phe Ile Leu Glu Asp Ala Ala
             100                 105                 110
Ser Pro Lys Cys Ile Met Lys Glu Lys Lys Pro Gly Glu Thr Phe
             115                 120                 125
Phe Met Cys Ser Cys Ser Ser Asp Glu Cys Asn Asp Asn Ile Ile Phe
         130                 135                 140
Ser Glu Glu Tyr Asn Thr Ser Asn Pro Asp Gly Gly Gly Ser Gly
145                 150                 155                 160
Gly Gly Gly Ser Gly Gly Gly Ser Ile Pro Pro His Val Gln Lys
             165                 170                 175
Ser Val Asn Asn Asp Met Ile Val Thr Asp Asn Asn Gly Ala Val Lys
             180                 185                 190
Phe Pro Gln Leu Cys Lys Phe Cys Asp Val Arg Phe Ser Thr Cys Asp
             195                 200                 205
Asn Gln Lys Ser Cys Met Ser Asn Cys Ser Ile Thr Ser Ile Cys Glu
 210                 215                 220
Lys Pro Gln Glu Val Cys Val Ala Val Trp Arg Lys Asn Asp Glu Asn
 225                 230                 235                 240
Ile Thr Leu Glu Thr Val Cys His Asp Pro Lys Leu Pro Tyr His Asp
                 245                 250                 255
Phe Ile Leu Glu Asp Ala Ala Ser Pro Lys Cys Ile Met Lys Glu Lys
             260                 265                 270
Lys Lys Pro Gly Glu Thr Phe Phe Met Cys Ser Cys Ser Ser Asp Glu
         275                 280                 285
Cys Asn Asp Asn Ile Ile Phe Ser Glu Glu Tyr Asn Thr Ser Asn Pro
 290                 295                 300
Asp Ile Thr Cys Pro Pro Pro Met Ser Val Glu His Ala Asp Ile Trp
 305                 310                 315                 320
Val Lys Ser Tyr Ser Leu Tyr Ser Arg Glu Arg Tyr Ile Cys Asn Ser
                 325                 330                 335
Gly Phe Lys Arg Lys Ala Gly Thr Ser Ser Leu Thr Glu Cys Val Leu
             340                 345                 350
Asn Lys Ala Thr Asn Val Ala His Trp Thr Thr Pro Ser Leu Lys Cys
             355                 360                 365
Ile Arg
 370

<210> SEQ ID NO 73
<211> LENGTH: 1509
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
```

```
atgaagtggg tgaccttcat cagcctgctg ttcctgttct ccagcgccta ctccgattgc    60
gacatcgagg caaggacgg caagcagtac gagagcgtgc tgatggtgtc catcgaccag   120
ctgctggaca gcatgaagga gatcggctcc aactgcctca caacgagtt caacttcttc   180
aagcggcaca tctgcgacgc caacaaggag ggcatgttcc tgttcagggc cgccaggaaa   240
ctgcggcagt tcctgaagat gaactccacc ggcgacttcg acctgcacct gctgaaggtg   300
tccgagggca ccaccatcct gctgaactgc accggacagg tgaagggccg gaaacctgct   360
gctctgggag aggcccaacc caccaagagc ctggaggaga caagtccct gaaggagcag   420
aagaagctga cgacctgtg cttcctgaag aggctgctgc aggagatcaa gacctgctgg   480
aacaagatcc tgatgggcac caaggagcat agcggcacaa ccaacacagt cgctgcctat   540
aacctcactt ggaagagcac caacttcaaa accatcctcg aatgggaacc caaacccgtt   600
aaccaagttt acaccgtgca gatcagcacc aagtccggcg actggaagtc caaatgtttc   660
tataccaccg acaccgagtg cgatctcacc gatgagatcg tgaaagatgt gaaacagacc   720
tacctcgccc gggtgtttag ctaccccgcc ggcaatgtgg agagcactgg ttccgctggc   780
gagcctttat acgagaacag ccccgaattt accccttacc tcgagaccaa tttaggacag   840
cccaccatcc aaagctttga gcaagttggc acaaggtga atgtgacagt ggaggacgag   900
cggactttag tgcggcggaa caacaccttt ctcagcctcc gggatgtgtt cggcaaagat   960
ttaatctaca cactgtatta ctggaagtcc tcttcctccg gcaagaagac agctaaaacc  1020
aacacaaacg agttttttaat cgacgtggat aaaggcgaaa actactgttt cagcgtgcaa  1080
gctgtgatcc cctcccggac cgtgaatagg aaaagcaccg atagcccgt tgagtgcatg  1140
ggccaagaaa agggcgagtt ccggagagaac tgggtgaacg tcatcagcga tttaaagaag  1200
atcgaagatt taattcagtc catgcatatc gacgccactt tatacacaga atccgacgtg  1260
caccctctctt gtaaggtgac cgccatgaaa tgttttttac tggagctgca agttatctct  1320
ttagagagcg gagacgctag catccacgac accgtggaga atttaatcat tttagccaat  1380
aactctttat ccagcaacgg caacgtgaca gagtccggct gcaaggagtg cgaagagctg  1440
gaggagaaga acatcaagga gtttctgcaa tcctttgtgc acattgtcca gatgttcatc  1500
aatacctcc                                                          1509
```

<210> SEQ ID NO 74
<211> LENGTH: 503
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Met Lys Trp Val Thr Phe Ile Ser Leu Leu Phe Leu Phe Ser Ser Ala
1               5                   10                  15

Tyr Ser Asp Cys Asp Ile Glu Gly Lys Asp Gly Lys Gln Tyr Glu Ser
            20                  25                  30

Val Leu Met Val Ser Ile Asp Gln Leu Leu Asp Ser Met Lys Glu Ile
        35                  40                  45

Gly Ser Asn Cys Leu Asn Asn Glu Phe Asn Phe Phe Lys Arg His Ile
    50                  55                  60

Cys Asp Ala Asn Lys Glu Gly Met Phe Leu Phe Arg Ala Ala Arg Lys
65                  70                  75                  80

Leu Arg Gln Phe Leu Lys Met Asn Ser Thr Gly Asp Phe Asp Leu His

```
                    85                  90                  95
Leu Leu Lys Val Ser Glu Gly Thr Thr Ile Leu Leu Asn Cys Thr Gly
                100                 105                 110

Gln Val Lys Gly Arg Lys Pro Ala Ala Leu Gly Glu Ala Gln Pro Thr
                115                 120                 125

Lys Ser Leu Glu Glu Asn Lys Ser Leu Lys Glu Gln Lys Lys Leu Asn
        130                 135                 140

Asp Leu Cys Phe Leu Lys Arg Leu Leu Gln Glu Ile Lys Thr Cys Trp
145                 150                 155                 160

Asn Lys Ile Leu Met Gly Thr Lys Glu His Ser Gly Thr Thr Asn Thr
                165                 170                 175

Val Ala Ala Tyr Asn Leu Thr Trp Lys Ser Thr Asn Phe Lys Thr Ile
                180                 185                 190

Leu Glu Trp Glu Pro Lys Pro Val Asn Gln Val Tyr Thr Val Gln Ile
                195                 200                 205

Ser Thr Lys Ser Gly Asp Trp Lys Ser Lys Cys Phe Tyr Thr Thr Asp
        210                 215                 220

Thr Glu Cys Asp Leu Thr Asp Glu Ile Val Lys Asp Val Lys Gln Thr
225                 230                 235                 240

Tyr Leu Ala Arg Val Phe Ser Tyr Pro Ala Gly Asn Val Glu Ser Thr
                245                 250                 255

Gly Ser Ala Gly Glu Pro Leu Tyr Glu Asn Ser Pro Glu Phe Thr Pro
                260                 265                 270

Tyr Leu Glu Thr Asn Leu Gly Gln Pro Thr Ile Gln Ser Phe Glu Gln
                275                 280                 285

Val Gly Thr Lys Val Asn Val Thr Val Glu Asp Glu Arg Thr Leu Val
                290                 295                 300

Arg Arg Asn Asn Thr Phe Leu Ser Leu Arg Asp Val Phe Gly Lys Asp
305                 310                 315                 320

Leu Ile Tyr Thr Leu Tyr Tyr Trp Lys Ser Ser Ser Gly Lys Lys
                325                 330                 335

Thr Ala Lys Thr Asn Thr Asn Glu Phe Leu Ile Asp Val Asp Lys Gly
                340                 345                 350

Glu Asn Tyr Cys Phe Ser Val Gln Ala Val Ile Pro Ser Arg Thr Val
                355                 360                 365

Asn Arg Lys Ser Thr Asp Ser Pro Val Glu Cys Met Gly Gln Glu Lys
                370                 375                 380

Gly Glu Phe Arg Glu Asn Trp Val Asn Val Ile Ser Asp Leu Lys Lys
385                 390                 395                 400

Ile Glu Asp Leu Ile Gln Ser Met His Ile Asp Ala Thr Leu Tyr Thr
                405                 410                 415

Glu Ser Asp Val His Pro Ser Cys Lys Val Thr Ala Met Lys Cys Phe
                420                 425                 430

Leu Leu Glu Leu Gln Val Ile Ser Leu Glu Ser Gly Asp Ala Ser Ile
                435                 440                 445

His Asp Thr Val Glu Asn Leu Ile Ile Leu Ala Asn Asn Ser Leu Ser
                450                 455                 460

Ser Asn Gly Asn Val Thr Glu Ser Gly Cys Lys Glu Cys Glu Glu Leu
465                 470                 475                 480

Glu Glu Lys Asn Ile Lys Glu Phe Leu Gln Ser Phe Val His Ile Val
                485                 490                 495

Gln Met Phe Ile Asn Thr Ser
                500
```

<210> SEQ ID NO 75
<211> LENGTH: 1245
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75

```
atgaagtggg tgaccttcat cagcctgctg ttcctgttct ccagcgccta ctcccagggc      60
caggacaggc acatgatccg gatgaggcag ctcatcgaca tcgtcgacca gctgaagaac     120
tacgtgaacg acctggtgcc cgagtttctg cctgccccg aggacgtgga gaccaactgc     180
gagtggtccg ccttctcctg ctttcagaag gcccagctga agtccgccaa caccggcaac     240
aacgagcgga tcatcaacgt gagcatcaag aagctgaagc ggaagcctcc ctccacaaac     300
gccggcagga ggcagaagca caggctgacc tgccccagct gtgactccta cgagaagaag     360
ccccccaagg agttcctgga gaggttcaag tccctgctgc agaagatgat ccatcagcac     420
ctgtcctcca ggacccacgg ctccgaggac tccattacat gcccccctcc catgagcgtg     480
gagcacgccg acatctgggt gaagagctat agcctctaca gccgggagag gtatatctgt     540
aacagcggct tcaagaggaa ggccggcacc agcagcctca ccgagtgcgt gctgaataag     600
gctaccaacg tggctcactg gacaacaccc tctttaaagt gcatccgggg cggtggagga     660
tccggaggag gtggctccgg cggcggagga tctcgcgagg gtcccgagct ttcgcccgac     720
gatcccgccg gctcttggaa cctgcggcag ggcatgtttg cgcagctggt ggcccaaaat     780
gttctgctga tcgatgggcc cctgagctgg tacagtgacc caggcctggc aggcgtgtcc     840
ctgacggggg gcctgagcta caaagaggac acgaaggagc tggtggtggc caaggctgga     900
gtctactatg tcttctttca actagagctg cggcgcgtgg tggccggcga gggctcaggc     960
tccgtttcac ttgcgctgca cctgcagcca ctgcgctctg ctgctggggc cgccgccctg    1020
gctttgaccg tggacctgcc acccgcctcc tccgaggctc ggaactcggc cttcggtttc    1080
cagggccgct gctgcacct gagtgccggc cagcgcctgg cgtccatct tcacactgag    1140
gccagggcac gccatgcctg cagcttacc cagggcgcca cagtcttggg actcttccgg    1200
gtgacccccg aaatcccagc cggactccct tcaccgaggt cggaa                    1245
```

<210> SEQ ID NO 76
<211> LENGTH: 415
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

```
Met Lys Trp Val Thr Phe Ile Ser Leu Leu Phe Leu Phe Ser Ser Ala
1               5                   10                  15

Tyr Ser Gln Gly Gln Asp Arg His Met Ile Arg Met Arg Gln Leu Ile
                20                  25                  30

Asp Ile Val Asp Gln Leu Lys Asn Tyr Val Asn Asp Leu Val Pro Glu
            35                  40                  45

Phe Leu Pro Ala Pro Glu Asp Val Glu Thr Asn Cys Glu Trp Ser Ala
        50                  55                  60

Phe Ser Cys Phe Gln Lys Ala Gln Leu Lys Ser Ala Asn Thr Gly Asn
65                  70                  75                  80
```

```
Asn Glu Arg Ile Ile Asn Val Ser Ile Lys Lys Leu Lys Arg Lys Pro
                85                  90                  95

Pro Ser Thr Asn Ala Gly Arg Arg Gln Lys His Arg Leu Thr Cys Pro
            100                 105                 110

Ser Cys Asp Ser Tyr Glu Lys Lys Pro Pro Lys Glu Phe Leu Glu Arg
        115                 120                 125

Phe Lys Ser Leu Leu Gln Lys Met Ile His Gln His Leu Ser Ser Arg
    130                 135                 140

Thr His Gly Ser Glu Asp Ser Ile Thr Cys Pro Pro Met Ser Val
145                 150                 155                 160

Glu His Ala Asp Ile Trp Val Lys Ser Tyr Ser Leu Tyr Ser Arg Glu
                165                 170                 175

Arg Tyr Ile Cys Asn Ser Gly Phe Lys Arg Lys Ala Gly Thr Ser Ser
            180                 185                 190

Leu Thr Glu Cys Val Leu Asn Lys Ala Thr Asn Val Ala His Trp Thr
        195                 200                 205

Thr Pro Ser Leu Lys Cys Ile Arg Gly Gly Gly Ser Gly Gly Gly
    210                 215                 220

Gly Ser Gly Gly Gly Ser Arg Glu Gly Pro Glu Leu Ser Pro Asp
225                 230                 235                 240

Asp Pro Ala Gly Leu Leu Asp Leu Arg Gln Gly Met Phe Ala Gln Leu
                245                 250                 255

Val Ala Gln Asn Val Leu Leu Ile Asp Gly Pro Leu Ser Trp Tyr Ser
            260                 265                 270

Asp Pro Gly Leu Ala Gly Val Ser Leu Thr Gly Gly Leu Ser Tyr Lys
        275                 280                 285

Glu Asp Thr Lys Glu Leu Val Val Ala Lys Ala Gly Val Tyr Tyr Val
    290                 295                 300

Phe Phe Gln Leu Glu Leu Arg Arg Val Val Ala Gly Glu Gly Ser Gly
305                 310                 315                 320

Ser Val Ser Leu Ala Leu His Leu Gln Pro Leu Arg Ser Ala Ala Gly
                325                 330                 335

Ala Ala Ala Leu Ala Leu Thr Val Asp Leu Pro Pro Ala Ser Ser Glu
            340                 345                 350

Ala Arg Asn Ser Ala Phe Gly Phe Gln Gly Arg Leu Leu His Leu Ser
        355                 360                 365

Ala Gly Gln Arg Leu Gly Val His Leu His Thr Glu Ala Arg Ala Arg
    370                 375                 380

His Ala Trp Gln Leu Thr Gln Gly Ala Thr Val Leu Gly Leu Phe Arg
385                 390                 395                 400

Val Thr Pro Glu Ile Pro Ala Gly Leu Pro Ser Pro Arg Ser Glu
                405                 410                 415

<210> SEQ ID NO 77
<211> LENGTH: 1509
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
atgaagtggg tgaccttcat cagcctgctg ttcctgttct ccagcgccta ctccgattgc      60
gacatcgagg gcaaggacgg caagcagtac gagagcgtgc tgatggtgtc catcgaccag     120
```

```
ctgctggaca gcatgaagga gatcggctcc aactgcctca caacgagtt caacttcttc      180
aagcggcaca tctgcgacgc caacaaggag ggcatgttcc tgttcagggc cgccaggaaa      240
ctgcggcagt tcctgaagat gaactccacc ggcgacttcg acctgcacct gctgaaggtg      300
tccgagggca ccaccatcct gctgaactgc accggacagg tgaagggccg gaaacctgct      360
gctctgggag aggcccaacc caccaagagc ctggaggaga caagtccct gaaggagcag      420
aagaagctga cgacctgtg cttcctgaag aggctgctgc aggagatcaa gacctgctgg      480
aacaagatcc tgatgggcac caaggagcat agcggcacaa ccaacacagt cgctgcctat      540
aacctcactt ggaagagcac caacttcaaa accatcctcg aatgggaacc caaacccgtt      600
aaccaagttt acaccgtgca gatcagcacc aagtccggcg actggaagtc caaatgtttc      660
tataccaccg acaccgagtg cgatctcacc gatgagatcg tgaaagatgt gaaacagacc      720
tacctcgccc gggtgtttag ctaccccgcc ggcaatgtgg agagcactgg ttccgctggc      780
gagcctttat acgagaacag ccccgaattt accccttacc tcgagaccaa tttaggacag      840
cccaccatcc aaagctttga gcaagttggc acaaaggtga atgtgacagt ggaggacgag      900
cggactttag tgcggcggaa caacaccttt ctcagcctcc gggatgtgtt cggcaaagat      960
ttaatctaca cactgtatta ctggaagtcc tcttcctccg gcaagaagac agctaaaacc     1020
aacacaaacg agttttttaat cgacgtggat aaaggcgaaa actactgttt cagcgtgcaa     1080
gctgtgatcc cctcccggac cgtgaatagg aaaagcaccg atagcccgt tgagtgcatg      1140
ggccaagaaa agggcgagtt ccgggagaac tgggtgaacg tcatcagcga tttaaagaag     1200
atcgaagatt taattcagtc catgcatatc gacgccactt tatacacaga atccgacgtg     1260
cacccctctt gtaaggtgac cgccatgaaa tgttttttac tggagctgca agttatctct     1320
ttagagagcg gagacgctag catccacgac accgtggaga atttaatcat tttagccaat     1380
aactctttat ccagcaacgg caacgtgaca gagtccggct gcaaggagtg cgaagagctg     1440
gaggagaaga acatcaagga gtttctgcaa tcctttgtgc acattgtcca gatgttcatc     1500
aataccctcc                                                                     1509
```

<210> SEQ ID NO 78
<211> LENGTH: 503
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Met Lys Trp Val Thr Phe Ile Ser Leu Leu Phe Leu Phe Ser Ser Ala
1               5                   10                  15

Tyr Ser Asp Cys Asp Ile Glu Gly Lys Asp Gly Lys Gln Tyr Glu Ser
                20                  25                  30

Val Leu Met Val Ser Ile Asp Gln Leu Leu Asp Ser Met Lys Glu Ile
            35                  40                  45

Gly Ser Asn Cys Leu Asn Asn Glu Phe Asn Phe Phe Lys Arg His Ile
        50                  55                  60

Cys Asp Ala Asn Lys Glu Gly Met Phe Leu Phe Arg Ala Ala Arg Lys
65                  70                  75                  80

Leu Arg Gln Phe Leu Lys Met Asn Ser Thr Gly Asp Phe Asp Leu His
                85                  90                  95

Leu Leu Lys Val Ser Glu Gly Thr Thr Ile Leu Leu Asn Cys Thr Gly
                100                 105                 110

```
Gln Val Lys Gly Arg Lys Pro Ala Leu Gly Glu Ala Gln Pro Thr
            115                 120                 125
Lys Ser Leu Glu Glu Asn Lys Ser Leu Lys Glu Gln Lys Leu Asn
        130                 135                 140
Asp Leu Cys Phe Leu Lys Arg Leu Leu Gln Glu Ile Lys Thr Cys Trp
145                 150                 155                 160
Asn Lys Ile Leu Met Gly Thr Lys Glu His Ser Gly Thr Thr Asn Thr
                165                 170                 175
Val Ala Ala Tyr Asn Leu Thr Trp Lys Ser Thr Asn Phe Lys Thr Ile
            180                 185                 190
Leu Glu Trp Glu Pro Lys Pro Val Asn Gln Val Tyr Thr Val Gln Ile
        195                 200                 205
Ser Thr Lys Ser Gly Asp Trp Lys Ser Lys Cys Phe Tyr Thr Thr Asp
    210                 215                 220
Thr Glu Cys Asp Leu Thr Asp Glu Ile Val Lys Asp Val Lys Gln Thr
225                 230                 235                 240
Tyr Leu Ala Arg Val Phe Ser Tyr Pro Ala Gly Asn Val Glu Ser Thr
                245                 250                 255
Gly Ser Ala Gly Glu Pro Leu Tyr Glu Asn Ser Pro Glu Phe Thr Pro
            260                 265                 270
Tyr Leu Glu Thr Asn Leu Gly Gln Pro Thr Ile Gln Ser Phe Glu Gln
        275                 280                 285
Val Gly Thr Lys Val Asn Val Thr Val Glu Asp Glu Arg Thr Leu Val
    290                 295                 300
Arg Arg Asn Asn Thr Phe Leu Ser Leu Arg Asp Val Phe Gly Lys Asp
305                 310                 315                 320
Leu Ile Tyr Thr Leu Tyr Tyr Trp Lys Ser Ser Ser Gly Lys Lys
                325                 330                 335
Thr Ala Lys Thr Asn Thr Asn Glu Phe Leu Ile Asp Val Asp Lys Gly
            340                 345                 350
Glu Asn Tyr Cys Phe Ser Val Gln Ala Val Ile Pro Ser Arg Thr Val
        355                 360                 365
Asn Arg Lys Ser Thr Asp Ser Pro Val Glu Cys Met Gly Gln Glu Lys
    370                 375                 380
Gly Glu Phe Arg Glu Asn Trp Val Asn Val Ile Ser Asp Leu Lys Lys
385                 390                 395                 400
Ile Glu Asp Leu Ile Gln Ser Met His Ile Asp Ala Thr Leu Tyr Thr
                405                 410                 415
Glu Ser Asp Val His Pro Ser Cys Lys Val Thr Ala Met Lys Cys Phe
            420                 425                 430
Leu Leu Glu Leu Gln Val Ile Ser Leu Glu Ser Gly Asp Ala Ser Ile
        435                 440                 445
His Asp Thr Val Glu Asn Leu Ile Ile Leu Ala Asn Asn Ser Leu Ser
    450                 455                 460
Ser Asn Gly Asn Val Thr Glu Ser Gly Cys Lys Glu Cys Glu Glu Leu
465                 470                 475                 480
Glu Glu Lys Asn Ile Lys Glu Phe Leu Gln Ser Phe Val His Ile Val
                485                 490                 495
Gln Met Phe Ile Asn Thr Ser
            500

<210> SEQ ID NO 79
<211> LENGTH: 1188
```

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 79

```
atgaagtggg tgaccttcat cagcctgctg ttcctgttct ccagcgccta ctcccagggc      60
caggacaggc acatgatccg gatgaggcag ctcatcgaca tcgtcgacca gctgaagaac     120
tacgtgaacg acctggtgcc cgagtttctg cctgccccg aggacgtgga gaccaactgc      180
gagtggtccg ccttctcctg ctttcagaag gcccagctga gtccgccaa caccggcaac      240
aacgagcgga tcatcaacgt gagcatcaag aagctgaagc ggaagcctcc ctccacaaac    300
gccggcagga ggcagaagca caggctgacc tgccccagct gtgactccta cgagaagaag    360
cccccccaagg agttcctgga gaggttcaag tccctgctgc agaagatgat ccatcagcac  420
ctgtcctcca ggacccacgg ctccgaggac tccattacat gccccctcc catgagcgtg     480
gagcacgccg acatctgggt gaagagctat agcctctaca gccgggagag gtatatctgt    540
aacagcggct tcaagaggaa ggccggcacc agcagcctca ccgagtgcgt gctgaataag    600
gctaccaacg tggctcactg gacaacaccc tctttaaagt gcatccgggg cggtggagga    660
tccggaggag gtggctccgg cggcggagga tctgatcccg ccggcctctt ggacctgcgg    720
cagggcatgt ttgcgcagct ggtggcccaa aatgttctgc tgatcgatgg ccccctgagc    780
tggtacagtg acccaggcct ggcaggcgtg tccctgacgg ggggcctgag ctacaaagag    840
gacacgaagg agctggtggt ggccaaggct ggagtctact atgtcttctt tcaactagag    900
ctgcggcgcg tggtggccgg cgagggctca ggctccgttt cacttgcgct gcacctgcag    960
ccactgcgct ctgctgctgg ggccgccgcc tggctttga ccgtggacct gccacccgcc    1020
tcctccgagg ctcggaactc ggccttcggt ttccagggcc gcttgctgca cctgagtgcc   1080
ggccagcgcc tgggcgtcca tcttcacact gaggccaggg cacgccatgc ctggcagctt   1140
acccagggcg ccacagtctt gggactcttc cgggtgaccc ccgaaatc                1188
```

<210> SEQ ID NO 80
<211> LENGTH: 396
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 80

```
Met Lys Trp Val Thr Phe Ile Ser Leu Leu Phe Leu Phe Ser Ser Ala
1               5                   10                  15

Tyr Ser Gln Gly Gln Asp Arg His Met Ile Arg Met Arg Gln Leu Ile
            20                  25                  30

Asp Ile Val Asp Gln Leu Lys Asn Tyr Val Asn Asp Leu Val Pro Glu
        35                  40                  45

Phe Leu Pro Ala Pro Glu Asp Val Glu Thr Asn Cys Glu Trp Ser Ala
    50                  55                  60

Phe Ser Cys Phe Gln Lys Ala Gln Leu Lys Ser Ala Asn Thr Gly Asn
65                  70                  75                  80

Asn Glu Arg Ile Ile Asn Val Ser Ile Lys Lys Leu Lys Arg Lys Pro
                85                  90                  95

Pro Ser Thr Asn Ala Gly Arg Arg Gln Lys His Arg Leu Thr Cys Pro
            100                 105                 110
```

```
Ser Cys Asp Ser Tyr Glu Lys Lys Pro Pro Lys Glu Phe Leu Glu Arg
        115                 120                 125

Phe Lys Ser Leu Leu Gln Lys Met Ile His Gln His Leu Ser Ser Arg
    130                 135                 140

Thr His Gly Ser Glu Asp Ser Ile Thr Cys Pro Pro Met Ser Val
145                 150                 155                 160

Glu His Ala Asp Ile Trp Val Lys Ser Tyr Ser Leu Tyr Ser Arg Glu
                165                 170                 175

Arg Tyr Ile Cys Asn Ser Gly Phe Lys Arg Lys Ala Gly Thr Ser Ser
                180                 185                 190

Leu Thr Glu Cys Val Leu Asn Lys Ala Thr Asn Val Ala His Trp Thr
        195                 200                 205

Thr Pro Ser Leu Lys Cys Ile Arg Gly Gly Gly Ser Gly Gly Gly
    210                 215                 220

Gly Ser Gly Gly Gly Ser Asp Pro Ala Gly Leu Leu Asp Leu Arg
225                 230                 235                 240

Gln Gly Met Phe Ala Gln Leu Val Ala Gln Asn Val Leu Leu Ile Asp
                245                 250                 255

Gly Pro Leu Ser Trp Tyr Ser Asp Pro Gly Leu Ala Gly Val Ser Leu
        260                 265                 270

Thr Gly Gly Leu Ser Tyr Lys Glu Asp Thr Lys Glu Leu Val Val Ala
    275                 280                 285

Lys Ala Gly Val Tyr Tyr Val Phe Phe Gln Leu Glu Leu Arg Arg Val
    290                 295                 300

Val Ala Gly Glu Gly Ser Gly Ser Val Ser Leu Ala Leu His Leu Gln
305                 310                 315                 320

Pro Leu Arg Ser Ala Ala Gly Ala Ala Ala Leu Ala Leu Thr Val Asp
                325                 330                 335

Leu Pro Pro Ala Ser Ser Glu Ala Arg Asn Ser Ala Phe Gly Phe Gln
        340                 345                 350

Gly Arg Leu Leu His Leu Ser Ala Gly Gln Arg Leu Gly Val His Leu
    355                 360                 365

His Thr Glu Ala Arg Ala Arg His Ala Trp Gln Leu Thr Gln Gly Ala
    370                 375                 380

Thr Val Leu Gly Leu Phe Arg Val Thr Pro Glu Ile
385                 390                 395
```

<210> SEQ ID NO 81
<211> LENGTH: 1509
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81

```
atgaagtggg tgaccttcat cagcctgctg ttcctgttct ccagcgccta ctccgattgc      60
gacatcgagg gcaaggacgg caagcagtac gagagcgtgc tgatggtgtc catcgaccag     120
ctgctggaca gcatgaagga gatcggctcc aactgcctca caacgagtt caacttcttc     180 aagcggcaca tctgcgacgc caacaaggag ggcatgttcc tgttcagggc cgccaggaaa     240
ctgcggcagt cctgaagat gaactccacc ggcgacttcg acctgcacct gctgaaggtg     300
tccgagggca ccaccatcct gctgaactgc accggacagg tgaagggccg gaaacctgct     360
gctctgggag aggcccaacc caccaagagc ctggaggaga caagtccct gaaggagcag     420
```

-continued

```
aagaagctga acgacctgtg cttcctgaag aggctgctgc aggagatcaa gacctgctgg    480
aacaagatcc tgatgggcac caaggagcat agcggcacaa ccaacacagt cgctgcctat    540
aacctcactt ggaagagcac caacttcaaa accatcctcg aatgggaacc caaacccgtt    600
aaccaagttt acaccgtgca gatcagcacc aagtccggcg actggaagtc caaatgtttc    660
tataccaccg acaccgagtg cgatctcacc gatgagatcg tgaaagatgt gaaacagacc    720
tacctcgccc gggtgtttag ctaccccgcc ggcaatgtgg agagcactgg ttccgctggc    780
gagcctttat acgagaacag ccccgaattt acccttacc tcgagaccaa tttaggacag    840
cccaccatcc aaagctttga gcaagttggc acaaaggtga atgtgacagt ggaggacgag    900
cggactttag tgcggcggaa caacaccttt ctcagcctcc gggatgtgtt cggcaaagat    960
ttaatctaca cactgtatta ctggaagtcc tcttcctccg caagaagac agctaaaacc    1020 aacacaaacg agttttaat cgacgtggat aaaggcgaaa actactgttt cagcgtgcaa    1080
gctgtgatcc cctcccggac cgtgaatagg aaaagcaccg atagcccgt tgagtgcatg    1140 ggccaagaaa agggcgagtt ccgggagaac tgggtgaacg tcatcagcga tttaaagaag    1200
atcgaagatt taattcagtc catgcatatc gacgccactt tatacacaga atccgacgtg    1260 caccccctctt gtaaggtgac cgccatgaaa tgttttttac tggagctgca agttatctct    1320
ttagagagcg gagacgctag catccacgac accgtggaga atttaatcat tttagccaat    1380
aactctttat ccagcaacgg caacgtgaca gagtccggct gcaaggagtg cgaagagctg    1440
gaggagaaga acatcaagga gtttctgcaa tcctttgtgc acattgtcca gatgttcatc    1500
aatacctcc                                                           1509
```

<210> SEQ ID NO 82
<211> LENGTH: 503
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

```
Met Lys Trp Val Thr Phe Ile Ser Leu Leu Phe Leu Phe Ser Ser Ala
1               5                   10                  15

Tyr Ser Asp Cys Asp Ile Glu Gly Lys Asp Gly Lys Gln Tyr Glu Ser
            20                  25                  30

Val Leu Met Val Ser Ile Asp Gln Leu Leu Asp Ser Met Lys Glu Ile
        35                  40                  45

Gly Ser Asn Cys Leu Asn Asn Glu Phe Asn Phe Phe Lys Arg His Ile
    50                  55                  60

Cys Asp Ala Asn Lys Glu Gly Met Phe Leu Phe Arg Ala Ala Arg Lys
65                  70                  75                  80

Leu Arg Gln Phe Leu Lys Met Asn Ser Thr Gly Asp Phe Asp Leu His
                85                  90                  95

Leu Leu Lys Val Ser Glu Gly Thr Thr Ile Leu Leu Asn Cys Thr Gly
            100                 105                 110

Gln Val Lys Gly Arg Lys Pro Ala Ala Leu Gly Glu Ala Gln Pro Thr
        115                 120                 125

Lys Ser Leu Glu Glu Asn Lys Ser Leu Lys Glu Gln Lys Lys Leu Asn
    130                 135                 140

Asp Leu Cys Phe Leu Lys Arg Leu Leu Gln Glu Ile Lys Thr Cys Trp
145                 150                 155                 160
```

```
Asn Lys Ile Leu Met Gly Thr Lys Glu His Ser Gly Thr Thr Asn Thr
            165                 170                 175

Val Ala Ala Tyr Asn Leu Thr Trp Lys Ser Thr Asn Phe Lys Thr Ile
        180                 185                 190

Leu Glu Trp Glu Pro Lys Pro Val Asn Gln Val Tyr Thr Val Gln Ile
    195                 200                 205

Ser Thr Lys Ser Gly Asp Trp Lys Ser Lys Cys Phe Tyr Thr Thr Asp
210                 215                 220

Thr Glu Cys Asp Leu Thr Asp Glu Ile Val Lys Asp Val Lys Gln Thr
225                 230                 235                 240

Tyr Leu Ala Arg Val Phe Ser Tyr Pro Ala Gly Asn Val Glu Ser Thr
                245                 250                 255

Gly Ser Ala Gly Glu Pro Leu Tyr Glu Asn Ser Pro Glu Phe Thr Pro
            260                 265                 270

Tyr Leu Glu Thr Asn Leu Gly Gln Pro Thr Ile Gln Ser Phe Glu Gln
        275                 280                 285

Val Gly Thr Lys Val Asn Val Thr Val Glu Asp Glu Arg Thr Leu Val
    290                 295                 300

Arg Arg Asn Asn Thr Phe Leu Ser Leu Arg Asp Val Phe Gly Lys Asp
305                 310                 315                 320

Leu Ile Tyr Thr Leu Tyr Tyr Trp Lys Ser Ser Ser Gly Lys Lys
                325                 330                 335

Thr Ala Lys Thr Asn Thr Asn Glu Phe Leu Ile Asp Val Asp Lys Gly
            340                 345                 350

Glu Asn Tyr Cys Phe Ser Val Gln Ala Val Ile Pro Ser Arg Thr Val
        355                 360                 365

Asn Arg Lys Ser Thr Asp Ser Pro Val Glu Cys Met Gly Gln Glu Lys
370                 375                 380

Gly Glu Phe Arg Glu Asn Trp Val Asn Val Ile Ser Asp Leu Lys Lys
385                 390                 395                 400

Ile Glu Asp Leu Ile Gln Ser Met His Ile Asp Ala Thr Leu Tyr Thr
                405                 410                 415

Glu Ser Asp Val His Pro Ser Cys Lys Val Thr Ala Met Lys Cys Phe
            420                 425                 430

Leu Leu Glu Leu Gln Val Ile Ser Leu Glu Ser Gly Asp Ala Ser Ile
        435                 440                 445

His Asp Thr Val Glu Asn Leu Ile Ile Leu Ala Asn Asn Ser Leu Ser
450                 455                 460

Ser Asn Gly Asn Val Thr Glu Ser Gly Cys Lys Glu Cys Glu Glu Leu
465                 470                 475                 480

Glu Glu Lys Asn Ile Lys Glu Phe Leu Gln Ser Phe Val His Ile Val
                485                 490                 495

Gln Met Phe Ile Asn Thr Ser
            500
```

<210> SEQ ID NO 83
<211> LENGTH: 1110
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83
atgaagtggg tgaccttcat cagcctgctg ttcctgttct ccagcgccta ctccatcccc    60

```
cccatgtgc aaaagagcgt gaacaacgat atgatcgtga ccgacaacaa cggcgccgtg    120
aagtttcccc agctctgcaa gttctgcgat gtcaggttca gcacctgcga taatcagaag    180
tcctgcatgt ccaactgcag catcacctcc atctgcgaga agccccaaga agtgtgcgtg    240
gccgtgtggc ggaaaaatga cgagaacatc accctggaga ccgtgtgtca cgaccccaag    300
ctcccttatc acgacttcat tctggaggac gctgcctccc ccaaatgcat catgaaggag    360
aagaagaagc ccggagagac cttctttatg tgttcctgta gcagcgacga gtgtaacgac    420
aacatcatct tcagcgaaga gtacaacacc agcaaccctg atggaggtgg cggatccgga    480
ggtggaggtt ctggtggagg tgggagtatt cctccccacg tgcagaagag cgtgaataat    540
gacatgatcg tgaccgataa caatggcgcc gtgaaatttc cccagctgtg caaattctgc    600
gatgtgaggt tttccacctg cgacaaccag aagtcctgta tgagcaactg ctccatcacc    660
tccatctgtg agaagcctca ggaggtgtgc gtggctgtct ggcggaagaa tgacgagaat    720
atcacccctg gaaaccgtct gccacgatcc caagctgccct accacgattt catcctggaa    780
gacgccgcca gccctaagtg catcatgaaa gagaaaaaga gcctggcga gaccttttc    840 atgtgctcct gcagcagcga cgaatgcaac gacaatatca tctttagcga ggaatacaat    900
accagcaacc ccgacattac atgccccct cccatgagcg tggagcacgc cgacatctgg    960
gtgaagagct atagcctcta cagccgggag aggtatatct gtaacagcgg cttcaagagg    1020
aaggccggca ccagcagcct caccgagtgc gtgctgaata aggctaccaa cgtggctcac    1080
tggacaacac cctctttaaa gtgcatccgg                                     1110
```

<210> SEQ ID NO 84
<211> LENGTH: 370
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 84

```
Met Lys Trp Val Thr Phe Ile Ser Leu Leu Phe Leu Phe Ser Ser Ala
1               5                   10                  15

Tyr Ser Ile Pro Pro His Val Gln Lys Ser Val Asn Asn Asp Met Ile
            20                  25                  30

Val Thr Asp Asn Asn Gly Ala Val Lys Phe Pro Gln Leu Cys Lys Phe
        35                  40                  45

Cys Asp Val Arg Phe Ser Thr Cys Asp Asn Gln Lys Ser Cys Met Ser
    50                  55                  60

Asn Cys Ser Ile Thr Ser Ile Cys Glu Lys Pro Gln Glu Val Cys Val
65                  70                  75                  80

Ala Val Trp Arg Lys Asn Asp Glu Asn Ile Thr Leu Glu Thr Val Cys
                85                  90                  95

His Asp Pro Lys Leu Pro Tyr His Asp Phe Ile Leu Glu Asp Ala Ala
            100                 105                 110

Ser Pro Lys Cys Ile Met Lys Glu Lys Lys Lys Pro Gly Glu Thr Phe
        115                 120                 125

Phe Met Cys Ser Cys Ser Ser Asp Glu Cys Asn Asp Asn Ile Ile Phe
    130                 135                 140

Ser Glu Glu Tyr Asn Thr Ser Asn Pro Asp Gly Gly Gly Gly Ser Gly
145                 150                 155                 160

Gly Gly Gly Ser Gly Gly Gly Gly Ser Ile Pro Pro His Val Gln Lys
```

```
                165                 170                 175
Ser Val Asn Asn Asp Met Ile Val Thr Asp Asn Asn Gly Ala Val Lys
            180                 185                 190

Phe Pro Gln Leu Cys Lys Phe Cys Asp Val Arg Phe Ser Thr Cys Asp
        195                 200                 205

Asn Gln Lys Ser Cys Met Ser Asn Cys Ser Ile Thr Ser Ile Cys Glu
        210                 215                 220

Lys Pro Gln Glu Val Cys Val Ala Val Trp Arg Lys Asn Asp Glu Asn
225                 230                 235                 240

Ile Thr Leu Glu Thr Val Cys His Asp Pro Lys Leu Pro Tyr His Asp
                245                 250                 255

Phe Ile Leu Glu Asp Ala Ala Ser Pro Lys Cys Ile Met Lys Glu Lys
            260                 265                 270

Lys Lys Pro Gly Glu Thr Phe Phe Met Cys Ser Cys Ser Ser Asp Glu
        275                 280                 285

Cys Asn Asp Asn Ile Ile Phe Ser Glu Glu Tyr Asn Thr Ser Asn Pro
        290                 295                 300

Asp Ile Thr Cys Pro Pro Met Ser Val Glu His Ala Asp Ile Trp
305                 310                 315                 320

Val Lys Ser Tyr Ser Leu Tyr Ser Arg Glu Arg Tyr Ile Cys Asn Ser
                325                 330                 335

Gly Phe Lys Arg Lys Ala Gly Thr Ser Ser Leu Thr Glu Cys Val Leu
            340                 345                 350

Asn Lys Ala Thr Asn Val Ala His Trp Thr Thr Pro Ser Leu Lys Cys
        355                 360                 365

Ile Arg
    370

<210> SEQ ID NO 85
<211> LENGTH: 1914
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85
atgaagtggg tgaccttcat cagcctgctg ttcctgttct ccagcgccta ctccatcccc      60
ccccatgtgc aaaagagcgt gaacaacgat atgatcgtga ccgacaacaa cggcgccgtg     120
aagtttcccc agctctgcaa gttctgcgat gtcaggttca gcacctgcga taatcagaag     180
tcctgcatgt ccaactgcag catcacctcc atctgcgaga agccccaaga agtgtgcgtg     240
gccgtgtggc ggaaaaatga cgagaacatc accctggaga ccgtgtgtca cgaccccaag     300
ctcccttatc acgacttcat tctggaggac gctgcctccc ccaaatgcat catgaaggag     360
aagaagaagc ccggagagac cttctttatg tgttcctgta gcagcgacga gtgtaacgac     420
aacatcatct tcagcgaaga gtacaacacc agcaaccctg atgaggtggc ggatccgga      480 ggtggaggtt ctggtggagg tgggagtatt cctccccacg tgcagaagag cgtgaataat     540
gacatgatcg tgaccgataa caatggcgcc gtgaaatttc cccagctgtg caaattctgc     600
gatgtgaggt tttccacctg cgacaaccag aagtcctgta tgagcaactg ctccatcacc     660
tccatctgtg agaagcctca ggaggtgtgc gtggctgtct ggcggaagaa tgacgagaat     720
atcaccctgg aaaccgtctg ccacgatccc aagctgccct accacgattt catcctggaa     780
gacgccgcca gccctaagtg catcatgaaa gagaaaaaga gcctggcga gacctttttc     840
```

```
atgtgctcct gcagcagcga cgaatgcaac gacaatatca tctttagcga ggaatacaat    900
accagcaacc ccgacagcgg cacaaccaac acagtcgctg cctataacct cacttggaag    960
agcaccaact tcaaaaccat cctcgaatgg gaacccaaac ccgttaacca agtttacacc   1020
gtgcagatca gcaccaagtc cggcgactgg aagtccaaat gtttctatac caccgacacc   1080
gagtgcgatc tcaccgatga gatcgtgaaa gatgtgaaac agacctacct cgcccgggtg   1140
tttagctacc ccgccggcaa tgtggagagc actggttccg ctggcgagcc tttatacgag   1200
aacagccccg aatttacccc ttacctcgag accaatttag gacagcccac catccaaagc   1260
tttgagcaag ttggcacaaa ggtgaatgtg acagtggagg acgagcggac tttagtgcgg   1320
cggaacaaca cctttctcag cctccgggat gtgttcggca agatttaat  ctacacactg   1380
tattactgga agtcctcttc ctccggcaag aagacagcta aaaccaacac aaacgagttt   1440
ttaatcgacg tggataaagg cgaaaactac tgtttcagcg tgcaagctgt gatcccctcc   1500
cggaccgtga ataggaaaag caccgatagc cccgttgagt gcatgggcca agaaaagggc   1560
gagttccggg agaactgggt gaacgtcatc agcgatttaa agaagatcga agatttaatt   1620
cagtccatgc atatcgacgc cactttatac acagaatccg acgtgcaccc ctcttgtaag   1680
gtgaccgcca tgaaatgttt tttactggag ctgcaagtta tctctttaga gagcggagac   1740
gctagcatcc acgacaccgt ggagaattta atcattttag ccaataactc tttatccagc   1800
aacggcaacg tgacagagtc cggctgcaag gagtgcgaag agctggagga gaagaacatc   1860
aaggagtttc tgcaatcctt tgtgcacatt gtccagatgt tcatcaatac ctcc         1914
```

<210> SEQ ID NO 86
<211> LENGTH: 638
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 86

```
Met Lys Trp Val Thr Phe Ile Ser Leu Leu Phe Leu Phe Ser Ser Ala
1               5                   10                  15

Tyr Ser Ile Pro Pro His Val Gln Lys Ser Val Asn Asn Asp Met Ile
            20                  25                  30

Val Thr Asp Asn Asn Gly Ala Val Lys Phe Pro Gln Leu Cys Lys Phe
        35                  40                  45

Cys Asp Val Arg Phe Ser Thr Cys Asp Asn Gln Lys Ser Cys Met Ser
    50                  55                  60

Asn Cys Ser Ile Thr Ser Ile Cys Glu Lys Pro Gln Glu Val Cys Val
65                  70                  75                  80

Ala Val Trp Arg Lys Asn Asp Glu Asn Ile Thr Leu Glu Thr Val Cys
                85                  90                  95

His Asp Pro Lys Leu Pro Tyr His Asp Phe Ile Leu Glu Asp Ala Ala
            100                 105                 110

Ser Pro Lys Cys Ile Met Lys Glu Lys Lys Pro Gly Glu Thr Phe Phe
        115                 120                 125

Phe Met Cys Ser Cys Ser Ser Asp Glu Cys Asn Asp Asn Ile Ile Phe
    130                 135                 140

Ser Glu Glu Tyr Asn Thr Ser Asn Pro Asp Gly Gly Gly Ser Gly
145                 150                 155                 160

Gly Gly Gly Ser Gly Gly Gly Gly Ser Ile Pro Pro His Val Gln Lys
```

```
                165                 170                 175
Ser Val Asn Asn Asp Met Ile Val Thr Asp Asn Asn Gly Ala Val Lys
            180                 185                 190
Phe Pro Gln Leu Cys Lys Phe Cys Asp Val Arg Phe Ser Thr Cys Asp
        195                 200                 205
Asn Gln Lys Ser Cys Met Ser Asn Cys Ser Ile Thr Ser Ile Cys Glu
    210                 215                 220
Lys Pro Gln Glu Val Cys Val Ala Val Trp Arg Lys Asn Asp Glu Asn
225                 230                 235                 240
Ile Thr Leu Glu Thr Val Cys His Asp Pro Lys Leu Pro Tyr His Asp
                245                 250                 255
Phe Ile Leu Glu Asp Ala Ala Ser Pro Lys Cys Ile Met Lys Glu Lys
            260                 265                 270
Lys Lys Pro Gly Glu Thr Phe Phe Met Cys Ser Cys Ser Ser Asp Glu
        275                 280                 285
Cys Asn Asp Asn Ile Ile Phe Ser Glu Glu Tyr Asn Thr Ser Asn Pro
    290                 295                 300
Asp Ser Gly Thr Thr Asn Thr Val Ala Ala Tyr Asn Leu Thr Trp Lys
305                 310                 315                 320
Ser Thr Asn Phe Lys Thr Ile Leu Glu Trp Glu Pro Lys Pro Val Asn
                325                 330                 335
Gln Val Tyr Thr Val Gln Ile Ser Thr Lys Ser Gly Asp Trp Lys Ser
            340                 345                 350
Lys Cys Phe Tyr Thr Thr Asp Thr Glu Cys Asp Leu Thr Asp Glu Ile
        355                 360                 365
Val Lys Asp Val Lys Gln Thr Tyr Leu Ala Arg Val Phe Ser Tyr Pro
    370                 375                 380
Ala Gly Asn Val Glu Ser Thr Gly Ser Ala Gly Glu Pro Leu Tyr Glu
385                 390                 395                 400
Asn Ser Pro Glu Phe Thr Pro Tyr Leu Glu Thr Asn Leu Gly Gln Pro
                405                 410                 415
Thr Ile Gln Ser Phe Glu Gln Val Gly Thr Lys Val Asn Val Thr Val
            420                 425                 430
Glu Asp Glu Arg Thr Leu Val Arg Arg Asn Asn Thr Phe Leu Ser Leu
        435                 440                 445
Arg Asp Val Phe Gly Lys Asp Leu Ile Tyr Thr Leu Tyr Tyr Trp Lys
    450                 455                 460
Ser Ser Ser Ser Gly Lys Lys Thr Ala Lys Thr Asn Thr Asn Glu Phe
465                 470                 475                 480
Leu Ile Asp Val Asp Lys Gly Glu Asn Tyr Cys Phe Ser Val Gln Ala
                485                 490                 495
Val Ile Pro Ser Arg Thr Val Asn Arg Lys Ser Thr Asp Ser Pro Val
            500                 505                 510
Glu Cys Met Gly Gln Glu Lys Gly Glu Phe Arg Glu Asn Trp Val Asn
        515                 520                 525
Val Ile Ser Asp Leu Lys Lys Ile Glu Asp Leu Ile Gln Ser Met His
    530                 535                 540
Ile Asp Ala Thr Leu Tyr Thr Glu Ser Asp Val His Pro Ser Cys Lys
545                 550                 555                 560
Val Thr Ala Met Lys Cys Phe Leu Leu Glu Leu Gln Val Ile Ser Leu
                565                 570                 575
Glu Ser Gly Asp Ala Ser Ile His Asp Thr Val Glu Asn Leu Ile Ile
            580                 585                 590
```

Leu Ala Asn Asn Ser Leu Ser Ser Asn Gly Asn Val Thr Glu Ser Gly
            595                 600                 605

Cys Lys Glu Cys Glu Glu Leu Glu Glu Lys Asn Ile Lys Glu Phe Leu
        610                 615                 620

Gln Ser Phe Val His Ile Val Gln Met Phe Ile Asn Thr Ser
625                 630                 635

<210> SEQ ID NO 87
<211> LENGTH: 1245
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87
atgaagtggg tgaccttcat cagcctgctg ttcctgttct ccagcgccta ctcccagggc      60
caggacaggc acatgatccg gatgaggcag ctcatcgaca tcgtcgacca gctgaagaac     120
tacgtgaacg acctggtgcc cgagtttctg cctgccccg aggacgtgga gaccaactgc     180
gagtggtccg ccttctcctg ctttcagaag gcccagctga agtccgccaa caccggcaac     240
aacgagcgga tcatcaacgt gagcatcaag aagctgaagc ggaagcctcc ctccacaaac     300
gccggcagga ggcagaagca caggctgacc tgccccagct gtgactccta cgagaagaag     360 cccccaagg agttcctgga gaggttcaag tccctgctgc agaagatgat ccatcagcac     420
ctgtcctcca ggacccacgg ctccgaggac tccattacat gccccctcc catgagcgtg     480 gagcacgccg acatctgggt gaagagctat agcctctaca gccgggagag gtatatctgt     540
aacagcggct tcaagaggaa ggccggcacc agcagcctca ccgagtgcgt gctgaataag     600
gctaccaacg tggctcactg gacaacaccc tctttaaagt gcatccgggg cggtggagga     660
tccggaggag gtggctccgg cggcggagga tctcgcgagg gtcccgagct ttcgcccgac     720
gatcccgccg gcctcttgga cctgcggcag ggcatgtttg cgcagctggt ggcccaaaat     780
gttctgctga tcgatgggcc cctgagctgg tacagtgacc caggcctggc aggcgtgtcc     840
ctgacggggg gcctgagcta caagaggac acgaaggagc tggtggtggc caaggctgga     900
gtctactatg tcttctttca actagagctg cggcgcgtgg tggccggcga gggctcaggc     960
tccgtttcac ttgcgctgca cctgcagcca ctgcgctctg ctgctgggc cgccgccctg    1020 gctttgaccg tggacctgcc acccgcctcc tccgaggctc ggaactcggc cttcggtttc    1080
cagggccgct tgctgcacct gagtgccggc cagcgcctgg gcgtccatct tcacactgag    1140
gccagggcac gccatgcctg gcagcttacc cagggcgcca cagtcttggg actcttccgg    1200 gtgaccccg aaatcccagc cggactccct tcaccgaggt cggaa                     1245

<210> SEQ ID NO 88
<211> LENGTH: 415
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Met Lys Trp Val Thr Phe Ile Ser Leu Leu Phe Leu Phe Ser Ser Ala
1               5                   10                  15

Tyr Ser Gln Gly Gln Asp Arg His Met Ile Arg Met Arg Gln Leu Ile
                20                  25                  30

-continued

Asp Ile Val Asp Gln Leu Lys Asn Tyr Val Asn Asp Leu Val Pro Glu
              35                  40                  45

Phe Leu Pro Ala Pro Glu Asp Val Glu Thr Asn Cys Glu Trp Ser Ala
 50                  55                  60

Phe Ser Cys Phe Gln Lys Ala Gln Leu Lys Ser Ala Asn Thr Gly Asn
 65                  70                  75                  80

Asn Glu Arg Ile Ile Asn Val Ser Ile Lys Lys Leu Lys Arg Lys Pro
                  85                  90                  95

Pro Ser Thr Asn Ala Gly Arg Arg Gln Lys His Arg Leu Thr Cys Pro
             100                 105                 110

Ser Cys Asp Ser Tyr Glu Lys Lys Pro Pro Lys Glu Phe Leu Glu Arg
             115                 120                 125

Phe Lys Ser Leu Leu Gln Lys Met Ile His Gln His Leu Ser Ser Arg
130                 135                 140

Thr His Gly Ser Glu Asp Ser Ile Thr Cys Pro Pro Met Ser Val
145                 150                 155                 160

Glu His Ala Asp Ile Trp Val Lys Ser Tyr Ser Leu Tyr Ser Arg Glu
                 165                 170                 175

Arg Tyr Ile Cys Asn Ser Gly Phe Lys Arg Lys Ala Gly Thr Ser Ser
             180                 185                 190

Leu Thr Glu Cys Val Leu Asn Lys Ala Thr Asn Val Ala His Trp Thr
        195                 200                 205

Thr Pro Ser Leu Lys Cys Ile Arg Gly Gly Gly Ser Gly Gly Gly
210                 215                 220

Gly Ser Gly Gly Gly Ser Arg Glu Gly Pro Glu Leu Ser Pro Asp
225                 230                 235                 240

Asp Pro Ala Gly Leu Leu Asp Leu Arg Gln Gly Met Phe Ala Gln Leu
             245                 250                 255

Val Ala Gln Asn Val Leu Leu Ile Asp Gly Pro Leu Ser Trp Tyr Ser
             260                 265                 270

Asp Pro Gly Leu Ala Gly Val Ser Leu Thr Gly Gly Leu Ser Tyr Lys
        275                 280                 285

Glu Asp Thr Lys Glu Leu Val Val Ala Lys Ala Gly Val Tyr Tyr Val
        290                 295                 300

Phe Phe Gln Leu Glu Leu Arg Arg Val Val Ala Gly Glu Gly Ser Gly
305                 310                 315                 320

Ser Val Ser Leu Ala Leu His Leu Gln Pro Leu Arg Ser Ala Ala Gly
             325                 330                 335

Ala Ala Ala Leu Ala Leu Thr Val Asp Leu Pro Pro Ala Ser Ser Glu
        340                 345                 350

Ala Arg Asn Ser Ala Phe Gly Phe Gln Gly Arg Leu Leu His Leu Ser
        355                 360                 365

Ala Gly Gln Arg Leu Gly Val His Leu His Thr Glu Ala Arg Ala Arg
370                 375                 380

His Ala Trp Gln Leu Thr Gln Gly Ala Thr Val Leu Gly Leu Phe Arg
385                 390                 395                 400

Val Thr Pro Glu Ile Pro Ala Gly Leu Pro Ser Pro Arg Ser Glu
             405                 410                 415

<210> SEQ ID NO 89
<211> LENGTH: 1914
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 89

```
atgaagtggg tgaccttcat cagcctgctg ttcctgttct ccagcgccta ctccatcccc        60
ccccatgtgc aaaagagcgt gaacaacgat atgatcgtga ccgacaacaa cggcgccgtg       120
aagtttcccc agctctgcaa gttctgcgat gtcaggttca gcacctgcga taatcagaag       180
tcctgcatgt ccaactgcag catcacctcc atctgcgaga agcccaaga agtgtgcgtg        240
gccgtgtggc ggaaaaatga cgagaacatc accctggaga ccgtgtgtca cgaccccaag       300
ctcccttatc acgacttcat tctggaggac gctgcctccc ccaaatgcat catgaaggag       360
aagaagaagc ccggagagac cttctttatg tgttcctgta gcagcgacga gtgtaacgac       420
aacatcatct tcagcgaaga gtacaacacc agcaaccctg atggaggtgg cggatccgga       480
ggtggaggtt ctggtggagg tgggagtatt cctccccacg tgcagaagag cgtgaataat       540
gacatgatcg tgaccgataa caatggcgcc gtgaaatttc cccagctgtg caaattctgc       600
gatgtgaggt tttccacctg cgacaaccag aagtcctgta tgagcaactg ctccatcacc       660
tccatctgtg agaagcctca ggaggtgtgc gtggctgtct ggcggaagaa tgacgagaat       720
atcaccctgg aaaccgtctg ccacgatccc aagctgccct accacgattt catcctggaa       780
gacgccgcca gccctaagtg catcatgaaa gagaaaaaga gcctggcga gaccttttc        840
atgtgctcct gcagcagcga cgaatgcaac gacaatatca tctttagcga ggaatacaat       900
accagcaacc ccgacagcgg cacaaccaac acagtcgctg cctataacct cacttggaag       960
agcaccaact tcaaaaccat cctcgaatgg gaacccaaac ccgttaacca gtttacacc       1020
gtgcagatca gcaccaagtc cggcgactgg aagtccaaat gtttctatac caccgacacc      1080
gagtgcgatc tcaccgatga gatcgtgaaa gatgtgaaac agacctacct cgcccgggtg      1140
tttagctacc ccgccggcaa tgtggagagc actggttccg ctggcgagcc tttatacgag      1200
aacagccccg aatttacccc ttacctcgag accaatttag gacagcccac catccaaagc      1260
tttgagcaag ttggcacaaa ggtgaatgtg acagtggagg acgagcggac tttagtgcgg      1320
cggaacaaca ccttctcag cctccgggat gtgttcggca agatttaat ctacacactg        1380
tattactgga gtcctcttc ctccggcaag aagacagcta aaccaacac aaacgagttt        1440
ttaatcgacg tggataaagg cgaaaactac tgtttcagcg tgcaagctgt gatcccctcc      1500
cggaccgtga ataggaaaag caccgatagc cccgttgagt gcatgggcca agaaaagggc      1560
gagttccggg agaactgggt gaacgtcatc agcgatttaa agaagatcga agatttaatt      1620
cagtccatgc atatcgacgc cactttatac acagaatccg acgtgcaccc ctcttgtaag      1680
gtgaccgcca tgaaatgttt tttactggag ctgcaagtta tctctttaga gagcggagac      1740
gctagcatcc acgacaccgt ggagaattta atcattttag ccaataactc tttatccagc      1800
aacggcaacg tgacagagtc cggctgcaag gagtgcgaag agctggagga agaacatc        1860
aaggagtttc tgcaatcctt tgtgcacatt gtccagatgt tcatcaatac ctcc            1914
```

<210> SEQ ID NO 90
<211> LENGTH: 638
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 90

```
Met Lys Trp Val Thr Phe Ile Ser Leu Leu Phe Leu Phe Ser Ser Ala
1               5                   10                  15

Tyr Ser Ile Pro Pro His Val Gln Lys Ser Val Asn Asp Met Ile
                20                  25                  30

Val Thr Asp Asn Asn Gly Ala Val Lys Phe Pro Gln Leu Cys Lys Phe
            35                  40                  45

Cys Asp Val Arg Phe Ser Thr Cys Asp Asn Gln Lys Ser Cys Met Ser
    50                  55                  60

Asn Cys Ser Ile Thr Ser Ile Cys Glu Lys Pro Gln Glu Val Cys Val
65                  70                  75                  80

Ala Val Trp Arg Lys Asn Asp Glu Asn Ile Thr Leu Glu Thr Val Cys
                85                  90                  95

His Asp Pro Lys Leu Pro Tyr His Asp Phe Ile Leu Glu Asp Ala Ala
            100                 105                 110

Ser Pro Lys Cys Ile Met Lys Glu Lys Lys Pro Gly Glu Thr Phe
    115                 120                 125

Phe Met Cys Ser Cys Ser Ser Asp Glu Cys Asn Asp Asn Ile Ile Phe
    130                 135                 140

Ser Glu Glu Tyr Asn Thr Ser Asn Pro Asp Gly Gly Gly Gly Ser Gly
145                 150                 155                 160

Gly Gly Gly Ser Gly Gly Gly Ser Ile Pro Pro His Val Gln Lys
                165                 170                 175

Ser Val Asn Asn Asp Met Ile Val Thr Asp Asn Asn Gly Ala Val Lys
            180                 185                 190

Phe Pro Gln Leu Cys Lys Phe Cys Asp Val Arg Phe Ser Thr Cys Asp
            195                 200                 205

Asn Gln Lys Ser Cys Met Ser Asn Cys Ser Ile Thr Ser Ile Cys Glu
210                 215                 220

Lys Pro Gln Glu Val Cys Val Ala Val Trp Arg Lys Asn Asp Glu Asn
225                 230                 235                 240

Ile Thr Leu Glu Thr Val Cys His Asp Pro Lys Leu Pro Tyr His Asp
            245                 250                 255

Phe Ile Leu Glu Asp Ala Ala Ser Pro Lys Cys Ile Met Lys Glu Lys
            260                 265                 270

Lys Lys Pro Gly Glu Thr Phe Phe Met Cys Ser Cys Ser Ser Asp Glu
        275                 280                 285

Cys Asn Asp Asn Ile Ile Phe Ser Glu Glu Tyr Asn Thr Ser Asn Pro
    290                 295                 300

Asp Ser Gly Thr Thr Asn Thr Val Ala Ala Tyr Asn Leu Thr Trp Lys
305                 310                 315                 320

Ser Thr Asn Phe Lys Thr Ile Leu Glu Trp Glu Pro Lys Pro Val Asn
            325                 330                 335

Gln Val Tyr Thr Val Gln Ile Ser Thr Lys Ser Gly Asp Trp Lys Ser
            340                 345                 350

Lys Cys Phe Tyr Thr Thr Asp Thr Glu Cys Asp Leu Thr Asp Glu Ile
            355                 360                 365

Val Lys Asp Val Lys Gln Thr Tyr Leu Ala Arg Val Phe Ser Tyr Pro
370                 375                 380

Ala Gly Asn Val Glu Ser Thr Gly Ser Ala Gly Glu Pro Leu Tyr Glu
385                 390                 395                 400

Asn Ser Pro Glu Phe Thr Pro Tyr Leu Glu Thr Asn Leu Gly Gln Pro
                405                 410                 415
```

```
Thr Ile Gln Ser Phe Glu Gln Val Gly Thr Lys Val Asn Val Thr Val
                420                 425                 430

Glu Asp Glu Arg Thr Leu Val Arg Arg Asn Asn Thr Phe Leu Ser Leu
            435                 440                 445

Arg Asp Val Phe Gly Lys Asp Leu Ile Tyr Thr Leu Tyr Tyr Trp Lys
        450                 455                 460

Ser Ser Ser Ser Gly Lys Lys Thr Ala Lys Thr Asn Thr Asn Glu Phe
465                 470                 475                 480

Leu Ile Asp Val Asp Lys Gly Glu Asn Tyr Cys Phe Ser Val Gln Ala
                485                 490                 495

Val Ile Pro Ser Arg Thr Val Asn Arg Lys Ser Thr Asp Ser Pro Val
            500                 505                 510

Glu Cys Met Gly Gln Glu Lys Gly Glu Phe Arg Glu Asn Trp Val Asn
        515                 520                 525

Val Ile Ser Asp Leu Lys Lys Ile Glu Asp Leu Ile Gln Ser Met His
530                 535                 540

Ile Asp Ala Thr Leu Tyr Thr Glu Ser Asp Val His Pro Ser Cys Lys
545                 550                 555                 560

Val Thr Ala Met Lys Cys Phe Leu Leu Glu Leu Gln Val Ile Ser Leu
                565                 570                 575

Glu Ser Gly Asp Ala Ser Ile His Asp Thr Val Glu Asn Leu Ile Ile
            580                 585                 590

Leu Ala Asn Asn Ser Leu Ser Ser Asn Gly Asn Val Thr Glu Ser Gly
        595                 600                 605

Cys Lys Glu Cys Glu Glu Leu Glu Glu Lys Asn Ile Lys Glu Phe Leu
    610                 615                 620

Gln Ser Phe Val His Ile Val Gln Met Phe Ile Asn Thr Ser
625                 630                 635

<210> SEQ ID NO 91
<211> LENGTH: 1509
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91
atgaagtggg tgaccttcat cagcctgctg ttcctgttct ccagcgccta ctccatcccc    60
ccccatgtgc aaaagagcgt gaacaacgat atgatcgtga ccgacaacaa cggcgccgtg   120
aagtttcccc agctctgcaa gttctgcgat gtcaggttca gcacctgcga taatcagaag   180
tcctgcatgt ccaactgcag catcaccctcc atctgcgaga agccccaaga agtgtgcgtg   240
gccgtgtggc ggaaaaatga cgagaacatc accctggaga ccgtgtgtca cgaccccaag   300
ctcccttatc acgacttcat tctggaggac gctgcctccc ccaaatgcat catgaaggag   360
aagaagaagc ccggagagac cttctttatg tgttcctgta gcagcgacga gtgtaacgac   420
aacatcatct tcagcgaaga gtacaacacc agcaaccctg atggaggtgg cggatccgga   480
ggtggaggtt ctggtggagg tgggagtatt cctccccacg tgcagaagag cgtgaataat   540
gacatgatcg tgaccgataa caatggcgcc gtgaaatttc cccagctgtg caaattctgc   600
gatgtgaggt tttccacctg cgacaaccag aagtcctgta tgagcaactg ctccatcacc   660
tccatctgtg agaagcctca ggaggtgtgc gtggctgtct ggcggaagaa tgacgagaat   720
atcaccctgg aaaccgtctg ccacgatccc aagctgccct accacgattt catcctggaa   780
```

```
gacgccgcca gccctaagtg catcatgaaa gagaaaaaga agcctggcga gaccttttc      840
atgtgctcct gcagcagcga cgaatgcaac gacaatatca tctttagcga ggaatacaat      900
accagcaacc ccgacattac atgccccct cccatgagcg tggagcacgc cgacatctgg       960
gtgaagagct atagcctcta cagccgggag aggtatatct gtaacagcgg cttcaagagg      1020
aaggccggca ccagcagcct caccgagtgc gtgctgaata aggctaccaa cgtggctcac      1080
tggacaacac cctcttttaaa gtgcatccgg cagggccagg acaggcacat gatccggatg     1140
aggcagctca tcgacatcgt cgaccagctg aagaactacg tgaacgacct ggtgcccgag      1200
tttctgcctg cccccgagga cgtggagacc aactgcgagt ggtccgcctt ctcctgcttt      1260
cagaaggccc agctgaagtc cgccaacacc ggcaacaacg agcggatcat caacgtgagc      1320
atcaagaagc tgaagcggaa gcctccctcc acaaacgccg gcaggaggca gaagcacagg      1380
ctgacctgcc ccagctgtga ctcctacgag aagaagcccc caaggagtt cctggagagg       1440
ttcaagtccc tgctgcagaa gatgatccat cagcacctgt cctccaggac ccacggctcc      1500
gaggactcc                                                              1509
```

<210> SEQ ID NO 92
<211> LENGTH: 503
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 92

```
Met Lys Trp Val Thr Phe Ile Ser Leu Leu Phe Leu Phe Ser Ser Ala
1               5                   10                  15

Tyr Ser Ile Pro Pro His Val Gln Lys Ser Val Asn Asn Asp Met Ile
            20                  25                  30

Val Thr Asp Asn Asn Gly Ala Val Lys Phe Pro Gln Leu Cys Lys Phe
        35                  40                  45

Cys Asp Val Arg Phe Ser Thr Cys Asp Asn Gln Lys Ser Cys Met Ser
    50                  55                  60

Asn Cys Ser Ile Thr Ser Ile Cys Glu Lys Pro Gln Glu Val Cys Val
65                  70                  75                  80

Ala Val Trp Arg Lys Asn Asp Glu Asn Ile Thr Leu Glu Thr Val Cys
                85                  90                  95

His Asp Pro Lys Leu Pro Tyr His Asp Phe Ile Leu Glu Asp Ala Ala
            100                 105                 110

Ser Pro Lys Cys Ile Met Lys Glu Lys Lys Pro Gly Glu Thr Phe
            115                 120                 125

Phe Met Cys Ser Cys Ser Ser Asp Glu Cys Asn Asp Asn Ile Ile Phe
        130                 135                 140

Ser Glu Glu Tyr Asn Thr Ser Asn Pro Asp Gly Gly Gly Ser Gly
145                 150                 155                 160

Gly Gly Gly Ser Gly Gly Gly Ser Ile Pro Pro His Val Gln Lys
                165                 170                 175

Ser Val Asn Asn Asp Met Ile Val Thr Asp Asn Asn Gly Ala Val Lys
            180                 185                 190

Phe Pro Gln Leu Cys Lys Phe Cys Asp Val Arg Phe Ser Thr Cys Asp
        195                 200                 205

Asn Gln Lys Ser Cys Met Ser Asn Cys Ser Ile Thr Ser Ile Cys Glu
    210                 215                 220
```

```
Lys Pro Gln Glu Val Cys Val Ala Val Trp Arg Lys Asn Asp Glu Asn
225                 230                 235                 240

Ile Thr Leu Glu Thr Val Cys His Asp Pro Lys Leu Pro Tyr His Asp
            245                 250                 255

Phe Ile Leu Glu Asp Ala Ala Ser Pro Lys Cys Ile Met Lys Glu Lys
            260                 265                 270

Lys Lys Pro Gly Glu Thr Phe Phe Met Cys Ser Cys Ser Ser Asp Glu
        275                 280                 285

Cys Asn Asp Asn Ile Ile Phe Ser Glu Glu Tyr Asn Thr Ser Asn Pro
    290                 295                 300

Asp Ile Thr Cys Pro Pro Pro Met Ser Val Glu His Ala Asp Ile Trp
305                 310                 315                 320

Val Lys Ser Tyr Ser Leu Tyr Ser Arg Glu Arg Tyr Ile Cys Asn Ser
                325                 330                 335

Gly Phe Lys Arg Lys Ala Gly Thr Ser Ser Leu Thr Glu Cys Val Leu
            340                 345                 350

Asn Lys Ala Thr Asn Val Ala His Trp Thr Thr Pro Ser Leu Lys Cys
            355                 360                 365

Ile Arg Gln Gly Gln Asp Arg His Met Ile Arg Met Arg Gln Leu Ile
370                 375                 380

Asp Ile Val Asp Gln Leu Lys Asn Tyr Val Asn Asp Leu Val Pro Glu
385                 390                 395                 400

Phe Leu Pro Ala Pro Glu Asp Val Glu Thr Asn Cys Glu Trp Ser Ala
            405                 410                 415

Phe Ser Cys Phe Gln Lys Ala Gln Leu Lys Ser Ala Asn Thr Gly Asn
            420                 425                 430

Asn Glu Arg Ile Ile Asn Val Ser Ile Lys Lys Leu Lys Arg Lys Pro
            435                 440                 445

Pro Ser Thr Asn Ala Gly Arg Arg Gln Lys His Arg Leu Thr Cys Pro
        450                 455                 460

Ser Cys Asp Ser Tyr Glu Lys Lys Pro Pro Lys Glu Phe Leu Glu Arg
465                 470                 475                 480

Phe Lys Ser Leu Leu Gln Lys Met Ile His Gln His Leu Ser Ser Arg
                485                 490                 495

Thr His Gly Ser Glu Asp Ser
            500

<210> SEQ ID NO 93
<211> LENGTH: 1914
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93
atgaagtggg tgaccttcat cagcctgctg ttcctgttct ccagcgccta ctccatcccc        60
ccccatgtgc aaaagagcgt gaacaacgat atgatcgtga ccgacaacaa cggcgccgtg       120
aagtttcccc agctctgcaa gttctgcgat gtcaggttca gcacctgcga taatcagaag       180
tcctgcatgt ccaactgcag catcacctcc atctgcgaga agcccaagaa agtgtgcgtg       240
gccgtgtggc ggaaaaatga cgagaacatc accctggaga ccgtgtgtca cgaccccaag       300
ctcccttatc acgacttcat tctggaggac gctgcctccc ccaaatgcat catgaaggag       360
aagaagaagc ccggagagac cttctttatg tgttcctgta gcagcgacga gtgtaacgac       420
```

```
aacatcatct tcagcgaaga gtacaacacc agcaaccctg atggaggtgg cggatccgga    480
ggtggaggtt ctggtggagg tgggagtatt cctccccacg tgcagaagag cgtgaataat    540
gacatgatcg tgaccgataa caatggcgcc gtgaaatttc cccagctgtg caaattctgc    600
gatgtgaggt tttccacctg cgacaaccag aagtcctgta tgagcaactg ctccatcacc    660
tccatctgtg agaagcctca ggaggtgtgc gtggctgtct ggcggaagaa tgacgagaat    720
atcaccctgg aaaccgtctg ccacgatccc aagctgccct accacgattt catcctggaa    780
gacgccgcca gccctaagtg catcatgaaa gagaaaaaga agcctggcga gacctttttc    840
atgtgctcct gcagcagcga cgaatgcaac gacaatatca tctttagcga ggaatacaat    900
accagcaacc ccgacagcgg cacaaccaac acagtcgctg cctataacct cacttggaag    960
agcaccaact tcaaaaccat cctcgaatgg gaacccaaac ccgttaacca agtttacacc   1020
gtgcagatca gcaccaagtc cggcgactgg aagtccaaat gtttctatac caccgacacc   1080
gagtgcgatc tcaccgatga gatcgtgaaa gatgtgaaac agacctacct cgcccgggtg   1140
tttagctacc ccgccggcaa tgtggagagc actggttccg ctggcgagcc tttatacgag   1200
aacagccccg aatttacccc ttacctcgag accaatttag gacagcccac catccaaagc   1260
tttgagcaag ttggcacaaa ggtgaatgtg acagtggagg acgagcggac tttagtgcgg   1320
cggaacaaca cctttctcag cctccgggat gtgttcggca agatttaat ctacacactg   1380
tattactgga agtcctcttc ctccggcaag aagacagcta aaaccaacac aaacgagttt   1440
ttaatcgacg tggataaagg cgaaaactac tgtttcagcg tgcaagctgt gatcccctcc   1500
cggaccgtga taggaaaag caccgatagc cccgttgagt gcatgggcca agaaaagggc   1560
gagttccggg agaactgggt gaacgtcatc agcgatttaa agaagatcga agatttaatt   1620
cagtccatgc atatcgacgc cactttatac acagaatccg acgtgcaccc ctcttgtaag   1680
gtgaccgcca tgaaatgttt tttactggag ctgcaagtta tctctttaga gagcggagac   1740
gctagcatcc acgacaccgt ggagaattta atcattttag ccaataactc tttatccagc   1800
aacggcaacg tgacagagtc cggctgcaag gagtgcgaag agctggagga agaacatc   1860
aaggagtttc tgcaatcctt tgtgcacatt gtccagatgt tcatcaatac ctcc         1914
```

<210> SEQ ID NO 94
<211> LENGTH: 638
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 94

Met Lys Trp Val Thr Phe Ile Ser Leu Leu Phe Leu Phe Ser Ser Ala
1               5                   10                  15

Tyr Ser Ile Pro Pro His Val Gln Lys Ser Val Asn Asn Asp Met Ile
            20                  25                  30

Val Thr Asp Asn Asn Gly Ala Val Lys Phe Pro Gln Leu Cys Lys Phe
        35                  40                  45

Cys Asp Val Arg Phe Ser Thr Cys Asp Asn Gln Lys Ser Cys Met Ser
    50                  55                  60

Asn Cys Ser Ile Thr Ser Ile Cys Glu Lys Pro Gln Glu Val Cys Val
65                  70                  75                  80

Ala Val Trp Arg Lys Asn Asp Glu Asn Ile Thr Leu Glu Thr Val Cys
                85                  90                  95

-continued

His Asp Pro Lys Leu Pro Tyr His Asp Phe Ile Leu Glu Asp Ala Ala
            100                 105                 110

Ser Pro Lys Cys Ile Met Lys Glu Lys Lys Pro Gly Glu Thr Phe
115                 120                 125

Phe Met Cys Ser Cys Ser Ser Asp Glu Cys Asn Asp Asn Ile Ile Phe
        130                 135                 140

Ser Glu Glu Tyr Asn Thr Ser Asn Pro Asp Gly Gly Gly Ser Gly
145                 150                 155                 160

Gly Gly Gly Ser Gly Gly Gly Ser Ile Pro Pro His Val Gln Lys
                165                 170                 175

Ser Val Asn Asn Asp Met Ile Val Thr Asp Asn Asn Gly Ala Val Lys
                    180                 185                 190

Phe Pro Gln Leu Cys Lys Phe Cys Asp Val Arg Phe Ser Thr Cys Asp
                195                 200                 205

Asn Gln Lys Ser Cys Met Ser Asn Cys Ser Ile Thr Ser Ile Cys Glu
                210                 215                 220

Lys Pro Gln Glu Val Cys Val Ala Val Trp Arg Lys Asn Asp Glu Asn
225                 230                 235                 240

Ile Thr Leu Glu Thr Val Cys His Asp Pro Lys Leu Pro Tyr His Asp
                    245                 250                 255

Phe Ile Leu Glu Asp Ala Ala Ser Pro Lys Cys Ile Met Lys Glu Lys
                260                 265                 270

Lys Lys Pro Gly Glu Thr Phe Phe Met Cys Ser Cys Ser Ser Asp Glu
            275                 280                 285

Cys Asn Asp Asn Ile Ile Phe Ser Glu Glu Tyr Asn Thr Ser Asn Pro
        290                 295                 300

Asp Ser Gly Thr Thr Asn Thr Val Ala Ala Tyr Asn Leu Thr Trp Lys
305                 310                 315                 320

Ser Thr Asn Phe Lys Thr Ile Leu Glu Trp Glu Pro Lys Pro Val Asn
                325                 330                 335

Gln Val Tyr Thr Val Gln Ile Ser Thr Lys Ser Gly Asp Trp Lys Ser
                340                 345                 350

Lys Cys Phe Tyr Thr Thr Asp Thr Glu Cys Asp Leu Thr Asp Glu Ile
                355                 360                 365

Val Lys Asp Val Lys Gln Thr Tyr Leu Ala Arg Val Phe Ser Tyr Pro
370                 375                 380

Ala Gly Asn Val Glu Ser Thr Gly Ser Ala Gly Glu Pro Leu Tyr Glu
385                 390                 395                 400

Asn Ser Pro Glu Phe Thr Pro Tyr Leu Glu Thr Asn Leu Gly Gln Pro
                405                 410                 415

Thr Ile Gln Ser Phe Glu Gln Val Gly Thr Lys Val Asn Val Thr Val
                420                 425                 430

Glu Asp Glu Arg Thr Leu Val Arg Arg Asn Asn Thr Phe Leu Ser Leu
            435                 440                 445

Arg Asp Val Phe Gly Lys Asp Leu Ile Tyr Thr Leu Tyr Tyr Trp Lys
            450                 455                 460

Ser Ser Ser Ser Gly Lys Lys Thr Ala Lys Thr Asn Thr Asn Glu Phe
465                 470                 475                 480

Leu Ile Asp Val Asp Lys Gly Glu Asn Tyr Cys Phe Ser Val Gln Ala
                485                 490                 495

Val Ile Pro Ser Arg Thr Val Asn Arg Lys Ser Thr Asp Ser Pro Val
                500                 505                 510

Glu Cys Met Gly Gln Glu Lys Gly Glu Phe Arg Glu Asn Trp Val Asn

```
                515                 520                 525
Val Ile Ser Asp Leu Lys Lys Ile Glu Asp Leu Ile Gln Ser Met His
530                 535                 540

Ile Asp Ala Thr Leu Tyr Thr Glu Ser Asp Val His Pro Ser Cys Lys
545                 550                 555                 560

Val Thr Ala Met Lys Cys Phe Leu Leu Glu Leu Gln Val Ile Ser Leu
                565                 570                 575

Glu Ser Gly Asp Ala Ser Ile His Asp Thr Val Glu Asn Leu Ile Ile
            580                 585                 590

Leu Ala Asn Asn Ser Leu Ser Ser Asn Gly Asn Val Thr Glu Ser Gly
            595                 600                 605

Cys Lys Glu Cys Glu Glu Leu Glu Glu Lys Asn Ile Lys Glu Phe Leu
610                 615                 620

Gln Ser Phe Val His Ile Val Gln Met Phe Ile Asn Thr Ser
625                 630                 635

<210> SEQ ID NO 95
<211> LENGTH: 1830
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
atgaagtggg tgaccttcat cagcctgctg ttcctgttct ccagcgccta ctccatcccc      60
ccccatgtgc aaaagagcgt gaacaacgat atgatcgtga ccgacaacaa cggcgccgtg     120
aagtttcccc agctctgcaa gttctgcgat gtcaggttca gcacctgcga taatcagaag     180
tcctgcatgt ccaactgcag catcacctcc atctgcgaga agccccaaga agtgtgcgtg     240
gccgtgtggc ggaaaaatga cgagaacatc accctggaga ccgtgtgtca cgaccccaag     300
ctcccttatc acgacttcat tctggaggac gctgcctccc ccaaatgcat catgaaggag     360
aagaagaagc ccggagagac cttctttatg tgttcctgta gcagcgacga gtgtaacgac     420
aacatcatct tcagcgaaga gtacaacacc agcaaccctg atggaggtgg cggatccgga     480
ggtggaggtt ctggtggagg tgggagtatt cctccccacg tgcagaagag cgtgaataat     540
gacatgatcg tgaccgataa caatggcgcc gtgaaatttc cccagctgtg caaattctgc     600
gatgtgaggt tttccacctg cgacaaccag aagtcctgta tgagcaactg ctccatcacc     660
tccatctgtg agaagcctca ggaggtgtgc gtggctgtct ggcggaagaa tgacgagaat     720
atcaccctgg aaaccgtctg ccacgatccc aagctgccct accacgattt catcctggaa     780
gacgccgcca gccctaagtg catcatgaaa gagaaaaaga gcctggcga gaccttttc      840 atgtgctcct gcagcagcga cgaatgcaac gacaatatca tctttagcga ggaatacaat     900
accagcaacc ccgacattac atgccccct cccatgagcg tggagcacgc cgacatctgg     960
gtgaagagct atagcctcta cagccgggag aggtatatct gtaacagcgg cttcaagagg    1020
aaggccggca ccagcagcct caccgagtgc gtgctgaata aggctaccaa cgtggctcac    1080
tggacaacac cctcttttaaa gtgcatccgg tccgagctga cccaggaccc tgctgtgtcc    1140
gtggctctgg ccagaccgt gaggatcacc tgccagggcg actccctgag gtcctactac    1200
gcctcctggt accagcagaa gcccggccag gctcctgtgc tggtgatcta cggcaagaac    1260 aacaggcccct ccggcatccc tgacaggttc tccggatcct cctccggcaa caccgcctcc    1320
ctgaccatca caggcgctca ggccgaggac gaggctgact actactgcaa ctccagggac    1380
```

```
tcctccggca accatgtggt gttcggcggc ggcaccaagc tgaccgtggg ccatggcggc    1440
ggcggctccg gaggcggcgg cagcggcgga ggaggatccg aggtgcagct ggtggagtcc    1500
ggaggaggag tggtgaggcc tggaggctcc ctgaggctga gctgtgctgc ctccggcttc    1560
accttcgacg actacggcat gtcctgggtg aggcaggctc ctggaaaggg cctggagtgg    1620
gtgtccggca tcaactggaa cggcggatcc accggctacg ccgattccgt gaagggcagg    1680
ttcaccatca gcagggacaa cgccaagaac tccctgtacc tgcagatgaa ctccctgagg    1740
gccgaggaca ccgccgtgta ctactgcgcc agggggcaggt ccctgctgtt cgactactgg    1800
ggacagggca ccctggtgac cgtgtccagg                                    1830
```

<210> SEQ ID NO 96
<211> LENGTH: 610
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

```
Met Lys Trp Val Thr Phe Ile Ser Leu Leu Phe Leu Phe Ser Ser Ala
1               5                   10                  15

Tyr Ser Ile Pro Pro His Val Gln Lys Ser Val Asn Asn Asp Met Ile
            20                  25                  30

Val Thr Asp Asn Asn Gly Ala Val Lys Phe Pro Gln Leu Cys Lys Phe
        35                  40                  45

Cys Asp Val Arg Phe Ser Thr Cys Asp Asn Gln Lys Ser Cys Met Ser
    50                  55                  60

Asn Cys Ser Ile Thr Ser Ile Cys Glu Lys Pro Gln Glu Val Cys Val
65                  70                  75                  80

Ala Val Trp Arg Lys Asn Asp Glu Asn Ile Thr Leu Glu Thr Val Cys
                85                  90                  95

His Asp Pro Lys Leu Pro Tyr His Asp Phe Ile Leu Glu Asp Ala Ala
            100                 105                 110

Ser Pro Lys Cys Ile Met Lys Glu Lys Lys Pro Gly Glu Thr Phe
            115                 120                 125

Phe Met Cys Ser Cys Ser Ser Asp Glu Cys Asn Asp Asn Ile Ile Phe
        130                 135                 140

Ser Glu Glu Tyr Asn Thr Ser Asn Pro Asp Gly Gly Gly Ser Gly
145                 150                 155                 160

Gly Gly Gly Ser Gly Gly Gly Ser Ile Pro Pro His Val Gln Lys
                165                 170                 175

Ser Val Asn Asn Asp Met Ile Val Thr Asp Asn Asn Gly Ala Val Lys
            180                 185                 190

Phe Pro Gln Leu Cys Lys Phe Cys Asp Val Arg Phe Ser Thr Cys Asp
        195                 200                 205

Asn Gln Lys Ser Cys Met Ser Asn Cys Ser Ile Thr Ser Ile Cys Glu
    210                 215                 220

Lys Pro Gln Glu Val Cys Val Ala Val Trp Arg Lys Asn Asp Glu Asn
225                 230                 235                 240

Ile Thr Leu Glu Thr Val Cys His Asp Pro Lys Leu Pro Tyr His Asp
                245                 250                 255

Phe Ile Leu Glu Asp Ala Ala Ser Pro Lys Cys Ile Met Lys Glu Lys
            260                 265                 270
```

Lys Lys Pro Gly Glu Thr Phe Phe Met Cys Ser Cys Ser Ser Asp Glu
            275                 280                 285

Cys Asn Asp Asn Ile Ile Phe Ser Glu Glu Tyr Asn Thr Ser Asn Pro
        290                 295                 300

Asp Ile Thr Cys Pro Pro Met Ser Val Glu His Ala Asp Ile Trp
305                 310                 315                 320

Val Lys Ser Tyr Ser Leu Tyr Ser Arg Glu Arg Tyr Ile Cys Asn Ser
                325                 330                 335

Gly Phe Lys Arg Lys Ala Gly Thr Ser Ser Leu Thr Glu Cys Val Leu
            340                 345                 350

Asn Lys Ala Thr Asn Val Ala His Trp Thr Thr Pro Ser Leu Lys Cys
        355                 360                 365

Ile Arg Ser Glu Leu Thr Gln Asp Pro Ala Val Ser Val Ala Leu Gly
370                 375                 380

Gln Thr Val Arg Ile Thr Cys Gln Gly Asp Ser Leu Arg Ser Tyr Tyr
385                 390                 395                 400

Ala Ser Trp Tyr Gln Gln Lys Pro Gly Gln Ala Pro Val Leu Val Ile
                405                 410                 415

Tyr Gly Lys Asn Asn Arg Pro Ser Gly Ile Pro Asp Arg Phe Ser Gly
            420                 425                 430

Ser Ser Ser Gly Asn Thr Ala Ser Leu Thr Ile Thr Gly Ala Gln Ala
        435                 440                 445

Glu Asp Glu Ala Asp Tyr Tyr Cys Asn Ser Arg Asp Ser Ser Gly Asn
450                 455                 460

His Val Val Phe Gly Gly Gly Thr Lys Leu Thr Val Gly His Gly Gly
465                 470                 475                 480

Gly Gly Ser Gly Gly Gly Gly Ser Gly Gly Gly Gly Ser Glu Val Gln
                485                 490                 495

Leu Val Glu Ser Gly Gly Gly Val Val Arg Pro Gly Gly Ser Leu Arg
            500                 505                 510

Leu Ser Cys Ala Ala Ser Gly Phe Thr Phe Asp Asp Tyr Gly Met Ser
        515                 520                 525

Trp Val Arg Gln Ala Pro Gly Lys Gly Leu Glu Trp Val Ser Gly Ile
530                 535                 540

Asn Trp Asn Gly Gly Ser Thr Gly Tyr Ala Asp Ser Val Lys Gly Arg
545                 550                 555                 560

Phe Thr Ile Ser Arg Asp Asn Ala Lys Asn Ser Leu Tyr Leu Gln Met
                565                 570                 575

Asn Ser Leu Arg Ala Glu Asp Thr Ala Val Tyr Tyr Cys Ala Arg Gly
            580                 585                 590

Arg Ser Leu Leu Phe Asp Tyr Trp Gly Gln Gly Thr Leu Val Thr Val
        595                 600                 605

Ser Arg
    610

<210> SEQ ID NO 97
<211> LENGTH: 1914
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97
atgaagtggg tgaccttcat cagcctgctg ttcctgttct ccagcgccta ctccatcccc    60

```
cccatgtgc aaaagagcgt gaacaacgat atgatcgtga ccgacaacaa cggcgccgtg      120
aagtttcccc agctctgcaa gttctgcgat gtcaggttca gcacctgcga taatcagaag      180
tcctgcatgt ccaactgcag catcacctcc atctgcgaga agccccaaga agtgtgcgtg      240
gccgtgtggc ggaaaaatga cgagaacatc accctggaga ccgtgtgtca cgaccccaag      300
ctcccttatc acgacttcat tctggaggac gctgcctccc ccaaatgcat catgaaggag      360
aagaagaagc ccggagagac cttctttatg tgttcctgta gcagcgacga gtgtaacgac      420
aacatcatct tcagcgaaga gtacaacacc agcaaccctg atggaggtgg cggatccgga      480
ggtggaggtt ctggtggagg tgggagtatt cctccccacg tgcagaagag cgtgaataat      540
gacatgatcg tgaccgataa caatggcgcc gtgaaatttc cccagctgtg caaattctgc      600
gatgtgaggt tttccacctg cgacaaccag aagtcctgta tgagcaactg ctccatcacc      660
tccatctgtg agaagcctca ggaggtgtgc gtggctgtct ggcggaagaa tgacgagaat      720
atcaccctgg aaaccgtctg ccacgatccc aagctgccct accacgattt catcctggaa      780
gacgccgcca gccctaagtg catcatgaaa gagaaaaaga gcctggcga gacctttttc      840
atgtgctcct gcagcagcga cgaatgcaac gacaatatca tctttagcga ggaatacaat      900
accagcaacc ccgacagcgg cacaaccaac acagtcgctg cctataacct cacttggaag      960
agcaccaact tcaaaaccat cctcgaatgg aacccaaac ccgttaacca agtttacacc     1020
gtgcagatca gcaccaagtc cggcgactgg aagtccaaat gtttctatac caccgacacc     1080
gagtgcgatc tcaccgatga gatcgtgaaa gatgtgaaac agacctacct cgcccgggtg     1140
tttagctacc ccgccggcaa tgtggagagc actggttccg ctggcgagcc tttatacgag     1200
aacagccccg aatttacccc ttacctcgag accaatttag gacagcccac catccaaagc     1260
tttgagcaag ttggcacaaa ggtgaatgtg acagtggagg acgagcggac tttagtgcgg     1320
cggaacaaca ccttttctcag cctccgggat gtgttcggca agatttaat ctacacactg     1380
tattactgga gtcctcttc ctccggcaag aagacagcta aaaccaacac aaacgagttt     1440
ttaatcgacg tggataaagg cgaaaactac tgtttcagcg tgcaagctgt gatcccctcc     1500
cggaccgtga ataggaaaag caccgatagc cccgttgagt gcatgggcca agaaaagggc     1560
gagttccggg agaactgggt gaacgtcatc agcgatttaa agaagatcga agatttaatt     1620
cagtccatgc atatcgacgc cactttatac acagaatccg acgtgcaccc ctcttgtaag     1680
gtgaccgcca tgaaatgttt tttactggag ctgcaagtta tctctttaga gagcggagac     1740
gctagcatcc acgacaccgt ggagaattta atcattttag ccataactc tttatccagc     1800
aacggcaacg tgacagagtc cggctgcaag gagtgcgaag agctggagga agaacatc     1860
aaggagtttc tgcaatcctt tgtgcacatt gtccagatgt tcatcaatac ctcc            1914
```

<210> SEQ ID NO 98
<211> LENGTH: 638
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 98

Met Lys Trp Val Thr Phe Ile Ser Leu Leu Phe Leu Phe Ser Ser Ala
1               5                   10                  15

Tyr Ser Ile Pro Pro His Val Gln Lys Ser Val Asn Asn Asp Met Ile
            20                  25                  30

-continued

```
Val Thr Asp Asn Asn Gly Ala Val Lys Phe Pro Gln Leu Cys Lys Phe
         35                  40                  45

Cys Asp Val Arg Phe Ser Thr Cys Asp Asn Gln Lys Ser Cys Met Ser
 50                  55                  60

Asn Cys Ser Ile Thr Ser Ile Cys Glu Lys Pro Gln Glu Val Cys Val
 65                  70                  75                  80

Ala Val Trp Arg Lys Asn Asp Glu Asn Ile Thr Leu Glu Thr Val Cys
                 85                  90                  95

His Asp Pro Lys Leu Pro Tyr His Asp Phe Ile Leu Glu Asp Ala Ala
                100                 105                 110

Ser Pro Lys Cys Ile Met Lys Glu Lys Lys Pro Gly Glu Thr Phe
            115                 120                 125

Phe Met Cys Ser Cys Ser Ser Asp Glu Cys Asn Asp Asn Ile Ile Phe
130                 135                 140

Ser Glu Glu Tyr Asn Thr Ser Asn Pro Asp Gly Gly Gly Ser Gly
145                 150                 155                 160

Gly Gly Gly Ser Gly Gly Gly Ser Ile Pro Pro His Val Gln Lys
                165                 170                 175

Ser Val Asn Asn Asp Met Ile Val Thr Asp Asn Gly Ala Val Lys
                180                 185                 190

Phe Pro Gln Leu Cys Lys Phe Cys Asp Val Arg Phe Ser Thr Cys Asp
195                 200                 205

Asn Gln Lys Ser Cys Met Ser Asn Cys Ser Ile Thr Ser Ile Cys Glu
    210                 215                 220

Lys Pro Gln Glu Val Cys Val Ala Val Trp Arg Lys Asn Asp Glu Asn
225                 230                 235                 240

Ile Thr Leu Glu Thr Val Cys His Asp Pro Lys Leu Pro Tyr His Asp
                245                 250                 255

Phe Ile Leu Glu Asp Ala Ala Ser Pro Lys Cys Ile Met Lys Glu Lys
                260                 265                 270

Lys Lys Pro Gly Glu Thr Phe Phe Met Cys Ser Cys Ser Ser Asp Glu
            275                 280                 285

Cys Asn Asp Asn Ile Ile Phe Ser Glu Glu Tyr Asn Thr Ser Asn Pro
290                 295                 300

Asp Ser Gly Thr Thr Asn Thr Val Ala Ala Tyr Asn Leu Thr Trp Lys
305                 310                 315                 320

Ser Thr Asn Phe Lys Thr Ile Leu Glu Trp Glu Pro Lys Pro Val Asn
                325                 330                 335

Gln Val Tyr Thr Val Gln Ile Ser Thr Lys Ser Gly Asp Trp Lys Ser
                340                 345                 350

Lys Cys Phe Tyr Thr Thr Asp Thr Glu Cys Asp Leu Thr Asp Glu Ile
            355                 360                 365

Val Lys Asp Val Lys Gln Thr Tyr Leu Ala Arg Val Phe Ser Tyr Pro
370                 375                 380

Ala Gly Asn Val Glu Ser Thr Gly Ser Ala Gly Glu Pro Leu Tyr Glu
385                 390                 395                 400

Asn Ser Pro Glu Phe Thr Pro Tyr Leu Glu Thr Asn Leu Gly Gln Pro
                405                 410                 415

Thr Ile Gln Ser Phe Glu Gln Val Gly Thr Lys Val Asn Val Thr Val
                420                 425                 430

Glu Asp Glu Arg Thr Leu Val Arg Arg Asn Asn Thr Phe Leu Ser Leu
            435                 440                 445

Arg Asp Val Phe Gly Lys Asp Leu Ile Tyr Thr Leu Tyr Tyr Trp Lys
```

| | | | | | | | | | | | | |
|---|---|---|---|---|---|---|---|---|---|---|---|---|
| | | | | 450 | | | | 455 | | | | 460 |
| Ser | Ser | Ser | Gly | Lys | Lys | Thr | Ala | Lys | Thr | Asn | Thr | Asn | Glu | Phe |
| 465 | | | | 470 | | | | 475 | | | | 480 |

Ser Ser Ser Gly Lys Lys Thr Ala Lys Thr Asn Thr Asn Glu Phe
465                 470                 475                 480

Leu Ile Asp Val Asp Lys Gly Glu Asn Tyr Cys Phe Ser Val Gln Ala
            485                 490                 495

Val Ile Pro Ser Arg Thr Val Asn Arg Lys Ser Thr Asp Ser Pro Val
            500                 505                 510

Glu Cys Met Gly Gln Glu Lys Gly Glu Phe Arg Glu Asn Trp Val Asn
            515                 520                 525

Val Ile Ser Asp Leu Lys Lys Ile Glu Asp Leu Ile Gln Ser Met His
            530                 535                 540

Ile Asp Ala Thr Leu Tyr Thr Glu Ser Asp Val His Pro Ser Cys Lys
545                 550                 555                 560

Val Thr Ala Met Lys Cys Phe Leu Leu Glu Leu Gln Val Ile Ser Leu
            565                 570                 575

Glu Ser Gly Asp Ala Ser Ile His Asp Thr Val Glu Asn Leu Ile Ile
            580                 585                 590

Leu Ala Asn Asn Ser Leu Ser Ser Asn Gly Asn Val Thr Glu Ser Gly
            595                 600                 605

Cys Lys Glu Cys Glu Glu Leu Glu Glu Lys Asn Ile Lys Glu Phe Leu
            610                 615                 620

Gln Ser Phe Val His Ile Val Gln Met Phe Ile Asn Thr Ser
625                 630                 635

<210> SEQ ID NO 99
<211> LENGTH: 1707
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99

```
atgaagtggg tgaccttcat cagcctgctg ttcctgttct ccagcgccta ctccatcccc      60
ccccatgtgc aaaagagcgt gaacaacgat atgatcgtga ccgacaacaa cggcgccgtg     120
aagtttcccc agctctgcaa gttctgcgat gtcaggttca gcacctgcga taatcagaag     180
tcctgcatgt ccaactgcag catcacctcc atctgcgaga agcccaagaa gtgtgcgtg      240 gccgtgtggc ggaaaaatga cgagaacatc accctggaga ccgtgtgtca cgaccccaag     300
ctcccttatc acgacttcat tctggaggac gctgcctccc ccaaatgcat catgaaggag     360
aagaagaagc ccggagagac cttctttatg tgttcctgta gcagcgacga gtgtaacgac     420
aacatcatct tcagcgaaga gtacaacacc agcaacccctg atggaggtgg cggatccgga     480
ggtggaggtt ctggtggagg tgggagtatt cctccccacg tgcagaagag cgtgaataat     540
gacatgatcg tgaccgataa caatggcgcc gtgaaatttc cccagctgtg caaattctgc     600
gatgtgaggt tttccacctg cgacaaccag aagtcctgta tgagcaactg ctccatcacc     660
tccatctgtg agaagcctca ggaggtgtgc gtggctgtct ggcggaagaa tgacgagaat     720
atcaccctgg aaaccgtctg ccacgatccc aagctgccct accacgattt catcctggaa     780
gacgccgcca gccctaagtg catcatgaaa gagaaaaaga gcctggcgga gacctttttc     840
atgtgctcct gcagcagcga cgaatgcaac gacaatatca tctttagcga ggaatacaat     900
accagcaacc ccgacattac atgcccccct cccatgagcg tggagcacgc cgacatctgg     960
gtgaagagct atagcctcta cagccgggag aggtatatct gtaacagcgg cttcaagagg    1020
```

```
aaggccggca ccagcagcct caccgagtgc gtgctgaata aggctaccaa cgtggctcac   1080
tggacaacac cctctttaaa gtgcatccgg ggcggtggag gatccggagg aggtggctcc   1140
ggcggcggag gatctcgcga gggtcccgag ctttcgcccg acgatcccgc cggcctcttg   1200
gacctgcggc agggcatgtt tgcgcagctg gtggcccaaa atgttctgct gatcgatggg   1260
cccctgagct ggtacagtga cccaggcctg gcaggcgtgt ccctgacggg gggcctgagc   1320
tacaaagagg acacgaagga gctggtggtg gccaaggctg gagtctacta tgtcttcttt   1380
caactagagc tgcggcgcgt ggtggccggc gagggctcag gctccgtttc acttgcgctg   1440
cacctgcagc cactgcgctc tgctgctggg ccgccgccc tggctttgac cgtggacctg   1500
ccacccgcct cctccgaggc tcggaactcg gccttcggtt tccagggccg cttgctgcac   1560
ctgagtgccg gccagcgcct gggcgtccat cttcacactg aggccagggc acgccatgcc   1620
tggcagctta cccagggcgc cacagtcttg ggactcttcc gggtgacccc cgaaatccca   1680
gccggactcc cttcaccgag gtcggaa                                       1707
```

<210> SEQ ID NO 100
<211> LENGTH: 569
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 100

```
Met Lys Trp Val Thr Phe Ile Ser Leu Leu Phe Leu Phe Ser Ser Ala
1               5                   10                  15

Tyr Ser Ile Pro Pro His Val Gln Lys Ser Val Asn Asn Asp Met Ile
            20                  25                  30

Val Thr Asp Asn Asn Gly Ala Val Lys Phe Pro Gln Leu Cys Lys Phe
        35                  40                  45

Cys Asp Val Arg Phe Ser Thr Cys Asp Asn Gln Lys Ser Cys Met Ser
    50                  55                  60

Asn Cys Ser Ile Thr Ser Ile Cys Glu Lys Pro Gln Glu Val Cys Val
65                  70                  75                  80

Ala Val Trp Arg Lys Asn Asp Glu Asn Ile Thr Leu Glu Thr Val Cys
                85                  90                  95

His Asp Pro Lys Leu Pro Tyr His Asp Phe Ile Leu Glu Asp Ala Ala
            100                 105                 110

Ser Pro Lys Cys Ile Met Lys Glu Lys Lys Pro Gly Glu Thr Phe Phe
        115                 120                 125

Phe Met Cys Ser Cys Ser Ser Asp Glu Cys Asn Asp Asn Ile Ile Phe
    130                 135                 140

Ser Glu Glu Tyr Asn Thr Ser Asn Pro Asp Gly Gly Gly Ser Gly
145                 150                 155                 160

Gly Gly Gly Ser Gly Gly Gly Ser Ile Pro Pro His Val Gln Lys
                165                 170                 175

Ser Val Asn Asn Asp Met Ile Val Thr Asp Asn Asn Gly Ala Val Lys
            180                 185                 190

Phe Pro Gln Leu Cys Lys Phe Cys Asp Val Arg Phe Ser Thr Cys Asp
        195                 200                 205

Asn Gln Lys Ser Cys Met Ser Asn Cys Ser Ile Thr Ser Ile Cys Glu
    210                 215                 220

Lys Pro Gln Glu Val Cys Val Ala Val Trp Arg Lys Asn Asp Glu Asn
```

```
            225                 230                 235                 240
Ile Thr Leu Glu Thr Val Cys His Asp Pro Lys Leu Pro Tyr His Asp
            245                 250                 255

Phe Ile Leu Glu Asp Ala Ala Ser Pro Lys Cys Ile Met Lys Glu Lys
            260                 265                 270

Lys Lys Pro Gly Glu Thr Phe Phe Met Cys Ser Cys Ser Ser Asp Glu
            275                 280                 285

Cys Asn Asp Asn Ile Ile Phe Ser Glu Glu Tyr Asn Thr Ser Asn Pro
            290                 295                 300

Asp Ile Thr Cys Pro Pro Met Ser Val Glu His Ala Asp Ile Trp
305                 310                 315                 320

Val Lys Ser Tyr Ser Leu Tyr Ser Arg Glu Arg Tyr Ile Cys Asn Ser
            325                 330                 335

Gly Phe Lys Arg Lys Ala Gly Thr Ser Ser Leu Thr Glu Cys Val Leu
            340                 345                 350

Asn Lys Ala Thr Asn Val Ala His Trp Thr Thr Pro Ser Leu Lys Cys
            355                 360                 365

Ile Arg Gly Gly Gly Gly Ser Gly Gly Gly Ser Gly Gly Gly Gly
            370                 375                 380

Ser Arg Glu Gly Pro Glu Leu Ser Pro Asp Asp Pro Ala Gly Leu Leu
385                 390                 395                 400

Asp Leu Arg Gln Gly Met Phe Ala Gln Leu Val Ala Gln Asn Val Leu
            405                 410                 415

Leu Ile Asp Gly Pro Leu Ser Trp Tyr Ser Asp Pro Gly Leu Ala Gly
            420                 425                 430

Val Ser Leu Thr Gly Gly Leu Ser Tyr Lys Glu Asp Thr Lys Glu Leu
            435                 440                 445

Val Val Ala Lys Ala Gly Val Tyr Tyr Val Phe Phe Gln Leu Glu Leu
            450                 455                 460

Arg Arg Val Val Ala Gly Glu Gly Ser Gly Ser Val Ser Leu Ala Leu
465                 470                 475                 480

His Leu Gln Pro Leu Arg Ser Ala Ala Gly Ala Ala Leu Ala Leu
            485                 490                 495

Thr Val Asp Leu Pro Pro Ala Ser Ser Glu Ala Arg Asn Ser Ala Phe
            500                 505                 510

Gly Phe Gln Gly Arg Leu Leu His Leu Ser Ala Gly Gln Arg Leu Gly
            515                 520                 525

Val His Leu His Thr Glu Ala Arg Ala Arg His Ala Trp Gln Leu Thr
            530                 535                 540

Gln Gly Ala Thr Val Leu Gly Leu Phe Arg Val Thr Pro Glu Ile Pro
545                 550                 555                 560

Ala Gly Leu Pro Ser Pro Arg Ser Glu
            565

<210> SEQ ID NO 101
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Met Lys Trp Val Thr Phe Ile Ser Leu Leu Phe Leu Phe Ser Ser Ala
1               5                   10                  15
```

```
Tyr Ser Gln Gly Gln Asp Arg His Met Ile Arg Met Arg Gln Leu Ile
            20                  25                  30

Asp Ile Val Asp Gln Leu Lys Asn Tyr Val Asn Asp Leu Val Pro Glu
        35                  40                  45

Phe Leu Pro Ala Pro Glu Asp Val Glu Thr Asn Cys Glu Trp Ser Ala
50                  55                  60

Phe Ser Cys Phe Gln Lys Ala Gln Leu Lys Ser Ala Asn Thr Gly Asn
65                  70                  75                  80

Asn Glu Arg Ile Ile Asn Val Ser Ile Lys Lys Leu Lys Arg Lys Pro
                85                  90                  95

Pro Ser Thr Asn Ala Gly Arg Arg Gln Lys His Arg Leu Thr Cys Pro
            100                 105                 110

Ser Cys Asp Ser Tyr Glu Lys Lys Pro Pro Lys Glu Phe Leu Glu Arg
        115                 120                 125

Phe Lys Ser Leu Leu Gln Lys Met Ile His Gln His Leu Ser Ser Arg
130                 135                 140

Thr His Gly Ser Glu Asp Ser Ile Thr Cys Pro Pro Pro Met Ser Val
145                 150                 155                 160

Glu His Ala Asp Ile Trp Val Lys Ser Tyr Ser Leu Tyr Ser Arg Glu
                165                 170                 175

Arg Tyr Ile Cys Asn Ser Gly Phe Lys Arg Lys Ala Gly Thr Ser Ser
            180                 185                 190

Leu Thr Glu Cys Val Leu Asn Lys Ala Thr Asn Val Ala His Trp Thr
        195                 200                 205

Thr Pro Ser Leu Lys Cys Ile Arg
210                 215

<210> SEQ ID NO 102
<211> LENGTH: 332
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Glu Phe Ala Ser Thr Lys Gly Pro Ser Val Phe Pro Leu Ala Pro Ser
1               5                   10                  15

Ser Lys Ser Thr Ser Gly Gly Thr Ala Ala Leu Gly Cys Leu Val Lys
            20                  25                  30

Asp Tyr Phe Pro Glu Pro Val Thr Val Ser Trp Asn Ser Gly Ala Leu
        35                  40                  45

Thr Ser Gly Val His Thr Phe Pro Ala Val Leu Gln Ser Ser Gly Leu
50                  55                  60

Tyr Ser Leu Ser Ser Val Val Thr Val Pro Ser Ser Ser Leu Gly Thr
65                  70                  75                  80

Gln Thr Tyr Ile Cys Asn Val Asn His Lys Pro Ser Asn Thr Lys Val
                85                  90                  95

Asp Lys Lys Val Glu Pro Lys Ser Cys Asp Lys Thr His Thr Cys Pro
            100                 105                 110

Pro Cys Pro Ala Pro Glu Leu Leu Gly Gly Pro Ser Val Phe Leu Phe
        115                 120                 125

Pro Pro Lys Pro Lys Asp Thr Leu Met Ile Ser Arg Thr Pro Glu Val
130                 135                 140

Thr Cys Val Val Val Asp Val Ser His Glu Asp Pro Glu Val Lys Phe
145                 150                 155                 160
```

Asn Trp Tyr Val Asp Gly Val Glu Val His Asn Ala Lys Thr Lys Pro
               165                 170                 175

Arg Glu Glu Gln Tyr Asn Ser Thr Tyr Arg Val Val Ser Val Leu Thr
            180                 185                 190

Val Leu His Gln Asp Trp Leu Asn Gly Lys Glu Tyr Lys Cys Lys Val
        195                 200                 205

Ser Asn Lys Ala Leu Pro Ala Pro Ile Glu Lys Thr Ile Ser Lys Ala
    210                 215                 220

Lys Gly Gln Pro Arg Glu Pro Gln Val Tyr Thr Leu Pro Pro Ser Arg
225                 230                 235                 240

Asp Glu Leu Thr Lys Asn Gln Val Ser Leu Thr Cys Leu Val Lys Gly
                245                 250                 255

Phe Tyr Pro Ser Asp Ile Ala Val Glu Trp Glu Ser Asn Gly Gln Pro
            260                 265                 270

Glu Asn Asn Tyr Lys Thr Thr Pro Pro Val Leu Asp Ser Asp Gly Ser
        275                 280                 285

Phe Phe Leu Tyr Ser Lys Leu Thr Val Asp Lys Ser Arg Trp Gln Gln
    290                 295                 300

Gly Asn Val Phe Ser Cys Ser Val Met His Glu Ala Leu His Asn His
305                 310                 315                 320

Tyr Thr Gln Lys Ser Leu Ser Leu Ser Pro Gly Lys
                325                 330

<210> SEQ ID NO 103
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Glu Phe Ala Ser Thr Lys Gly Pro Ser Val Phe Pro Leu Ala Pro Cys
1               5                   10                  15

Ser Arg Ser Thr Ser Glu Ser Thr Ala Ala Leu Gly Cys Leu Val Lys
            20                  25                  30

Asp Tyr Phe Pro Glu Pro Val Thr Val Ser Trp Asn Ser Gly Ala Leu
        35                  40                  45

Thr Ser Gly Val His Thr Phe Pro Ala Val Leu Gln Ser Ser Gly Leu
    50                  55                  60

Tyr Ser Leu Ser Ser Val Val Thr Val Pro Ser Ser Ser Leu Gly Thr
65                  70                  75                  80

Lys Thr Tyr Thr Cys Asn Val Asp His Lys Pro Ser Asn Thr Lys Val
                85                  90                  95

Asp Lys Arg Val Glu Ser Lys Tyr Gly Pro Pro Cys Pro Ser Cys Pro
            100                 105                 110

Ala Pro Glu Phe Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser Gln Glu Asp Pro Glu Val Gln Phe Asn Trp Tyr
145                 150                 155                 160

Val Asp Gly Val Glu Val His Asn Ala Lys Thr Lys Pro Arg Glu Glu
                165                 170                 175

Gln Phe Asn Ser Thr Tyr Arg Val Val Ser Val Leu Thr Val Leu His

```
            180                 185                 190
Gln Asp Trp Leu Asn Gly Lys Glu Tyr Lys Cys Lys Val Ser Asn Lys
            195                 200                 205

Gly Leu Pro Ser Ser Ile Glu Lys Thr Ile Ser Lys Ala Lys Gly Gln
            210                 215                 220

Pro Arg Glu Pro Gln Val Tyr Thr Leu Pro Pro Ser Gln Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
            275                 280                 285

Tyr Ser Arg Leu Thr Val Asp Lys Ser Arg Trp Gln Glu Gly Asn Val
            290                 295                 300

Phe Ser Cys Ser Val Met His Glu Ala Leu His Asn His Tyr Thr Gln
305                 310                 315                 320

Lys Ser Leu Ser Leu Ser Leu Gly Lys
                325
```

<210> SEQ ID NO 104
<211> LENGTH: 133
<212> TYPE: PRT
<213> ORGANISM: Homo sapiens

<400> SEQUENCE: 104

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
        130
```

<210> SEQ ID NO 105
<211> LENGTH: 133
<212> TYPE: PRT
<213> ORGANISM: Homo sapiens

<400> SEQUENCE: 105

```
Ala Pro Met Thr Gln Thr Thr Pro Leu Lys Thr Ser Trp Val Asn Cys
1               5                   10                  15

Ser Asn Met Ile Asp Glu Ile Ile Thr His Leu Lys Gln Pro Pro Leu
            20                  25                  30

Pro Leu Leu Asp Phe Asn Asn Leu Asn Gly Glu Asp Gln Asp Ile Leu
```

-continued

```
                35                  40                  45
Met Glu Asn Asn Leu Arg Arg Pro Asn Leu Glu Ala Phe Asn Arg Ala
 50                  55                  60

Val Lys Ser Leu Gln Asn Ala Ser Ala Ile Glu Ser Ile Leu Lys Asn
 65                  70                  75                  80

Leu Leu Pro Cys Leu Pro Leu Ala Thr Ala Ala Pro Thr Arg His Pro
                 85                  90                  95

Ile His Ile Lys Asp Gly Asp Trp Asn Glu Phe Arg Lys Leu Thr
                100                 105                 110

Phe Tyr Leu Lys Thr Leu Glu Asn Ala Gln Ala Gln Gln Thr Thr Leu
                115                 120                 125

Ser Leu Ala Ile Phe
                130
```

<210> SEQ ID NO 106
<211> LENGTH: 152
<212> TYPE: PRT
<213> ORGANISM: Homo sapiens

<400> SEQUENCE: 106

```
Asp Cys Asp Ile Glu Gly Lys Asp Gly Lys Gln Tyr Glu Ser Val Leu
 1               5                  10                  15

Met Val Ser Ile Asp Gln Leu Leu Asp Ser Met Lys Glu Ile Gly Ser
                20                  25                  30

Asn Cys Leu Asn Asn Glu Phe Asn Phe Phe Lys Arg His Ile Cys Asp
                35                  40                  45

Ala Asn Lys Glu Gly Met Phe Leu Phe Arg Ala Ala Arg Lys Leu Arg
 50                  55                  60

Gln Phe Leu Lys Met Asn Ser Thr Gly Asp Phe Asp Leu His Leu Leu
 65                  70                  75                  80

Lys Val Ser Glu Gly Thr Thr Ile Leu Leu Asn Cys Thr Gly Gln Val
                 85                  90                  95

Lys Gly Arg Lys Pro Ala Ala Leu Gly Glu Ala Gln Pro Thr Lys Ser
                100                 105                 110

Leu Glu Glu Asn Lys Ser Leu Lys Glu Gln Lys Lys Leu Asn Asp Leu
                115                 120                 125

Cys Phe Leu Lys Arg Leu Leu Gln Glu Ile Lys Thr Cys Trp Asn Lys
                130                 135                 140

Ile Leu Met Gly Thr Lys Glu His
145                 150
```

<210> SEQ ID NO 107
<211> LENGTH: 79
<212> TYPE: PRT
<213> ORGANISM: Homo sapiens

<400> SEQUENCE: 107

```
Glu Gly Ala Val Leu Pro Arg Ser Ala Lys Glu Leu Arg Cys Gln Cys
 1               5                  10                  15

Ile Lys Thr Tyr Ser Lys Pro Phe His Pro Lys Phe Ile Lys Glu Leu
                20                  25                  30

Arg Val Ile Glu Ser Gly Pro His Cys Ala Asn Thr Glu Ile Ile Val
                35                  40                  45

Lys Leu Ser Asp Gly Arg Glu Leu Cys Leu Asp Pro Lys Glu Asn Trp
 50                  55                  60

Val Gln Arg Val Val Glu Lys Phe Leu Lys Arg Ala Glu Asn Ser
```

```
                65                  70                  75

<210> SEQ ID NO 108
<211> LENGTH: 160
<212> TYPE: PRT
<213> ORGANISM: Homo sapiens

<400> SEQUENCE: 108

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
                20                  25                  30

Val Lys Thr Phe Phe Gln Met Lys Asp Gln Leu Asp Asn Leu Leu Leu
            35                  40                  45

Lys Glu Ser Leu Leu Glu Asp Phe Lys Gly Tyr Leu Gly Cys Gln Ala
        50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

<210> SEQ ID NO 109
<211> LENGTH: 114
<212> TYPE: PRT
<213> ORGANISM: Homo sapiens

<400> SEQUENCE: 109

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
        50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 110
<211> LENGTH: 132
<212> TYPE: PRT
<213> ORGANISM: Homo sapiens

<400> SEQUENCE: 110
```

```
Gly Ile Thr Ile Pro Arg Asn Pro Gly Cys Pro Asn Ser Glu Asp Lys
1               5                   10                  15

Asn Phe Pro Arg Thr Val Met Val Asn Leu Asn Ile His Asn Arg Asn
                20                  25                  30

Thr Asn Thr Asn Pro Lys Arg Ser Ser Asp Tyr Tyr Asn Arg Ser Thr
            35                  40                  45

Ser Pro Trp Asn Leu His Arg Asn Glu Asp Pro Glu Arg Tyr Pro Ser
    50                  55                  60

Val Ile Trp Glu Ala Lys Cys Arg His Leu Gly Cys Ile Asn Ala Asp
65                  70                  75                  80

Gly Asn Val Asp Tyr His Met Asn Ser Val Pro Ile Gln Gln Glu Ile
                85                  90                  95

Leu Val Leu Arg Arg Glu Pro Pro His Cys Pro Asn Ser Phe Arg Leu
                100                 105                 110

Glu Lys Ile Leu Val Ser Val Gly Cys Thr Cys Val Thr Pro Ile Val
            115                 120                 125

His His Val Ala
        130
```

<210> SEQ ID NO 111
<211> LENGTH: 157
<212> TYPE: PRT
<213> ORGANISM: Homo sapiens

<400> SEQUENCE: 111

```
Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
                20                  25                  30

Met Thr Asp Ser Asp Cys Arg Asp Asn Ala Pro Arg Thr Ile Phe Ile
            35                  40                  45

Ile Ser Met Tyr Lys Asp Ser Gln Pro Arg Gly Met Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155
```

<210> SEQ ID NO 112
<211> LENGTH: 352
<212> TYPE: PRT
<213> ORGANISM: Homo sapiens

<400> SEQUENCE: 112

```
Arg Asp Thr Ser Ala Thr Pro Gln Ser Ala Ser Ile Lys Ala Leu Arg
1               5                   10                  15

Asn Ala Asn Leu Arg Arg Asp Glu Ser Asn His Leu Thr Asp Leu Tyr
                20                  25                  30
```

Arg Arg Asp Glu Thr Ile Gln Val Lys Gly Asn Gly Tyr Val Gln Ser
            35                  40                  45

Pro Arg Phe Pro Asn Ser Tyr Pro Arg Asn Leu Leu Leu Thr Trp Arg
 50                  55                  60

Leu His Ser Gln Glu Asn Thr Arg Ile Gln Leu Val Phe Asp Asn Gln
65                  70                  75                  80

Phe Gly Leu Glu Glu Ala Glu Asn Asp Ile Cys Arg Tyr Asp Phe Val
                85                  90                  95

Glu Val Glu Asp Ile Ser Glu Thr Ser Thr Ile Ile Arg Gly Arg Trp
            100                 105                 110

Cys Gly His Lys Glu Val Pro Pro Arg Ile Lys Ser Arg Thr Asn Gln
            115                 120                 125

Ile Lys Ile Thr Phe Lys Ser Asp Asp Tyr Phe Val Ala Lys Pro Gly
130                 135                 140

Phe Lys Ile Tyr Tyr Ser Leu Leu Glu Asp Phe Gln Pro Ala Ala Ala
145                 150                 155                 160

Ser Glu Thr Asn Trp Glu Ser Val Thr Ser Ser Ile Ser Gly Val Ser
                165                 170                 175

Tyr Asn Ser Pro Ser Val Thr Asp Pro Thr Leu Ile Ala Asp Ala Leu
            180                 185                 190

Asp Lys Lys Ile Ala Glu Phe Asp Thr Val Glu Asp Leu Leu Lys Tyr
            195                 200                 205

Phe Asn Pro Glu Ser Trp Gln Glu Asp Leu Glu Asn Met Tyr Leu Asp
            210                 215                 220

Thr Pro Arg Tyr Arg Gly Arg Ser Tyr His Asp Arg Lys Ser Lys Val
225                 230                 235                 240

Asp Leu Asp Arg Leu Asn Asp Asp Ala Lys Arg Tyr Ser Cys Thr Pro
                245                 250                 255

Arg Asn Tyr Ser Val Asn Ile Arg Glu Glu Leu Lys Leu Ala Asn Val
            260                 265                 270

Val Phe Phe Pro Arg Cys Leu Leu Val Gln Arg Cys Gly Gly Asn Cys
            275                 280                 285

Gly Cys Gly Thr Val Asn Trp Arg Ser Cys Thr Cys Asn Ser Gly Lys
290                 295                 300

Thr Val Lys Lys Tyr His Glu Val Leu Gln Phe Glu Pro Gly His Ile
305                 310                 315                 320

Lys Arg Arg Gly Arg Ala Lys Thr Met Ala Leu Val Asp Ile Gln Leu
                325                 330                 335

Asp His His Glu Arg Cys Asp Cys Ile Cys Ser Ser Arg Pro Pro Arg
            340                 345                 350

<210> SEQ ID NO 113
<211> LENGTH: 248
<212> TYPE: PRT
<213> ORGANISM: Homo sapiens

<400> SEQUENCE: 113

Glu Gly Ile Cys Arg Asn Arg Val Thr Asn Asn Val Lys Asp Val Thr
1               5                   10                  15

Lys Leu Val Ala Asn Leu Pro Lys Asp Tyr Met Ile Thr Leu Lys Tyr
            20                  25                  30

Val Pro Gly Met Asp Val Leu Pro Ser His Cys Trp Ile Ser Glu Met
            35                  40                  45

Val Val Gln Leu Ser Asp Ser Leu Thr Asp Leu Leu Asp Lys Phe Ser
        50                  55                  60

```
Asn Ile Ser Glu Gly Leu Ser Asn Tyr Ser Ile Ile Asp Lys Leu Val
 65                  70                  75                  80

Asn Ile Val Asp Asp Leu Val Glu Cys Val Lys Glu Asn Ser Ser Lys
                 85                  90                  95

Asp Leu Lys Lys Ser Phe Lys Ser Pro Glu Pro Arg Leu Phe Thr Pro
            100                 105                 110

Glu Glu Phe Phe Arg Ile Phe Asn Arg Ser Ile Asp Ala Phe Lys Asp
            115                 120                 125

Phe Val Val Ala Ser Glu Thr Ser Asp Cys Val Val Ser Ser Thr Leu
        130                 135                 140

Ser Pro Glu Lys Asp Ser Arg Val Ser Val Thr Lys Pro Phe Met Leu
145                 150                 155                 160

Pro Pro Val Ala Ala Ser Ser Leu Arg Asn Asp Ser Ser Ser Ser Asn
                165                 170                 175

Arg Lys Ala Lys Asn Pro Pro Gly Asp Ser Ser Leu His Trp Ala Ala
            180                 185                 190

Met Ala Leu Pro Ala Leu Phe Ser Leu Ile Ile Gly Phe Ala Phe Gly
        195                 200                 205

Ala Leu Tyr Trp Lys Lys Arg Gln Pro Ser Leu Thr Arg Ala Val Glu
        210                 215                 220

Asn Ile Gln Ile Asn Glu Glu Asp Asn Glu Ile Ser Met Leu Gln Glu
225                 230                 235                 240

Lys Glu Arg Glu Phe Gln Glu Val
            245

<210> SEQ ID NO 114
<211> LENGTH: 209
<212> TYPE: PRT
<213> ORGANISM: Homo sapiens

<400> SEQUENCE: 114

Thr Gln Asp Cys Ser Phe Gln His Ser Pro Ile Ser Ser Asp Phe Ala
  1               5                  10                  15

Val Lys Ile Arg Glu Leu Ser Asp Tyr Leu Leu Gln Asp Tyr Pro Val
             20                  25                  30

Thr Val Ala Ser Asn Leu Gln Asp Glu Glu Leu Cys Gly Gly Leu Trp
         35                  40                  45

Arg Leu Val Leu Ala Gln Arg Trp Met Glu Arg Leu Lys Thr Val Ala
 50                  55                  60

Gly Ser Lys Met Gln Gly Leu Leu Glu Arg Val Asn Thr Glu Ile His
 65                  70                  75                  80

Phe Val Thr Lys Cys Ala Phe Gln Pro Pro Pro Ser Cys Leu Arg Phe
                 85                  90                  95

Val Gln Thr Asn Ile Ser Arg Leu Leu Gln Glu Thr Ser Glu Gln Leu
            100                 105                 110

Val Ala Leu Lys Pro Trp Ile Thr Arg Gln Asn Phe Ser Arg Cys Leu
        115                 120                 125

Glu Leu Gln Cys Gln Pro Asp Ser Ser Thr Leu Pro Pro Pro Trp Ser
        130                 135                 140

Pro Arg Pro Leu Glu Ala Thr Ala Pro Thr Ala Pro Gln Pro Pro Leu
145                 150                 155                 160

Leu Leu Leu Leu Leu Leu Pro Val Gly Leu Leu Leu Leu Ala Ala Ala
                165                 170                 175

Trp Cys Leu His Trp Gln Arg Thr Arg Arg Arg Thr Pro Arg Pro Gly
```

```
                180                 185                 190
Glu Gln Val Pro Pro Val Pro Ser Pro Gln Asp Leu Leu Leu Val Glu
        195                 200                 205

His

<210> SEQ ID NO 115
<211> LENGTH: 360
<212> TYPE: PRT
<213> ORGANISM: Homo sapiens

<400> SEQUENCE: 115

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Lys Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
        195                 200                 205

Pro Trp Asn Ile Thr Leu Ser Trp Arg Gln Asp Gly Val Ser Leu Ser
    210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
            260                 265                 270

Pro Ser Gly Lys Val Leu Val Leu Gln Ser His Trp Gln Thr Phe His
        275                 280                 285

Val Ser Ala Val Ala Ala Ala Ile Phe Val Ile Ile Ile Phe Tyr
    290                 295                 300

Val Arg Cys Cys Lys Lys Lys Thr Ser Ala Ala Glu Gly Pro Glu Leu
305                 310                 315                 320

Val Ser Leu Gln Val Leu Asp Gln His Pro Val Gly Thr Ser Asp His
                325                 330                 335

Arg Asp Ala Thr Gln Leu Gly Phe Gln Pro Leu Met Ser Asp Leu Gly
```

Ser Thr Gly Ser Thr Glu Gly Ala
         355                 360

<210> SEQ ID NO 116
<211> LENGTH: 361
<212> TYPE: PRT
<213> ORGANISM: Homo sapiens

<400> SEQUENCE: 116

Ala Glu Pro His Ser Leu Arg Tyr Asn Leu Met Val Leu Ser Gln Asp
1               5                   10                  15

Glu Ser Val Gln Ser Gly Phe Leu Ala Glu Gly His Leu Asp Gly Gln
            20                  25                  30

Pro Phe Leu Arg Tyr Asp Arg Gln Lys Arg Arg Ala Lys Pro Gln Gly
        35                  40                  45

Gln Trp Ala Glu Asp Val Leu Gly Ala Lys Thr Trp Asp Thr Glu Thr
50                  55                  60

Glu Asp Leu Thr Glu Asn Gly Gln Asp Leu Arg Arg Thr Leu Thr His
65                  70                  75                  80

Ile Lys Asp Gln Lys Gly Gly Leu His Ser Leu Gln Glu Ile Arg Val
                85                  90                  95

Cys Glu Ile His Glu Asp Ser Ser Thr Arg Gly Ser Arg His Phe Tyr
            100                 105                 110

Tyr Asp Gly Glu Leu Phe Leu Ser Gln Asn Leu Glu Thr Gln Glu Ser
        115                 120                 125

Thr Val Pro Gln Ser Ser Arg Ala Gln Thr Leu Ala Met Asn Val Thr
130                 135                 140

Asn Phe Trp Lys Glu Asp Ala Met Lys Thr Lys Thr His Tyr Arg Ala
145                 150                 155                 160

Met Gln Ala Asp Cys Leu Gln Lys Leu Gln Arg Tyr Leu Lys Ser Gly
                165                 170                 175

Val Ala Ile Arg Arg Thr Val Pro Pro Met Val Asn Val Thr Cys Ser
            180                 185                 190

Glu Val Ser Glu Gly Asn Ile Thr Val Thr Cys Arg Ala Ser Ser Phe
        195                 200                 205

Tyr Pro Arg Asn Ile Thr Leu Thr Trp Arg Gln Asp Gly Val Ser Leu
210                 215                 220

Ser His Asn Thr Gln Gln Trp Gly Asp Val Leu Pro Asp Gly Asn Gly
225                 230                 235                 240

Thr Tyr Gln Thr Trp Val Ala Thr Arg Ile Arg Gln Gly Glu Glu Gln
                245                 250                 255

Arg Phe Thr Cys Tyr Met Glu His Ser Gly Asn His Gly Thr His Pro
            260                 265                 270

Val Pro Ser Gly Lys Val Leu Val Leu Gln Ser Gln Arg Thr Asp Phe
        275                 280                 285

Pro Tyr Val Ser Ala Ala Met Pro Cys Phe Val Ile Ile Ile Ile Leu
290                 295                 300

Cys Val Pro Cys Cys Lys Lys Lys Thr Ser Ala Ala Glu Gly Pro Glu
305                 310                 315                 320

Leu Val Ser Leu Gln Val Leu Asp Gln His Pro Val Gly Thr Gly Asp
                325                 330                 335

His Arg Asp Ala Ala Gln Leu Gly Phe Gln Pro Leu Met Ser Ala Thr
            340                 345                 350

```
Gly Ser Thr Gly Ser Thr Glu Gly Ala
        355                 360

<210> SEQ ID NO 117
<211> LENGTH: 190
<212> TYPE: PRT
<213> ORGANISM: Homo sapiens

<400> SEQUENCE: 117

Trp Val Asp Thr His Cys Leu Cys Tyr Asp Phe Ile Ile Thr Pro Lys
1               5                   10                  15

Ser Arg Pro Glu Pro Gln Trp Cys Glu Val Gln Gly Leu Val Asp Glu
            20                  25                  30

Arg Pro Phe Leu His Tyr Asp Cys Val Asn His Lys Ala Lys Ala Phe
        35                  40                  45

Ala Ser Leu Gly Lys Lys Val Asn Val Thr Lys Thr Trp Glu Glu Gln
    50                  55                  60

Thr Glu Thr Leu Arg Asp Val Val Asp Phe Leu Lys Gly Gln Leu Leu
65                  70                  75                  80

Asp Ile Gln Val Glu Asn Leu Ile Pro Ile Glu Pro Leu Thr Leu Gln
                85                  90                  95

Ala Arg Met Ser Cys Glu His Glu Ala His Gly His Gly Arg Gly Ser
            100                 105                 110

Trp Gln Phe Leu Phe Asn Gly Gln Lys Phe Leu Leu Phe Asp Ser Asn
        115                 120                 125

Asn Arg Lys Trp Thr Ala Leu His Pro Gly Ala Lys Lys Met Thr Glu
    130                 135                 140

Lys Trp Glu Lys Asn Arg Asp Val Thr Met Phe Phe Gln Lys Ile Ser
145                 150                 155                 160

Leu Gly Asp Cys Lys Met Trp Leu Glu Glu Phe Leu Met Tyr Trp Glu
                165                 170                 175

Gln Met Leu Asp Pro Thr Lys Pro Pro Ser Leu Ala Pro Gly
            180                 185                 190

<210> SEQ ID NO 118
<211> LENGTH: 191
<212> TYPE: PRT
<213> ORGANISM: Homo sapiens

<400> SEQUENCE: 118

Gly Arg Ala Asp Pro His Ser Leu Cys Tyr Asp Ile Thr Val Ile Pro
1               5                   10                  15

Lys Phe Arg Pro Gly Pro Arg Trp Cys Ala Val Gln Gly Gln Val Asp
            20                  25                  30

Glu Lys Thr Phe Leu His Tyr Asp Cys Gly Asn Lys Thr Val Thr Pro
        35                  40                  45

Val Ser Pro Leu Gly Lys Lys Leu Asn Val Thr Thr Ala Trp Lys Ala
    50                  55                  60

Gln Asn Pro Val Leu Arg Glu Val Val Asp Ile Leu Thr Glu Gln Leu
65                  70                  75                  80

Arg Asp Ile Gln Leu Glu Asn Tyr Thr Pro Lys Glu Pro Leu Thr Leu
                85                  90                  95

Gln Ala Arg Met Ser Cys Glu Gln Lys Ala Glu Gly His Ser Ser Gly
            100                 105                 110

Ser Trp Gln Phe Ser Phe Asp Gly Gln Ile Phe Leu Leu Phe Asp Ser
        115                 120                 125
```

```
Glu Lys Arg Met Trp Thr Thr Val His Pro Gly Ala Arg Lys Met Lys
130                 135                 140

Glu Lys Trp Glu Asn Asp Lys Val Val Ala Met Ser Phe His Tyr Phe
145                 150                 155                 160

Ser Met Gly Asp Cys Ile Gly Trp Leu Glu Asp Phe Leu Met Gly Met
                165                 170                 175

Asp Ser Thr Leu Glu Pro Ser Ala Gly Ala Pro Leu Ala Met Ser
            180                 185                 190

<210> SEQ ID NO 119
<211> LENGTH: 188
<212> TYPE: PRT
<213> ORGANISM: Homo sapiens

<400> SEQUENCE: 119

Asp Ala His Ser Leu Trp Tyr Asn Phe Thr Ile Ile His Leu Pro Arg
1               5                   10                  15

His Gly Gln Gln Trp Cys Glu Val Gln Ser Gln Val Asp Gln Lys Asn
                20                  25                  30

Phe Leu Ser Tyr Asp Cys Gly Ser Asp Lys Val Leu Ser Met Gly His
            35                  40                  45

Leu Glu Glu Gln Leu Tyr Ala Thr Asp Ala Trp Gly Lys Gln Leu Glu
50                  55                  60

Met Leu Arg Glu Val Gly Gln Arg Leu Arg Leu Glu Leu Ala Asp Thr
65                  70                  75                  80

Glu Leu Glu Asp Phe Thr Pro Ser Gly Pro Leu Thr Leu Gln Val Arg
                85                  90                  95

Met Ser Cys Glu Cys Glu Ala Asp Gly Tyr Ile Arg Gly Ser Trp Gln
            100                 105                 110

Phe Ser Phe Asp Gly Arg Lys Phe Leu Leu Phe Asp Ser Asn Asn Arg
        115                 120                 125

Lys Trp Thr Val Val His Ala Gly Ala Arg Arg Met Lys Glu Lys Trp
130                 135                 140

Glu Lys Asp Ser Gly Leu Thr Thr Phe Phe Lys Met Val Ser Met Arg
145                 150                 155                 160

Asp Cys Lys Ser Trp Leu Arg Asp Phe Leu Met His Arg Lys Lys Arg
                165                 170                 175

Leu Glu Pro Thr Ala Pro Pro Thr Met Ala Pro Gly
            180                 185

<210> SEQ ID NO 120
<211> LENGTH: 233
<212> TYPE: PRT
<213> ORGANISM: Homo sapiens

<400> SEQUENCE: 120

His Ser Leu Cys Phe Asn Phe Thr Ile Lys Ser Leu Ser Arg Pro Gly
1               5                   10                  15

Gln Pro Trp Cys Glu Ala Gln Val Phe Leu Asn Lys Asn Leu Phe Leu
                20                  25                  30

Gln Tyr Asn Ser Asp Asn Asn Met Val Lys Pro Leu Gly Leu Leu Gly
            35                  40                  45

Lys Lys Val Tyr Ala Thr Ser Thr Trp Gly Glu Leu Thr Gln Thr Leu
50                  55                  60

Gly Glu Val Gly Arg Asp Leu Arg Met Leu Leu Cys Asp Ile Lys Pro
65                  70                  75                  80
```

```
Gln Ile Lys Thr Ser Asp Pro Ser Thr Leu Gln Val Glu Met Phe Cys
                85                  90                  95

Gln Arg Glu Ala Glu Arg Cys Thr Gly Ala Ser Trp Gln Phe Ala Thr
            100                 105                 110

Asn Gly Glu Lys Ser Leu Leu Phe Asp Ala Met Asn Met Thr Trp Thr
        115                 120                 125

Val Ile Asn His Glu Ala Ser Lys Ile Lys Glu Thr Trp Lys Lys Asp
    130                 135                 140

Arg Gly Leu Glu Lys Tyr Phe Arg Lys Leu Ser Lys Gly Asp Cys Asp
145                 150                 155                 160

His Trp Leu Arg Glu Phe Leu Gly His Trp Glu Ala Met Pro Glu Pro
                165                 170                 175

Thr Val Ser Pro Val Asn Ala Ser Asp Ile His Trp Ser Ser Ser Ser
            180                 185                 190

Leu Pro Asp Arg Trp Ile Ile Leu Gly Ala Phe Ile Leu Leu Val Leu
        195                 200                 205

Met Gly Ile Val Leu Ile Cys Val Trp Trp Gln Asn Gly Glu Trp Gln
    210                 215                 220

Ala Gly Leu Trp Pro Leu Arg Thr Ser
225                 230

<210> SEQ ID NO 121
<211> LENGTH: 193
<212> TYPE: PRT
<213> ORGANISM: Homo sapiens

<400> SEQUENCE: 121

Gly Leu Ala Asp Pro His Ser Leu Cys Tyr Asp Ile Thr Val Ile Pro
1               5                   10                  15

Lys Phe Arg Pro Gly Pro Arg Trp Cys Ala Val Gln Gly Gln Val Asp
            20                  25                  30

Glu Lys Thr Phe Leu His Tyr Asp Cys Gly Ser Lys Thr Val Thr Pro
        35                  40                  45

Val Ser Pro Leu Gly Lys Lys Leu Asn Val Thr Thr Ala Trp Lys Ala
50                  55                  60

Gln Asn Pro Val Leu Arg Glu Val Val Asp Ile Leu Thr Glu Gln Leu
65                  70                  75                  80

Leu Asp Ile Gln Leu Glu Asn Tyr Ile Pro Lys Glu Pro Leu Thr Leu
                85                  90                  95

Gln Ala Arg Met Ser Cys Glu Gln Lys Ala Glu Gly His Gly Ser Gly
            100                 105                 110

Ser Trp Gln Leu Ser Phe Asp Gly Gln Ile Phe Leu Leu Phe Asp Ser
        115                 120                 125

Glu Asn Arg Met Trp Thr Thr Val His Pro Gly Ala Arg Lys Met Lys
    130                 135                 140

Glu Lys Trp Glu Asn Asp Lys Asp Met Thr Met Ser Phe His Tyr Ile
145                 150                 155                 160

Ser Met Gly Asp Cys Thr Gly Trp Leu Glu Asp Phe Leu Met Gly Met
                165                 170                 175

Asp Ser Thr Leu Glu Pro Ser Ala Gly Ala Pro Pro Thr Met Ser Ser
            180                 185                 190

Gly

<210> SEQ ID NO 122
<211> LENGTH: 193
```

<212> TYPE: PRT
<213> ORGANISM: Homo sapiens

<400> SEQUENCE: 122

```
Arg Arg Asp Asp Pro His Ser Leu Cys Tyr Asp Ile Thr Val Ile Pro
1               5                   10                  15

Lys Phe Arg Pro Gly Pro Arg Trp Cys Ala Val Gln Gly Gln Val Asp
            20                  25                  30

Glu Lys Thr Phe Leu His Tyr Asp Cys Gly Asn Lys Thr Val Thr Pro
        35                  40                  45

Val Ser Pro Leu Gly Lys Lys Leu Asn Val Thr Met Ala Trp Lys Ala
    50                  55                  60

Gln Asn Pro Val Leu Arg Glu Val Val Asp Ile Leu Thr Glu Gln Leu
65                  70                  75                  80

Leu Asp Ile Gln Leu Glu Asn Tyr Thr Pro Lys Glu Pro Leu Thr Leu
                85                  90                  95

Gln Ala Arg Met Ser Cys Glu Gln Lys Ala Glu Gly His Ser Ser Gly
            100                 105                 110

Ser Trp Gln Phe Ser Ile Asp Gly Gln Thr Phe Leu Leu Phe Asp Ser
        115                 120                 125

Glu Lys Arg Met Trp Thr Thr Val His Pro Gly Ala Arg Lys Met Lys
    130                 135                 140

Glu Lys Trp Glu Asn Asp Lys Asp Val Ala Met Ser Phe His Tyr Ile
145                 150                 155                 160

Ser Met Gly Asp Cys Ile Gly Trp Leu Glu Asp Phe Leu Met Gly Met
                165                 170                 175

Asp Ser Thr Leu Glu Pro Ser Ala Gly Ala Pro Leu Ala Met Ser Ser
            180                 185                 190

Gly
```

<210> SEQ ID NO 123
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

```
Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg
65
```

<210> SEQ ID NO 124
<211> LENGTH: 195
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 124

```
attacatgcc cccctcccat gagcgtggag cacgccgaca tctgggtgaa gagctatagc    60
ctctacagcc gggagaggta tatctgtaac agcggcttca agaggaaggc cggcaccagc   120
agcctcaccg agtgcgtgct gaataaggct accaacgtgg ctcactggac aacaccctct   180
ttaaagtgca tccgg                                                    195
```

<210> SEQ ID NO 125
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser
```

<210> SEQ ID NO 126
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 126

```
aactgggtga acgtcatcag cgatttaaag aagatcgaag atttaattca gtccatgcat    60
atcgacgcca ctttatacac agaatccgac gtgcacccct cttgtaaggt gaccgccatg   120
aaatgttttt tactggagct gcaagttatc tctttagaga gcggagacgc tagcatccac   180
gacaccgtgg agaatttaat cattttagcc aataactctt tatccagcaa cggcaacgtg   240
acagagtccg gctgcaagga gtgcgaagag ctggaggaga agaacatcaa ggagtttctg   300
caatcctttg tgcacattgt ccagatgttc atcaatacct cc                      342
```

<210> SEQ ID NO 127
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

```
Gln Ile Gln Leu Val Gln Ser Gly Gly Glu Val Lys Lys Pro Gly Ala
1               5                   10                  15
```

```
Ser Val Arg Val Ser Cys Lys Ala Ser Gly Tyr Ser Phe Thr Asp Tyr
            20                  25                  30

Asn Val Tyr Trp Val Arg Gln Ser Pro Gly Lys Gly Leu Glu Trp Ile
        35                  40                  45

Gly Tyr Ile Asp Pro Tyr Asn Gly Ile Thr Ile Tyr Asp Gln Asn Phe
50                  55                  60

Lys Gly Lys Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Asp Val Thr Thr Ala Leu Asp Phe Trp Gly Gln Gly Thr Thr
            100                 105                 110

Val Thr Val Ser Ser Glu Phe Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430
```

Ala Leu His Asn His Tyr Thr Gln Lys Ser Leu Ser Leu Ser Pro Gly
            435                 440                 445

Lys

<210> SEQ ID NO 128
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 128

| | | | | | |
|---|---|---|---|---|---|
| cagatccagc | tggtgcagag | cggcggcgag | gtgaagaagc | ccggcgccag | cgtgagggtg | 60 |
| agctgcaagg | ccagcggcta | cagcttcacc | gactacaacg | tgtactgggt | gaggcagagc | 120 |
| cccggcaagg | gcctggagtg | gatcggctac | atcgacccct | acaacggcat | caccatctac | 180 |
| gaccagaact | tcaagggcaa | ggccaccctg | accgtggaca | gagcaccag | caccgcctac | 240 |
| atggagctga | gcagcctgag | gagcgaggac | accgccgtgt | acttctgcgc | cagggacgtg | 300 |
| accaccgccc | tggacttctg | gggccagggc | accaccgtga | ccgtgagcag | cgagttcgcc | 360 |
| agcaccaagg | gccccagcgt | gttccccctg | gcccccagca | gcaagagcac | cagcggcggc | 420 |
| accgccgccc | tgggctgcct | ggtgaaggac | tacttccccg | agcccgtgac | cgtgagctgg | 480 |
| aacagcggcg | ccctgaccag | cggcgtgcac | accttccccg | ccgtgctgca | gagcagcggc | 540 |
| ctgtacagcc | tgagcagcgt | ggtgaccgtg | cccagcagca | gcctgggcac | ccagacctac | 600 |
| atctgcaacg | tgaaccacaa | gcccagcaac | accaaggtgg | acaagaaggt | ggagcccaag | 660 |
| agctgcgaca | agacccacac | ctgcccccca | tgccccgccc | ccgagctgct | gggcggcccc | 720 |
| agcgtgttcc | tgttcccccc | caagcccaag | gacaccctga | tgatcagcag | gacccccgag | 780 |
| gtgacctgcg | tggtggtgga | cgtgagccac | gaggaccccg | aggtgaagtt | caactggtac | 840 |
| gtggacggcg | tggaggtgca | caacgccaag | accaagccca | gggaggagca | gtacaacagc | 900 |
| acctacaggg | tggtgagcgt | gctgaccgtg | ctgcaccagg | actggctgaa | cggcaaggag | 960 |
| tacaagtgca | aggtgagcaa | caaggccctg | cccgccccca | tcgagaagac | catcagcaag | 1020 |
| gccaagggcc | agccccaggga | gccccaggtg | tacaccctgc | cccccagcag | ggacgagctg | 1080 |
| accaagaacc | aggtgagcct | gacctgcctg | gtgaagggct | tctaccccag | cgacatcgcc | 1140 |
| gtggagtggg | agagcaacgg | ccagcccgag | aacaactaca | agaccacccc | ccccgtgctg | 1200 |
| gacagcgacg | gcagcttctt | cctgtacagc | aagctgaccg | tggacaagag | caggtggcag | 1260 |
| cagggcaacg | tgttcagctg | cagcgtgatg | cacgaggccc | tgcacaacca | ctacacccag | 1320 |
| aagagcctga | gcctgagccc | cggcaagtga | | | | 1350 |

<210> SEQ ID NO 129
<211> LENGTH: 210
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Asp Ile Gln Met Thr Gln Ser Pro Ala Ser Leu Ser Ala Ser Val Gly
1               5                   10                  15

Arg Val Thr Ile Thr Cys Leu Ala Ser Gln Thr Ile Asp Thr Trp Leu
            20                  25                  30

```
Ala Trp Leu Gln Lys Pro Gly Lys Ser Pro Gln Leu Leu Ile Tyr Ala
             35                  40                  45
Ala Thr Asn Leu Asp Gly Val Pro Ser Arg Phe Ser Gly Ser Gly Ser
 50                      55                  60
Gly Thr Asp Phe Ser Phe Ile Ser Ser Leu Gln Pro Glu Asp Phe Ala
 65                  70                  75                  80
Thr Tyr Tyr Cys Gln Gln Val Tyr Ser Ser Pro Phe Thr Phe Gly Gln
                 85                  90                  95
Gly Thr Lys Leu Glu Ile Lys Arg Thr Val Ala Ala Pro Ser Val Phe
            100                 105                 110
Ile Phe Pro Pro Ser Asp Glu Gln Leu Lys Ser Gly Thr Ala Ser Val
        115                 120                 125
Val Cys Leu Leu Asn Asn Phe Tyr Pro Arg Glu Ala Lys Val Gln Trp
130                 135                 140
Lys Val Asp Asn Ala Leu Gln Ser Gly Asn Ser Gln Glu Ser Val Thr
145                 150                 155                 160
Glu Gln Asp Ser Lys Asp Ser Thr Tyr Ser Leu Ser Ser Thr Leu Thr
                165                 170                 175
Leu Ser Lys Ala Asp Tyr Glu Lys His Lys Val Tyr Ala Cys Glu Val
            180                 185                 190
Thr His Gln Gly Leu Ser Ser Pro Val Thr Lys Ser Phe Asn Arg Gly
        195                 200                 205
Glu Cys
    210

<210> SEQ ID NO 130
<211> LENGTH: 647
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 130
gacatccaga tgacccagag ccccgccagc ctgagcgcca gcgtgggcga cagggtgacc      60
atcacctgcc tggccagcca gaccatcgac acctggctgg cctggtacct gcagaagccc    120
ggcaagagcc cccagctgct gatctacgcc gccaccaacc tggccgacgg cgtgcccagc    180
aggttcagcg gcagcggcag cggcaccgac ttcagcttca ccatcagca gcctgcagcc    240 cgaggacttc gccacctact actgccagca ggtgtactag cagccccttc accttcggcc    300
agggcaccaa gctggagatc aagaggaccg tggccgcccc cagcgtgttc atcttccccc    360
ccagcgacga gcagctgaag agcggcaccg ccagcgtggt gtgcctgctg aacaacttct    420
accccaggga ggccaaggtg cagtggaagg tggacaacgc cctgcagagc ggcaacagcc    480
aggagagcgt gaccgagcag gacagcaagg acagcaccta cagcctgagc agcaccctga    540
ccctgagcaa ggccgactac gagaagcaca aggtgtacgc ctgcgaggtg acccaccagg    600
gcctgagcag ccccgtgacc aagagcttca cagggggcga gtgctga                  647

<210> SEQ ID NO 131
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
```

```
atgaaatggg tgacctttat ttctttactg ttcctcttta gcagcgccta ctcc         54
```

```
<210> SEQ ID NO 132
<211> LENGTH: 918
<212> TYPE: DNA
<213> ORGANISM: Homo sapiens

<400> SEQUENCE: 132
atttgggaac tgaagaagga cgtctacgtg gtcgaactgg actggtatcc cgatgctccc    60
ggcgaaatgg tggtgctcac ttgtgacacc cccgaagaag acggcatcac ttggaccctc   120
gatcagagca gcgaggtgct gggctccgga aagacccctca caatccaagt taaggagttc   180
ggagacgctg ccaatacaca atgccacaag ggaggcgagg tgctcagcca ttccttatta   240
ttattacaca agaaggaaga cggaatctgg tccaccgaca ttttaaaaga tcagaaggag   300
cccaagaata agacctttt aaggtgtgag gccaaaaact acagcggtcg tttcacttgt   360
tggtggctga ccaccatttc caccgattta accttctccg tgaaaagcag ccggggaagc   420
tccgaccctc aaggtgtgac atgtggagcc gctaccctca gcgctgagag ggttcgtggc   480
gataacaagg aatacgagta cagcgtggag tgccaagaag atagcgcttg tcccgctgcc   540
gaagaatctt tacccattga ggtgatggtg gacgccgtgc acaaactcaa gtacgagaac   600
tacacctcct ccttctttat ccgggacatc attaagcccg atcctcctaa gaatttacag   660
ctgaagcctc tcaaaatag ccggcaagtt gaggtctctt gggaatatcc cgacacttgg   720
agcacacccc acagctactt ctctttaacc tttttgtgtgc aagttcaagg taaaagcaag   780
cgggagaaga aagaccgggt gtttaccgac aaaaccagcg ccaccgtcat ctgtcggaag   840
aacgcctcca tcagcgtgag ggctcaagat cgttattact ccagcagctg gtccgagtgg   900
gccagcgtgc cttgttcc                                                  918
```

```
<210> SEQ ID NO 133
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
ggcggtggag gatccggagg aggtggctcc ggcggcggag gatct                    45
```

```
<210> SEQ ID NO 134
<211> LENGTH: 591
<212> TYPE: DNA
<213> ORGANISM: Homo sapiens

<400> SEQUENCE: 134
cgtaacctcc ccgtggctac ccccgatccc ggaatgttcc cttgtttaca ccacagccag    60
aatttactga gggccgtgag caacatgctg cagaaagcta gcagactttt agaatttac   120 ccttgcacca gcgaggagat cgaccatgaa gatatcacca aggacaagac atccaccgtg   180
gaggcttgtt tacctctgga gctgacaaag aacgagtctt gtctcaactc tcgtgaaacc   240
agcttcatca caaatggctc ttgtttagct tcccggaaga cctcctttat gatggcttta   300
tgcctcagct ccatctacga ggatttaaag atgtaccaag tggagttcaa gaccatgaac   360
gccaagctgc tcatggaccc taaacggcag atctttttag accagaacat gctggctgtg   420
attgatgagc tgatgcaagc tttaaacttc aactccgaga ccgtccctca gaagtcctcc   480
```

-continued

```
ctcgaggagc ccgattttta caagacaaag atcaaactgt gcattttact ccacgccttt      540
aggatccggg ccgtgaccat tgaccgggtc atgagctatt taaacgccag c               591

<210> SEQ ID NO 135
<211> LENGTH: 195
<212> TYPE: DNA
<213> ORGANISM: Homo sapiens

<400> SEQUENCE: 135
attacatgcc ccctcccat gagcgtggag cacgccgaca tctgggtgaa gagctatagc       60
ctctacagcc gggagaggta tatctgtaac agcggcttca agaggaaggc cggcaccagc     120
agcctcaccg agtgcgtgct gaataaggct accaacgtgg ctcactggac aacaccctct     180
ttaaagtgca tccgg                                                      195

<210> SEQ ID NO 136
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Met Lys Trp Val Thr Phe Ile Ser Leu Leu Phe Leu Phe Ser Ser Ala
1               5                   10                  15

Tyr Ser

<210> SEQ ID NO 137
<211> LENGTH: 306
<212> TYPE: PRT
<213> ORGANISM: Homo sapiens

<400> SEQUENCE: 137

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
                20                  25                  30

Glu Asp Gly Ile Thr Trp Thr Leu Asp Gln Ser Ser Glu Val Leu Gly
            35                  40                  45

Ser Gly Lys Thr Leu Thr Ile Gln Val Lys Glu Phe Gly Asp Ala Gly
        50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
```

```
                    180                 185                 190
Val His Lys Leu Lys Tyr Glu Asn Tyr Thr Ser Ser Phe Phe Ile Arg
                195                 200                 205

Asp Ile Ile Lys Pro Asp Pro Pro Lys Asn Leu Gln Leu Lys Pro Leu
            210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
                275                 280                 285

Gln Asp Arg Tyr Tyr Ser Ser Trp Ser Glu Trp Ala Ser Val Pro
            290                 295                 300

Cys Ser
305

<210> SEQ ID NO 138
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Gly Gly Gly Gly Ser Gly Gly Gly Ser Gly Gly Gly Gly Ser
1               5                   10                  15

<210> SEQ ID NO 139
<211> LENGTH: 197
<212> TYPE: PRT
<213> ORGANISM: Homo sapiens

<400> SEQUENCE: 139

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
                20                  25                  30

Ala Arg Gln Thr Leu Glu Phe Tyr Pro Cys Thr Ser Glu Glu Ile Asp
            35                  40                  45

His Glu Asp Ile Thr Lys Asp Lys Thr Ser Thr Val Glu Ala Cys Leu
50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
```

```
                165                 170                 175
Leu His Ala Phe Arg Ile Arg Ala Val Thr Ile Asp Arg Val Met Ser
            180                 185                 190

Tyr Leu Asn Ala Ser
        195

<210> SEQ ID NO 140
<211> LENGTH: 65
<212> TYPE: PRT
<213> ORGANISM: Homo sapiens

<400> SEQUENCE: 140

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg
65

<210> SEQ ID NO 141
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
atgaagtggg tcacatttat ctctttactg ttcctcttct ccagcgccta cagc          54

<210> SEQ ID NO 142
<211> LENGTH: 471
<212> TYPE: DNA
<213> ORGANISM: Homo sapiens

<400> SEQUENCE: 142
tacttcggca aactggaatc caagctgagc gtgatccgga atttaaacga ccaagttctg    60
tttatcgatc aaggtaaccg gcctctgttc gaggacatga ccgactccga ttgccgggac   120 aatgccccc ggaccatctt cattatctcc atgtacaagg acagccagcc ccggggcatg    180
gctgtgacaa ttagcgtgaa gtgtgagaaa atcagcactt tatcttgtga gaacaagatc   240
atctccttta aggaaatgaa ccccccgat aacatcaagg acaccaagtc cgatatcatc     300
ttcttccagc ggtccgtgcc cggtcacgat aacaagatgc agttcgaatc ctcctcctac   360
gagggctact ttttagcttg tgaaaaggag agggatttat tcaagctgat cctcaagaag   420
gaggacgagc tgggcgatcg ttccatcatg ttcaccgtcc aaaacgagga t            471

<210> SEQ ID NO 143
<211> LENGTH: 657
<212> TYPE: DNA
<213> ORGANISM: Homo sapiens

<400> SEQUENCE: 143
agcggcacaa ccaacacagt cgctgcctat aacctcactt ggaagagcac caacttcaaa    60
accatcctcg aatgggaacc caaacccgtt aaccaagttt acaccgtgca gatcagcacc   120
```
aagtccggcg actggaagtc caaatgtttc tataccaccg acaccgagtg cgatctcacc    180
gatgagatcg tgaaagatgt gaaacagacc tacctcgccc gggtgtttag ctaccccgcc    240
ggcaatgtgg agagcactgg ttccgctggc gagcctttat acgagaacag ccccgaattt    300
accccttacc tcgagaccaa tttaggacag cccaccatcc aaagctttga gcaagttggc    360
acaaaggtga atgtgacagt ggaggacgag cggactttag tgcggcggaa caacaccttt    420
ctcagcctcc gggatgtgtt cggcaaagat ttaatctaca cactgtatta ctggaagtcc    480
tcttcctccg gcaagaagac agctaaaacc aacacaaacg agtttttaat cgacgtggat    540
aaaggcgaaa actactgttt cagcgtgcaa gctgtgatcc cctcccggac cgtgaatagg    600
aaaagcaccg atagccccgt tgagtgcatg ggccaagaaa agggcgagtt ccgggag      657

<210> SEQ ID NO 144
<211> LENGTH: 342
<212> TYPE: DNA
<213> ORGANISM: Homo sapiens

<400> SEQUENCE: 144
aactgggtga acgtcatcag cgatttaaag aagatcgaag atttaattca gtccatgcat     60
atcgacgcca ctttatacac agaatccgac gtgcacccct cttgtaaggt gaccgccatg    120
aaatgttttt tactggagct gcaagttatc tctttagaga gcggagacgc tagcatccac    180
gacaccgtgg agaatttaat cattttagcc aataactctt tatccagcaa cggcaacgtg    240
acagagtccg gctgcaagga gtgcgaagag ctggaggaga gaacatcaa ggagtttctg    300 caatcctttg tgcacattgt ccagatgttc atcaatacct cc                      342

<210> SEQ ID NO 145
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Met Lys Trp Val Thr Phe Ile Ser Leu Leu Phe Leu Phe Ser Ser Ala
1               5                   10                  15

Tyr Ser

<210> SEQ ID NO 146
<211> LENGTH: 157
<212> TYPE: PRT
<213> ORGANISM: Homo sapiens

<400> SEQUENCE: 146

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
                20                  25                  30

Met Thr Asp Ser Asp Cys Arg Asp Asn Ala Pro Arg Thr Ile Phe Ile
            35                  40                  45

Ile Ser Met Tyr Lys Asp Ser Gln Pro Arg Gly Met Ala Val Thr Ile
        50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys

```
                85                  90                  95
Ser Asp Ile Ile Phe Gln Arg Ser Val Pro Gly His Asp Asn Lys
            100                 105                 110

Met Gln Phe Glu Ser Ser Tyr Glu Gly Tyr Phe Leu Ala Cys Glu
            115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155

<210> SEQ ID NO 147
<211> LENGTH: 219
<212> TYPE: PRT
<213> ORGANISM: Homo sapiens

<400> SEQUENCE: 147

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
    130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu
    210                 215

<210> SEQ ID NO 148
<211> LENGTH: 114
<212> TYPE: PRT
<213> ORGANISM: Homo sapiens

<400> SEQUENCE: 148

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
```

```
        35                  40                  45
Val Ile Ser Leu Glu Ser Gly Asp Ala Ser Ile His Asp Thr Val Glu
 50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Gln Met Phe Ile Asn
            100                 105                 110

Thr Ser

<210> SEQ ID NO 149
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
atgaaatggg tgacctttat ttctttactg ttcctctttta gcagcgccta ctcc         54

<210> SEQ ID NO 150
<211> LENGTH: 918
<212> TYPE: DNA
<213> ORGANISM: Homo sapiens

<400> SEQUENCE: 150
atttgggaac tgaagaagga cgtctacgtg gtcgaactgg actggtatcc cgatgctccc     60
ggcgaaatgg tggtgctcac ttgtgacacc cccgaagaag acggcatcac ttggaccctc    120
gatcagagca gcgaggtgct gggctccgga aagaccctca caatccaagt taaggagttc    180
ggagacgctg gccaatacac atgccacaag ggaggcgagg tgctcagcca ttccttatta    240
ttattacaca agaaggaaga cggaatctgg tccaccgaca ttttaaaaga tcagaaggag    300
cccaagaata agacctttt aaggtgtgag gccaaaaact acagcggtcg tttcacttgt    360
tggtggctga ccaccatttc caccgattta accttctccg tgaaaagcag ccggggaagc    420
tccgaccctc aaggtgtgac atgtggagcc gctaccctca gcgctgagag ggttcgtggc    480
gataacaagg aatacgagta cagcgtggag tgccaagaag atagcgcttg cccgctgcc    540 gaagaatctt tacccattga ggtgatggtg gacgccgtgc acaaactcaa gtacgagaac    600
tacacctcct ccttctttat ccgggacatc attaagcccg atcctcctaa gaatttacag    660
ctgaagcctc tcaaaaatag ccggcaagtt gaggtctctt gggaatatcc cgacacttgg    720
agcacacccc acagctactt ctctttaacc ttttgtgtgc aagttcaagg taaaagcaag    780
cgggagaaga agaccgggt gtttaccgac aaaaccagcg ccaccgtcat ctgtcggaag    840
aacgcctcca tcagcgtgag ggctcaagat cgttattact ccagcagctg gtccgagtgg    900
gccagcgtgc cttgttcc                                                  918

<210> SEQ ID NO 151
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
```

```
ggcggtggag gatccggagg aggtggctcc ggcggcggag gatct            45
```

<210> SEQ ID NO 152
<211> LENGTH: 591
<212> TYPE: DNA
<213> ORGANISM: Homo sapiens

<400> SEQUENCE: 152

```
cgtaacctcc ccgtggctac ccccgatccc ggaatgttcc cttgtttaca ccacagccag     60
aatttactga gggccgtgag caacatgctg cagaaagcta ggcagacttt agaattttac    120
ccttgcacca gcgaggagat cgaccatgaa gatatcacca aggacaagac atccaccgtg    180
gaggcttgtt tacctctgga gctgacaaag aacgagtctt gtctcaactc tcgtgaaacc    240
agcttcatca caaatggctc ttgtttagct tcccggaaga cctcctttat gatggcttta    300
tgcctcagct ccatctacga ggatttaaag atgtaccaag tggagttcaa gaccatgaac    360
gccaagctgc tcatggaccc taaacggcag atcttttag accagaacat gctggctgtg    420
attgatgagc tgatgcaagc tttaaacttc aactccgaga ccgtccctca gaagtcctcc    480
ctcgaggagc ccgattttta caagacaaag atcaaactgt gcattttact ccacgccttt    540
aggatccggg ccgtgaccat tgaccgggtc atgagctatt taaacgccag c              591
```

<210> SEQ ID NO 153
<211> LENGTH: 195
<212> TYPE: DNA
<213> ORGANISM: Homo sapiens

<400> SEQUENCE: 153

```
attacatgcc cccctcccat gagcgtggag cacgccgaca tctgggtgaa gagctatagc     60
ctctacagcc gggagaggta tatctgtaac agcggcttca agaggaaggc cggcaccagc    120
agcctcaccg agtgcgtgct gaataaggct accaacgtgg ctcactggac aacaccctct    180
ttaaagtgca tccgg                                                     195
```

<210> SEQ ID NO 154
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 154

```
tccgagctga cccaggaccc tgctgtgtcc gtggctctgg gccagaccgt gaggatcacc     60
tgccagggcg actccctgag gtcctactac gcctcctggt accagcagaa gcccggccag    120
gctcctgtgc tggtgatcta cggcaagaac aacaggccct ccggcatccc tgacaggttc    180
tccggatcct cctccggcaa caccgcctcc ctgaccatca caggcgctca ggccgaggac    240
gaggctgact actactgcaa ctccaggga ctcctccggca accatgtggt gttcggcggc    300
ggcaccaagc tgaccgtggg ccat                                           324
```

<210> SEQ ID NO 155
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155

```
ggcggcggcg gctccggagg cggcggcagc ggcggaggag gatcc              45
```

<210> SEQ ID NO 156
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 156

```
gaggtgcagc tggtggagtc cggaggagga gtggtgaggc ctggaggctc cctgaggctg    60
agctgtgctg cctccggctt caccttcgac gactacggca tgtcctgggt gaggcaggct   120
cctggaaagg gcctggagtg ggtgtccggc atcaactgga acggcggatc caccggctac   180
gccgattccg tgaagggcag gttcaccatc agcagggaca cgccaagaa ctccctgtac    240 ctgcagatga actccctgag ggccgaggac accgccgtgt actactgcgc caggggcagg   300
tccctgctgt tcgactactg gggacagggc accctggtga ccgtgtccag g            351
```

<210> SEQ ID NO 157
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

```
Met Lys Trp Val Thr Phe Ile Ser Leu Leu Phe Leu Phe Ser Ala
1               5                   10                  15

Tyr Ser
```

<210> SEQ ID NO 158
<211> LENGTH: 306
<212> TYPE: PRT
<213> ORGANISM: Homo sapiens

<400> SEQUENCE: 158

```
Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
```

```
                145                 150                 155                 160
Asp Asn Lys Glu Tyr Glu Tyr Ser Val Glu Cys Gln Glu Asp Ser Ala
                    165                 170                 175

Cys Pro Ala Ala Glu Glu Ser Leu Pro Ile Glu Val Met Val Asp Ala
                    180                 185                 190

Val His Lys Leu Lys Tyr Glu Asn Tyr Thr Ser Ser Phe Phe Ile Arg
                    195                 200                 205

Asp Ile Ile Lys Pro Asp Pro Pro Lys Asn Leu Gln Leu Lys Pro Leu
            210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
                260                 265                 270

Ser Ala Thr Val Ile Cys Arg Lys Asn Ala Ser Ile Ser Val Arg Ala
                275                 280                 285

Gln Asp Arg Tyr Tyr Ser Ser Ser Trp Ser Glu Trp Ala Ser Val Pro
            290                 295                 300

Cys Ser
305

<210> SEQ ID NO 159
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Gly Gly Gly Gly Ser Gly Gly Gly Ser Gly Gly Gly Gly Ser
1               5                   10                  15

<210> SEQ ID NO 160
<211> LENGTH: 197
<212> TYPE: PRT
<213> ORGANISM: Homo sapiens

<400> SEQUENCE: 160

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
                20                  25                  30

Ala Arg Gln Thr Leu Glu Phe Tyr Pro Cys Thr Ser Glu Glu Ile Asp
            35                  40                  45

His Glu Asp Ile Thr Lys Asp Lys Thr Ser Thr Val Glu Ala Cys Leu
        50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
                100                 105                 110

Gln Val Glu Phe Lys Thr Met Asn Ala Lys Leu Leu Met Asp Pro Lys
            115                 120                 125

Arg Gln Ile Phe Leu Asp Gln Asn Met Leu Ala Val Ile Asp Glu Leu
```

```
                130                 135                 140
Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser
        195

<210> SEQ ID NO 161
<211> LENGTH: 65
<212> TYPE: PRT
<213> ORGANISM: Homo sapiens

<400> SEQUENCE: 161

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
        50                  55                  60

Arg
65

<210> SEQ ID NO 162
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Ser Glu Leu Thr Gln Asp Pro Ala Val Ser Val Ala Leu Gly Gln Thr
1               5                   10                  15

Val Arg Ile Thr Cys Gln Gly Asp Ser Leu Arg Ser Tyr Tyr Ala Ser
                20                  25                  30

Trp Tyr Gln Gln Lys Pro Gly Gln Ala Pro Val Leu Val Ile Tyr Gly
            35                  40                  45

Lys Asn Asn Arg Pro Ser Gly Ile Pro Asp Arg Phe Ser Gly Ser Ser
        50                  55                  60

Ser Gly Asn Thr Ala Ser Leu Thr Ile Thr Gly Ala Gln Ala Glu Asp
65                  70                  75                  80

Glu Ala Asp Tyr Tyr Cys Asn Ser Arg Asp Ser Ser Gly Asn His Val
                85                  90                  95

Val Phe Gly Gly Gly Thr Lys Leu Thr Val Gly His
            100                 105

<210> SEQ ID NO 163
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163
```

Gly Gly Gly Gly Ser Gly Gly Gly Ser Gly Gly Gly Ser
1               5                   10                  15

<210> SEQ ID NO 164
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Glu Val Gln Leu Val Glu Ser Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Ser Leu Leu Phe Asp Tyr Trp Gly Gln Gly Thr Leu
            100                 105                 110

Val Thr Val Ser Arg
        115

<210> SEQ ID NO 165
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
atgaagtggg tcacatttat ctctttactg ttcctcttct ccagcgccta cagc        54

<210> SEQ ID NO 166
<211> LENGTH: 471
<212> TYPE: DNA
<213> ORGANISM: Homo sapiens

<400> SEQUENCE: 166
tacttcggca aactggaatc caagctgagc gtgatccgga atttaaacga ccaagttctg    60
tttatcgatc aaggtaaccg gcctctgttc gaggacatga ccgactccga ttgccgggac   120
aatgcccccc ggaccatctt cattatctcc atgtacaagg acagccagcc ccggggcatg   180
gctgtgacaa ttagcgtgaa gtgtgagaaa atcagcactt tatcttgtga gaacaagatc   240
atctccttta aggaaatgaa cccccccgat aacatcaagg acaccaagtc cgatatcatc   300
ttcttccagc ggtccgtgcc cggtcacgat aacaagatgc agttcgaatc ctcctcctac   360
gagggctact ttttagcttg tgaaaaggag agggatttat tcaagctgat cctcaagaag   420
gaggacgagc tgggcgatcg ttccatcatg ttcaccgtcc aaaacgagga t            471

<210> SEQ ID NO 167
<211> LENGTH: 195

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 167
attacatgcc cccctcccat gagcgtggag cacgccgaca tctgggtgaa gagctatagc     60
ctctacagcc gggagaggta tatctgtaac agcggcttca agaggaaggc cggcaccagc    120
agcctcaccg agtgcgtgct gaataaggct accaacgtgg ctcactggac aacaccctct    180
ttaaagtgca tccgg                                                    195

<210> SEQ ID NO 168
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Met Lys Trp Val Thr Phe Ile Ser Leu Leu Phe Leu Phe Ser Ser Ala
1               5                   10                  15

Tyr Ser

<210> SEQ ID NO 169
<211> LENGTH: 157
<212> TYPE: PRT
<213> ORGANISM: Homo sapiens

<400> SEQUENCE: 169

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
                20                  25                  30

Met Thr Asp Ser Asp Cys Arg Asp Asn Ala Pro Arg Thr Ile Phe Ile
            35                  40                  45

Ile Ser Met Tyr Lys Asp Ser Gln Pro Arg Gly Met Ala Val Thr Ile
        50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155

<210> SEQ ID NO 170
<211> LENGTH: 65
<212> TYPE: PRT
<213> ORGANISM: Homo sapiens

<400> SEQUENCE: 170

Ile Thr Cys Pro Pro Pro Met Ser Val Glu His Ala Asp Ile Trp Val
```

```
               1               5                  10                 15
             Lys Ser Tyr Ser Leu Tyr Ser Arg Glu Arg Tyr Ile Cys Asn Ser Gly
                              20                 25                 30
             Phe Lys Arg Lys Ala Gly Thr Ser Ser Leu Thr Glu Cys Val Leu Asn
                         35                 40                 45
             Lys Ala Thr Asn Val Ala His Trp Thr Thr Pro Ser Leu Lys Cys Ile
                    50                 55                 60
             Arg
             65
```

<210> SEQ ID NO 171
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171

```
atgaaatggg tgacctttat ttctttactg ttcctcttta gcagcgccta ctcc              54
```

<210> SEQ ID NO 172
<211> LENGTH: 918
<212> TYPE: DNA
<213> ORGANISM: Homo sapiens

<400> SEQUENCE: 172

```
atttgggaac tgaagaagga cgtctacgtg gtcgaactgg actggtatcc cgatgctccc         60
ggcgaaatgg tggtgctcac ttgtgacacc cccgaagaag acggcatcac ttggaccctc        120
gatcagagca gcgaggtgct gggctccgga aagacccctca caatccaagt taaggagttc       180
ggagacgctg gccaatacac atgccacaag ggaggcgagg tgctcagcca ttccttatta       240
ttattacaca agaaggaaga cggaatctgg tccaccgaca ttttaaaaga tcagaaggag       300
cccaagaata agacctttt aaggtgtgag gccaaaaact acagcggtcg tttcacttgt       360
tggtggctga ccaccatttc caccgattta accttctccg tgaaaagcag ccggggaagc       420
tccgaccctc aaggtgtgac atgtggagcc gctacccta gcgctgagag ggttcgtggc       480
gataacaagg aatacgagta cagcgtggag tgccaagaag atagcgcttg tcccgctgcc       540
gaagaatctt tacccattga ggtgatggtg gacgccgtgc acaaactcaa gtacgagaac       600
tacacctcct ccttctttat ccgggacatc attaagcccg atcctcctaa gaatttacag       660
ctgaagcctc tcaaaaatag ccggcaagtt gaggtctctt gggaatatcc cgacacttgg       720
agcacacccc acagctactt ctctttaacc ttttgtgtgc aagttcaagg taaaagcaag       780
cgggagaaga aagaccgggt gtttaccgac aaaaccagcg ccaccgtcat ctgtcggaag       840
aacgcctcca tcagcgtgag ggctcaagat cgttattact ccagcagctg gtccgagtgg       900
gccagcgtgc cttgttcc                                                    918
```

<210> SEQ ID NO 173
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173

```
ggcggtggag gatccggagg aggtggctcc ggcggcggag gatct                        45
```

<210> SEQ ID NO 174
<211> LENGTH: 591
<212> TYPE: PRT
<213> ORGANISM: Homo sapiens

<400> SEQUENCE: 174

Cys Gly Thr Ala Ala Cys Cys Thr Cys Cys Cys Gly Thr Gly Gly
1               5                   10                  15

Cys Thr Ala Cys Cys Cys Cys Gly Ala Thr Cys Cys Gly Gly
            20                  25                  30

Ala Ala Thr Gly Thr Thr Cys Cys Thr Thr Gly Thr Thr Ala
            35                  40                  45

Cys Ala Cys Cys Ala Cys Ala Gly Cys Ala Gly Ala Thr Thr
        50                  55                  60

Thr Ala Cys Thr Gly Ala Gly Gly Cys Cys Gly Thr Gly Ala Gly
65                  70                  75                  80

Cys Ala Ala Cys Ala Thr Gly Cys Thr Gly Cys Ala Gly Ala Ala
                85                  90                  95

Gly Cys Thr Ala Gly Gly Cys Ala Gly Ala Cys Thr Thr Ala Gly
                100                 105                 110

Ala Ala Thr Thr Thr Ala Cys Cys Cys Thr Thr Gly Cys Ala Cys
            115                 120                 125

Cys Ala Gly Cys Gly Ala Gly Ala Gly Ala Thr Cys Gly Ala Cys
            130                 135                 140

Cys Ala Thr Gly Ala Ala Gly Ala Thr Ala Cys Ala Cys Cys Ala
145                 150                 155                 160

Ala Gly Gly Ala Cys Ala Ala Gly Ala Cys Thr Cys Cys Ala Cys
                165                 170                 175

Cys Gly Thr Gly Gly Ala Gly Gly Cys Thr Thr Gly Thr Thr Ala
            180                 185                 190

Cys Cys Thr Cys Thr Gly Gly Ala Gly Cys Thr Gly Ala Cys Ala
                195                 200                 205

Ala Gly Ala Ala Cys Gly Ala Gly Thr Cys Thr Thr Gly Thr Cys Thr
            210                 215                 220

Cys Ala Ala Cys Thr Cys Thr Cys Gly Thr Gly Ala Ala Cys Cys
225                 230                 235                 240

Ala Gly Cys Thr Thr Cys Ala Thr Cys Ala Ala Thr Gly
                245                 250                 255

Gly Cys Thr Cys Thr Thr Gly Thr Thr Thr Ala Gly Cys Thr Thr Cys
                260                 265                 270

Cys Cys Gly Gly Ala Ala Gly Ala Cys Cys Thr Cys Thr Thr
            275                 280                 285

Ala Thr Gly Ala Thr Gly Gly Cys Thr Thr Ala Thr Gly Cys Cys
        290                 295                 300

Thr Cys Ala Gly Cys Thr Cys Cys Ala Thr Cys Ala Cys Gly Ala
305                 310                 315                 320

Gly Gly Ala Thr Thr Ala Ala Ala Gly Ala Thr Gly Thr Ala Cys
                325                 330                 335

Cys Ala Ala Gly Thr Gly Gly Ala Thr Thr Cys Ala Ala Gly Ala
            340                 345                 350

Cys Cys Ala Thr Gly Ala Ala Cys Gly Cys Ala Ala Gly Cys Thr
            355                 360                 365

Gly Cys Thr Cys Ala Thr Gly Gly Ala Cys Cys Cys Thr Ala Ala Ala

```
                370                 375                 380
Cys Gly Gly Cys Ala Gly Ala Thr Cys Thr Thr Thr Thr Ala Gly
385                 390                 395                 400

Ala Cys Cys Ala Gly Ala Ala Cys Ala Thr Gly Cys Thr Gly Cys
                405                 410                 415

Thr Gly Thr Gly Ala Thr Thr Gly Ala Thr Gly Ala Gly Cys Thr Gly
                420                 425                 430

Ala Thr Gly Cys Ala Ala Gly Cys Thr Thr Ala Ala Ala Cys Thr
                435                 440                 445

Thr Cys Ala Ala Cys Thr Cys Cys Gly Ala Gly Ala Cys Cys Gly Thr
                450                 455                 460

Cys Cys Cys Thr Cys Ala Gly Ala Ala Gly Thr Cys Cys Thr Cys Cys
465                 470                 475                 480

Cys Thr Cys Gly Ala Gly Gly Ala Gly Cys Cys Cys Gly Ala Thr Thr
                485                 490                 495

Thr Thr Thr Ala Cys Ala Gly Ala Cys Ala Ala Gly Ala Thr
                500                 505                 510

Cys Ala Ala Cys Thr Gly Thr Gly Cys Ala Thr Thr Thr Ala
515                 520                 525

Cys Thr Cys Thr Ala Cys Gly Cys Cys Thr Thr Thr Ala Gly Gly Ala
                530                 535                 540

Thr Cys Cys Gly Gly Gly Cys Cys Gly Thr Gly Ala Cys Cys Ala Thr
545                 550                 555                 560

Thr Gly Ala Cys Cys Gly Gly Gly Thr Cys Ala Thr Gly Ala Gly Cys
                565                 570                 575

Thr Ala Thr Thr Thr Ala Ala Ala Cys Gly Cys Cys Ala Gly Cys
                580                 585                 590
```

<210> SEQ ID NO 175
<211> LENGTH: 657
<212> TYPE: DNA
<213> ORGANISM: Homo sapiens

<400> SEQUENCE: 175

```
agcggcacaa ccaacacagt cgctgcctat aacctcactt ggaagagcac caacttcaaa      60
accatcctcg aatgggaacc caaacccgtt aaccaagttt acaccgtgca gatcagcacc     120
aagtccggcg actggaagtc caaatgtttc tataccaccg acaccgagtg cgatctcacc     180
gatgagatcg tgaaagatgt gaaacagacc tacctcgccc gggtgtttag ctaccccgcc     240
ggcaatgtgg agagcactgg ttccgctggc gagcctttat acgagaacag ccccgaattt     300
accccttacc tcgagaccaa tttaggacag cccaccatcc aaagctttga gcaagttggc     360
acaaaggtga atgtgacagt ggaggacgag cggactttag tgcggcggaa caacaccttt     420
ctcagcctcc gggatgtgtt cggcaaagat ttaatctaca cactgtatta ctggaagtcc     480
tcttcctccg gcaagaagac agctaaaacc aacacaaacg agttttaat cgacgtggat     540
aaaggcgaaa actactgttt cagcgtgcaa gctgtgatcc cctcccggac cgtgaatagg     600
aaaagcaccg atagcccccgt tgagtgcatg ggccaagaaa agggcgagtt ccgggag      657
```

<210> SEQ ID NO 176
<211> LENGTH: 342
<212> TYPE: DNA
<213> ORGANISM: Homo sapiens

<400> SEQUENCE: 176

```
aactgggtga acgtcatcag cgatttaaag aagatcgaag atttaattca gtccatgcat    60
atcgacgcca ctttatacac agaatccgac gtgcacccct cttgtaaggt gaccgccatg   120
aaatgttttt tactggagct gcaagttatc tctttagaga gcggagacgc tagcatccac   180
gacaccgtgg agaatttaat cattttagcc aataactctt tatccagcaa cggcaacgtg   240
acagagtccg gctgcaagga gtgcgaagag ctggaggaga agaacatcaa ggagtttctg   300
caatcctttg tgcacattgt ccagatgttc atcaatacct cc                      342
```

<210> SEQ ID NO 177
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Met Lys Trp Val Thr Phe Ile Ser Leu Leu Phe Leu Phe Ser Ser Ala
1               5                   10                  15

Tyr Ser

<210> SEQ ID NO 178
<211> LENGTH: 306
<212> TYPE: PRT
<213> ORGANISM: Homo sapiens

<400> SEQUENCE: 178

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
                20                  25                  30

Glu Asp Gly Ile Thr Trp Thr Leu Asp Gln Ser Ser Glu Val Leu Gly
            35                  40                  45

Ser Gly Lys Thr Leu Thr Ile Gln Val Lys Glu Phe Gly Asp Ala Gly
        50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp

```
                225                 230                 235                 240
Ser Thr Pro His Ser Tyr Phe Ser Leu Thr Phe Cys Val Gln Val Gln
                    245                 250                 255

Gly Lys Ser Lys Arg Glu Lys Lys Asp Arg Val Phe Thr Asp Lys Thr
                260                 265                 270

Ser Ala Thr Val Ile Cys Arg Lys Asn Ala Ser Ile Ser Val Arg Ala
                275                 280                 285

Gln Asp Arg Tyr Tyr Ser Ser Ser Trp Ser Glu Trp Ala Ser Val Pro
                290                 295                 300

Cys Ser
305

<210> SEQ ID NO 179
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Gly Gly Gly Gly Ser Gly Gly Gly Gly Ser Gly Gly Gly Gly Ser
1               5                   10                  15

<210> SEQ ID NO 180
<211> LENGTH: 197
<212> TYPE: PRT
<213> ORGANISM: Homo sapiens

<400> SEQUENCE: 180

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
                20                  25                  30

Ala Arg Gln Thr Leu Glu Phe Tyr Pro Cys Thr Ser Glu Glu Ile Asp
            35                  40                  45

His Glu Asp Ile Thr Lys Asp Lys Thr Ser Thr Val Glu Ala Cys Leu
        50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser
        195
```

```
<210> SEQ ID NO 181
<211> LENGTH: 219
<212> TYPE: PRT
<213> ORGANISM: Homo sapiens

<400> SEQUENCE: 181

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
    130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu
    210                 215

<210> SEQ ID NO 182
<211> LENGTH: 114
<212> TYPE: PRT
<213> ORGANISM: Homo sapiens

<400> SEQUENCE: 182

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser
```

<210> SEQ ID NO 183
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 183
atgaagtggg tgaccttcat cagcctgctg ttcctgttct ccagcgccta ctcc                54

<210> SEQ ID NO 184
<211> LENGTH: 408
<212> TYPE: DNA
<213> ORGANISM: Homo sapiens

<400> SEQUENCE: 184 atccccccc atgtgcaaaa gagcgtgaac aacgatatga tcgtgaccga caacaacggc        60
gccgtgaagt ttccccagct ctgcaagttc tgcgatgtca ggttcagcac ctgcgataat      120
cagaagtcct gcatgtccaa ctgcacgatc acctccatct gcgagaagcc caagaagtg      180
tgcgtggccg tgtggcggaa aaatgacgag aacatcaccc tggagaccgt gtgtcacgac      240
cccaagctcc cttatcacga cttcattctg gaggacgctg cctcccccaa atgcatcatg      300
aaggagaaga gaagcccgg agagaccttc tttatgtgtt cctgtagcag cgacgagtgt      360
aacgacaaca tcatcttcag cgaagagtac aacaccagca accctgat                  408

<210> SEQ ID NO 185
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 185
ggaggtggcg gatccggagg tggaggttct ggtggaggtg ggagt                       45

<210> SEQ ID NO 186
<211> LENGTH: 408
<212> TYPE: DNA
<213> ORGANISM: Homo sapiens

<400> SEQUENCE: 186
attcctcccc acgtgcagaa gagcgtgaat aatgacatga tcgtgaccga taacaatggc        60
gccgtgaaat ttccccagct gtgcaaattc tgcgatgtga ggttttccac ctgcgacaac      120
cagaagtcct gtatgagcaa ctgcacaatc acctccatct gtgagaagcc tcaggaggtg      180
tgcgtggctg tctggcggaa gaatgacgag aatatcaccc tggaaaccgt ctgccacgat      240
cccaagctgc cctaccacga tttcatcctg gaagacgccg ccagccctaa gtgcatcatg      300
aaagagaaaa agaagcctgg cgagaccttt ttcatgtgct cctgcagcag cgacgaatgc      360
aacgacaata tcatctttag cgaggaatac aataccagca accccgac                  408

<210> SEQ ID NO 187
<211> LENGTH: 195
<212> TYPE: PRT
<213> ORGANISM: Homo sapiens

<400> SEQUENCE: 187

Ala Thr Cys Ala Cys Gly Thr Gly Thr Cys Thr Cys Cys Thr Cys
1               5                   10                  15

Cys Thr Ala Thr Gly Thr Cys Cys Gly Thr Gly Gly Ala Ala Cys Ala
            20                  25                  30

Cys Gly Cys Ala Gly Ala Cys Ala Thr Cys Thr Gly Gly Gly Thr Cys
            35                  40                  45

Ala Ala Gly Ala Gly Cys Thr Ala Cys Ala Gly Cys Thr Thr Gly Thr
50                      55                  60

Ala Cys Thr Cys Cys Ala Gly Gly Gly Ala Gly Cys Gly Gly Thr Ala
65                  70                  75                  80

Cys Ala Thr Thr Thr Gly Thr Ala Ala Cys Thr Cys Thr Gly Gly Thr
                85                  90                  95

Thr Thr Cys Ala Ala Gly Cys Gly Thr Ala Ala Ala Gly Cys Cys Gly
            100                 105                 110

Gly Cys Ala Cys Gly Thr Cys Ala Gly Cys Cys Thr Gly Ala Cys
        115                 120                 125

Gly Gly Ala Gly Thr Gly Cys Gly Thr Gly Thr Gly Ala Ala Cys
        130                 135                 140

Ala Ala Gly Gly Cys Cys Ala Cys Gly Ala Ala Thr Gly Thr Cys Gly
145                 150                 155                 160

Cys Cys Cys Ala Cys Thr Gly Gly Ala Cys Ala Ala Cys Cys Cys Cys
                165                 170                 175

Cys Ala Gly Thr Cys Thr Cys Ala Ala Ala Thr Gly Thr Ala Thr Thr
            180                 185                 190

Ala Gly Ala
        195

<210> SEQ ID NO 188
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Met Lys Trp Val Thr Phe Ile Ser Leu Leu Phe Leu Phe Ser Ser Ala
1               5                   10                  15

Tyr Ser

<210> SEQ ID NO 189
<211> LENGTH: 218
<212> TYPE: PRT
<213> ORGANISM: Homo sapiens

<400> SEQUENCE: 189

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro

```
                    85                  90                  95
Lys Cys Ile Met Lys Glu Lys Lys Pro Gly Glu Thr Phe Phe Met
                100                 105                 110

Cys Ser Cys Ser Ser Asp Glu Cys Asn Asp Asn Ile Ile Phe Ser Glu
                115                 120                 125

Glu Tyr Asn Thr Ser Asn Pro Asp Pro Ser Cys Lys Val Thr Ala Met
    130                 135                 140

Lys Cys Phe Leu Leu Glu Leu Gln Val Ile Ser Leu Glu Ser Gly Asp
145                 150                 155                 160

Ala Ser Ile His Asp Thr Val Glu Asn Leu Ile Ile Leu Ala Asn Asn
                165                 170                 175

Ser Leu Ser Ser Asn Gly Asn Val Thr Glu Ser Gly Cys Lys Glu Cys
                180                 185                 190

Glu Glu Leu Glu Glu Lys Asn Ile Lys Glu Phe Leu Gln Ser Phe Val
                195                 200                 205

His Ile Val Gln Met Phe Ile Asn Thr Ser
    210                 215
```

<210> SEQ ID NO 190
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

```
Gly Gly Gly Gly Ser Gly Gly Gly Ser Gly Gly Gly Gly Ser
1               5                   10                  15
```

<210> SEQ ID NO 191
<211> LENGTH: 136
<212> TYPE: PRT
<213> ORGANISM: Homo sapiens

<400> SEQUENCE: 191

```
Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
                20                  25                  30

Val Arg Phe Ser Thr Cys Asp Asn Gln Lys Ser Cys Met Ser Asn Cys
                35                  40                  45

Ser Ile Thr Ser Ile Cys Glu Lys Pro Gln Glu Val Cys Val Ala Val
            50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
                100                 105                 110

Cys Ser Cys Ser Ser Asp Glu Cys Asn Asp Asn Ile Ile Phe Ser Glu
                115                 120                 125

Glu Tyr Asn Thr Ser Asn Pro Asp
    130                 135
```

<210> SEQ ID NO 192
<211> LENGTH: 65
<212> TYPE: PRT

<213> ORGANISM: Homo sapiens

<400> SEQUENCE: 192

```
Ile Thr Cys Pro Pro Met Ser Val Glu His Ala Asp Ile Trp Val
1               5                   10                  15
Lys Ser Tyr Ser Leu Tyr Ser Arg Glu Arg Tyr Ile Cys Asn Ser Gly
            20                  25                  30
Phe Lys Arg Lys Ala Gly Thr Ser Ser Leu Thr Glu Cys Val Leu Asn
        35                  40                  45
Lys Ala Thr Asn Val Ala His Trp Thr Thr Pro Ser Leu Lys Cys Ile
    50                  55                  60
Arg
65
```

<210> SEQ ID NO 193
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 193

| atgaagtggg tgaccttcat cagcctgctg ttcctgttct ccagcgccta ctcc | 54 |
|---|---|

<210> SEQ ID NO 194
<211> LENGTH: 399
<212> TYPE: DNA
<213> ORGANISM: Homo sapiens

<400> SEQUENCE: 194

| cagggccagg acaggcacat gatccggatg aggcagctca tcgacatcgt cgaccagctg | 60 |
|---|---|
| aagaactacg tgaacgacct ggtgcccgag tttctgcctg cccccgagga cgtggagacc | 120 |
| aactgcgagt ggtccgcctt ctcctgcttt cagaaggccc agctgaagtc cgccaacacc | 180 |
| ggcaacaacg agcggatcat caacgtgagc atcaagaagc tgaagcggaa gcctccctcc | 240 |
| acaaacgccg gcaggaggca gaagcacagg ctgacctgcc ccagctgtga ctcctacgag | 300 |
| aagaagcccc ccaaggagtt cctggagagg ttcaagtccc tgctgcagaa gatgatccat | 360 |
| cagcacctgt cctccaggac ccacggctcc gaggactcc | 399 |

<210> SEQ ID NO 195
<211> LENGTH: 657
<212> TYPE: DNA
<213> ORGANISM: Homo sapiens

<400> SEQUENCE: 195

| tccggcacca ccaataccgt ggccgcttat aacctcacat ggaagagcac caacttcaag | 60 |
|---|---|
| acaattctgg aatgggaacc caagcccgtc aatcaagttt acaccgtgca gatctccacc | 120 |
| aaatccggag actggaagag caagtgcttc tacacaacag acaccgagtg tgatttaacc | 180 |
| gacgaaatcg tcaaggacgt caagcaaacc tatctggctc gggtcttttc ctaccccgct | 240 |
| ggcaatgtcg agtccaccgg ctccgctggc gagcctctct acgagaattc ccccgaattc | 300 |
| acccccttatt tagagaccaa tttaggccag cctaccatcc agagcttcga gcaagttggc | 360 |
| accaaggtga acgtcaccgt cgaggatgaa aggactttag tgcggcggaa taacacattt | 420 |
| ttatccctcc gggatgtgtt cggcaaagac ctcatctaca cactgtacta ttggaagtcc | 480 |
| agctcctccg gcaaaaagac cgctaagacc aacaccaacg agttttttaat tgacgtggac | 540 |

```
aaaggcgaga actactgctt cagcgtgcaa gccgtgatcc cttctcgtac cgtcaaccgg    600
aagagcacag attcccccgt tgagtgcatg ggccaagaaa agggcgagtt ccgggag       657
```

<210> SEQ ID NO 196
<211> LENGTH: 342
<212> TYPE: DNA
<213> ORGANISM: Homo sapiens

<400> SEQUENCE: 196

```
aactgggtga acgtcatcag cgatttaaag aagatcgaag atttaattca gtccatgcat    60
atcgacgcca ctttatacac agaatccgac gtgcacccct cttgtaaggt gaccgccatg   120
aaatgttttt tactggagct gcaagttatc tctttagaga gcggagacgc tagcatccac   180
gacaccgtgg agaatttaat cattttagcc aataactctt tatccagcaa cggcaacgtg   240
acagagtccg gctgcaagga gtgcgaagag ctggaggaga agaacatcaa ggagtttctg   300
caatcctttg tgcacattgt ccagatgttc atcaataccct cc                     342
```

<210> SEQ ID NO 197
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Met Lys Trp Val Thr Phe Ile Ser Leu Leu Phe Leu Phe Ser Ser Ala
1               5                   10                  15

Tyr Ser

<210> SEQ ID NO 198
<211> LENGTH: 133
<212> TYPE: PRT
<213> ORGANISM: Homo sapiens

<400> SEQUENCE: 198

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
                20                  25                  30

Pro Ala Pro Glu Asp Val Glu Thr Asn Cys Glu Trp Ser Ala Phe Ser
            35                  40                  45

Cys Phe Gln Lys Ala Gln Leu Lys Ser Ala Asn Thr Gly Asn Asn Glu
        50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
                100                 105                 110

Ser Leu Leu Gln Lys Met Ile His Gln His Leu Ser Ser Arg Thr His
            115                 120                 125

Gly Ser Glu Asp Ser
        130

<210> SEQ ID NO 199
<211> LENGTH: 219

```
<212> TYPE: PRT
<213> ORGANISM: Homo sapiens

<400> SEQUENCE: 199

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Pro Leu Tyr Glu Asn
                85                  90                  95

Ser Pro Glu Phe Thr Pro Tyr Leu Glu Thr Asn Leu Gly Gln Pro Thr
                100                 105                 110

Ile Gln Ser Phe Glu Gln Val Gly Thr Lys Val Asn Val Thr Val Glu
                115                 120                 125

Asp Glu Arg Thr Leu Val Arg Arg Asn Asn Thr Phe Leu Ser Leu Arg
                130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
                180                 185                 190

Ile Pro Ser Arg Thr Val Asn Arg Lys Ser Thr Asp Ser Pro Val Glu
                195                 200                 205

Cys Met Gly Gln Glu Lys Gly Glu Phe Arg Glu
    210                 215

<210> SEQ ID NO 200
<211> LENGTH: 114
<212> TYPE: PRT
<213> ORGANISM: Homo sapiens

<400> SEQUENCE: 200

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
        50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
                100                 105                 110

Thr Ser
```

```
<210> SEQ ID NO 201
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
atgaagtggg tgaccttcat cagcctgctg ttcctgttct ccagcgccta ctcc          54

<210> SEQ ID NO 202
<211> LENGTH: 399
<212> TYPE: DNA
<213> ORGANISM: Homo sapiens

<400> SEQUENCE: 202
cagggccagg acaggcacat gatccggatg aggcagctca tcgacatcgt cgaccagctg    60
aagaactacg tgaacgacct ggtgcccgag tttctgcctg cccccgagga cgtggagacc   120
aactgcgagt ggtccgcctt ctcctgcttt cagaaggccc agctgaagtc cgccaacacc   180
ggcaacaacg agcggatcat caacgtgagc atcaagaagc tgaagcggaa gcctccctcc   240
acaaacgccg gcaggaggca gaagcacagg ctgacctgcc ccagctgtga ctcctacgag   300
aagaagcccc ccaaggagtt cctggagagg ttcaagtccc tgctgcagaa gatgatccat   360
cagcacctgt cctccaggac ccacggctcc gaggactcc                          399

<210> SEQ ID NO 203
<211> LENGTH: 657
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 203
tccggcacca ccaataccgt ggccgcttat aacctcacat ggaagagcac caacttcgcg    60
acagctctgg aatgggaacc caagcccgtc aatcaagttt acaccgtgca gatctccacc   120
aaatccggag actggaagag caagtgcttc tacacaacga cacccgagtg tgctttaacc   180
gacgaaatcg tcaaggacgt caagcaaacc tatctggctc gggtcttttc ctaccccgct   240
ggcaatgtcg agtccaccgg ctccgctggc gagcctctct acgagaattc ccccgaattc   300 acccccttatt tagagaccaa tttaggccag cctaccatcc agagcttcga gcaagttggc   360
accaaggtga acgtcaccgt cgaggatgaa aggactttag tggcgcggaa taacacagct   420
ttatccctcc gggatgtgtt cggcaaagac ctcatctaca cactgtacta ttggaagtcc   480
agctcctccg gcaaaaagac cgctaagacc aacaccaacg agttttttaat tgacgtggac   540 aaaggcgaga actactgctt cagcgtgcaa gccgtgatcc cttctcgtac cgtcaaccgg   600
aagagcacag attccccccgt tgagtgcatg ggccaagaaa agggcgagtt ccgggag     657

<210> SEQ ID NO 204
<211> LENGTH: 342
<212> TYPE: DNA
<213> ORGANISM: Homo sapiens

<400> SEQUENCE: 204
aactgggtga acgtcatcag cgatttaaag aagatcgaag atttaattca gtccatgcat    60
atcgacgcca ctttatacac agaatccgac gtgcacccct cttgtaaggt gaccgccatg   120
```

```
aaatgttttt tactggagct gcaagttatc tctttagaga gcggagacgc tagcatccac    180
gacaccgtgg agaatttaat catttagcc aataactctt tatccagcaa cggcaacgtg    240
acagagtccg gctgcaagga gtgcgaagag ctggaggaga agaacatcaa ggagtttctg    300
caatcctttg tgcacattgt ccagatgttc atcaataccct cc                      342
```

<210> SEQ ID NO 205
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Met Lys Trp Val Thr Phe Ile Ser Leu Leu Phe Leu Phe Ser Ser Ala
1               5                   10                  15

Tyr Ser

<210> SEQ ID NO 206
<211> LENGTH: 133
<212> TYPE: PRT
<213> ORGANISM: Homo sapiens

<400> SEQUENCE: 206

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
                20                  25                  30

Pro Ala Pro Glu Asp Val Glu Thr Asn Cys Glu Trp Ser Ala Phe Ser
            35                  40                  45

Cys Phe Gln Lys Ala Gln Leu Lys Ser Ala Asn Thr Gly Asn Asn Glu
        50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser
    130

<210> SEQ ID NO 207
<211> LENGTH: 219
<212> TYPE: PRT
<213> ORGANISM: Homo sapiens

<400> SEQUENCE: 207

Ser Gly Thr Thr Asn Thr Val Ala Ala Tyr Asn Leu Thr Trp Lys Ser
1               5                   10                  15

Thr Asn Phe Ala Thr Ala Leu Glu Trp Glu Pro Lys Pro Val Asn Gln
                20                  25                  30

Val Tyr Thr Val Gln Ile Ser Thr Lys Ser Gly Asp Trp Lys Ser Lys
            35                  40                  45

Cys Phe Tyr Thr Thr Asp Thr Glu Cys Ala Leu Thr Asp Glu Ile Val
        50                  55                  60

```
Lys Asp Val Lys Gln Thr Tyr Leu Ala Arg Val Phe Ser Tyr Pro Ala
 65                  70                  75                  80

Gly Asn Val Glu Ser Thr Gly Ser Ala Gly Glu Pro Leu Tyr Glu Asn
                 85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Ala Arg Asn Asn Thr Ala Leu Ser Leu Arg
    130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu
    210                 215

<210> SEQ ID NO 208
<211> LENGTH: 114
<212> TYPE: PRT
<213> ORGANISM: Homo sapiens

<400> SEQUENCE: 208

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
        50                  55                  60

Asn Leu Ile Ile Leu Ala Asn Asn Ser Leu Ser Ser Asn Gly Asn Val
 65                 70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 209
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
atgaagtggg tgaccttcat cagcctgctg ttcctgttct ccagcgccta ctcc          54

<210> SEQ ID NO 210
<211> LENGTH: 399
<212> TYPE: DNA
<213> ORGANISM: Homo sapiens
```

<400> SEQUENCE: 210

```
cagggccagg acaggcacat gatccggatg aggcagctca tcgacatcgt cgaccagctg    60
aagaactacg tgaacgacct ggtgcccgag tttctgcctg ccccgagga cgtggagacc   120
aactgcgagt ggtccgcctt ctcctgcttt cagaaggccc agctgaagtc cgccaacacc   180
ggcaacaacg agcggatcat caacgtgagc atcaagaagc tgaagcggaa gcctccctcc   240
acaaacgccg caggaggca gaagcacagg ctgacctgcc ccagctgtga ctcctacgag   300
aagaagcccc ccaaggagtt cctggagagg ttcaagtccc tgctgcagaa gatgatccat   360
cagcacctgt cctccaggac ccacggctcc gaggactcc                          399
```

<210> SEQ ID NO 211
<211> LENGTH: 195
<212> TYPE: DNA
<213> ORGANISM: Homo sapiens

<400> SEQUENCE: 211

```
attacatgcc cccctcccat gagcgtggag cacgccgaca tctgggtgaa gagctatagc    60
ctctacagcc gggagaggta tatctgtaac agcggcttca agaggaaggc cggcaccagc   120
agcctcaccg agtgcgtgct gaataaggct accaacgtgg ctcactggac aacaccctct   180
ttaaagtgca tccgg                                                    195
```

<210> SEQ ID NO 212
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Met Lys Trp Val Thr Phe Ile Ser Leu Leu Phe Leu Phe Ser Ser Ala
1               5                   10                  15

Tyr Ser

<210> SEQ ID NO 213
<211> LENGTH: 133
<212> TYPE: PRT
<213> ORGANISM: Homo sapiens

<400> SEQUENCE: 213

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
                20                  25                  30

Pro Ala Pro Glu Asp Val Glu Thr Asn Cys Glu Trp Ser Ala Phe Ser
            35                  40                  45

Cys Phe Gln Lys Ala Gln Leu Lys Ser Ala Asn Thr Gly Asn Asn Glu
        50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His

```
              115                 120                 125
Gly Ser Glu Asp Ser
    130

<210> SEQ ID NO 214
<211> LENGTH: 65
<212> TYPE: PRT
<213> ORGANISM: Homo sapiens

<400> SEQUENCE: 214

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg
65

<210> SEQ ID NO 215
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
atgaagtggg tgaccttcat cagcctgctg ttcctgttct ccagcgccta ctcc        54

<210> SEQ ID NO 216
<211> LENGTH: 408
<212> TYPE: DNA
<213> ORGANISM: Homo sapiens

<400> SEQUENCE: 216
atcccccccc atgtgcaaaa gagcgtgaac aacgatatga tcgtgaccga caacaacggc    60
gccgtgaagt ttccccagct ctgcaagttc tgcgatgtca ggttcagcac ctgcgataat   120
cagaagtcct gcatgtccaa ctgcacgatc acctccatct gcgagaagcc ccaagaagtg   180
tgcgtggccg tgtggcggaa aaatgacgag aacatcaccc tggagaccgt gtgtcacgac   240
cccaagctcc cttatcacga cttcattctg gaggacgctg cctcccccaa atgcatcatg   300
aaggagaaga gaagcccggg agagaccttc tttatgtgtt cctgtagcag cgacgagtgt   360
aacgacaaca tcatcttcag cgaagagtac aacaccagca accctgat               408

<210> SEQ ID NO 217
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
ggaggtggcg gatccggagg tggaggttct ggtggaggtg ggagt                   45

<210> SEQ ID NO 218
<211> LENGTH: 408
```

<212> TYPE: DNA
<213> ORGANISM: Homo sapiens

<400> SEQUENCE: 218

```
attcctcccc acgtgcagaa gagcgtgaat aatgacatga tcgtgaccga taacaatggc    60
gccgtgaaat ttccccagct gtgcaaattc tgcgatgtga ggttttccac ctgcgacaac   120
cagaagtcct gtatgagcaa ctgcacaatc acctccatct gtgagaagcc tcaggaggtg   180
tgcgtggctg tctggcggaa gaatgacgag aatatcaccc tggaaaccgt ctgccacgat   240
cccaagctgc cctaccacga tttcatcctg gaagacgccg ccagccctaa gtgcatcatg   300
aaagagaaaa agaagcctgg cgagaccttt ttcatgtgct cctgcagcag cgacgaatgc   360
aacgacaata tcatctttag cgaggaatac aataccagca accccgac              408
```

<210> SEQ ID NO 219
<211> LENGTH: 657
<212> TYPE: DNA
<213> ORGANISM: Homo sapiens

<400> SEQUENCE: 219

```
tccggcacca ccaataccgt ggccgcttat aacctcacat ggaagagcac caacttcaag    60
acaattctgg aatgggaacc caagcccgtc aatcaagttt acaccgtgca gatctccacc   120
aaatccggag actggaagag caagtgcttc tacacaacag acaccgagtg tgatttaacc   180
gacgaaatcg tcaaggacgt caagcaaacc tatctggctc gggtcttttc ctaccccgct   240
ggcaatgtcg agtccaccgg ctccgctggc gagcctctct acgagaattc ccccgaattc   300
acccccttatt tagagaccaa tttaggccag cctaccatcc agagcttcga gcaagttggc   360
accaaggtga acgtcaccgt cgaggatgaa aggactttag tgcggcggaa taacacattt   420
ttatccctcc gggatgtgtt cggcaaagac ctcatctaca cactgtacta ttggaagtcc   480
agctcctccg gcaaaaagac cgctaagacc aacaccaacg agttttaat tgacgtggac   540
aaaggcgaga actactgctt cagcgtgcaa gccgtgatcc cttctcgtac cgtcaaccgg   600
aagagcacag attcccccgt tgagtgcatg ggccaagaaa agggcgagtt ccgggag    657
```

<210> SEQ ID NO 220
<211> LENGTH: 342
<212> TYPE: DNA
<213> ORGANISM: Homo sapiens

<400> SEQUENCE: 220

```
aactgggtga acgtcatcag cgatttaaag aagatcgaag atttaattca gtccatgcat    60
atcgacgcca ctttatacac agaatccgac gtgcaccccct cttgtaaggt gaccgccatg   120
aaatgttttt tactggagct gcaagttatc tctttagaga gcggagacgc tagcatccac   180
gacaccgtgg agaatttaat cattttagcc aataactctt tatccagcaa cggcaacgtg   240
acagagtccg gctgcaagga gtgcgaagag ctggaggaga gaacatcaa ggagtttctg   300
caatcctttg tgcacattgt ccagatgttc atcaataccct cc                    342
```

<210> SEQ ID NO 221
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

```
Met Lys Trp Val Thr Phe Ile Ser Leu Leu Phe Leu Phe Ser Ser Ala
1               5                   10                  15

Tyr Ser

<210> SEQ ID NO 222
<211> LENGTH: 136
<212> TYPE: PRT
<213> ORGANISM: Homo sapiens

<400> SEQUENCE: 222

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
                20                  25                  30

Val Arg Phe Ser Thr Cys Asp Asn Gln Lys Ser Cys Met Ser Asn Cys
            35                  40                  45

Ser Ile Thr Ser Ile Cys Glu Lys Pro Gln Glu Val Cys Val Ala Val
        50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
                100                 105                 110

Cys Ser Cys Ser Ser Asp Glu Cys Asn Asp Asn Ile Ile Phe Ser Glu
            115                 120                 125

Glu Tyr Asn Thr Ser Asn Pro Asp
        130                 135

<210> SEQ ID NO 223
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Gly Gly Gly Gly Ser Gly Gly Gly Ser Gly Gly Gly Gly Ser
1               5                   10                  15

<210> SEQ ID NO 224
<211> LENGTH: 136
<212> TYPE: PRT
<213> ORGANISM: Homo sapiens

<400> SEQUENCE: 224

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
                20                  25                  30

Val Arg Phe Ser Thr Cys Asp Asn Gln Lys Ser Cys Met Ser Asn Cys
            35                  40                  45

Ser Ile Thr Ser Ile Cys Glu Lys Pro Gln Glu Val Cys Val Ala Val
        50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
```

-continued

```
                     85                  90                  95

Lys Cys Ile Met Lys Glu Lys Lys Pro Gly Glu Thr Phe Phe Met
                100                 105                 110

Cys Ser Cys Ser Ser Asp Glu Cys Asn Asp Asn Ile Ile Phe Ser Glu
            115                 120                 125

Glu Tyr Asn Thr Ser Asn Pro Asp
        130                 135

<210> SEQ ID NO 225
<211> LENGTH: 219
<212> TYPE: PRT
<213> ORGANISM: Homo sapiens

<400> SEQUENCE: 225

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
                20                  25                  30

Val Tyr Thr Val Gln Ile Ser Thr Lys Ser Gly Asp Trp Lys Ser Lys
            35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
                100                 105                 110

Ile Gln Ser Phe Glu Gln Val Gly Thr Lys Val Asn Val Thr Val Glu
            115                 120                 125

Asp Glu Arg Thr Leu Val Arg Arg Asn Asn Thr Phe Leu Ser Leu Arg
        130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu
    210                 215

<210> SEQ ID NO 226
<211> LENGTH: 114
<212> TYPE: PRT
<213> ORGANISM: Homo sapiens

<400> SEQUENCE: 226

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
```

```
              50                  55                  60
Asn Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Gln Met Phe Ile Asn
            100                 105                 110

Thr Ser
```

<210> SEQ ID NO 227
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227

```
atgggagtga aagttctttt tgcccttatt tgtattgctg tggccgaggc c          51
```

<210> SEQ ID NO 228
<211> LENGTH: 456
<212> TYPE: DNA
<213> ORGANISM: Homo sapiens

<400> SEQUENCE: 228

```
gattgtgata ttgaaggtaa agatggcaaa caatatgaga gtgttctaat ggtcagcatc    60
gatcaattat tggacagcat gaaagaaatt ggtagcaatt gcctgaataa tgaatttaac   120
ttttttaaaa gacatatctg tgatgctaat aaggaaggta tgttttttatt ccgtgctgct   180 cgcaagttga ggcaatttct taaaatgaat agcactggtg attttgatct ccacttatta   240
aaagtttcag aaggcacaac aatactgttg aactgcactg gccaggttaa aggaagaaaa   300
ccagctgccc tgggtgaagc ccaaccaaca aagagtttgg aagaaaataa atctttaaag   360
gaacagaaaa aactgaatga cttgtgtttc ctaaagagac tattacaaga gataaaaact   420
tgttggaata aaattttgat gggcactaaa gaacac                              456
```

<210> SEQ ID NO 229
<211> LENGTH: 195
<212> TYPE: DNA
<213> ORGANISM: Homo sapiens

<400> SEQUENCE: 229

```
atcacgtgcc ctccccccat gtccgtggaa cacgcagaca tctgggtcaa gagctacagc    60
ttgtactcca gggagcggta catttgtaac tctggtttca gcgtaaagc cggcacgtcc    120 agcctgacgg agtgcgtgtt gaacaaggcc acgaatgtcg cccactggac aacccccagt   180
ctcaaatgca ttaga                                                      195
```

<210> SEQ ID NO 230
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

```
Met Lys Trp Val Thr Phe Ile Ser Leu Leu Phe Leu Phe Ser Ser Ala
 1               5                  10                  15
```

Tyr Ser

<210> SEQ ID NO 231
<211> LENGTH: 152
<212> TYPE: PRT
<213> ORGANISM: Homo sapiens

<400> SEQUENCE: 231

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Phe Lys Arg His Ile Cys Asp
        35                  40                  45

Ala Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140

Ile Leu Met Gly Thr Lys Glu His
145                 150

<210> SEQ ID NO 232
<211> LENGTH: 219
<212> TYPE: PRT
<213> ORGANISM: Homo sapiens

<400> SEQUENCE: 232

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
            35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
    130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
            165                 170                 175

Ile Asp Val Asp Lys Gly Glu Asn Tyr Cys Phe Ser Val Gln Ala Val
        180                 185                 190

Ile Pro Ser Arg Thr Val Asn Arg Lys Ser Thr Asp Ser Pro Val Glu
            195                 200                 205

Cys Met Gly Gln Glu Lys Gly Glu Phe Arg Glu
        210                 215

```
<210> SEQ ID NO 233
<211> LENGTH: 114
<212> TYPE: PRT
<213> ORGANISM: Homo sapiens

<400> SEQUENCE: 233
```

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

```
<210> SEQ ID NO 234
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
atgggagtga agttcttttt tgcccttatt tgtattgctg tggccgaggc c          51

<210> SEQ ID NO 235
<211> LENGTH: 399
<212> TYPE: DNA
<213> ORGANISM: Homo sapiens

<400> SEQUENCE: 235
caaggtcaag atcgccacat gattagaatg cgtcaactta tagatattgt tgatcagctg     60
aaaaattatg tgaatgactt ggtccctgaa tttctgccag ctccagaaga tgtagagaca    120
aactgtgagt ggtcagcttt ttcctgtttt cagaaggccc aactaaagtc agcaaataca    180
ggaaacaatg aaaggataat caatgtatca attaaaaagc tgaagaggaa accaccttcc    240
acaaatgcag ggagaagaca gaaacacaga ctaacatgcc cttcatgtga ttcttatgag    300
aaaaaaccac ccaaagaatt cctagaaaga ttcaaatcac ttctccaaaa gatgattcat    360
cagcatctgt cctctagaac acacggaagt gaagattcc                          399
```

<210> SEQ ID NO 236
<211> LENGTH: 657
<212> TYPE: DNA
<213> ORGANISM: Homo sapiens

<400> SEQUENCE: 236

```
tcaggcacta caaatactgt ggcagcatat aatttaactt ggaaatcaac taatttcaag    60
acaattttgg agtgggaacc caaacccgtc aatcaagtct acactgttca ataagcact    120
aagtcaggag attggaaaag caaatgcttt tacacaacag acacagagtg tgacctcacc   180
gacgagattg tgaaggatgt gaagcagacg tacttggcac gggtcttctc ctacccggca   240
gggaatgtgg agagcaccgg ttctgctggg gagcctctgt atgagaactc cccagagttc   300
acaccttacc tggagacaaa cctcggacag ccaacaattc agagttttga acaggtggga   360
acaaaagtga atgtgaccgt agaagatgaa cggactttag tcagaaggaa caacactttc   420
ctaagcctcc gggatgtttt tggcaaggac ttaatttata cactttatta ttggaaatct   480
tcaagttcag gaaagaaaac agccaaaaca aacactaatg agttttttgat tgatgtggat   540
aaaggagaaa actactgttt cagtgttcaa gcagtgattc cctcccgaac agttaaccgg   600
aagagtacag acagcccggt agagtgtatg ggccaggaga aggggaatt cagagaa       657
```

<210> SEQ ID NO 237
<211> LENGTH: 342
<212> TYPE: DNA
<213> ORGANISM: Homo sapiens

<400> SEQUENCE: 237

```
aactgggtga acgtcatcag cgatttaaag aagatcgaag atttaattca gtccatgcat    60
atcgacgcca ctttatacac agaatccgac gtgcacccct cttgtaaggt gaccgccatg   120
aaatgttttt tactggagct gcaagttatc tctttagaga gcggagacgc tagcatccac   180
gacaccgtgg agaatttaat cattttagcc aataactctt tatccagcaa cggcaacgtg   240
acagagtccg gctgcaagga gtgcgaagag ctggaggaga gaacatcaa ggagtttctg   300
caatcctttg tgcacattgt ccagatgttc atcaatacct cc                      342
```

<210> SEQ ID NO 238
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

```
Met Gly Val Lys Val Leu Phe Ala Leu Ile Cys Ile Ala Val Ala Glu
1               5                   10                  15

Ala
```

<210> SEQ ID NO 239
<211> LENGTH: 133
<212> TYPE: PRT
<213> ORGANISM: Homo sapiens

<400> SEQUENCE: 239

```
Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
                20                  25                  30
```

```
Pro Ala Pro Glu Asp Val Glu Thr Asn Cys Glu Trp Ser Ala Phe Ser
         35                  40                  45

Cys Phe Gln Lys Ala Gln Leu Lys Ser Ala Asn Thr Gly Asn Asn Glu
 50                  55                  60

Arg Ile Ile Asn Val Ser Ile Lys Lys Leu Lys Arg Lys Pro Pro Ser
 65                  70                  75                  80

Thr Asn Ala Gly Arg Arg Gln Lys His Arg Leu Thr Cys Pro Ser Cys
                 85                  90                  95

Asp Ser Tyr Glu Lys Lys Pro Pro Lys Glu Phe Leu Glu Arg Phe Lys
                100                 105                 110

Ser Leu Leu Gln Lys Met Ile His Gln His Leu Ser Ser Arg Thr His
            115                 120                 125

Gly Ser Glu Asp Ser
        130

<210> SEQ ID NO 240
<211> LENGTH: 219
<212> TYPE: PRT
<213> ORGANISM: Homo sapiens

<400> SEQUENCE: 240

Ser Gly Thr Thr Asn Thr Val Ala Ala Tyr Asn Leu Thr Trp Lys Ser
 1               5                  10                  15

Thr Asn Phe Lys Thr Ile Leu Glu Trp Glu Pro Lys Pro Val Asn Gln
             20                  25                  30

Val Tyr Thr Val Gln Ile Ser Thr Lys Ser Gly Asp Trp Lys Ser Lys
         35                  40                  45

Cys Phe Tyr Thr Thr Asp Thr Glu Cys Asp Leu Thr Asp Glu Ile Val
 50                  55                  60

Lys Asp Val Lys Gln Thr Tyr Leu Ala Arg Val Phe Ser Tyr Pro Ala
 65                  70                  75                  80

Gly Asn Val Glu Ser Thr Gly Ser Ala Gly Glu Pro Leu Tyr Glu Asn
                 85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
            115                 120                 125

Asp Glu Arg Thr Leu Val Arg Arg Asn Asn Thr Phe Leu Ser Leu Arg
            130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
            195                 200                 205

Cys Met Gly Gln Glu Lys Gly Glu Phe Arg Glu
210                 215

<210> SEQ ID NO 241
<211> LENGTH: 114
<212> TYPE: PRT
<213> ORGANISM: Homo sapiens

<400> SEQUENCE: 241
```

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser
```

<210> SEQ ID NO 242
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 242

```
atgaagtggg tgaccttcat cagcctgctg ttcctgttct ccagcgccta ctcc        54
```

<210> SEQ ID NO 243
<211> LENGTH: 399
<212> TYPE: DNA
<213> ORGANISM: Homo sapiens

<400> SEQUENCE: 243

```
cagggccagg acaggcacat gatccggatg aggcagctca tcgacatcgt cgaccagctg    60
aagaactacg tgaacgacct ggtgcccgag tttctgcctg cccccgagga cgtggagacc   120
aactgcgagt ggtccgcctt ctcctgcttt cagaaggccc agctgaagtc cgccaacacc   180
ggcaacaacg agcggatcat caacgtgagc atcaagaagc tgaagcggaa gcctccctcc   240
acaaacgccg gcaggaggca gaagcacagg ctgacctgcc ccagctgtga ctcctacgag   300
aagaagcccc ccaaggagtt cctggagagg ttcaagtccc tgctgcagaa gatgatccat   360
cagcacctgt cctccaggac ccacggctcc gaggactcc                          399
```

<210> SEQ ID NO 244
<211> LENGTH: 195
<212> TYPE: DNA
<213> ORGANISM: Homo sapiens

<400> SEQUENCE: 244

```
attacatgcc ccctcccat gagcgtggag cacgccgaca tctgggtgaa gagctatagc     60
ctctacagcc gggagaggta tctgtgtaac agcggcttca gaggaaggc cggcaccagc    120
agcctcaccg agtgcgtgct gaataaggct accaacgtgg ctcactggac aacaccctct   180
ttaaagtgca tccgg                                                    195
```

<210> SEQ ID NO 245
<211> LENGTH: 18
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 245

Met Lys Trp Val Thr Phe Ile Ser Leu Leu Phe Leu Phe Ser Ser Ala
1               5                   10                  15

Tyr Ser

<210> SEQ ID NO 246
<211> LENGTH: 133
<212> TYPE: PRT
<213> ORGANISM: Homo sapiens

<400> SEQUENCE: 246

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
                20                  25                  30

Pro Ala Pro Glu Asp Val Glu Thr Asn Cys Glu Trp Ser Ala Phe Ser
            35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser
    130

<210> SEQ ID NO 247
<211> LENGTH: 65
<212> TYPE: PRT
<213> ORGANISM: Homo sapiens

<400> SEQUENCE: 247

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
    50                  55                  60

Arg
65

<210> SEQ ID NO 248
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
```

```
atgaagtggg tgaccttcat cagcctgctg ttcctgttct ccagcgccta ctcc         54
```

<210> SEQ ID NO 249
<211> LENGTH: 456
<212> TYPE: DNA
<213> ORGANISM: Homo sapiens

<400> SEQUENCE: 249

```
gattgcgaca tcgagggcaa ggacggcaag cagtacgaga gcgtgctgat ggtgtccatc    60
gaccagctgc tggacagcat gaaggagatc ggctccaact gcctcaacaa cgagttcaac   120
ttcttcaagc ggcacatctg cgacgccaac aaggagggca tgttcctgtt cagggccgcc   180
aggaaactgc ggcagttcct gaagatgaac tccaccggcg acttcgacct gcacctgctg   240
aaggtgtccg agggcaccac catcctgctg aactgcaccg acaggtgaa gggccggaaa    300
cctgctgctc tgggagaggc ccaacccacc aagagcctgg aggagaacaa gtccctgaag   360
gagcagaaga agctgaacga cctgtgcttc ctgaagaggc tgctgcagga gatcaagacc   420
tgctggaaca agatcctgat gggcaccaag gagcat                             456
```

<210> SEQ ID NO 250
<211> LENGTH: 657
<212> TYPE: DNA
<213> ORGANISM: Homo sapiens

<400> SEQUENCE: 250

```
agcggcacaa ccaacacagt cgctgcctat aacctcactt ggaagagcac caacttcaaa    60
accatcctcg aatgggaacc caaacccgtt aaccaagttt acaccgtgca gatcagcacc   120
aagtccggcg actggaagtc caaatgtttc tataccaccg acaccgagtg cgatctcacc   180
gatgagatcg tgaaagatgt gaaacagacc tacctcgccc gggtgtttag ctaccccgcc   240
ggcaatgtgg agagcactgg ttccgctggc gagcctttat acgagaacag ccccgaattt   300
acccccttacc tcgagaccaa tttaggacag cccaccatcc aaagctttga gcaagttggc   360
acaaaggtga atgtgacagt ggaggacgag cggactttag tgcggcggaa caacaccttt   420
ctcagcctcc gggatgtgtt cggcaaagat ttaatctaca cactgtatta ctggaagtcc   480
tcttcctccg gcaagaagac agctaaaacc aacacaaacg agttttaat cgacgtggat   540
aaaggcgaaa actactgttt cagcgtgcaa gctgtgatcc cctcccggac cgtgaatagg   600
aaaagcaccg atagccccgt tgagtgcatg ggccaagaaa agggcgagtt ccgggag      657
```

<210> SEQ ID NO 251
<211> LENGTH: 342
<212> TYPE: DNA
<213> ORGANISM: Homo sapiens

<400> SEQUENCE: 251

```
aactgggtga acgtcatcag cgatttaaag aagatcgaag atttaattca gtccatgcat    60
atcgacgcca ctttatacac agaatccgac gtgcacccct cttgtaaggt gaccgccatg   120
aaatgttttt tactggagct gcaagttatc tctttagaga gcggagacgc tagcatccac   180
gacaccgtgg agaatttaat cattttagcc aataactctt tatccagcaa cggcaacgtg   240
acagagtccg gctgcaagga gtgcgaagag ctggaggaga gaacatcaa ggagtttctg    300
caatcctttg tgcacattgt ccagatgttc atcaataccct cc                     342
```

<210> SEQ ID NO 252

```
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Met Lys Trp Val Thr Phe Ile Ser Leu Leu Phe Leu Phe Ser Ser Ala
1               5                   10                  15

Tyr Ser

<210> SEQ ID NO 253
<211> LENGTH: 152
<212> TYPE: PRT
<213> ORGANISM: Homo sapiens

<400> SEQUENCE: 253

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
                20                  25                  30

Asn Cys Leu Asn Asn Glu Phe Asn Phe Phe Lys Arg His Ile Cys Asp
            35                  40                  45

Ala Asn Lys Glu Gly Met Phe Leu Phe Arg Ala Ala Arg Lys Leu Arg
        50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
130                 135                 140

Ile Leu Met Gly Thr Lys Glu His
145                 150

<210> SEQ ID NO 254
<211> LENGTH: 219
<212> TYPE: PRT
<213> ORGANISM: Homo sapiens

<400> SEQUENCE: 254

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
                20                  25                  30

Val Tyr Thr Val Gln Ile Ser Thr Lys Ser Gly Asp Trp Lys Ser Lys
            35                  40                  45

Cys Phe Tyr Thr Thr Asp Thr Glu Cys Asp Leu Thr Asp Glu Ile Val
        50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
```

```
                100             105             110
Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
    130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu
        210                 215
```

<210> SEQ ID NO 255
<211> LENGTH: 114
<212> TYPE: PRT
<213> ORGANISM: Homo sapiens

<400> SEQUENCE: 255

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser
```

<210> SEQ ID NO 256
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 256
atgaagtggg tgaccttcat cagcctgctg ttcctgttct ccagcgccta ctcc        54

<210> SEQ ID NO 257
<211> LENGTH: 456
<212> TYPE: DNA
<213> ORGANISM: Homo sapiens

<400> SEQUENCE: 257
gattgcgaca tcgagggcaa ggacggcaag cagtacgaga gcgtgctgat ggtgtccatc      60
gaccagctgc tggacagcat gaaggagatc ggctccaact gcctcaacaa cgagttcaac     120

```
ttcttcaagc ggcacatctg cgacgccaac aaggagggca tgttcctgtt cagggccgcc        180
aggaaactgc ggcagttcct gaagatgaac tccaccggcg acttcgacct gcacctgctg        240
aaggtgtccg agggcaccac catcctgctg aactgcaccg acaggtgaa gggccggaaa         300 cctgctgctc tgggagaggc ccaacccacc aagagcctgg aggagaacaa gtccctgaag        360
gagcagaaga agctgaacga cctgtgcttc ctgaagaggc tgctgcagga gatcaagacc        420
tgctggaaca agatcctgat gggcaccaag gagcat                                  456
```

```
<210> SEQ ID NO 258
<211> LENGTH: 657
<212> TYPE: DNA
<213> ORGANISM: Homo sapiens

<400> SEQUENCE: 258
agcggcacaa ccaacacagt cgctgcctat aacctcactt ggaagagcac caacttcaaa         60
accatcctcg aatgggaacc caaacccgtt aaccaagttt acaccgtgca gatcagcacc        120
aagtccggcg actggaagtc caaatgtttc tataccaccg acaccgagtg cgatctcacc        180
gatgagatcg tgaaagatgt gaaacagacc tacctcgccc gggtgtttag ctaccccgcc        240
ggcaatgtgg agagcactgg ttccgctggc gagcctttat acgagaacag ccccgaattt        300 acccccttacc tcgagaccaa tttaggacag cccaccatcc aaagctttga gcaagttggc        360
acaaaggtga atgtgacagt ggaggacgag cggactttag tgcggcggaa caacaccttt        420
ctcagcctcc gggatgtgtt cggcaaagat ttaatctaca cactgtatta ctggaagtcc        480
tcttcctccg gcaagaagac agctaaaacc aacacaaacg agtttttaat cgacgtggat        540
aaaggcgaaa actactgttt cagcgtgcaa gctgtgatcc cctcccggac cgtgaatagg        600
aaaagcaccg atagccccgt tgagtgcatg ggccaagaaa agggcgagtt ccgggag          657
```

```
<210> SEQ ID NO 259
<211> LENGTH: 342
<212> TYPE: DNA
<213> ORGANISM: Homo sapiens

<400> SEQUENCE: 259
aactgggtga acgtcatcag cgatttaaag aagatcgaag atttaattca gtccatgcat         60
atcgacgcca ctttatacac agaatccgac gtgcaccct cttgtaaggt gaccgccatg        120
aaatgttttt tactggagct gcaagttatc tctttagaga gcggagacgc tagcatccac        180
gacaccgtgg agaatttaat cattttagcc aataactctt tatccagcaa cggcaacgtg        240
acagagtccg gctgcaagga gtgcgaagag ctggaggaga gaacatcaa ggagtttctg        300 caatccttgt tgcacattgt ccagatgttc atcaataccc tcc                         342
```

```
<210> SEQ ID NO 260
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Met Lys Trp Val Thr Phe Ile Ser Leu Leu Phe Leu Phe Ser Ser Ala
1               5                   10                  15

Tyr Ser
```

```
<210> SEQ ID NO 261
<211> LENGTH: 152
<212> TYPE: PRT
<213> ORGANISM: Homo sapiens

<400> SEQUENCE: 261

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Lys Arg His Ile Cys Asp
        35                  40                  45

Ala Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140

Ile Leu Met Gly Thr Lys Glu His
145                 150

<210> SEQ ID NO 262
<211> LENGTH: 219
<212> TYPE: PRT
<213> ORGANISM: Homo sapiens

<400> SEQUENCE: 262

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
    130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
```

```
                180             185                 190
Ile Pro Ser Arg Thr Val Asn Arg Lys Ser Thr Asp Ser Pro Val Glu
        195                 200                 205

Cys Met Gly Gln Glu Lys Gly Glu Phe Arg Glu
        210                 215

<210> SEQ ID NO 263
<211> LENGTH: 114
<212> TYPE: PRT
<213> ORGANISM: Homo sapiens

<400> SEQUENCE: 263

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 264
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
atgaagtggg tgaccttcat cagcctgctg ttcctgttct ccagcgccta ctcc          54

<210> SEQ ID NO 265
<211> LENGTH: 720
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 265
tccgagctga cccaggaccc tgctgtgtcc gtggctctgg ccagaccgt gaggatcacc      60 tgccagggcg actccctgag gtcctactac gcctcctggt accagcagaa gcccggccag    120
gctcctgtgc tggtgatcta cggcaagaac aacaggccct ccggcatccc tgacaggttc    180
tccggatcct cctccggcaa caccgcctcc ctgaccatca caggcgctca ggccgaggac    240
gaggctgact actactgcaa ctccagggac tcctccggca accatgtggt gttcggcggc    300
ggcaccaagc tgaccgtggg ccatggcggc ggcggctccg gaggcggcgg cagcggcgga    360
ggaggatccg aggtgcagct ggtggagtcc ggaggaggag tggtgaggcc tggaggctcc    420
ctgaggctga gctgtgctgc ctccggcttc accttcgacg actacggcat gtcctgggtg    480
```

```
aggcaggctc ctggaaaggg cctggagtgg gtgtccggca tcaactggaa cggcggatcc      540
accggctacg ccgattccgt gaagggcagg ttcaccatca gcagggacaa cgccaagaac      600
tccctgtacc tgcagatgaa ctccctgagg gccgaggaca ccgccgtgta ctactgcgcc      660
aggggcaggt ccctgctgtt cgactactgg ggacagggca cctggtgac cgtgtccagg      720

<210> SEQ ID NO 266
<211> LENGTH: 195
<212> TYPE: DNA
<213> ORGANISM: Homo sapiens

<400> SEQUENCE: 266
attacatgcc cccctcccat gagcgtggag cacgccgaca tctgggtgaa gagctatagc       60
ctctacagcc gggagaggta tatctgtaac agcggcttca agaggaaggc cggcaccagc      120
agcctcaccg agtgcgtgct gaataaggct accaacgtgg ctcactggac aacaccctct      180
ttaaagtgca tccgg                                                      195

<210> SEQ ID NO 267
<211> LENGTH: 399
<212> TYPE: DNA
<213> ORGANISM: Homo sapiens

<400> SEQUENCE: 267
cagggccagg acaggcacat gatccggatg aggcagctca tcgacatcgt cgaccagctg       60
aagaactacg tgaacgacct ggtgcccgag tttctgcctg ccccgagga cgtggagacc      120 aactgcgagt ggtccgcctt ctcctgcttt cagaaggccc agctgaagtc cgccaacacc      180
ggcaacaacg agcggatcat caacgtgagc atcaagaagc tgaagcggaa gcctccctcc      240
acaaacgccg gcaggaggca gaagcacagg ctgacctgcc ccagctgtga ctcctacgag      300
aagaagcccc ccaaggagtt cctggagagg ttcaagtccc tgctgcagaa gatgatccat      360
cagcacctgt cctccaggac ccacggctcc gaggactcc                            399

<210> SEQ ID NO 268
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Met Lys Trp Val Thr Phe Ile Ser Leu Leu Phe Leu Phe Ser Ser Ala
1               5                   10                  15

Tyr Ser

<210> SEQ ID NO 269
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 269

Ser Glu Leu Thr Gln Asp Pro Ala Val Ser Val Ala Leu Gly Gln Thr
1               5                   10                  15

Val Arg Ile Thr Cys Gln Gly Asp Ser Leu Arg Ser Tyr Tyr Ala Ser
                20                  25                  30
```

Trp Tyr Gln Gln Lys Pro Gly Gln Ala Pro Val Leu Val Ile Tyr Gly
              35                  40                  45

Lys Asn Asn Arg Pro Ser Gly Ile Pro Asp Arg Phe Ser Gly Ser Ser
 50                  55                  60

Ser Gly Asn Thr Ala Ser Leu Thr Ile Thr Gly Ala Gln Ala Glu Asp
 65                  70                  75                  80

Glu Ala Asp Tyr Tyr Cys Asn Ser Arg Asp Ser Ser Gly Asn His Val
                 85                  90                  95

Val Phe Gly Gly Gly Thr Lys Leu Thr Val Gly His Gly Gly Gly Gly
             100                 105                 110

Ser Gly Gly Gly Gly Ser Gly Gly Gly Ser Glu Val Gln Leu Val
             115                 120                 125

Glu Ser Gly Gly Gly Val Val Arg Pro Gly Gly Ser Leu Arg Leu Ser
130                 135                 140

Cys Ala Ala Ser Gly Phe Thr Phe Asp Asp Tyr Gly Met Ser Trp Val
145                 150                 155                 160

Arg Gln Ala Pro Gly Lys Gly Leu Glu Trp Val Ser Gly Ile Asn Trp
                165                 170                 175

Asn Gly Gly Ser Thr Gly Tyr Ala Asp Ser Val Lys Gly Arg Phe Thr
            180                 185                 190

Ile Ser Arg Asp Asn Ala Lys Asn Ser Leu Tyr Leu Gln Met Asn Ser
        195                 200                 205

Leu Arg Ala Glu Asp Thr Ala Val Tyr Tyr Cys Ala Arg Gly Arg Ser
    210                 215                 220

Leu Leu Phe Asp Tyr Trp Gly Gln Gly Thr Leu Val Thr Val Ser Arg
225                 230                 235                 240

<210> SEQ ID NO 270
<211> LENGTH: 65
<212> TYPE: PRT
<213> ORGANISM: Homo sapiens

<400> SEQUENCE: 270

Ile Thr Cys Pro Pro Pro Met Ser Val Glu His Ala Asp Ile Trp Val
 1               5                  10                  15

Lys Ser Tyr Ser Leu Tyr Ser Arg Glu Arg Tyr Ile Cys Asn Ser Gly
             20                  25                  30

Phe Lys Arg Lys Ala Gly Thr Ser Ser Leu Thr Glu Cys Val Leu Asn
         35                  40                  45

Lys Ala Thr Asn Val Ala His Trp Thr Thr Pro Ser Leu Lys Cys Ile
 50                  55                  60

Arg
 65

<210> SEQ ID NO 271
<211> LENGTH: 133
<212> TYPE: PRT
<213> ORGANISM: Homo sapiens

<400> SEQUENCE: 271

Gln Gly Gln Asp Arg His Met Ile Arg Met Arg Gln Leu Ile Asp Ile
 1               5                  10                  15

Val Asp Gln Leu Lys Asn Tyr Val Asn Asp Leu Val Pro Glu Phe Leu
             20                  25                  30

Pro Ala Pro Glu Asp Val Glu Thr Asn Cys Glu Trp Ser Ala Phe Ser
         35                  40                  45

| Cys | Phe | Gln | Lys | Ala | Gln | Leu | Lys | Ser | Ala | Asn | Thr | Gly | Asn | Asn | Glu |
| --- | --- | --- | --- | --- | --- | --- | --- | --- | --- | --- | --- | --- | --- | --- | --- |
| | 50 | | | | 55 | | | | 60 | | | | | | |

| Arg | Ile | Ile | Asn | Val | Ser | Ile | Lys | Lys | Leu | Lys | Arg | Lys | Pro | Pro | Ser |
| --- | --- | --- | --- | --- | --- | --- | --- | --- | --- | --- | --- | --- | --- | --- | --- |
| 65 | | | | | 70 | | | | | 75 | | | | | 80 |

| Thr | Asn | Ala | Gly | Arg | Arg | Gln | Lys | His | Arg | Leu | Thr | Cys | Pro | Ser | Cys |
| --- | --- | --- | --- | --- | --- | --- | --- | --- | --- | --- | --- | --- | --- | --- | --- |
| | | | | 85 | | | | | 90 | | | | | 95 | |

| Asp | Ser | Tyr | Glu | Lys | Lys | Pro | Pro | Lys | Glu | Phe | Leu | Glu | Arg | Phe | Lys |
| --- | --- | --- | --- | --- | --- | --- | --- | --- | --- | --- | --- | --- | --- | --- | --- |
| | | | 100 | | | | | 105 | | | | | 110 | | |

| Ser | Leu | Leu | Gln | Lys | Met | Ile | His | Gln | His | Leu | Ser | Ser | Arg | Thr | His |
| --- | --- | --- | --- | --- | --- | --- | --- | --- | --- | --- | --- | --- | --- | --- | --- |
| | | | | 115 | | | | 120 | | | | 125 | | | |

| Gly | Ser | Glu | Asp | Ser |
| --- | --- | --- | --- | --- |
| | | | 130 | |

<210> SEQ ID NO 272
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272

```
atgaagtggg tgaccttcat cagcctgctg ttcctgttct ccagcgccta ctcc         54
```

<210> SEQ ID NO 273
<211> LENGTH: 861
<212> TYPE: DNA
<213> ORGANISM: Homo sapiens

<400> SEQUENCE: 273

```
atcccccccc atgtgcaaaa gagcgtgaac aacgatatga tcgtgaccga caacaacggc    60
gccgtgaagt tcccccagct ctgcaagttc tgcgatgtca ggttcagcac ctgcgataat   120
cagaagtcct gcatgtccaa ctgcagcatc acctccatct gcgagaagcc caagaagtg   180 tgcgtggccg tgtggcggaa aaatgacgag aacatcaccc tggagaccgt gtgtcacgac   240
cccaagctcc cttatcacga cttcattctg gaggacgctg cctcccccaa atgcatcatg   300
aaggagaaga agaagcccgg agagaccttc tttatgtgtt cctgtagcag cgacgagtgt   360
aacgacaaca tcatcttcag cgaagagtac aacaccagca accctgatgg aggtggcgga   420
tccggaggtg gaggttctgg tggaggtggg agtattcctc ccacgtgca gaagagcgtg    480 aataatgaca tgatcgtgac cgataacaat ggcgccgtga atttcccca gctgtgcaaa    540 ttctgcgatg tgaggttttc cacctgcgac aaccagaagt cctgtatgag caactgctcc   600
atcacctcca tctgtgagaa gcctcaggag gtgtgcgtgg ctgtctggcg gaagaatgac   660
gagaatatca ccctggaaac cgtctgccac gatcccaagc tgccctacca cgatttcatc   720
ctggaagacg ccgccagccc taagtgcatc atgaaagaga aaagaagcc tggcgagacc    780 ttttcatgt gctcctgcag cagcgacgaa tgcaacgaca tatcatctt agcgaggaa     840 tacaatacca gcaaccccga c                                              861
```

<210> SEQ ID NO 274
<211> LENGTH: 657
<212> TYPE: DNA
<213> ORGANISM: Homo sapiens

<400> SEQUENCE: 274

```
agcggcacaa ccaacacagt cgctgcctat aacctcactt ggaagagcac caacttcaaa    60
```

```
accatcctcg aatgggaacc caaacccgtt aaccaagttt acaccgtgca gatcagcacc      120
aagtccggcg actggaagtc caaatgtttc tataccaccg acaccgagtg cgatctcacc      180
gatgagatcg tgaaagatgt gaaacagacc tacctcgccc gggtgtttag ctaccccgcc      240
ggcaatgtgg agagcactgg ttccgctggc gagcctttat acgagaacag ccccgaattt      300
accccttacc tcgagaccaa tttaggacag cccaccatcc aaagctttga gcaagttggc      360
acaaaggtga atgtgacagt ggaggacgag cggactttag tgcggcggaa caacaccttt      420
ctcagcctcc gggatgtgtt cggcaaagat ttaatctaca cactgtatta ctggaagtcc      480
tcttcctccg gcaagaagac agctaaaacc aacacaaacg agtttttaat cgacgtggat      540
aaaggcgaaa actactgttt cagcgtgcaa gctgtgatcc cctcccggac cgtgaatagg      600
aaaagcaccg atagccccgt tgagtgcatg ggccaagaaa agggcgagtt ccgggag       657
```

```
<210> SEQ ID NO 275
<211> LENGTH: 342
<212> TYPE: DNA
<213> ORGANISM: Homo sapiens

<400> SEQUENCE: 275
aactgggtga acgtcatcag cgatttaaag aagatcgaag atttaattca gtccatgcat      60
atcgacgcca ctttatacac agaatccgac gtgcaccct cttgtaaggt gaccgccatg      120
aaatgttttt tactggagct gcaagttatc tctttagaga gcgagacgc tagcatccac      180 gacaccgtgg agaatttaat cattttagcc aataactctt tatccagcaa cggcaacgtg      240
acagagtccg gctgcaagga gtgcgaagag ctggaggaga gaacatcaa ggagtttctg      300 caatcctttg tgcacattgt ccagatgttc atcaatacct cc                        342
```

```
<210> SEQ ID NO 276
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Met Lys Trp Val Thr Phe Ile Ser Leu Leu Phe Leu Phe Ser Ser Ala
1               5                   10                  15

Tyr Ser
```

```
<210> SEQ ID NO 277
<211> LENGTH: 287
<212> TYPE: PRT
<213> ORGANISM: Homo sapiens

<400> SEQUENCE: 277

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
                20                  25                  30

Val Arg Phe Ser Thr Cys Asp Asn Gln Lys Ser Cys Met Ser Asn Cys
            35                  40                  45

Ser Ile Thr Ser Ile Cys Glu Lys Pro Gln Glu Val Cys Val Ala Val
        50                  55                  60

Trp Arg Lys Asn Asp Glu Asn Ile Thr Leu Glu Thr Val Cys His Asp
65                  70                  75                  80
```

Pro Lys Leu Pro Tyr His Asp Phe Ile Leu Glu Asp Ala Ala Ser Pro
            85                  90                  95

Lys Cys Ile Met Lys Glu Lys Lys Pro Gly Glu Thr Phe Phe Met
        100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp Gly Gly Gly Ser Gly Gly Gly
        130                 135                 140

Gly Ser Gly Gly Gly Ser Ile Pro Pro His Val Gln Lys Ser Val
145                 150                 155                 160

Asn Asn Asp Met Ile Val Thr Asp Asn Gly Ala Val Lys Phe Pro
                165                 170                 175

Gln Leu Cys Lys Phe Cys Asp Val Arg Phe Ser Thr Cys Asp Asn Gln
        180                 185                 190

Lys Ser Cys Met Ser Asn Cys Ser Ile Thr Ser Ile Cys Glu Lys Pro
        195                 200                 205

Gln Glu Val Cys Val Ala Val Trp Arg Lys Asn Asp Glu Asn Ile Thr
        210                 215                 220

Leu Glu Thr Val Cys His Asp Pro Lys Leu Pro Tyr His Asp Phe Ile
225                 230                 235                 240

Leu Glu Asp Ala Ala Ser Pro Lys Cys Ile Met Lys Glu Lys Lys Lys
                245                 250                 255

Pro Gly Glu Thr Phe Phe Met Cys Ser Cys Ser Ser Asp Glu Cys Asn
        260                 265                 270

Asp Asn Ile Ile Phe Ser Glu Glu Tyr Asn Thr Ser Asn Pro Asp
        275                 280                 285

<210> SEQ ID NO 278
<211> LENGTH: 219
<212> TYPE: PRT
<213> ORGANISM: Homo sapiens

<400> SEQUENCE: 278

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
    130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu
    210                 215

<210> SEQ ID NO 279
<211> LENGTH: 114
<212> TYPE: PRT
<213> ORGANISM: Homo sapiens

<400> SEQUENCE: 279

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 280
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
atgaagtggg tgaccttcat cagcctgctg ttcctgttct ccagcgccta ctcc         54

<210> SEQ ID NO 281
<211> LENGTH: 720
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 281
tccgagctga cccaggaccc tgctgtgtcc gtggctctgg ccagaccgt gaggatcacc      60 tgccagggcg actccctgag gtcctactac gcctcctggt accagcagaa gcccggccag    120
gctcctgtgc tggtgatcta cggcaagaac aacaggccct ccggcatccc tgacaggttc    180
tccggatcct cctccggcaa caccgcctcc ctgaccatca caggcgctca ggccgaggac    240
gaggctgact actactgcaa ctccagggac tcctccggca accatgtggt gttcggcggc    300
ggcaccaagc tgaccgtggg ccatggcggc ggcggctccg gaggcggcgg cagcggcgga    360
ggaggatccg aggtgcagct ggtggagtcc ggaggaggag tggtgaggcc tggaggctcc    420

```
ctgaggctga gctgtgctgc ctccggcttc accttcgacg actacggcat gtcctgggtg    480
aggcaggctc ctggaaaggg cctggagtgg gtgtccggca tcaactgaa cggcggatcc    540 accggctacg ccgattccgt gaagggcagg ttcaccatca gcagggacaa cgccaagaac    600
tccctgtacc tgcagatgaa ctccctgagg gccgaggaca ccgccgtgta ctactgcgcc    660
aggggcaggt ccctgctgtt cgactactgg ggacagggca cctggtgac cgtgtccagg    720
```

<210> SEQ ID NO 282
<211> LENGTH: 195
<212> TYPE: DNA
<213> ORGANISM: Homo sapiens

<400> SEQUENCE: 282

```
attacatgcc cccctcccat gagcgtggag cacgccgaca tctgggtgaa gagctatagc    60
ctctacagcc gggagaggta tatctgtaac agcggcttca agaggaaggc cggcaccagc   120
agcctcaccg agtgcgtgct gaataaggct accaacgtgg ctcactggac aacaccctct   180
ttaaagtgca tccgg                                                    195
```

<210> SEQ ID NO 283
<211> LENGTH: 399
<212> TYPE: DNA
<213> ORGANISM: Homo sapiens

<400> SEQUENCE: 283

```
cagggccagg acaggcacat gatccggatg aggcagctca tcgacatcgt cgaccagctg    60
aagaactacg tgaacgacct ggtgcccgag tttctgcctg cccccgagga cgtggagacc   120
aactgcgagt ggtccgcctt ctcctgcttt cagaaggccc agctgaagtc cgccaacacc   180
ggcaacaacg agcggatcat caacgtgagc atcaagaagc tgaagcggaa gcctccctcc   240
acaaacgccg gcaggaggca aagcacagg ctgacctgcc ccagctgtga ctcctacgag   300
aagaagcccc ccaaggagtt cctggagagg ttcaagtccc tgctgcagaa gatgatccat   360
cagcacctgt cctccaggac ccacggctcc gaggactcc                          399
```

<210> SEQ ID NO 284
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

```
Met Lys Trp Val Thr Phe Ile Ser Leu Leu Phe Leu Phe Ser Ser Ala
1               5                   10                  15

Tyr Ser
```

<210> SEQ ID NO 285
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 285

```
Ser Glu Leu Thr Gln Asp Pro Ala Val Ser Val Ala Leu Gly Gln Thr
1               5                   10                  15

Val Arg Ile Thr Cys Gln Gly Asp Ser Leu Arg Ser Tyr Tyr Ala Ser
```

```
                 20                  25                  30

Trp Tyr Gln Gln Lys Pro Gly Gln Ala Pro Val Leu Val Ile Tyr Gly
             35                  40                  45

Lys Asn Asn Arg Pro Ser Gly Ile Pro Asp Arg Phe Ser Gly Ser Ser
     50                  55                  60

Ser Gly Asn Thr Ala Ser Leu Thr Ile Thr Gly Ala Gln Ala Glu Asp
     65                  70                  75                  80

Glu Ala Asp Tyr Tyr Cys Asn Ser Arg Asp Ser Ser Gly Asn His Val
                     85                  90                  95

Val Phe Gly Gly Gly Thr Lys Leu Thr Val Gly His Gly Gly Gly Gly
                100                 105                 110

Ser Gly Gly Gly Gly Ser Gly Gly Gly Ser Glu Val Gln Leu Val
                115                 120                 125

Glu Ser Gly Gly Gly Val Val Arg Pro Gly Gly Ser Leu Arg Leu Ser
                130                 135                 140

Cys Ala Ala Ser Gly Phe Thr Phe Asp Asp Tyr Gly Met Ser Trp Val
    145                 150                 155                 160

Arg Gln Ala Pro Gly Lys Gly Leu Glu Trp Val Ser Gly Ile Asn Trp
                    165                 170                 175

Asn Gly Gly Ser Thr Gly Tyr Ala Asp Ser Val Lys Gly Arg Phe Thr
                    180                 185                 190

Ile Ser Arg Asp Asn Ala Lys Asn Ser Leu Tyr Leu Gln Met Asn Ser
                    195                 200                 205

Leu Arg Ala Glu Asp Thr Ala Val Tyr Tyr Cys Ala Arg Gly Arg Ser
                    210                 215                 220

Leu Leu Phe Asp Tyr Trp Gly Gln Gly Thr Leu Val Thr Val Ser Arg
    225                 230                 235                 240

<210> SEQ ID NO 286
<211> LENGTH: 65
<212> TYPE: PRT
<213> ORGANISM: Homo sapiens

<400> SEQUENCE: 286

Ile Thr Cys Pro Pro Met Ser Val Glu His Ala Asp Ile Trp Val
     1               5                  10                  15

Lys Ser Tyr Ser Leu Tyr Ser Arg Glu Arg Tyr Ile Cys Asn Ser Gly
                     20                  25                  30

Phe Lys Arg Lys Ala Gly Thr Ser Ser Leu Thr Glu Cys Val Leu Asn
                 35                  40                  45

Lys Ala Thr Asn Val Ala His Trp Thr Thr Pro Ser Leu Lys Cys Ile
     50                  55                  60

Arg
    65

<210> SEQ ID NO 287
<211> LENGTH: 133
<212> TYPE: PRT
<213> ORGANISM: Homo sapiens

<400> SEQUENCE: 287

Gln Gly Gln Asp Arg His Met Ile Arg Met Arg Gln Leu Ile Asp Ile
     1               5                  10                  15

Val Asp Gln Leu Lys Asn Tyr Val Asn Asp Leu Val Pro Glu Phe Leu
                     20                  25                  30

Pro Ala Pro Glu Asp Val Glu Thr Asn Cys Glu Trp Ser Ala Phe Ser
```

```
                35                  40                  45
Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser
    130
```

<210> SEQ ID NO 288
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288

```
atgaagtggg tgaccttcat cagcctgctg ttcctgttct ccagcgccta ctcc         54
```

<210> SEQ ID NO 289
<211> LENGTH: 456
<212> TYPE: DNA
<213> ORGANISM: Homo sapiens

<400> SEQUENCE: 289

```
gattgcgaca tcgagggcaa ggacggcaag cagtacgaga gcgtgctgat ggtgtccatc    60
gaccagctgc tggacagcat gaaggagatc ggctccaact gcctcaacaa cgagttcaac   120
ttcttcaagc ggcacatctg cgacgccaac aaggagggca tgttcctgtt cagggccgcc   180
aggaaactgc ggcagttcct gaagatgaac tccaccggcg acttcgacct gcacctgctg   240
aaggtgtccg agggcaccac catcctgctg aactgcaccg acaggtgaa gggccggaaa   300 cctgctgctc tgggagaggc ccaacccacc aagagcctgg aggagaacaa gtccctgaag   360
gagcagaaga agctgaacga cctgtgcttc ctgaagaggc tgctgcagga gatcaagacc   420
tgctggaaca agatcctgat gggcaccaag gagcat                            456
```

<210> SEQ ID NO 290
<211> LENGTH: 657
<212> TYPE: DNA
<213> ORGANISM: Homo sapiens

<400> SEQUENCE: 290

```
agcggcacaa ccaacacagt cgctgcctat aacctcactt ggaagagcac caacttcaaa    60
accatcctcg aatgggaacc caaacccgtt aaccaagttt acaccgtgca gatcagcacc   120
aagtccggcg actggaagtc caatgttttc tataccaccg acaccgagtg cgatctcacc   180
gatgagatcg tgaaagatgt gaaacagacc tacctcgccc gggtgtttag ctaccccgcc   240
ggcaatgtgg agagcactgg ttccgctggc gagcctttat acgagaacag ccccgaattt   300
accccttacc tcgagaccaa tttaggacag cccaccatcc aaagctttga gcaagttggc   360
acaaaggtga atgtgacagt ggaggacgag cggactttag tgcggcggaa caacaccttt   420
```

```
ctcagcctcc gggatgtgtt cggcaaagat ttaatctaca cactgtatta ctggaagtcc    480
tcttcctccg gcaagaagac agctaaaacc aacacaaacg agtttttaat cgacgtggat    540
aaaggcgaaa actactgttt cagcgtgcaa gctgtgatcc cctcccggac cgtgaatagg    600
aaaagcaccg atagccccgt tgagtgcatg ggccaagaaa agggcgagtt ccgggag      657
```

<210> SEQ ID NO 291
<211> LENGTH: 342
<212> TYPE: DNA
<213> ORGANISM: Homo sapiens

<400> SEQUENCE: 291

```
aactgggtga acgtcatcag cgatttaaag aagatcgaag atttaattca gtccatgcat     60
atcgacgcca ctttatacac agaatccgac gtgcacccct cttgtaaggt gaccgccatg    120
aaatgttttt tactggagct gcaagttatc tctttagaga gcggagacgc tagcatccac    180
gacaccgtgg agaatttaat cattttagcc aataactctt tatccagcaa cggcaacgtg    240
acagagtccg gctgcaagga gtgcgaagag ctggaggaga gaacatcaa ggagtttctg     300 caatcctttg tgcacattgt ccagatgttc atcaatacct cc                      342
```

<210> SEQ ID NO 292
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Met Lys Trp Val Thr Phe Ile Ser Leu Leu Phe Leu Phe Ser Ser Ala
1               5                   10                  15

Tyr Ser

<210> SEQ ID NO 293
<211> LENGTH: 152
<212> TYPE: PRT
<213> ORGANISM: Homo sapiens

<400> SEQUENCE: 293

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
                20                  25                  30

Asn Cys Leu Asn Asn Glu Phe Asn Phe Lys Arg His Ile Cys Asp
                35                  40                  45

Ala Asn Lys Glu Gly Met Phe Leu Phe Arg Ala Ala Arg Lys Leu Arg
        50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
                100                 105                 110

Leu Glu Glu Asn Lys Ser Leu Lys Glu Gln Lys Lys Leu Asn Asp Leu
                115                 120                 125

Cys Phe Leu Lys Arg Leu Leu Gln Glu Ile Lys Thr Cys Trp Asn Lys
        130                 135                 140

Ile Leu Met Gly Thr Lys Glu His
145                 150

<210> SEQ ID NO 294
<211> LENGTH: 219
<212> TYPE: PRT
<213> ORGANISM: Homo sapiens

<400> SEQUENCE: 294

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
    130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu
    210                 215

<210> SEQ ID NO 295
<211> LENGTH: 114
<212> TYPE: PRT
<213> ORGANISM: Homo sapiens

<400> SEQUENCE: 295

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 296
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
atgggagtga aagttctttt tgcccttatt tgtattgctg tggccgaggc c          51

<210> SEQ ID NO 297
<211> LENGTH: 456
<212> TYPE: DNA
<213> ORGANISM: Homo sapiens

<400> SEQUENCE: 297
gattgtgata ttgaaggtaa agatggcaaa caatatgaga gtgttctaat ggtcagcatc    60
gatcaattat tggacagcat gaaagaaatt ggtagcaatt gcctgaataa tgaatttaac   120
ttttttaaaa gacatatctg tgatgctaat aaggaaggta tgttttttatt ccgtgctgct   180 cgcaagttga ggcaatttct taaaatgaat agcactggtg attttgatct ccacttatta   240
aaagtttcag aaggcacaac aatactgttg aactgcactg ccaggttaa aggaagaaaa    300 ccagctgccc tgggtgaagc ccaaccaaca aagagtttgg aagaaaataa atctttaaag   360
gaacagaaaa aactgaatga cttgtgtttc ctaaagagac tattacaaga gataaaaact   420
tgttggaata aaattttgat gggcactaaa gaacac                            456

<210> SEQ ID NO 298
<211> LENGTH: 195
<212> TYPE: DNA
<213> ORGANISM: Homo sapiens

<400> SEQUENCE: 298
atcacgtgcc ctcccccat gtccgtggaa cacgcagaca tctgggtcaa gagctacagc    60
ttgtactcca gggagcggta catttgtaac tctggtttca agcgtaaagc cggcacgtcc   120
agcctgacgg agtgcgtgtt gaacaaggcc acgaatgtcg cccactggac aaccccagt   180 ctcaaatgca ttaga                                                   195

<210> SEQ ID NO 299
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Met Gly Val Lys Val Leu Phe Ala Leu Ile Cys Ile Ala Val Ala Glu
1               5                   10                  15

Ala

<210> SEQ ID NO 300
<211> LENGTH: 152
<212> TYPE: PRT
<213> ORGANISM: Homo sapiens

<400> SEQUENCE: 300

Asp Cys Asp Ile Glu Gly Lys Asp Gly Lys Gln Tyr Glu Ser Val Leu
1               5                   10                  15
Met Val Ser Ile Asp Gln Leu Leu Asp Ser Met Lys Glu Ile Gly Ser
            20                  25                  30
Asn Cys Leu Asn Asn Glu Phe Asn Phe Phe Lys Arg His Ile Cys Asp
        35                  40                  45
Ala Asn Lys Glu Gly Met Phe Leu Phe Arg Ala Ala Arg Lys Leu Arg
    50                  55                  60
Gln Phe Leu Lys Met Asn Ser Thr Gly Asp Phe Asp Leu His Leu Leu
65                  70                  75                  80
Lys Val Ser Glu Gly Thr Thr Ile Leu Leu Asn Cys Thr Gly Gln Val
                85                  90                  95
Lys Gly Arg Lys Pro Ala Ala Leu Gly Glu Ala Gln Pro Thr Lys Ser
            100                 105                 110
Leu Glu Glu Asn Lys Ser Leu Lys Glu Gln Lys Lys Leu Asn Asp Leu
        115                 120                 125
Cys Phe Leu Lys Arg Leu Leu Gln Glu Ile Lys Thr Cys Trp Asn Lys
    130                 135                 140
Ile Leu Met Gly Thr Lys Glu His
145                 150

<210> SEQ ID NO 301
<211> LENGTH: 65
<212> TYPE: PRT
<213> ORGANISM: Homo sapiens

<400> SEQUENCE: 301

Ile Thr Cys Pro Pro Pro Met Ser Val Glu His Ala Asp Ile Trp Val
1               5                   10                  15
Lys Ser Tyr Ser Leu Tyr Ser Arg Glu Arg Tyr Ile Cys Asn Ser Gly
            20                  25                  30
Phe Lys Arg Lys Ala Gly Thr Ser Ser Leu Thr Glu Cys Val Leu Asn
        35                  40                  45
Lys Ala Thr Asn Val Ala His Trp Thr Thr Pro Ser Leu Lys Cys Ile
    50                  55                  60
Arg
65

<210> SEQ ID NO 302
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302
atgaagtggg tgaccttcat cagcctgctg ttcctgttct ccagcgccta ctcc         54

<210> SEQ ID NO 303
<211> LENGTH: 861
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 303

```
atcccccccc atgtgcaaaa gagcgtgaac aacgatatga tcgtgaccga caacaacggc    60
gccgtgaagt ttccccagct ctgcaagttc tgcgatgtca ggttcagcac ctgcgataat   120
cagaagtcct gcatgtccaa ctgcagcatc acctccatct gcgagaagcc caagaagtg    180 tgcgtggccg tgtggcggaa aaatgacgag aacatcaccc tggagaccgt gtgtcacgac   240
cccaagctcc cttatcacga cttcattctg gaggacgctg cctcccccaa atgcatcatg   300
aaggagaaga gaagcccgg agagaccttc tttatgtgtt cctgtagcag cgacgagtgt    360
aacgacaaca tcatcttcag cgaagagtac aacaccagca accctgatgg aggtggcgga   420
tccggaggtg gaggttctgg tggaggtggg agtattcctc cccacgtgca gaagagcgtg   480
aataatgaca tgatcgtgac cgataacaat ggcgccgtga atttccccca gctgtgcaaa   540
ttctgcgatg tgaggttttc cacctgcgac aaccagaagt cctgtatgag caactgctcc   600
atcacctcca tctgtgagaa gcctcaggag gtgtgcgtgg ctgtctggcg gaagaatgac   660
gagaatatca ccctggaaac cgtctgccac gatcccaagc tgccctacca cgatttcatc   720
ctggaagacg ccgccagccc taagtgcatc atgaaagaga aaagaagcc tggcgagacc    780 tttttcatgt gctcctgcag cagcgacgaa tgcaacgaca atatcatctt tagcgaggaa   840
tacaatacca gcaaccccga c                                             861

<210> SEQ ID NO 304
<211> LENGTH: 657
<212> TYPE: DNA
<213> ORGANISM: Homo sapiens

<400> SEQUENCE: 304
agcggcacaa ccaacacagt cgctgcctat aacctcactt ggaagagcac caacttcaaa    60
accatcctcg aatgggaacc caaacccgtt aaccaagttt acaccgtgca gatcagcacc   120
aagtccggcg actggaagtc caaatgtttc tataccaccg acaccgagtg cgatctcacc   180
gatgagatcg tgaaagatgt gaaacagacc tacctcgccc gggtgtttag ctaccccgcc   240
ggcaatgtgg agagcactgg ttccgctggc gagccttat acgagaacag ccccgaattt    300 acccccttacc tcgagaccaa tttaggacag cccaccatcc aaagctttga gcaagttggc   360
acaaaggtga atgtgacagt ggaggacgag cggactttag tgcggcggaa caacaccttt   420
ctcagcctcc gggatgtgtt cggcaaagat ttaatctaca cactgtatta ctggaagtcc   480
tcttcctccg gcaagaagac agctaaaacc aacacaaacg agttttaat cgacgtggat    540 aaaggcgaaa actactgttt cagcgtgcaa gctgtgatcc cctcccggac cgtgaatagg   600
aaaagcaccg atagcccgt tgagtgcatg ggccaagaaa agggcgagtt ccgggag       657

<210> SEQ ID NO 305
<211> LENGTH: 342
<212> TYPE: DNA
<213> ORGANISM: Homo sapiens

<400> SEQUENCE: 305
aactgggtga acgtcatcag cgatttaaag aagatcgaag atttaattca gtccatgcat    60
atcgacgcca cttatacac agaatccgac gtgcacccct cttgtaaggt gaccgccatg    120
aaatgttttt tactggagct gcaagttatc tctttagaga gcggagacgc tagcatccac   180
gacaccgtgg agaatttaat catttttagcc aataactctt tatccagcaa cggcaacgtg   240
acagagtccg gctgcaagga gtgcgaagag ctggaggaga gaacatcaa ggagtttctg    300
```

```
caatcctttg tgcacattgt ccagatgttc atcaatacct cc                              342
```

<210> SEQ ID NO 306
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Met Lys Trp Val Thr Phe Ile Ser Leu Leu Phe Leu Phe Ser Ser Ala
1               5                   10                  15

Tyr Ser

<210> SEQ ID NO 307
<211> LENGTH: 287
<212> TYPE: PRT
<213> ORGANISM: Homo sapiens

<400> SEQUENCE: 307

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
                20                  25                  30

Val Arg Phe Ser Thr Cys Asp Asn Gln Lys Ser Cys Met Ser Asn Cys
            35                  40                  45

Ser Ile Thr Ser Ile Cys Glu Lys Pro Gln Glu Val Cys Val Ala Val
        50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
                100                 105                 110

Cys Ser Cys Ser Ser Asp Glu Cys Asn Asp Asn Ile Ile Phe Ser Glu
            115                 120                 125

Glu Tyr Asn Thr Ser Asn Pro Asp Gly Gly Gly Ser Gly Gly Gly
        130                 135                 140

Gly Ser Gly Gly Gly Ser Ile Pro Pro His Val Gln Lys Ser Val
145                 150                 155                 160

Asn Asn Asp Met Ile Val Thr Asp Asn Asn Gly Ala Val Lys Phe Pro
                165                 170                 175

Gln Leu Cys Lys Phe Cys Asp Val Arg Phe Ser Thr Cys Asp Asn Gln
            180                 185                 190

Lys Ser Cys Met Ser Asn Cys Ser Ile Thr Ser Ile Cys Glu Lys Pro
        195                 200                 205

Gln Glu Val Cys Val Ala Val Trp Arg Lys Asn Asp Glu Asn Ile Thr
    210                 215                 220

Leu Glu Thr Val Cys His Asp Pro Lys Leu Pro Tyr His Asp Phe Ile
225                 230                 235                 240

Leu Glu Asp Ala Ala Ser Pro Lys Cys Ile Met Lys Glu Lys Lys Lys
                245                 250                 255

Pro Gly Glu Thr Phe Phe Met Cys Ser Cys Ser Ser Asp Glu Cys Asn
            260                 265                 270

Asp Asn Ile Ile Phe Ser Glu Glu Tyr Asn Thr Ser Asn Pro Asp
        275                 280                 285

<210> SEQ ID NO 308
<211> LENGTH: 219
<212> TYPE: PRT
<213> ORGANISM: Homo sapiens

<400> SEQUENCE: 308

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
    130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu
    210                 215

<210> SEQ ID NO 309
<211> LENGTH: 114
<212> TYPE: PRT
<213> ORGANISM: Homo sapiens

<400> SEQUENCE: 309

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 310
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
atgaagtggg tgaccttcat cagcctgctg ttcctgttct ccagcgccta ctcc        54

<210> SEQ ID NO 311
<211> LENGTH: 861
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 311 atccccccc atgtgcaaaa gagcgtgaac aacgatatga tcgtgaccga caacaacggc        60
gccgtgaagt ttccccagct ctgcaagttc tgcgatgtca ggttcagcac ctgcgataat       120
cagaagtcct gcatgtccaa ctgcagcatc acctccatct gcgagaagcc ccagaagtg       180 tgcgtggccg tgtggcggaa aaatgacgag aacatcaccc tggagaccgt gtgtcacgac       240
cccaagctcc cttatcacga cttcattctg gaggacgctg cctcccccaa atgcatcatg       300
aaggagaaga gaagcccgg agagaccttc tttatgtgtt cctgtagcag cgacgagtgt       360
aacgacaaca tcatcttcag cgaagagtac aacaccagca accctgatgg aggtggcgga       420
tccggaggtg gaggttctgg tggaggtggg agtattcctc cccacgtgca gaagagcgtg       480
aataatgaca tgatcgtgac cgataacaat ggcgccgtga aatttcccca gctgtgcaaa       540
ttctgcgatg tgaggttttc cacctgcgac aaccagaagt cctgtatgag caactgctcc       600
atcacctcca tctgtgagaa gcctcaggag gtgtgcgtgg ctgtctggcg gaagaatgac       660
gagaatatca ccctggaaac cgtctgccac gatcccaagc tgccctacca cgatttcatc       720
ctggaagacg ccgccagccc taagtgcatc atgaaagaga aaagaagcc tggcgagacc       780 ttttttcatgt gctcctgcag cagcgacgaa tgcaacgaca atatcatctt tagcgaggaa       840
tacaatacca gcaaccccga c                                                 861

<210> SEQ ID NO 312
<211> LENGTH: 195
<212> TYPE: DNA
<213> ORGANISM: Homo sapiens

<400> SEQUENCE: 312
attacatgcc ccctcccat gagcgtggag cacgccgaca tctgggtgaa gagctatagc        60
ctctacagcc gggagaggta tatctgtaac agcggcttca gaggaaggc cggcaccagc       120 agcctcaccg agtgcgtgct gaataaggct accaacgtgg ctcactggac aacaccctct       180
ttaaagtgca tccgg                                                        195

<210> SEQ ID NO 313
<211> LENGTH: 18
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 313

Met Lys Trp Val Thr Phe Ile Ser Leu Leu Phe Leu Phe Ser Ser Ala
1               5                   10                  15

Tyr Ser

<210> SEQ ID NO 314
<211> LENGTH: 287
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 314

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
                20                  25                  30

Val Arg Phe Ser Thr Cys Asp Asn Gln Lys Ser Cys Met Ser Asn Cys
            35                  40                  45

Ser Ile Thr Ser Ile Cys Glu Lys Pro Gln Glu Val Cys Val Ala Val
        50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
                100                 105                 110

Cys Ser Cys Ser Ser Asp Glu Cys Asn Asp Asn Ile Ile Phe Ser Glu
            115                 120                 125

Glu Tyr Asn Thr Ser Asn Pro Asp Gly Gly Gly Ser Gly Gly Gly
        130                 135                 140

Gly Ser Gly Gly Gly Ser Ile Pro Pro His Val Gln Lys Ser Val
145                 150                 155                 160

Asn Asn Asp Met Ile Val Thr Asp Asn Asn Gly Ala Val Lys Phe Pro
                165                 170                 175

Gln Leu Cys Lys Phe Cys Asp Val Arg Phe Ser Thr Cys Asp Asn Gln
            180                 185                 190

Lys Ser Cys Met Ser Asn Cys Ser Ile Thr Ser Ile Cys Glu Lys Pro
        195                 200                 205

Gln Glu Val Cys Val Ala Val Trp Arg Lys Asn Asp Glu Asn Ile Thr
    210                 215                 220

Leu Glu Thr Val Cys His Asp Pro Lys Leu Pro Tyr His Asp Phe Ile
225                 230                 235                 240

Leu Glu Asp Ala Ala Ser Pro Lys Cys Ile Met Lys Glu Lys Lys
                245                 250                 255

Pro Gly Glu Thr Phe Phe Met Cys Ser Cys Ser Ser Asp Glu Cys Asn
            260                 265                 270

Asp Asn Ile Ile Phe Ser Glu Tyr Asn Thr Ser Asn Pro Asp
        275                 280                 285

<210> SEQ ID NO 315
<211> LENGTH: 65
<212> TYPE: PRT

<213> ORGANISM: Homo sapiens

<400> SEQUENCE: 315

Ile Thr Cys Pro Pro Met Ser Val Glu His Ala Asp Ile Trp Val
1               5                   10                  15
Lys Ser Tyr Ser Leu Tyr Ser Arg Glu Arg Tyr Ile Cys Asn Ser Gly
            20                  25                  30
Phe Lys Arg Lys Ala Gly Thr Ser Ser Leu Thr Glu Cys Val Leu Asn
        35                  40                  45
Lys Ala Thr Asn Val Ala His Trp Thr Thr Pro Ser Leu Lys Cys Ile
    50                  55                  60
Arg
65

<210> SEQ ID NO 316
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
atgaagtggg tgaccttcat cagcctgctg ttcctgttct ccagcgccta ctcc          54

<210> SEQ ID NO 317
<211> LENGTH: 456
<212> TYPE: DNA
<213> ORGANISM: Homo sapiens

<400> SEQUENCE: 317
gattgcgaca tcgagggcaa ggacggcaag cagtacgaga gcgtgctgat ggtgtccatc    60
gaccagctgc tggacagcat gaaggagatc ggctccaact gcctcaacaa cgagttcaac   120
ttcttcaagc ggcacatctg cgacgccaac aaggagggca tgttcctgtt cagggccgcc   180
aggaaactgc ggcagttcct gaagatgaac tccaccggcg acttcgacct gcacctgctg   240
aaggtgtccg agggcaccac catcctgctg aactgcaccg acaggtgaa gggccggaaa    300 cctgctgctc tgggagaggc ccaacccacc aagagcctgg aggagaacaa gtccctgaag   360
gagcagaaga gctgaacga cctgtgcttc ctgaagaggc tgctgcagga gatcaagacc    420
tgctggaaca agatcctgat gggcaccaag gagcat                             456

<210> SEQ ID NO 318
<211> LENGTH: 657
<212> TYPE: DNA
<213> ORGANISM: Homo sapiens

<400> SEQUENCE: 318
agcggcacaa ccaacacagt cgctgcctat aacctcactt ggaagagcac caacttcaaa    60
accatcctcg aatgggaacc caaacccgtt aaccaagttt acaccgtgca gatcagcacc   120
aagtccggcg actggaagtc caaatgtttc tataccaccg acaccgagtg cgatctcacc   180
gatgagatcg tgaaagatgt gaaacagacc tacctcgccc gggtgtttag ctaccccgcc   240
ggcaatgtgg agagcactgg ttccgctggc gagcctttat acgagaacag ccccgaattt   300
accccttacc tcgagaccaa tttaggacag cccaccatcc aaagctttga gcaagttggc   360
acaaaggtga atgtgacagt ggaggacgag cggactttag tgcggcggaa caacaccttt   420
ctcagcctcc gggatgtgtt cggcaaagat ttaatctaca cactgtatta ctggaagtcc   480

```
tcttcctccg gcaagaagac agctaaaacc aacacaaacg agttttaat cgacgtggat    540 aaaggcgaaa actactgttt cagcgtgcaa gctgtgatcc cctcccggac cgtgaatagg    600
aaaagcaccg atagccccgt tgagtgcatg ggccaagaaa agggcgagtt ccgggag       657
```

<210> SEQ ID NO 319
<211> LENGTH: 342
<212> TYPE: DNA
<213> ORGANISM: Homo sapiens

<400> SEQUENCE: 319

```
aactgggtga acgtcatcag cgatttaaag aagatcgaag atttaattca gtccatgcat     60
atcgacgcca ctttatacac agaatccgac gtgcacccct cttgtaaggt gaccgccatg    120
aaatgttttt tactggagct gcaagttatc tctttagaga gcggagacgc tagcatccac    180
gacaccgtgg agaatttaat catttagcc aataactctt tatccagcaa cggcaacgtg    240
acagagtccg gctgcaagga gtgcgaagag ctggaggaga gaacatcaa ggagtttctg    300 caatcctttg tgcacattgt ccagatgttc atcaatacct cc                       342
```

<210> SEQ ID NO 320
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

```
Met Lys Trp Val Thr Phe Ile Ser Leu Leu Phe Leu Phe Ser Ser Ala
1               5                   10                  15

Tyr Ser
```

<210> SEQ ID NO 321
<211> LENGTH: 152
<212> TYPE: PRT
<213> ORGANISM: Homo sapiens

<400> SEQUENCE: 321

```
Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
                20                  25                  30

Asn Cys Leu Asn Asn Glu Phe Asn Phe Phe Lys Arg His Ile Cys Asp
            35                  40                  45

Ala Asn Lys Glu Gly Met Phe Leu Phe Arg Ala Ala Arg Lys Leu Arg
        50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
130                 135                 140

Ile Leu Met Gly Thr Lys Glu His
                145                 150
```

<210> SEQ ID NO 322
<211> LENGTH: 219
<212> TYPE: PRT
<213> ORGANISM: Homo sapiens

<400> SEQUENCE: 322

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu
    210                 215

<210> SEQ ID NO 323
<211> LENGTH: 114
<212> TYPE: PRT
<213> ORGANISM: Homo sapiens

<400> SEQUENCE: 323

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn

Thr Ser

<210> SEQ ID NO 324
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 324
atgaagtggg tgaccttcat cagcctgctg ttcctgttct ccagcgccta ctcc      54

<210> SEQ ID NO 325
<211> LENGTH: 399
<212> TYPE: DNA
<213> ORGANISM: Homo sapiens

<400> SEQUENCE: 325
cagggccagg acaggcacat gatccggatg aggcagctca tcgacatcgt cgaccagctg      60
aagaactacg tgaacgacct ggtgcccgag tttctgcctg cccccgagga cgtggagacc     120
aactgcgagt ggtccgcctt ctcctgcttt cagaaggccc agctgaagtc cgccaacacc     180
ggcaacaacg agcggatcat caacgtgagc atcaagaagc tgaagcggaa gcctcccctcc    240 acaaacgccg gcaggaggca gaagcacagg ctgacctgcc ccagctgtga ctcctacgag     300
aagaagcccc ccaaggagtt cctggagagg ttcaagtccc tgctgcagaa gatgatccat     360
cagcacctgt cctccaggac ccacggctcc gaggactcc                             399

<210> SEQ ID NO 326
<211> LENGTH: 195
<212> TYPE: DNA
<213> ORGANISM: Homo sapiens

<400> SEQUENCE: 326
attacatgcc cccctcccat gagcgtggag cacgccgaca tctgggtgaa gagctatagc      60
ctctacagcc gggagaggta tatctgtaac agcggcttca gaggaaggc cggcaccagc     120 agcctcaccg agtgcgtgct gaataaggct accaacgtgg ctcactggac aacaccctct     180
ttaaagtgca tccgg                                                      195

<210> SEQ ID NO 327
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 327
ggcggtggag gatccggagg aggtggctcc ggcggcggag gatct                       45

<210> SEQ ID NO 328
<211> LENGTH: 552
<212> TYPE: DNA
<213> ORGANISM: Homo sapiens

<400> SEQUENCE: 328
cgcgagggtc ccgagctttc gcccgacgat cccgccggcc tcttggacct gcggcagggc      60
atgtttgcgc agctggtggc ccaaaatgtt ctgctgatcg atgggcccct gagctggtac     120

```
agtgacccag gcctggcagg cgtgtccctg acggggggcc tgagctacaa agaggacacg      180
aaggagctgg tggtggccaa ggctggagtc tactatgtct tctttcaact agagctgcgg      240
cgcgtggtgg ccggcgaggg ctcaggctcc gtttcacttg cgctgcacct gcagccactg      300
cgctctgctg ctggggccgc cgccctggct ttgaccgtgg acctgccacc cgcctcctcc      360
gaggctcgga actcggcctt cggtttccag ggccgcttgc tgcacctgag tgccggccag      420
cgcctgggcg tccatcttca cactgaggcc agggcacgcc atgcctggca gcttacccag      480
ggcgccacag tcttgggact cttccgggtg acccccgaaa tcccagccgg actcccttca      540
ccgaggtcgg aa                                                          552
```

<210> SEQ ID NO 329
<211> LENGTH: 18
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 329

Met Lys Trp Val Thr Phe Ile Ser Leu Leu Phe Leu Phe Ser Ser Ala
1               5                   10                  15

Tyr Ser

<210> SEQ ID NO 330
<211> LENGTH: 133
<212> TYPE: PRT
<213> ORGANISM: Homo sapiens

<400> SEQUENCE: 330

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
                20                  25                  30

Pro Ala Pro Glu Asp Val Glu Thr Asn Cys Glu Trp Ser Ala Phe Ser
            35                  40                  45

Cys Phe Gln Lys Ala Gln Leu Lys Ser Ala Asn Thr Gly Asn Asn Glu
        50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser
    130

<210> SEQ ID NO 331
<211> LENGTH: 65
<212> TYPE: PRT
<213> ORGANISM: Homo sapiens

<400> SEQUENCE: 331

Ile Thr Cys Pro Pro Pro Met Ser Val Glu His Ala Asp Ile Trp Val
1               5                   10                  15

-continued

```
Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
 50                  55                  60

Arg
 65

<210> SEQ ID NO 332
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Gly Gly Gly Gly Ser Gly Gly Gly Ser Gly Gly Gly Gly Ser
1               5                  10                  15

<210> SEQ ID NO 333
<211> LENGTH: 184
<212> TYPE: PRT
<213> ORGANISM: Homo sapiens

<400> SEQUENCE: 333

Arg Glu Gly Pro Glu Leu Ser Pro Asp Asp Pro Ala Gly Leu Leu Asp
1               5                  10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
 50                  55                  60

Val Ala Lys Ala Gly Val Tyr Tyr Val Phe Phe Gln Leu Glu Leu Arg
 65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Pro Ser Pro Arg Ser Glu
            180

<210> SEQ ID NO 334
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 334
atgaagtggg tgaccttcat cagcctgctg ttcctgttct ccagcgccta ctcc        54

<210> SEQ ID NO 335
<211> LENGTH: 456
<212> TYPE: DNA
<213> ORGANISM: Homo sapiens

<400> SEQUENCE: 335
gattgcgaca tcgagggcaa ggacggcaag cagtacgaga gcgtgctgat ggtgtccatc    60
gaccagctgc tggacagcat gaaggagatc ggctccaact gcctcaacaa cgagttcaac   120
ttcttcaagc ggcacatctg cgacgccaac aaggagggca tgttcctgtt cagggccgcc   180
aggaaactgc ggcagttcct gaagatgaac tccaccggcg acttcgacct gcacctgctg   240
aaggtgtccg agggcaccac catcctgctg aactgcaccg acaggtgaa gggccggaaa    300
cctgctgctc tgggagaggc ccaacccacc aagagcctgg aggagaacaa gtccctgaag   360
gagcagaaga agctgaacga cctgtgcttc ctgaagaggc tgctgcagga gatcaagacc   420
tgctggaaca agatcctgat gggcaccaag gagcat                             456

<210> SEQ ID NO 336
<211> LENGTH: 657
<212> TYPE: DNA
<213> ORGANISM: Homo sapiens

<400> SEQUENCE: 336
agcggcacaa ccaacacagt cgctgcctat aacctcactt ggaagagcac caacttcaaa    60
accatcctcg aatgggaacc caaacccgtt aaccaagttt acaccgtgca gatcagcacc   120
aagtccggcg actggaagtc caaatgtttc tataccaccg acaccgagtg cgatctcacc   180
gatgagatcg tgaaagatgt gaaacagacc tacctcgccc gggtgtttag ctaccccgcc   240
ggcaatgtgg agagcactgg ttccgctggc gagcctttat acgagaacag ccccgaattt   300
acccccttacc tcgagaccaa tttaggacag cccaccatcc aaagctttga gcaagttggc   360
acaaaggtga atgtgacagt ggaggacgag cggactttag tgcggcggaa caacaccttt   420
ctcagcctcc gggatgtgtt cggcaaagat ttaatctaca cactgtatta ctggaagtcc   480
tcttcctccg gcaagaagac agctaaaacc aacacaaacg agttttttaat cgacgtggat   540
aaaggcgaaa actactgttt cagcgtgcaa gctgtgatcc cctcccggac cgtgaatagg   600
aaaagcaccg atagccccgt tgagtgcatg ggccaagaaa agggcgagtt ccgggag      657

<210> SEQ ID NO 337
<211> LENGTH: 342
<212> TYPE: DNA
<213> ORGANISM: Homo sapiens

<400> SEQUENCE: 337
aactgggtga acgtcatcag cgatttaaag aagatcgaag atttaattca gtccatgcat    60
atcgacgcca ctttatacac agaatccgac gtgcaccect cttgtaaggt gaccgccatg   120
aaatgttttt tactgagct gcaagttatc tctttagaga gcggagacgc tagcatccac   180
gacaccgtgg agaatttaat catttttagcc aataactctt tatccagcaa cggcaacgtg   240
acagagtccg gctgcaagga gtgcgaagag ctggaggaga gaacatcaa ggagtttctg   300
caatccttg tgcacattgt ccagatgttc atcaataccct cc                      342

```
<210> SEQ ID NO 338
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Met Lys Trp Val Thr Phe Ile Ser Leu Leu Phe Leu Phe Ser Ser Ala
1               5                   10                  15

Tyr Ser

<210> SEQ ID NO 339
<211> LENGTH: 152
<212> TYPE: PRT
<213> ORGANISM: Homo sapiens

<400> SEQUENCE: 339

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
                20                  25                  30

Asn Cys Leu Asn Asn Glu Phe Asn Phe Lys Arg His Ile Cys Asp
            35                  40                  45

Ala Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
130                 135                 140

Ile Leu Met Gly Thr Lys Glu His
145                 150

<210> SEQ ID NO 340
<211> LENGTH: 219
<212> TYPE: PRT
<213> ORGANISM: Homo sapiens

<400> SEQUENCE: 340

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
                20                  25                  30

Val Tyr Thr Val Gln Ile Ser Thr Lys Ser Gly Asp Trp Lys Ser Lys
            35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95
```

```
Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
    130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu
    210                 215
```

```
<210> SEQ ID NO 341
<211> LENGTH: 114
<212> TYPE: PRT
<213> ORGANISM: Homo sapiens

<400> SEQUENCE: 341

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser
```

```
<210> SEQ ID NO 342
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 342
atgaagtggg tgaccttcat cagcctgctg ttcctgttct ccagcgccta ctcc        54

<210> SEQ ID NO 343
<211> LENGTH: 399
<212> TYPE: DNA
<213> ORGANISM: Homo sapiens

<400> SEQUENCE: 343
cagggccagg acaggcacat gatccggatg aggcagctca tcgacatcgt cgaccagctg        60
aagaactacg tgaacgacct ggtgcccgag tttctgcctg cccccgagga cgtggagacc       120
```

```
aactgcgagt ggtccgcctt ctcctgcttt cagaaggccc agctgaagtc cgccaacacc      180
ggcaacaacg agcggatcat caacgtgagc atcaagaagc tgaagcggaa gcctccctcc      240
acaaacgccg gcaggaggca gaagcacagg ctgacctgcc ccagctgtga ctcctacgag      300
aagaagcccc ccaaggagtt cctggagagg ttcaagtccc tgctgcagaa gatgatccat      360
cagcacctgt cctccaggac ccacggctcc gaggactcc                             399

<210> SEQ ID NO 344
<211> LENGTH: 195
<212> TYPE: DNA
<213> ORGANISM: Homo sapiens

<400> SEQUENCE: 344
attacatgcc cccctcccat gagcgtggag cacgccgaca tctgggtgaa gagctatagc       60
ctctacagcc gggagaggta tatctgtaac agcggcttca agaggaaggc cggcaccagc      120
agcctcaccg agtgcgtgct gaataaggct accaacgtgg ctcactggac aacaccctct      180
ttaaagtgca tccgg                                                      195

<210> SEQ ID NO 345
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 345
ggcggtggag gatccggagg aggtggctcc ggcggcggag gatct                       45

<210> SEQ ID NO 346
<211> LENGTH: 495
<212> TYPE: DNA
<213> ORGANISM: Homo sapiens

<400> SEQUENCE: 346
gatcccgccg gcctcttgga cctgcggcag ggcatgtttg cgcagctggt ggcccaaaat       60
gttctgctga tcgatgggcc cctgagctgg tacagtgacc caggcctggc aggcgtgtcc      120
ctgacggggg gcctgagcta caaagaggac acgaaggagc tggtggtggc caaggctgga      180
gtctactatg tcttctttca actagagctg cggcgcgtgg tggccggcga gggctcaggc      240
tccgtttcac ttgcgctgca cctgcagcca ctgcgctctg ctgctgggc cgccgccctg      300 gctttgaccg tggacctgcc acccgcctcc tccgaggctc ggaactcggc cttcggtttc      360
cagggccgct tgctgcacct gagtgccggc cagcgcctgg cgtccatct tcacactgag      420 gccagggcac gccatgcctg gcagcttacc cagggcgcca cagtcttggg actcttccgg      480 gtgaccccg aaatc                                                      495

<210> SEQ ID NO 347
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Met Lys Trp Val Thr Phe Ile Ser Leu Leu Phe Leu Phe Ser Ser Ala
1               5                   10                  15
```

Tyr Ser

<210> SEQ ID NO 348
<211> LENGTH: 133
<212> TYPE: PRT
<213> ORGANISM: Homo sapiens

<400> SEQUENCE: 348

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser
    130

<210> SEQ ID NO 349
<211> LENGTH: 65
<212> TYPE: PRT
<213> ORGANISM: Homo sapiens

<400> SEQUENCE: 349

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg
65

<210> SEQ ID NO 350
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Gly Gly Gly Gly Ser Gly Gly Gly Ser Gly Gly Gly Gly Ser
1               5                   10                  15

<210> SEQ ID NO 351
<211> LENGTH: 165
<212> TYPE: PRT

-continued

<213> ORGANISM: Homo sapiens

<400> SEQUENCE: 351

```
Asp Pro Ala Gly Leu Asp Leu Arg Gln Gly Met Phe Ala Gln Leu
1               5                   10                  15
Val Ala Gln Asn Val Leu Leu Ile Asp Gly Pro Leu Ser Trp Tyr Ser
            20                  25                  30
Asp Pro Gly Leu Ala Gly Val Ser Leu Thr Gly Gly Leu Ser Tyr Lys
        35                  40                  45
Glu Asp Thr Lys Glu Leu Val Val Ala Lys Ala Gly Val Tyr Tyr Val
    50                  55                  60
Phe Phe Gln Leu Glu Leu Arg Arg Val Val Ala Gly Glu Gly Ser Gly
65                  70                  75                  80
Ser Val Ser Leu Ala Leu His Leu Gln Pro Leu Arg Ser Ala Ala Gly
                85                  90                  95
Ala Ala Ala Leu Ala Leu Thr Val Asp Leu Pro Pro Ala Ser Ser Glu
            100                 105                 110
Ala Arg Asn Ser Ala Phe Gly Phe Gln Gly Arg Leu Leu His Leu Ser
        115                 120                 125
Ala Gly Gln Arg Leu Gly Val His Leu His Thr Glu Ala Arg Ala Arg
    130                 135                 140
His Ala Trp Gln Leu Thr Gln Gly Ala Thr Val Leu Gly Leu Phe Arg
145                 150                 155                 160
Val Thr Pro Glu Ile
                165
```

<210> SEQ ID NO 352
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 352

```
atgaagtggg tgaccttcat cagcctgctg ttcctgttct ccagcgccta ctcc        54
```

<210> SEQ ID NO 353
<211> LENGTH: 456
<212> TYPE: DNA
<213> ORGANISM: Homo sapiens

<400> SEQUENCE: 353

```
gattgcgaca tcgagggcaa ggacggcaag cagtacgaga gcgtgctgat ggtgtccatc    60
gaccagctgc tggacagcat gaaggagatc ggctccaact gcctcaacaa cgagttcaac   120
ttcttcaagc ggcacatctg cgacgccaac aaggagggca tgttcctgtt cagggccgcc   180
aggaaactgc ggcagttcct gaagatgaac tccaccggcg acttcgacct gcacctgctg   240
aaggtgtccg agggcaccac catcctgctg aactgcaccg acaggtgaa gggccggaaa   300
cctgctgctc tgggagaggc ccaacccacc aagagcctgg aggagaacaa gtccctgaag   360
gagcagaaga agctgaacga cctgtgcttc ctgaagaggc tgctgcagga gatcaagacc   420
tgctggaaca agatcctgat gggcaccaag gagcat                             456
```

<210> SEQ ID NO 354
<211> LENGTH: 657
<212> TYPE: DNA
<213> ORGANISM: Homo sapiens

<400> SEQUENCE: 354

```
agcggcacaa ccaacacagt cgctgcctat aacctcactt ggaagagcac caacttcaaa        60
accatcctcg aatgggaacc caaacccgtt aaccaagttt acaccgtgca gatcagcacc       120
aagtccggcg actggaagtc caaatgtttc tataccaccg acaccgagtg cgatctcacc       180
gatgagatcg tgaaagatgt gaaacagacc tacctcgccc gggtgtttag ctaccccgcc       240
ggcaatgtgg agagcactgg ttccgctggc gagcctttat acgagaacag ccccgaattt       300
accccttacc tcgagaccaa tttaggacag cccaccatcc aaagctttga gcaagttggc       360
acaaaggtga atgtgacagt ggaggacgag cggactttag tgcggcggaa caacaccttt       420
ctcagcctcc gggatgtgtt cggcaaagat ttaatctaca cactgtatta ctggaagtcc       480
tcttcctccg gcaagaagac agctaaaacc aacacaaacg agttttaat cgacgtggat        540
aaaggcgaaa actactgttt cagcgtgcaa gctgtgatcc cctcccggac cgtgaatagg       600
aaaagcaccg atagcccgt tgagtgcatg ggccaagaaa agggcgagtt ccgggag          657
```

<210> SEQ ID NO 355
<211> LENGTH: 342
<212> TYPE: DNA
<213> ORGANISM: Homo sapiens

<400> SEQUENCE: 355

```
aactgggtga acgtcatcag cgatttaaag aagatcgaag atttaattca gtccatgcat        60
atcgacgcca ctttatacac agaatccgac gtgcaccct cttgtaaggt gaccgccatg       120
aaatgttttt tactggagct gcaagttatc tctttagaga gcggagacgc tagcatccac       180
gacaccgtgg agaatttaat catttagcc aataactctt tatccagcaa cggcaacgtg       240
acagagtccg gctgcaagga gtgcgaagag ctggaggaga gaacatcaa ggagttctg        300
caatcctttg tgcacattgt ccagatgttc atcaatacct cc                         342
```

<210> SEQ ID NO 356
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 356

Met Lys Trp Val Thr Phe Ile Ser Leu Leu Phe Leu Phe Ser Ser Ala
1               5                   10                  15

Tyr Ser

<210> SEQ ID NO 357
<211> LENGTH: 152
<212> TYPE: PRT
<213> ORGANISM: Homo sapiens

<400> SEQUENCE: 357

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
                20                  25                  30

Asn Cys Leu Asn Asn Glu Phe Asn Phe Phe Lys Arg His Ile Cys Asp
            35                  40                  45

Ala Asn Lys Glu Gly Met Phe Leu Phe Arg Ala Ala Arg Lys Leu Arg

```
Gln Phe Leu Lys Met Asn Ser Thr Gly Asp Phe Asp Leu His Leu Leu
 65                  70                  75                  80

Lys Val Ser Glu Gly Thr Thr Ile Leu Leu Asn Cys Thr Gly Gln Val
                 85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140

Ile Leu Met Gly Thr Lys Glu His
145                 150
```

<210> SEQ ID NO 358
<211> LENGTH: 219
<212> TYPE: PRT
<213> ORGANISM: Homo sapiens

<400> SEQUENCE: 358

```
Ser Gly Thr Thr Asn Thr Val Ala Ala Tyr Asn Leu Thr Trp Lys Ser
  1               5                  10                  15

Thr Asn Phe Lys Thr Ile Leu Glu Trp Glu Pro Lys Pro Val Asn Gln
                 20                  25                  30

Val Tyr Thr Val Gln Ile Ser Thr Lys Ser Gly Asp Trp Lys Ser Lys
             35                  40                  45

Cys Phe Tyr Thr Thr Asp Thr Glu Cys Asp Leu Thr Asp Glu Ile Val
 50                  55                  60

Lys Asp Val Lys Gln Thr Tyr Leu Ala Arg Val Phe Ser Tyr Pro Ala
 65                  70                  75                  80

Gly Asn Val Glu Ser Thr Gly Ser Ala Gly Glu Pro Leu Tyr Glu Asn
                 85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
    130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu
    210                 215
```

<210> SEQ ID NO 359
<211> LENGTH: 114
<212> TYPE: PRT
<213> ORGANISM: Homo sapiens

<400> SEQUENCE: 359

```
Asn Trp Val Asn Val Ile Ser Asp Leu Lys Lys Ile Glu Asp Leu Ile
```

```
            1               5                  10                  15
       Gln Ser Met His Ile Asp Ala Thr Leu Tyr Thr Glu Ser Asp Val His
                       20                  25                  30
       Pro Ser Cys Lys Val Thr Ala Met Lys Cys Phe Leu Leu Glu Leu Gln
                       35                  40                  45
       Val Ile Ser Leu Glu Ser Gly Asp Ala Ser Ile His Asp Thr Val Glu
                       50                  55                  60
       Asn Leu Ile Ile Leu Ala Asn Asn Ser Leu Ser Ser Asn Gly Asn Val
       65                  70                  75                  80
       Thr Glu Ser Gly Cys Lys Glu Cys Glu Glu Leu Glu Glu Lys Asn Ile
                       85                  90                  95
       Lys Glu Phe Leu Gln Ser Phe Val His Ile Val Gln Met Phe Ile Asn
                       100                 105                 110
       Thr Ser
```

<210> SEQ ID NO 360
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 360

```
atgaagtggg tgaccttcat cagcctgctg ttcctgttct ccagcgccta ctcc         54
```

<210> SEQ ID NO 361
<211> LENGTH: 861
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 361

```
atccccccccc atgtgcaaaa gagcgtgaac aacgatatga tcgtgaccga caacaacggc    60
gccgtgaagt ttccccagct ctgcaagttc tgcgatgtca ggttcagcac ctgcgataat   120
cagaagtcct gcatgtccaa ctgcagcatc acctccatct gcgagaagcc caagaagtg    180
tgcgtggccg tgtggcggaa aaatgacgag aacatcaccc tggagaccgt gtgtcacgac   240
cccaagctcc cttatcacga cttcattctg gaggacgctg cctcccccaa atgcatcatg   300
aaggagaaga agaagcccgg agagaccttc tttatgtgtt cctgtagcag cgacgagtgt   360
aacgacaaca tcatcttcag cgaagagtac aacaccagca ccctgatgg aggtggcgga   420
tccggaggtg gaggttctgg tggaggtggg agtattcctc ccacgtgca gaagagcgtg   480
aataatgaca tgatcgtgac cgataacaat ggcgccgtga atttcccca gctgtgcaaa   540
ttctgcgatg tgaggttttc cacctgcgac aaccagaagt cctgtatgag caactgctcc   600
atcacctcca tctgtgagaa gcctcaggag gtgtgcgtgg ctgtctggcg gaagaatgac   660
gagaatatca ccctggaaac cgtctgccac gatcccaagc tgccctacca cgatttcatc   720
ctggaagacg ccgccagccc taagtgcatc atgaaagaga aaagaagcc tggcgagacc   780
tttttcatgt gctcctgcag cagcgacgaa tgcaacgaca atatcatctt tagcgaggaa   840
tacaatacca gcaaccccga c                                            861
```

<210> SEQ ID NO 362
<211> LENGTH: 195

<212> TYPE: DNA
<213> ORGANISM: Homo sapiens

<400> SEQUENCE: 362

```
attacatgcc cccctcccat gagcgtggag cacgccgaca tctgggtgaa gagctatagc    60
ctctacagcc gggagaggta tatctgtaac agcggcttca agaggaaggc cggcaccagc   120
agcctcaccg agtgcgtgct gaataaggct accaacgtgg ctcactggac aacaccctct   180
ttaaagtgca tccgg                                                    195
```

<210> SEQ ID NO 363
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 363

```
Met Lys Trp Val Thr Phe Ile Ser Leu Leu Phe Leu Phe Ser Ser Ala
1               5                   10                  15

Tyr Ser
```

<210> SEQ ID NO 364
<211> LENGTH: 287
<212> TYPE: PRT
<213> ORGANISM: Homo sapiens

<400> SEQUENCE: 364

```
Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
                20                  25                  30

Val Arg Phe Ser Thr Cys Asp Asn Gln Lys Ser Cys Met Ser Asn Cys
            35                  40                  45

Ser Ile Thr Ser Ile Cys Glu Lys Pro Gln Glu Val Cys Val Ala Val
        50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
                100                 105                 110

Cys Ser Cys Ser Ser Asp Glu Cys Asn Asp Asn Ile Ile Phe Ser Glu
            115                 120                 125

Glu Tyr Asn Thr Ser Asn Pro Asp Gly Gly Gly Ser Gly Gly Gly
        130                 135                 140

Gly Ser Gly Gly Gly Ser Ile Pro Pro His Val Gln Lys Ser Val
145                 150                 155                 160

Asn Asn Asp Met Ile Val Thr Asp Asn Asn Gly Ala Val Lys Phe Pro
                165                 170                 175

Gln Leu Cys Lys Phe Cys Asp Val Arg Phe Ser Thr Cys Asp Asn Gln
            180                 185                 190

Lys Ser Cys Met Ser Asn Cys Ser Ile Thr Ser Ile Cys Glu Lys Pro
        195                 200                 205

Gln Glu Val Cys Val Ala Val Trp Arg Lys Asn Asp Glu Asn Ile Thr
    210                 215                 220
```

```
Leu Glu Thr Val Cys His Asp Pro Lys Leu Pro Tyr His Asp Phe Ile
225                 230                 235                 240

Leu Glu Asp Ala Ala Ser Pro Lys Cys Ile Met Lys Glu Lys Lys
                245                 250                 255

Pro Gly Glu Thr Phe Phe Met Cys Ser Cys Ser Ser Asp Glu Cys Asn
            260                 265                 270

Asp Asn Ile Ile Phe Ser Glu Glu Tyr Asn Thr Ser Asn Pro Asp
        275                 280                 285

<210> SEQ ID NO 365
<211> LENGTH: 65
<212> TYPE: PRT
<213> ORGANISM: Homo sapiens

<400> SEQUENCE: 365

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
        50                  55                  60

Arg
65

<210> SEQ ID NO 366
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 366
atgaagtggg tgaccttcat cagcctgctg ttcctgttct ccagcgccta ctcc          54

<210> SEQ ID NO 367
<211> LENGTH: 861
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 367
atcccccccc atgtgcaaaa gagcgtgaac aacgatatga tcgtgaccga caacaacggc    60
gccgtgaagt tcccccagct ctgcaagttc tgcgatgtca ggttcagcac ctgcgataat   120
cagaagtcct gcatgtccaa ctgcagcatc acctccatct gcgagaagcc ccaagaagtg   180
tgcgtggccg tgtggcggaa aaatgacgag aacatcaccc tggagaccgt gtgtcacgac   240
cccaagctcc cttatcacga cttcattctg gaggacgctg cctcccccaa atgcatcatg   300
aaggagaaga gaagcccgg agagaccttc tttatgtgtt cctgtagcag cgacgagtgt   360
aacgacaaca tcatcttcag cgaagagtac aacaccagca accctgatgg aggtggcgga   420
tccggaggtg gaggttctgg tggaggtggg agtattcctc ccacgtgca gaagagcgtg    480 aataatgaca tgatcgtgac cgataacaat ggcgccgtga atttcccca gctgtgcaaa    540 ttctgcgatg tgaggttttc cacctgcgac aaccagaagt cctgtatgag caactgctcc   600
```

```
atcacctcca tctgtgagaa gcctcaggag gtgtgcgtgg ctgtctggcg gaagaatgac    660
gagaatatca ccctggaaac cgtctgccac gatcccaagc tgccctacca cgatttcatc    720
ctggaagacg ccgccagccc taagtgcatc atgaaagaga aaaagaagcc tggcgagacc    780
tttttcatgt gctcctgcag cagcgacgaa tgcaacgaca atatcatctt tagcgaggaa    840
tacaatacca gcaaccccga c                                              861
```

<210> SEQ ID NO 368
<211> LENGTH: 657
<212> TYPE: DNA
<213> ORGANISM: Homo sapiens

<400> SEQUENCE: 368

```
agcggcacaa ccaacacagt cgctgcctat aacctcactt ggaagagcac caacttcaaa     60
accatcctcg aatgggaacc caaacccgtt aaccaagttt acaccgtgca gatcagcacc    120
aagtccggcg actggaagtc caatgttttc tataccaccg acaccgagtg cgatctcacc    180
gatgagatcg tgaaagatgt gaaacagacc tacctcgccc gggtgtttag ctaccccgcc    240
ggcaatgtgg agagcactgg ttccgctggc gagcctttat acgagaacag ccccgaattt    300
accccttacc tcgagaccaa tttaggacag cccaccatcc aaagctttga gcaagttggc    360
acaaaggtga atgtgacagt ggaggacgag cggactttag tgcggcggaa caacaccttt    420
ctcagcctcc gggatgtgtt cggcaaagat ttaatctaca cactgtatta ctggaagtcc    480
tcttcctccg gcaagaagac agctaaaacc aacacaaacg agttttttaat cgacgtggat    540 aaaggcgaaa actactgttt cagcgtgcaa gctgtgatcc cctcccggac cgtgaatagg    600
aaaagcaccg atagccccgt tgagtgcatg ggccaagaaa agggcgagtt ccgggag       657
```

<210> SEQ ID NO 369
<211> LENGTH: 342
<212> TYPE: DNA
<213> ORGANISM: Homo sapiens

<400> SEQUENCE: 369

```
aactgggtga acgtcatcag cgatttaaag aagatcgaag atttaattca gtccatgcat     60
atcgacgcca ctttatacac agaatccgac gtgcacccct cttgtaaggt gaccgccatg    120
aaatgttttt tactggagct gcaagttatc tctttagaga gcggagacgc tagcatccac    180
gacaccgtgg agaatttaat cattttagcc aataactctt tatccagcaa cggcaacgtg    240
acagagtccg gctgcaagga gtgcgaagag ctggaggaga gaacatcaa ggagtttctg    300 caatcctttg tgcacattgt ccagatgttc atcaatacct cc                      342
```

<210> SEQ ID NO 370
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Met Lys Trp Val Thr Phe Ile Ser Leu Leu Phe Leu Phe Ser Ser Ala
1               5                   10                  15

Tyr Ser

<210> SEQ ID NO 371
<211> LENGTH: 287

<212> TYPE: PRT
<213> ORGANISM: Homo sapiens

<400> SEQUENCE: 371

```
Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp Gly Gly Gly Ser Gly Gly Gly
    130                 135                 140

Gly Ser Gly Gly Gly Ser Ile Pro Pro His Val Gln Lys Ser Val
145                 150                 155                 160

Asn Asn Asp Met Ile Val Thr Asp Asn Asn Gly Ala Val Lys Phe Pro
                165                 170                 175

Gln Leu Cys Lys Phe Cys Asp Val Arg Phe Ser Thr Cys Asp Asn Gln
            180                 185                 190

Lys Ser Cys Met Ser Asn Cys Ser Ile Thr Ser Ile Cys Glu Lys Pro
        195                 200                 205

Gln Glu Val Cys Val Ala Val Trp Arg Lys Asn Asp Glu Asn Ile Thr
    210                 215                 220

Leu Glu Thr Val Cys His Asp Pro Lys Leu Pro Tyr His Asp Phe Ile
225                 230                 235                 240

Leu Glu Asp Ala Ala Ser Pro Lys Cys Ile Met Lys Glu Lys Lys
                245                 250                 255

Pro Gly Glu Thr Phe Phe Met Cys Ser Cys Ser Ser Asp Glu Cys Asn
            260                 265                 270

Asp Asn Ile Ile Phe Ser Glu Glu Tyr Asn Thr Ser Asn Pro Asp
        275                 280                 285
```

<210> SEQ ID NO 372
<211> LENGTH: 219
<212> TYPE: PRT
<213> ORGANISM: Homo sapiens

<400> SEQUENCE: 372

```
Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60
```

```
Lys Asp Val Lys Gln Thr Tyr Leu Ala Arg Val Phe Ser Tyr Pro Ala
 65                  70                  75                  80

Gly Asn Val Glu Ser Thr Gly Ser Ala Gly Glu Pro Leu Tyr Glu Asn
                 85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
    130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu
    210                 215

<210> SEQ ID NO 373
<211> LENGTH: 114
<212> TYPE: PRT
<213> ORGANISM: Homo sapiens

<400> SEQUENCE: 373

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 374
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 374
atgaagtggg tgaccttcat cagcctgctg ttcctgttct ccagcgccta ctcc        54

<210> SEQ ID NO 375
<211> LENGTH: 399
<212> TYPE: DNA
<213> ORGANISM: Homo sapiens
```

<400> SEQUENCE: 375

```
cagggccagg acaggcacat gatccggatg aggcagctca tcgacatcgt cgaccagctg      60
aagaactacg tgaacgacct ggtgcccgag tttctgcctg cccccgagga cgtggagacc     120
aactgcgagt ggtccgcctt ctcctgcttt cagaaggccc agctgaagtc cgccaacacc     180
ggcaacaacg agcggatcat caacgtgagc atcaagaagc tgaagcggaa gcctccctcc     240
acaaacgccg gcaggaggca gaagcacagg ctgacctgcc ccagctgtga ctcctacgag     300
aagaagcccc ccaaggagtt cctggagagg ttcaagtccc tgctgcagaa gatgatccat     360
cagcacctgt cctccaggac ccacggctcc gaggactcc                            399
```

<210> SEQ ID NO 376
<211> LENGTH: 195
<212> TYPE: DNA
<213> ORGANISM: Homo sapiens

<400> SEQUENCE: 376

```
attacatgcc ccctcccat gagcgtggag cacgccgaca tctgggtgaa gagctatagc       60
ctctacagcc gggagaggta tatctgtaac agcggcttca agaggaaggc cggcaccagc     120
agcctcaccg agtgcgtgct gaataaggct accaacgtgg ctcactggac aacaccctct     180
ttaaagtgca tccgg                                                     195
```

<210> SEQ ID NO 377
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 377

```
ggcggtggag gatccggagg aggtggctcc ggcggcggag gatct                      45
```

<210> SEQ ID NO 378
<211> LENGTH: 552
<212> TYPE: DNA
<213> ORGANISM: Homo sapiens

<400> SEQUENCE: 378

```
cgcgagggtc ccgagctttc gcccgacgat cccgccggcc tcttggacct gcggcagggc      60
atgtttgcgc agctggtggc ccaaaatgtt ctgctgatcg atgggcccct gagctggtac     120
agtgacccag gcctggcagg cgtgtccctg acgggggggcc tgagctacaa agaggacacg     180
aaggagctgg tggtggccaa ggctggagtc tactatgtct tctttcaact agagctgcgg     240
cgcgtggtgg ccggcgaggg ctcaggctcc gtttcacttg cgctgcacct gcagccactg     300
cgctctgctg ctggggccgc cgccctggct ttgaccgtgg acctgccacc gcctcctcc     360
gaggctcgga actcggcctt cggtttccag ggccgcttgc tgcacctgag tgccggccag     420
cgcctgggcg tccatcttca cactgaggcc agggcacgcc atgcctggca gcttacccag     480
ggcgccacag tcttgggact cttccgggtg accccgaaa tcccagccgg actcccttca     540
ccgaggtcgg aa                                                        552
```

<210> SEQ ID NO 379
<211> LENGTH: 18
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 379

Met Lys Trp Val Thr Phe Ile Ser Leu Leu Phe Leu Phe Ser Ser Ala
1               5                   10                  15

Tyr Ser

<210> SEQ ID NO 380
<211> LENGTH: 133
<212> TYPE: PRT
<213> ORGANISM: Homo sapiens

<400> SEQUENCE: 380

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
                20                  25                  30

Pro Ala Pro Glu Asp Val Glu Thr Asn Cys Glu Trp Ser Ala Phe Ser
            35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser
        130

<210> SEQ ID NO 381
<211> LENGTH: 65
<212> TYPE: PRT
<213> ORGANISM: Homo sapiens

<400> SEQUENCE: 381

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
    50                  55                  60

Arg
65

<210> SEQ ID NO 382
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382
```

Gly Gly Gly Gly Ser Gly Gly Gly Ser Gly Gly Gly Ser
1               5                   10                  15

<210> SEQ ID NO 383
<211> LENGTH: 184
<212> TYPE: PRT
<213> ORGANISM: Homo sapiens

<400> SEQUENCE: 383

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Pro Ser Pro Arg Ser Glu
            180

<210> SEQ ID NO 384
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 384
atgaagtggg tgaccttcat cagcctgctg ttcctgttct ccagcgccta ctcc         54

<210> SEQ ID NO 385
<211> LENGTH: 861
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 385
atcccccccc atgtgcaaaa gagcgtgaac aacgatatga tcgtgaccga caacaacggc    60
gccgtgaagt tcccccagct ctgcaagttc tgcgatgtca ggttcagcac ctgcgataat   120
cagaagtcct gcatgtccaa ctgcagcatc acctccatct gcgagaagcc ccaagaagtg   180
tgcgtggccg tgtggcggaa aaatgacgag aacatcaccc tggagaccgt gtgtcacgac   240

```
cccaagctcc cttatcacga cttcattctg gaggacgctg cctcccccaa atgcatcatg    300
aaggagaaga agaagcccgg agagaccttc tttatgtgtt cctgtagcag cgacgagtgt    360
aacgacaaca tcatcttcag cgaagagtac aacaccagca accctgatgg aggtggcgga    420
tccggaggtg gaggttctgg tggaggtggg agtattcctc cccacgtgca gaagagcgtg    480
aataatgaca tgatcgtgac cgataacaat ggcgccgtga aatttcccca gctgtgcaaa    540
ttctgcgatg tgaggttttc cacctgcgac aaccagaagt cctgtatgag caactgctcc    600
atcacctcca tctgtgagaa gcctcaggag gtgtgcgtgg ctgtctggcg gaagaatgac    660
gagaatatca ccctggaaac cgtctgccac gatcccaagc tgccctacca cgatttcatc    720
ctggaagacg ccgccagccc taagtgcatc atgaaagaga aaagaagcc tggcgagacc    780 ttttttcatgt gctcctgcag cagcgacgaa tgcaacgaca atatcatctt tagcgaggaa    840
tacaatacca gcaaccccga c                                              861
```

```
<210> SEQ ID NO 386
<211> LENGTH: 657
<212> TYPE: DNA
<213> ORGANISM: Homo sapiens

<400> SEQUENCE: 386
agcggcacaa ccaacacagt cgctgcctat aacctcactt ggaagagcac caacttcaaa     60
accatcctcg aatgggaacc caaacccgtt aaccaagttt acaccgtgca gatcagcacc    120
aagtccggcg actggaagtc caatgttttc tataccaccg acaccgagtg cgatctcacc    180
gatgagatcg tgaaagatgt gaaacagacc tacctcgccc gggtgtttag ctaccccgcc    240
ggcaatgtgg agagcactgg ttccgctggc gagcctttat acgagaacag ccccgaattt    300
accccttacc tcgagaccaa tttaggacag cccaccatcc aaagctttga gcaagttggc    360
acaaaggtga atgtgacagt ggaggacgag cggactttag tgcggcggaa caacaccttt    420
ctcagcctcc gggatgtgtt cggcaaagat ttaatctaca cactgtatta ctggaagtcc    480
tcttcctccg gcaagaagac agctaaaacc aacacaaacg agtttttaat cgacgtggat    540
aaaggcgaaa actactgttt cagcgtgcaa gctgtgatcc cctcccggac cgtgaatagg    600
aaaagcaccg atagccccgt tgagtgcatg ggccaagaaa agggcgagtt ccgggag      657
```

```
<210> SEQ ID NO 387
<211> LENGTH: 342
<212> TYPE: DNA
<213> ORGANISM: Homo sapiens

<400> SEQUENCE: 387
aactgggtga acgtcatcag cgatttaaag aagatcgaag atttaattca gtccatgcat     60
atcgacgcca ctttatacac agaatccgac gtgcacccct cttgtaaggt gaccgccatg    120
aaatgttttt tactggagct gcaagttatc tctttagaga gcggagacgc tagcatccac    180
gacaccgtgg agaatttaat catttttagcc aataactctt tatccagcaa cggcaacgtg    240
acagagtccg gctgcaagga gtgcgaagag ctggaggaga gaacatcaa ggagtttctg    300 caatcctttg tgcacattgt ccagatgttc atcaatacct cc                        342
```

```
<210> SEQ ID NO 388
<211> LENGTH: 18
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 388

Met Lys Trp Val Thr Phe Ile Ser Leu Leu Phe Leu Phe Ser Ser Ala
1               5                   10                  15

Tyr Ser

<210> SEQ ID NO 389
<211> LENGTH: 287
<212> TYPE: PRT
<213> ORGANISM: Homo sapiens

<400> SEQUENCE: 389

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
                20                  25                  30

Val Arg Phe Ser Thr Cys Asp Asn Gln Lys Ser Cys Met Ser Asn Cys
            35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
                100                 105                 110

Cys Ser Cys Ser Ser Asp Glu Cys Asn Asp Asn Ile Ile Phe Ser Glu
            115                 120                 125

Glu Tyr Asn Thr Ser Asn Pro Asp Gly Gly Gly Ser Gly Gly Gly
    130                 135                 140

Gly Ser Gly Gly Gly Ser Ile Pro Pro His Val Gln Lys Ser Val
145                 150                 155                 160

Asn Asn Asp Met Ile Val Thr Asp Asn Asn Gly Ala Val Lys Phe Pro
                165                 170                 175

Gln Leu Cys Lys Phe Cys Asp Val Arg Phe Ser Thr Cys Asp Asn Gln
            180                 185                 190

Lys Ser Cys Met Ser Asn Cys Ser Ile Thr Ser Ile Cys Glu Lys Pro
        195                 200                 205

Gln Glu Val Cys Val Ala Val Trp Arg Lys Asn Asp Glu Asn Ile Thr
    210                 215                 220

Leu Glu Thr Val Cys His Asp Pro Lys Leu Pro Tyr His Asp Phe Ile
225                 230                 235                 240

Leu Glu Asp Ala Ala Ser Pro Lys Cys Ile Met Lys Glu Lys Lys Lys
                245                 250                 255

Pro Gly Glu Thr Phe Phe Met Cys Ser Cys Ser Ser Asp Glu Cys Asn
                260                 265                 270

Asp Asn Ile Ile Phe Ser Glu Glu Tyr Asn Thr Ser Asn Pro Asp
            275                 280                 285

<210> SEQ ID NO 390
<211> LENGTH: 219
<212> TYPE: PRT
<213> ORGANISM: Homo sapiens

<400> SEQUENCE: 390
```

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65              70                  75                  80

Gly Asn Val Glu Ser Thr Gly Ser Ala Gly Pro Leu Tyr Glu Asn
                85                  90                  95

Ser Pro Glu Phe Thr Pro Tyr Leu Glu Thr Asn Leu Gly Gln Pro Thr
                100                 105                 110

Ile Gln Ser Phe Glu Gln Val Gly Thr Lys Val Asn Val Thr Val Glu
            115                 120                 125

Asp Glu Arg Thr Leu Val Arg Arg Asn Asn Thr Phe Leu Ser Leu Arg
    130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
            195                 200                 205

Cys Met Gly Gln Glu Lys Gly Glu Phe Arg Glu
210                 215

<210> SEQ ID NO 391
<211> LENGTH: 114
<212> TYPE: PRT
<213> ORGANISM: Homo sapiens

<400> SEQUENCE: 391

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65              70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
                100                 105                 110

Thr Ser

<210> SEQ ID NO 392
<211> LENGTH: 54
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 392
atgaagtggg tgaccttcat cagcctgctg ttcctgttct ccagcgccta ctcc          54

<210> SEQ ID NO 393
<211> LENGTH: 861
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 393
atcccccccc atgtgcaaaa gagcgtgaac aacgatatga tcgtgaccga caacaacggc    60
gccgtgaagt ttccccagct ctgcaagttc tgcgatgtca ggttcagcac ctgcgataat   120
cagaagtcct gcatgtccaa ctgcagcatc acctccatct gcgagaagcc caagaagtg    180 tgcgtggccg tgtggcggaa aaatgacgag aacatcaccc tggagaccgt gtgtcacgac   240
cccaagctcc cttatcacga cttcattctg gaggacgctg cctcccccaa atgcatcatg   300
aaggagaaga agaagcccgg agagaccttc tttatgtgtt cctgtagcag cgacgagtgt   360
aacgacaaca tcatcttcag cgaagagtac aacaccagca accctgatgg aggtggcgga   420
tccggaggtg gaggttctgg tggaggtggg agtattcctc cccacgtgca gagagcgtg    480 aataatgaca tgatcgtgac cgataacaat ggcgccgtga aatttcccca gctgtgcaaa   540
ttctgcgatg tgaggttttc cacctgcgac aaccagaagt cctgtatgag caactgctcc   600
atcacctcca tctgtgagaa gcctcaggag gtgtgcgtgg ctgtctggcg gaagaatgac   660
gagaatatca ccctggaaac cgtctgccac gatcccaagc tgccctacca cgatttcatc   720
ctggaagacg ccgccagccc taagtgcatc atgaaagaga aaaagaagcc tggcgagacc   780
tttttcatgt gctcctgcag cagcgacgaa tgcaacgaca atatcatctt tagcgaggaa   840
tacaatacca gcaaccccga c                                             861

<210> SEQ ID NO 394
<211> LENGTH: 195
<212> TYPE: DNA
<213> ORGANISM: Homo sapiens

<400> SEQUENCE: 394
attacatgcc cccctcccat gagcgtggag cacgccgaca tctgggtgaa gagctatagc    60
ctctacagcc gggagaggta tatctgtaac agcggcttca gaggaaggc cggcaccagc    120 agcctcaccg agtgcgtgct gaataaggct accaacgtgg ctcactggac aacaccctct   180
ttaaagtgca tccgg                                                    195

<210> SEQ ID NO 395
<211> LENGTH: 399
<212> TYPE: DNA
<213> ORGANISM: Homo sapiens

<400> SEQUENCE: 395
cagggccagg acaggcacat gatccggatg aggcagctca tcgacatcgt cgaccagctg    60
aagaactacg tgaacgacct ggtgcccgag tttctgcctg cccccgagga cgtggagacc   120
aactgcgagt ggtccgcctt ctcctgcttt cagaaggccc agctgaagtc cgccaacacc   180
```

```
ggcaacaacg agcggatcat caacgtgagc atcaagaagc tgaagcggaa gcctccctcc    240
acaaacgccg gcaggaggca gaagcacagg ctgacctgcc ccagctgtga ctcctacgag    300
aagaagcccc ccaaggagtt cctggagagg ttcaagtccc tgctgcagaa gatgatccat    360
cagcacctgt cctccaggac ccacggctcc gaggactcc                          399
```

```
<210> SEQ ID NO 396
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 396
```

Met Lys Trp Val Thr Phe Ile Ser Leu Leu Phe Leu Phe Ser Ser Ala
1               5                   10                  15

Tyr Ser

```
<210> SEQ ID NO 397
<211> LENGTH: 287
<212> TYPE: PRT
<213> ORGANISM: Homo sapiens

<400> SEQUENCE: 397
```

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
                20                  25                  30

Val Arg Phe Ser Thr Cys Asp Asn Gln Lys Ser Cys Met Ser Asn Cys
            35                  40                  45

Ser Ile Thr Ser Ile Cys Glu Lys Pro Gln Glu Val Cys Val Ala Val
        50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
                100                 105                 110

Cys Ser Cys Ser Ser Asp Glu Cys Asn Asp Asn Ile Ile Phe Ser Glu
            115                 120                 125

Glu Tyr Asn Thr Ser Asn Pro Asp Gly Gly Gly Ser Gly Gly Gly
        130                 135                 140

Gly Ser Gly Gly Gly Ser Ile Pro Pro His Val Gln Lys Ser Val
145                 150                 155                 160

Asn Asn Asp Met Ile Val Thr Asp Asn Asn Gly Ala Val Lys Phe Pro
                165                 170                 175

Gln Leu Cys Lys Phe Cys Asp Val Arg Phe Ser Thr Cys Asp Asn Gln
            180                 185                 190

Lys Ser Cys Met Ser Asn Cys Ser Ile Thr Ser Ile Cys Glu Lys Pro
        195                 200                 205

Gln Glu Val Cys Val Ala Val Trp Arg Lys Asn Asp Glu Asn Ile Thr
    210                 215                 220

Leu Glu Thr Val Cys His Asp Pro Lys Leu Pro Tyr His Asp Phe Ile
225                 230                 235                 240

Leu Glu Asp Ala Ala Ser Pro Lys Cys Ile Met Lys Glu Lys Lys Lys
                245                 250                 255

```
Pro Gly Glu Thr Phe Phe Met Cys Ser Cys Ser Ser Asp Glu Cys Asn
            260                 265                 270

Asp Asn Ile Ile Phe Ser Glu Tyr Asn Thr Ser Asn Pro Asp
        275                 280                 285

<210> SEQ ID NO 398
<211> LENGTH: 65
<212> TYPE: PRT
<213> ORGANISM: Homo sapiens

<400> SEQUENCE: 398

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg
65

<210> SEQ ID NO 399
<211> LENGTH: 133
<212> TYPE: PRT
<213> ORGANISM: Homo sapiens

<400> SEQUENCE: 399

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser
    130

<210> SEQ ID NO 400
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 400
atgaagtggg tgaccttcat cagcctgctg ttcctgttct ccagcgccta ctcc        54
```

```
<210> SEQ ID NO 401
<211> LENGTH: 861
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 401
atcccccccc atgtgcaaaa gagcgtgaac aacgatatga tcgtgaccga caacaacggc      60
gccgtgaagt ttccccagct ctgcaagttc tgcgatgtca ggttcagcac ctgcgataat     120
cagaagtcct gcatgtccaa ctgcagcatc acctccatct gcgagaagcc caagaagtg     180 tgcgtggccg tgtggcggaa aaatgacgag aacatcaccc tggagaccgt gtgtcacgac     240
cccaagctcc cttatcacga cttcattctg gaggacgctg cctcccccaa atgcatcatg     300
aaggagaaga agaagcccgg agagaccttc tttatgtgtt cctgtagcag cgacgagtgt     360
aacgacaaca tcatcttcag cgaagagtac aacaccagca accctgatgg aggtggcgga     420
tccggaggtg gaggttctgg tggaggtggg agtattcctc cccacgtgca gaagagcgtg     480
aataatgaca tgatcgtgac cgataacaat ggcgccgtga aatttcccca gctgtgcaaa     540
ttctgcgatg tgaggttttc cacctgcgac aaccagaagt cctgtatgag caactgctcc     600
atcacctcca tctgtgagaa gcctcaggag gtgtgcgtgg ctgtctggcg gaagaatgac     660
gagaatatca ccctggaaac cgtctgccac gatcccaagc tgccctacca cgatttcatc     720
ctggaagacg ccgccagccc taagtgcatc atgaaagaga aaaagaagcc tggcgagacc     780 ttttttcatgt gctcctgcag cagcgacgaa tgcaacgaca atatcatctt tagcgaggaa     840
tacaatacca gcaaccccga c                                                861

<210> SEQ ID NO 402
<211> LENGTH: 657
<212> TYPE: DNA
<213> ORGANISM: Homo sapiens

<400> SEQUENCE: 402
agcggcacaa ccaacacagt cgctgcctat aacctcactt ggaagagcac caacttcaaa      60
accatcctcg aatgggaacc caaacccgtt aaccaagttt acaccgtgca gatcagcacc     120
aagtccggcg actggaagtc caaatgtttc tataccaccg acaccgagtg cgatctcacc     180
gatgagatcg tgaaagatgt gaaacagacc tacctcgccc gggtgtttag ctaccccgcc     240
ggcaatgtgg agagcactgg ttccgctggc gagcctttat acgagaacag ccccgaattt     300
accccttacc tcgagaccaa tttaggacag cccaccatcc aaagctttga gcaagttggc     360
acaaaggtga atgtgacagt ggaggacgag cggactttag tgcggcggaa caacaccttt     420
ctcagcctcc gggatgtgtt cggcaaagat ttaatctaca cactgtatta ctggaagtcc     480
tcttcctccg gcaagaagac agctaaaacc aacacaaacg agtttttaat cgacgtggat     540
aaaggcgaaa actactgttt cagcgtgcaa gctgtgatcc cctcccggac cgtgaatagg     600
aaaagcaccg atagcccccgt tgagtgcatg gccaagaaaa agggcgagtt ccggggag      657

<210> SEQ ID NO 403
<211> LENGTH: 342
<212> TYPE: DNA
<213> ORGANISM: Homo sapiens

<400> SEQUENCE: 403
aactgggtga acgtcatcag cgatttaaag aagatcgaag atttaattca gtccatgcat      60
```

```
atcgacgcca ctttatacac agaatccgac gtgcacccct cttgtaaggt gaccgccatg    120
aaatgttttt tactggagct gcaagttatc tctttagaga gcggagacgc tagcatccac    180
gacaccgtgg agaatttaat cattttagcc aataactctt tatccagcaa cggcaacgtg    240
acagagtccg gctgcaagga gtgcgaagag ctggaggaga gaacatcaa ggagtttctg     300 caatcctttg tgcacattgt ccagatgttc atcaatacct cc                      342
```

<210> SEQ ID NO 404
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

Met Lys Trp Val Thr Phe Ile Ser Leu Leu Phe Leu Phe Ser Ser Ala
1               5                   10                  15

Tyr Ser

<210> SEQ ID NO 405
<211> LENGTH: 287
<212> TYPE: PRT
<213> ORGANISM: Homo sapiens

<400> SEQUENCE: 405

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
                20                  25                  30

Val Arg Phe Ser Thr Cys Asp Asn Gln Lys Ser Cys Met Ser Asn Cys
            35                  40                  45

Ser Ile Thr Ser Ile Cys Glu Lys Pro Gln Glu Val Cys Val Ala Val
        50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp Gly Gly Gly Ser Gly Gly Gly
        130                 135                 140

Gly Ser Gly Gly Gly Ser Ile Pro Pro His Val Gln Lys Ser Val
145                 150                 155                 160

Asn Asn Asp Met Ile Val Thr Asp Asn Asn Gly Ala Val Lys Phe Pro
                165                 170                 175

Gln Leu Cys Lys Phe Cys Asp Val Arg Phe Ser Thr Cys Asp Asn Gln
            180                 185                 190

Lys Ser Cys Met Ser Asn Cys Ser Ile Thr Ser Ile Cys Glu Lys Pro
        195                 200                 205

Gln Glu Val Cys Val Ala Val Trp Arg Lys Asn Asp Glu Asn Ile Thr
        210                 215                 220

Leu Glu Thr Val Cys His Asp Pro Lys Leu Pro Tyr His Asp Phe Ile
225                 230                 235                 240

```
Leu Glu Asp Ala Ala Ser Pro Lys Cys Ile Met Lys Glu Lys Lys
                245                 250                 255

Pro Gly Glu Thr Phe Phe Met Cys Ser Cys Ser Ser Asp Glu Cys Asn
            260                 265                 270

Asp Asn Ile Ile Phe Ser Glu Glu Tyr Asn Thr Ser Asn Pro Asp
        275                 280                 285

<210> SEQ ID NO 406
<211> LENGTH: 219
<212> TYPE: PRT
<213> ORGANISM: Homo sapiens

<400> SEQUENCE: 406

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu
    210                 215

<210> SEQ ID NO 407
<211> LENGTH: 114
<212> TYPE: PRT
<213> ORGANISM: Homo sapiens

<400> SEQUENCE: 407

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
50                  55                  60
```

```
Asn Leu Ile Ile Leu Ala Asn Asn Ser Leu Ser Ser Asn Gly Asn Val
 65                  70                  75                  80

Thr Glu Ser Gly Cys Lys Glu Cys Glu Leu Glu Glu Lys Asn Ile
                 85                  90                  95

Lys Glu Phe Leu Gln Ser Phe Val His Ile Val Gln Met Phe Ile Asn
            100                 105                 110

Thr Ser
```

<210> SEQ ID NO 408
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 408

```
atgaagtggg tgaccttcat cagcctgctg ttcctgttct ccagcgccta ctcc        54
```

<210> SEQ ID NO 409
<211> LENGTH: 861
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 409

```
atccccccc  atgtgcaaaa gagcgtgaac aacgatatga tcgtgaccga caacaacggc    60
gccgtgaagt tcccccagct ctgcaagttc tgcgatgtca ggttcagcac ctgcgataat   120
cagaagtcct gcatgtccaa ctgcagcatc acctccatct gcgagaagcc caagaagtg   180 tgcgtggccg tgtggcggaa aaatgacgag aacatcaccc tggagaccgt gtgtcacgac   240
cccaagctcc cttatcacga cttcattctg gaggacgctg cctcccccaa atgcatcatg   300
aaggagaaga agaagcccgg agagaccttc tttatgtgtt cctgtagcag cgacgagtgt   360
aacgacaaca tcatcttcag cgaagagtac aacaccagca ccctgatgg  aggtggcgga   420 tccggaggtg gaggttctgg tggaggtggg agtattcctc ccacgtgca  gaagagcgtg   480 aataatgaca tgatcgtgac cgataacaat ggcgccgtga atttcccca  gctgtgcaaa   540 ttctgcgatg tgaggttttc cacctgcgac aaccagaagt cctgtatgag caactgctcc   600
atcacctcca tctgtgagaa gcctcaggag gtgtgcgtgg ctgtctggcg gaagaatgac   660
gagaatatca ccctggaaac cgtctgccac gatcccaagc tgccctacca cgatttcatc   720
ctggaagacg ccgccagccc taagtgcatc atgaaagaga aaagaagcc  tggcgagacc   780 tttttcatgt gctcctgcag cagcgacgaa tgcaacgaca tatcatctt  tagcgaggaa   840 tacaatacca gcaaccccga c                                            861
```

<210> SEQ ID NO 410
<211> LENGTH: 195
<212> TYPE: DNA
<213> ORGANISM: Homo sapiens

<400> SEQUENCE: 410

```
attacatgcc ccctcccat gagcgtggag cacgccgaca tctgggtgaa gagctatagc    60
ctctacagcc gggagaggta tatctgtaac agcggcttca gaggaaggc  cggcaccagc   120 agcctcaccg agtgcgtgct gaataaggct accaacgtgg ctcactggac  aacaccctct   180
```
ttaaagtgca tccgg                                                       195

<210> SEQ ID NO 411
<211> LENGTH: 720
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 411
tccgagctga cccaggaccc tgctgtgtcc gtggctctgg ccagaccgt gaggatcacc        60
tgccagggcg actccctgag gtcctactac gcctcctggt accagcagaa gcccggccag      120
gctcctgtgc tggtgatcta cggcaagaac aacaggccct ccggcatccc tgacaggttc      180
tccggatcct cctccggcaa caccgcctcc ctgaccatca caggcgctca ggccgaggac      240
gaggctgact actactgcaa ctccaggac tcctccggca accatgtggt gttcggcggc       300
ggcaccaagc tgaccgtggg ccatggcggc ggcggctccg gaggcggcgg cagcggcgga      360
ggaggatccg aggtgcagct ggtggagtcc ggaggaggag tggtgaggcc tggaggctcc      420
ctgaggctga gctgtgctgc ctccggcttc accttcgacg actacggcat gtcctgggtg      480
aggcaggctc ctggaaaggg cctggagtgg gtgtccggca tcaactggaa cggcggatcc      540
accggctacg ccgattccgt gaagggcagg ttcaccatca gcagggacaa cgccaagaac      600
tccctgtacc tgcagatgaa ctccctgagg gccgaggaca ccgccgtgta ctactgcgcc      660
aggggcaggt ccctgctgtt cgactactgg ggacagggca ccctggtgac cgtgtccagg      720

<210> SEQ ID NO 412
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 412

Met Lys Trp Val Thr Phe Ile Ser Leu Leu Phe Leu Phe Ser Ser Ala
1               5                   10                  15

Tyr Ser

<210> SEQ ID NO 413
<211> LENGTH: 287
<212> TYPE: PRT
<213> ORGANISM: Homo sapiens

<400> SEQUENCE: 413

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

```
Lys Cys Ile Met Lys Glu Lys Lys Pro Gly Glu Thr Phe Phe Met
            100                 105                 110
Cys Ser Cys Ser Ser Asp Glu Cys Asn Asp Asn Ile Ile Phe Ser Glu
            115                 120                 125
Glu Tyr Asn Thr Ser Asn Pro Asp Gly Gly Gly Ser Gly Gly Gly
        130                 135                 140
Gly Ser Gly Gly Gly Ser Ile Pro Pro His Val Gln Lys Ser Val
145                 150                 155                 160
Asn Asn Asp Met Ile Val Thr Asp Asn Asn Gly Ala Val Lys Phe Pro
                165                 170                 175
Gln Leu Cys Lys Phe Cys Asp Val Arg Phe Ser Thr Cys Asp Asn Gln
                180                 185                 190
Lys Ser Cys Met Ser Asn Cys Ser Ile Thr Ser Ile Cys Glu Lys Pro
                195                 200                 205
Gln Glu Val Cys Val Ala Val Trp Arg Lys Asn Asp Glu Asn Ile Thr
            210                 215                 220
Leu Glu Thr Val Cys His Asp Pro Lys Leu Pro Tyr His Asp Phe Ile
225                 230                 235                 240
Leu Glu Asp Ala Ala Ser Pro Lys Cys Ile Met Lys Glu Lys Lys Lys
                245                 250                 255
Pro Gly Glu Thr Phe Phe Met Cys Ser Cys Ser Ser Asp Glu Cys Asn
            260                 265                 270
Asp Asn Ile Ile Phe Ser Glu Glu Tyr Asn Thr Ser Asn Pro Asp
            275                 280                 285

<210> SEQ ID NO 414
<211> LENGTH: 65
<212> TYPE: PRT
<213> ORGANISM: Homo sapiens

<400> SEQUENCE: 414

Ile Thr Cys Pro Pro Pro Met Ser Val Glu His Ala Asp Ile Trp Val
1               5                   10                  15
Lys Ser Tyr Ser Leu Tyr Ser Arg Glu Arg Tyr Ile Cys Asn Ser Gly
            20                  25                  30
Phe Lys Arg Lys Ala Gly Thr Ser Ser Leu Thr Glu Cys Val Leu Asn
        35                  40                  45
Lys Ala Thr Asn Val Ala His Trp Thr Thr Pro Ser Leu Lys Cys Ile
    50                  55                  60
Arg
65

<210> SEQ ID NO 415
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 415

Ser Glu Leu Thr Gln Asp Pro Ala Val Ser Val Ala Leu Gly Gln Thr
1               5                   10                  15
Val Arg Ile Thr Cys Gln Gly Asp Ser Leu Arg Ser Tyr Tyr Ala Ser
            20                  25                  30
Trp Tyr Gln Gln Lys Pro Gly Gln Ala Pro Val Leu Val Ile Tyr Gly
        35                  40                  45
```

Lys Asn Asn Arg Pro Ser Gly Ile Pro Asp Arg Phe Ser Gly Ser Ser
            50                  55                  60

Ser Gly Asn Thr Ala Ser Leu Thr Ile Thr Gly Ala Gln Ala Glu Asp
 65                  70                  75                  80

Glu Ala Asp Tyr Tyr Cys Asn Ser Arg Asp Ser Ser Gly Asn His Val
                85                  90                  95

Val Phe Gly Gly Gly Thr Lys Leu Thr Val Gly His Gly Gly Gly Gly
                100                 105                 110

Ser Gly Gly Gly Gly Ser Gly Gly Gly Gly Ser Glu Val Gln Leu Val
                115                 120                 125

Glu Ser Gly Gly Gly Val Val Arg Pro Gly Gly Ser Leu Arg Leu Ser
130                 135                 140

Cys Ala Ala Ser Gly Phe Thr Phe Asp Asp Tyr Gly Met Ser Trp Val
145                 150                 155                 160

Arg Gln Ala Pro Gly Lys Gly Leu Glu Trp Val Ser Gly Ile Asn Trp
                165                 170                 175

Asn Gly Gly Ser Thr Gly Tyr Ala Asp Ser Val Lys Gly Arg Phe Thr
                180                 185                 190

Ile Ser Arg Asp Asn Ala Lys Asn Ser Leu Tyr Leu Gln Met Asn Ser
                195                 200                 205

Leu Arg Ala Glu Asp Thr Ala Val Tyr Tyr Cys Ala Arg Gly Arg Ser
210                 215                 220

Leu Leu Phe Asp Tyr Trp Gly Gln Gly Thr Leu Val Thr Val Ser Arg
225                 230                 235                 240

<210> SEQ ID NO 416
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 416
atgaagtggg tgaccttcat cagcctgctg ttcctgttct ccagcgccta ctcc        54

<210> SEQ ID NO 417
<211> LENGTH: 861
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 417
atcccccccc atgtgcaaaa gagcgtgaac aacgatatga tcgtgaccga caacaacggc      60
gccgtgaagt tcccccagct ctgcaagttc tgcgatgtca ggttcagcac ctgcgataat     120
cagaagtcct gcatgtccaa ctgcagcatc acctccatct gcgagaagcc caagaagtg     180 tgcgtggccg tgtggcggaa aaatgacgag aacatcaccc tggagaccgt gtgtcacgac     240
cccaagctcc cttatcacga cttcattctg gaggacgctg cctcccccaa atgcatcatg     300
aaggagaaga agagcccgg agagaccttc tttatgtgtt cctgtagcag cgacgagtgt     360
aacgacaaca tcatcttcag cgaagagtac aacaccagca accctgatgg aggtggcgga     420
tccggaggtg gaggttctgg tggaggtggg agtattcctc ccacgtgca gaagagcgtg      480 aataatgaca tgatcgtgac cgataacaat ggcgccgtga atttcccca gctgtgcaaa     540

```
ttctgcgatg tgaggttttc cacctgcgac aaccagaagt cctgtatgag caactgctcc    600
atcacctcca tctgtgagaa gcctcaggag gtgtgcgtgg ctgtctggcg aagaatgac     660 gagaatatca ccctggaaac cgtctgccac gatcccaagc tgccctacca cgatttcatc    720
ctggaagacg ccgccagccc taagtgcatc atgaaagaga aaaagaagcc tggcgagacc    780
tttttcatgt gctcctgcag cagcgacgaa tgcaacgaca atatcatctt tagcgaggaa    840
tacaatacca gcaaccccga c                                              861
```

<210> SEQ ID NO 418
<211> LENGTH: 657
<212> TYPE: DNA
<213> ORGANISM: Homo sapiens

<400> SEQUENCE: 418

```
agcggcacaa ccaacacagt cgctgcctat aacctcactt ggaagagcac caacttcaaa     60
accatcctcg aatgggaacc caaacccgtt aaccaagttt acaccgtgca gatcagcacc    120
aagtccggcg actggaagtc caaatgtttc tataccaccg acaccgagtg cgatctcacc    180
gatgagatcg tgaaagatgt gaaacagacc tacctcgccc gggtgtttag ctaccccgcc    240
ggcaatgtgg agagcactgg ttccgctggc gagcctttat acgagaacag ccccgaattt    300
accccttacc tcgagaccaa tttaggacag cccaccatcc aaagctttga gcaagttggc    360
acaaaggtga atgtgacagt ggaggacgag cggactttag tgcggcggaa caacaccttt    420
ctcagcctcc gggatgtgtt cggcaaagat ttaatctaca cactgtatta ctggaagtcc    480
tcttcctccg gcaagaagac agctaaaacc aacacaaacg agttttttaat cgacgtggat    540 aaaggcgaaa actactgttt cagcgtgcaa gctgtgatcc cctcccggac cgtgaatagg    600
aaaagcaccg atagccccgt tgagtgcatg ggccaagaaa agggcgagtt ccgggag      657
```

<210> SEQ ID NO 419
<211> LENGTH: 342
<212> TYPE: DNA
<213> ORGANISM: Homo sapiens

<400> SEQUENCE: 419

```
aactgggtga acgtcatcag cgatttaaag aagatcgaag atttaattca gtccatgcat     60
atcgacgcca ctttatacac agaatccgac gtgcaccccct cttgtaaggt gaccgccatg    120
aaatgttttt tactggagct gcaagttatc tctttagaga gcggagacgc tagcatccac    180
gacaccgtgg agaatttaat catttttagcc aataactctt tatccagcaa cggcaacgtg    240
acagagtccg gctgcaagga gtgcgaagag ctggaggaga agaacatcaa ggagtttctg    300
caatcctttg tgcacattgt ccagatgttc atcaataccc cc                        342
```

<210> SEQ ID NO 420
<211> LENGTH: 18
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 420

```
Met Lys Trp Val Thr Phe Ile Ser Leu Leu Phe Leu Phe Ser Ser Ala
1               5                   10                  15

Tyr Ser
```

```
<210> SEQ ID NO 421
<211> LENGTH: 287
<212> TYPE: PRT
<213> ORGANISM: Homo sapiens

<400> SEQUENCE: 421

Ile Pro Pro His Val Gln Lys Ser Val Asn Asn Asp Met Ile Val Thr
1               5                   10                  15

Asp Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp Gly Gly Gly Ser Gly Gly Gly
    130                 135                 140

Gly Ser Gly Gly Gly Ser Ile Pro Pro His Val Gln Lys Ser Val
145                 150                 155                 160

Asn Asn Asp Met Ile Val Thr Asp Asn Gly Ala Val Lys Phe Pro
                165                 170                 175

Gln Leu Cys Lys Phe Cys Asp Val Arg Phe Ser Thr Cys Asp Asn Gln
            180                 185                 190

Lys Ser Cys Met Ser Asn Cys Ser Ile Thr Ser Ile Cys Glu Lys Pro
        195                 200                 205

Gln Glu Val Cys Val Ala Val Trp Arg Lys Asn Asp Glu Asn Ile Thr
    210                 215                 220

Leu Glu Thr Val Cys His Asp Pro Lys Leu Pro Tyr His Asp Phe Ile
225                 230                 235                 240

Leu Glu Asp Ala Ala Ser Pro Lys Cys Ile Met Lys Glu Lys Lys
                245                 250                 255

Pro Gly Glu Thr Phe Phe Met Cys Ser Cys Ser Ser Asp Glu Cys Asn
            260                 265                 270

Asp Asn Ile Ile Phe Ser Glu Glu Tyr Asn Thr Ser Asn Pro Asp
        275                 280                 285

<210> SEQ ID NO 422
<211> LENGTH: 219
<212> TYPE: PRT
<213> ORGANISM: Homo sapiens

<400> SEQUENCE: 422

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
```

```
            50                  55                  60
Lys Asp Val Lys Gln Thr Tyr Leu Ala Arg Val Phe Ser Tyr Pro Ala
 65                  70                  75                  80

Gly Asn Val Glu Ser Thr Gly Ser Ala Gly Glu Pro Leu Tyr Glu Asn
                 85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu
    210                 215

<210> SEQ ID NO 423
<211> LENGTH: 114
<212> TYPE: PRT
<213> ORGANISM: Homo sapiens

<400> SEQUENCE: 423

Asn Trp Val Asn Val Ile Ser Asp Leu Lys Lys Ile Glu Asp Leu Ile
 1               5                  10                  15

Gln Ser Met His Ile Asp Ala Thr Leu Tyr Thr Glu Ser Asp Val His
             20                  25                  30

Pro Ser Cys Lys Val Thr Ala Met Lys Cys Phe Leu Leu Glu Leu Gln
         35                  40                  45

Val Ile Ser Leu Glu Ser Gly Asp Ala Ser Ile His Asp Thr Val Glu
     50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Gln Met Phe Ile Asn
            100                 105                 110

Thr Ser

<210> SEQ ID NO 424
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 424
atgaagtggg tgaccttcat cagcctgctg ttcctgttct ccagcgccta ctcc        54

<210> SEQ ID NO 425
<211> LENGTH: 861
```

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 425 atccccccccc atgtgcaaaa gagcgtgaac aacgatatga tcgtgaccga caacaacggc      60
gccgtgaagt ttccccagct ctgcaagttc tgcgatgtca ggttcagcac ctgcgataat     120
cagaagtcct gcatgtccaa ctgcagcatc acctccatct gcgagaagcc ccaagaagtg     180
tgcgtggccg tgtggcggaa aaatgacgag aacatcaccc tggagaccgt gtgtcacgac     240
cccaagctcc cttatcacga cttcattctg gaggacgctg cctcccccaa atgcatcatg     300
aaggagaaga agaagcccgg agagaccttc tttatgtgtt cctgtagcag cgacgagtgt     360
aacgacaaca tcatcttcag cgaagagtac aacaccagca ccctgatgg aggtggcgga     420 tccggaggtg gaggttctgg tggaggtggg agtattcctc cccacgtgca gaagagcgtg     480
aataatgaca tgatcgtgac cgataacaat ggcgccgtga atttccccca gctgtgcaaa     540
ttctgcgatg tgaggttttc cacctgcgac aaccagaagt cctgtatgag caactgctcc     600
atcacctcca tctgtgagaa gcctcaggag gtgtgcgtgg ctgtctggcg gaagaatgac     660
gagaatatca ccctggaaac cgtctgccac gatcccaagc tgccctacca cgatttcatc     720
ctggaagacg ccgccagccc taagtgcatc atgaaagaga aaagaagcc tggcgagacc     780 tttttcatgt gctcctgcag cagcgacgaa tgcaacgaca atatcatctt tagcgaggaa     840
tacaatacca gcaaccccga c                                              861

<210> SEQ ID NO 426
<211> LENGTH: 195
<212> TYPE: DNA
<213> ORGANISM: Homo sapiens

<400> SEQUENCE: 426
attacatgcc ccctcccat gagcgtggag cacgccgaca tctgggtgaa gagctatagc       60
ctctacagcc gggagaggta tatctgtaac agcggcttca agaggaaggc cggcaccagc     120
agcctcaccg agtgcgtgct gaataaggct accaacgtgg ctcactggac aacaccctct     180
ttaaagtgca tccgg                                                     195

<210> SEQ ID NO 427
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 427
ggcggtggag gatccggagg aggtggctcc ggcggcggag gatct                      45

<210> SEQ ID NO 428
<211> LENGTH: 552
<212> TYPE: DNA
<213> ORGANISM: Homo sapiens

<400> SEQUENCE: 428
cgcgagggtc ccgagctttc gcccgacgat ccgccggcc tcttggacct gcggcagggc       60
atgtttgcgc agctggtggc ccaaaatgtt ctgctgatcg atgggccct gagctggtac     120
```

```
agtgacccag gcctggcagg cgtgtccctg acgggggggcc tgagctacaa agaggacacg    180
aaggagctgg tggtggccaa ggctggagtc tactatgtct tctttcaact agagctgcgg    240
cgcgtggtgg ccggcgaggg ctcaggctcc gtttcacttg cgctgcacct gcagccactg    300
cgctctgctg ctggggccgc cgccctggct ttgaccgtgg acctgccacc cgcctcctcc    360
gaggctcgga actcggcctt cggtttccag ggccgcttgc tgcacctgag tgccggccag    420
cgcctgggcg tccatcttca cactgaggcc agggcacgcc atgcctggca gcttacccag    480
ggcgccacag tcttgggact cttccgggtg accccgaaa tcccagccgg actcccttca    540
ccgaggtcgg aa                                                         552
```

```
<210> SEQ ID NO 429
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 429

Met Lys Trp Val Thr Phe Ile Ser Leu Leu Phe Leu Phe Ser Ser Ala
1               5                   10                  15

Tyr Ser

<210> SEQ ID NO 430
<211> LENGTH: 287
<212> TYPE: PRT
<213> ORGANISM: Homo sapiens

<400> SEQUENCE: 430

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
                20                  25                  30

Val Arg Phe Ser Thr Cys Asp Asn Gln Lys Ser Cys Met Ser Asn Cys
            35                  40                  45

Ser Ile Thr Ser Ile Cys Glu Lys Pro Gln Glu Val Cys Val Ala Val
        50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
                100                 105                 110

Cys Ser Cys Ser Ser Asp Glu Cys Asn Asp Asn Ile Ile Phe Ser Glu
            115                 120                 125

Glu Tyr Asn Thr Ser Asn Pro Asp Gly Gly Gly Ser Gly Gly Gly
        130                 135                 140

Gly Ser Gly Gly Gly Ser Ile Pro Pro His Val Gln Lys Ser Val
145                 150                 155                 160

Asn Asn Asp Met Ile Val Thr Asp Asn Asn Gly Ala Val Lys Phe Pro
                165                 170                 175

Gln Leu Cys Lys Phe Cys Asp Val Arg Phe Ser Thr Cys Asp Asn Gln
            180                 185                 190

Lys Ser Cys Met Ser Asn Cys Ser Ile Thr Ser Ile Cys Glu Lys Pro
        195                 200                 205
```

-continued

```
Gln Glu Val Cys Val Ala Val Trp Arg Lys Asn Asp Glu Asn Ile Thr
    210                 215                 220
Leu Glu Thr Val Cys His Asp Pro Lys Leu Pro Tyr His Asp Phe Ile
225                 230                 235                 240
Leu Glu Asp Ala Ala Ser Pro Lys Cys Ile Met Lys Glu Lys Lys
                245                 250                 255
Pro Gly Glu Thr Phe Phe Met Cys Ser Cys Ser Ser Asp Glu Cys Asn
                260                 265                 270
Asp Asn Ile Ile Phe Ser Glu Tyr Asn Thr Ser Asn Pro Asp
            275                 280                 285

<210> SEQ ID NO 431
<211> LENGTH: 65
<212> TYPE: PRT
<213> ORGANISM: Homo sapiens

<400> SEQUENCE: 431

Ile Thr Cys Pro Pro Pro Met Ser Val Glu His Ala Asp Ile Trp Val
1               5                   10                  15
Lys Ser Tyr Ser Leu Tyr Ser Arg Glu Arg Tyr Ile Cys Asn Ser Gly
            20                  25                  30
Phe Lys Arg Lys Ala Gly Thr Ser Ser Leu Thr Glu Cys Val Leu Asn
        35                  40                  45
Lys Ala Thr Asn Val Ala His Trp Thr Thr Pro Ser Leu Lys Cys Ile
    50                  55                  60
Arg
65

<210> SEQ ID NO 432
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 432

Gly Gly Gly Gly Ser Gly Gly Gly Ser Gly Gly Gly Ser
1               5                   10                  15

<210> SEQ ID NO 433
<211> LENGTH: 184
<212> TYPE: PRT
<213> ORGANISM: Homo sapiens

<400> SEQUENCE: 433

Arg Glu Gly Pro Glu Leu Ser Pro Asp Asp Pro Ala Gly Leu Leu Asp
1               5                   10                  15
Leu Arg Gln Gly Met Phe Ala Gln Leu Val Ala Gln Asn Val Leu Leu
            20                  25                  30
Ile Asp Gly Pro Leu Ser Trp Tyr Ser Asp Pro Gly Leu Ala Gly Val
        35                  40                  45
Ser Leu Thr Gly Gly Leu Ser Tyr Lys Glu Asp Thr Lys Glu Leu Val
    50                  55                  60
Val Ala Lys Ala Gly Val Tyr Tyr Val Phe Phe Gln Leu Glu Leu Arg
65                  70                  75                  80
Arg Val Val Ala Gly Glu Gly Ser Gly Ser Val Ser Leu Ala Leu His
                85                  90                  95
Leu Gln Pro Leu Arg Ser Ala Ala Gly Ala Ala Ala Leu Ala Leu Thr
```

-continued

```
                100              105              110
Val Asp Leu Pro Pro Ala Ser Ser Glu Ala Arg Asn Ser Ala Phe Gly
        115              120              125

Phe Gln Gly Arg Leu Leu His Leu Ser Ala Gly Gln Arg Leu Gly Val
        130              135              140

His Leu His Thr Glu Ala Arg Ala Arg His Ala Trp Gln Leu Thr Gln
145              150              155              160

Gly Ala Thr Val Leu Gly Leu Phe Arg Val Thr Pro Glu Ile Pro Ala
                165              170              175

Gly Leu Pro Ser Pro Arg Ser Glu
                180
```

What is claimed is:

1. A method of purifying a multi-chain chimeric polypeptide, the method comprising:
   loading an affinity chromatography resin with a liquid comprising the multi-chain chimeric polypeptide;
   washing the affinity chromatography resin using one or more wash buffer(s); and
   eluting the multi-chain chimeric polypeptide using an elution buffer, wherein:
   the affinity chromatography resin comprises an anti-tissue factor antibody or antigen-binding fragment thereof comprising a heavy chain variable domain comprising a CDR1 of SEQ ID NO: 1, a CDR2 of SEQ ID NO: 2 or 9, and a CDR3 of SEQ ID NO: 3, and a light chain variable domain comprising a CDR1 of SEQ ID NO: 4, a CDR2 of SEQ ID NO: 5, and a CDR3 of SEQ ID NO: 6, attached to a base resin;
   the multi-chain chimeric polypeptide comprises:
   (a) a first chimeric polypeptide comprising:
      (i) a first target-binding domain comprising a sequence that is at least 80% identical to amino acids 19 to 305 of SEQ ID NO: 70;
      (ii) a soluble tissue factor domain comprising a sequence that is at least 80% identical to SEQ ID NO: 10; and
      (iii) a first domain of a pair of affinity domains comprising a sequence that is at least 80% identical to SEQ ID NO: 125; and
   (b) a second chimeric polypeptide comprising:
      (i) a second domain of a pair of affinity domains comprising a sequence that is at least 80% identical to SEQ ID NO: 123; and
      (ii) a second target-binding domain comprising a sequence that is at least 80% identical to amino acids 19 to 305 of SEQ ID NO: 70;
   the first chimeric polypeptide and the second chimeric polypeptide associate through the binding of the first domain and the second domain of the pair of affinity domains; and
   the multi-chain chimeric polypeptide does not stimulate blood coagulation in a mammal.

2. The method of claim 1, wherein the liquid comprising the multi-chain chimeric polypeptide is a clarified liquid culture medium.

3. The method of claim 1, wherein the liquid comprising the multi-chain chimeric polypeptide comprises a cell lysate.

4. The method of claim 1, wherein the one or more wash buffer(s) are:
   (i) a first wash buffer comprising phosphate buffered saline; and
   (ii) a second wash buffer comprising 0.01 M to 0.2 M citrate and having a pH of 4.5 to 5.5.

5. The method of claim 4, wherein:
   (i) the first wash buffer is phosphate buffered saline; and
   (ii) the second wash buffer is 0.1 M citrate, pH 5.0.

6. The method of claim 1, wherein the elution buffer comprises 0.01 M to 0.2 M acetate and has a pH of 2.5 to 3.5.

7. The method of claim 6, wherein the elution buffer comprises 0.1 M acetate and has a pH of 2.9.

8. The method of claim 1, wherein the method further comprises:
   performing one or more additional unit operations on an eluate obtained from the step of eluting the multi-chain chimeric polypeptide.

9. The method of claim 8, wherein the one or more additional unit operations comprises, in sequential order:
   performing low pH viral inactivation;
   performing depth filtration;
   performing polishing chromatography;
   performing nanofiltration; and
   performing ultrafiltration and diafiltration (UF/DF).

10. The method of claim 1, wherein the heavy chain variable domain comprises a sequence that is at least 90% identical to SEQ ID NO: 7, and the light chain variable domain comprises a sequence that is at least 90% identical to SEQ ID NO: 8.

11. The method of claim 10, wherein the heavy chain variable domain comprises SEQ ID NO: 7, and the light chain variable domain comprises SEQ ID NO: 8.

12. The method of claim 1, wherein the base resin is sepharose.

13. The method of claim 1, wherein the base resin is any support material.

14. The method of claim 13, wherein the support material is agarose or a capto resin.

15. The method of claim 1, wherein the anti-tissue factor antibody or antigen-binding fragment thereof is non-covalently attached to the base resin.

16. The method of claim 1, wherein the anti-tissue factor antibody or antigen-binding fragment thereof is covalently attached to the base resin.

17. The method of claim 16, wherein the anti-tissue factor antibody or antigen-binding fragment thereof is covalently attached to the base resin through the formation of a disulfide bond between a cysteine in the anti-tissue factor antibody or antigen-binding fragment thereof and a chemical group on the base resin.

18. The method of claim 16, wherein the anti-tissue factor antibody or antigen-binding fragment thereof is covalently attached to the base resin through the formation of a covalent bond between a free amine of the anti-tissue factor antibody or antigen-binding domain and a chemical group on the base resin.

19. The method of claim 18, wherein the base resin is CNBr-activated or N-hydroxysuccinimide (NHS)-activated solid support material.

20. The method of claim 18, wherein the covalent bond is represented by Formula I below:

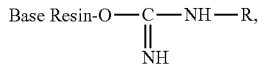

wherein R represents the anti-tissue factor antibody or antigen-binding fragment thereof.

21. The method of claim 1, wherein the first target-binding domain and the soluble tissue factor domain directly abut each other in the first chimeric polypeptide.

22. The method of claim 1, wherein the first chimeric polypeptide further comprises a linker sequence between the first target-binding domain and the soluble tissue factor domain in the first chimeric polypeptide.

23. The method of claim 1, wherein the soluble tissue factor domain and the first domain of the pair of affinity domains directly abut each other in the first chimeric polypeptide.

24. The method of claim 1, wherein the first chimeric polypeptide further comprises a linker sequence between the soluble tissue factor domain and the first domain of the pair of affinity domains in the first chimeric polypeptide.

25. The method of claim 1, wherein the second domain of the pair of affinity domains and the second target-binding domain directly abut each other in the second chimeric polypeptide.

26. The method of claim 1, wherein the second chimeric polypeptide further comprises a linker sequence between the second domain of the pair of affinity domains and the second target-binding domain in the second chimeric polypeptide.

27. The method of claim 1, wherein the soluble tissue factor domain is a soluble human tissue factor domain.

28. The method of claim 1, wherein:
the first target-binding domain comprises a sequence that is at least 90% identical to amino acids 19 to 305 of SEQ ID NO: 70;
the soluble tissue factor domain comprises a sequence that is at least 90% identical to SEQ ID NO: 10;
the first domain of the pair of affinity domains comprises a sequence that is at least 90% identical to SEQ ID NO: 125;
the second target-binding domain comprises a sequence that is at least 90% identical to amino acids 19 to 305 of SEQ ID NO: 70; and
the second domain of the pair of affinity domains comprises a sequence that is at least 90% identical to SEQ ID NO: 123.

29. The method of claim 28, wherein:
the first target-binding domain comprises a sequence that is at least 95% identical to amino acids 19 to 305 of SEQ ID NO: 70;
the soluble tissue factor domain comprises a sequence that is at least 95% identical to SEQ ID NO: 10;
the first domain of the pair of affinity domains comprises a sequence that is at least 95% identical to SEQ ID NO: 125;
the second target-binding domain comprises a sequence that is at least 95% identical to amino acids 19 to 305 of SEQ ID NO: 70; and
the second domain of the pair of affinity domains comprises a sequence that is at least 95% identical to SEQ ID NO: 123.

30. The method of claim 29, wherein:
the first target-binding domain comprises a sequence of amino acids 19 to 305 of SEQ ID NO: 70;
the soluble tissue factor domain comprises SEQ ID NO: 10;
the first domain of the pair of affinity domains comprises SEQ ID NO: 125;
the second target-binding domain comprises a sequence of amino acids 19 to 305 of SEQ ID NO: 70; and
the second domain of the pair of affinity domains comprises SEQ ID NO: 123.

* * * * *